(12) United States Patent
Curtiss, III et al.

(10) Patent No.: US 9,050,285 B2
(45) Date of Patent: Jun. 9, 2015

(54) **RECOMBINANT BACTERIUM CAPABLE OF ELICITING AN IMMUNE RESPONSE AGAINST *STREPTOCOCCUS PNEUMONIAE***

(75) Inventors: Roy Curtiss, III, Paradise Valley, AZ (US); Javier Santander-Morales, Tempe, AZ (US); Soo-Young Wanda, Chandler, AZ (US); Shifeng Wang, Tempe, AZ (US); Karen Brenneman, Phoenix, AZ (US); Huoying Shi, Tempe, AZ (US); Wei Xin, Tempe, AZ (US); Qingke Kong, Tempe, AZ (US)

(73) Assignee: The United States of America National Institutes of Health (NH), U.S. Dept. of Health and Human Services (DHHS), Washington, DC (US)

( * ) Notice: Subject to any disclaimer, the term of this patent is extended or adjusted under 35 U.S.C. 154(b) by 240 days.

(21) Appl. No.: 13/088,141

(22) Filed: Apr. 15, 2011

(65) Prior Publication Data

US 2011/0287052 A1 Nov. 24, 2011

Related U.S. Application Data

(63) Continuation-in-part of application No. PCT/US2009/061100, filed on Oct. 16, 2009.

(60) Provisional application No. 61/106,367, filed on Oct. 17, 2008.

(51) Int. Cl.
*A61K 39/275* (2006.01)
*A61K 39/09* (2006.01)
*A61K 39/00* (2006.01)

(52) U.S. Cl.
CPC ......... *A61K 39/092* (2013.01); *A61K 2039/522* (2013.01); *A61K 2039/523* (2013.01)

(58) Field of Classification Search
CPC ... A61K 39/092; A61K 2039/523; C12N 1/21
USPC ................................. 435/252.3; 424/200.1
See application file for complete search history.

(56) References Cited

U.S. PATENT DOCUMENTS 4,190,495 A 2/1980 Curtiss, III
4,888,170 A * 12/1989 Curtiss, III ................. 424/200.1

(Continued)

FOREIGN PATENT DOCUMENTS

EP 0315682 B1 12/1993
EP 0381706 B1 4/1995

(Continued)

OTHER PUBLICATIONS

Xin, W et al, Infection and Immunity, Jul. 2008, vol. 76(7), pp. 3241-3254, Analysis of Type II secretion of Recombinant Pneumococcal PspA andPspC in *Salmonella enterica* serovar typhimurium vaccine with regulated delayed antigen synthesis.*

(Continued)

*Primary Examiner* — Albert Navarro
*Assistant Examiner* — Ginny Portner
(74) *Attorney, Agent, or Firm* — Rebecca C. Riley-Vargas; Polsinelli PC

(57) ABSTRACT

The invention encompasses a recombinant bacterium capable of eliciting an immune response against *Streptococcus pneumoniae*, a vaccine comprising the bacterium, and methods of using the bacterium.

10 Claims, 152 Drawing Sheets

(56) References Cited

U.S. PATENT DOCUMENTS

| | | | |
|---|---|---|---|
| 4,968,619 | A | 11/1990 | Curtiss, III |
| 5,210,035 | A | 5/1993 | Stocker |
| 5,294,441 | A | 3/1994 | Curtiss, III |
| 5,387,744 | A | 2/1995 | Curtiss et al. |
| 5,389,368 | A * | 2/1995 | Curtiss, III ............... 424/200.1 |
| 5,424,065 | A | 6/1995 | Curtiss et al. |
| 5,468,485 | A | 11/1995 | Curtiss, III |
| 5,654,184 | A | 8/1997 | Curtiss, III |
| 5,656,488 | A | 8/1997 | Curtiss, III |
| 5,672,345 | A * | 9/1997 | Curtiss, III ................. 424/93.2 |
| 5,679,880 | A | 10/1997 | Curtiss, III |
| 5,686,079 | A | 11/1997 | Curtiss, III |
| 5,695,983 | A * | 12/1997 | Miller et al. ............... 435/252.8 |
| 5,817,317 | A | 10/1998 | Titball |
| 5,827,705 | A | 10/1998 | Dean |
| 5,840,483 | A | 11/1998 | Curtiss, III |
| 5,855,879 | A | 1/1999 | Curtiss III |
| 5,855,880 | A | 1/1999 | Curtiss, III |
| 5,919,663 | A * | 7/1999 | Brey et al. ................... 435/69.3 |
| 5,961,983 | A * | 10/1999 | Brey et al. ................. 424/200.1 |
| 6,024,961 | A * | 2/2000 | Curtiss et al. ............. 424/200.1 |
| 6,180,614 | B1 | 1/2001 | Davis |
| 6,248,329 | B1 | 6/2001 | Chandrashekar et al. |
| 6,350,454 | B1 | 2/2002 | Thune |
| 6,383,496 | B1 * | 5/2002 | Curtiss et al. ............. 424/200.1 |
| 6,399,074 | B1 | 6/2002 | Roland |
| 6,403,094 | B1 | 6/2002 | Titball |
| 6,610,529 | B1 | 8/2003 | Curtiss, III |
| 6,780,405 | B1 | 8/2004 | Curtiss, III |
| 6,872,547 | B1 * | 3/2005 | Curtiss, III ................... 435/69.1 |
| 6,969,513 | B2 | 11/2005 | Galen |
| 7,083,794 | B2 * | 8/2006 | Curtiss et al. ............. 424/200.1 |
| 7,195,757 | B2 | 3/2007 | Curtiss, III |
| 7,205,125 | B2 | 4/2007 | Castillo |
| 7,341,860 | B2 | 3/2008 | Curtiss, III |
| 7,871,604 | B1 | 1/2011 | Curtiss, III |
| 7,968,101 | B2 | 6/2011 | Kawaoka |
| 8,133,493 | B2 * | 3/2012 | Curtiss, III ................ 424/200.1 |
| 8,445,254 | B2 * | 5/2013 | Curtiss, III et al. ........ 435/252.3 |
| 8,465,755 | B2 * | 6/2013 | Curtiss, III et al. ........ 424/258.1 |
| 8,889,121 | B2 * | 11/2014 | Curtiss, III et al. ........ 424/93.48 |
| 2003/0031683 | A1 | 2/2003 | Curtiss, III |
| 2003/0175772 | A1 | 9/2003 | Wang |
| 2004/0077556 | A1 * | 4/2004 | Chinery .......................... 514/27 |
| 2004/0101531 | A1 * | 5/2004 | Curtiss, et al. ............. 424/184.1 |
| 2004/0120962 | A1 | 6/2004 | Curtiss, III |
| 2004/0137003 | A1 | 7/2004 | Curtiss, III |
| 2004/0203039 | A1 | 10/2004 | Hensel |
| 2005/0036987 | A1 | 2/2005 | Pawelek |
| 2005/0106175 | A1 | 5/2005 | Montaines |
| 2005/0106176 | A1 | 5/2005 | Curtiss, III |
| 2005/0118193 | A1 | 6/2005 | Andino-Pavlovsky et al. |
| 2006/0140975 | A1 | 6/2006 | Curtiss, III |
| 2006/0171917 | A1 | 8/2006 | Campbell |
| 2006/0206961 | A1 | 9/2006 | Cirpus |
| 2006/0233829 | A1 * | 10/2006 | Curtiss ....................... 424/200.1 |
| 2006/0234346 | A1 | 10/2006 | Retallack |
| 2006/0275255 | A1 | 12/2006 | Gudkov |
| 2007/0025981 | A1 | 2/2007 | Szalay |
| 2008/0248066 | A1 | 10/2008 | Dubensky, Jr. |
| 2009/0175829 | A1 | 7/2009 | Forbes |
| 2010/0124558 | A1 * | 5/2010 | Curtiss, III et al. ........ 424/200.1 |
| 2010/0285592 | A1 | 11/2010 | Curtiss, III |
| 2010/0317084 | A1 * | 12/2010 | Curtiss, III ................. 435/252.3 |
| 2011/0033501 | A1 * | 2/2011 | Curtiss, III et al. ........ 424/258.1 |
| 2011/0256181 | A1 * | 10/2011 | Curtiss, III et al. ........ 424/258.1 |
| 2011/0287052 | A1 * | 11/2011 | Curtiss, III et al. ........ 424/200.1 |
| 2012/0087946 | A1 | 4/2012 | Curtiss, III |
| 2013/0004537 | A1 * | 1/2013 | Curtiss, III et al. ........ 424/200.1 |
| 2013/0171190 | A1 * | 7/2013 | Curtiss, III et al. ........ 424/200.1 |

FOREIGN PATENT DOCUMENTS

| | | | |
|---|---|---|---|
| EP | 0465560 | B1 | 6/1996 |
| EP | 0500699 | B1 | 6/1998 |
| EP | 0558631 | B1 | 3/1999 |
| EP | 0433372 | B1 | 6/2002 |
| EP | 1030690 | B1 | 7/2002 |
| EP | 0556333 | B1 | 3/2003 |
| EP | 1326960 | B1 | 12/2004 |
| EP | 0832255 | B1 | 12/2005 |
| EP | 1537214 | B1 | 3/2006 |
| EP | 1292687 | B1 | 8/2006 |
| WO | 88/09669 | A1 | 12/1988 |
| WO | 89/03427 | A1 | 4/1989 |
| WO | 90/02484 | A1 | 3/1990 |
| WO | 90/11687 | A1 | 10/1990 |
| WO | 90/11688 | A1 | 10/1990 |
| WO | 90/12086 | A1 | 10/1990 |
| WO | 91/06317 | A1 | 5/1991 |
| WO | 92/08486 | A1 | 5/1992 |
| WO | 92/09684 | A1 | 6/1992 |
| WO | 93/04202 | A1 | 3/1993 |
| WO | 94/24291 | A2 | 10/1994 |
| WO | 94/24291 | A3 | 12/1994 |
| WO | 96/40947 | A1 | 12/1996 |
| WO | 99/25387 | A1 | 5/1999 |
| WO | 01/83785 | A2 | 11/2001 |
| WO | 02/30457 | A2 | 4/2002 |
| WO | 2001/083785 | A3 | 6/2002 |
| WO | 02/059292 | A2 | 8/2002 |
| WO | 2002/030457 | A3 | 1/2003 |
| WO | 2002/030457 | A3 | 7/2003 |
| WO | 2002/059292 | A3 | 7/2003 |
| WO | 03/079792 | A1 | 10/2003 |
| WO | 03/096812 | A1 | 11/2003 |
| WO | 2004/020643 | A2 | 3/2004 |
| WO | 2004/020643 | A3 | 4/2004 |
| WO | 2005/001069 | A1 | 1/2005 |
| WO | 2008/141226 | A2 | 11/2008 |
| WO | 2009/025888 | * | 2/2009 ............... C12N 1/21 |
| WO | 2009/025888 | A2 | 2/2009 |
| WO | 2009/046449 | A1 | 4/2009 |
| WO | 2009/046451 | A1 | 4/2009 |
| WO | 2010/045620 | A1 | 4/2010 |
| WO | 2010/078584 | A1 | 8/2010 |
| WO | 2010/135563 | A1 | 11/2010 |
| WO | 2011/091291 | A1 | 7/2011 |
| WO | 2011/150421 | A2 | 12/2011 |
| WO | 2012087483 | A1 | 6/2012 |

OTHER PUBLICATIONS

PCT/US2008/063303 (WO 2008/141226)—International Search Report and Written Opinion of the International Searching Authority, Nov. 26, 2008.

U.S. Appl. No. 12/759,842, Office Action dated Oct. 4, 2010.

PCT/US2008/078991 (WO 2009/046449)—International Search Report and Written Opinion of the International Searching Authority, Dec. 15, 2008.

PCT/US2008/078993 (WO 2009/046451)—International Search Report and Written Opinion of the International Searching Authority, Dec. 15, 2008.

PCT/US2010/035630 (WO 2010/135563)—International Search Report and Written Opinion of the International Searching Authority, Sep. 29, 2010.

PCT/US2009/061100 (WO 2010/045620)—International Search Report and Written Opinion of the International Searching Authority, Dec. 4, 2009.

PCT/US2010/020137 (WO 2010/078584)—International Search Report and Written Opinion of the International Searching Authority, Mar. 9, 2010.

PCT/US2011/022110 (WO 2011/091291)—International Search Report and Written Opinion of the International Searching Authority, Apr. 11, 2011.

PCT/US2011/038588 (WO 2011/150421)—International Search Report and Written Opinion of the International Searching Authority, Nov. 22, 2011.

(56) References Cited

OTHER PUBLICATIONS

PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar Typhimurium. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydeJ. Biol. Chem., 1955, pp. 39-50, vol. 213.
Briles et al., Immunization of humans with recombinant pneumococcal surface protein A (rPspA) elicits antibodies that passively protect

(56) References Cited

OTHER PUBLICATIONS mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.
Brosius et al., Spacing of the −10 and −35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., Il-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for *Salmonella* virulence in mice. J. Clin. Invest., 1995, pp. 1047-1053, vol. 95.
Bumann, Regulated antigen expression in live recombinant *Salmonella enterica* serovar Typhimurium strongly affects colonization capabilities and specific CD4(+)-T-cell responses. Infect Immun, 2001. pp. 7493-7500, vol. 69, No. 12.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of *Bordetella pertussis* using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* KIM delivered by live attenuated *Salmonella typhimurium* elicits a protective immune response against plague. Adv Exp Med Biol, 2007, pp. 3873-3899, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to *Yersiniae*: roles of Yops and LcrV (V antigen). Infect Immun, 2003, pp. 3673-3681, vol. 71.
Brubaker, The Vwa+ virulence factor of *Yersiniae*: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.

Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL Is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murl gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.

(56) References Cited

OTHER PUBLICATIONS

Giannella et al., Gastric acidity and cholera. Ann Intern Med, 1973, p. 780, vol. 78.

Gilbert, The lac repressor and the lac operator. Ciba Found Symp, 1972, pp. 24-59, vol. 7.

Gong et al., Characterization of the *Yersinia pestis* Yfu ABC inorganic iron transport system. Infect Immun, 2001, pp. 2829-2837, vol. 69.

Gor et al., TH1-TH2: a Procrustean paradigm. Nat Immunol, 2003, p. 503-5, vol. 4.

Grillot-Courvalin et al., Functional gene transfer from intracellular bacteria to mammalian cells. Nat. Biotechnol., 1998, pp. 862-866, vol. 16.

Guerrant et al., Magnitude and Impact of Diarrheal Diseases. Arch. Med. Res., 2002, pp. 351-355, vol. 33.

Gunn, Mechanisms of bacterial resistance and response to bile. Microbes Infect, 2000, pp. 907-913, vol. 2.

Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.

CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.

Chen et al., Genetic mapping of the cold-adapted phenotype of B/Ann Arbor/1/66, the master donor virus for live attenuated influenza vaccines (FluMist). Virology, 2006, pp. 416-423, vol. 345.

U.S. Appl. No. 13/006,072, Office Action dated Apr. 19, 2012.

Sun et al., Highly efficient method for introducing successive multiple scarless gene deletions and markerless gene insertions into the *Yersinia pestis* chromosome. Appl Environ Microbiol, 2008, pp. 4241-4245, vol. 74.

Curtiss et al., New technologies in using recombinant attenuated *Salmonella* vaccine vectors. Crit. Rev. Immunol., 2010, pp. 255-270, vol. 30.

Curtiss et al., *Salmonella* strains with regulated delayed attenuation in vivo. Infect. Immun., 2009, pp. 1071-1082, vol. 77.

Curtiss et al., *Salmonella typhimurium* deletion mutants lacking adenylate cyclase and cyclic AMP receptor protein are avirulent and immunogenic. Infect Immun, 1987, pp. 3035-3043, vol. 55.

Waltman et al., Biochemical Characteristics of *Edwardsiella ictaluri*. Applied and Enviornmental Microbiology, 1986, pp. 101-104, vol. 51, No. 1.

Curtiss, Bacterial infectious disease control by vaccine development. J. Clin. Investig., 2002, pp. 1061-1066, vol. 110.

Curtiss, Chromosomal aberrations associated with mutations to bacteriophage resistance in *Escherichia coli*. J. Bacteriol., 1965, pp. 28-40, vol. 89.

Daigle et al., Identification of *Salmonella typhi* genes expressed within macrophages by selective capture of transcribed sequences (SCOTS). Mol Microbiol, 2001, pp. 1211-1222, vol. 41.

Takaya et al., The ATP-Dependent Lon Protease of *Salmonella enterica* Serovar Typhimurium Regulates Invasion and Expression of Genes Carried on *Salmonella* Pathogenicity Island 1. Journal of Bacteriology, 2002, pp. 224-232, vol. 184, No. 1.

Dean, 1997. Import of plasmid DNA into the nucleus is sequence specific. Exp. Cell Res., 1997, pp. 293-302, vol. 230.

Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.

Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.

Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.

Pickard et al., Characterization of defined ompR mutants of *Salmonella typhi*: ompR is involved in the regulation of Vi polysaccharide expression. Infect Immun, 1994, pp. 3984-3993, vol. 62, No. 9.

Egorov et al., Transfectant influenza A viruses with long deletions in the NS1 protein grow efficiently in Vero cells. J. Virol., 1998, pp. 6437-6441, vol. 72.

Enami et al., Introduction of site-specific mutations into the genome of influenza virus. Proc. Natl. Acad. Sci. USA, 1990, pp. 3802-3805, vol. 87.

Fodor et al., Rescue of influenza A virus from recombinant DNA. J. Virol., 1999, pp. 9679-9682, vol. 73.

Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.

Fraser et al., The amino acid composition of T3 bacteriophage. J Biol Chem, 1953, pp. 291-295, vol. 205, No. 1.

Galan et al., Cloning and molecular characterization of genes whose products allow *Salmonella typhimurium* to penetrate tissue culture cells. Proc Natl Acad Sci U S A, 1989, pp. 6383-6387, vol. 86.

Galen et al., Optimization of Plasmid Maintenance in the Attenuated Live Vector Vaccine Strain *Salmonella typhi* CVD 908-htrA. Infect. Immun., 1999, pp. 6424-6433, vol. 67.

Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.

Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.

Gerdil, The annual production cycle for influenza vaccine. Vaccine, 2003, pp. 1776-1779, vol. 21.

Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.

Greenwood, The epidemiology of pneumococcal infection in children in the developing world. Philos. Trans. R. Soc. Lond. B. Biol. Sci., 1999, pp. 777-785, vol. 354.

Gulig et al., Plasmid-associated virulence of *Salmonella typhimurium*. Infect Immun, 1987, pp. 2891-2901, vol. 55.

Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.

Hoffmann et al., "Ambisense" approach for the generation of influenza A virus: vRNA and mRNA synthesis from one template. Virology, 2000, pp. 310-317, vol. 267.

Hohmann et al., Macrophage-inducible expression of a model antigen in *Salmonella typhimurium* enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

(56) References Cited

OTHER PUBLICATIONS

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.
Kang et al., Immune responses to recombinant pneumococcal PspA antigen delivered by live attenuated *Salmonella enterica* serovar typhimurium vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Hurme et al, A Proteinaceous Gene Regulator Thermameter in *Salmonella*. Cell, 1997, pp. 55-64, vol. 90.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.
Konjufca et al., A Recombinant Attenuated *Salmonella enterica* Serovar Typhimurium Vaccine Encoding *Eimeria acervulina* Antigen Offers Protection against *E. acervulina* Challenge. Infect. Immun., 2006, pp. 6785-6796, vol. 74.
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in *Xenopus oocytes*. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of *Yersinia pestis* by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spv and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to *Yersiniae* mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.

(56) References Cited

OTHER PUBLICATIONS

Perry et al., Temperature regulation of the hemin storage (Hms+) phenotype of *Yersinia pestis* is posttranscriptional. J Bacteriol, 2004, pp. 1638-1647, vol. 186.

Petersen et al., Essential role for cyclic AMP and its receptor protein in *Yersinia enterocolitica* virulence. Infect Immun, 2004, pp. 3665-3672, vol. 70.

Ramarathinam et al., *Salmonella typhimurium* induces IFN-gamma production in murine splenocytes. Role of natural killer cells and macrophages. J Immunol, 1993, pp. 3973-3981, vol. 150.

Raupach et al., Bacterial virulence, proinflammatory cytokines and host immunity: how to choose the appropriate *Salmonella* vaccine strain? Microbes and Infection, 2001, p. 1261, vol. 3.

Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.

Sarubbi et al., (1989) Characterization of the spoT gene of *Escherichia coli*. J Biol Chem, 1989, pp. 15074-15082, vol. 264.

Schmieger et al., Altered cotransduction frequencies exhibited by HT-mutants of *Salmonella*-phage P22. Mol Gen Genet, 1976, pp. 307-309, vol. 143.

Schmieger, Phage P22-mutants with increased or decreased transduction abilities. Mol Gen Genet, 1972, pp. 75-88, vol. 119.

Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.

Schodel, Prospects for oral vaccination using recombinant bacteria expressing viral epitopes. Adv. Virus Res., 1992, pp. 409-446, vol. 41.

Schwyn et al., Universal chemical assay for the detection and determination of siderophores. Analytical Biochemistry, 1987, p. 47, vol. 160.

Sedgwick et al., A solid-phase immunoenzymatic technique for the enumeration of specific antibody-secreting cells. Journal of Immunological Methods, 1983, p. 301, vol. 57.

Shalaby, Development of oral vaccines to stimulate mucosal and systemic immunity: barriers and novel strategies. Clin Immunol Immunopathol, 1995, pp. 127-134, vol. 74, No. 2.

Sheehan et al., Generation and characterization of hamster monoclonal antibodies that neutralize murine tumor necrosis factors. J Immunol, 1989, pp. 3884-3893, vol. 142.

Sizemore et al., Attenuated bacteria as a DNA delivery vehicle for DNA-mediated immunization. Vaccine, 1997, pp. 804-807, vol. 15.

Snapper et al., Distinct types of T-cell help for the induction of a humoral immune response to *Streptococcus pneumoniae*. Trends Immunol, 2001, pp. 308-311, vol. 22.

Sodeinde et al., Plasminogen activator/coagulase gene of *Yersinia pestis* is responsible for degradation of plasmid-encoded outer membrane proteins. Infect Immun, 1988, pp. 2749-2752, vol. 56.

Sternberg et al., Bacteriophage-mediated nucleic acid sequenceralized transduction in *Escherichia coli* and *Salmonella typhimurium*. Methods Enzymol, 1991, pp. 18-43, vol. 204.

Straley et al., Virulence genes regulated at the transcriptional level by Ca2+ in *Yersinia pestis* include structural genes for outer membrane proteins. Infect Immun, 1986, pp. 445-454, vol. 51.

Sun et al., The role of relA and spoT in *Yersinia pestis* KIM5+ pathogenicity. PLoS One, 2009, pp. E6720, vol. 4.

Thompson et al., The bacterial signal molecule, ppGpp, mediates the environmental regulation of both the invasion and intracellular virulence gene programs of *Salmonella*. J Biol Chem, 2006, pp. 30112-30121, vol. 281.

Une et al., In vivo comparison of avirulent Vwa- and Pgm- or Pstr phenotypes of *Yersiniae*. Infect Immun, 1984, pp. 895-900, vol. 43.

Uzzau et al., Epitope tagging of chromosomal genes in *Salmonella*. Proc Natl Acad Sci U S A, 2001, pp. 15264-15269, vol. 98.

Viboud et al., *Yersinia* outer proteins: role in modulation of host cell signaling responses and pathogenesis. Annu Rev Microbiol, 2005, pp. 69-89, vol. 59.

Wasserman et al., Two alanine racemase genes in *Salmonella typhimurium* that differ in structure and function. J. Bacteriol., 1983, pp. 1439-1450, vol. 153.

Whitfield, Biosynthesis and assembly of capsular polysaccharides in *Escherichia coli*. Annu Rev. Biochem., 2006, pp. 39-68, vol. 75.

Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.

Wolf et al., Evolution of aminoacyl tRNA synthetases-analysis of unique domain architectures and phylogenetic trees reveals a complex history of horizontal gene transfer events. Genome Res, 1999, pp. 689-710, vol. 9.

Xiao et al., Residual guanosine 39,59-bispyrophosphate synthetic activity of relA null mutants can be eliminated by spoT null mutations. J Biol Chem, 1991, pp. 5980-5990, vol. 266.

Zahorchak et al., Effect of exogenous nucleotides on Ca2+ dependence and V antigen synthesis in *Yersinia pestis*. Infect Immun, 1982, pp. 953-959, vol. 38.

Zhang et al., A "one-plasmid" system to generate influenza virus in cultured chicken cells for potential use in influenza vaccine. J. Virol., 2009, pp. 9296-9303, vol. 83.

Zhang et al., Transcription activation parameters at ara pBAD. J Mol Biol, 1996, pp. 14-24, vol. 258, No. 1.

Zinkernagel et al., Antigen localisation regulates immune responses in a dose- and time-dependent fashion: a geographical view of immune reactivity. Immunol Rev, 1997, pp. 199-209, vol. 156.

Briles et al., PspA, a protection-eliciting pneumococcal protein: immunogenicity of isolated native PspA in mice. Vaccine, 1996, pp. 858-867, vol. 14.

Hanisch, et al, The *Ralstonia eutropha* H16 phasin PhaP1 is targeted to intracellular triacylglycerol inclusions in *Rhodococcus opacus* PD630 and *Mycobacterium smegmatis* mc2155, and provides an anchor to target other proteins. Microbiology, 2006, pp. 3271-3280, vol. 152.

Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.

Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.

Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.

Navasa et al, Temperature has reciprocal effects on colanic acid and polysialic acid biosynthesis in *E. coli* K92. Appl Microbiol Biotechnol, 2009, pp. 721-729, vol. 82.

Stevens, Immunization with the C-Domain of alpha-Toxin Prevents Lethal Infection, Localizes Tissue Injury, and Promotes Host Responses to Challenge with *Clostridium perfringens*. JID, 2004, pp. 767-773, vol. 190.

Verjan et al, Genetic Loci of Major Antigenic Protein Genes of *Edwardsiella tarda*. Applied and Environmental Microbiology, 2005, pp. 5654-5658, vol. 71, No. 9.

U.S. Appl. No. 12/599,655 Office Action dated Jul. 2, 2012.

U.S. Appl. No. 12/681,721, Office Action dated May 24, 2012.

U.S. Appl. No. 12/759,842, Office Action dated Jun. 7, 2012.

Ellis, New Technologies for Making Vaccines. Vaccines, 1988, pp. 568-574, Chapter 29, WB Saunders Company, United States.

Greenspan et al, Defining eptiopes: It's not as easy as it seems. Nature Biotechnology, 1999, pp. 936-937, vol. 17.

Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.

U.S. Appl. No. 12/615,872 Office Action dated Oct. 23, 2012.

PCT/US2011/061896—International Search Report and Written Opinion of the International Searching Authority, Apr. 5, 2012.

Spellberg et al., Type 1/type 2 immunity in infectious diseases. Clin. Infect. Dis., 2001, pp. 76-102, vol. 32.

(56) References Cited

OTHER PUBLICATIONS

Schnaitman et al., Genetics of Lipopolysaccharide Biosynthesis in Enteric Bacteria. Microbiological Reviews, 1993, pp. 655-682, vol. 57, No. 3.
Byl et al, Sequence of the Genomore of *Salmonella* Bacteriophage P22. Journal of Bacteriology, 2000, pp. 6472-6484, vol. 182, 22.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.
U.S. Appl. No. 12/615,872, Office Action dated Mar. 14, 2012.
Collins et al, Mutation at rfc or pmi Attenuate *Salmonella typhimurium* Virulence for Mice. Infect and Immun, 1991, pp. 1079-1085, vol. 59, No. 3.
Curtiss et al., Stabilization of Recombinant Avirulent Vaccine Strains in vivo. Res. Microbiol., 1990, pp. 797-805, vol. 141.
Curtiss et al, Avirulent *Salmonell typhimurim* cyc crp oral vaccine strains expressing a streptococcal colonization and virulence antigen. Vaccine, 1988, pp. 155-160, vol. 6.
Darzins et al., Nucleotide sequence analysis of the phosphomannose isomerase gene (pmi) of *Pseudomonas aeruginose* and comparison with the corresponding *Escherichia coli* gene manA. Gene, 1986, pp. 293-302, vol. 42.
Doggett et al., Immune Responses to *Streptococcus sobrinus* Surface Protein Antigen A Expressed by Recombinant *Salmonella typhimurium*. Infect and Immun, 1993, pp. 1859-1866, vol. 61, No. 5.
Egan et al., A Regulatory Cascade in the Induction of rhaBAD. J. Mol. Biol., 1993, pp. 87-98, vol. 234.
Guzman et al., Tight regulations, Modulations, and High-Level Expression by Vectors Containing the Arabinose Pbad Promotor. Journal of Bacteriology, 1995, pp. 4121-4130, vol. 177, No. 14.
Kennedy et al., Attenuation and Immunogenicity of cya crp Derivatives of *Salmonella choleraeuis* in Pigs. Infect Immun, 1999, pp. 4628-4636, vol. 67, No. 9.
Nickerson et al., Role of Sigma Factor RpoS in Initial Stages of *Salmonella typhimurium* Infection. Infect Immun, 1997, p. 1814-23, vol. 65, No. 5.
Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.
Schodel, Recombinant Avirulent *Salmonellae* as Oral Vaccine Carriers. Infection, 1992, pp. 5-12, No. 1.
Siegele et al., Gene Expression from plasmids containing the araBAD promoter at subsaturating inducer concentrations represents mixed populations. PNAS, 1997, pp. 8168-8172, vol. 94.
Song et al., Organization and Regulation of the d-Xylose Operons in *Escherichia coli* K-12: XylR Acts as a Transcriptional Activator. Journal of Bacteriology, 1997, pp. 7025-7032, vol. 197, No. 22.
Srinivasan et al., Oral Immunization with Attenuated *Salmonella* Expressing Human Sperm Antigen Induces Antibodies in Serum and the Reproductive Tract. Biology of Reproduction, 1995, p. 462-71 vol. 53.
PCT/US2008/063293 (WO 2009/025888)—International Search Report and Written Opinion of the International Searching Authority, Feb. 12, 2009.
Kotton et al., Enteric pathogens as vaccine vectors for foreign antigen delivery. Infect. Immun., 2004, pp. 5535-5547, vol. 72.
Lee et al., Characterization of recent H5 subtype avian influenza viruses from US poultry. Avian Pathol., 2004, pp. 288-297, vol. 33.
Lee et al., Mechanism of araC autoregulation and the domains of two overlapping promoters, PC and PBAD, in the L-arabinose regulatory region of *Escherichia coli.* Proc. Natl. Acad. Sci. U S A, 1981, pp. 752-756, vol. 78.
Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.
Lee et al., Trigger factor retards protein export in *Escherichia coli.* J Biol Chem, 2002, pp. 43527-43535, vol. 277.
Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.
Loessner et al., Differential effect of auxotrophies on the release of macromolecules by *Salmonella enterica* vaccine strains. FEMS Microbiol. Lett., 2006, pp. 81-88, vol. 265.
Loewen et al., Genetic mapping of katF, a locus that with katE affects the synthesis of a second catalase species in *Escherichia coli.* J Bacteriol, 1984, pp. 668-675, vol. 160.
Luytjes et al., Amplification, expression, and packaging of foreign gene by influenza virus. Cell, 1989, pp. 1107-1113, vol. 59.
Malley et al., CD4+ T cells mediate antibody-independent acquired immunity to pneumococcal colonization. PNAS, 2005, pp. 4848-4853, vol. 102.
Massin et al., Cloning of the chicken RNA polymerase I promoter and use for reverse genetics of influenza A viruses in avian cells. J. Virol., 2005, pp. 13811-13816, vol. 79.
Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.
McClelland et al., Complete genome sequence of *Salmonella enterica* serovar Typhimurium LT2. Nature, 2001, pp. 852-856, vol. 413, No. 6858.
McDaniel et al., Monoclonal antibodies against protease sensitive pneumococcal antigens can protect mice from fatal infection with *Streptococcus pneumoniae*. J. Exp. Med., 1984, pp. 368-397, vol. 160.
McDaniel et al., Use of insertional inactivation to facilitate studies of biological properties of pneumococcal surface protein A (PspA). J. Exp. Med., 1987, pp. 381-394, vol. 165.
Mesika et al., A regulated, NF κB-assisted import of plasmid DNA into mammalian cell nuclei. Mol. Ther., 2001, pp. 653-657, vol. 3.

(56) References Cited

OTHER PUBLICATIONS

Miller et al., A novel suicide vector and its use in construction of insertion mutations: osmoregulation of outer membrane proteins and virulence determinants in *Vibrio cholerae* requires toxR. J Bacteriol, 1988, pp. 2575-2783, vol. 170.

Miller et al., Bacteriophage T4 genome. Microbiol Mol Biol Rev, 2003, pp. 86-156, vol. 67, No. 1.

Molinari et al., The annual impact of seasonal influenza in the US: measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect. Immun., 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs. Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of *Streptococcus pneumoniae* D39 in a Mouse Model. Infect. Immun., 2007, pp. 1843-1851, vol. 75.

Osterholm, Preparing for the next pandemic. N. Engl. J. Med., 2005, pp. 1839-1842, vol. 352.

Ozaki et al., Generation of high-yielding influenza A viruses in African green monkey kidney (Vero) cells by reverse genetics. J. Virol., 2004, pp. 1851-1857, vol. 78.

Park et al., Engineered viral vaccine constructs with dual specificity: avian influenza and Newcastle disease. Proc. Natl. Acad. Sci. USA, 2006, pp. 8203-8208, vol. 103.

Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.

Pashine et al., Th1 dominance in the immune response to live *Salmonella typhimurium* requires bacterial invasiveness but not persistence. Int. Immunol., 1999, pp. 481-489, vol. 11.

Peterson et al., RpoS proteolysis is regulated by a mechanism that does not require the SprE (RssB) response regulator phosphorylation site. J Bacteriol, 2004, pp. 7403-7410, vol. 186.

Pizarro-Cerda et al., The bacterial signal molecule, ppGpp, regulates *Salmonella virulence* nucleic acid sequence expression. Mol Microbiol, 2004, pp. 1827-1844, vol. 52, No. 6.

Prouty et al., *Salmonella enterica* serovar Typhimurium invasion is repressed in the presence of bile. Infect Immun, 2000, pp. 6763-6769, vol. 68.

Quinlivan et al., Attenuation of equine influenza viruses through truncations of the NS1 protein. J. Virol., 2005, pp. 8431-8439, vol. 79.

Rand, Crystal violet can be used to visualize DNA bands during gel electrophoresis and to improve cloning efficiency. Tech. Tips Online, 1996 http://www.science-direct.com/science/journal/13662120.

Roberts et al., Oral vaccination against tetanus: comparison of the immunogenicities of *Salmonella* strains expressing fragment C from the nirB and htrA promoters. Infect. Immun., 1998, pp. 3080-3087, vol. 66.

Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.

Sadler et al., A perfectly symmetric lac operator binds the lac repressor very tightly. Proc Natl Acad Sci U S A, 1983, pp. 6785-6789, vol. 80, No. 22.

Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.

Hori et al, Construction of selt-disruptive *Bacillus megaterium* in response to substrate exhaustion for polyhydroxybutryrate production. Appl Microbiol Biotechnol, 2002, pp. 211-216, vol. 59.

Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.

Schuchat et al., *Bacterial meningitis* in the United States in 1995. Active Surveillance Team. N Engl J Med, 1997, pp. 970-976, vol. 337.

Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.

Simonsen et al., The impact of influenza epidemics on hospitalizations. J. Infect. Dis., 2000, pp. 831-837, vol. 181.

Quenee, Lauriane E., et al., *Yersinia pestis* caf1 Variants and the Limits of Plague Vaccine Protection, Infection and Immunity, May 2008, vol. 76, No. 5, pp. 2025-2036.

U.S. Appl. No. 13/088,141, Office Action dated Dec. 6, 2012 (Ginny Portner).

U.S. Appl. No. 13/006,072, Office Action dated Dec. 11, 2012 (Ja'Na Hines).

Kong, W., T-10-, Improving DNA Vaccine Vector for Efficient Vaccine Delivery Using Live Attenuated Bacterial Carrier, The Society, vol. 2008, No. 108, pp. 668.

Mesika, Adi, et al., A Regulated, NF κB-Assisted Import of Plasmid DNA into Mammalian Cell Nuclei, Molecular Therapy, vol. 3, No. 5, May 2001, pp. 653-657.

Ribeiro, Sofia C., et al., The Role of Polyadenylation Signal Secondary Structures on the Resistance of Plasmid Vectors to Nucleases, The Journal of Gene Medicine, vol. 6, 2004, pp. 565-573.

Rytkonen, Anne, et al.,. SseL, a *Salmonella* Deubiquitinase Required for Macrophage Killing and Virulence, PNAS, vol. 104, No. 9, Feb. 27, 2007, pp. 3502-3507.

Wang, Shixia, et al., Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines, Journal of Virology, vol. 80, No. 23, Dec. 2006, pp. 11628-11637.

U.S. Appl. No. 13/302,575, Office Action dated Sep. 25, 2012 (Oluwatosin Ogunbiyi).

U.S. Appl. No. 12/615,872, Office Action dated Oct. 23, 2012 (Jennifer Graser).

American Society of Microbiology, vol. 108; 2008: (p668).

\* cited by examiner

```
                                                                     Primer 1
GTT AGC GCT TCC GGC GCG ACT TTC AGG ATC TCT TGT CCT TCG AAT TCG GCG ACG GAA ACA
TGT TCG CTG GTC AAC AAG TAG TAC TCG GTA TCG TCC TTT TTG AGG GGA AAA GGG TCT TGA
TAA AAG AAG GGT TTG TTT GAC ATT GTG CTC TCA CTT ACC GCT CGG TAT GGT TAT TCT CTG
GGC AGG TGT TCC ATT GCC CGA CTC AAA GCG AGT AAC ACT ATC CTA CAC AAT TTT TTA ACA
AAA ACT GAG ACA AGT ACG ACT TTT TAC GCC CGG AGG TTA CTT CAT GCG GGT TTC TTG GTT
TAA TAC CTC CCA TTG ATC TCC ACA TTG AAA CAG GGC TTG ATA [ATG CAA AAA CTC ATT AAC
                                                         M   Q   K   L   I   N
                                                        Δpmi of 1176 bp
TCA GTG CAA AAC TAT GCC TGG GGA AGT AAA ACT GCG TTA ACG GAA CTT TAT GGC ATC GCC
 S   V   Q   N   Y   A   W   G   S   K   T   A   L   T   E   L   Y   G   I   A
AAT CCG CAG CAG CAG CCA ATG GCT GAA CTC TGG ATG GGC GCG CAT CCC AAA AGC AGC TCG
 N   P   Q   Q   Q   P   M   A   E   L   W   M   G   A   H   P   K   S   S   S
CGA ATC ACC ACC GCC AAC GGC GAA ACC GTC TCC CTG CGT GAC GCC ATC GAA AAG AAT AAA
 R   I   T   T   A   N   G   E   T   V   S   L   R   D   A   I   E   K   N   K
ACC GCC ATG CTG GGC GAA GCG GTA GCC AAC CGT TTC GGC GAA CTG CCG TTT CTG TTT AAA
 T   A   M   L   G   E   A   V   A   N   R   F   G   E   L   P   F   L   F   K
GTA CTG TGC GCC GCA CAA CCG CTC TCT ATT CAG GTG CAC CCG AAT AAA CGC AAC TCC GAA
 V   L   C   A   A   Q   P   L   S   I   Q   V   H   P   N   K   R   N   S   E
ATC GGT TTC GCG AAA GAA AAT GCG GCG GGT ATC CCC ATG GAT GCC GCA GAG CGG AAC TAT
 I   G   F   A   K   E   N   A   A   G   I   P   M   D   A   A   E   R   N   Y
AAA GAT CCT AAC CAT AAA CCA GAG CTG GTT TTT GCC CTG ACG CCT TTC CTG GCG ATG AAC
 K   D   P   N   H   K   P   E   L   V   F   A   L   T   P   F   L   A   M   N
GCG TTC CGC GAA TTT TCT GAC ATT GTC TCT TTA CTG CAA CCT GTC GCC GGC GCG CAT TCC
 A   F   R   E   F   S   D   I   V   S   L   L   Q   P   V   A   G   A   H   S
GCT ATC GCC CAC TTT TTG CAG GTG CCG AAT GCT GAA CGT CTG AGC CAG CTT TTC GCC AGC
 A   I   A   H   F   L   Q   V   P   N   A   E   R   L   S   Q   L   F   A   S
CTG TTG AAT ATG CAA GGC GAA GAA AAA TCC CGC GCG TTA GCC GTA CTC AAA GCG GCG CTT
 L   L   N   M   Q   G   E   E   K   S   R   A   L   A   V   L   K   A   A   L
AAC AGC CAG CAA GGC GAA CCG TGG CAA ACG ATC CGC GTG ATT TCA GAG TAT TAT CCT GAC
 N   S   Q   Q   G   E   P   W   Q   T   I   R   V   I   S   E   Y   Y   P   D
GAC AGC GGG CTT TTC TCT CCT TTG TTG CTG AAT GTG GTC AAA CTG AAT CCC GGC GAG GCG
 D   S   G   L   F   S   P   L   L   L   N   V   V   K   L   N   P   G   E   A
ATG TTC CTG TTT GCT GAA ACG CCT CAT GCT TAT CTG CAG GGC GTT GCG CTG GAA GTC ATG
 M   F   L   F   A   E   T   P   H   A   Y   L   Q   G   V   A   L   E   V   M
GCG AAC TCC GAT AAC GTT CTG CGC GCT GGC CTT ACG CCA AAA TAT ATC GAC ATC CCT GAG
 A   N   S   D   N   V   L   R   A   G   L   T   P   K   Y   I   D   I   P   E
CTG GTC GCG AAC GTG AAG TTC GAA CCT AAG CCT GCC GGC GAG TTG CTG ACT GCC CCG GTG
 L   V   A   N   V   K   F   E   P   K   P   A   G   E   L   L   T   A   P   V
AAA AGC GGC GCG GAG CTG GAC TTC CCA ATT CCG GTT GAC GAT TTT GCT TTT TCA CTG CAC
 K   S   G   A   E   L   D   F   P   I   P   V   D   D   F   A   F   S   L   H
GAC CTG GCG CTT CAG GAG ACG AGC ATC GGC CAA CAC AGC GCC GCG ATT CTG TTC TGC GTT
 D   L   A   L   Q   E   T   S   I   G   Q   H   S   A   A   I   L   F   C   V
GAG GGT GAG GCG GTG TTA CGT AAA GAT GAA CAG CGT CTG GTA CTG AAG CCG GGT GAA TCT
 E   G   E   A   V   L   R   K   D   E   Q   R   L   V   L   K   P   G   E   S
GCC TTT ATC GGC GCG GAT GAG TCT CCG GTT AAC GCC AGC GGC ACG GGC CGT TTA GCG CGT
 A   F   I   G   A   D   E   S   P   V   N   A   S   G   T   G   R   L   A   R
GTT TAT AAC AAG CTG TAG] CAA CGT ACT GAA TTT TTT AAC AAC TCT TGC TAA GCT TAT AAC
 V   Y   N   K   L   *   pmi₁₁₇₆
AGA CGT AAA ACT CCT CCA GGC GGT TTA ATC CGC CTG GTT TCA TTT TTA TGG ACA ATT GAT
ATG AAA AAA ACA CTG GTA GCT GCA GGT GTA GTA ATT GCA CTT GGC ATC GTC TGG ACA GGC
GGC GCC TGG TAT ACG GGG AAA AAG CTG GAG AAC CAT CTT GCA GAA ATG GTG ACT CAG GCC
AAT GAA CAG CTC AAG CGT ACT GCG CCG GAG GCC GGT GTC GAA TTA AGT TAT CAA AAC TAC
CAG CGC GGC GTG TTC AGT AGC CAT CTG CAA CTG GTT GTC AAA CCG GTT    primer 2
```

FIG. 3A

1176 bp *pmi* gene deleted (from ATG to TAG)

```
                                                             primer wcaF-SmaI
GGC GGT ACA GGC GAC ATT ATT CGC CGG GTC GCC GCA AAT ATT GTA TCG CTG GCG AGC CTT
TTT GCT GCG TCT GTT TGG CGC CAA AAT TGG AAA GAA TGT GGT TAT TCG ACC GTC AGT AAA
AAT TAC CTA TCC GTG GAA ATT AAC CGT CGG CGA TTA TGC CTG GGT AGG CGA CGA CGC TGT
GTT ATA TAC GTT GGG TGA AAT TAA TAT TGG CGC ACA TGC GGT TAT TTC ACA AAA AGG GTA
TTT GTG TAC CGG TAG CCA TGA TTA TAC CAG CGC CCA TTT CGA TAT TAA TGC CGC GCC GAT
TGT TAT TGG CGA AAA ATG TTG GCT GGC GAC CGA TGT TTT TGT CGC GCC CGG CGT GAC GAT
AGG TCA TGG CAC CGT CGT CGG CGC GCG CAG CAG CGT ATT TAA ATC ATT ACC GGC AAA TGC
GAT TTG TCG GGG CAA TCC CGC AGT GGT AAC GCG CCA GCG CGT TCA GAA AGT TAC TCC CTA
ACG GGA CTA TTT GAG GA[A ATG AAA ATG TCA AAA GTC GCT CTC ATT ACT GGC GTA ACC GGA
                    gmd₋₇        M   S   K   V
                                 gmd →
CAG GAT GGG TCT TAC CTG GCA GAA TTT CTG CTG GAA AAA GGG TAT GAG GTG CAT GGT ATC
AAG CGC CGC GCG TCA TCG TTT AAT ACC GAG CGC GTG GAC CAT ATT TAT CAG GAC CCG CAC
AGC TGC AAC CCG AAA TTT CAT CTG CAT TAT GGC GAC CTG ACC GAC GCC TCC AAC CTG ACC
CGC ATT TTA CAG GAA GTG CAG CCG GAT GAG GTC TAC AAC CTG GGC GCG ATG AGC CAT GTG
GCG GTG TCG TTT GAG TCG CCG GAA TAT ACC GCC GAT GTG GAT GCG ATG GGC ACG CTG CGC
CTG CTG GAG GCG ATC CGC TTC CTC GGT CTT GAA AAG AAA ACG CGG TTC TAC CAG GCC TCC
ACC TCT GAA CTG TAC GGG CTG GTG CAG GAG ATC CCG CAG AAA GAG ACC ACG CCG TTC TAC
CCG CGT TCC CCC TAT GCG GTG GCG AAA CTG TAC GCC TAC TGG ATC ACC GTT AAC TAC CGT
GAA TCC TAC GGT ATT TAC GCC TGT AAC GGC ATT CTG TTT AAC CAC GAG TCC CCG CGT CGC
GGC GAA ACC TTC GTC ACC CGT AAG ATC ACC CGC GCC ATC GCC AAT ATC GCC CAG GGA CTA
GAG TCC TGC CTG TAT CTC GGC AAC ATG GAC TCG CTG CGC GAC TGG GGT CAT GCG AAA GAT
TAC GTG CGG ATG CAG TGG ATG ATG TTA CAG CAG GAG CAG CCG GAA GAT TTC GTG ATT GCC
ACC GGC GTG CAG TAT TCC GTA CGC CAG TTT GTG GAG CTG GCA GCG GCG CAA CTG GGG ATA
AAA CTG CGC TTT GAA GGC GAA GGC ATT AAT GAG AAA GGG ATC GTG GTA TCC GTT ACC GGA
CAC GAT GCG CCG GGC GTG AAA CCG GGG GAT GTG ATT GTG GCC GTT GAT CCG CGT TAT TTC
CGT CCG GCG GAA GTG GAA ACC CTG CTG GGC GAC CCG TCC AAA GCG CAT GAG AAA CTG GGC
TGG AAA CCG GAA ATC ACC CTG TCG GAG ATG GTC TCC GAG ATG GTG GCG AAC GAT CTG GAG
GCC GCG AAA AAA CAC TCA CTG TTG AAA TCT CAC GGT TAT GAG GTG GCC ATC GCG CTG GAG
TCC TGA GAA TGA ATA AGC AAC GAA TTT TTG TGG CGG GCC ATC GCG GAA TGG TGG GCT CCG
 S   *   M   N   Q
         fcl/wcaG
CCA TTG TAC GGC AGC TTG CGC AGC GCG GCG ACG TGG AAC TGG TAC TGC GCA CCC GCG ATG
AGC TGG ATC TGC TCG ACG GGC GCG CGG TAC AGG CGT TCT TTG CCG GGG CGG GTA TCG ACC
AGG TTT ATC TGG CGG CGG CGA AAG TGG GCG GCA TTG TCG CCA ACA ACA CGT ATC GGC GG
ATT TTA TTT ATG AAA ACA TGA TGA TAG AGA CGA ACA TTA TTC ACG CCG CGC ACC TGC ACA
ACG TGA ACA AAC TGC TGT TTC TCG GTT CGT CCT GTA TCT ATC CGA AAC TGG CAA GGC AGC
CGA TGG CGG AAA GCG AGC TGC TGC AGG GGA CGC TGG AGC CGA CCA ACG AGC CGT ACG CCA
TCG CCA AGA TCG CCG GGA TTA AAC TGT GCG AGT CCT ACA ACC GGC AGT ACG TCG CGA CT
ACC GTT CGG TGA TGC CAA CCA ACC TGT ACG CCC GCA TGA TAT TCC ACC GGA CAA TT
CAC ATG TGA TCC CGG CGC TGC TGC GTC GCT TTC ATG AGG CTG CGC AGA GCC ACG CGC GG
AGG TGG TGG TGT GGG CAG CGC GCA CGC CGA TGC GTG AAT TTC TGC ACG TTG ACG ATA TGG
CGG CGG CCA GTA TTC ACG TGA TGG AGC TGG CGC GCG AAG TGT GGC AGG AGA ACA CTG CCC
CGA TGC TGT CGC ACA TTA ACG TCG GCA CTG CGT GGA CTG CCA TCC GCG AGC TGG CGC
AGA CCA TCG CAA AGG TGG TGG GTT ACC AGG CCG GGT GGT GTC GAT GCC GGA GCG G
ACG GCA CGC CGC GTA AAT TGC TCG ACG TCA CGC CGC TGC ATC AGC TTG GCT GGT ATC ACG
AAA TTT CAC TGG AGG CAG GGC TTG CCG GTA CTT ACC AGT GGT CCC TTG AGA TCA GCA AC
GGT TCC GGG GGT GA]C AAT GTT TTT ACG TCA GGA AGA TTT CGC CGC CGT GGT GCG GCC ACG
  F   R   G   *   fcl₉₆₆/₉₆₆
```

FIG. 4A

```
CCC CTC ATC TCC CTC GAT TTC ATC GTG GAA AAC GGC CAG GGG GAA ATT TTA CTG GGC CAG CGT
CTC AAC CGT CCG GCG CAG GGC TAC TGG TTT GTG CCG GGG GGG CGG GTG TGC AAA GAC
GAA ACG CTG GAG GCC GCC TTT GCA CGC CTG ACG CAG GCG GAA CTG GGC GTG CGT CTG CCG CTG
GCG GCA GGG ACG TTT TAT GGC GTC TGG CAG CAC TTC TAT GAC GAC AAC TTT TCC GGT
GAG GAT TTT TCA ACT CAC TAC ATC GTG CTC GGC TTT CGT CTG CGC GTG GCG GAG AGC GAT TTA
CGC CTG CCT GAT GCC CAG CAT GGC AGT TAC CGC TGG CTG ACG CCG GAA CAG CTT
Primer gmm/wcaH-SphI
```

FIG. 4B

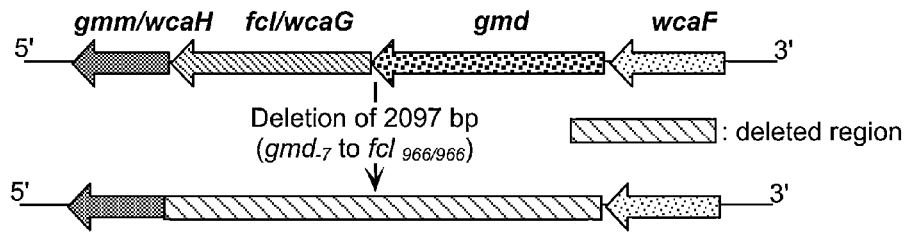

FIG. 4C

```
                                          primer araE C-BamHI
TGA TTA TAT TAA CGG CTA TAC CAT AGC GGT AGA TGG CGG TTG GCT GGC GCG TTA ATC CGC
TAC TGA CAA ATG CGT TTC TGG GAA AAT CGA CGC TTT GGC CGA AAA AAC TGA TAA AGC CCT
GTC CTC GTA CAG GGT TTT TTT ATG ATC TCA TTA GCA TAG TCC ATA TTG TGG GTT TAA CTT
AAT CCA TAT ATT GTT AAA TAA TAG CTA TGA TCA ATG CTT TAA TTC ATT GAA ATA TTG GTG
GTT TAA AAA AAT ACC CGG CAA CGG CGT TAA ATT TAA AAA GTG TAA TAT CCA TCA CAT ATC
GCT ATA GCG TAG CCA TTT AAT CCA TAT TTA TGC CGT TTC CAG CCT GAC ACT TGA GGA AGA
                                                                    araE →
GTA TCC CGT ACT TTC AGG CTA TGT CTT ACT CTG TTG TGG CAG G[AA AAT ATG GTC TCT ATT
                                    deletion of 1432 bp ara_{B-5}  M   V   S   I
AAT CAT GAC TCT GCT TTA ACG CCG CGT TCG CTT CGC GAC ACA CGA CGT ATG AAT ATG TTT
 N   H   D   S   A   L   T   P   R   S   L   R   D   T   R   R   M   N   M   F
GTT TCG GTT TGT TCT GCA GCG GTA GCG GGA CTG TTA TTT GGT CTG GAT ATC GGC GTT ATC GCC
 V   S   V   S   A   A   V   A   G   L   L   F   G   L   D   I   G   V   I   A
GGG GCG CTG CCT TTT ATT ACC GAC CAT TTC GTA CTG ACC AGC CGG CTG CAG GAA TGG GTC
 G   A   L   P   F   I   T   D   H   F   V   L   T   S   R   L   Q   E   W   V
GTC AGC AGC ATG ATG CTT GGC GCG GCA ATT GGC GCA TTA TTT AAC GGC TGG CTT TCA TTC
 V   S   S   M   M   L   G   A   A   I   G   A   L   F   N   G   W   L   S   F
CGG CTG GGG CGT AAG TAT AGC CTG ATG GCT GGC GCG ATT TTG TTC GTG CTC GGC TCG CTG
 R   L   G   R   K   Y   S   L   M   A   G   A   I   L   F   V   L   G   S   L
GGG TCG GCG TTT GCT TCC AGC GTG GAA GTA TTG ATT GGC GCC CGC GTG ATA CTG GGC GTA
 G   S   A   F   A   S   S   V   E   V   L   I   G   A   R   V   I   L   G   V
GCA GTA GGG ATT GCC TCC TAT ACC GCG CCG CTT TAT CTC TCT GAA ATG GCA AGT GAA AAT
 A   V   G   I   A   S   Y   T   A   P   L   Y   L   S   E   M   A   S   E   N
GTT CGC GGC AAA ATG ATC AGT ATG TAT CAA CTG ATG GTG ACG TTA GGC ATT GTG CTG GCT
 V   R   G   K   M   I   S   M   Y   Q   L   M   V   T   L   G   I   V   L   A
TTT TTA TCC GAT ACG GCA TTC AGC TAC AGC GGC AAC TGG CGC GCG ATG TTG GGC GTG CTG
 F   L   S   D   T   A   F   S   Y   S   G   N   W   R   A   M   L   G   V   L
GCG CTG CCT GCG GTG TTG CTC ATT ATT CTG GTG GTA TTC CTG CCG AAT AGT CCG CGT TGG
 A   L   P   A   V   L   L   I   I   L   V   V   F   L   P   N   S   P   R   W
CTG GCG CAA AAA GGT CGC CAT ATT GAA GCG GAA GAG GTG CTG CGT ATG CTG CGC GAT ACC
 L   A   Q   K   G   R   H   I   E   A   E   E   V   L   R   M   L   R   D   T
TCG GAA AAA GCC CGT GAT GAA CTG AAT GAG ATT CGG GAA AGC CTC AAA CTC AAG CAG GGA
 S   E   K   A   R   D   E   L   N   E   I   R   E   S   L   K   L   K   Q   G
GGG TGG GCA TTA TTT AAA GCT AAC CGC AAT GTT CGC CGC GCC GTG TTC CTC GGT ATG CTG
 G   W   A   L   F   K   A   N   R   N   V   R   R   A   V   F   L   G   M   L
CTA CAG GCA ATG CAG CAG TTC ACC GGC ATG AAC ATC ATT ATG TAC TAT GCG CCG CGC ATT
 L   Q   A   M   Q   Q   F   T   G   M   N   I   I   M   Y   Y   A   P   R   I
TTT AAA ATG GCC GGC TTT ACC ACC ACG GAA CAG CAA ATG ATC GCC ACG CTG GTG GTC GGA
 F   K   M   A   G   F   T   T   T   E   Q   Q   M   I   A   T   L   V   V   G
CTG ACT TTT ATG TTC GCG ACG TTT ATC GCC GTC TTT ACG GTC GAT AAG GCC GGG CGT AAA
 L   T   F   M   F   A   T   F   I   A   V   F   T   V   D   K   A   G   R   K
CCG GCG TTA AAA ATC GGT TTC AGC GTA ATG GCG TTA GGG ACA TTG GTG TTG GGC TAC TGC
 P   A   L   K   I   G   F   S   V   M   A   L   G   T   L   V   L   G   Y   C
CTG ATG CAG TTT GAT AAC GGT ACG GCA TCA AGC GGT CTC TCC TGG CTT TCC GTT GGG ATG
 L   M   Q   F   D   N   G   T   A   S   S   G   L   S   W   L   S   V   G   M
ACG ATG ATG TGT ATC GCC GGT TAC GCG ATG AGC GCC GCT CCG GTG TGG ATA CTG TGT
 T   M   M   C   I   A   G   Y   A   M   S   A   A   P   V   V   W   I   L   C
TCG GAA ATC CAG CCG CTG AAA TGC CGT GAT TTT GGC ATT ACC TGT TCA ACC ACG ACA AAC
 S   E   I   Q   P   L   K   C   R   D   F   G   I   T   C   S   T   T   T   N
TGG GTA TCG AAC ATG ATC ATC GGC GCG ACA TTC CTG ACA CTG TTG GAC AGC ATT GGC GCG
 W   V   S   N   M   I   I   G   A   T   F   L   T   L   L   D   S   I   G   A
GCA GGT ACA TTC TGG CTC TAC ACC GCG CTG AAT ATC GCT TTT ATC GGC ATC ACT TTC TGG
 A   G   T   F   W   L   Y   T   A   L   N   I   A   F   I   G   I   T   F   W
CTG ATT CCG GAA ACC AAA AAT GTC ACC CTG GAG CAC ATC GAA CGC AAG CTG ATG GCG GGC
 L   I   P   E   T   K   N   V   T   L   E   H   I   E   R   K   L   M   A   G
GAG AAG CTA AGA AAT ATT GGC GTG TAA TCC CCC CT]C CCA TGC CGG ATG ACG CCT GTT ATC
 E   K   L   R   N   I   G   V   *           ara_{B+9}
```

FIG. 5A

```
CGG CAT GAT GAA AAA TAG ACT GGA AAC GGA TGT GTA AGT TTG CTT CAC TGC CAT AAT GCT
TTA CAA AAA GGA GAG CGC AGT GAA AAC GAT CGG ACT GTT GGG GGG GAT GAG CTG GGA ATC
GAC TAT CCC TTA TTA CCG TTT AAT CAA TGA AGG TAT TAA ACA GCA GTT GGG AGG CCT GCA
CTC GGC GAG CTT ACT GCT GCA TAG CGT AGA TTT CCA CGA TAT TGA AGT ATG TCA ACG CCG
CGA CGA GTG GGA TAA AGC GGG CGA TAT CCT GGC GCA GGC CGC CCA TGG GTT ACA GCA GGC
GGG CGC AGA AGG CAT TGT GCT GTG TAC CAA CAC CAT GCA TAA AAT CGC GCA CGT TAT TGA
                                 primer araE N-SphI
```

FIG. 5B

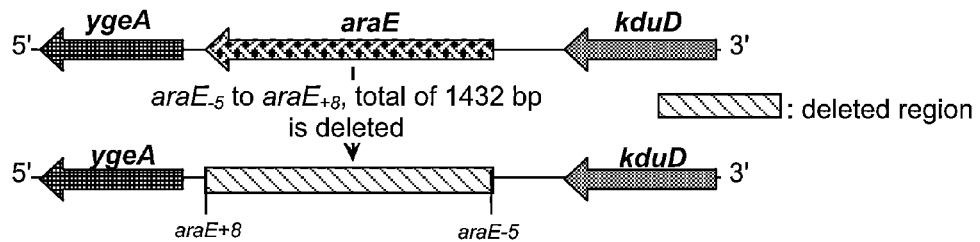

FIG. 5C

```
      primer araC-SphI
AAC GGA CGA TCG ATA AAA AAA TCC AGA TAT CCA TTC GCT TCA ATT GGC GTC AGC CCG GCG
ACC AGA TGG GCA TTA AAT GAA TAT CCC GGC AAT AGC GGA TCA TTT TGC GTT TCA GCC ATG
ATT TCT CTA CCC CCC GAT GTT CAG AGA AGA AAC AAA TTG TCC ATA TCG ACC AGG ACG ACA
GAG CTT CCG TCT CCG CAA GAC TTT GCG CTT GAT GAA AGC ACG TAT CAA CCC CGC TTG TGA
AAA GCG CTT TGT AAC AAA AGC GTA CAG TTC AGG CGA TAA AAT TAA GTA ACA GAA GTG TCT
ATA ACT ATG GCT GGA ATG TCC ACA TTG AAT ATT TGC ACA GCG TCA CAC TTT GCA AAG CAT
TAG CAT TTT TGT CCA TAA GAT TAG CGG ATC CTG CCT GAC GGT TTT TGC CGC GAC TCT CTA
                                                       araBAD₂
CTG TTT CTC CAT ACC TGT TTT TCT GGA TGG AGT AAG ACG A[TG GCA ATT GCA ATT GGC CTC
                                                       M   A   I   A
                                                       araB →
GAT TTT GGC AGT GAT TCA GTG CGC GCT CTG GCA GTG GAC TGC GCC ACC GGC GAC GAG ATC
GCC ACC AGC GCA GTA GAG TGG TAT CCG CGC TGG CAA GAA GGC CGT TAT TGC GAC GGC CCG AAC
AAC CAG TTC CGT CAT CAT CCG CGC GAC TAC ATG GAG TCA ATG GAG GCC GCG CTG AAA GCC
GTT CTG GCA CAA TTA AGC GCC GCG CAA CGC GCA AAT GTC GTT GGC ATT GGC GTT GAC AGC
ACC GGC TCT ACG CCA GCG CCG ATT GAC GCC GAC GGT AAC GTC CTG GCG CTG CGT CCA GAG
TTC GCC GAG AAC CCG AAT GCG ATG TTT GTG CTG TGG AAA GAT CAC ACC GCC GTG GAA GAG
GCC GAC GAA ATC ACT CGT CTG TGC CAT AAG CCA GGC AAG GTC GAC TAC TCC CGC TAT ATT
GGC GGC ATT TAC TCC AGC GAA TGG TTC TGG GCG AAG ATT CTG CAC GTC ACC CGG CAG GAT
AGC GCC GTC GCG CAG GCC GCC GTC TCG TGG ATT GAG CTG TGC GAC TGG GTG CCG GCG CTG
CTT TCC GGC ACC ACT CGC CCG CAG GAT ATC CGC CGT GGC CGC TGC AGC GCC GGG CAC AAA
ACG CTG TGG CAT GAA AGC TGG GGC GGT CTG CCG CCC GCG AGC TTC TTT GAT GAA CTC GAT
CCG TGC ATT AAC CGT CAT CTG CGC TAC CCG TTA TTT AGC GAA ACC TTC ACC GCC GAT CTG
CCC GTG GGC ACC CTG TGC GCC GAA TGG GCG CAG CGC CTC GAC TTG CCG GAA AGC GTA GTG
ATT TCC GGC GGC GCG TTC GAC TGT CAC ATG GGC GCG GTC GGC GCG GGC GCA CAG CCC AAT
ACG CTG GTG AAA GTC ATC GGC ACG TCT ACC TGC GAC ATT CTG ATT GCG GAT AAA CAG AGC
GTC GGG GAT CGC GCC GTG AAA GGC ATT TGC GGT CAG GTT GAC GGC AGC GTG GTG CCG GAA
TTT ATC GGT CTG GAA GCG GGG CAA TCT GCT TTC GGC GAT ATC TAC GCC TGG TTT AGC CGC
GTG TTG AGC TGG CCG CTG GAG CAA CTT GCC GCG CAG CAC CCG GAA CTG AAA CCC CAG ATT
AAC GCC AGC CAG AAG CAG CTA CTG CCA GCG CTC ACC GAC GCC TGG GCG AAA AAT CCG TCC
CTG GAT CAC CTG CCG GTG GTG CTC GAC TGG TTT AAC GGT CGC CGC ACG CCA AAC GCT AAT
CAG CGT CTG AAA GGC GTC ATT ACC GAT CTC AAT ACC GCC ACC GAC GCG CCA GCG CTG TTT
GGC GGT CTG GTC GCT TCG ACC GCC TTC GGC GCG CGC GCC ATT CAG GAG TGT TTT ACC GAT
CAG GGT ATC GCG GTC AAT AAC GTG ATG GCG CTT GGC GGC ATC GCC CGT AAA AAT CAG GTC
ATT ATG CAG GTC TGC TGC GAC GTA CTG AAT CGT CCG TTG CAG ATC GTC GCT TCC GAC CAG
TGT TGC GCA TTA GGC GCC GCT ATC TTT GCC GCC GTC GCT GCG AAA GTC CAT GCC GAC ATT
CCA GCC GCC CAG CAA AGC ATG GCG AGC GCG GTA GAA CGC ACT CTG CGC CCC CAC CCT GAA
CAG GCG CAA CGC TTC GAA CAG CTT TAC CGC CGC TAC CAG CAG TGG GCG CTA AGC GCA GAA
CAA CAT TAT CTT CCG ACT GCC GCG CCG GCG CCA ACG ACC CCG GCC AAT CAG GCA ATC CTG
ACT CAT TAA GGA CAC GAC AAT GAC GAT TTT TGA TAA TTA TGA AGT ATG GTT TGT GAT TGG
 T   H   *           M   T   I   F
                                                       araA →
CAG CCA GCA TTT GTA TGG CGC AGA AAC CCT GCG TCA GGT CAC CCA ACA TGC CGA GCA TGT
GGT CAA CGC GCT GAA TAC CGA AGC CAA ACT GCC ATG TAA ACT GGT ATT AAA ACC GCT GGG
CAC CTC GCC GGA TGA GAT TAC CGC CAT TTG TCG TGA CGC CAA TTA CGA TCG CTG CGC
AGG GCT GGT GGT CTG GCT GCA CAC CTT CTC CCC GGC CAA AAT GTG GAT CAA CGG GCT GAG
TAT CCT TAA CAA ACC ACT ACT GCA TTC CAT ACC CAT TAA CGC CGC CCT GCC GTG GGA
CAG CAT TGA TAT GGA CTT TAT GAA CCT GAA CCA GAC TGC GCA GGG GGT CGA GTT CGG
TTT TAT CGG CGC GCG GAT GCG CCA GCA GCA CGC GGT CGT CAC CGG TCA CTG CAG GAA TAA
AGA GGC CCA TAC GCG TAT CGG TGC CTG GAT GCG CCA GGC GGT CTC TAA ACA GGA TAC CCG
CCA GCT AAA AGT CTG CCG CTT CGG CGA CAA TAT GCG TGA AGT CGC AGT GAC TGA CGG TGA
TAA AGT GGC CGC GCA AAT CAA ATT TGG CTT TTC GGT CAA TAC CTG GGC GGT CGG CGA TCT
GGT GCA GGT GGT GAA TTC TAT CGG CGA CGG CGA TAT CAA CGC TCT GAT TGA CGA GTA TGA
AAG CAG CTA TAC CCT GAC GCC CGC CAC CCA AAT CCA CGG CGA TAA CGC CGA ACG TGC G
GGA GGC GGC GCG TAT TGA ACT CGG TAT GAA GCG TTT CCT GGA ACA GGG CGG CTT CCA CGC
ATT CAC TAC TAC CTT TGA AGA TTT ACA CGG TCT GAA ACA GCT CCG GGT CTG GCC GTA CA
GCG TCT GAT GCA GCA AGG CTA CGG CTT TGC GGG CGA AGG CGA CTG GAA AAC GCC GCT CT
```

```
GCT TCG CAT TAT GAA AGT GAT GTC AAC CGG TCT GCA GGG CGG CAC CTC ATT TAT GGA GGA
TTA CAC CTA CCA CTT CGA GAA AGG CAA CGA TCT GGT GCT CGG CTC GCA CAT GCT GGA AGT
GTG TCC GTC CAT CGC GGT GGA AGA GAA ACC GAT CCT CGA CGT CCA GCA CCT CGG CAT TGG
CGG CAA GGA AGA TCC GGC GCG TTT GAT TTT CAA TAC CCA AAC CGG CCC GGC GAT CGT CGC
CAG CCT GAT CGA CCT CGG CGA TCG TTA TCG CCT GCT GGT CAA CTG CAT TGA CAC CGT AAA
AAC GCC GCA CTC CCT GCC GAA ACT GCC GGT GGC TAA CGC GCT GTG GAA GGC GCA GCC GGA
TCT GCC GAC CGC CTC CGA AGC GTG GAT TCT GGC TGG CGG CGC GCA CCA TAC CGT CTT CAG
CCA CGC GCT GGA TCT GAA CGA TAT GCG CCA GTT TGC AGA AAT ACA CGA TAT CGA AAT CGC
GGT GAT TGA TAA CGA TAC CCA TCT GCC GGC CTT TAA GGA CGC GCT GCG CTG GAA CGA GGT
GTA TTA CGG GTT CAA ACG TTA ATT GGT GAA ACG GAT TGC CCG GTG GCA CTG CGT TTA CCG
             G   F   K   R   *
GGC CTA CGG TCC TGT AGG CCG AAT AAG GCA TTT ATG TCG CCA TCC GGC ACA CCG TCG CTC
GTA GGC CGG ATA AGC GAA GCG CCA TCC GGC AGG GAG AAA ACA ATG TTA GAA GAT CTC AAA
                                                         M   L   E   D
                                                         araD →
CGC CAG GTA CTG GAA GCT AAT CTG GCG CTG CCA AAA CAC AAC CTG GTC ACC CTT ACC TGG
GGT AAC GTT AGC GCC GTC GAT CGC GAA CGC GGC GTA CTG GTG ATT AAG CCG TCC GGC GTC
GAT TAT AGC GTC ATG ACC GCT GAC GAT ATG GTG GTG GTC AGC CTG GAG AGC GGT GAA GTC
GTT GAA GGT CAT AAG AAA CCG TCG TCC GAT ACG CCA ACC CAC CGT CTG TTG TAC CAG GCA
TTT CCG ACT ATC GGC GGC ATC GCA CAT TCG CGC CAC GCG ACT ATC TGG GCG CAG
GCG GGT CAG CCA ATT CCG GCG ACG GGA ACC ACC CAT GCC GAC TAT TTC TAC GGT ACG ATT
CCC TGC ACT CGC AAA ATG ACC GAG GCG GAA ATT AAT GGC GAG TAT GAA TGG GAA ACG GGC
AAT GTC ATT GTT GAA ACC TTT GAA AAA CAA GGC ATT GAC GCC GCT CAA ATG CCC GGC GTG
CTT GTC CAT TCG CAC GGC CCG TTT GCC TGG GGT AAA AAT GCC GAG GAT GCA GTG CAT AAC
GCC ATC GTG CTG GAA GAA GTG GCC TAT ATG GGG ATC TTC TGC CGC CAG CTT GCG CCG CAG
TTG CCC GAC ATG CAG CAA TCC CTG CTG GAT AAA CAC TAT CTA CGC AAA CAC GGC GCA AAA
GCC TAT TAC GGG CAG TAA TGC CTC TAA AAA CGC GTC CCA TGG GGG GCG CGT TGA TGA ATC
         Y   Y   G   Q   *
                 araD ends
TGG TCG GTG A]TA TAT TCA GCA AAT GCG CTT TGA TAG ACG TAA TGA TCA GAA CTC ACA TAT
            araD₊₅₂
TCA ATA ATA TTG TCA TAA TGT CCC TGC CAC GCT TTT CCT TCC AGC GCA TGG AAG AAA ATA
TAA TCT TCG ATT GTT GAC TGC AGC GT TGC CCA TTT AAC AGA TAG TTA ATA ATG GTA TCC
CGA TGT CCG TTT TTT CTG TCG TGT CCT TGC CAG TGA AAA AAA GCA TTG CCG TTT TCA ATA
ATC TCG GTA CGC CAA ATC TGT TCT GTC CAT GTT TTA TAC TCA AAA AAT CGA CTC ACG GTT
TTT ATG GAA GGG TTA GCG CGT TGA GTA TTG ACG AAA AGA TAA CGG TCG TTC CCT ACC AGA
CGC GCC TGC ATA CTC ACA                                    primer araD-BamHI
```

FIG. 6B

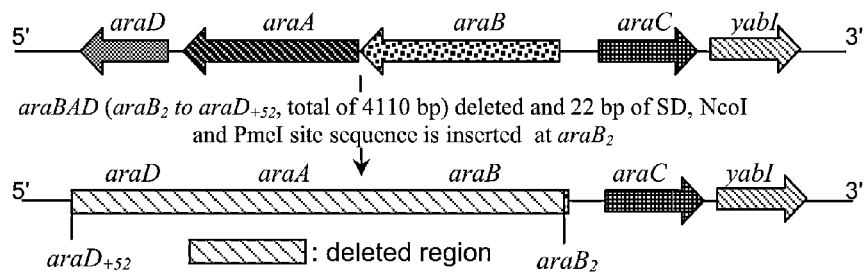

FIG. 6C

```
            primer N-SphI
GGC ATA CAC ACA CCT GTA TAA CAT TTG ATG TAA CGC CGT TAC TTT ACG CAG GAG TAA ATC
GGT GAA TTT GAT CTG AGT CAA GAA GGT GGG TTT TCA ATA AAA GTT GTG CCA TAA ATT GTG
AAG TTT GTA GAT TTT ATG AAC ATT TGA TGT ACC GAT CTC CCC CAT GAT CGC CAC TAC GTA
TGG ACG TCA GGA TGC CTC CCC GCC TGA TCA GAA GCG TTT CCT CAT TAA AAA GGA CAT TTT
TTT AAA GTT CCT GGT GCA TAA AAG TCA CAT CCT TTT AAA GGG TTG TTA ACC CTG TTG AAT
GTT CCC ACT CCC CTA TTC [AGG AAT ATT AAA AAC GCT ATG CAA ATA CAG AGC TTC TAT CAC
                         sopB₋₁₈                   M   Q   I   Q   S   F   Y   H
                                                              sopB →
TCA GCT TCA CTA AAA ACC CAG GAG GCT TTT AAA AGC CTA CAA AAA ACC TTA TAC AAC GGA
 S   A   S   L   K   T   Q   E   A   F   K   S   L   Q   K   T   L   Y   N   G
ATG CAG ATT CTC TCA GGC CAG GGC AAA GCG CCG GCT AAA GCG CCC GAC GCT CGC CCG GAA
 M   Q   I   L   S   G   Q   G   K   A   P   A   K   A   P   D   A   R   P   E
ATT ATT GTC CTG CGA GAA CCC GGC GCG ACA TGG GGG AAT TAT CTA CAG CAT CAG AAG GCG
 I   I   V   L   R   E   P   G   A   T   W   G   N   Y   L   Q   H   Q   K   A
TCT AAC CAC TCG CTG CAT AAC CTC TAT AAC TTA CAG CGC GAT CTT CTT ACC GTC GCG GCA
 S   N   H   S   L   H   N   L   Y   N   L   Q   R   D   L   L   T   V   A   A
ACC GTT CTG GGT AAA CAA GAC CCG GTT CTA ACG TCA ATG GCA AAC CAA ATG GAG TTA GCC
 T   V   L   G   K   Q   D   P   V   L   T   S   M   A   N   Q   M   E   L   A
AAA GTT AAA GCG GAC CGG CCA GCA ACA AAA CAA GAA GAA GCC GCG GCA AAA GCA TTG AAG
 K   V   K   A   D   R   P   A   T   K   Q   E   E   A   A   A   K   A   L   K
AAA AAT CTT ATC GAA CTT ATT GCA GCA CGC ACT CAG CAG CAG GAT GGC TTA CCT GCA AAA
 K   N   L   I   E   L   I   A   A   R   T   Q   Q   Q   D   G   L   P   A   K
GAA GCT CAT CGC TTT GCG GCA GTA GCG TTT AGA GAT GCT CAG GTC AAG CAG CTT AAT AAC
 E   A   H   R   F   A   A   V   A   F   R   D   A   Q   V   K   Q   L   N   N
CAG CCC TGG CAA ACC ATA AAA AAT ACA CTC ACG CAT AAC GGG CAT CAC TAT ACC AAC ACG
 Q   P   W   Q   T   I   K   N   T   L   T   H   N   G   H   H   Y   T   N   T
CAG CTC CCT GCA GCA GAG ATG AAA ATC GGC GCA AAA GAT ATC TTT CCC AGT GCT TAT GAG
 Q   L   P   A   A   E   M   K   I   G   A   K   D   I   F   P   S   A   Y   E
GGA AAG GGC GTA TGC AGT TGG GAT ACC AAG AAT ATT CAT CAC GCC AAT AAT TTG TGG ATG
 G   K   G   V   C   S   W   D   T   K   N   I   H   H   A   N   N   L   W   M
TCC ACG GTG AGT GTG CAT GAG GAC GGT AAA GAT AAA ACG CTT TTT TGC GGG ATA CGT CAT
 S   T   V   S   V   H   E   D   G   K   D   K   T   L   F   C   G   I   R   H
GGC GTG CTT TCC CCC TAT CAT GAA AAA GAT CCG CTT CTG CGT CAC GTC GGC GCT GAA AAC
 G   V   L   S   P   Y   H   E   K   D   P   L   L   R   H   V   G   A   E   N
AAA GCC AAA GAA GTA TTA ACT GCG GCA CTT TTT AGT AAA CCT GAG TTG CTT AAC AAA GCC
 K   A   K   E   V   L   T   A   A   L   F   S   K   P   E   L   L   N   K   A
TTA GCG GGC GAG GCG GTA AGC CTG AAA CTG GTA TCC GTC GGG TTA CTC ACC GCG TCG AAT
 L   A   G   E   A   V   S   L   K   L   V   S   V   G   L   L   T   A   S   N
ATT TTC GGC AAA GAG GGA ACG ATG GTC GAG GAC CAA ATG CGC GCA TGG CAA TCG TTG ACC
 I   F   G   K   E   G   T   M   V   E   D   Q   M   R   A   W   Q   S   L   T
CAG CCG GGA AAA ATG ATT CAT TTA AAA ATC CGC AAT AAA GAT GGC GAT CTA CAG ACG GTA
 Q   P   G   K   M   I   H   L   K   I   R   N   K   D   G   D   L   Q   T   V
AAA ATA AAA CCG GAC GTC GCC GCA TTT AAT GTG GGT GTT AAT GAG CTG GCG CTC AAG CTC
 K   I   K   P   D   V   A   A   F   N   V   G   V   N   E   L   A   L   K   L
GGC TTT GGC CTT AAG GCA TCG GAT AGC TAT AAT GCC GAG GCG CTA CAT CAG TTA TTA GGC
 G   F   G   L   K   A   S   D   S   Y   N   A   E   A   L   H   Q   L   L   G
AAT GAT TTA CGC CCT GAA GCC AGA CCA GGT GGC TGG GTT GGC GAA TGG CTG GCG CAA TAC
 N   D   L   R   P   E   A   R   P   G   G   W   V   G   E   W   L   A   Q   Y
CCG GAT AAT TAT GAG GTC GTC AAT ACA TTA GCG CGC CAG ATT AAG GAT ATA TGG AAA AAT
 P   D   N   Y   E   V   V   N   T   L   A   R   Q   I   K   D   I   W   K   N
AAC CAA CAT CAT AAA GAT GGC GGC GAA CCC TAT AAA CTC GCA CAA CGC TTT GCC ATG TTA
 N   Q   H   H   K   D   G   G   E   P   Y   K   L   A   Q   R   L   A   M   L
GCC CAT GAA ATT GAC GCG GTA CCC GCC TGG AAT TGT AAA AGC GGC AAA GAT CGT ACA GGG
 A   H   E   I   D   A   V   P   A   W   N   C   K   S   G   K   D   R   T   G
ATG ATG GAT TCA GAA ATC AAG CGA GAG ATC ATT TCC TTA CAT CAG ACC CAT ATG TTA AGT
 M   M   D   S   E   I   K   R   E   I   I   S   L   H   Q   T   H   M   L   S
GCG CCT GGT AGT CTT CCG GAT AGC GGT GGA CAG AAA ATT TTC CAA AAA GTA TTA CTG AAT
 A   P   G   S   L   P   D   S   G   G   Q   K   I   F   Q   K   V   L   L   N
```

FIG. 7A

```
AGC GGT AAC CTG GAG ATT CAG AAA CAA AAT ACG GGC GGG GCG GGA AAC AAA GTA ATG AAA
 S   G   N   L   E   I   Q   K   Q   N   T   G   G   A   G   N   K   V   M   K
AAT TTA TCG CCA GAG GTG CTC AAT CTT TCC TAT CAA AAA CGA GTT GGG GAT GAA AAT ATT
 N   L   S   P   E   V   L   N   L   S   Y   Q   K   R   V   G   D   E   N   I
TGG CAG TCA GTA AAA GGC ATT TCT TCA TTA ATC ACA TCT TGA] GTC TTG AGG TAA CTA TAT
 W   Q   S   V   K   G   I   S   S   L   I   T   S   *  sopB_{1645/1646}
GGA AAG TCT ATT AAA TCG TTT ATA TGA CGC GTT AGG CCT GGA TGC GCC AGA AGA TGA GCC
ACT GCT TAT CAT TGA TGA TGG GAT ACA GGT TTA TTT TAA TGA ATC CGA TCA TAC ACT GGA
AAT GTG CTG TCC CTT TAT GCC ATT GCC TGA CGA CAT CCT GAC TTT GCA GCA TTT TTT ACG
TCT GAA CTA CAC CAG CGC CGT CAC TAT CGG CGC TGA CGC AGA CAA TAC TGC TTT AGT GGC
                                            primer C-XmaI
```

FIG. 7B

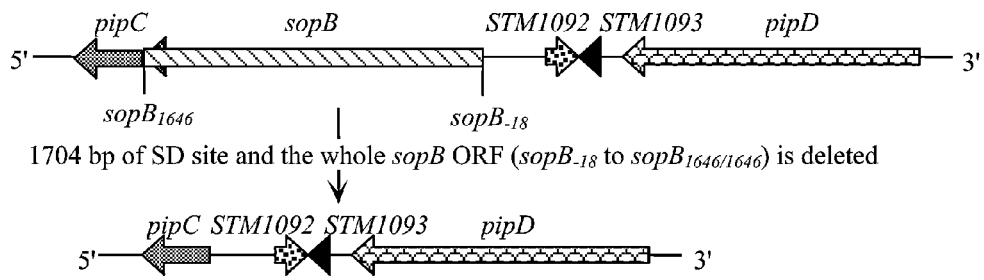

FIG. 7C

```
AGC CTG TGA TTC TGT ACA GTT AAG GTT TAA CCC CAA AGG TGC AAA CAA TTA AAT TTG TAA
      primer UtviA-5 SmaI
CAG ATT ATT TCA AAT ACG ATT AGG AAT ATT CTT ATT TTG AGG AAT GGC TTA GCA TTT TTT
ATG GTC GCC AGG ATT AAA AAA TAC GCC CTA TCC AAA CAA TTT AGC ATA ATT TAT CAT TCG
ATT TTC TAG ACT AAA TAA GAT TTT TTG ATA GGT ACA AAC AAT GAA TTG TGC AGG TTT GAC
ATC AAT TCT CTG TTG TGT AAA AAT CCC GTT TAG GCC GTT AGT ACT ATT AAA ATT AGG GTA
ATA ATT TTA TTG TTA GTT AAT TGT TAA CAG GAG CAA AGA ATT AGA TAT TGC TTG TAC CTT
                                                                   tviA↓
TTC TAT GGA TGA AAT TAG GTT ATT TCA GCA TAA GGA GAC TTC [ATG AGG TTT CAT CAT TTC
                                                         M   R   F   H
                                                     tviA→
TGG CCT CCG AAT GAT ATC TAT TTC GGG GTT GGA GCT GCT GGC ATT ATT GAA GAA GTG TCA
CTG ATA ACA GAC AGA AAT TAT TTG TTT GTG AAC CTA AAT CGC TAC AGC CTG TTA AAT
GCC CTG AAT TTT TTC ACG CGA ATG AGT GAT ATT AAT AAA ATA ATC GTT ATC ATT TCA GTT
TCG CGA CTA ATG CCC CTT GCA CGT TTT TGG TTG ACA GAG TGC AAA AAT GTT ATT GCT GTT
TTC GAT GCG GCA ACA TCA GTC CAG GAT ATT ATC AGA AAT GTC AGT CAA CAC CAA AGT GGT
GAA AAG ATC TTG ACG GAG CAG AGA GAT TAT CGT TTC AGA ATT AAC CGT AAG GAT ATA GTA
AAG ATG AAA TAT TTC CTT TCG GAA AGT GGT ATG GAA GAG CTT CAG GAT AGA TTT ATG AAC
TCA TCA TCG ACT ATG TAT CGC TGG AGA AAA GAA TTG GCA GTA AAA TTT GGA GTA CGT GAG
CCG CGC TAT CTG TTA TTG CCG GAT TCA GTT ACT TTA CTG TAA TGC GGT AAT TTT TAT TGA
 P   R   Y   L   L   P   D   S   V   T   L   L   *
GTA AAA CAC GGA CAA GTA TTT CGT TTC AGC ACA AAA TTA TTT TCG TTA CTC ATT GGC GTT
AAT ACA TAT ATT CTC AGC GAC TTC TGT TCT ATT CAA GTA AGA AAG GGG TAC GGT TAT ACG
TTT TCA TTA ACC ATA CTG GCT GCT ACG GCC AGG GGC GGT AGC GTA TCT GAA TAA ACA CCT
AGA ATT AAC TTT GTA AAT ATA AAA TTT TAG TAA AGG ATT AAT AAG AGT GTT CGG TAT AGA
                                                                 M   F   G   I
                                                             tviB →
CGA GGT AAA AAT CGC GAT TAT TGG GCT GGG ATA TGT TGG GCT TCC TCT GGC AGT TGA ATT
TGG CAA ATC TCG TCA GGT GTT TGG CTT CGA CGT TAA TAA AAA GCG TAT TCT TGA ATT AAA
GAA TGG GGT GGA TGT CAA TCT GGA AAC CAC TGA AGA AGA ATT ACG TGA GGC TCG TTA TCT
GAA ATT TAC TTC CGA GAT TGA GAA GAT CAA AGA ATG TAA TTT TTA CAT CAT CAC CGT CCC
GAC GCC GAT AAA TAC CTA CAA GCA ACC AGA CCT CAC CCC ACT AAT CAA GGC GAG TGA AAC
CGT TGG TAC AGT GCT GAA TCG GGG AGA TAT TGT GGT ATA TGA ATC TAC GGT ATA TCC GGG
ATG TAC CGA AGA AGA ATG CGT GCC GAT CCT TGC TCG TAT GTC CGG AAT GAC TTT CAA CCA
GGA TTT CTA TGT CGG TTA TAG CCC GGA AAG GAT CAA TCC CGG TGA TAA AAA GCA CCG TTT
AAC CAA CAT CAA GAA AAT CAC CTC CGG TTC AAC CGC ACA GAT CGC CGA ACT TAT CGA TGA
AGT ATA TCA GCA GAT CAT CAG CGC AGG TAC ATA TAA AGC AGA GAG CAT CAA AGT TGC TGA
GGC AGC GAA GGT GAT TGA AAA TAC GCA ACG TCT GAA TAT TGC CTT GGT CAA TGA GCT
GGC GAT TAT TTT TAA TCG TTT AAA TAT CGA TAC TGA AGC CGT GCT ACG TGC CGC TGG CAG
CAA ATG GAA TTT CCT GCC ATT CCG TCC GGG ACT GGT CGG TGG TCA CTG TAT TGG CGT AGA
TCC CTA TTA TCT GAC ACA TAA ATC TCA GGG CAT TGG CTA TTA TCC AGA AAT CAT ACT TGC
AGG ACG CCG CCT GAA CGA CAA CAT GGG CAA CTA TGT CTC CGA GCA GTT GAT CAA AGC AAT
GAT CAA AAA AGG AAT TAA CGT TGA TGG GTT CAG CGT GCT GAT TCT CGG CTT TAC CTT TAA
AGA AAA CTG TCC GGA CAT CAG AAA TAC ACG CAT TAT TGA TGT GGT AAA GGA ACT CGG TAA
ATA TAG TTG TAA AGT GGA TAT TTT TGA TCC ATG GGT GGA TGC CGA AGA GGT AAG ACG AGA
GTA TGG CAT TAT CCC GGT ATC GGA AGT CAA ATC AAG CCA CTA CGA TGC GAT CAT TGT TGC
AGT AGG ACA TCA GCA ATT AAA ACA GAT GGG AAG TGA GGA TAT TCG CGG CTT CGG AAA AGA
TAA ACA TGT ACT TTA TGA TTT GAA GTA TGT TCT TCC GGC TGA GCA GTC AGA TGT GAG ATT
                                                                             R   L
GTA ATC ATG ACG GCT TAC GAA GAA CTA CGG ACC AAA CTG GTT CTG GCA CCA AAG CGC TGG
 *   M   T   A   Y
         tviC →
CTG ATC ACT GGC GTA GCA GGC TTT ATT GGC TCC GGC TTA TTA GAA GAA TTA CTC TTT CTC
AAC CAG ACT GTC ATT GGA CTG GAT AAC TTT TCC ACC GGT TAT CAG CAT AAT CTA GAC GAC
GTT CGC ACG TCC GTC AGT GAG GAG CAA TGG TCG CGA TTT ATT TTT ATT CAG GGT GAC ATC
AGG AAA TTT ACT GAC TGT CAG AAA GCG TGT AAG AAC GTT GAC TAT GTT CTC CAC CAA GCC
GCG CTA GGA AGC GTG CCA CGT TCC CTA AAG GAT CCC ATC GCG ACT AAT AGC GCC AAT ATT
GAT GGT TTT TTA AAT ATG TTG ACG GCG AGA GAT GCT CAT GTC TCT AGT TTC ACC TAC
GCC GCA AGC AGT AGC ACC TAT GGA GAC CAT CCC GAT TTA CCT AAA ATT GAG GAA CGG ATC
GGT CGA CCA CTC AGC CCG TAT GCG GTA ACA AAA TAC GTC AAT GAA TTG TAC GCT GAT GTG
TTT GCA CGT AGC TAT GAA TTT AAC GCT ATT GGC CTA CGC TAC TTT AAT GTC TTT GGT CGC
```

FIG. 8A

```
CGC CAA AAT CCT AAC GGA GCG TAC TCG GCA GTT ATT CCT CGC TGG ATA CTA TCG CTT CTT
AAA GAT GAA CCA ATT TAT ATC AAT GGC GAT GGC TCA ACA AGC AGG GAT TTT TGC TAT ATA
GAG AAT GTG ATT CAG GCC AAT CTA TTA TCA GCA ACA ACT AAT GAT TTA GCC TCT AAA AAT
AAG GTC TAT AAT GTG GCA GTT GGA GAT AGA ACT TCG TTA AAT GAG CTT TAT TAT CTA ATT
CGC GAT GGG CTT AAT TTA TGG CGG AAC GAA CAA AGT AGA GCT GAA CCA ATT TAT AAA GAT
TTT CGT GAC GGT GAC GTT AAG CAT AGC CAG GCA GAT ATT ACC AAA ATA AAA ACA TTT CTT
TCA TAT GAG CCT GAA TTT GAT ATC AAA GAA GGA CTT AAG CAG ACT CTA AAA TGG TAT ATC
GAT AAA CAT TCT ACT TTG TAT TCC TCG GTA TAA CTA CTC ACT TTC CTT TCA CGT GGA TGA
                                Y   S   S   V   *                               M   N
                                                                               tviD→
ATT TAA TGA AAT CGT CAG GGA TGT TTA CGC TTA CAG CCA TTG GCA GTT GCC GTA TTG TGA
 L   M
GTC CGG TAA AAC GAG CTC AGC CTT ATT TTA ATT TTC AGG CAA ACT TTA AGA GAA TAT ATG
GTT TTA CGC ATA CGA GCA GCG AGG CAT TAC AGC AGA TTC GGT TTA TTT TGG GCT GAA TAG
ACA TTC CTG AAA AGG TCC GAC CAT TTA TTT TTA GAC CTA ATG TAA ACT ATT CAA ACA CCG
ACG TAC ATA GTC GTT CTG ATT TCT ATA TCA TTG AGA TTT CAA GTC AGA AGA AGA TTA TGG
CCT ATG GGT TCT GCT TAC AAA TAA ATT ATT TAA CTC GTC ATT TCT ATG AAT TTT TTA GCC
AAA CAG AGC GGG CGT GCA TGT ACT GGT CGT TGG CCA CGC AAG GAA ATC GAC ACA AAC TGC
TGG CCT ATC TCA AAG ACG ATC CCT GTT TTG CCG GAA TGT CGG AAG ACG ATC GTG CCT TAT
TAA GCA ATA TCA ATG TCG AGC AGA TGG ATG AGC ATG CTA TCG AAC AGG ATA TGA TGG AAA
TCG TTC AGC TTC TTG GTC GCG ATC GCG TTA TGT TTA TGA CAC ATG TTG ATG CCG TGA CTC
GTG CTG GAA CCG TCA TTC TAT CCC GTA GTC GGT TGA TTA AAA ATG TCG ACA CCA TCG TCG
CCA GGA TGG ATA TTC CCT GCG TTA ACC CGA CAA ATT TGA TGG AAA AGT GGG GGC AGA AAC
GAG CCC TGG AAA AAA ATG GCG ACG ATC TTA CTC ATT ATA CCG ATA TGT TTG GTG ACG CGA
TCG TTG CGG CTA TTT TTA AGG GAG TGA TCA ATA ATA CTA ATC ATC ATC TTG ATG AGG GGC
GAC AAG AGA AAC AGG ACC AAA TAC GTG AGA TTA CCT TAT CGA TCA CTA AGC AGC TTG CAG
ATG GCG ACA TTA TTG CTG CAT CAC AAC ACT TTT TTG CCG CAT TAA GAA ATC AGC AGC AAG
ATC CCG TTC TAA TCC AAC TTC GGT CCG TAA TCT TCA GCC ATT TAG GTT ATT ATG AAC AGG
CTT ATC AGG ATA TTA GTG ATG TTG AGA AAA TTA TCG GTA CGA CTG ACA GTA CAT TAC GTT
GTC GGC TGA GGT CTC TAC ATG GAT TAG CGC GTT GGC GGG AAG CCT TAT CGA CGG CAG AGA
TGA TGC TTT CCA ATG AAA TTG AAG ATG AAG AAG TCC TTA CCG TTG CCG CCG GCT CAG CCG
ATG CTT TAC AGC TGT TTG ATA AGT TAT ATC ATT ATT GGA AAC GTG TAC TAT TAT TGA ATC
CTG AAA CTC AAA GCG GAT GGG TTA ATT TCC TGA GCA GCA CGC AAT ATT TCA ATG ATG GCA
ACG CAT TCT CTG AAG CTT TCC ATG CCG GCA TTC AAT CGC AGC GCC TAA ATG ATA CGT TTA
TGG AAA CGG CGT TAT CTT TGG CAA TCA AAT TCA GTG ATG AAT TGA TTT TCA TGC ATG CGC
TCG AGC AGC TAC TCC GCC ATG AGT CAG AAT TTG CGC TGA CGG TAT TGT CGA CGA TTC ATG
ATA CCG GTC GCG TTA TCC GCA CAG CTT TCT GCA TCA AGA ATA TGA GCT ATC ATC AAG CGC
TTC GCA CCT CGT ATA AAG ATA AAA TCC ACG ACG TTT TTG AGG CAT GGA ACA ATA CCG CGC
TGT CGC TAC ATT CGG TTG ATG ATT TGT CTC ACT GAA GTA CTT CGC TAG CCT ATA GCT ACT
CTG CAT TTA TGG TTT ATC CCC ATT CAC GTA TTT CTC GCT TTA ATA ATG AAG TTA AAA TGG
CAT GGC GCG ATA AAT TAA GAG AAA TGT ATG AGC GTG AGG ATT ATG AAA ATA TCC TGG CAG
GGG CGA AAA TAG TGT GGC CAC TTC TGA AGT TTG ATC CCG TTG GCA CCG TAT ATT GTG CAA
GAA CGC TGG TGA ATC TTG GTG CCT GGA AAG ACG CGT GCA CGT GGC CCC ACA TGA CCT TGA
TTC GTA ACT CGA ACA TTA CCA GCC TGC AGT CGA TTA TGT TAC GCA GCA TAC GTC ATA TTA
ACA ACA TTC CGT TCC TCA TTG ATT TGA TTG CTA ACG TCA TGA GCA TTA CTC TAT CAT TCC
AGA ATG CCT CAA TGA ACA AGT TGT TTG AGA AAG AGT GTC GCA ATG TTG CAA CCA GAG CCC
TTA AAT ATG TAC GCC AGA AGA AAA CTG AGG GGC GTC TGG ATG AAG CAT TGT CTG TAT TGA
TTA GCC TGA AAC GAA TTG AGC CTG ATG TTT CTC GTC TGA TGC GTG AAT ATA AGC AAA TTA
TCA GAT TAT TTA ATG AGT CAC GGA AGG ATG GCG TTA GCA CTA TCA CGT CTT ATG AAC ATC
TAG ACT ATG CGA AAA AAT TAC TCG TTT TTG ATA GCG AAA ATG CCT ATG CCT TGA AAT ATG
CCG CAT TAA ATG CAA TGC ATT TAC GCG ACT ACA CGC AGG CTT TGC AGT ATT GGC AGC GAC
TGG AGA AAG TGA ATG GAC CAA CGG AGC CGG TGA CAA GGC AGA TCT CGA CCT GCA TAA CCG
CAT TAC AAA AAA ATA CAT CAG GGA AGT CGT AAT GAT TAC GCA GGA AGA AAA GTT AGC TGC
                                           S   G   K   S   *   M   I   T   Q
                                                             tviE →
ACT AGG AAA AAC GTG TTT AAC ATT AAA ACA AGA GAA GAA GCT TGC GCA AGC TGT TGC GTT
AAT TGA CAG TGA ATT ACC GAC TGA GGC TTT AAC TTC ATT AGC GAT GCT AAA AAA GCA GAG
GTT TCT TCA TGA TGT CAA TGA AAC GGA AGC GCG TGC ATA CGC GCT CTA CGA AAC GCT GAT
ACA AAA CAA TGA TGA ACG ACG TTA TGA GTA TGC ACG TCG TTT ATA TAA TAC GGG GCT AGC
CAA AGA TGC TCA GCT AAT TCT TAA AAA GGT TAG CAA TGG TGT GCA GAA AAA ATA TAA CAA
TTA TTT AGG CAA AAT AAA TAA GAT CTG TGA TTT GCT TGA ACG CCT TGA AGG GAA AGC GAT
```

FIG. 8B

```
CCC TGT GGG GAC CAA CAC CTG TAT TAT TGC AAT GAA GCA TGC CAT CTT GTT CTA TAG AAA
TCG TCA ACC CAG GCA GCT TCC CGT CGG GTC TTT CGG TCG TCT TGC GCT CTG TAC TGG CTC
GCT AGG TAG CGG TGG TGC AGA GCG TCA GAT TTC CAG GCT GGC TAT CGA AAT CGC CAG AAA
ATA TCG GCA AAA GGG GAA AAT TGG CGG CCT GAA AGT AGA AGA ACC GGT AGA ACT AAT TAT
TCG CTC CCT GAC ACC GGA ACT CAG GCA AGA CTT TTT CCT GAA AGA AGT GCT GGA AGA ACA
GGT CGA GGT TCT TGA AAT CGC GAA GAT TAC CGG AAA CTT GTT TGA CGA TGC GAC AAT AGA
ATC TCC AGA GTT GCG CTT ATT GCT ATC GCA TCT ACC GCC GGT GTG TAA ATA CGG CAT CAA
GCA TCT GGT CCC CCA TTT ATG CGA GCG CAA GCT GGA TTA TCT CTC CGT TTG CAG GGA TGG
CGC TTG TCT GAT GAT TGC GCT TGC AGC ATT GAT TGC TGG CGT GCC CAG AAT TCA ACT GGG
ATT ACG TGG GTT ACC GCC GGT GGT TAG AAA GCC TCT GTT CAA GCC GGA ATA TGA GCC TCT
CTA CCA GGC GCT GGC GGT CGT GCC TGG CGT TGA TTT TAT GAG TAA CAA CCA TTG TGT GAC
TCG CCA TTA TGC CGA CTG GCT GAA GTT GGA GGC GAA GCA CTT CCA GGT TGT ATA TAA CGG
CGT CTT ACC GCC ATC TAC TGA ACC CTC TTC TGA GGT GCC ACA TAA AAT CTG GCA GCA GTT
TAC GCA AAA AAC CCA GGA TGC GGA CAC GAC TAT TGG TGG CGT TTT CCG CTT TGT AGG CGA
TAA GAA CCC TTT TGC ATG GAT TGA TTT TGC AGC ACG CTA TTT ACA ACA CCA CCC CGC CAC
GCG CTT TGT GCT GGT AGG CGA TGG TGA TTT ACG CGC TGA AGC GCA GAA ACG CGC CGA ACA
GTT AGG GAT TCT GGA GAG AAT ACT ATT CGT TGG CGC CTC GCG TGA CGT AGG GTA TTG GCT
GCA AAA AAT GAA TGT ATT CAT TTT GTT TTC GCG TTA TGA AGG GCT ACC TAA TGT GCT TAT
TGA AGC ACA AAT GGT CGG GGT GCC GGT GAT TTC AAC CCC TGC AGG TGG ATC GGC AGA ATG
CTT TAT TGA GGG TGT TTC GGG TTT CAT TGT TGA TGA TGC ACA GAC GGT CAA TCT TGA CCA
GGC TTG CCG CTA TGC AGA AAA GTT GGT CAA TTT ATG GCG CAG CAG AAC CGG TAT TTG CCA
ACA GAC GCA GTC ATT TTT ACA AGA ACG CTT CAC CGT GGA ACA TAT GGT GGG AAC GTT TGT
AAA AAC CAT TGC CTC TCA GCC TCG TTA ATT AAT GGG CAT CAT TTT TCA GCT ATT TCA TTT
                                 S   Q   P   R   *
                                     tviE ends↑
ATA AAA TAA GTT] ATG AAA AAA ATC ATC ATA TTA CTA ACG ACA TTT TTC CTG CTT TCG GGA
         tviE₊₄₄
TGC ACT ATT CCC AGG GCG GTA TTT AAA TCC AGC CTT ATT AAT CAG GAC GAT CCT CGT TAT
AAT CTG GTC GAA GTC ACG CCG ACA TTA AAA CTA GCG GCT CCC GAT ACT GTG CCG AAA ACT
ATT GTC GAT CCG GTT TTT GCC GCA AAT AAC TGG CAC TGG ACA TCT TTG GCT AAA GGC GAT
GTG CTG CAT ATC ACT ATT TTA TCC TCG GGC GGG GCT GGA TAT TTA TCC AAT AAC GCG AGC
GGC GAC CGT GCG GAT TTT GAA AAT ATT CTT GTG ACT GAC AGT AAT ACC GTT CAG GTG CCT
                                  primer vexA-3 SphI
```

FIG. 8C vexE   vexD vexC vexB vexA   tviE     tviD    tviC  tviB    tviA    T4355

7410 bp of ΔtviABCDE (tviA₁ to tviE₊₄₄)

vexE   vexD vexC vexB vexA                                          T4355 tviE₊₄₄                          tviA₁

FIG. 8D

```
AAT AAT GTT TTT ATA TTA TTG TTT TTG CGG CTT AAA TTA TCC TGC CAA TAG TGG ATA AGC
TTC TTA TCC GCT TCC ATC ATA TCC ATT AAA ACA ATG CAA CCG GCC GAG ATA TCT TCC AGA
GAA CGT TGA ATA TTA TGC AGT TTT CCG GTT ATG GCC AGC GAT TGC TTT AAA TGT TGC AAT
AAT GCC GTA GCT TGC AGA GAT GGC TTT GTG ATC AAC AAT AGT GTG ACC TGA CTA CTA
TGG ACT TCA TTA AAC ATG ATG AAA CTC CAC TTT TTT TAA TCG CAC ATC TGA CAG CTG CCC
                                                                 primer UagfB
CCA TAA AAT AAA GGC ACC AGA AGT ACT GAC AGA TGT TGC ACT GCT GTG GGT TGA AAT AGC
CCA TTA TCC AGA AAG AGA AAA ATA TTT ACG AAA ATA CTT TTA ACT GTT TTC AAT CTA GCC
ATT ACA AAT CTT AAA GCA AGT GTT AAA CTT GTA ACC AAA TGT AAA AAT ATA TAT AAA ATT
GTT GTT TTT GGG TTT TTT TGA AGT TTA GAT TTG ATA GTA AAG TTG TAC ATT TCG CTG TTA
TTG CAT AGA TTT AAA AAA TCA TAC AAA TTA TAA TAA TTC ATT GAT TTT TAA TCA TTT TAA
TTA TTA TAT GTT ATG TTT TGA TTT TAT TTT TTC TTA AAA TTT GAG ACG TGG CAT TAA CCT
GGA CAG CAC AAA GAC AAA AAA AAC GAA GTG TGT CAC GTC TTG TGC GTA TTG CCC CAC ATG
GGA AGC ATA AGA ACA TCC C[CA TGG CGG CAT AAC ACA CAC CAA CAC TTC ATT TTT TAG GTG
                        NcoI  agfB₋₂₇₂
CGC GAT ACA CTA TCT TCT GTG GCC AAA AAT CAA TTA TAA AAA ATC ACA TGG CTA TCG TTT
TAT TAG CAC TTT GGT ATG AGC TTA AAT AAC AAA ATA CCA CGC GTG GGT GAG TTA TTA AAA
ATG TTT CCA CGG ACA TAC TCT TCA TCG TAA CGA CGC GTT AAC AAA AAA CGC ATG TCG CTA
ACA AGG TAA TAG ATA ATT TTC GCT ATG TAC GAC CAG GTC CAG GGT GAC AGC ATG AAA AAC
                                                                  M   K   N
                                                                agfB/csgB →
AAA TTG TTA TTT ATG ATG TTG ACA ATA CTG GGT GCG CCT GGG ATT GCA ACC GCG ACA AAT
TAT GAT CTG GCT CGT TCA GAG TAT AAT TTT GCG GTA AAT GAA TTA AGC AAG TCT TCA TTT
AAT CAG GCG GCC ATT ATT GGT CAA GTC GGC ACG GAT AAT AGT GCC AGA GTA CGC CAG GAA
GGA TCA AAA CTA TTG TCC GTT ATT TCA CAA GAA GGA GGA AAT AAT CGG GCG AAA GTC GAC
CAG GCA GGG AAT TAT AAC TTT GCG TAT ATT GAG CAA ACG GGC AAT GCC AAC GAT GCC AGT
ATA TCG CAA AGC GCT TAC GGT AAT AGT GCG GCT ATT ATC CAG AAA GGT TCT GGA AAT AAG
GCC AAT ATT ACC CAG TAC GGT ACG CAG AAA ACA GCA GTT GTA GTG CAG AAA CAG TCG CAT
ATG GCT ATT CGC GTC ACC CAA CGC TAA TAC CGT TAC GAC TTT TAA ATC AAT CCG ATG GGG
                V   T   Q   R   *
GTT TTA CCA TGA AAC TTT TAA AAG TGG CAG CAT TCG CAG CAA TCG TAG TTT CTG GCA GTG
           M   K   L   L   K   V   A
            agfA/csgA →
CTC TGG CTG GCG TCG TTC CAC AAT GGG GCG GCG GCG GTA ATC ATA ACG GCG GCG GCA ATA
GTT CCG GCC CGG ATT CCA CGT TCA GCA TTT ATC AGT ACG GTT CCG CTA ACG CTG CGC TTG
CTC TGC AAA GCG ATG CCC GTA AAT CTG AAA CGA CCA TTA CCC AGA GCG GTT ATG GTA ACG
GCG CCG ATG TAG GCC AGG GTG CGG ATA ACA GTA CTA TTG AAC TGA CTC AGA ATG GTT TCA
GAA ACA ATG CCA CCA TCG ACC AGT GGA ACG CTA AAA CTC CGA TTA CTG TCG GTC AAT
ACG GCG GTA ATA ACG CCG CGC TGG TTA ATC AGA CCG CAT CTG ATT CCA GCG TAA TGG TGC
GTC AGG TTG GTT TTG GCA ACA ACG CCA CGG CTA ACC AGT ATT AAT TTA GCG TCT GCG CTA
ATA AAA AAA CAG GGC ATA AGC CCT GTT TTT TTT CGG GAG GAA ATT ATG CAT ACT TTA TTG
                                                             M   H   T   L
                                                            agfC/csgC →
CTC CTT GCC GCA CTT TCA AAT CAG ATT ACG TTT ACC ACG ACT CAG CAA GGC GAT ATT TAC
ACG GTG ATC CCT CAG GTC ACA TTA AAC GAA CCC TGC GTC TGT CAG GTG CAA ATT CTC TCT
GTG CGC GAC GGC GTC GGG GGA CAA AGC CAT ACA CAG CAA AAA CAA ACG CTA TCT TTA CCT
GCT AAT CAA CCG ATT GAG TTG TCT CGT CTT AGT GTA AAT ATA TCT TCA GAG GAC TCG GTT
AAA ATT ATT GTT ACT GTT TCG GAC GGA CAA TCA CTG CAT TTA TCA CAA CAA TGG CCG CCT
TCT GCA CAG TAG TTT TTG ATG GTG GCG GAA ATG GAT TGG CTG ACC TGG GTA TAA AGA GGC
  S   A   Q   *
GAT AAA AGC GTC TCA TCG TCT CGG CAT GTC GCT ATA AGG TAA CGC CGA ACC C]TC GAG GAT
                                                        agfC₊₁₀₀   XhoI
GAC TAA TCA TTG AGG AGT TAA CAT GTC CGT AAT CAA GAA AAA TAT CCC TGC CAT AGG CCT
                              M   S   V   I
                              ymdA →
GTG TAT CTG CGC TTT TTT TAT CCA TTC TGC GGT AGG CAA ACA AAC GGT ACA GGG CGG CGT
TAT CCA TTT TCG CGG CGC GAT TGT TGA GCC ACT GTG CGA TAT TTC TAC TCA CGC CGA AAA
                                               primer ymdA
```

FIG. 9A

```
CGG GCA CAT ATC GAT ACC GTA AGC CGG GTA AGG CGT AAT CGC TAC CCG GTT TTT TTA TTG
AGG TGT GCA TGG CAA TCG CCC AAC GAC ATT TTG CCT CGC CAT GTT TCA GTA CGC GCA TAA
        primer Uasd N-XbaI
AAG CAG GCA AAT TTC TAC GCT GAT CCA TAA TTA GGA TCA ATA AAA CAG CGA CGG AAA TGA
TTC CCT TCC TAA CGC AAA TTC CCT GAT AAT CGC CAC TGG ACT TTC TGC TTG CGC GGT AAG
GCA GGA TAA GTC GCA TTA CTG ATG GCT TCG CTA TCA TTG ATT AAT TTC ACT TGC GAC TTT
GGC TGC TTT TTG TAT GGT GAA GGA TGC GCC ACA GGA TAC TGG CGC GCA TAC ACA GCA CAT
                                          asd₁
CTC TTT GCA GGA AAA AAC GCT [ATG AAA AAT GTT GGT TTT ATC GGC TGG CGC GGA ATG GTC
                             M   K   N   V   G   F   I   G   W   R   G   M   V
                            asd →
GGC TCT GTT CTC ATG CAA CGC ATG GTA GAG GAG CGC GAT TTC GAC GCT ATT CGC CCT GTT
G   S   V   L   M   Q   R   M   V   E   E   R   D   F   D   A   I   R   P   V
TTC TTT TCT ACC TCC CAG TTT GGA CAG GCG GCG CCC ACC TTC GGC GAC ACC TCC ACC GGC
F   F   S   T   S   Q   F   G   Q   A   A   P   T   F   G   D   T   S   T   G
ACG CTA CAG GAC GCT TTT GAT CTG GAT GCG CTA AAA GCG CTC GAT ATC ATC GTG ACC TGC
T   L   Q   D   A   F   D   L   D   A   L   K   A   L   D   I   I   V   T   C
CAG GGC GGC GAT TAT ACC AAC GAA ATT TAT CCA AAG CTG CGC GAA AGC GGA TGG CAG GGT
Q   G   G   D   Y   T   N   E   I   Y   P   K   L   R   E   S   G   W   Q   G
TAC TGG ATT GAC GCG GCT TCT ACG CTG CGC ATG AAA GAT GAT GCC ATT ATT ATT CTC GAC
Y   W   I   D   A   A   S   T   L   R   M   K   D   D   A   I   I   I   L   D
CCG GTC AAC CAG GAC GTG ATT ACC GAC GGA CTG AAC AAT GGC GTG AAG ACC TTT GTG GGC
P   V   N   Q   D   V   I   T   D   G   L   N   N   G   V   K   T   F   V   G
GGT AAC TGT ACC GTT AGC CTG ATG TTG ATG TCG CTG GGC GGT CTC TTT GCC CAT AAT CTC
G   N   C   T   V   S   L   M   L   M   S   L   G   G   L   F   A   H   N   L
GTT GAC TGG GTA TCC GTC GCG ACC TAT CAG GCC GCC TCC GGC GGC GGC GCG CGC CAT ATG
V   D   W   V   S   V   A   T   Y   Q   A   A   S   G   G   G   A   R   H   M
CGC GAG CTG TTA ACC CAA ATG GGG CAG TTG TAT GGC CAT GTC GCC GAT GAA CTG GCG ACG
R   E   L   L   T   Q   M   G   Q   L   Y   G   H   V   A   D   E   L   A   T
CCG TCT TCC GCA ATT CTT GAT ATT GAA CGC AAA GTT ACG GCA TTG ACC CGC AGC GGC GAG
P   S   S   A   I   L   D   I   E   R   K   V   T   A   L   T   R   S   G   E
CTG CCG GTG GAT AAC TTT GGC GTA CCG CTG GCG GGA AGC CTG ATC CCC TGG ATC GAC AAA
L   P   V   D   N   F   G   V   P   L   A   G   S   L   I   P   W   I   D   K
CAG CTT GAT AAC GGC CAA AGC CGC GAA GAG TGG AAA GGC CAG GCG GAA ACC AAC AAG ATC
Q   L   D   N   G   Q   S   R   E   E   W   K   G   Q   A   E   T   N   K   I
CTC AAT ACT GCC TCT GTG ATC CCG GTT GAT GGT TTG TGC GTG CGC GTC GGC GCG CTG CGC
L   N   T   A   S   V   I   P   V   D   G   L   C   V   R   V   G   A   L   R
TGT CAC AGC CAG GCG TTC ACC ATT AAG CTG AAA AAA GAG GTA TCC ATT CCG ACG GTG GAA
C   H   S   Q   A   F   T   I   K   L   K   K   E   V   S   I   P   T   V   E
GAA CTG CTG GCG GCA CAT AAT CCC TGG GCG AAA GTG GTG CCG AAC GAT CGT GAT ATC ACT
E   L   L   A   A   H   N   P   W   A   K   V   V   P   N   D   R   D   I   T
ATG CGC GAA TTA ACC CCG GCG GCG GTG ACC GGC ACG TTG ACT ACG CCG GTT GGT CGT CTG
M   R   E   L   T   P   A   A   V   T   G   T   L   T   T   P   V   G   R   L
CGT AAG CTG AAC ATG GGG CCA GAG TTC TTG TCG GCG TTT ACC GTA GGC GAC CAG TTG TTA
R   K   L   N   M   G   P   E   F   L   S   A   F   T   V   G   D   Q   L   L
TGG GGC GCC GCC GAG CCG CTG CGT CGA ATG CTG CGC CAG TTG GCG] TAG TGG CTA TTG CAG
W   G   A   A   E   P   L   R   R   M   L   R   Q   L   A   *
                                                              asd₁₁₀₄/₁₁₀₇
CGC TTA TCG GGC CTG CGT GTG GTT CTG TAG GCC GGA TAA GGC GTG TCA GCG CCG CCA TCC
GGC AAT ATC CGC CAG ATA AGG CGT AGT CGG CAA GCA GAC GTC AGA TTG ATA TGT AGG GTG
CAT CGT CAC CTT TTT TTG CGT AAT ACA GGA GTA AAC GCA GAT GTT TCA TTT TTA TCA GGA
GTT AAG CAG AGC ATT GGC TAT TCT TTA AGG GTA GCT TAA TCC CAC GGG TAT TAA GCC TAA
CCT GAA GGT AGG ACG ACG CAG ATA GGA TGC ACA GTG TGC TGC GCC GTT CAG GTC AAA GAA
        primer asd-C XmaI
```

FIG. 10A

```
                                                    primer Ucrp-N SphI
CTA CAT CCG CCA GCC GCC ATT AAT ACC ATC TCC ATC GGA CTC GGC GCT TTG TCA CCG GAG
TTG CCA TCC ATT AAA ATC TGG TGG CCG GAG GAG GAC TCT CCG AGG AAC GTG AGC CCT TCA
ACC CAC TTT ACA CGC GCT TGC ATA TTT CGT AAC TCC AAT GTT TCA ATT TTC CTG AAA GAT
TAC GCG CAT ACA ACA AAA GTC GCA ATG GAA GGC GAC CTG GGT CAT GCT GAA GCG AGA CAC
CAG GAG ACA CAC GGC GAA AGC TAT GCT AAA ACA GAC AAG ATG CTA CAG TAA TAC ATT GAC
GTA CTG CAT GTA TGC AGA GGA CAT CAC ATT ACA GGC TAC AA[T CTA TTT TCG TAG CCC CCT
                                                 ΔP_crp   crp_-109
TCC CAG GTA GCG GGA AGT ATA TTT TTG CAA CCC CAG AGA CAG TGC CGT TTT CTG GCT CTG
GAG ACA GCT TAT AAC A]GA GGA TAA CCG CGC ATG GTG CTT GGC AAA CCG CAA ACA GAC CCG
    to          crp_-15                        M   V   L   G   K   P   Q   T   D   P
                                            crp →
ACT CTT GAA TGG TTC TTG TCT CAT TGC CAC ATT CAT AAG TAC CCG TCA AAG AGC ACG CTG
 T   L   E   W   F   L   S   H   C   H   I   H   K   Y   P   S   K   S   T   L
ATT CAC CAG GGT GAA AAA GCA GAA ACG CTG TAC TAC ATC GTT AAA GGC TCC GTG GCA GTG
 I   H   Q   G   E   K   A   E   T   L   Y   Y   I   V   K   G   S   V   A   V
CTG ATC AAA GAT GAA GAA GGG AAA GAA ATG ATC CTT TCT TAT CTG AAT CAG GGT GAT TTT
 L   I   K   D   E   E   G   K   E   M   I   L   S   Y   L   N   Q   G   D   F
ATT GGT GAA CTG GGC CTG TTT GAA GAA GGC CAG GAA CGC AGC GCC TGG GTA CGT GCG AAA
 I   G   E   L   G   L   F   E   E   G   Q   E   R   S   A   W   V   R   A   K
ACC GCA TGT GAA GTC GCT GCA GAA ATT TCC TAC AAA AAA TTT CGC CAA TTA ATC CAG GTC AAC
 T   A   C   E   V   A   E   I   S   Y   K   K   F   R   Q   L   I   Q   V   N
                                                                primer crp C-SacI
CCG GAT ATT CTG ATG CGC CTC TCT TCC CAG ATG GCT CGT CGC TTA CAA GTC ACC TCT GAA
 P   D   I   L   M   R   L   S   S   Q   M   A   R   R   L   Q   V   T   S   E
```

FIG. 11A

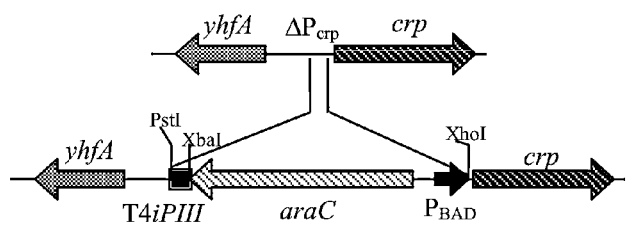

95 bp of *crp* promoter region (-15 to -109) is deleted and
1335 bp P_BAD *araC* TT inserted

FIG. 11B

```
                                                 Primer Ucrp-N SphI
TAC ATC CGC CAG CCG CCA TTA ATA CCA TCT CCA TCG GAC TCG GCG CTT TGT CAC CGG AGT
TGC CAT CCA TTA AAA TCT GGT GGC CGG AGG AGG ACT CTC CGA GGA ACG TGA GCC CTT CAA
CCC ACT TTA CAC GCG CTT GCA TAT TTC GTA ACT CCA ATG TTT CAA TTT TCC TGA AAG ATT
ACG CGC ATA CAA CAA AAG TCG CAA TGG AAG GCG ACC TGG GTC ATG CTG AAG CGA GAC ACC
AGG AGA CAC ACG GCG AAA GCT ATG CTA AAA CAG ACA AGA TGC TAC AGT AAT ACA TTG ACG
TAC TGC ATG TAT GCA GAG GAC ATC ACA TTA CAG GCT ACA ACT GCA GAG ATC TTT TAT TAT
TCT ATC CTA GAA TTG TGA TAA TAT ATT CAC AAT TCT AGG AGT TGT AAA CTG CTT TTA TTT
                                  T4iPIII TT
ATC TAG AGT CAA GCC GTC AAT TGT CTG ATT CGT TAC CAA TTA TGA CAA CTT GAC GGC TAC
TAG ATC TCA GTT CGG CAG TTA ACA GAC TAA GCA ATG GTT AAT ACT GTT GAA CTG CCG ATG
                                              araC ends  *  S   L   K   V   A   V
ATC ATT CAC TTT TTC TTC ACA ACC GGC ACG AAA CTC GCT CGG GCT GGC CCC GGT GCA TTT
TAG TAA GTG AAA AAG AAG TGT TGG CCG TGC TTT GAG CGA GCC CGA CCG GGG CCA CGT AAA
 D   N   V   K   E   E   C   G   A   R   F   E   S   P   S   A   G   T   C   K
TTT AAA TAC TCG CGA GAA ATA GAG TTG ATC GTC AAA ACC AAC ATT GCG ACC GAC GGT GGC
AAA TTT ATG AGC GCT CTT TAT CTC AAC TAG CAG TTT TGG TTG TAA CGC TGG CTG CCA CCG
 K   F   V   R   S   F   Y   L   Q   D   D   F   G   V   N   R   G   V   T   A
GAT AGG CAT CCG GGT AGT GCT CAA AAG CAG CTT CGC CTG ACT AAT GCG TTG GTC CTC GCG
CTA TCC GTA GGC CCA TCA CGA GTT TTC GTC GAA GCG GAC TGA TTA CGC AAC CAG GAG CGC
 I   P   M   R   T   T   S   L   L   K   A   Q   S   I   R   Q   D   E   R
CCA GCT TAA GAC GCT AAT CCC TAA CTG CTG GCG AAA AAG ATG TGA CAG ACG CGA CGG CGA
GGT CGA ATT CTG CGA TTA GGG ATT GAC GAC CGC TTT TTC TAC ACT GTC TGC GCT GCC GCT
 W   S   L   V   S   I   G   L   Q   Q   R   F   L   H   S   L   R   S   P   S
CAA GCA AAC ATG CTG TGC GAC GCT GGC GAT ATC AAA ATT GCT GTC TGC CAG GTG ATC GCT
GTT CGT TTG TAC GAC ACG CTG CGA CCG CTA TAG TTT TAA CGA CAG ACG GTC CAC TAG CGA
 L   C   V   H   Q   A   V   S   A   I   D   F   N   S   D   A   L   H   D   S
GAT GTA CTG ACA AGC CTC GCG TAC CCG ATT ATC CAT CGG TGG ATG GAG CGA CTC GTT AAT
CTA CAT GAC TGT TCG GAG CGC ATG GGC TAA TAG GTA GCC ACC TAC CTC GCT GAG CAA TTA
 I   Y   Q   C   A   E   R   V   R   N   D   M   P   P   H   L   S   E   N   I
CGC TTC CAT GCG CCG CAG TAA CAA TTG CTC AAG CAG ATT TAT CGC CAG CAG CTC CGA ATA
GCG AAG GTA CGC GGC GTC ATT GTT AAC GAG TTC GTC TAA ATA GCG GTC GTC GAG GCT TAT
 A   E   M   R   R   L   L   Q   E   L   N   I   A   L   L   E   S   Y
GCG CCC TTC CCC TTG CCC GGC GTT AAT GAT TTG CCC AAA CAG GTC GCT GAA ATG CGG CTG
CGC GGG AAG GGG AAC GGG CCG CAA TTA CTA AAC GGG TTT GTC CAG CGA CTT TAC GCC GAC
 R   G   E   G   N   I   I   Q   G   F   L   D   S   F   H   P   Q
GTG CGC TTC ATC CGG GCG AAA GAA ACC CGT ATT GGC AAA TAT TGA CGG CCA GTT AAG CCA
CAC GCG AAG TAG GCC CGC TTT CTT TGG GCA TAA CCG TTT ATA ACT GCC GGT CAA TTC GGT
 H   A   E   D   P   R   F   F   G   T   N   A   F   I   S   P   W   N   L   W
TTC ATG CCA GTA GGC GCG CGG ACG AAA GTA AAC CCA CTG GTG ATA CCA TTC GCG AGC CTC
AAG TAC GGT CAT CCG CGC GCC TGC TTT CAT TTG GGT GAC CAC TAT GGT AAG CGC TCG GAG
 E   H   W   Y   A   R   P   R   F   Y   V   W   Q   H   Y   W   E   R   A   E
CGG ATG ACG ACC GTA GTG ATG AAT CTC TCC TGG CGG GAA CAG CAA ATA TCA CCG GTC G
GCC TAC TGC TGG CAT CAC TAC TTA GAG AGG ACC GCC CTT GTC GTT TAG TGG CCA GC
 P   H   R   G   Y   H   H   I   E   G   P   P   F   L   L   I   D   G   P   R
GCA GAC AAA TTC TCG TCC CTG ATT TTT CAC CAC CCC CTG ACC GCG AAT GGT GAG ATT GAG
CGT CTG TTT AAG AGC AGG GAC TAA AAA GTG GTG GGG GAC TGG CGC TTA CCA CTC TAA CTC
 C   V   F   E   R   G   Q   N   K   V   V   G   Q   G   R   I   T   L   N   L
AAT ATA ACC TTT CAT TCC CAG CGG TCG GTC GAT AAA AAA ATC GAG ATA ACC GTT GGC CTC
TTA TAT TGG AAA GTA AGG GTC GCC AGC CAG CTA TTT TTT TAG CTC TAT TGG CAA CCG GAG
 I   Y   G   K   M   G   L   P   R   D   I   F   F   D   L   Y   G   N   A   E
AAT CGG CGT TAA CCG CGC CAC CAG ATG GGC GTT AAA CGA GTA TCC CGG CAG CAG GGG ATC
TTA GCC GCA ATT GGC GCG GTG GTC TAC CCG CAA TTT GCT CAT AGG GCC GTC GTC CCC TAG
 I   P   T   L   G   A   V   L   H   A   N   F   S   Y   G   P   L   L   P   D
ATT TTG CGC TTC AGC CAT ACT TTT CAT ACT CCC ACC ATT CAG AGA AGA AAC CAA TTG TCC
TAA AAC GCG AAG TCG GTA TGA AAA GTA TGA GGG TGG TAA GTC TCT TCT TTG GTT AAC AGG
 N   Q   A   E   A   M  ←araC
```

FIG. 12A

```
ATA TTG CAT CAG ACA TTG CCG TCA CTG CGT CTT TTA CTG GCT CTT CTC GCT AAC CCA ACC
GGT AAC CCC GCT TAT TAA AAG CAT TCT GTA ACA AAG CGG GAC CAA AGC CAT GAC AAA AAC
GCG TAA CAA AAG TGT CTA TAA TCA CGG CAG AAA AGT CCA CAT TGA TTA TTT GCA CGG CGT
                                                                   P   -35
                                                                    BAD
CAC ACT TTG CTA TGC CAT AGC ATT TTT ATC CAT AAG ATT AGC GGA TCC TAC CTG ACG CTT
                P   -10                                            SD
                 BAD
TTT ATC GCA ACT CTC TAC TGT TTC TCC ATA CCC GTT TTT TTG GGC TAG CCT CGA GGA GGA
TAA CCG CGC ATG GTG CTT GGC AAA CCG CAA ACA GAC CCG ACT CTT GAA TGG TTC TTG TCT
                 M   V   L   G   K   P   Q   T   D   P   T   L   E   W   F   L   S
                 crp →
CAT TGC CAC ATT CAT AAG TAC CCG TCA AAG AGC ACG CTG ATT CAC CAG GGT GAA AAA GCA
 H   C   H   I   H   K   Y   P   S   K   S   T   L   I   H   Q   G   E   K   A GAA ACG CTG TAC TAC ATC GTT AAA GGC TCC GTG GCA GTG CTG ATC AAA GAT GAA GAA GGG
 E   T   L   Y   Y   I   V   K   G   S   V   A   V   L   I   K   D   E   E   G
AAA GAA ATG ATC CTT TCT TAT CTG AAT CAG GGT GAT TTT ATT GGT GAA CTG GGC CTG TTT
 K   E   M   I   L   S   Y   L   N   Q   G   D   F   I   G   E   L   G   L   F
GAA GAA GGC CAG GAA CGC AGC GCC TGG GTA CGT GCG AAA ACC GCA TGT GAG GTC GCT GAA
 E   E   G   Q   E   R   S   A   W   V   R   A   K   T   A   C   E   V   A   E
                                                      Primer crpC-SacI
ATT TCC TAC AAA AAA TTT CGC CAA TTA ATC CAG GTC AAC CCG GAT ATT CTG ATG CGC CTC
 I   S   Y   K   K   F   R   Q   L   I   Q   V   N   P   D   I   L   M   R   L
TCT TCC CAG ATG GCT CGT CGC TTA CAA GTC ACC TCT GAA
 S   S   Q   M   A   R   R   L   Q   V   T   S   E
```

FIG. 12B

```
                Primer 1
GAA GCG CAA TGT GAC TGG GAT GAC TTC TTC CCG ACT CTC GAA GAG ATT GAC TTT AAC GGT
 E   A   Q   C   D   W   D   D   F   F   P   T   L   E   E   I   D   F   N   G
AAG CTG GTG GCG CTG TTT GGC TGT GGC GAT CAG GAA GAC TAC GCG GAA TAC TTC TGT GAT
 K   L   V   A   L   F   G   C   G   D   Q   E   D   Y   A   E   Y   F   C   D
GCG CTG GGC ACG ATT CGC GAC ATT ATT GAG CCG CGC GGC GCC ACG ATT GTG GGT CAC TGG
 A   L   G   T   I   R   D   I   I   E   P   R   G   A   T   I   V   G   H   W
CCA ACC GCA GGC TAT CAT TTT GAA GCC TCT AAA GGT CTG GCT GAC GAC GAT CAT TTT GTC
 P   T   A   G   Y   H   F   E   A   S   K   G   L   A   D   D   D   H   F   V
GGC CTG GCG ATT GAC GAA GAC CGT CAG CCT GAA CTG ACC GCC GAG CGT GTT GAA AAA TGG
 G   L   A   I   D   E   D   R   Q   P   E   L   T   A   E   R   V   E   K   W
GTT AAG CAA GTT TCG GCT GAA TTG CAC CTC GGC GAC ATC CTC AAC GCC TAA TCT TAT GCG
 V   K   Q   V   S   A   E   L   H   L   G   D   I   L   N   A   *  fldA ends
GCG CAG CGT TAT ATC TGC G[CC GCA TCA ATA GAC AAG ACC AAT CAA AAT TGC TAC AAA
                Fur₋₂₅₃           OxyR binding site
TTT GTA ACT TTC GCA CCC ATC CCT GTA CAA TGT CCG GGT GTA ATC AGG TGG CGC CAG AAT
                                                                -35
TTG CAG GCA AAA CCA CAG TTT TAT TAA CAT CTG CGA GAG ACT GCC GGT TTT CAT TTC GGC
         CRP binding site
                      -10
ATG GCA GTC CTA TAA TGA TAC GCA TTA TCT TGA GTG CAA TTT CTG TCA CTT CTC TAA TGA
            Fur consensus
AGT GAA TCG TTT AGC AAC] AGG ACA GAT TCC GC ATG ACT GAC AAC AAT ACC GCA TTA AAG
                 Fur₋₁₅ SD             M   T   D   N   N   T   A   L   K
                                    Fur →
AAG GCT GGC CTG AAA GTA ACG CTT CCT CGT TTA AAA ATT CTG GAA GTT CTT CAG GAA CCA
 K   A   G   L   K   V   T   L   P   R   L   K   I   L   E   V   L   Q   E   P
GAT AAC CAT CAC GTC AGT GCG GAA GAT TTA TAC AAA CGC CTG ATC GAC ATG GGT GAA GAA
 D   N   H   H   V   S   A   E   D   L   Y   K   R   L   I   D   M   G   E   E
ATC GGT CTG GCA ACC GTA TAC CGT GTG CTG AAC CAG TTT GAC GAT GCC GGT ATC GTG ACC
 I   G   L   A   T   V   Y   R   V   L   N   Q   F   D   D   A   G   I   V   T
CGC CAT AAC TTT GAA GGC GGT AAA TCC GTT TTT GAA CTG ACG CAA CAG CAT CAT CAC GAC
 R   H   N   F   E   G   G   K   S   V   F   E   L   T   Q   Q   H   H   H   D
CAT CTT ATC TGC CTT GAC TGC GGA AAA GTG ATT GAA TTT AGT GAT GAC TCT ATT GAA GCG
 H   L   I   C   L   D   C   G   K   V   I   E   F   S   D   D   S   I   E   A
                primer 2
CGC CAG CGT GAA ATT GCG GCG AAA CAC GGT ATT CGT TTA ACT AAT CAC AGC CTC TAT CTT
 R   Q   R   E   I   A   A   K   H   G   I   R   L   T   N   H   S   L   Y   L
TAC GGC CAC TGC GCT GAA GGC GAC TGC CGC GAA GAC GAG CAC GCG CAC GAT GAC GCG ACT Y
 G   H   C   A   E   G   D   C   R   E   D   E   H   A   H   D   D   A   T
AAA TAA GTG TAA ATC TTT CGA AGA GCC AAC CGC CCG GTT GGC TTT TTT ATA
 K   *
```

FIG. 13A

```
                           primer 1
GAA GCG CAA TGT GAC TGG GAT GAC TTC TTC CCG ACT CTC GAA GAG ATT GAC TTT AAC GGT
 E   A   Q   C   D   W   D   D   F   F   P   T   L   E   E   I   D   F   N   G
AAG CTG GTG GCG CTG TTT GGC TGT GGC GAT CAG GAA GAC TAC GCG GAA TAC TTC TGT GAT
 K   L   V   A   L   F   G   C   G   D   Q   E   D   Y   A   E   Y   F   C   D
GCG CTG GGC ACG ATT CGC GAC ATT ATT GAG CCG CGC GGC GCC ACG ATT GTG GGT CAC TGG
 A   L   G   T   I   R   D   I   I   E   P   R   G   A   T   I   V   G   H   W
CCA ACC GCA GGC TAT CAT TTT GAA GCC TCT AAA GGT CTG GCT GAC GAC GAT CAT TTT GTC
 P   T   A   G   Y   H   F   E   A   S   K   G   L   A   D   D   D   H   F   V
GGC CTG GCG ATT GAC GAA GAC CGT CAG CCT GAA CTG ACC GCC GAG CGT GTT GAA AAA TGG
 G   L   A   I   D   E   D   R   Q   P   E   L   T   A   E   R   V   E   K   W
GTT AAG CAA GTT TCG GCT GAA TTG CAC CTC GGC GAC ATC CTC AAC GCC TAA TCT TAT GCG
 V   K   Q   V   S   A   E   L   H   L   G   D   I   L   N   A   *
GCG CAG CGT TAT ATC TGC GCT GCA GAG ATC TTT TAT TAT TCT ATC CTA GAA TTG TGA TAA
                                                      T4iPIII TT
TAT ATT CAC AAT TCT AGG AGT TGT AAA CTG CTT TTA TTT ATC TAG AGT CAA GCC GTC AAT TGT CTG ATT CGT TAC CAA TTA TGA CAA CTT GAC GGC TAC ATC ATT CAC TTT TTC TTC ACA
ACA GAC TAA GCA ATG GTT AAT ACT GTT GAA CTG CCG ATG TAG TAA GTG AAA AAG AAG TGT
             araC ends *   S   L   K   V   A   V   D   N   V   K   E   E   C
ACC GGC ACG AAA CTC GCT CGG GCT GGC CCC GGT GCA TTT TTT AAA TAC TCG CGA GAA ATA
TGG CCG TGC TTT GAG CGA GCC CGA CCG GGG CCA CGT AAA AAA TTT ATG AGC GCT CTT TAT
 G   A   R   F   E   S   P   S   A   G   T   C   K   K   F   V   R   S   F   Y
GAG TTG ATC GTC AAA ACC AAC ATT GCG ACC GAC GGT GGC GAT AGG CAT CCG GGT AGT GCT
CTC AAC TAG CAG TTT TGG TTG TAA CGC TGG CTG CCA CCG CTA TCC GTA GGC CCA TCA CGA
 L   Q   D   D   F   G   V   N   R   G   V   T   A   I   P   M   R   T   T   S
CAA AAG CAG CTT CGC CTG ACT AAT GCG TTG GTC CTC GCG CCA GCT TAA GAC GCT AAT CCC
GTT TTC GTC GAA GCG GAC TGA TTA CGC AAC CAG GAG CGC GGT CGA ATT CTG CGA TTA GGG
 L   L   L   K   A   Q   S   I   R   Q   D   E   R   W   S   L   V   S   I   G
TAA CTG CTG GCG GAA AAG ATG TGA CAG ACG CGA CGG CGA CAA GCA AAC ATG CTG TGC GAC
ATT GAC GAC GCC CTT TTC TAC ACT GTC TGC GCT GCC GCT GTT CGT TTG TAC GAC ACG CTG
 L   Q   Q   R   F   L   H   S   L   R   S   P   S   L   C   V   H   Q   A   V
GCT GGC GAT ATC AAA ATT GCT GTC TGC CAG GTG ATC GCT GAT GTA CTG ACA AGC CTC GCG
CGA CCG CTA TAG TTT TAA CGA CAG ACG GTC CAC TAG CGA CTA CAT GAC TGT TCG GAG CGC
 S   A   I   D   F   N   S   D   A   L   H   D   S   I   Y   Q   C   A   E   R
TAC CCG ATT ATC CAT CGG TGG ATG GAG CGA CTC GTT AAT CGC TTC CAT GCG CCG CAG TAA
ATG GGC TAA TAG GTA GCC ACC TAC CTC GCT GAG CAA TTA GCG AAG GTA CGC GGC GTC ATT
 V   R   N   D   M   P   P   H   L   S   E   N   I   A   E   M   R   R   L   L
CAA TTG CTC AAG CAG ATT TAT CGC CAG CAG CTC CGA ATA GCG CCC TTC CCC TTG CCC GGC
GTT AAC GAG TTC GTC TAA ATA GCG GTC GTC GAG GCT TAT CGC GGG AAG GGG AAC GGG CCG
 L   Q   E   L   L   N   I   A   L   L   E   S   Y   R   G   E   G   Q   G   A
GTT AAT GAT TTG CCC AAA CAG GTC GCT GAA ATG CGG CTG GTG CGC TTC ATC GGG GCG AAA
CAA TTA CTA AAC GGG TTT GTC CAG CGA CTT TAC GCC GAC CAC GCG AAG TAG CCC CGC TTT
 N   I   I   Q   G   F   L   D   S   F   H   P   Q   H   A   E   D   P   R   F
GAA ACC CGT ATT GGC AAA TAT TGA CCG CCA GTT AAG CCA TTC ATG CCA GTA GGC GCG CGG
CTT TGG GCA TAA CCG TTT ATA ACT GGC GGT CAA TTC GGT AAG TAC GGT CAT CCG CGC GCC
 F   G   T   N   A   F   I   S   P   W   N   L   W   E   H   W   Y   A   R   P
ACG AAA GTA AAC CCA CTG GTG ATA CCA TTC GCG AGC CTC CGG ATG ACG ACC GTA GTG ATG
TGC TTT CAT TTG GGT GAC CAC TAT GGT AAG CGC TCG GAG GCC TAC TGC TGG CAT CAC TAC
 R   F   Y   V   W   Q   H   Y   W   E   R   A   E   P   H   R   G   Y   H   H
AAT CTC TCC TGG CGG GAA CAG CAA AAT ATC ACC GGT CGC GCA GAC AAA TTC TCG TCC CTG
TTA GAG AGG ACC GCC CTT GTC GTT TTA TAG TGG CCA GCG CGT CTG TTT AAG AGC AGG GAC
 I   E   G   P   P   F   L   L   I   D   G   P   R   C   V   F   E   R   G   Q
```

FIG. 13B

```
ATT TTT CAC CAC CCC CTG ACC GCG AAT GGT GAG ATT GAG AAT ATA ACC TTT CAT TCC CAG
TAA AAA GTG GTG GGG GAC TGG CGC TTA CCA CTC TAA CTC TTA TAT GGA AAA GTA AGG GTC
 N   K   V   V   G   Q   G   R   I   T   L   N   L   I   Y   G   K   M   G   L
CGG TCG GTC GAT AAA AAA ATC GAG ATA ACC GTT GGC CTC AAT CGG CGT TAA ACC CGC CAC
GCC AGC CAG CTA TTT TTT TAG CTC TAT TGG CAA CCG GAG TTA GCC GCA ATT TGG GCG GTG
 P   R   D   I   F   F   D   L   Y   G   N   A   E   I   P   T   L   G   A   V
CAG ATG GGC GTT AAA CGA GTA TCC CGG CAG CAG GGG ATC ATT TTG CGC TTC AGC CAT ACT
GTC TAC CCG CAA TTT GCT CAT AGG GCC GTC GTC CCC TAG TAA AAC GCG AAG TCG GTA TGA
 L   H   A   N   F   S   Y   G   P   L   L   P   D   N   Q   A   E   A   M
                                                                          ← araC
TTT CAT ACT CCC ACC ATT CAG AGA AGA AAC CAA TTG TCC ATA TTG CAT CAG ACA TTG CCG
TCA CTG CGT CTT TTA CTG GCT CTT CTC GCT AAC CCA ACC GGT AAC CCC GCT ATT TAA AAG
CAT TCT GTA ACA AAG CGG GAC CAA AGC CAT GAC AAA AAC GCG TAA CAA AAG TGT CTA TAA
TCA CGG CAG AAA AGT CCA CAT TGA TTA TTT GCA CGG CGT CAC ACT TTG CTA TGC CAT AGC
                                            P_BAD    -35                     -10
ATT TTT ATC CAT AAG ATT AGC GGA TCC TAC CTG ACG CTT TTT ATC GCA ACT CTC TAC TGT
                                        AGGA to AAGG            ATG changed to GTG
TTC TCC ATA CCC GTT TTT TTG GGC TAG CCT CGA GAA GGC AGA TTC GCG TGA CT GAC AAC
                                            weaker SD              M   T   D   N
                                                                        fur →
AAT ACC GCA TTA AAG AAG GCT GGC CTG AAA GTA ACG CTT CCT CGT TTA AAA ATT CTG GAA
 N   T   A   L   K   K   A   G   L   K   V   T   L   P   R   L   K   I   L   E
GTT CTT CAG GAA CCA GAT AAC CAT CAC GTC AGT GCG GAA GAT TTA TAC AAA CGC CTG ATC
 V   L   Q   E   P   D   N   H   H   V   S   A   E   D   L   Y   K   R   L   I
GAC ATG GGT GAA GAA ATC GGT CTG GCA ACC GTA TAC CGT GTG CTG AAC CAG TTT GAC GAT
 D   M   G   E   E   I   G   L   A   T   V   Y   R   V   L   N   Q   F   D   D
GCC GGT ATC GTG ACC CGC CAT AAC TTT GAA GGC GGT AAA TCC GTT TTT GAA CTG ACG CAA
 A   G   I   V   T   R   H   N   F   E   G   G   K   S   V   F   E   L   T   Q
                                                    primer 2
CAG CAT CAT CAC GAC CAT CTT ATC TGC CTT GAC TGC GGA AAA GTG ATT GAA TTT AGT GAT
 Q   H   H   H   D   H   L   I   C   L   D   C   G   K   V   I   E   F   S   D
GAC TCT ATT GAA GCG CGC CAG CGT GAA ATT GCG GCG AAA CAC GGT ATT CGT TTA ACT AAT
 D   S   I   E   A   R   Q   R   E   I   A   A   K   H   G   I   R   L   T   N
CAC AGC CTC TAT CTT TAC GGC CAC TGC GCT GAA GGC GAC TGC CGC GAA GAC GAG CAC GCG
 H   S   L   Y   L   Y   G   H   C   A   E   G   D   C   R   E   D   E   H   A
CAC GAT GAC GCG ACT AAA TAA TGA GCT CTC CCG
 H   D   D   A   T   K   *  fur ends
```

FIG. 13C

```
                                                                    primer 1
GCA AGC GTG ATT GGG GTT GAG GGC GTT CCG GCG CTG GTA GAA AAA GGC CGT GAA AAC GCC
ATC CGC AAT GGT TTA CAT AAT GTG ACA TTC TTC CAT GAG AAC CTG GAG GAA GAT GTC ACG
AAG CAG CCG TGG GCG AAA AAC GGC TTT GAC AAA GTC TTA CTC GAT CCT GCG CGT GCG GGG
GCT ACA GGA GTG ATG CGA CAT ATT ATA AAA TTA AAA CCT ATT CGC ATT GTT TAT GTA TCC
TGT AAC CCG GCG ACG CTG GCG CGC GAT AGT GAA GCG CTG GTC AAT GCG GGA TAT GAG GTT
ACG CGT TTA GCG ATG CTC GAC ATG TTC CCG CAC ACA GGA CAT CTG GAA TCA ATG GTT CTG
TTC GAG CGC ATG TAA TGA TTA CCG GCT TAC CGA CTT CGG TAG GCC TGG TCC CTT [AAG GAG
                                                                          relA₁₂
AGG ACG ATG GTC GCG GTA AGA AGT GCA CAT ATT AAT AAA GCT GGT GAA TTT GAT CCG AAG
            M   V   A   V   R   S   A   H   I   N   K   A   G   E   F   D   P   K
            relA →
AAG TGG ATC GCA AGC CTG GGA ATT TCC AGC CAG CAG TCG TGT GAG CGC TTA GCC GAA ACC
 K   W   I   A   S   L   G   I   S   S   Q   Q   S   C   E   R   L   A   E   T
TGG GCG TAT TGC CTG CAA CAG ACA CAA GGA CAT CCG GAT GCG GAT CTG TTG CTG TGG CGT
 W   A   Y   C   L   Q   Q   T   Q   G   H   P   D   A   D   L   L   L   W   R
GGC GTG GAG ATG GTA GAA ATT CTT TCC ACG CTG AGT ATG GAT ATC GAC ACG CTG CGG GCG
 G   V   E   M   V   E   I   L   S   T   L   S   M   D   I   D   T   L   R   A
GCG CTA CTG TTC CCT CTG GCC GAC GCC AAC GTA GTC AGC GAA GAT GTA CTG CGC GAA AGC
 A   L   L   F   P   L   A   D   A   N   V   V   S   E   D   V   L   R   E   S
GTC GGC AAA TCT ATC GTT ACC CTG ATT CAT GGC GTG CGC GAT ATG GCG GCG ATC CGT CAG
 V   G   K   S   I   V   T   L   I   H   G   V   R   D   M   A   A   I   R   Q
CTA AAC GCC ACT CAT AAC GAC TCT GTT TCT TCG GAG CAG GTT GAT AAC GTC CGT CGA ATG
 L   N   A   T   H   N   D   S   V   S   S   E   Q   V   D   N   V   R   R   M
TTA TTG GCG ATG GTG GAT GAT TTC CGC TGC GTG GTG ATC AAA CTG GCC GAG CGA ATC GCT
 L   L   A   M   V   D   D   F   R   C   V   V   I   K   L   A   E   R   I   A
CAT TTG CGC GAA GTG AAA GAG GCG CCG GAA GAT GAG CGC GTG CTG GCG GCG AAA GAA TGT
 H   L   R   E   V   K   E   A   P   E   D   E   R   V   L   A   A   K   E   C
ACC AAC ATC TAT GCG CCG CTC GCC AAT CGT CTG GGC ATC GGG CAA CTG AAG TGG GAA CTG
 T   N   I   Y   A   P   L   A   N   R   L   G   I   G   Q   L   K   W   E   L
GAA GAC TAC TGT TTC CGC TAC CTG CAT CCG GCG GAA TAC AAA CGC ATC GCC AAA CTG CTG
 E   D   Y   C   F   R   Y   L   H   P   A   E   Y   K   R   I   A   K   L   L
CAT GAG CGC CGT CTC GAT CGC GAA CAT TAC ATC GAA GAG TTT GTT GGA CAT CTG CGC GCC
 H   E   R   R   L   D   R   E   H   Y   I   E   E   F   V   G   H   L   R   A
GAA ATG AAA AAC GAA GGC GTG CAG GCG GAG GTC TAC GGA CGA CCA AAA CAT ATT TAT AGC
 E   M   K   N   E   G   V   Q   A   E   V   Y   G   R   P   K   H   I   Y   S
ATC TGG CGC AAA ATG CAG AAA AAG CAT CTG GCG TTT GAT GAA CTC TTT GAC GTG CGC GCC
 I   W   R   K   M   Q   K   K   H   L   A   F   D   E   L   F   D   V   R   A
GTG CGT ATT GTC GCT GAA CGT CTG CAG GAC TGC TAC GCC GCG TTG GGG ATA GTG CAT ACG
 V   R   I   V   A   E   R   L   Q   D   C   Y   A   A   L   G   I   V   H   T
CAC TAT CGT CAC CTG CCG GAT GAA TTC GAT GAT TAT GTC GCT AAC CCG AAA CCG AAC GGT
 H   Y   R   H   L   P   D   E   F   D   D   Y   V   A   N   P   K   P   N   G
TAC CAG TCT ATC CAC ACC GTG GTC CTG GGA CCG GGC GGT AAA ACC GTT GAG ATC CAG ATC
 Y   Q   S   I   H   T   V   V   L   G   P   G   G   K   T   V   E   I   Q   I
CGT ACC AAA CAG ATG CAT GAA GAC GCC GAA CTG GGC GTG GCG GCA CAC TGG AAG TAT AAA
 R   T   K   Q   M   H   E   D   A   E   L   G   V   A   A   H   W   K   Y   K
GAA GGC GCC GCG TCC GGC GGC GTG CGC TCC GGT CAT GAA GAC AGA ATT GCG TGG CTG CGT
 E   G   A   A   S   G   G   V   R   S   G   H   E   D   R   I   A   W   L   R
AAG CTG ATC GCC TGG CAG GAA GAG ATG GCC GAT TCC GGC GAA ATG CTG GAT GAA GTG CGC
 K   L   I   A   W   Q   E   E   M   A   D   S   G   E   M   L   D   E   V   R
AGC CAG GTG TTT GAC GAT CGG GTC TAC GTT TTT ACG CCA AAA GGC GAC GTG GTT GAC TTG
 S   Q   V   F   D   D   R   V   Y   V   F   T   P   K   G   D   V   V   D   L
CCT GCC GGA TCT ACG CCG CTC GAT TTT TAC CAC ATC CAC AGC GAT GTT GGG CAC CGC
 P   A   G   S   T   P   L   D   F   A   Y   H   I   H   S   D   V   G   H   R
TGC ATT GGC GCT AAA ATC GGC GGC CGT ATT GTG CCA TTC ACC TAT CAG TTG CAG ATG GGT
 C   I   G   A   K   I   G   G   R   I   V   P   F   T   Y   Q   L   Q   M   G
```

FIG. 14A

```
GAT CAA ATT GAA ATT ATC ACT CAG AAG CAG CCG AAT CCC AGC CGC GAC TGG CTG AAT CCA
 D   Q   I   E   I   I   T   Q   K   Q   P   N   P   S   R   D   W   L   N   P
AAC CTG GGC TAT GTG ACG ACC AGC CGC GGA CGC TCG AAA ATT CAC GCC TGG TTC CGC AAG
 N   L   G   Y   V   T   T   S   R   G   R   S   K   I   H   A   W   F   R   K
CAG GAT CGT GAC AAA AAT ATC CAG GCT GGA CGG CAG ATC CTC GAC GAT GAG CTG GCG CAT
 Q   D   R   D   K   N   I   Q   A   G   R   Q   I   L   D   D   E   L   A   H
TTG GGG ATT AGC CTG AAA GAG GCC GAA AAA CAT CTG CTG CCG CGC TAC AAC TTT AAT GAG
 L   G   I   S   L   K   E   A   E   K   H   L   L   P   R   Y   N   F   N   E
CTG GAA GAG TTG CTG GCG GCG ATA GGC GGC GGC GAT ATC CGT CTT AAT CAG ATG GTG AAT
 L   E   E   L   L   A   A   I   G   G   G   D   I   R   L   N   Q   M   V   N
TTC CTG CAA TCA CAG TTC AAT AAG CCG AGT GCA GAG GAG CAG GAT GCA GCG GCG CTG AAA
 F   L   Q   S   Q   F   N   K   P   S   A   E   E   Q   D   A   A   A   L   K
CAG CTT CAG CAA AAA ACA TAC GCG CCG CAA AAT CGT CGT AAA GAC GAC GGG CGC GTG GTG
 Q   L   Q   Q   K   T   Y   A   P   Q   N   R   R   K   D   D   G   R   V   V
GTA GAA GGC GTG GGT AAT TTG ATG CAC CAC ATC GCC CGC TGC TGC CAG CCG ATT CCG GGG
 V   E   G   V   G   N   L   M   H   H   I   A   R   C   C   Q   P   I   P   G
GAT GAA ATT GTC GGC TTC ATT ACT CAA GGG CGA GGG ATT TCC GTG CAC CGG GCC GAC TGC
 D   E   I   V   G   F   I   T   Q   G   R   G   I   S   V   H   R   A   D   C
GAA CAG CTG GCG GAA CTG CGC TCC CAT GCG CCG GAG CGG ATC GTA GAG GCG GTA TGG GGC
 E   Q   L   A   E   L   R   S   H   A   P   E   R   I   V   E   A   V   W   G
GAG AGC TAC TCG GCG GGA TAT TCG CTG GTG GTG CGC GTC CAG GCC AAC GAT CGC AGC GGC
 E   S   Y   S   A   G   Y   S   L   V   V   R   V   Q   A   N   D   R   S   G
TTG CTA CGC GAT ATC ACC ACC ATT CTG GCT AAC GAA AAA GTC AAC GTG CTG GGC GTC GCC
 L   L   R   D   I   T   T   I   L   A   N   E   K   V   N   V   L   G   V   A
AGC CGC AGC GAC ATT AAA CAG CAG ATC GCC ACC ATT GAT ATG ACC ATC GAG ATC TAC AAC
 S   R   S   D   I   K   Q   Q   I   A   T   I   D   M   T   I   E   I   Y   N
CTG CAG GTG CTG GGC CGG GTG CTC GGT AAG CTG AAC CAG GTG CCG GAT GTG ATT GAT GCA
 L   Q   V   L   G   R   V   L   G   K   L   N   Q   V   P   D   V   I   D   A
CGG CGA CTG CAC GGG GGG TAA] ACC CCA GAC AGT AAT CAT GTA GCG GCT TTG CTA CTC GTT
 R   R   L   H   G   G    *  ΔrelA₂₂₃₅/₂₂₃₅

CAG CAA AGC CGC ATT AGC AAC CCC ATA AGC ATG AGA TAT GGG GTA TGT TTT TGA CGT ACA
TTT CAT TTC CGG TGT ACT CTT ATG TAA GAT TTA TAC TTA CAG TGG AGG CTG TTA TGG CCA
GAA CAA TGA CCG TTG ATC TTG GCG ATG AAC TGC CGC AGT TTA TTG AAT CGC TCA TAG AAT
CAG GTG ATT ACA GAA CAC AAA GTG AAG TGA TCA GAG AGT CTC TTC GTC TGC TGA GGG AAA
AAC AGG CCG AGT CAC GAC TTC AGG CGT TAC GTG AAC TTC TGG CTG AAG GTC TGA ACA GCG
GAG AGC CGC AGG CCT GGG AAA GGG ATG CCT TTT ACG GAA GGT CAA ACA GGA TGA TCA
AAC CCG ATG AGA ATG GTA AAA TTA ACG CCA AAG GCC AGT GAA GAT CTG AAA AT ATC TGG
                                           ─────────────────────────────────
                                                                    primer 2
CAT TAC GGC TGG CAG CAT TTT GGC GAA ATA CAG GCC GAT CGA TAT ATT AAT CAT CTA TCA
```

FIG. 14B

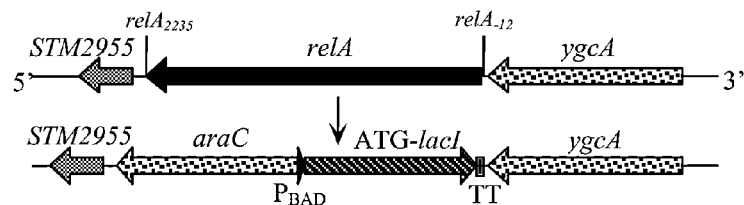

FIG. 14C

```
                              primer 1
GAG CTC GAG GGC GTT CCG GCG CTG GTA GAA AAA GGC CGT GAA AAC GCC ATC CGC AAT GGT
TTA CAT AAT GTG ACA TTC TTC CAT GAG AAC CTG GAG GAA GAT GTC ACG AAG CAG CCG TGG
GCG AAA AAC GGC TTT GAC AAA GTC TTA CTC GAT CCT GCG CGT GCG GGG GCT ACA GGA GTG
ATG CGA CAT ATT ATA AAA TTA AAA CCT ATT CGC ATT GTT TAT GTA TCC TGT AAC CCG ACG
ACG CTG GCG CGC GAT AGT GAA GCG CTG GTC AAT GCG GGA TAT GAG GTT ACG CGT TTA GCG
ATG CTC GAC ATG TTC CCG CAC ACA GGA CAT CTG GAA TCA ATG GTT CTG TTC GAG CGC ATG
TAA TGA TTA CCG GCT TAC CGA CTT CGG TAG GCC TGG TCC CTT AGA TCT TTT ATT ATT CTA
TCC TAG AAT TGT GAT AAT ATA TTC ACA ATT CTA GGA GTT GTA AAC TGC TTT TAT TTA TCT
                              T4iPIII TT sequence
       ↓ lacI ends          T          T              original   sequence
AGA TCA CTG CCC GCT TTC CAG ACG GGA AAC CTG ACG TGC CAG CTG CAT TAA TGA ATC GGC
TCT AGT GAC GGG CGA AAG GTC TGC CCT TTG GAC TGC ACG GTC GAC GTA ATT ACT AGC CG
 S   *   Q   G   S   E   L   R   S   V   Q   R   A   L   Q   M   L   S   D   A
                                                                          TCT
CAA CGC GCG CGG AGA GGC GGT TTG CGT ATT CGG CGC CAG GGT GGT TTT ACG TTT CAC CAG
GTT GCG CGC GCC TCT CCG CCA AAC GCA TAA GCC GCG GTC CCA CCA AAA TGC AAA GTG GTC
 L   A   R   P   S   A   T   Q   T   N   P   A   L   T   T   K   R   K   V   L
TGA GAC CGG CAA CAG CTG ATT GCC CTT CAC CGC CTG GCC CTG AGA GAG TTG CAG CAA GCG
ACT CTG GCC GTT GTC GAC TAA CGG GAA GTG GCG GAC CGG GAC TCT CTC AAC GTC GTT CGC
 S   V   P   L   L   Q   N   G   K   V   A   Q   G   Q   S   L   Q   L   L   R
GTC CAC GCT GGT TTG CCC CAG CAG GCG AAA ATC CTG TTT GAT GGT GGT TAA CGG CGG GAT
CAG GTG CGA CCA AAC GGG GTC GTC CGC TTT TAG GAC AAA CTA CCA CCA ATT GCC GCC CTA
 D   V   S   T   Q   G   L   L   R   F   D   Q   K   I   T   T   L   P   P   I
                                                T
ATA ACA TGA GCT GTC TTC GGT ATC GTC GTA ACC CAC TAC CGA GAT ATC CGC ACC AAC GCG
TAT TGT ACT CGA CAG AAG CCA TAG CAG CAT TGG GTG ATG GCT CTA TAG GCG TGG TTG CGC
 Y   C   S   S   D   E   T   D   D   Y   G   V   V   S   I   D   A   G   V   R
CAG CCC GGA CTC GGT AAT GGC GCG CAT TGC GCC CAG CGC CAT CTG ATC GTT GGC AAC CAG
GTC GGG CCT GAG CCA TTA CCG CGC GTA ACG CGG GTC GCG GTA GAC TAG CAA CCG TTG GTC
 L   G   S   E   T   I   A   R   M   A   G   L   A   M   Q   D   N   A   V   L
CAT CGC AGT CGG AAC GAT GCC CTC ATT CAG CAT TTG CAT GGT TTG TTG AAA ACC GGA CAT
GTA GCG TCA GCC TTG CTA CGG GAG TAA GTC GTA AAC GTA CCA AAC AAC TTT GGC CCT GTA
 M   A   T   P   V   I   G   E   N   L   M   Q   M   T   Q   Q   F   G   S   M
                              C                T
GGC ACT CCA GTC GCC TTC ACG TTC CGC GAT CGG CTG AAT TTG ATT GCG AGT GAG ATA TTT
CCG TGA GGT CAG CGG AAG TGC AAG GCG CTA GCC GAC TTA AAC TAA CGC TCA CTC TAT AAA
 A   S   W   D   G   E   R   E   A   I   P   Q   I   Q   N   R   T   L   Y   K
ATG CCA GCC AGC AGC ACG CAG ACG CGC CGA GAC AGA ACT TAA TGG GCC CGC TAA CAG CGC
TAC GGT CGG TCG TCG TGC GTC TGC GCG GCT CTG TCT TGA ATT ACC GGG CGA TTG TCG CG
 H   W   G   A   L   R   L   R   A   S   V   S   S   L   P   G   A   L   L   A
                                                                        T
GAT TTG CTG GTG ACC CAA TGC GAC CAG ATG CTC CAC GCC CAG ACG CGT ACC GTC TTC ATG
CTA AAC GAC CAC TGG GTT ACG CTG GTC TAC GAG GTG CGG GTC TGC GCA TGG CAG AAG TAC
 I   Q   Q   H   G   L   A   V   L   H   E   V   G   L   R   T   G   D   E   H
                                 G
GGA GAA AAT AAT ACT GTT GAT CGG TGT CTG GTC AGA GAC ATC AAG AAA TAA CGC CGG AAC
CCT CTT TTA TTA TGA CAA CTA GCC ACA GAC CAG TCT CTG TAG TTC TTT ATT GCG GCC TTG
 S   F   I   I   S   N   I   P   T   Q   D   S   V   D   L   F   L   A   P   V
ATT AGT GCA GGC AGC TTC CAC AGC AAT GGC ATC CTG GTC ATC AGC GGA TAG TTA ATG AT
TAA TCA CGT CCG TCG AAG GTG TCG TTA CCG TAG GAC CAG TAG GTC GCC TAT CAA TTA CTA
 N   T   C   A   A   E   V   A   I   A   D   Q   D   D   L   P   Y   N   I   I
CAG CCC ACT GAC GCG TTG CGC GAG AAG ATT GTG CAC CGC CGC TTT ACA AGC TTC GAC GCC
GTC GGG TGA CTG CGC AAC GCG CTC TTC TAA CAC GTG GCG GCG AAA TGT TCG AAG CTG CGG
 L   G   S   V   R   Q   A   L   L   N   H   V   A   A   K   C   A   E   V   G
   T
GCT ACG TTC TAC CAT CGA CAC CAC CAC GCT GGC ACC CAG TTG ATC GGC GCG AGA TTT AAT
CGA TGC AAG ATG GTA GCT GTG GTG GTG CGA CCG TGG GTC AAC TAG CCG CGC TCT AAA TTA
 S   R   E   V   M   S   V   V   V   S   A   G   L   Q   D   A   R   S   K   I
CGC CGC GAC AAT TTG CGA CGG CGC GTG CAG GGC CAG ACT GGA GGT GGC AAC GCC AAT CAG
GCG GCG CTG TTA AAC GCT GCC GCG CAC GTC CCG GTC TGA CCT CCA CCG TTG CGG TTA GTC
 A   A   V   I   Q   S   P   A   H   L   A   L   S   S   T   A   V   G   I   L
```

FIG. 14D

```
CAA CGA CTG TTT GCC CGC CAG TTG TTG TGC CAC GCG GTT CGG AAT GTA ATT CAG CTC CGC
GTT GCT GAC AAA CGG GCG GTC AAC AAC ACG GTG CGC CAA GCC TTA CAT TAA GTC GAG GCG
 L   S   Q   K   G   A   L   Q   Q   A   V   R   N   P   I   Y   N   L   E   A
                                                C
CAT CGC CGC TTC CAC TTT TTC ACG CGT TTT CGC AGA AAC GTG GCT GGC CTG GTT CAC CAC
GTA GCG GCG AAG GTG AAA AAG TGC GCA AAA GCG TCT TTG CAC CGA CCG GAC CAA GTG GTG
 M   A   A   E   V   K   E   R   T   K   A   S   V   H   S   A   Q   N   V   V
GCG GGA AAC GGT CTG ATA AGA GAC ACC GGC ATA CTC TGC GAC ATC GTA TAA CGT TAC TGG
CGC CCT TTG CCA GAC TAT TCT CTG TGG CCG TAT GAG ACG CTG TAG CAT ATT GCA ATG ACC
 R   S   V   T   Q   Y   S   V   G   A   Y   E   A   V   D   Y   L   T   V   P
                                         primer 4                    primer 3
TTT CAT ATT CAC CAT CCT CTC GAG GCT AGC CCA AAA AAA CGG GTA TGG AGA AAC AGT AGA
AAA GTA TAA GTG GTA GGA GAG CTC CGA TCG GGT TTT TTT GCC CAT ACC TCT TTG TCA TCT
 K   M                SD                                              P_BAD -10
   ← lacI        P_BAD -35
GAG TTG CGA TAA AAA GCG TCA GGT AGG ATC CGC TAA TCT TAT GGA TAA AAA TGC TAT GGC
ATA GCA AAG TGT GAC GCC GTG CAA ATA ATC AAT GTG GAC TTT TCT GCC GTG ATT ATA GAC
ACT TTT GTT ACG CGT TTT TGT CAT GGC TTT GGT CCC GCT TTG TTA CAG AAT GCT TTT AAT
AAG CGG GGT TAC CGG TTG GGT TAG CGA GAA GAG CCA GTA AAA GAC GCA GTG ACG GCA ATG
TCT GAT GCA ATA TGG ACA ATT GGT TTC TTC TCT GAA TGG TGG GAG TAT GAA AAG T
araC →
ATG GCT GAA GCG CAA AAT GAT CCC CTG CTG CCG GGA TAC TCG TTT AAC GCC CAT CTG GTG
 M   A   E   A   Q   N   D   P   L   L   P   G   Y   S   F   N   A   H   L   V
GCG GGT TTA ACG CCG ATT GAG GCC AAC GGT TAT CTC GAT TTT TTT ATC GAC CGA CCG CTG
 A   G   L   T   P   I   E   A   N   G   Y   L   D   F   F   I   D   R   P   L
GGA ATG AAA GGT TAT ATT CTC AAT CTC ACC ATT CGC GGT CAG GGG GTG GTG AAA AAT CAG
 G   M   K   G   Y   I   L   N   L   T   I   R   G   Q   G   V   V   K   N   Q
GGA CGA GAA TTT GTC TGC CGA CCG GGT GAT ATT TTG CTG TTC CCG CCA GGA GAG ATT CAT
 G   R   E   F   V   C   R   P   G   D   I   L   L   F   P   P   G   E   I   H
CAC TAC GGT CGT CAT CCG GAG GCT CGC GAA TGG TAT CAC CAG TGG GTT TAC TTT CGT CCG
 H   Y   G   R   H   P   E   A   R   E   W   Y   H   Q   W   V   Y   F   R   P
CGC GCC TAC TGG CAT GAA TGG CTT AAC TGG CCG TCA ATA TTT GCC AAT ACG GGT TTC TTT
 R   A   Y   W   H   E   W   L   N   W   P   S   I   F   A   N   T   G   F   F
CGC CCG GAT GAA GCG CAC CAG CCG CAT TTC AGC GAC CTG TTT GGG CAA ATC ATT AAC GCC
 R   P   D   E   A   H   Q   P   H   F   S   D   L   F   G   Q   I   I   N   A
GGG CAA GGG GAA GGG CGC TAT TCG GAG CTG CTG GCG ATA AAT CTG CTT GAG CAA TTG TTA
 G   Q   G   E   G   R   Y   S   E   L   L   A   I   N   L   L   E   Q   L   L
CTG CGG CGC ATG GAA GCG ATT AAC GAG TCG CTC CAT CCA CCG ATG GAT AAT CGG GTA CGC
 L   R   R   M   E   A   I   N   E   S   L   H   P   P   M   D   N   R   V   R
GAG GCT TGT CAG TAC ATC AGC GAT CAC CTG GCA GAC AGC AAT TTT GAT ATC GCC AGC GTC
 E   A   C   Q   Y   I   S   D   H   L   A   D   S   N   F   D   I   A   S   V
GCA CAG CAT GTT TGC TTG TCG CCG TCG CGT CTG TCA CAT CTT TTC CGC CAG CAG TTA GGG
 A   Q   H   V   C   L   S   P   S   R   L   S   H   L   F   R   Q   Q   L   G
ATT AGC GTC TTA AGC TGG CGC GAG GAC CAA CGC ATT AGT CAG GCG AAG CTG CTT TTG AGC
 I   S   V   L   S   W   R   E   D   Q   R   I   S   Q   A   K   L   L   L   S
ACT ACC CGG ATG CCT ATC GCC ACC GTC GGT CGC AAT GTT GGT TTT GAC GAT CAA CTC TAT
 T   T   R   M   P   I   A   T   V   G   R   N   V   G   F   D   D   Q   L   Y
TTC TCG CGA GTA TTT AAA AAA TGC ACC GGG GCC AGC CCG AGC GAG TTT CGT GCC GGT TGT
 F   S   R   V   F   K   K   C   T   G   A   S   P   S   E   F   R   A   G   C
GAA GAA AAA GTG AAT GAT GTA GCC GTC AAG TTG TCA TAA TTG GTA ACG AAT CAG ACA ATT
 E   E   K   V   N   D   V   A   V   K   L   S   *
                                         araC ends ↑
GAC GGC TTG ACT CGG AAT TCA CCC CAG ACA GTA ATC ATG TAG CGG CTT TGC TAC TCG TTC
AGC AAA GCC GCA TTA GCA ACC CCA TAA GCA TGA GAT ATG GGG TAT GTT TTT GAC GTA CAT
TTC ATT TCC GGT GTA CTC TTA TGT AAG ATT TAT ACT TAC AGT GGA GGC TGT TAT GGC CAG
AAC AAT GAC CGT TGA TCT TGG CGA TGA ACT GCG CGA GTT TAT TGA TCT CAT AGA ATC
AGG TGA TTA CAG AAC ACA AAG TGA AGT GAT CAG AGA GTC TCT TCG TCT GCT GAG GGA AAA
ACA GGC CGA GTC ACG ACT TCA GGC GTT ACG TGA ACT TCT GGC TGA GGT CTG AAA CAG CGG
AGA GCC GCA GGC CTG GGA AAA GGA TGC CTT TTT ACG AAG GTC AAA ACA GGG ATG ATC AA
ACC CGA TGA GAA TGG TAA AAT TAA CGC CAA AGG CCA GTG AAG ATC TGG AAA ATA TCT GGG
GTA CC                                               primer 2
```

FIG. 14E

```
   1    GGATCTTCCG GAAGACCTTC CATTCTGAAA TGAGCTGTTG ACAATTAATC ATCCGGCTCG
  61    TATAATGTGT GGAATTGTGA GCGGATAACA ATTTCACACA GGAAACAGAC CATGAGTATT
 121    CAACATTTCC GTGTCGCCCT TATTCCCTTT TTTGCGGCAT TTTGCCTTCC TGTTTTTGCT
 181    CACCCAGAAA CGCTGGTGAA AGTAAAAGAT GCTGAAGAAT TCGCAATTCC CGGGGATCCG
 241    TCGACCTGCA GCCAAGCTCC CAAGCTTGGC TGTTTTGGCG GATGAGAGAA GATTTTCAGC
 301    CTGATACAGA TTAAATCAGA ACGCAGAAGC GGTCTGATAA AACAGAATTT GCCTGGCGGC
 361    AGTAGCGCGG TGGTCCCACC TGACCCCATG CCGAACTCAG AAGTGAAACG CCGTAGCGCC
 421    GATGGTAGTG TGGGGTCTCC CCATGCGAGA GTAGGGAACT GCCAGGCATC AAATAAAACG
 481    AAAGGCTCAG TCGAAAGACT GGGCCTTTCG TTTTATCTGT TGTTTGTCGG TGAACGCTCT
 541    CCTGAGTAGG ACAAATCCGC CGGGAGCGGA TTTGAACGTT GCGAAGCAAC GGCCCGGAGG
 601    GTGGCGGGCA GGACGCCCGC CATAAACTGC CAGGCATCAA ATTAAGCAGA AGGCCATCCT
 661    GACGGATGGC CTTTTTGCGT TTCTACAAAC TCTTTTGTTT ATTTTTCTAA ATACATTCAA
 721    ATATGTATCC GCTCATGAGA CAATAACCCT GATAAATGCT TCAATAATGG AAGATCTTCC
 781    AACATCACAG GTAAACAGAA ACGTCGGGTC GATCGGGAAA TTCTTTCCCG GACGGCGCGG
 841    GGTTGGGCAA GCCGCAGGCG CGTCAGTGCT TTTAGCGGGT GTCGGGCGC AGCCATGACC
 901    CAGTCACGTA GCGATAGCGG AGTGTATACT GGCTTAACTA TGCGGCATCA GAGCAGATTG
 961    TACTGAGAGT GCACCATATG CGGTGTGAAA TACCGCACAG ATGCGTAAGG AGAAAATACC
1021    GCATCAGGCG CTCTTCCGCT TCCTCGCTCA CTGACTCGCT GCGCTCGGTC GTTCGGCTGC
1081    GGCGAGCGGT ATCAGCTCAC TCAAAGGCGG TAATACGGTT ATCCACAGAA TCAGGGGATA
1141    ACGCAGGAAA GAACATGTGA GCAAAAGGCC AGCAAAACCGT CAGGAACCGT AAAAAGGCCG
1201    CGTTGCTGGC GTTTTTCCAT AGGCTCCGCC CCCCTGACGA GCATCACAAA AATCGACGCT
1261    CAAGTCAGAG GTGGCGAAAC CCGACAGGAC TATAAAGATA CCAGGCGTTT CCCCCTGGAA
1321    GCTCCCTCGT GCGCTCTCCT GTTCCGACCC TGCCGCTTAC CGGATACCTG TCCGCCTTTC
1381    TCCCTTCGGG AAGCGTGGCG CTTTCTCATA GCTCACGCTG TAGGTATCTC AGTTCGGTGT
1441    AGGTCGTTCG CTCCAAGCTG GGCTGTGTGC ACGAACCCCC CGTTCAGCCC GACCGCTGCG
1501    CCTTATCCGG TAACTATCGT CTTGAGTCCA ACCCGGTAAG ACACGACTTA TCGCCACTGG
1561    CAGCAGCCAC TGGTAACAGG ATTAGCAGAG CGAGGTATGT AGGCGGTGCT ACAGAGTTCT
1621    TGAAGTGGTG GCCTAACTAC GGCTACACTA GAAGGACAGT ATTTGGTATC TGCGCTCTGC
1681    TGAAGCCAGT TACCTTCGGA AAAAGAGTTG GTAGCTCTTG ATCCGGCAAA CAAACCACCG
1741    CTGGTAGCGG TGGTTTTTTT GTTTGCAAGC AGCAGATTAC GCGCAGAAAA AAAGGATCTC
1801    AAGAAGATCC TTTGATCTTT TCTACGGGGT CTGACGCTCA GTGGAACGAA AACTCACGTT
1861    AAGGGATTTT GGTCATGAGA TTATCAAAAA GGATCTTCAC CTAGATCCTT TTAAATTAAA
1921    AATGAAGTTT TAAATCAATC TAAAGTATAT ATGAGTAAAC TTGGTCTGAC AGTCTAGACT
1981    AGGCCAACTG GCGCAGCATT CGACGCAGCG GCTCGGCGGC GCCCCATAAC AACTGGTCGC
2041    CTACGGTAAA CGCCGACAAG AACTCTGGCC CCATGTTCAG CTTACGCAGA CGACCAACCG
2101    GCGTAGTCAA CGTGCCGGTC ACCGCCGCCG GGGTTAATTC GCGCATAGTG ATATCACGAT
2161    CGTTCGGCAC CACTTTCGCC CACGGATTAT GTGCCGCCAA CAGTTCTTCC ACCGTCGGAA
2221    TGGATACCTC TTTTTTCAGC TTGATGGTGA ACGCCTGGCT GTGACAGCGC AGCGCGCCGA
2281    CGCGCACACA CAAACCATCA ACCGGAATCA CAGAGGCAGT ATTGAGAATC TTGTTGGTTT
2341    CCGCCTGGCC TTTCCACTCT TCGCGGCTCT GGCCGTTATC GAGCTGTTTG TCGATCCAGG
2401    GGATCAGGCT TCCCGCCAGC GGTACGCCAA AGTTATCAAC CGGCAGCTCG CCGCTGCGGG
2461    TCAATGCCGT AACTTTGCGT TCAATATCAA GAATTGCGGA AGACGGCGTC GCCAGTTCAT
2521    CGGCGACATG GCCATACAAC TGACCCATCT GGGTTAACAG CTCGCGCATA TGGCGCGCGC
2581    CGCCGCCGGA GGCGGCCTGA TAGGTCGCGA CGGATACCCA GTCAACGAGA TTATGGGCAA
2641    AGAGACCGCC CAGCGACATC AACATCAGGC TAACGGTACA GTTACCGCCC ACAAAGGTCT
2701    TCACGCCATT GTTCAGGCCG TCGGTAATCA CGTCCTGGTT GACCGGGTCG AGAATAATAA
2761    TGGCATCATC TTTCATGCGC AGCGTAGAAG CCGCATCAAT CCAGTAACCC TGCCATCCGC
2821    TTTCGCGCAG CTTTGGATAA ATTTCGTTGG TATAATCGCC GCCCTGGCAG GTCACGATGA
2881    TATCGAGCGC TTTTAGCGCA TCCAGATCAA AAGCGTCCTG TAGCGTGCCG GTGGAGGTGT
2941    CGCCGAAGGT GGGCGCCGCC TGTCCAAACT GGGAGGTAGA AAAGAAAACA GGGCGAATAG
3001    CGTCGAAATC GCGCTCCTCT ACCATGCGTT GCATGAGAAC AGAGCCGACC ATTCCGCGCC
3061    AGCCGATAAA ACCAACATTT TTCATAGCGT TTTTTTCCTG CAAAGAGATG TGC
```

FIG. 15B

```
   1   GGATCTTCCG GAAGACCTTC CATTCTGAAA TGAGCTGTTG ACAATTAATC ATCCGGCTCG
  61   TATAATGTGT GGAATTGTGA GCGGATAACA ATTTCACACA GGAAACAGAC CATGAGTATT
 121   CAACATTTCC GTGTCGCCCT TATTCCCTTT TTTGCGGCAT TTTGCCTTCC TGTTTTTGCT
 181   CACCCAGAAA CGCTGGTGAA AGTAAAAGAT GCTGAAGAAT TCTCTCCGGT AGCCAGTCAG
 241   TCTAAAGCTG AGAAAGACTA TGATGCAGCG AAGAAAGATG CTAAGAATGC TAAAAAAGCA
 301   GTAGAAGATG CTCAAAAGGC TTTAGATGAT GCAAAGCTG CTCAGAAAAA ATATGACGAG
 361   GATCAGAAGA AAACTGAGGA GAAAGCCGCG CTGGAAAAAG CAGCGTCTGA AGAGATGGAT
 421   AAGGCAGTGG CAGCAGTTCA ACAAGCGTAT CTGGCCTATC AACAAGCTAC AGACAAAGCC
 481   GCAAAAGACG CAGCAGATAA GATGATCGAT GAAGCTAAGA ACGCGAAGA AGAGGCAAAA
 541   ACTAAATTTA ATACTGTTCG TGCAATGGTA GTTCCTGAGC CAGAGCAGTT GGCGGAGACT
 601   AAGAAAAAAT CAGAAGAAGC TAAACAAAAA GCACCAGAAC TTACTAAAAA ACTGGAAGAA
 661   GCTAAAGCAA AATTAGAAGA GGCTGAGAAA AAAGCTACTG AAGCCAAACA AAAAGTGGAT
 721   GCTGAAGAAG TCGCTCCTCA AGCTAAAATC GCTGAATTGG AAAATCAAGT TCATCGTCTG
 781   GAACAAGAGC TCAAAGAGAT TGATGAGTCT GAATCAGAAG ATTATGCTAA AGAAGGTTTC
 841   CGTGCTCCTC TTCAATCTAA ATTGGATGCC AAAAAAGCTA AACTGTCAAA ACTTGAAGAG
 901   TTAAGTGATA AGATTGATGA GTTAGACGCT GAAATTGCAA AACTTGAAGA TCAACTTAAA
 961   GCTGCTGAAG AAAACAATAA TGTAGAAGAC TACTTTAAAG AAGGTTTAGA GAAAACTATT
1021   GCTGCTAAAA AAGCTGAATT AGAAAAAACT GAAGCTGACC TTAAGAAAGC ATAATAAGCT
1081   TGGCTGTTTT GGCGGATGAG AGAAGATTTT CAGCCTGATA CAGATTAAAT CAGAACGCAG
1141   AAGCGGTCTG ATAAAACAGA ATTTGCCTGG CGGCAGTAGC GCGGTGGTCC CACCTGACCC
1201   CATGCCGAAC TCAGAAGTGA AACGCCGTAG CGCCGATGGT AGTGTGGGGT CTCCCCATGC
1261   GAGAGTAGGG AACTGCCAGG CATCAAATAA AACGAAAGGC TCAGTCGAAA GACTGGGCCT
1321   TTCGTTTTAT CTGTTGTTTG TCGGTGAACG CTCTCCTGAG TAGGACAAAT CCGCCGGGAG
1381   CGGATTTGAA CGTTGCGAAG CAACGGCCCG GAGGGTGGCG GGCAGGACGC CCGCCATAAA
1441   CTGCCAGGCA TCAAATTAAG CAGAAGGCCA TCCTGACGGA TGGCCTTTTT GCGTTTCTAC
1501   AAACTCTTTT GTTTATTTTT CTAAATACAT TCAAATATGT ATCCGCTCAT GAGACAATAA
1561   CCCTGATAAA TGCTTCAATA ATGGAAGATC TTCCAACATC ACAGGTAAAC AGAAACGTCG
1621   GGTCGATCGG GAAATTCTTT CCCGGACGGC GCGGGGTTGG GCAAGCCGCA GGCGCGTCAG
1681   TGCTTTTAGC GGGTGTCGGG GCGCAGCCAT GACCCAGTCA CGTAGCGATA GCGGAGTGTA
1741   TACTGGCTTA ACTATGCGGC ATCAGAGCAG ATTGTACTGA GAGTGCACCA TATGCGGTGT
1801   GAAATACCGC ACAGATGCGT AAGGAGAAAA TACCGCATCA GGCGCTCTTC CGCTTCCTCG
1861   CTCACTGACT CGCTGCGCTC GGTCGTTCGG CTGCGGCGAG CGGTATCAGC TCACTCAAAG
1921   GCGGTAATAC GGTTATCCAC AGAATCAGGG GATAACGCAG GAAAGAACAT GTGAGCAAAA
1981   GGCCAGCAAA AGGCCAGGAA CCGTAAAAAG GCCGCGTTGC TGGCGTTTTT CCATAGGCTC
2041   CGCCCCCCTG ACGAGCATCA CAAAAATCGA CGCTCAAGTC AGAGGTGGCG AAACCCGACA
2101   GGACTATAAA GATACCAGGC GTTTCCCCCT GGAAGCTCCC TCGTGCGCTC TCCTGTTCCG
2161   ACCCTGCCGC TTACCGGATA CCTGTCCGCC TTTCTCCCTT CGGGAAGCGT GGCGCTTTCT
2221   CATAGCTCAC GCTGTAGGTA TCTCAGTTCG GTGTAGGTCG TTCGCTCCAA GCTGGGCTGT
2281   GTGCACGAAC CCCCCGTTCA GCCCGACCGC TGCGCCTTAT CCGGTAACTA TCGTCTTGAG
2341   TCCAACCCGG TAAGACACGA CTTATCGCCA CTGGCAGCAG CCACTGGTAA CAGGATTAGC
2401   AGAGCGAGGT ATGTAGGCGG TGCTACAGAG TTCTTGAAGT GGTGGCCTAA CTACGGCTAC
2461   ACTAGAAGGA CAGTATTTGG TATCTGCGCT CTGCTGAAGC CAGTTACCTT CGGAAAAAGA
2521   GTTGGTAGCT CTTGATCCGG CAAACAAACC ACCGCTGGTA GCGGTGGTTT TTTTGTTTGC
2581   AAGCAGCAGA TTACGCGCAG AAAAAAAGGA TCTCAAGAAG ATCCTTTGAT CTTTTCTACG
2641   GGGTCTGACG CTCAGTGGAA CGAAAACTCA CGTTAAGGGA TTTTGGTCAT GAGATTATCA
2701   AAAAGGATCT TCACCTAGAT CCTTTTAAAT TAAAAATGAA GTTTTAAATC AATCTAAAGT
2761   ATATATGAGT AAACTTGGTC TGACAGTCTA GACTAGGCCA ACTGGCGCAG CATTCGACGC
2821   AGCGGCTCAG CGGCGCCCCA TAACACTGG TCGCCTACGG TAAACGCCGA CAAGAACTCT
2881   GGCCCCATGT TCAGCTTACG CAGACGACCA ACCGCGTAG TCAACGTGCC GGTCACCGCC
2941   GCCGGGGTTA ATTCGCGCAT AGTGATATCA CGATCGTTCG GCACCACTTT CGCCCACGGA
3001   TTATGTGCCG CCAGCAGTTC TTCCACCGTC GGAATGGATA CCTCTTTTTT CAGCTTGATG
3061   GTGAACGCCT GGCTGTGACA GCGCAGCGCG CCGACGCGCA CACACAAACC ATCAACCGGA
3121   ATCACAGAGG CAGTATTGAG AATCTTGTTG GTTTCCGCCT GGCCTTTCCA CTCTTCGCGG
```

FIG. 16B

```
3181    CTCTGGCCGT TATCGAGCTG TTTGTCGATC CAGGGGATCA GGCTTCCCGC CAGCGGTACG
3241    CCAAAGTTAT CAACCGGCAG CTCGCCGCTG CGGGTCAATG CCGTAACTTT GCGTTCAATA
3301    TCAAGAATTG CGGAAGACGG CGTCGCCAGT TCATCGGCGA CATGGCCATA CAACTGACCC
3361    ATCTGGGTTA ACAGCTCGCG CATATGGCGC GCGCCGCCGC CGGAGGCGGC CTGATAGGTC
3421    GCGACGGATA CCCAGTCAAC GAGATTATGG GCAAAGAGAC CGCCCAGCGA CATCAACATC
3481    AGGCTAACGG TACAGTTACC GCCCACAAAG GTCTTCACGC CATTGTTCAG GCCGTCGGTA
3541    ATCACGTCCT GGTTGACCGG GTCGAGAATA ATAATGGCAT CATCTTTCAT GCGCAGCGTA
3601    GAAGCCGCAT CAATCCAGTA ACCCTGCCAT CCGCTTTCGC GCAGCTTTGG ATAAATTTCG
3661    TTGGTATAAT CGCCGCCCTG GCAGGTCACG ATGATATCGA GCGCTTTTAG CGCATCCAGA
3721    TCAAAAGCGT CCTGTAGCGT GCCGGTGGAG GTGTCGCCGA AGGTGGGCGC CGCCTGTCCA
3781    AACTGGGAGG TAGAAAAGAA AACAGGGCGA ATAGCGTCGA AATCGCGCTC CTCTACCATG
3841    CGTTGCATGA GAACAGAGCC GACCATTCCG CGCCAGCCGA TAAAACCAAC ATTTTTCATA
3901    GCGTTTTTTT CCTGCAAAGA GATGTGC
```

FIG. 16C beta lactamase N-terminal signal→
                                                                              M   S   I
112                                                                           ATGAGTATT
      Q   H   F   R   V   A   L     I   P   F     F   A   A   F     C   L   P     V   F   A
121   CAACATTTCC  GTGTCGCCCT  TATTCCCTTT  TTTGCGGCAT  TTTGCCTTCC  TGTTTTTGCT
                                                            PspA Rx1 →
      H   P   E   T     L   V   K     V   K   D     A   E   E   F     S   P   V     A   S   Q
181   CACCCAGAAA  CGCTGGTGAA  AGTAAAAGAT  GCTGAAGAAT  TCTCTCCGGT  AGCCAGTCAG
      S   K   A   E     K   D   Y     D   A   A     K   K   D     A   K   N   A     K   K   A
241   TCTAAAGCTG  AAAAGACTA   TGATGCAGCG  AAGAAAGATG  CTAAGAATGC  TAAAAAAGCA
      V   E   D   A     Q   K   A     L   D   D     A   K   A   A     Q   K   K     Y   D   E
301   GTAGAAGATG  CTCAAAAGGC  TTTAGATGAT  GCAAAAGCTG  CTCAGAAAAA  ATATGACGAG
      D   Q   K   K     T   E   E     K   A   A     L   E   K   A     A   S   E     E   M   D
361   GATCAGAAGA  AAACTGAGGA  GAAAGCCGCG  CTGGAAAAAG  CAGCGTCTGA  AGAGATGGAT
      K   A   V   A   A   V   Q   Q   A   Y     L   A   Y   Q   Q   A   T     D   K   A
421   AAGGCAGTGG  CAGCAGTTCA  ACAAGCGTAT  CTGGCCTATC  AACAAGCTAC  AGACAAAGCC
      A   K   D   A   A   D   K     M   I   D     E   A   K   K     R   E   E     E   A   K
481   GCAAAAGACG  CAGCAGATAA  GATGATCGAT  GAAGCTAAGA  AACGCGAAGA  AGAGGCAAAA
      T   K   F   N     T   V   R     A   M   V     V   P   E   P     E   Q   L     A   E   T
541   ACTAAATTTA  ATACTGTTCG  TGCAATGGTA  GTTCCTGAGC  CAGAGCAGTT  GGCGGAGACT
      K   K   K   S     E   E   A     Q   K     A   P   E   L     T   K   K     L   E   E
601   AAGAAAAAAT  CAGAAGAAGC  TAAACAAAAA  GCACCAGAAC  TTACTAAAAA  ACTGGAAGAA
      A   K   A   K     L   E   E     A   E   K     K   A   T   E     A   K   Q     K   V   D
661   GCTAAAGCAA  AATTAGAAGA  GGCTGAGAAA  AAAGCTACTG  AAGCCAAACA  AAAAGTGGAT
      A   E   E   V     A   P   Q     A   K   I     A   E   L     N   Q   V     H   R   L
721   GCTGAAGAAG  TCGCTCCTCA  AGCTAAAATC  GCTGAATTGG  AAAATCAAGT  TCATCGTCTG
      E   Q   E   L     K   E   I     D   E   S     E   S   E   D     Y   A   K     E   G   F
781   GAACAAGAGC  TCAAAGAGAT  TGATGAGTCT  GAATCAGAAG  ATTATGCTAA  AGAAGGTTTC
      R   A   P   L     Q   S   K     L   D   A     K   K   A   K     L   S   K     L   E   E
841   CGTGCTCCTC  TTCAATCTAA  ATTGGATGCC  AAAAAAGCTA  AACTGTCAAA  ACTTGAAGAG
      L   S   D   K     I   D   E     L   D   A     E   I   A   K     L   E   D     Q   L   K
901   TTAAGTGATA  AGATTGATGA  GTTAGACGCT  GAAATTGCAA  AACTTGAAGA  TCAACTTAAA
      A   A   E   E   N   N     V   E   D     Y   F   K   E     G   L   E   K     T   I
961   GCTGCTGAAG  AAAACAATAA  TGTAGAAGAC  TACTTTAAAG  AAGGTTTAGA  GAAAACTATT
      A   A   K   K     A   E   L     E   K   T     E   A   D     L   K   K   A
1021  GCTGCTAAAA  AAGCTGAATT  AGAAAAAACT  GAAGCTGACC  TTAAGAAAGC  ATAA

FIG. 17

```
112                                                                ATGAGTATT
121    CAACATTTCC GTGTCGCCCT TATTCCCTTT TTTGCGGCAT TTTGCCTTCC TGTTTTTGCT
181    CACCCAGAAA CGCTGGTGAA AGTAAAAGAT GCTGAAGAAT CTCTCCGGT AGCCAGTCAG
241    TCTAAAGCTG AGAAAGACTA TGATGCAGCG AAGAAAGATG CTAAGAATGC TAAAAAAGCA
301    GTAGAAGATG CTCAAAAGGC TTTAGATGAT GCAAAAGCTG CTCAGAAAAA ATATGACGAG
361    GATCAGAAGA AAACTGAGGA GAAAGCCGCG CTGGAAAAAG CAGCGTCTGA AGAGATGGAT
421    AAGGCAGTGG CAGCAGTTCA ACAAGCGTAT CTGGCCTATC AACAAGCTAC AGACAAAGCC
481    GCAAAAGACG CAGCAGATAA GATGATCGAT GAAGCTAAGA AACGCGAAGA AGAGGCAAAA
541    ACTAAATTTA ATACTGTTCG TGCAATGGTA GTTCCTGAGC CAGAGCAGTT GGCGGAGACT
601    AAGAAAAAAT CAGAAGAAGC TAAACAAAAA GCACCAGAAC TTACTAAAAA ACTGGAAGAA
661    GCTAAAGCAA AATTAGAAGA GGCTGAGAAA AAAGCTACTG AAGCCAAACA AAAAGTGGAT
721    GCTGAAGAAG TCGCTCCTCA AGCTAAAATC GCTGAATTGG AAAATCAAGT TCATCGTCTG
781    GAACAAGAGC TCAAAGAGAT TGATGAGTCT GAATCAGAAG ATTATGCTAA AGAAGGTTTC
841    CGTGCTCCTC TTCAATCTAA ATTGGATGCC AAAAAAGCTA AACTGTCAAA ACTTGAAGAG
901    TTAAGTGATA AGATTGATGA GTTAGACGCT GAAATTGCAA AACTTGAAGA TCAACTTAAA
961    GCTGCTGAAG AAAACAATAA TGTAGAAGAC TACTTTAAAG AAGGTTTAGA GAAAACTATT
1021   GCTGCTAAAA AAGCTGAATT AGAAAAAACT GAAGCTGACC TTAAGAAAGC ATAA
```

FIG. 18

```
223                                                        TCTCCGGT AGCCAGTCAG
241    TCTAAAGCTG AGAAAGACTA TGATGCAGCG AAGAAAGATG CTAAGAATGC TAAAAAAGCA
301    GTAGAAGATG CTCAAAAGGC TTTAGATGAT GCAAAAGCTG CTCAGAAAAA ATATGACGAG
361    GATCAGAAGA AAACTGAGGA GAAAGCCGCG CTGGAAAAAG CAGCGTCTGA AGAGATGGAT
421    AAGGCAGTGG CAGCAGTTCA ACAAGCGTAT CTGGCCTATC AACAAGCTAC AGACAAAGCC
481    GCAAAAGACG CAGCAGATAA GATGATCGAT GAAGCTAAGA AACGCGAAGA AGAGGCAAAA
541    ACTAAATTTA ATACTGTTCG TGCAATGGTA GTTCCTGAGC CAGAGCAGTT GGCGGAGACT
601    AAGAAAAAAT CAGAAGAAGC TAAACAAAAA GCACCAGAAC TTACTAAAAA ACTGGAAGAA
661    GCTAAAGCAA AATTAGAAGA GGCTGAGAAA AAAGCTACTG AAGCCAAACA AAAAGTGGAT
721    GCTGAAGAAG TCGCTCCTCA AGCTAAAATC GCTGAATTGG AAAATCAAGT TCATCGTCTG
781    GAACAAGAGC TCAAAGAGAT TGATGAGTCT GAATCAGAAG ATTATGCTAA AGAAGGTTTC
841    CGTGCTCCTC TTCAATCTAA ATTGGATGCC AAAAAAGCTA AACTGTCAAA ACTTGAAGAG
901    TTAAGTGATA AGATTGATGA GTTAGACGCT GAAATTGCAA AACTTGAAGA TCAACTTAAA
961    GCTGCTGAAG AAAACAATAA TGTAGAAGAC TACTTTAAAG AAGGTTTAGA GAAAACTATT
1021   GCTGCTAAAA AAGCTGAATT AGAAAAAACT GAAGCTGACC TTAAGAAAGC ATAA
```

FIG. 19

```
  1    MSIQHFRVAL IPFFAAFCLP VFAHPETLVK VKDAEEFSPV ASQSKAEKDY
 51    DAAKKDAKNA KKAVEDAQKA LDDAKAAQKK YDEDQKKTEE KAALEKAASE
101    EMDKAVAAVQ QAYLAYQQAT DKAAKDAADK MIDEAKKREE EAKTKFNTVR
151    AMVVPEPEQL AETKKKSEEA KQKAPELTKK LEEAKAKLEE AEKKATEAKQ
201    KVDAEEVAPQ AKIAELENQV HRLEQELKEI DESESEDYAK EGFRAPLQSK
251    LDAKKAKLSK LEELSDKIDE LDAEIAKLED QLKAAEENNN VEDYFKEGLE
301    KTIAAKKAEL EKTEADLKKA
```

FIG. 20

```
 38                                           SPV ASQSKAEKDY
 51    DAAKKDAKNA KKAVEDAQKA LDDAKAAQKK YDEDQKKTEE KAALEKAASE
101    EMDKAVAAVQ QAYLAYQQAT DKAAKDAADK MIDEAKKREE EAKTKFNTVR
151    AMVVPEPEQL AETKKKSEEA KQKAPELTKK LEEAKAKLEE AEKKATEAKQ
201    KVDAEEVAPQ AKIAELENQV HRLEQELKEI DESESEDYAK EGFRAPLQSK
251    LDAKKAKLSK LEELSDKIDE LDAEIAKLED QLKAAEENNN VEDYFKEGLE
301    KTIAAKKAEL EKTEADLKKA
```

FIG. 21

```
 24                                 HPETLVK VKDAEEFSPV ASQSKAEKDY
 51    DAAKKDAKNA KKAVEDAQKA LDDAKAAQKK YDEDQKKTEE KAALEKAASE
101    EMDKAVAAVQ QAYLAYQQAT DKAAKDAADK MIDEAKKREE EAKTKFNTVR
151    AMVVPEPEQL AETKKKSEEA KQKAPELTKK LEEAKAKLEE AEKKATEAKQ
201    KVDAEEVAPQ AKIAELENQV HRLEQELKEI DESESEDYAK EGFRAPLQSK
251    LDAKKAKLSK LEELSDKIDE LDAEIAKLED QLKAAEENNN VEDYFKEGLE
301    KTIAAKKAEL EKTEADLKKA
```

FIG. 22

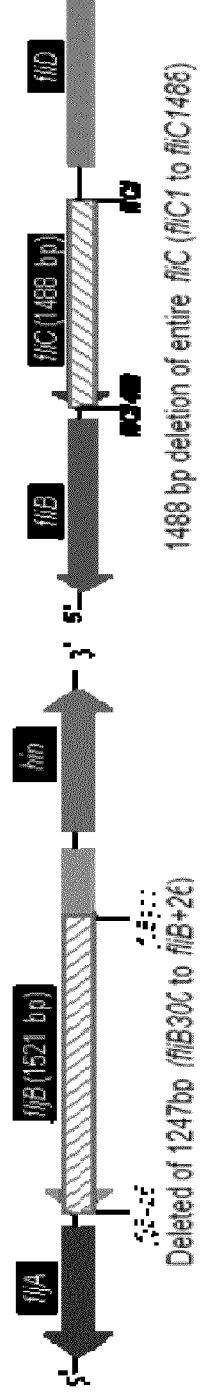
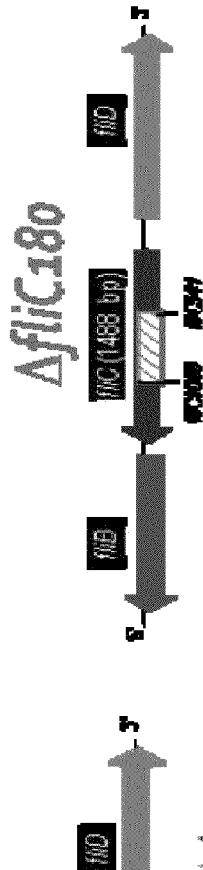
FIG. 49
FIG. 50

```
                                                                    45
ori  TCT CCC GTA GCC AGT CAG TCT AAA GCT GAG AAA GAC TAT GAT GCA
      S   P   V   A   S   Q   S   K   A   E   K   D   Y   D   A
opt  TCT CCG GTA GCC AGT CAG TCT AAA GCT GAG AAA GAC TAT GAT GCA
      S   P   V   A   S   Q   S   K   A   E   K   D   Y   D   A
     *** **  *** *** *** *** *** *** *** *** *** *** *** *** ***

90
ori  GCG AAG AAA GAT GCT AAG AAT GCG AAA AAA GCA GTA GAA GAT GCT
      A   K   K   D   A   K   N   A   K   K   A   V   E   D   A
opt  GCG AAG AAA GAT GCT AAG AAT GCT AAA AAA GCA GTA GAA GAT GCT
      A   K   K   D   A   K   N   A   K   K   A   V   E   D   A
     *** *** *** *** *** *** *** **  *** *** *** *** *** *** ***

135
ori  CAA AAG GCT TTA GAT GAT GCA AAA GCT GCT CAG AAA AAA TAT GAC
      Q   K   A   L   D   D   A   K   A   A   Q   K   K   Y   D
opt  CAA AAG GCT TTA GAT GAT GCA AAA GCT GCT CAG AAA AAA TAT GAC
      Q   K   A   L   D   D   A   K   A   A   Q   K   K   Y   D
     *** *** *** *** *** *** *** *** *** *** *** *** *** *** ***

180
ori  GAG GAT CAG AAG AAA ACT GAG GAG AAA GCC GCG CTA GAA AAA GCA
      E   D   Q   K   K   T   E   E   K   A   A   L   E   K   A
opt  GAG GAT CAG AAG AAA ACT GAG GAG AAA GCC GCG CTG GAA AAA GCA
      E   D   Q   K   K   T   E   E   K   A   A   L   E   K   A
     *** *** *** *** *** *** *** *** *** *** *** **  *** *** ***

225
ori  GCG TCT GAA GAG ATG GAT AAG GCA GTG GCA GCA GTT CAA CAA GCG
      A   S   E   E   M   D   K   A   V   A   A   V   Q   Q   A
opt  GCG TCT GAA GAG ATG GAT AAG GCA GTG GCA GCA GTT CAA CAA GCG
      A   S   E   E   M   D   K   A   V   A   A   V   Q   Q   A
     *** *** *** *** *** *** *** *** *** *** *** *** *** *** ***

270
ori  AAT CTG GCC TAT CAA CAA GCT ACA GAC AAA GCC GCA AAA GAC GCA
      N   L   A   Y   Q   Q   A   T   D   K   A   A   K   D   A
opt  TAT CTG GCC TAT CAA CAA GCT ACA GAC AAA GCC GCA AAA GAC GCA
      Y   L   A   Y   Q   Q   A   T   D   K   A   A   K   D   A
     **  *** *** *** *** *** *** *** *** *** *** *** *** *** ***

315
ori  GCA GAT AAG ATG ATA GAT GAA GCT AAG AAA CGC GAA GAA GAG GCA
      A   D   K   M   I   D   E   A   K   K   R   E   E   E   A
opt  GCA GAT AAG ATG ATC GAT GAA GCT AAG AAA CGC GAA GAA GAG GCA
      A   D   K   M   I   D   E   A   K   K   R   E   E   E   A
     *** *** *** *** **  *** *** *** *** *** *** *** *** *** ***
```

FIG. 57A

```
                                                                        360
ori AAA ACT AAA TTT AAT ACT GTT CGA GCA ATG GTA GTT CCT GAG CCA
     K   T   K   F   N   T   V   R   A   M   V   V   P   E   P
opt AAA ACT AAA TTT AAT ACT GTT CGT GCA ATG GTA GTT CCT GAG CCA
     K   T   K   F   N   T   V   R   A   M   V   V   P   E   P
    *** *** *** *** *** *** *** **  *** *** *** *** *** *** ***

405
ori GAG CAG TTG GCT GAG ACT AAG AAA AAA TCA GAA GAA GCT AAA CAA
     E   Q   L   A   E   T   K   K   K   S   E   E   A   K   Q
opt GAG CAG TTG GCG GAG ACT AAG AAA AAA TCA GAA GAA GCT AAA CAA
     E   Q   L   A   E   T   K   K   K   S   E   E   A   K   Q
    *** *** *** **  *** *** *** *** *** *** *** *** *** *** ***

450
ori AAA GCA CCA GAA CTT ACT AAA AAA CTA GAA GAA GCT AAA GCA AAA
     K   A   P   E   L   T   K   K   L   E   E   A   K   A   K
opt AAA GCA CCA GAA CTT ACT AAA AAA CTG GAA GAA GCT AAA GCA AAA
     K   A   P   E   L   T   K   K   L   E   E   A   K   A   K
    *** *** *** *** *** *** *** *** **  *** *** *** *** *** ***

495
ori TTA GAA GAG GCT GAG AAA AAA GCT ACT GAA GCC AAA CAA AAA GTG
     L   E   E   A   E   K   K   A   T   E   A   K   Q   K   V
opt TTA GAA GAG GCT GAG AAA AAA GCT ACT GAA GCC AAA CAA AAA GTG
     L   E   E   A   E   K   K   A   T   E   A   K   Q   K   V
    *** *** *** *** *** *** *** *** *** *** *** *** *** *** ***

540
ori GAT GCT GAA GAA GTC GCT CCT CAA GCT AAA ATC GCT GAA TTG GAA
     D   A   E   E   V   A   P   Q   A   K   I   A   E   L   E
opt GAT GCT GAA GAA GTC GCT CCT CAA GCT AAA ATC GCT GAA TTG GAA
     D   A   E   E   V   A   P   Q   A   K   I   A   E   L   E
    *** *** *** *** *** *** *** *** *** *** *** *** *** *** ***

585
ori AAT CAA GTT CAT AGA CTA GAA CAA GAG CTC AAA GAG ATT GAT GAG
     N   Q   V   H   R   L   E   Q   E   L   K   E   I   D   E
opt AAT CAA GTT CAT CGT CTG GAA CAA GAG CTC AAA GAG ATT GAT GAG
     N   Q   V   H   R   L   E   Q   E   L   K   E   I   D   E
    *** *** *** *** *   **  *** *** *** *** *** *** *** *** ***

630
ori TCT GAA TCA GAA GAT TAT GCT AAA GAA GGT TTC CGT GCT CCT CTT
     S   E   S   E   D   Y   A   K   E   G   F   R   A   P   L
opt TCT GAA TCA GAA GAT TAT GCT AAA GAA GGT TTC CGT GCT CCT CTT
     S   E   S   E   D   Y   A   K   E   G   F   R   A   P   L
    *** *** *** *** *** *** *** *** *** *** *** *** *** *** ***
```

FIG. 57B

```
                                                                    675
ori CAA TCT AAA TTG GAT GCC AAA AAA GCT AAA CTA TCA AAA CTT GAA
     Q   S   K   L   D   A   K   K   A   K   L   S   K   L   E
opt CAA TCT AAA TTG GAT GCC AAA AAA GCT AAA CTG TCA AAA CTT GAA
     Q   S   K   L   D   A   K   K   A   K   L   S   K   L   E
    *** *** *** *** *** *** *** *** *** *** **  *** *** *** ***

720
ori GAG TTA AGT GAT AAG ATT GAT GAG TTA GAC GCT GAA ATT GCA AAA
     E   L   S   D   K   I   D   E   L   D   A   E   I   A   K
opt GAG TTA AGT GAT AAG ATT GAT GAG TTA GAC GCT GAA ATT GCA AAA
     E   L   S   D   K   I   D   E   L   D   A   E   I   A   K
    *** *** *** *** *** *** *** *** *** *** *** *** *** *** ***

765
ori CTT GAA GAT CAA CTT AAA GCT GCT GAA GAA AAC AAT AAT GTA GAA
     L   E   D   Q   L   K   A   A   E   E   N   N   N   V   E
opt CTT GAA GAT CAA CTT AAA GCT GCT GAA GAA AAC AAT AAT GTA GAA
     L   E   D   Q   L   K   A   A   E   E   N   N   N   V   E
    *** *** *** *** *** *** *** *** *** *** *** *** *** *** ***

810
ori GAC TAC TTT AAA GAA GGT TTA GAG AAA ACT ATT GCT GCT AAA AAA
     D   Y   F   K   E   G   L   E   K   T   I   A   A   K   K
opt GAC TAC TTT AAA GAA GGT TTA GAG AAA ACT ATT GCT GCT AAA AAA
     D   Y   F   K   E   G   L   E   K   T   I   A   A   K   K
    *** *** *** *** *** *** *** *** *** *** *** *** *** *** ***

852
ori GCT GAA TTA GAA AAA ACT GAA GCT GAC CTT AAG AAA GCA TAA
     A   E   L   E   K   T   E   A   D   L   K   K   A   *
opt GCT GAA TTA GAA AAA ACT GAA GCT GAC CTT AAG AAA GCA TAA
     A   E   L   E   K   T   E   A   D   L   K   K   A   *
    *** *** *** *** *** *** *** *** *** *** *** *** *** ***
```

FIG. 57C

```
ori  TCT CCC GTA GCC AGT CAG TCT AAA GCT GAG AAA GAC TAT GAT GCA
      S   P   V   A   S   Q   S   K   A   E   K   D   Y   D   A
opt  TCT CCG GTA GCC AGT CAG TCT AAA GCT GAG AAA GAC TAT GAT GCA
      S   P   V   A   S   Q   S   K   A   E   K   D   Y   D   A
     *** **  *** *** *** *** *** *** *** *** *** *** *** *** ***
                                                                 90
ori  GCG AAG AAA GAT GCT AAG AAT GCG AAA AAA GCA GTA GAA GAT GCT
      A   K   K   D   A   K   N   A   K   K   A   V   E   D   A
opt  GCG AAG AAA GAT GCT AAG AAT GCT AAA AAA GCA GTA GAA GAT GCT
      A   K   K   D   A   K   N   A   K   K   A   V   E   D   A
     *** *** *** *** *** *** *** **  *** *** *** *** *** *** ***
                                                                 135
ori  CAA AAG GCT TTA GAT GAT GCA AAA GCT GCT CAG AAA AAA TAT GAC
      Q   K   A   L   D   D   A   K   A   A   Q   K   K   Y   D
opt  CAA AAG GCT TTA GAT GAT GCA AAA GCT GCT CAG AAA AAA TAT GAC
      Q   K   A   L   D   D   A   K   A   A   Q   K   K   Y   D
     *** *** *** *** *** *** *** *** *** *** *** *** *** *** ***
                                                                 180
ori  GAG GAT CAG AAG AAA ACT GAG GAG AAA GCC GCG CTA GAA AAA GCA
      E   D   Q   K   K   T   E   E   K   A   A   L   E   K   A
opt  GAG GAT CAG AAG AAA ACT GAG GAG AAA GCC GCG CTG GAA AAA GCA
      E   D   Q   K   K   T   E   E   K   A   A   L   E   K   A
     *** *** *** *** *** *** *** *** *** *** *** **  *** *** ***
                                                                 225
ori  GCG TCT GAA GAG ATG GAT AAG GCA GTG GCA GCA GTT CAA CAA GCG
      A   S   E   E   M   D   K   A   V   A   A   V   Q   Q   A
opt  GCG TCT GAA GAG ATG GAT AAG GCA GTG GCA GCA GTT CAA CAA GCG
      A   S   E   E   M   D   K   A   V   A   A   V   Q   Q   A
     *** *** *** *** *** *** *** *** *** *** *** *** *** *** ***
                                                                 270
ori  AAT CTG GCC TAT CAA CAA GCT ACA GAC AAA GCC GCA AAA GAC GCA
      N   L   A   Y   Q   Q   A   T   D   K   A   A   K   D   A
opt  TAT CTG GCC TAT CAA CAA GCT ACA GAC AAA GCC GCA AAA GAC GCA
      Y   L   A   Y   Q   Q   A   T   D   K   A   A   K   D   A
     **  *** *** *** *** *** *** *** *** *** *** *** *** *** ***
                                                                 315
ori  GCA GAT AAG ATG ATA GAT GAA GCT AAG AAA CGC GAA GAA GAG GCA
      A   D   K   M   I   D   E   A   K   K   R   E   E   E   A
opt  GCA GAT AAG ATG ATC GAT GAA GCT AAG AAA CGC GAA GAA GAG GCA
      A   D   K   M   I   D   E   A   K   K   R   E   E   E   A
     *** *** *** *** **  *** *** *** *** *** *** *** *** *** ***
```

FIG. 58A

```
                                                                      360
ori AAA ACT AAA TTT AAT ACT GTT CGA GCA ATG GTA GTT CCT GAG CCA
     K   T   K   F   N   T   V   R   A   M   V   V   P   E   P
opt AAA ACT AAA TTT AAT ACT GTT CGT GCA ATG GTA GTT CCT GAG CCA
     K   T   K   F   N   T   V   R   A   M   V   V   P   E   P
    *** *** *** *** *** *** *** **  *** *** *** *** *** *** ***

405
ori GAG CAG TTG GCT GAG ACT AAG AAA AAA TCA GAA GAA GCT AAA CAA
     E   Q   L   A   E   T   K   K   K   S   E   E   A   K   Q
opt GAG CAG TTG GCG GAG ACT AAG AAA AAA TCA GAA GAA GCT AAA CAA
     E   Q   L   A   E   T   K   K   K   S   E   E   A   K   Q
    *** *** *** **  *** *** *** *** *** *** *** *** *** *** ***

450
ori AAA GCA CCA GAA CTT ACT AAA AAA CTA GAA GAA GCT AAA GCA AAA
     K   A   P   E   L   T   K   K   L   E   E   A   K   A   K
opt AAA GCA CCA GAA CTT ACT AAA AAA CTG GAA GAA GCT AAA GCA AAA
     K   A   P   E   L   T   K   K   L   E   E   A   K   A   K
    *** *** *** *** *** *** *** *** **  *** *** *** *** *** ***

495
ori TTA GAA GAG GCT GAG AAA AAA GCT ACT GAA GCC AAA CAA AAA GTG
     L   E   E   A   E   K   K   A   T   E   A   K   Q   K   V
opt TTA GAA GAG GCT GAG AAA AAA GCT ACT GAA GCC AAA CAA AAA GTG
     L   E   E   A   E   K   K   A   T   E   A   K   Q   K   V
    *** *** *** *** *** *** *** *** *** *** *** *** *** *** ***

540
ori GAT GCT GAA GAA GTC GCT CCT CAA GCT AAA ATC GCT GAA TTG GAA
     D   A   E   E   V   A   P   Q   A   K   I   A   E   L   E
opt GAT GCT GAA GAA GTC GCT CCT CAA GCT AAA ATC GCT GAA TTG GAA
     D   A   E   E   V   A   P   Q   A   K   I   A   E   L   E
    *** *** *** *** *** *** *** *** *** *** *** *** *** *** ***

585
ori AAT CAA GTT CAT AGA CTA GAA CAA GAG CTC AAA GAG ATT GAT GAG
     N   Q   V   H   R   L   E   Q   E   L   K   E   I   D   E
opt AAT CAA GTT CAT CGT CTG GAA CAA GAG CTC AAA GAG ATT GAT GAG
     N   Q   V   H   R   L   E   Q   E   L   K   E   I   D   E
    *** *** *** ***  *   ** *** *** *** *** *** *** *** *** ***

630
ori TCT GAA TCA GAA GAT TAT GCT AAA GAA GGT TTC CGT GCT CCT CTT
     S   E   S   E   D   Y   A   K   E   G   F   R   A   P   L
opt TCT GAA TCA GAA GAT TAT GCT AAA GAA GGT TTC CGT GCT CCT CTT
     S   E   S   E   D   Y   A   K   E   G   F   R   A   P   L
    *** *** *** *** *** *** *** *** *** *** *** *** *** *** ***
```

FIG. 58B

```
                                                                    675
ori CAA TCT AAA TTG GAT GCC AAA AAA GCT AAA CTA TCA AAA CTT GAA
     Q   S   K   L   D   A   K   K   A   K   L   S   K   L   E
opt CAA TCT AAA TTG GAT GCC AAA AAA GCT AAA CTG TCA AAA CTT GAA
     Q   S   K   L   D   A   K   K   A   K   L   S   K   L   E
    *** *** *** *** *** *** *** *** *** *** **  *** *** *** ***

720
ori GAG TTA AGT GAT AAG ATT GAT GAG TTA GAC GCT GAA ATT GCA AAA
     E   L   S   D   K   I   D   E   L   D   A   E   I   A   K
opt GAG TTA AGT GAT AAG ATT GAT GAG TTA GAC GCT GAA ATT GCA AAA
     E   L   S   D   K   I   D   E   L   D   A   E   I   A   K
    *** *** *** *** *** *** *** *** *** *** *** *** *** *** ***

765
ori CTT GAA GAT CAA CTT AAA GCT GCT GAA GAA AAC AAT AAT GTA GAA
     L   E   D   Q   L   K   A   A   E   E   N   N   N   V   E
opt CTT GAA GAT CAA CTT AAA GCT GCT GAA GAA AAC AAT AAT GTA GAA
     L   E   D   Q   L   K   A   A   E   E   N   N   N   V   E
    *** *** *** *** *** *** *** *** *** *** *** *** *** *** ***
```

FIG. 58C

```
                                                                    45
opt  AAC CAG TCT AAA GCT GAG AAA GAC TAT GAT GCA GCA GTG AAA AAA
      N   Q   S   K   A   E   K   D   Y   D   A   A   V   K   K
ori  AAC CAG TCT AAA GCT GAG AAA GAC TAT GAT GCA GCA GTG AAA AAA
      N   Q   S   K   A   E   K   D   Y   D   A   A   V   K   K
     *** *** *** *** *** *** *** *** *** *** *** *** *** *** ***

90
opt  TCT GAA GCT GCT AAG AAA GAT TAC GAA ACG GCT AAA AAG AAA GCA
      S   E   A   A   K   K   D   Y   E   T   A   K   K   K   A
ori  TCT GAA GCT GCT AAG AAA GAT TAC GAA ACG GCT AAA AAG AAA GCA
      S   E   A   A   K   K   D   Y   E   T   A   K   K   K   A
     *** *** *** *** *** *** *** *** *** *** *** *** *** *** ***

135
opt  GAA GAC GCT CAG AAG AAA TAT GAT GAG GAT CAG AAG AAA ACT GAG
      E   D   A   Q   K   K   Y   D   E   D   Q   K   K   T   E
ori  GAA GAC GCT CAG AAG AAA TAT GAT GAG GAT CAG AAG AAA ACT GAG
      E   D   A   Q   K   K   Y   D   E   D   Q   K   K   T   E
     *** *** *** *** *** *** *** *** *** *** *** *** *** *** ***

180
opt  GCA AAA GCG GAA AAA GAA CGT AAA GCT TCT GAA AAG ATC GCT GAG
      A   K   A   E   K   E   R   K   A   S   E   K   I   A   E
ori  GCA AAA GCG GAA AAA GAA AGA AAA GCT TCT GAA AAG ATA GCT GAG
      A   K   A   E   K   E   R   K   A   S   E   K   I   A   E
     *** *** *** *** *** ***  *  *** *** *** *** *** **  *** ***

225
opt  GCA ACA AAA GAA GTT CAA CAA GCG TAC CTA GCT TAT CTA CAA GCT
      A   T   K   E   V   Q   Q   A   Y   L   A   Y   L   Q   A
ori  GCA ACA AAA GAA GTT CAA CAA GCG TAC CTA GCT TAT CTA CAA GCT
      A   T   K   E   V   Q   Q   A   Y   L   A   Y   L   Q   A
     *** *** *** *** *** *** *** *** *** *** *** *** *** *** ***

270
opt  AGC AAC GAA AGT CAG CGT AAA GAG GCA GAT AAG AAG ATC AAA GAA
      S   N   E   S   Q   R   K   E   A   D   K   K   I   K   E
ori  AGC AAC GAA AGT CAG AGA AAA GAG GCA GAT AAG AAG ATA AAA GAA
      S   N   E   S   Q   R   K   E   A   D   K   K   I   K   E
     *** *** *** *** ***  *  *** *** *** *** *** *** **  *** ***

315
opt  GCT ACG CAA CGC AAA GAT GAG GCG GAA GCT GCA TTT GCT ACT ATT
      A   T   Q   R   K   D   E   A   E   A   A   F   A   T   I
ori  GCT ACG CAA CGC AAA GAT GAG GCG GAA GCT GCA TTT GCT ACT ATT
      A   T   Q   R   K   D   E   A   E   A   A   F   A   T   I
     *** *** *** *** *** *** *** *** *** *** *** *** *** *** ***
```

FIG. 59A

```
                                                                        360
opt CGT ACA ACA ATT GTA GTT CCT GAA CCA AGT GAG TTA GCT GAG ACT
    R   T   T   I   V   V   P   E   P   S   E   L   A   E   T
ori CGA ACA ACA ATT GTA GTT CCT GAA CCA AGT GAG TTA GCT GAG ACT
    R   T   T   I   V   V   P   E   P   S   E   L   A   E   T
    **  *** *** *** *** *** *** *** *** *** *** *** *** *** ***
                                                                        405
opt AAG AAA AAA GCA GAA GAG GCA ACA AAA GAA GCA GAA GTA GCT AAG
    K   K   K   A   E   E   A   T   K   E   A   E   V   A   K
ori AAG AAA AAA GCA GAA GAG GCA ACA AAA GAA GCA GAA GTA GCT AAG
    K   K   K   A   E   E   A   T   K   E   A   E   V   A   K
    *** *** *** *** *** *** *** *** *** *** *** *** *** *** ***
                                                                        450
opt AAA AAA TCT GAA GAG GCA GCT AAA GAG GTA GAA GTA GAG AAA AAT
    K   K   S   E   E   A   A   K   E   V   E   V   E   K   N
ori AAA AAA TCT GAA GAG GCA GCT AAA GAG GTA GAA GTA GAG AAA AAT
    K   K   S   E   E   A   A   K   E   V   E   V   E   K   N
    *** *** *** *** *** *** *** *** *** *** *** *** *** *** ***
                                                                        495
opt AAA ATC CTT GAA CAA GAT GCT GAA AAC GAA AAG AAA ATT GAC GTA
    K   I   L   E   Q   D   A   E   N   E   K   K   I   D   V
ori AAA ATA CTT GAA CAA GAT GCT GAA AAC GAA AAG AAA ATT GAC GTA
    K   I   L   E   Q   D   A   E   N   E   K   K   I   D   V
    *** **  *** *** *** *** *** *** *** *** *** *** *** *** ***
                                                                        540
opt CTT CAA AAC AAA GTC GCT GAT TTA GAA AAA GGA ATT GCT CCT TAT
    L   Q   N   K   V   A   D   L   E   K   G   I   A   P   Y
ori CTT CAA AAC AAA GTC GCT GAT TTA GAA AAA GGA ATT GCT CCT TAT
    L   Q   N   K   V   A   D   L   E   K   G   I   A   P   Y
    *** *** *** *** *** *** *** *** *** *** *** *** *** *** ***
                                                                        585
opt CAA AAC GAA GTC GCT GAA TTA AAT AAA GAA ATT GCT CGT CTT CAA
    Q   N   E   V   A   E   L   N   K   E   I   A   R   L   Q
ori CAA AAC GAA GTC GCT GAA TTA AAT AAA GAA ATT GCT AGA CTT CAA
    Q   N   E   V   A   E   L   N   K   E   I   A   R   L   Q
    *** *** *** *** *** *** *** *** *** *** *** *** *   *** ***
                                                                        630
opt AGC GAT TTA AAA GAT GCT GAA GAA AAT AAT GTA GAA GAC TAC ATT
    S   D   L   K   D   A   E   E   N   N   V   E   D   Y   I
ori AGC GAT TTA AAA GAT GCT GAA GAA AAT AAT GTA GAA GAC TAC ATT
    S   D   L   K   D   A   E   E   N   N   V   E   D   Y   I
    *** *** *** *** *** *** *** *** *** *** *** *** *** *** ***
```

FIG. 59B

```
                                                                      675
opt AAA GAA GGT TTA GAG CAA GCT ATC ACT AAT AAA AAA GCT GAA TTA
     K   E   G   L   E   Q   A   I   T   N   K   K   A   E   L
ori AAA GAA GGT TTA GAG CAA GCT ATC ACT AAT AAA AAA GCT GAA TTA
     K   E   G   L   E   Q   A   I   T   N   K   K   A   E   L
    *** *** *** *** *** *** *** *** *** *** *** *** *** *** ***

720
opt GCT ACA ACT CAA CAA AAC ATC GAT AAA ACT CAA AAA GAT TTA GAG
     A   T   T   Q   Q   N   I   D   K   T   Q   K   D   L   E
ori GCT ACA ACT CAA CAA AAC ATA GAT AAA ACT CAA AAA GAT TTA GAG
     A   T   T   Q   Q   N   I   D   K   T   Q   K   D   L   E
    *** *** *** *** *** *** **  *** *** *** *** *** *** *** ***

765
opt GAT GCT GAA TTA GAA CTT GAA AAA GTA TTA GCT ACA TTA GAC CCT
     D   A   E   L   E   L   E   K   V   L   A   T   L   D   P
ori GAT GCT GAA TTA GAA CTT GAA AAA GTA TTA GCT ACA TTA GAC CCT
     D   A   E   L   E   L   E   K   V   L   A   T   L   D   P
    *** *** *** *** *** *** *** *** *** *** *** *** *** *** ***

810
opt GAA GGT AAA ACT CAA GAT GAA TTA GAT AAA GAA GCT GCT GAA GCT
     E   G   K   T   Q   D   E   L   D   K   E   A   A   E   A
ori GAA GGT AAA ACT CAA GAT GAA TTA GAT AAA GAA GCT GCT GAA GCT
     E   G   K   T   Q   D   E   L   D   K   E   A   A   E   A
    *** *** *** *** *** *** *** *** *** *** *** *** *** *** ***

855
opt GAG TTG AAT GAA AAA GTT GAA GCT CTT CAA AAC CAA GTT GCT GAA
     E   L   N   E   K   V   E   A   L   Q   N   Q   V   A   E
ori GAG TTG AAT GAA AAA GTT GAA GCT CTT CAA AAC CAA GTT GCT GAA
     E   L   N   E   K   V   E   A   L   Q   N   Q   V   A   E
    *** *** *** *** *** *** *** *** *** *** *** *** *** *** ***

900
opt TTA GAA GAA GAA CTT TCA AAA CTT GAA GAT AAT CTT AAA GAT GCT
     L   E   E   E   L   S   K   L   E   D   N   L   K   D   A
ori TTA GAA GAA GAA CTT TCA AAA CTT GAA GAT AAT CTT AAA GAT GCT
     L   E   E   E   L   S   K   L   E   D   N   L   K   D   A
    *** *** *** *** *** *** *** *** *** *** *** *** *** *** ***

945
opt GAA ACA AAC AAC GTT GAA GAC TAC ATT AAA GAA GGT TTA GAA GAA
     E   T   N   N   V   E   D   Y   I   K   E   G   L   E   E
ori GAA ACA AAC AAC GTT GAA GAC TAC ATT AAA GAA GGT TTA GAA GAA
     E   T   N   N   V   E   D   Y   I   K   E   G   L   E   E
    *** *** *** *** *** *** *** *** *** *** *** *** *** *** ***
```

FIG. 59C

```
                                                                       990
opt GCT ATC GCG ACT AAA AAA GCT GAA TTG GAA AAA ACT CAA AAA GAA
     A   I   A   T   K   K   A   E   L   E   K   T   Q   K   E
ori GCT ATC GCG ACT AAA AAA GCT GAA TTG GAA AAA ACT CAA AAA GAA
     A   I   A   T   K   K   A   E   L   E   K   T   Q   K   E
    *** *** *** *** *** *** *** *** *** *** *** *** *** *** ***

1035
opt TTA GAT GCA GCT CTT AAT GAG TTA GGC CCT GAT GGA GAT GAA GAA
     L   D   A   A   L   N   E   L   G   P   D   G   D   E   E
ori TTA GAT GCA GCT CTT AAT GAG TTA GGC CCT GAT GGA GAT GAA GAA
     L   D   A   A   L   N   E   L   G   P   D   G   D   E   E
    *** *** *** *** *** *** *** *** *** *** *** *** *** *** ***

1080
opt GAG ACT CCA GCG CCG GCT CCT CAA CCA GAA AAA CCA GCT GAA GAG
     E   T   P   A   P   A   P   Q   P   E   K   P   A   E   E
ori GAG ACT CCA GCG CCG GCT CCT CAA CCA GAA AAA CCA GCT GAA GAG
     E   T   P   A   P   A   P   Q   P   E   K   P   A   E   E
    *** *** *** *** *** *** *** *** *** *** *** *** *** *** ***

1125
opt CCT GAG AAT CCA GCT CCA GCA CCA AAA CCA GAG AAG TCA GCA GAT
     P   E   N   P   A   P   A   P   K   P   E   K   S   A   D
ori CCT GAG AAT CCA GCT CCA GCA CCA AAA CCA GAG AAG TCA GCA GAT
     P   E   N   P   A   P   A   P   K   P   E   K   S   A   D
    *** *** *** *** *** *** *** *** *** *** *** *** *** *** ***

1170
opt CAA CAA GCT GAA GAA GAC TAT GCT CGT AGA TCA GAA GAA GAA TAT
     Q   Q   A   E   E   D   Y   A   R   R   S   E   E   E   Y
ori CAA CAA GCT GAA GAA GAC TAT GCT CGT AGA TCA GAA GAA GAA TAT
     Q   Q   A   E   E   D   Y   A   R   R   S   E   E   E   Y
    *** *** *** *** *** *** *** *** *** *** *** *** *** *** ***

1215
opt AAT CGC TTG ACC CAA CAG CAA CCG CCA AAA GCA GAA AAA CCA GCT
     N   R   L   T   Q   Q   Q   P   P   K   A   E   K   P   A
ori AAT CGC TTG ACC CAA CAG CAA CCG CCA AAA GCA GAA AAA CCA GCT
     N   R   L   T   Q   Q   Q   P   P   K   A   E   K   P   A
    *** *** *** *** *** *** *** *** *** *** *** *** *** *** ***

1256
opt CCT GCA CCA CAA CCA GAG CAA CCA GCT CCT GCA CCA ATA AT
     P   A   P   Q   P   E   Q   P   A   P   A   P   I
ori CCT GCA CCA CAA CCA GAG CAA CCA GCT CCT GCA CCA --- --
     P   A   P   Q   P   E   Q   P   A   P   A   P
    *** *** *** *** *** *** *** *** *** *** *** ***
```

FIG. 59D gaattctctccggtagccagtcagtctaaagctgagaaagactatgatgcagcgaagaaagatgctaagaatgctaaaaaag
cagtagaagatgctcaaaaggctttagatgatgcaaaagctgctcagaaaaaatatgacgaggatcagaagaaaactgag
gagaaagccgcgctggaaaaagcagcgtctgaagagatggataaggcagtggcagcagttcaacaagcgtatctggccta
tcaacaagctacagacaaagccgcaaaagacgcagcagataagatgatcgatgaagctaagaaacgcgaagaagagg
caaaaactaaatttaatactgttcgtgcaatggtagttcctgagccagagcagttggcggagactaagaaaaaatcagaagaa
gctaaacaaaaagcaccagaacttactaaaaaactggaagaagctaaagcaaaattagaagaggctgagaaaaaagcta
ctgaagccaaacaaaaagtggatgctgaagaagtcgctcctcaagctaaaatcgctgaattggaaaatcaagttcatcgtctg
gaacaagagctcaaagagattgatgagtctgaatcagaagattatgctaaagaaggtttccgtgctcctcttcaatctaaattgg
atgccaaaaaagctaaactgtcaaaacttgaagagttaagtgataagattgatgagttagacgctgaaattgcaaaacttgaa
gatcaacttaaagctgctgaagaaaacaataatgtagaagactactttaaagaaggtttagagaaaactattgctgctaaaaa
agctgaattagaaaaaactgaagctgaccttaagaaagcactgcagaaccagtctaaagctgagaaagactatgatgcagc
agtgaaaaaatctgaagctgctaagaaagattacgaaacggctaaaaagaaagcagaagacgctcagaagaaatatgat
gaggatcagaagaaactgaggcaaaagcggaaaaagaacgtaaagcttctgaaaagatcgctgaggcaacaaaaga
agttcaacaagcgtacctagcttatctacaagctagcaacgaaagtcagcgtaaagaggcagataagaagatcaaagaag
ctacgcaacgcaaagatgaggcggaagctgcatttgctactattcgtacaacaattgtagttcctgaaccaagtgagttagctga
gactaagaaaaaagcagaagaggcaacaaaagaagcagaagtagctaagaaaaaatctgaagaggcagctaaagag
gtagaagtagagaaaaataaaatccttgaacaagatgctgaaaacgaaaagaaattgacgtacttcaaaacaaagtcgct
gatttagaaaaaggaattgctccttatcaaaacgaagtcgctgaattaaataaagaaattgctcgtcttcaaagcgatttaaaag
atgctgaagaaaataatgtagaagactacattaaagaaggtttagagcaagctatcactaataaaaaagctgaattagctaca
actcaacaaaacatcgataaaactcaaaaagatttagaggatgctgaattagaacttgaaaaagtattagctacattagaccct
gaaggtaaaactcaagatgaattagataaagaagctgctgaagctgagttgaatgaaaaagttgaagctcttcaaaaccaag
ttgctgaattagaagaagaactttcaaaacttgaagataatcttaaagatgctgaaacaaacaacgttgaagactacattaaag
aaggtttagaagaagctatcgcgactaaaaaagctgaattggaaaaaaactcaaaaagaattagatgcagctcttaatgagtta
ggccctgatggagatgaagaagagactccagcgccggctcctcaaccagaaaaaccagctgaagagcctgagaatccag
ctccagcaccaaaaccagagaagtcagcagatcaacaagctgaagaagactatgctcgtagatcagaagaagaatataat
cgcttgacccaacagcaaccgccaaaagcagaaaaaccagctcctgcaccacaaccagagcaaccagctcctgcaccaa
taat
</p>

FIG. 60A

SPVASQSKAEKDYDAAKKDAKNAKKAVEDAQKALDDAKAAQKKYDEDQKKTEEKAALEK
AASEEMDKAVAAVQQAYLAYQQATDKAAKDAADKMIDEAKKREEEAKTKFNTVRAMVVP
EPEQLAETKKKSEEAKQKAPELTKKLEEAKAKLEEAEKKATEAKQKVDAEEVAPQAKIAEL
ENQVHRLEQELKEIDESESEDYAKEGFRAPLQSKLDAKKAKLSKLEELSDKIDELDAEIAKL
EDQLKAAEENNNVEDYFKEGLEKTIAAKKAELEKTEADLKKAKAEKDYDAAVKKSEAAKKD
YETAKKKAEDAQKKYDEDQKKTEAKAEKERKASEKIAEATKEVQQAYLAYLQASNESQRK
EADKKIKEATQRKDEAEAAFATIRTTIVVPEPSELAETKKKAEEATKEAEVAKKKSEEAAKE
VEVEKNKILEQDAENEKKIDVLQNKVADLEKGIAPYQNEVAELNKEIARLQSDLKDAEENNV
EDYIKEGLEQAITNKKAELATTQQNIDKTQKDLEDAELELEKVLATLDPEGKTQDELDKEAA
EAELNEKVEALQNQVAELEEELSKLEDNLKDAETNNVEDYIKEGLEEAIATKKAELEKTQKE
LDAALNELGPDGDEEETPAPAPQPEKPAEEPENPAPAPKPEKSADQQAEEDYARRSEEE
YNRLTQQQPPKAEKPAPAPQPEQPAPAP

FIG. 60B gaattcaaccagtctaaagctgagaaagactatgatgcagcagtgaaaaaatctgaagctgctaagaaagattacgaaacg
gctaaaaagaaagcagaagacgctcagaagaaatatgatgaggatcagaagaaaactgaggcaaaagcggaaaaga
acgtaaagcttctgaaaagatcgctgaggcaacaaaagaagttcaacaagcgtacctagcttatctacaagctagcaacgaa
agtcagcgtaaagaggcagataagaagatcaaagaagctacgcaacgcaaagatgaggcggaagctgcatttgctactatt
cgtacaacaattgtagttcctgaaccaagtgagttagctgagactaagaaaaaagcagaagaggcaacaaaagaagcaga
agtagctaagaaaaaatctgaagaggcagctaaagaggtagaagtagagaaaaataaaatccttgaacaagatgctgaaa
acgaaaagaaaattgacgtacttcaaaacaaagtcgctgatttagaaaaaggaattgctccttatcaaaacgaagtcgctgaa
ttaaataaagaaattgctcgtcttcaaagcgatttaaaagatgctgaagaaaataatgtagaagactacattaaagaaggttag
agcaagctatcactaataaaaaagctgaattagctacaactcaacaaaacatcgataaaactcaaaaagatttagaggatgc
tgaattagaacttgaaaaagtattagctacattagaccctgaaggtaaaactcaagatgaattagataaagaagctgctgaag
ctgagttgaatgaaaaagttgaagctctcaaaaccaagttgctgaattagaagaagaactttcaaaacttgaagataatcttaa
agatgctgaaacaaacaacgttgaagactacattaaagaaggtttagaagaagctatcgcgactaaaaaagctgaattgga
aaaaactcaaaagaattagatgcagctcttaatgagttaggccctgatggagatgaagaagagactccagcgccggctcct
caaccagaaaaaccagctgaagagcctgagaatccagctccagcaccaaaaccagagaagtcagcagatcaacaagct
gaagaagactatgctcgtagatcagaagaagaatataatcgcttgacccaacagcaaccgccaaaagcagaaaaaccag
ctcctgcaccacaaccagagcaaccagctcctgcaccaagaattctctccggtagccagtcagtctaaagctgagaaagact
atgatgcagcgaagaaagatgctaagaatgctaaaaaagcagtagaagatgctcaaaaggctttagatgatgcaaaagctg
ctcagaaaaatatgacgaggatcagaagaaaactgaggagaaagccgcgctggaaaaagcagcgtctgaagagatgg
ataaggcagtggcagcagttcaacaagcgtatctggcctatcaacaagctacagacaaagccgcaaaagacgcagcagat
aagatgatcgatgaagctaagaaacgcgaagaagaggcaaaaactaaatttaatactgttcgtgcaatggtagttcctgagcc
agagcagttggcggagactaagaaaaaatcagaagaagctaaacaaaaagcaccagaacttactaaaaaactggaaga
agctaaagcaaattagaagaggctgagaaaaaagctactgaagccaaacaaaaagtggatgctgaagaagtcgctcctc
aagctaaaatcgctgaattggaaaatcaagttcatcgtctggaacaagagctcaaagagattgatgagtctgaatcagaagatt
atgctaaagaaggtttccgtgctcctcttcaatctaaattggatgccaaaaaagctaaactgtcaaaacttgaagagttaagtgat
aagattgatgagttagacgctgaaattgcaaaacttgaagatcaacttaaagctgctgaagaaacaataatgtagaagacta
ctttaaagaaggtttagagaaaactattgctgctaaaaaagctgaattagaaaaaactgaagctgaccttaagaaagcataat

FIG. 61A

KAEKDYDAAVKKSEAAKKDYETAKKKAEDAQKKYDEDQKKTEAKAEKERKASEKIAEATK
EVQQAYLAYLQASNESQRKEADKKIKEATQRKDEAEAAFATIRTTIVVPEPSELAETKKKAE
EATKEAEVAKKKSEEAAKEVEVEKNKILEQDAENEKKIDVLQNKVADLEKGIAPYQNEVAE
LNKEIARLQSDLKDAEENNVEDYIKEGLEQAITNKKAELATTQQNIDKTQKDLEDAELELEK
VLATLDPEGKTQDELDKEAAEAELNEKVEALQNQVAELEEELSKLEDNLKDAETNNVEDYI
KEGLEEAIATKKAELEKTQKELDAALNELGPDGDEEETPAPAPQPEKPAEEPENPAPAPKP
EKSADQQAEEDYARRSEEEYNRLTQQQPPKAEKPAPAPQPEQPAPAPSPVASQSKAEKD
YDAAKKDAKNAKKAVEDAQKALDDAKAAQKKYDEDQKKTEEKAALEKAASEEMDKAVAA
VQQAYLAYQQATDKAAKDAADKMIDEAKKREEEAKTKFNTVRAMVVPEPEQLAETKKKSE
EAKQKAPELTKKLEEAKAKLEEAEKKATEAKQKVDAEEVAPQAKIAELENQVHRLEQELKE
IDESESEDYAKEGFRAPLQSKLDAKKAKLSKLEELSDKIDELDAEIAKLEDQLKAAEENNNV
EDYFKEGLEKTIAAKKAELEKTEADLKKA

FIG. 61B

```
                                                               45
opt GAG AAC GAA GGC CTG CCA AGT ACC ACT TCT TCT AAT CGC GCA AAT
     E   N   E   G   L   P   S   T   T   S   S   N   R   A   N
ori GAG AAC GAA GGA CTA CCA AGT ACC ACT TCT TCT AAT AGG GCA AAT
     E   N   E   G   L   P   S   T   T   S   S   N   R   A   N
    * * *     * * * * * * *  *  * *

90
opt GAA AGT CAG GCA GAA CAA GGC GAA CAA CCT AAA AAA CTC GAT TCA
     E   S   Q   A   E   Q   G   E   Q   P   K   K   L   D   S
ori GAA AGT CAG GCA GAA CAA GGA GAA CAA CCT AAA AAA CTC GAT TCA
     E   S   Q   A   E   Q   G   E   Q   P   K   K   L   D   S
    * * * * * *   * * * * * * * ***

135
opt GAA CGC GAT AAG GCA CGC AAA GAG GTC GAG GAA TAT GTA AAA AAA
     E   R   D   K   A   R   K   E   V   E   E   Y   V   K   K
ori GAA CGA GAT AAG GCA AGG AAA GAG GTC GAG GAA TAT GTA AAA AAA
     E   R   D   K   A   R   K   E   V   E   E   Y   V   K   K
    *   * * ***  *  * * * * * * * * ***

180
opt ATC GTG GGT GAG AGC TAT GCA AAA TCA ACT AAA AAG CGC CAT ACA
     I   V   G   E   S   Y   A   K   S   T   K   K   R   H   T
ori ATA GTG GGT GAG AGC TAT GCA AAA TCA ACT AAA AAG CGA CAT ACA
     I   V   G   E   S   Y   A   K   S   T   K   K   R   H   T
      * * * * * * * * * * *   * ***

225
opt ATT ACT GTA GCT CTG GTT AAC GAG TTG AAC AAC ATT AAG AAC GAG
     I   T   V   A   L   V   N   E   L   N   N   I   K   N   E
ori ATT ACT GTA GCT CTA GTT AAC GAG TTG AAC AAC ATT AAG AAC GAG
     I   T   V   A   L   V   N   E   L   N   N   I   K   N   E
    * * * *   * * * * * * * * * ***

270
opt TAT TTG AAT AAA ATC GTT GAA TCA ACC TCA GAA AGC CAA CTA CAG
     Y   L   N   K   I   V   E   S   T   S   E   S   Q   L   Q
ori TAT TTG AAT AAA ATA GTT GAA TCA ACC TCA GAA AGC CAA CTA CAG
     Y   L   N   K   I   V   E   S   T   S   E   S   Q   L   Q
    * * * *   * * * * * * * * * ***

315
opt ATC CTG ATG ATG GAG AGT CGC TCA AAA GTA GAT GAA GCT GTG TCT
     I   L   M   M   E   S   R   S   K   V   D   E   A   V   S
ori ATA CTG ATG ATG GAG AGT CGA TCA AAA GTA GAT GAA GCT GTG TCT
     I   L   M   M   E   S   R   S   K   V   D   E   A   V   S
      * * * * *   * * * * * * * ***
```

FIG. 62A

```
                                                                    360
opt AAG TTT GAA AAG GAC TCA TCT TCT TCG TCA AGT TCA GAC TCT TCC
     K   F   E   K   D   S   S   S   S   S   S   S   D   S   S
ori AAG TTT GAA AAG GAC TCA TCT TCT TCG TCA AGT TCA GAC TCT TCC
     K   F   E   K   D   S   S   S   S   S   S   S   D   S   S
    *** *** *** *** *** *** *** *** *** *** *** *** *** *** ***

405
opt ACT AAA CCG GAA GCT TCA GAT ACA GCG AAG CCA AAC AAG CCG ACA
     T   K   P   E   A   S   D   T   A   K   P   N   K   P   T
ori ACT AAA CCG GAA GCT TCA GAT ACA GCG AAG CCA AAC AAG CCG ACA
     T   K   P   E   A   S   D   T   A   K   P   N   K   P   T
    *** *** *** *** *** *** *** *** *** *** *** *** *** *** ***

450
opt GAA CCA GGC GAA AAG GTA GCA GAA GCT AAG AAG AAG GTT GAA GAA
     E   P   G   E   K   V   A   E   A   K   K   K   V   E   E
ori GAA CCA GGA GAA AAG GTA GCA GAA GCT AAG AAG AAG GTT GAA GAA
     E   P   G   E   K   V   A   E   A   K   K   K   V   E   E
    *** *** **  *** *** *** *** *** *** *** *** *** *** *** ***

495
opt GCT GAG AAA AAA GCC AAG GAT CAA AAA GAA GAA GAT CGT CGT AAC
     A   E   K   K   A   K   D   Q   K   E   E   D   R   R   N
ori GCT GAG AAA AAA GCC AAG GAT CAA AAA GAA GAA GAT CGT CGT AAC
     A   E   K   K   A   K   D   Q   K   E   E   D   R   R   N
    *** *** *** *** *** *** *** *** *** *** *** *** *** *** ***

540
opt TAC CCA ACC ATT ACT TAC AAA ACG CTT GAA CTT GAA ATT GCT GAG
     Y   P   T   I   T   Y   K   T   L   E   L   E   I   A   E
ori TAC CCA ACC ATT ACT TAC AAA ACG CTT GAA CTT GAA ATT GCT GAG
     Y   P   T   I   T   Y   K   T   L   E   L   E   I   A   E
    *** *** *** *** *** *** *** *** *** *** *** *** *** *** ***

585
opt TCC GAT GTG GAA GTT AAA AAA GCG GAG CTT GAA CTA GTA AAA GTG
     S   D   V   E   V   K   K   A   E   L   E   L   V   K   V
ori TCC GAT GTG GAA GTT AAA AAA GCG GAG CTT GAA CTA GTA AAA GTG
     S   D   V   E   V   K   K   A   E   L   E   L   V   K   V
    *** *** *** *** *** *** *** *** *** *** *** *** *** *** ***

630
opt AAA GCT AAC GAA CCT CGC GAC GAG CAA AAA ATT AAG CAA GCA GAA
     K   A   N   E   P   R   D   E   Q   K   I   K   Q   A   E
ori AAA GCT AAC GAA CCT CGA GAC GAG CAA AAA ATT AAG CAA GCA GAA
     K   A   N   E   P   R   D   E   Q   K   I   K   Q   A   E
    *** *** *** *** *** **  *** *** *** *** *** *** *** *** ***
```

FIG. 62B

```
                                                                        675
opt GCG GAA GTT GAG AGT AAA CAA GCT GAG GCT ACA CGC TTA AAA AAA
     A   E   V   E   S   K   Q   A   E   A   T   R   L   K   K
ori GCG GAA GTT GAG AGT AAA CAA GCT GAG GCT ACA AGG TTA AAA AAA
     A   E   V   E   S   K   Q   A   E   A   T   R   L   K   K
    *** *** *** *** *** *** *** *** *** *** ***  *  *** *** ***

720
opt ATC AAG ACA GAT CGT GAA GAA GCA GAA GAA GAA GCT AAA CGC CGC
     I   K   T   D   R   E   E   A   E   E   E   A   K   R   R
ori ATC AAG ACA GAT CGT GAA GAA GCA GAA GAA GAA GCT AAA CGA AGA
     I   K   T   D   R   E   E   A   E   E   E   A   K   R   R
    *** *** *** *** *** *** *** *** *** *** *** *** ***  **   *

765
opt GCA GAT GCT AAA GAG CAA GGT AAA CCA AAG GGG CGC GCA AAA CGC
     A   D   A   K   E   Q   G   K   P   K   G   R   A   K   R
ori GCA GAT GCT AAA GAG CAA GGT AAA CCA AAG GGG CGG GCA AAA CGA
     A   D   A   K   E   Q   G   K   P   K   G   R   A   K   R
    *** *** *** *** *** *** *** *** *** *** ***  ** *** ***  **

810
opt GGA GTT CCT GGC GAG CTG GCA ACA CCT GAT AAA AAA GAA AAT GAT
     G   V   P   G   E   L   A   T   P   D   K   K   E   N   D
ori GGA GTT CCT GGA GAG CTA GCA ACA CCT GAT AAA AAA GAA AAT GAT
     G   V   P   G   E   L   A   T   P   D   K   K   E   N   D
    * * *   *   * * * * * * * * ***

855
opt GCG AAG TCT TCA GAT TCT AGC GTA GGT GAA GAA ACT CTT CCA AGC
     A   K   S   S   D   S   S   V   G   E   E   T   L   P   S
ori GCG AAG TCT TCA GAT TCT AGC GTA GGT GAA GAA ACT CTT CCA AGC
     A   K   S   S   D   S   S   V   G   E   E   T   L   P   S
    *** *** *** *** *** *** *** *** *** *** *** *** *** *** ***

900
opt CCA TCC CTG AAA CCA GAA AAA AAG GTA GCA GAA GCT GAG AAG AAG
     P   S   L   K   P   E   K   K   V   A   E   A   E   K   K
ori CCA TCC CTG AAA CCA GAA AAA AAG GTA GCA GAA GCT GAG AAG AAG
     P   S   L   K   P   E   K   K   V   A   E   A   E   K   K
    *** *** *** *** *** *** *** *** *** *** *** *** *** *** ***

945
opt GTT GAA GAA GCT AAG AAA AAA GCC GAG GAT CAA AAA GAA GAA GAT
     V   E   E   A   K   K   K   A   E   D   Q   K   E   E   D
ori GTT GAA GAA GCT AAG AAA AAA GCC GAG GAT CAA AAA GAA GAA GAT
     V   E   E   A   K   K   K   A   E   D   Q   K   E   E   D
    *** *** *** *** *** *** *** *** *** *** *** *** *** *** ***
```

FIG. 62C

```
                                                                           990
opt CGC CGT AAC TAC CCA ACC AAT ACT TAC AAA ACG CTT GAA CTT GAA
     R   R   N   Y   P   T   N   T   Y   K   T   L   E   L   E
ori CGC CGT AAC TAC CCA ACC AAT ACT TAC AAA ACG CTT GAA CTT GAA
     R   R   N   Y   P   T   N   T   Y   K   T   L   E   L   E
    *** *** *** *** *** *** *** *** *** *** *** *** *** *** ***

1035
opt ATT GCT GAG TCC GAT GTG GAA GTT AAA AAA GCG GAG CTT GAA CTG
     I   A   E   S   D   V   E   V   K   K   A   E   L   E   L
ori ATT GCT GAG TCC GAT GTG GAA GTT AAA AAA GCG GAG CTT GAA CTA
     I   A   E   S   D   V   E   V   K   K   A   E   L   E   L
    *** *** *** *** *** *** *** *** *** *** *** *** *** *** **

1080
opt GTA AAA GAG GAA GCT AAG GAA CCT CGC AAC GAG GAA AAA GTT AAG
     V   K   E   E   A   K   E   P   R   N   E   E   K   V   K
ori GTA AAA GAG GAA GCT AAG GAA CCT CGA AAC GAG GAA AAA GTT AAG
     V   K   E   E   A   K   E   P   R   N   E   E   K   V   K
    *** *** *** *** *** *** *** *** **  *** *** *** *** *** ***

1125
opt CAA GCA AAA GCG GAA GTT GAG AGT AAA AAA GCT GAG GCT ACT CGC
     Q   A   K   A   E   V   E   S   K   K   A   E   A   T   R
ori CAA GCA AAA GCG GAA GTT GAG AGT AAA AAA GCT GAG GCT ACT AGG
     Q   A   K   A   E   V   E   S   K   K   A   E   A   T   R
    *** *** *** *** *** *** *** *** *** *** *** *** *** ***  *

1170
opt TTA GAA AAA ATC AAG ACA GAT CGT AAA AAA GCA GAA GAA GAA GCT
     L   E   K   I   K   T   D   R   K   K   A   E   E   E   A
ori TTA GAA AAA ATC AAG ACA GAT CGT AAA AAA GCA GAA GAA GAA GCT
     L   E   K   I   K   T   D   R   K   K   A   E   E   E   A
    *** *** *** *** *** *** *** *** *** *** *** *** *** *** ***

1215
opt AAA CGC AAA GCA GCA GAA GAA GAT AAA GTT AAA GAA AAA CCA GCT
     K   R   K   A   A   E   E   D   K   V   K   E   K   P   A
ori AAA CGA AAA GCA GCA GAA GAA GAT AAA GTT AAA GAA AAA CCA GCT
     K   R   K   A   A   E   E   D   K   V   K   E   K   P   A
    *** **  *** *** *** *** *** *** *** *** *** *** *** *** ***
```

FIG. 62D

```
                                                                              45
opt  GAG AAC GAA GGC CTG CCA AGT ACC ACT TCT TCT AAT CGC GCA AAT
      E   N   E   G   L   P   S   T   T   S   S   N   R   A   N
ori  GAG AAC GAA GGA CTA CCA AGT ACC ACT TCT TCT AAT AGG GCA AAT
      E   N   E   G   L   P   S   T   T   S   S   N   R   A   N
     * * *     * * * * * * *  *  * *

90
opt  GAA AGT CAG GCA GAA CAA GGC GAA CAA CCT AAA AAA CTC GAT TCA
      E   S   Q   A   E   Q   G   E   Q   P   K   K   L   D   S
ori  GAA AGT CAG GCA GAA CAA GGA GAA CAA CCT AAA AAA CTC GAT TCA
      E   S   Q   A   E   Q   G   E   Q   P   K   K   L   D   S
     * * * * * *   * * * * * * * ***

135
opt  GAA CGC GAT AAG GCA CGC AAA GAG GTC GAG GAA TAT GTA AAA AAA
      E   R   D   K   A   R   K   E   V   E   E   Y   V   K   K
ori  GAA CGA GAT AAG GCA AGG AAA GAG GTC GAG GAA TAT GTA AAA AAA
      E   R   D   K   A   R   K   E   V   E   E   Y   V   K   K
     *   * * ***  *  * * * * * * * * ***

180
opt  ATC GTG GGT GAG AGC TAT GCA AAA TCA ACT AAA AAG CGC CAT ACA
      I   V   G   E   S   Y   A   K   S   T   K   K   R   H   T
ori  ATA GTG GGT GAG AGC TAT GCA AAA TCA ACT AAA AAG CGA CAT ACA
      I   V   G   E   S   Y   A   K   S   T   K   K   R   H   T
       * * * * * * * * * * *   * ***

225
opt  ATT ACT GTA GCT CTG GTT AAC GAG TTG AAC AAC ATT AAG AAC GAG
      I   T   V   A   L   V   N   E   L   N   N   I   K   N   E
ori  ATT ACT GTA GCT CTA GTT AAC GAG TTG AAC AAC ATT AAG AAC GAG
      I   T   V   A   L   V   N   E   L   N   N   I   K   N   E
     * * * *   * * * * * * * * * ***

270
opt  TAT TTG AAT AAA ATC GTT GAA TCA ACC TCA GAA AGC CAA CTA CAG
      Y   L   N   K   I   V   E   S   T   S   E   S   Q   L   Q
ori  TAT TTG AAT AAA ATA GTT GAA TCA ACC TCA GAA AGC CAA CTA CAG
      Y   L   N   K   I   V   E   S   T   S   E   S   Q   L   Q
     * * * *   * * * * * * * * * ***

315
opt  ATC CTG ATG ATG GAG AGT CGC TCA AAA GTA GAT GAA GCT GTG TCT
      I   L   M   M   E   S   R   S   K   V   D   E   A   V   S
ori  ATA CTG ATG ATG GAG AGT CGA TCA AAA GTA GAT GAA GCT GTG TCT
      I   L   M   M   E   S   R   S   K   V   D   E   A   V   S
       * * * * *   * * * * * * * ***
```

FIG. 63A

```
                                                                    360
opt AAG TTT GAA AAG GAC TCA TCT TCT TCG TCA AGT TCA GAC TCT TCC
     K   F   E   K   D   S   S   S   S   S   S   S   D   S   S
ori AAG TTT GAA AAG GAC TCA TCT TCT TCG TCA AGT TCA GAC TCT TCC
     K   F   E   K   D   S   S   S   S   S   S   S   D   S   S
    *** *** *** *** *** *** *** *** *** *** *** *** *** *** ***

405
opt ACT AAA CCG GAA GCT TCA GAT ACA GCG AAG CCA AAC AAG CCG ACA
     T   K   P   E   A   S   D   T   A   K   P   N   K   P   T
ori ACT AAA CCG GAA GCT TCA GAT ACA GCG AAG CCA AAC AAG CCG ACA
     T   K   P   E   A   S   D   T   A   K   P   N   K   P   T
    *** *** *** *** *** *** *** *** *** *** *** *** *** *** ***

450
opt GAA CCA GGC GAA AAG GTA GCA GAA GCT AAG AAG AAG GTT GAA GAA
     E   P   G   E   K   V   A   E   A   K   K   K   V   E   E
ori GAA CCA GGA GAA AAG GTA GCA GAA GCT AAG AAG AAG GTT GAA GAA
     E   P   G   E   K   V   A   E   A   K   K   K   V   E   E
    *** *** **  *** *** *** *** *** *** *** *** *** *** *** ***

495
opt GCT GAG AAA AAA GCC AAG GAT CAA AAA GAA GAA GAT CGT CGT AAC
     A   E   K   K   A   K   D   Q   K   E   E   D   R   R   N
ori GCT GAG AAA AAA GCC AAG GAT CAA AAA GAA GAA GAT CGT CGT AAC
     A   E   K   K   A   K   D   Q   K   E   E   D   R   R   N
    *** *** *** *** *** *** *** *** *** *** *** *** *** *** ***

540
opt TAC CCA ACC ATT ACT TAC AAA ACG CTT GAA CTT GAA ATT GCT GAG
     Y   P   T   I   T   Y   K   T   L   E   L   E   I   A   E
ori TAC CCA ACC ATT ACT TAC AAA ACG CTT GAA CTT GAA ATT GCT GAG
     Y   P   T   I   T   Y   K   T   L   E   L   E   I   A   E
    *** *** *** *** *** *** *** *** *** *** *** *** *** *** ***

585
opt TCC GAT GTG GAA GTT AAA AAA GCG GAG CTT GAA CTA GTA AAA GTG
     S   D   V   E   V   K   K   A   E   L   E   L   V   K   V
ori TCC GAT GTG GAA GTT AAA AAA GCG GAG CTT GAA CTA GTA AAA GTG
     S   D   V   E   V   K   K   A   E   L   E   L   V   K   V
    *** *** *** *** *** *** *** *** *** *** *** *** *** *** ***

630
opt AAA GCT AAC GAA CCT CGC GAC GAG CAA AAA ATT AAG CAA GCA GAA
     K   A   N   E   P   R   D   E   Q   K   I   K   Q   A   E
ori AAA GCT AAC GAA CCT CGA GAC GAG CAA AAA ATT AAG CAA GCA GAA
     K   A   N   E   P   R   D   E   Q   K   I   K   Q   A   E
    *** *** *** *** *** **  *** *** *** *** *** *** *** *** ***
```

FIG. 63B

```
                                                                    675
opt GCG GAA GTT GAG AGT AAA CAA GCT GAG GCT ACA CGC TTA AAA AAA
     A   E   V   E   S   K   Q   A   E   A   T   R   L   K   K
ori GCG GAA GTT GAG AGT AAA CAA GCT GAG GCT ACA AGG TTA AAA AAA
     A   E   V   E   S   K   Q   A   E   A   T   R   L   K   K
    *** *** *** *** *** *** *** *** *** *** ***  *  *** *** ***

720
opt ATC AAG ACA GAT CGT GAA GAA GCA GAA GAA GAA GCT AAA CGC CGC
     I   K   T   D   R   E   E   A   E   E   E   A   K   R   R
ori ATC AAG ACA GAT CGT GAA GAA GCA GAA GAA GAA GCT AAA CGA AGA
     I   K   T   D   R   E   E   A   E   E   E   A   K   R   R
    *** *** *** *** *** *** *** *** *** *** *** *** *** **   *

765
opt GCA GAT GCT AAA GAG CAA GGT AAA CCA AAG GGG CGC GCA AAA CGC
     A   D   A   K   E   Q   G   K   P   K   G   R   A   K   R
ori GCA GAT GCT AAA GAG CAA GGT AAA CCA AAG GGG CGG GCA AAA CGA
     A   D   A   K   E   Q   G   K   P   K   G   R   A   K   R
    *** *** *** *** *** *** *** *** *** *** *** **  *** *** **

810
opt GGA GTT CCT GGC GAG CTG GCA ACA CCT GAT AAA AAA GAA AAT GAT
     G   V   P   G   E   L   A   T   P   D   K   K   E   N   D
ori GGA GTT CCT GGA GAG CTA GCA ACA CCT GAT AAA AAA GAA AAT GAT
     G   V   P   G   E   L   A   T   P   D   K   K   E   N   D
    * * *   *   * * * * * * * * ***

855
opt GCG AAG TCT TCA GAT TCT AGC GTA GGT GAA GAA ACT CTT CCA AGC
     A   K   S   S   D   S   S   V   G   E   E   T   L   P   S
ori GCG AAG TCT TCA GAT TCT AGC GTA GGT GAA GAA ACT CTT CCA AGC
     A   K   S   S   D   S   S   V   G   E   E   T   L   P   S
    *** *** *** *** *** *** *** *** *** *** *** *** *** *** ***

900
opt CCA TCC CTG AAA CCA GAA AAA AAG GTA GCA GAA GCT GAG AAG AAG
     P   S   L   K   P   E   K   K   V   A   E   A   E   K   K
ori CCA TCC CTG AAA CCA GAA AAA AAG GTA GCA GAA GCT GAG AAG AAG
     P   S   L   K   P   E   K   K   V   A   E   A   E   K   K
    *** *** *** *** *** *** *** *** *** *** *** *** *** *** ***

945
opt GTT GAA GAA GCT AAG AAA AAA GCC GAG GAT CAA AAA GAA GAA GAT
     V   E   E   A   K   K   K   A   E   D   Q   K   E   E   D
ori GTT GAA GAA GCT AAG AAA AAA GCC GAG GAT CAA AAA GAA GAA GAT
     V   E   E   A   K   K   K   A   E   D   Q   K   E   E   D
    *** *** *** *** *** *** *** *** *** *** *** *** *** *** ***
```

FIG. 63C

```
                                                                              990
opt CGC CGT AAC TAC CCA ACC AAT ACT TAC AAA ACG CTT GAA CTT GAA
     R   R   N   Y   P   T   N   T   Y   K   T   L   E   L   E
ori CGC CGT AAC TAC CCA ACC AAT ACT TAC AAA ACG CTT GAA CTT GAA
     R   R   N   Y   P   T   N   T   Y   K   T   L   E   L   E
    *** *** *** *** *** *** *** *** *** *** *** *** *** *** ***

1035
opt ATT GCT GAG TCC GAT GTG GAA GTT AAA AAA GCG GAG CTT GAA CTG
     I   A   E   S   D   V   E   V   K   K   A   E   L   E   L
ori ATT GCT GAG TCC GAT GTG GAA GTT AAA AAA GCG GAG CTT GAA CTA
     I   A   E   S   D   V   E   V   K   K   A   E   L   E   L
    *** *** *** *** *** *** *** *** *** *** *** *** *** *** **

1080
opt GTA AAA GAG GAA GCT AAG GAA CCT CGC AAC GAG GAA AAA GTT AAG
     V   K   E   E   A   K   E   P   R   N   E   E   K   V   K
ori GTA AAA GAG GAA GCT AAG GAA CCT CGA AAC GAG GAA AAA GTT AAG
     V   K   E   E   A   K   E   P   R   N   E   E   K   V   K
    *** *** *** *** *** *** *** *** **  *** *** *** *** *** ***

1125
opt CAA GCA AAA GCG GAA GTT GAG AGT AAA AAA GCT GAG GCT ACT CGC
     Q   A   K   A   E   V   E   S   K   K   A   E   A   T   R
ori CAA GCA AAA GCG GAA GTT GAG AGT AAA AAA GCT GAG GCT ACT AGG
     Q   A   K   A   E   V   E   S   K   K   A   E   A   T   R
    *** *** *** *** *** *** *** *** *** *** *** *** *** ***  *

1170
opt TTA GAA AAA ATC AAG ACA GAT CGT AAA AAA GCA GAA GAA GAA GCT
     L   E   K   I   K   T   D   R   K   K   A   E   E   E   A
ori TTA GAA AAA ATC AAG ACA GAT CGT AAA AAA GCA GAA GAA GAA GCT
     L   E   K   I   K   T   D   R   K   K   A   E   E   E   A
    *** *** *** *** *** *** *** *** *** *** *** *** *** *** ***

1215
opt AAA CGC AAA GCA GCA GAA GAA GAT AAA GTT AAA GAA AAA CCA GCT
     K   R   K   A   A   E   E   D   K   V   K   E   K   P   A
ori AAA CGA AAA GCA GCA GAA GAA GAT AAA GTT AAA GAA AAA CCA GCT
     K   R   K   A   A   E   E   D   K   V   K   E   K   P   A
    *** **  *** *** *** *** *** *** *** *** *** *** *** *** ***

1260
opt GAA CAA CCA CAA CCA GCG CCG GCT CCA AAA GCA GAA AAA CCA GCT
     E   Q   P   Q   P   A   P   A   P   K   A   E   K   P   A
ori GAA CAA CCA CAA CCA GCG CCG GCT CCA AAA GCA GAA AAA CCA GCT
     E   Q   P   Q   P   A   P   A   P   K   A   E   K   P   A
    *** *** *** *** *** *** *** *** *** *** *** *** *** *** ***
```

FIG. 63D

```
                                                                    1305
opt CCA GCT CCA AAA CCA GAG AAT CCA GCT GAA CAA CCA AAA GCA GAA
     P   A   P   K   P   E   N   P   A   E   Q   P   K   A   E
ori CCA GCT CCA AAA CCA GAG AAT CCA GCT GAA CAA CCA AAA GCA GAA
     P   A   P   K   P   E   N   P   A   E   Q   P   K   A   E
    *** *** *** *** *** *** *** *** *** *** *** *** *** *** ***

1350
opt AAA CCA GCT GAT CAA CAA GCT GAA GAA GAG TAT GCT CGT AGA TCA
     K   P   A   D   Q   Q   A   E   E   E   Y   A   R   R   S
ori AAA CCA GCT GAT CAA CAA GCT GAA GAA GAG TAT GCT CGT AGA TCA
     K   P   A   D   Q   Q   A   E   E   E   Y   A   R   R   S
    *** *** *** *** *** *** *** *** *** *** *** *** *** *** ***

1395
opt GAA GAA GAA TAT AAT CGC TTG ACT CTA CAG CAA CCG CCA AAA ACT
     E   E   E   Y   N   R   L   T   L   Q   Q   P   P   K   T
ori GAA GAA GAA TAT AAT CGC TTG ACT CTA CAG CAA CCG CCA AAA ACT
     E   E   E   Y   N   R   L   T   L   Q   Q   P   P   K   T
    *** *** *** *** *** *** *** *** *** *** *** *** *** *** ***

1433
opt GAA AAA CCA GCA CAA CCA TCT ACT CCA AAA ACA AAT AC
     E   K   P   A   Q   P   S   T   P   K   T   N
ori GAA AAA CCA GCA CAA CCA TCT ACT CCA AAA ACA AAT AC
     E   K   P   A   Q   P   S   T   P   K   T   N
    *** *** *** *** *** *** *** *** *** *** *** *** **
```

FIG. 63E

```
                                                                          45
ori GTC CAT GCA GAA GGG GTT AGA AGT GGG AAT AAC CTC ACG GTT ACA
     V   H   A   E   G   V   R   S   G   N   N   L   T   V   T
opt GTC CAT GCA GAA GGG GTT CGC AGT GGG AAT AAC CTC ACG GTT ACA
     V   H   A   E   G   V   R   S   G   N   N   L   T   V   T
    *** *** *** *** *** ***  *  *** *** *** *** *** *** *** ***

90
ori TCT AGT GGG CAA GAT ATA TCG AAG AAG TAT GCT GAT GAA GTC GAG
     S   S   G   Q   D   I   S   K   K   Y   A   D   E   V   E
opt TCT AGT GGG CAA GAT ATC TCG AAG AAG TAT GCT GAT GAA GTC GAG
     S   S   G   Q   D   I   S   K   K   Y   A   D   E   V   E
    *** *** *** *** *** **  *** *** *** *** *** *** *** *** ***

135
ori TCG CAT CTA GAA AGT ATA TTG AAG GAT GTC AAA AAA AAT TTG AAA
     S   H   L   E   S   I   L   K   D   V   K   K   N   L   K
opt TCG CAT CTG GAA AGT ATC TTG AAG GAT GTC AAA AAA AAT TTG AAA
     S   H   L   E   S   I   L   K   D   V   K   K   N   L   K
    *** *** **  *** *** **  *** *** *** *** *** *** *** *** ***

180
ori AAA GTT CAA CAT ACC CAA AAT GTC GGC TTA ATT ACA AAG TTG AGC
     K   V   Q   H   T   Q   N   V   G   L   I   T   K   L   S
opt AAA GTT CAA CAT ACC CAA AAT GTC GGC TTA ATT ACA AAG TTG AGC
     K   V   Q   H   T   Q   N   V   G   L   I   T   K   L   S
    *** *** *** *** *** *** *** *** *** *** *** *** *** *** ***

225
ori GAA ATT AAA AAG AAG TAT TTG TAT GAC TTA AAA GTT AAT GTT TTA
     E   I   K   K   K   Y   L   Y   D   L   K   V   N   V   L
opt GAA ATT AAA AAG AAG TAT TTG TAT GAC TTA AAA GTT AAT GTT TTA
     E   I   K   K   K   Y   L   Y   D   L   K   V   N   V   L
    *** *** *** *** *** *** *** *** *** *** *** *** *** *** ***

270
ori TCG GAA GCT GAG TTG ACG TCA AAA ACA AAA GAA ACA AAA GAA AAG
     S   E   A   E   L   T   S   K   T   K   E   T   K   E   K
opt TCG GAA GCT GAG TTG ACG TCA AAA ACA AAA GAA ACA AAA GAA AAG
     S   E   A   E   L   T   S   K   T   K   E   T   K   E   K
    *** *** *** *** *** *** *** *** *** *** *** *** *** *** ***

315
ori TTA ACC GCA ACT TTT GAG CAG TTT AAA AAA GAT ACA TTA CCA ACA
     L   T   A   T   F   E   Q   F   K   K   D   T   L   P   T
opt TTA ACC GCA ACT TTT GAG CAG TTT AAA AAA GAT ACA TTA CCA ACA
     L   T   A   T   F   E   Q   F   K   K   D   T   L   P   T
    *** *** *** *** *** *** *** *** *** *** *** *** *** *** ***
```

FIG. 64A

```
                                                                        360
ori GAA CCA GAA AAA AAG GTA GCA GAA GCT CAG AAG AAG GTT GAA GAA
     E   P   E   K   K   V   A   E   A   Q   K   K   V   E   E
opt GAA CCA GAA AAA AAG GTA GCA GAA GCT CAG AAG AAG GTT GAA GAA
     E   P   E   K   K   V   A   E   A   Q   K   K   V   E   E
    *** *** *** *** *** *** *** *** *** *** *** *** *** *** ***

405
ori GCT AAG AAA AAA GCC GAG GAT CAA AAA GAA AAA GAT CGC CGT AAC
     A   K   K   K   A   E   D   Q   K   E   K   D   R   R   N
opt GCT AAG AAA AAA GCC GAG GAT CAA AAA GAA AAA GAT CGC CGT AAC
     A   K   K   K   A   E   D   Q   K   E   K   D   R   R   N
    *** *** *** *** *** *** *** *** *** *** *** *** *** *** ***

450
ori TAC CCA ACC ATT ACT TAC AAA ACG CTT GAA CTT GAA ATT GCT GAG
     Y   P   T   I   T   Y   K   T   L   E   L   E   I   A   E
opt TAC CCA ACC ATT ACT TAC AAA ACG CTT GAA CTT GAA ATT GCT GAG
     Y   P   T   I   T   Y   K   T   L   E   L   E   I   A   E
    *** *** *** *** *** *** *** *** *** *** *** *** *** *** ***

495
ori TCC GAT GTG GAA GTT AAA AAA GCG GAG CTT GAA CTA GTA AAA GTG
     S   D   V   E   V   K   K   A   E   L   E   L   V   K   V
opt TCC GAT GTG GAA GTT AAA AAA GCG GAG CTT GAA CTG GTA AAA GTG
     S   D   V   E   V   K   K   A   E   L   E   L   V   K   V
    *** *** *** *** *** *** *** *** *** *** *** **  *** *** ***

540
ori AAA GCT AAG GAA TCT CAA GAC GAG GAA AAA ATT AAG CAA GCA GAA
     K   A   K   E   S   Q   D   E   E   K   I   K   Q   A   E
opt AAA GCT AAG GAA TCT CAA GAC GAG GAA AAA ATT AAG CAA GCA GAA
     K   A   K   E   S   Q   D   E   E   K   I   K   Q   A   E
    *** *** *** *** *** *** *** *** *** *** *** *** *** *** ***

585
ori GCG GAA GTT GAG AGT AAA CAA GCT GAG GCT ACA AGG TTA AAA AAA
     A   E   V   E   S   K   Q   A   E   A   T   R   L   K   K
opt GCG GAA GTT GAG AGT AAA CAA GCT GAG GCT ACA CGC TTA AAA AAA
     A   E   V   E   S   K   Q   A   E   A   T   R   L   K   K
    *** *** *** *** *** *** *** *** *** *** ***  *  *** *** ***

630
ori ATC AAG ACA GAT CGT GAA GAA GCT AAA CGA AAA GCA GAT GCT AAG
     I   K   T   D   R   E   E   A   K   R   K   A   D   A   K
opt ATC AAG ACA GAT CGT GAA --- GCT AAA CGC AAA GCA GAT GCT AAG
     I   K   T   D   R       A   K   R   K   A   D   A   K
    *** *** *** *** *** ***     *** *** **  *** *** *** *** ***
```

FIG. 64B

```
                                                                    675
ori TTG AAG GAA GCT GTT GAA AAG AAT GTA GCG ACT TCA GAG CAA GAT
     L   K   E   A   V   E   K   N   V   A   T   S   E   Q   D
opt TTG AAG GAA GCT GTT GAA AAG AAT GTA GCG ACT TCA GAG CAA GAT
     L   K   E   A   V   E   K   N   V   A   T   S   E   Q   D
    *** *** *** *** *** *** *** *** *** *** *** *** *** *** ***

720
ori AAA CCA AAG AGG CGG GCA AAA CGA GGA GTT TCT GGA GAG CTA GCA
     K   P   K   R   R   A   K   R   G   V   S   G   E   L   A
opt AAA CCA AAG CGG CGC GCA AAA CGC GGC GTT TCT GGC GAG CTG GCA
     K   P   K   R   R   A   K   R   G   V   S   G   E   L   A
    *** *** ***  ** **  *** ***  **  ** *** *** **  *** **  ***

765
ori ACA CCT GAT AAA AAA GAA AAT GAT GCG AAG TCT TCA GAT TCT AGC
     T   P   D   K   K   E   N   D   A   K   S   S   D   S   S
opt ACA CCT GAT AAA AAA GAA AAT GAT GCG AAG TCT TCA GAT TCT AGC
     T   P   D   K   K   E   N   D   A   K   S   S   D   S   S
    *** *** *** *** *** *** *** *** *** *** *** *** *** *** ***

810
ori GTA GGT GAA GAA ACT CTT CCA AGC CCA TCC CTT AAT ATG GCA AAT
     V   G   E   E   T   L   P   S   P   S   L   N   M   A   N
opt GTA GGT GAA GAA ACT CTT CCA AGC CCA TCC CTT AAT ATG GCA AAT
     V   G   E   E   T   L   P   S   P   S   L   N   M   A   N
    *** *** *** *** *** *** *** *** *** *** *** *** *** *** ***

855
ori GAA AGT CAG ACA GAA CAT AGG AAA GAT GTC GAT GAA TAT ATA AAA
     E   S   Q   T   E   H   R   K   D   V   D   E   Y   I   K
opt GAA AGT CAG ACA GAA CAT CGG AAA GAT GTC GAT GAA TAT ATC AAA
     E   S   Q   T   E   H   R   K   D   V   D   E   Y   I   K
    *** *** *** *** *** *** *** *** *** *** *** *** ***  ** ***

900
ori AAA ATG TTG AGT GAG ATC CAA TTA GAT AGA AGA AAA CAT ACC CAA
     K   M   L   S   E   I   Q   L   D   R   R   K   H   T   Q
opt AAA ATG TTG AGT GAG ATC CAA TTA GAT CGC CGC AAA CAT ACC CAA
     K   M   L   S   E   I   Q   L   D   R   R   K   H   T   Q
    *** *** *** *** *** *** *** *** ***  *   *  *** *** *** ***

945
ori AAT GTC AAC TTA AAC ATA AAG TTG AGC GCA ATT AAA ACG AAG TAT
     N   V   N   L   N   I   K   L   S   A   I   K   T   K   Y
opt AAT GTC AAC TTA AAC ATC AAG TTG AGC GCA ATT AAA ACG AAG TAT
     N   V   N   L   N   I   K   L   S   A   I   K   T   K   Y
    *** *** *** *** *** **  *** *** *** *** *** *** *** *** ***
```

FIG. 64C

```
                                                                     990
ori TTG TAT GAA TTA AGT GTT TTA AAA GAG AAC TCG AAA AAA GAA GAG
     L   Y   E   L   S   V   L   K   E   N   S   K   K   E   E
opt TTG TAT GAA TTA AGT GTT TTA AAA GAG AAC TCG AAA AAA GAA GAG
     L   Y   E   L   S   V   L   K   E   N   S   K   K   E   E
    *** *** *** *** *** *** *** *** *** *** *** *** *** *** ***
                                                                    1035
ori TTG ACG TCA AAA ACC AAA GCA GAG TTA ACC GCA GCT TTT GAG CAG
     L   T   S   K   T   K   A   E   L   T   A   A   F   E   Q
opt TTG ACG TCA AAA ACC AAA GCA GAG TTA ACC GCA GCT TTT GAG CAG
     L   T   S   K   T   K   A   E   L   T   A   A   F   E   Q
    *** *** *** *** *** *** *** *** *** *** *** *** *** *** ***
                                                                    1080
ori TTT AAA AAA GAT ACA TTG AAA CCA GAA AAA AAG GTA GCA GAA GCT
     F   K   K   D   T   L   K   P   E   K   K   V   A   E   A
opt TTT AAA AAA GAT ACA TTG AAA CCA GAA AAA AAG GTA GCA GAA GCT
     F   K   K   D   T   L   K   P   E   K   K   V   A   E   A
    *** *** *** *** *** *** *** *** *** *** *** *** *** *** ***
                                                                    1125
ori GAG AAG AAG GTT GAA GAA GCT AAG AAA AAA GCC AAG GAT CAA AAA
     E   K   K   V   E   E   A   K   K   K   A   K   D   Q   K
opt GAG AAG AAG GTT GAA GAA GCT AAG AAA AAA GCC AAG GAT CAA AAA
     E   K   K   V   E   E   A   K   K   K   A   K   D   Q   K
    *** *** *** *** *** *** *** *** *** *** *** *** *** *** ***
                                                                    1170
ori GAA GAA GAT CGC CGT AAC TAC CCA ACC AAT ACT TAC AAA ACG CTT
     E   E   D   R   R   N   Y   P   T   N   T   Y   K   T   L
opt GAA GAA GAT CGC CGT AAC TAC CCA ACC AAT ACT TAC AAA ACG CTT
     E   E   D   R   R   N   Y   P   T   N   T   Y   K   T   L
    *** *** *** *** *** *** *** *** *** *** *** *** *** *** ***
                                                                    1215
ori GAA CTT GAA ATT GCT GAG TCC GAT GTG AAA GTT AAA GAA GCG GAG
     E   L   E   I   A   E   S   D   V   K   V   K   E   A   E
opt GAA CTT GAA ATT GCT GAG TCC GAT GTG AAA GTT AAA GAA GCG GAG
     E   L   E   I   A   E   S   D   V   K   V   K   E   A   E
    *** *** *** *** *** *** *** *** *** *** *** *** *** *** ***
                                                                    1260
ori CTT GAA CTA GTA AAA GAG GAA GCT AAC GAA TCT CGA AAC GAG GAA
     L   E   L   V   K   E   E   A   N   E   S   R   N   E   E
opt CTC GAA CTA GTA AAA GAG GAA GCT AAC GAA TCT CGC AAC GAG GAA
     L   E   L   V   K   E   E   A   N   E   S   R   N   E   E
    **  *** *** *** *** *** *** *** *** *** *** **  *** *** ***
```

FIG. 64D

```
                                                                        1305
ori AAA ATT AAG CAA GCA AAA GAG AAA GTT GAG AGT AAA AAA GCT GAG
     K   I   K   Q   A   K   E   K   V   E   S   K   K   A   E
opt AAA ATT AAG CAA GCA AAA GAG AAA GTT GAG AGT AAA AAA GCT GAG
     K   I   K   Q   A   K   E   K   V   E   S   K   K   A   E
    *** *** *** *** *** *** *** *** *** *** *** *** *** *** ***

1350
ori GCT ACA AGG TTA GAA AAA ATC AAG ACA GAT CGT AAA AAA GCA GAA
     A   T   R   L   E   K   I   K   T   D   R   K   K   A   E
opt GCT ACA CGC TTA GAA AAA ATC AAG ACA GAT CGT AAA AAA GCA GAA
     A   T   R   L   E   K   I   K   T   D   R   K   K   A   E
    *** ***  *  *** *** *** *** *** *** *** *** *** *** *** ***

1395
ori GAA GAA GCT AAA CGA AAA GCA GAA GAA TCT GAG AAA AAA GCT GCT
     E   E   A   K   R   K   A   E   E   S   E   K   K   A   A
opt GAA GAA GCT AAA CGC AAA GCA GAA GAA TCT GAG AAA AAA GCT GCT
     E   E   A   K   R   K   A   E   E   S   E   K   K   A   A
    *** *** *** *** **  *** *** *** *** *** *** *** *** *** ***

1440
ori GAA GCC AAA CAA AAA GTG GAT GCT GAA GAA TAT GCT CTT GAA GCT
     E   A   K   Q   K   V   D   A   E   E   Y   A   L   E   A
opt GAA GCC AAA CAA AAA GTG GAT GCT GAA GAA TAT GCT CTT GAA GCT
     E   A   K   Q   K   V   D   A   E   E   Y   A   L   E   A
    *** *** *** *** *** *** *** *** *** *** *** *** *** *** ***

1485
ori AAA ATC GCT GAG TTG GAA TAT GAA GTT CAG AGA CTA GAA AAA GAG
     K   I   A   E   L   E   Y   E   V   Q   R   L   E   K   E
opt AAA ATC GCT GAG TTG GAA TAT GAA GTT CAG CGC CTG GAA AAA GAG
     K   I   A   E   L   E   Y   E   V   Q   R   L   E   K   E
    *** *** *** *** *** *** *** *** *** ***  *  ** *** *** ***

1530
ori CTC AAA GAG ATT GAT GAG TCT GAC TCA GAA GAT TAT CTT AAA GAA
     L   K   E   I   D   E   S   D   S   E   D   Y   L   K   E
opt CTC AAA GAG ATT GAT GAG TCT GAC TCA GAA GAT TAT CTT AAA GAA
     L   K   E   I   D   E   S   D   S   E   D   Y   L   K   E
    *** *** *** *** *** *** *** *** *** *** *** *** *** *** ***

1575
ori GGC CTC CGT GCT CCT CTT CAA TCT AAA TTG GAT ACC AAA AAA GCT
     G   L   R   A   P   L   Q   S   K   L   D   T   K   K   A
opt GGC CTC CGT GCT CCT CTT CAA TCT AAA TTG GAT ACC AAA AAA GCT
     G   L   R   A   P   L   Q   S   K   L   D   T   K   K   A
    *** *** *** *** *** *** *** *** *** *** *** *** *** *** ***
```

FIG. 64E

```
                                                                    1620
ori AAA CTA TCA AAA CTT GAA GAG TTG AGT GAT AAG ATT GAT GAG TTA
     K   L   S   K   L   E   E   L   S   D   K   I   D   E   L
opt AAA CTG TCA AAA CTT GAA GAG TTG AGT GAT AAG ATT GAT GAG TTA
     K   L   S   K   L   E   E   L   S   D   K   I   D   E   L
    *** **  *** *** *** *** *** *** *** *** *** *** *** *** ***

1665
ori GAC GCT GAA ATT GCA AAA CTT GAA GTT CAA CTT AAA GAT GCT GAA
     D   A   E   I   A   K   L   E   V   Q   L   K   D   A   E
opt GAC GCT GAA ATT GCA AAA CTT GAA GTT CAA CTT AAA GAT GCT GAA
     D   A   E   I   A   K   L   E   V   Q   L   K   D   A   E
    *** *** *** *** *** *** *** *** *** *** *** *** *** *** ***

1710
ori GGA AAC AAT AAT GTA GAA GCC TAC TTT AAA GAA GGT TTA GAG AAA
     G   N   N   N   V   E   A   Y   F   K   E   G   L   E   K
opt GGA AAC AAT AAT GTA GAA GCC TAC TTT AAA GAA GGT TTA GAG AAA
     G   N   N   N   V   E   A   Y   F   K   E   G   L   E   K
    *** *** *** *** *** *** *** *** *** *** *** *** *** *** ***

1755
ori ACT ACT GCT GAG AAA AAA GCT GAA TTA GAA AAA GCT GAA GCT GAC
     T   T   A   E   K   K   A   E   L   E   K   A   E   A   D
opt ACT ACT GCT GAG AAA AAA GCT GAA TTA GAA AAA GCT GAA GCT GAC
     T   T   A   E   K   K   A   E   L   E   K   A   E   A   D
    *** *** *** *** *** *** *** *** *** *** *** *** *** *** ***

1800
ori CTT AAG AAA GCA GTT GAT GAG CCA GAA ACT CCA GCT CCG GCT CCT
     L   K   K   A   V   D   E   P   E   T   P   A   P   A   P
opt CTT AAG AAA GCA GTT GAT GAG CCA GAA ACT CCA GCT CCG GCT CCT
     L   K   K   A   V   D   E   P   E   T   P   A   P   A   P
    *** *** *** *** *** *** *** *** *** *** *** *** *** *** ***

1845
ori CAA CCA GCT CCA GCT CCA GAA AAA CCA GCT GAA AAA CCA GCT CCA
     Q   P   A   P   A   P   E   K   P   A   E   K   P   A   P
opt CAA CCA GCT CCA GCT CCA GAA AAA CCA GCT GAA AAA CCA GCT CCA
     Q   P   A   P   A   P   E   K   P   A   E   K   P   A   P
    *** *** *** *** *** *** *** *** *** *** *** *** *** *** ***

1890
ori GCT CCA GAA AAA CCA GCT CCA GCT CCA GAA AAA CCA GCT CCA GCT
     A   P   E   K   P   A   P   A   P   E   K   P   A   P   A
opt GCT CCA GAA AAA CCA GCT CCA GCT CCA GAA AAA CCA GCT CCA GCT
     A   P   E   K   P   A   P   A   P   E   K   P   A   P   A
    *** *** *** *** *** *** *** *** *** *** *** *** *** *** ***
```

FIG. 64F

```
                                                                   1935
ori CCA GAA AAA CCA GCT CCA GCT CCA GAA AAA CCA GCT CCA GCT CCA
     P   E   K   P   A   P   A   P   E   K   P   A   P   A   P
opt CCA GAA AAA CCA GCT CCA GCT CCA GAA AAA CCA GCT CCA GCT CCA
     P   E   K   P   A   P   A   P   E   K   P   A   P   A   P
    *** *** *** *** *** *** *** *** *** *** *** *** *** *** ***

1980
ori GAA AAA CCA GCT CCA ACT CCA GAA ACT CCA AAA ACA GGC TGG AAA
     E   K   P   A   P   T   P   E   T   P   K   T   G   W   K
opt GAA AAA CCA GCT CCA ACT CCA GAA ACT CCA AAA ACA GGC TGG AAA
     E   K   P   A   P   T   P   E   T   P   K   T   G   W   K
    *** *** *** *** *** *** *** *** *** *** *** *** *** *** ***

2025
ori CAA GAA AAC GGT ATG TGG TAC TTC TAC AAT ACT GAT GGT TCA ATG
     Q   E   N   G   M   W   Y   F   Y   N   T   D   G   S   M
opt CAA GAA AAC GGT ATG TGG TAC TTC TAC AAT ACT GAT GGT TCA ATG
     Q   E   N   G   M   W   Y   F   Y   N   T   D   G   S   M
    *** *** *** *** *** *** *** *** *** *** *** *** *** *** ***

2070
ori GCA ACA GGC TGG CTC CAA AAC AAT GGC TCA TGG TAC TAC CTC AAC
     A   T   G   W   L   Q   N   N   G   S   W   Y   Y   L   N
opt GCA ACA GGC TGG CTC CAA AAC AAT GGC TCA TGG TAC TAC CTC AAC
     A   T   G   W   L   Q   N   N   G   S   W   Y   Y   L   N
    *** *** *** *** *** *** *** *** *** *** *** *** *** *** ***
```

FIG. 64G

```
GAATTCGAGAACGAAGGCCTGCCAAGTACCACTTCTTCTAATCGCGCAAATGAAAGTCA
GGCAGAACAAGGCGAACAACCTAAAAAACTCGATTCAGAACGCGATAAGGCACGCAA
AGAGGTCGAGGAATATGTAAAAAAAATCGTGGGTGAGAGCTATGCAAAATCAACTAAA
AAGCGCCATACAATTACTGTAGCTCTGGTTAACGAGTTGAACAACATTAAGAACGAGTA
TTTGAATAAAATCGTTGAATCAACCTCAGAAAGCCAACTACAGATCCTGATGATGGAGA
GTCGCTCAAAAGTAGATGAAGCTGTGTCTAAGTTTGAAAAGGACTCATCTTCTTCGTCA
AGTTCAGACTCTTCCACTAAACCGGAAGCTTCAGATACAGCGAAGCCAAACAAGCCGA
CAGAACCAGGCGAAAAGGTAGCAGAAGCTAAGAAGAAGGTTGAAGAAGCTGAGAAAA
AAGCCAAGGATCAAAAGAAGAAGATCGTCGTAACTACCCAACCATTACTTACAAAAC
GCTTGAACTTGAAATTGCTGAGTCCGATGTGGAAGTTAAAAAAGCGGAGCTTGAACTAG
TAAAAGTGAAAGCTAACGAACCTCGCGACGAGCAAAAAATTAAGCAAGCAGAAGCGG
AAGTTGAGAGTAAACAAGCTGAGGCTACACGCTTAAAAAAAATCAAGACAGATCGTGA
AGAAGCAGAAGAAGAAGCTAAACGCCGCGCAGATGCTAAAGAGCAAGGTAAACCAAA
GGGGCGCGCAAAACGCGGAGTTCCTGGCGAGCTGGCAACACCTGATAAAAAAGAAAAT
GATGCGAAGTCTTCAGATTCTAGCGTAGGTGAAGAAACTCTTCCAAGCCCATCCCTGAA
ACCAGAAAAAAGGTAGCAGAAGCTGAGAAGAAGGTTGAAGAAGCTAAGAAAAAAGC
CGAGGATCAAAAGAAGAAGATCGCCGTAACTACCCAACCAATACTTACAAAACGCTT
GAACTTGAAATTGCTGAGTCCGATGTGGAAGTTAAAAAAGCGGAGCTTGAACTGGTAA
AGAGGAAGCTAAGGAACCTCGCAACGAGGAAAAAGTTAAGCAAGCAAAGCGGAAG
TTGAGAGTAAAAAAGCTGAGGCTACTCGCTTAGAAAAAATCAAGACAGATCGTAAAAA
AGCAGAAGAAGAAGCTAAACGCAAAGCAGCAGAAGAAGATAAAGTTAAAGAAAAACC
AGCTGAACAACCACAACCAGCGCCGGCTCCAAAAGCAGAAAAACCAGCTCCAGCTCCA
AAACCAGAGAATCCAGCTGAACAACCAAAAGCAGAAAAACCAGCTGATCAACAAGCT
GAAGAAGAGTATGCTCGTAGATCAGAAGAAGAATATAATCGCTTGACTCTACAGCAAC
CGCCAAAAACTGAAAAACCAGCACAACCATCTACTCCAAAAACACTGCAGGTTCGCAG
TGGGAATAACCTCACGGTTACATCTAGTGGGCAAGATATCTCGAAGAAGTATGCTGATG
AAGTCGAGTCGCATCTGGAAAGTATCTTGAAGGATGTCAAAAAAAATTTGAAAAAAGT
TCAACATACCCAAAATGTCGGCTTAATTACAAAGTTGAGCGAAATTAAAAAGAAGTATT
TGTATGACTTAAAAGTTAATGTTTTATCGGAAGCTGAGTTGACGTCAAAAACAAAAGAA
ACAAAAGAAAAGTTAACCGCAACTTTTGAGCAGTTTAAAAAAGATACATTACCAACAG
AAACTACCCAAGCACCCACTTCTTCTAATAGGGGAAATGAAAGTCAGGCAGAACAACG
TAGAGAACTCGATTTAGAACGAGATAAGGTAAAGAAAGAGGTCAGGGAATATAAAGA
AAAAAAAGTGAAAGAGCTCTATTCAAAATCAACTAAAAGTCGACATAAGAAGACTGTA
GATATAGTTAACAAGTTGCAAAACATTAATAACGAGTATTTGAATAAAATAATTCAATC
AACCTCAACATACGAAGAACTGCAGAAACTGATGATGGAGAGTCAATCCCTTAATATG
GCAAATGAAAGTCAGACAGAACATCGGAAAGATGTCGATGAATATATCAAAAAAATGT
TGAGTGAGATCCAATTAGATCGCCGCAAACATACCCAAAATGTCAACTTAAACATCAAG
TTGAGCGCAATTAAAACGAAGTATTTGTATGAATTAAGTGTTTTAAAAGAGAACTCGAA
AAAAGAAGAGTTGACGTCAAAAACCAAAGCAGAGTTAACCGCAGCTTTTGAGCAGTTT
AAAAAAGATGATTATTTTGAAAAAGACTTCCGTCCAGCTTTCAATAAAAACCGGCAGAT
```

FIG. 65A

```
GGTAGCCATTCAAGAATCCTTGAACAAACTAGATGGTGAAACAAAAACTGTTCCAGAT
GGGGCTAAACTCACAGGAGAAGCTGGAAATGCCTATAATGAGGTCAGAGATTATGCAA
TAAAAGTTGTTTCTGAAAACAAGAAACTTCTATCACAGACAGCAGTGACAATGGATGA
ACTGGCAATGCAATTAACCAAATTGAACGATGCCATGTCTAAATTGAGAGAGGCTAAA
GCGAAATTGGTAAAAGAAAAAGATCGCCGTAACTACCCAACCATTACTTACAAAACGA
AAGCTGCTGAAGCCAAACAAAAAGTGGATGCTGAAGAATATGCTCTTGAAGCTAAAAT
CGCTGAGTTGGAATATGAAGTTCAGCGCCTGGAAAAAGAGCTCAAAGAGATTGATGAG
TCTGACTCAGAAGATTATCTTAAAGAAGGCCTCCGTGCTCCTCTTCAATCTAAATTGGAT
ACCAAAAAAGCTAAACTGTCAAAACTTGAAGAGTTGAGTGATAAGATTGATGAGTTAG
ACGCTGAAATTGCAAAACTTGAAGTTCAACTTAAAGATGCTGAAGGAAACAATAATGT
AGAAGCCTACTTTAAAGAAGGTTTAGAGAAAACTACTGCTGAGAAAAAAGCTGAATTA
GAAAAAGCTGAAGCTGACCTTAAGAAAGCAGTTGATGAGCCAGAAACTCCAGCTCCGG
CTCCTCAACCAGCTCCAGCTCCAGAAAAACCAGCTGAAAAACCAGCTCCAGCTCCAGA
AAAACCAGCTCCAGCTCCAGAAAAACCAGCTCCAGCTCCAGAAAAACCAGCTCCAGCT
CCAGAAAAACCAGCTCCAGCTCCAGAAAAACCAGCTCCAACTCCAGAAACTCCAAAAA
CAGGCTGGAAACAAGAAAACGGTATGAAGCTT
```

FIG. 65B

EGLPSTTSSNRANESQAEQGEQPKKLDSERDKARKEVEEYVKKIVGESYAKSTKKRHTIT
VALVNELNNIKNEYLNKIVESTSESQLQILMMESRSKVDEAVSKFEKDSSSSSSSDSSTKP
EASDTAKPNKPTEPGEKVAEAKKKVEEAEKKAKDQKEEDRRNYPTITYKTLELEIAESDVE
VKKAELELVKVKANEPRDEQKIKQAEAEVESKQAEATRLKKIKTDREEAEEEAKRRADAKE
QGKPKGRAKRGVPGELATPDKKENDAKSSDSSVGEETLPSPSLKPEKKVAEAEKKVEEA
KKKAEDQKEEDRRNYPTNTYKTLELEIAESDVEVKKAELELVKEEAKEPRNEEKVKQAKAE
VESKKAEATRLEKIKTDRKKAEEEAKRKAAEEDKVKEKPAEQPQPAPAPKAEKPAPAPKP
ENPAEQPKAEKPADQQAEEEYARRSEEEYNRLTLQQPPKTEKPAQPSTPKTLQVRSGNN
LTVTSSGQDISKKYADEVESHLESILKDVKKNLKKVQHTQNVGLITKLSEIKKKYLYDLKVNV
LSEAELTSKTKETKEKLTATFEQFKKDTLPTETTQAPTSSNRGNESQAEQRRELDLERDKV
KKEVREYKEKKVKELYSKSTKSRHKKTVDIVNKLQNINNEYLNKIIQSTSTYEELQKLMMES
QSLNMANESQTEHRKDVDEYIKKMLSEIQLDRRKHTQNVNLNIKLSAIKTKYLYELSVLKEN
SKKEELTSKTKAELTAAFEQFKKDDYFEKDFRPAFNKNRQMVAIQESLNKLDGETKTVPD
GAKLTGEAGNAYNEVRDYAIKVVSENKKLLSQTAVTMDELAMQLTKLNDAMSKLREAKAK
LVKEKDRRNYPTITYKTKAAEAKQKVDAEEYALEAKIAELEYEVQRLEKELKEIDESDSEDY
LKEGLRAPLQSKLDTKKAKLSKLEELSDKIDELDAEIAKLEVQLKDAEGNNNVEAYFKEGLE
KTTAEKKAELEKAEADLKKAVDEPETPAPAPQPAPAPEKPAEKPAPAPEKPAPAPEKPAP
APEKPAPAPEKPAPAPEKPAPTPETPKTG

FIG. 65C

```
              1
original:     ACG ACT GAT GAC AAA ATT GCT GCT CAA GAT AAT AAA ATT AGT AAC TTA ACA GCA CAA CAA     60
Amino Acid:    T   T   D   D   K   I   A   A   Q   D   N   K   I   S   N   L   T   A   Q   Q
Optimi :                                                                   CTG ACC 61
original:     CAA GAA GCC CAA AAA CAA ATT CAG GAG CAA GTT GAC CAA ATT CAG GCT ATT CAA GCT GAG    120
Amino Acid:    Q   E   A   Q   K   Q   I   Q   E   Q   V   D   Q   I   Q   A   I   Q   A   E
Optimi :                                                   TCC 121
original:     CAG TCT AAC TTG CAA GCT GAA AAT GAT AGA TTA CAA GCA GAA TCT AAG AAA CTC GAG GGT    180
Amino Acid:    Q   S   N   L   Q   A   E   N   D   R   L   Q   A   E   S   K   K   L   E   G
Optimi :                                       CGC CTG 181
original:     GAG ATT ACA GAA CTT TCT AAA AAT ATT GTT TCT CGT AAC CAA TCG TTG GAA AAA CAA GCT    240
Amino Acid:    E   I   T   E   L   S   K   N   I   V   S   R   N   Q   S   L   E   K   Q   A
Optimi :              ACC 241
original:     CGT AGT GCT CAA ACA AAT GGA GCC GTA ACT AGC TAT ATC AAT ACC ATT GTA AAC TCA AAA    300
Amino Acid:    R   S   A   Q   T   N   G   A   V   T   S   Y   I   N   T   I   V   N   S   K
Optimi :              TCC                 GGC                                         TCC 301
original:     TCA ATT ACA GAA GCT ATT TCA CGT GTT GCT GCA ATG AGT GAA ATC GTA TCT GCA AAC AAC    360
Amino Acid:    S   I   T   E   A   I   S   R   V   A   A   M   S   E   I   V   S   A   N   N
Optimi :      TCC         ACC                                 TCC
```

```
original:    781 ATT GGA GAA TGT ACA TGG GGA GTA AAA ACA TTG GCA CCT TGG GCT GGA GAC TAC TGG GGT  840
Amino Acid:       I   G   E   C   T   W   G   V   K   T   L   A   P   W   A   G   D   Y   W   G
Optimi    :           GGC                 GGC                     ACC                 GGC original:    841 AAT GGA GCA CAG TGG GCT ACA AGT GCA GCA GCA GCA GGT TTC CGT ACA GGT TCA ACA CCT  900
Amino Acid:       N   G   A   Q   W   A   T   S   A   A   A   A   G   F   R   T   G   S   T   P
Optimi    :           GGC                 ACC TCC                         TCC ACC original:    901 CAA GTT GGA GCA ATT GCA TGT TGG AAT GAT GGT GGA TAT GGT CAC GTA GCG GTT GTT ACA  960
Amino Acid:       Q   V   G   A   I   A   C   W   N   D   G   G   Y   G   H   V   A   V   V   T
Optimi    :               GGC                                         GGC             ACC original:    961 GCT GTT GAA TCA ACA CGT ATC CAA GTA TCA GAA TCA AAT TAT GCA GGT AAT CGT ACA 1020
Amino Acid:       A   V   E   S   T   R   I   Q   V   S   E   S   N   Y   A   G   N   R   T
Optimi    :                   TCC ACC             TCC         TCC                         ACC original:   1021 ATT GGA AAT CAC CGT GGA TGG TTC AAT CCA ACA ACA ACT TCT GAA GGT TTT GTT ACA TAT 1080
Amino Acid:       I   G   N   H   R   G   W   F   N   P   T   T   T   S   E   G   F   V   T   Y
Optimi    :           GGC                                     ACC ACC original:   1081 ATT TAT GCA GAT TAA                                                              1140
Amino Acid:       I   Y   A   D   -
Optimi    :
```

FIG. 66C

```
  1
original:   ATG ATC CAA ATC GGC AAG ATT TTT GCC GGA CGC TAT CGG ATT GTC AAA CAG ATT GGT CGA   60
Amino Acid:  M   I   Q   I   G   K   I   F   A   G   R   Y   R   I   V   K   Q   I   G   R
Optimi :                                            GGT         CGT                         CGT 61
original:   GGA GGT ATG GCG GAT GTC TAC CTA GCC AAA GAC TTA ATC TTA GAT GGG GAA GAA GTG GCA  120
Amino Acid:  G   G   M   A   D   V   Y   L   A   K   D   L   I   L   D   G   E   E   V   A
Optimi :             GGT                                         CTG 121
original:   GTG AAG GTT CTG AGG ACC AAC TAC CAG ACG GAC CCG ATA GCT GTA CGT TTT CAG CGT      180
Amino Acid:  V   K   V   L   R   T   N   Y   Q   T   D   P   I   A   V   R   F   Q   R
Optimi :                         CGT                                 ATC 181
original:   GAA GCG AGA GCT ATG GCA GAT CTA GAC CAT CCT CAT ATC GTT CGG ATA ACA GAT ATT GGC  240
Amino Acid:  E   A   R   A   M   A   D   L   D   H   P   H   I   V   R   I   T   D   I   G
Optimi :         CGT                         CTG                                 ATC ACC 241
original:   GAG GAA GAC GGT CAA CAG TAC CTA GCT ATG GAG TAT GTG GCT GGA CTG GAC CTC AAA CGC  300
Amino Acid:  E   E   D   G   Q   Q   Y   L   A   M   E   Y   V   A   G   L   D   L   K   R
Optimi :                             CTG                                 GGT 301
original:   TAT ATC AAG GAA CAT TAT CCT CTT TCT AAT GAA CAT ACT CGT ATC ATG GGA CAA ATT      360
Amino Acid:  Y   I   K   E   H   Y   P   L   S   N   E   E   A   V   R   I   M   G   Q   I
Optimi :                                                                                 GGT 361
original:   CTC TTG GCT ATG CGC TTG GCC CAT ACT CGA GGA ATT GTT CAC AGG GAC TTG AAA CCT CAA  420
Amino Acid:  L   L   A   M   R   L   A   H   T   R   G   I   V   H   R   D   L   K   P   Q
Optimi :                                             CGT GGT                 CGT
```

FIG. 67A

```
                  450                    480
421 AAT ATC CTC TTG ACA CCA GAT GGG ACT GCC AAG GTC ACA GAC TTT GGG ATT GCT GTA GCC
original:
Amino Acid:  N   I   L   L   T   P   D   G   T   A   K   V   T   D   F   G   I   A   V   A
Optimi    :              ACC     GGT                                 ACC         GGT 510                    540
481 TTT GCA GAG ACA AGT CTG ACC CAG ACT AAC TCG ATG TTG GGC TCA GTT CAT TAC TTG TCA
original:
Amino Acid:  F   A   E   T   S   L   T   Q   T   N   S   M   L   G   S   V   H   Y   L   S
Optimi    :          ACC TCT                                             TCT 570                    600
541 CCA GAG CAG GCG CGT GGT TCG AAG GCG ACT GTG CAG AGT GAT ATC TAT GCC ATG GGG ATT
original:
Amino Acid:  P   E   Q   A   R   G   S   K   A   T   V   Q   S   D   I   Y   A   M   G   I
Optimi    :                                                  TCT                     GGT 630                    660
601 ATT TTC TAT GAG ATG CTG ACA GGC CAT ATC CCT TAT GAC GGG GAT AGC GCG GTG ACC ATT
original:
Amino Acid:  I   F   Y   E   M   L   T   G   H   I   P   Y   D   G   D   S   A   V   T   I
Optimi    :                          ACC                          GGT 690                    720
661 GCC CTC CAG CAT TTC CAG AAA CCC CTG CCG TCC GTT ATT GCA GAA AAT CCA TCT GTA CCT
original:
Amino Acid:  A   L   Q   H   F   Q   K   P   L   P   S   V   I   A   E   N   P   S   V   P
Optimi    :                                  CCG 750                    780
721 CAG GCT TTA GAA AAT GTT ATT ATC AAG GCA ACT GCT AAA AAG TTG ACC AAT CGC TAC CGC
original:
Amino Acid:  Q   A   L   E   N   V   I   I   K   A   T   A   K   K   L   T   N   R   Y   R
Optimi    :          CTG 810                    840
781 TCG GTT TCA GAG ATG TAT GTG GAC TTG TCT AGT AGC TTG TCC TAC AAT CGT AGA AAT GAA
original:
Amino Acid:  S   V   S   E   M   Y   V   D   L   S   S   S   L   S   Y   N   R   R   N   E
Optimi    :      TCT                              TCT                      CGT
```

FIG. 67B

```
         841                                                                           900
original:    AGT AAG TTA ATC TTT GAT GAA ACG AGC AAG GCA GAT ACC AAG ACC TTG CCG AAG GTT TCT
Amino Acid:   S   K   L   I   F   D   E   T   S   K   A   D   T   K   T   L   P   K   V   S
Optimi :          TCT CTG 901                                                                           960
original:    CAG AGT ACC TTG ACA TCT ATT CCT AAG GTT CAA GCG ACA GAA CAC AAA TCA ATC AAA
Amino Acid:   Q   S   T   L   T   S   I   P   K   V   Q   A   T   E   H   K   S   I   K
Optimi :          TCT ACC                                     ACC           TCT 961                                                                          1020
original:    AAC CCA AGC CAG GCT GTG ACA GAG GAA ACT TAC CAA CCA CAA GCA CCG AAA AAA CAT AGA
Amino Acid:   N   P   S   Q   A   V   T   E   E   T   Y   Q   P   Q   A   P   K   K   H   R
Optimi :                                                 ACC                                  CGT 1021                                                                          1080
original:    TTT AAG ATG CGT TAC CTG ATT TTG TTG GCC AGC CTT GTA TTG GTG GCA GCT TCT CTT ATT
Amino Acid:   F   K   M   R   Y   L   I   L   L   A   S   L   V   L   V   A   A   S   L   I
Optimi :                  CGT 1081                                                                          1140
original:    TGG ATA CTA TCC AGA ACT CCT GCA ACC ATT GCC ATT CCA GAT GTG GCA GGT CAG ACA GTT
Amino Acid:   W   I   L   S   R   T   P   A   T   I   A   I   P   D   V   A   G   Q   T   V
Optimi :          ATC CTG     CGT                                                             ACC 1141                                                                          1200
original:    GCA GAG GCC AAG GCA ACG CTC AAA AAA AAA GCC AAT TTT GAG ATT GGT GAG GAG AAG ACA GAG
Amino Acid:   A   E   A   K   A   T   L   K   K   K   A   N   F   E   I   G   E   E   K   T   E
Optimi :                                                                                         ACC 1201                                                                          1260
original:    GCT AGT GAA AAG GTG GAA GAA GGG CGG ATT ATC CGT ACA GAT CCT GGC GCT GGA ACT GGT
Amino Acid:   A   S   E   K   V   E   E   G   R   I   I   R   T   D   P   G   A   G   T   G
Optimi :          TCT                              GGT CGT         ACC                     GGT
```

FIG. 67C

```
original:     1261 CGA AAA GAA GGA ACG AAA ATC AAT TTG GTT GTC TCA TCA GGC AAG CAA TCT TTC CAA ATT 1320
Amino Acid:        R   K   E   G   T   K   I   N   L   V   V   S   S   G   K   Q   S   F   Q   I
Optimi     :       CGT             GGT                                 TCT TCT original:     1321 AGT AAT TAT GTC GGT CGG AAA TCC TCT GAT GTC ATT GCG GAA TTA AAA GAG AAA AAA GTT 1380
Amino Acid:        S   N   Y   V   G   R   K   S   S   D   V   I   A   E   L   K   E   K   K   V
Optimi     :       TCT                 CGT                                         CTG original:     1381 CCA GAT AAT TTG ATT AAA ATT GAG GAA GAG TCG AAT GAG GCT GAG AGT GAG GCT GGA ACG GTC 1440
Amino Acid:        P   D   N   L   I   K   I   E   E   E   S   N   E   S   E   A   G   T   V
Optimi     :                                                                     TCT                 GGT original:     1441 CTG AAG CAA AGT CTA CCA GAA GGT ACG ACC TAT GAC TTG AGC AAG GCA ACT CAA ATT GTT 1500
Amino Acid:        L   K   Q   S   L   P   E   G   T   T   Y   D   L   S   K   A   T   Q   I   V
Optimi     :               TCT CTG original:     1501 TTG ACA GTA GCT AAA AAA GCT ACG ACG ATT CAA TTA GGG AAC TAT ATT GGA CGG AAC TCT 1560
Amino Acid:        L   T   V   A   K   K   A   T   T   I   Q   L   G   N   Y   I   G   R   N   S
Optimi     :           ACC                                                                 GGT CGT original:     1561 ACA GAA GTA ATC TCA GAA CTC AAG CAG AAG GTT CCT GAG AAT TTG ATT AAG ATA GAG 1620
Amino Acid:        T   E   V   I   S   E   L   K   Q   K   V   P   E   N   L   I   K   I   E
Optimi     :       ACC             TCT                                                         ATC original:     1621 GAA GAG GAG TCC AGC GAA AGC GAA CCA GGA ACG ATT ATG AAA CAA AGT CCA GGT GCC GGA 1680
Amino Acid:        E   E   E   S   S   E   S   E   P   G   T   I   M   K   Q   S   P   G   A   G
Optimi     :                                                 GGT                     TCT         GGT
```

FIG. 67D

```
        1681                                          1710                                          1740
original:   ACG ACT TAT GAT GTG AGT AAA CCT ACT CAA ATT GTC TTG ACA GTA GCT AAA AAA GTT ACA
Amino Acid:  T   T   Y   D   V   S   K   P   T   Q   I   V   L   T   V   A   K   K   V   T
Optimi :                         TCT                             ACC                         ACC 1741                                          1770                                          1800
original:   AGT GTT GCC ATG CCG AGT TAC ATT GGT TCT AGC TTG GAG TTT ACT AAG AAC AAT TTG ATT
Amino Acid:  S   V   A   M   P   S   Y   I   G   S   S   L   E   F   T   K   N   N   L   I
Optimi :    TCT                 TCT 1801                                          1830                                          1860
original:   CAA ATT GTT GGG ATT AAG GAA GCT AAT ATA GAA GTT GTA GAA GTG ACG ACA GCG CCT GCA
Amino Acid:  Q   I   V   G   I   K   E   A   N   I   E   V   V   E   V   T   T   A   P   A
Optimi :            GGT                         ATC                             ACC 1861                                          1890                                          1920
original:   GGT AGT GCA GAA GGC ATG GTT GTT GAA CAA AGT CCT AGA GCA GGT GAA AAG GTA GAC CTC
Amino Acid:  G   S   A   E   G   M   V   V   E   Q   S   P   R   A   G   E   K   V   D   L
Optimi :    TCT                                     TCT         CGT 1921                                          1950                                          1980
original:   AAT AAG ACT AGA GTC AAG ATT TCA ATC TAC AAA CCT AAA ACA TCA GCT ACT CCT TAA
Amino Acid:  N   K   T   R   V   K   I   S   I   Y   K   P   K   T   S   A   T   P   -
Optimi :            CGT                 TCT                 ACC         TCT
```

FIG. 67E

Agcggaaaaaaagatacaacttctggtcaaaaactaaaagttgttgctacaaactcaatcatcgctg
atattactaaaaatattgctggtgacaaaattgaccttcatagtatcgttccgattgggcaagaccc
acacgaatacgaaccacttcctgaagacgttaagaaaacttctgaggctaatttgattttctataac
ggtatcaaccttgaaacaggtggcaatgcttggtttacaaaattggtagaaaatgccaagaaaactg
aaaacaaagactacttcgcagtcagcgacggcgttgatgttatctaccttgaaggtcaaaatgaaaa
aggaaaagaagacccacacgcttggcttaaccttgaaaacggtattattttttgctaaaaatatcgcc
aaacaattgagcgccaaagaccctaacaataaagaattctatgaaaaaaatctcaaagaatatactg
ataagttagacaaacttgataaagaaagtaaggataaatttaataagatccctgctgaaaagaaact
cattgtaaccagcgaaggagcattcaaatacttctctaaagcctatggtgtcccaagtgcttacatc
tgggaaatcaatactgaagaagaaggaactcctgaacaaatcaagaccttggttgaaaaacttcgcc
aaacaaagttccatcactctttgtagaatcaagtgtggatgaccgtccaatgaaaactgtttctca
agacacaaacatcccaatctacgctcaaatctttactgactctatcgcagaacaaggtaaagaaggc
gacagctactacagcatgatgaaatacaaccttgacaagattgctgaaggattggcaaaataa SGKKDTTSGQKLKVVATNSIIADITKNIAGDKIDLHSIVPIGQDPHEYEPLPEDVKKTSEANLIFYN
GINLETGGNAWFTKLVENAKKTENKDYFAVSDGVDVIYLEGQNEKGKEDPHAWLNLENGIIFAKNIA
KQLSAKDPNNKEFYEKNLKEYTDKLDKLDKESKDKFNKIPAEKKLIVTSEGAFKYFSKAYGVPSAYI
WEINTEEEGTPEQIKTLVEKLRQTKVPSLFVESSVDDRPMKTVSQDTNIPIYAQIFTDSIAEQGKEG
DSYYSMMKYNLDKIAEGLAK

```
Atgaaaaaattaggtacattactcgttctctttctttctgcaatcattcttgtagcatgtgctagcg
gaaaaaaagatacaacttctggtcaaaaactaaaagttgttgctacaaactcaatcatcgctgatat
tactaaaaatattgctggtgacaaaattgaccttcatagtatcgttccgattgggcaagacccacac
gaatacgaaccacttcctgaagacgttaagaaaacttctgaggctaatttgattttctataacggta
tcaaccttgaaacaggtggcaatgcttggtttacaaaattggtagaaaatgccaagaaaactgaaaa
caaagactacttcgcagtcagcgacggcgttgatgttatctaccttgaaggtcaaatgaaaaagga
aaagaagacccacacgcttggcttaaccttgaaaacggtattattttttgctaaaaatatcgccaaac
aattgagcgccaaagaccctaacaataaagaattctatgaaaaaaatctcaaagaatatactgataa
gttagacaaacttgataaagaaagtaaggataaatttaataagatccctgctgaaaagaaactcatt
gtaaccagcgaaggagcattcaaatacttctctaaagcctatggtgtcccaagtgcttacatctggg
aaatcaatactgaagaagaaggaactcctgaacaaatcaagaccttggttgaaaaacttcgccaaac
aaaagttccatcactctttgtagaatcaagtgtggatgaccgtccaatgaaaactgtttctcaagac
acaaacatcccaatctacgctcaaatctttactgactctatcgcagaacaaggtaaagaaggcgaca
gctactacagcatgatgaaatacaaccttgacaagattgctgaaggattggcaaaataa
```

FIG. 69A

```
MKKLGTLLVLFLSAIILVACASGKKDTTSGQKLKVVATNSIIADITKNIAGDKIDLHSIVPIGQDPH
EYEPLPEDVKKTSEANLIFYNGINLETGGNAWFTKLVENAKKTENKDYFAVSDGVDVIYLEGQNEKG
KEDPHAWLNLENGIIFAKNIAKQLSAKDPNNKEFYEKNLKEYTDKLDKLDKESKDKFNKIPAEKKLI
VTSEGAFKYFSKAYGVPSAYIWEINTEEEGTPEQIKTLVEKLRQTKVPSLFVESSVDDRPMKTVSQD
TNIPIYAQIFTDSIAEQGKEGDSYYSMMKYNLDKIAEGLAK
```

FIG. 69B

```
ATGGCAAATAAAGCAGTAAATGACTTTATACTAGCTATGAATTACGATAAAAAGAAACTCTTGACCC
ATCAGGGAGAAAGTATTGAAAATCGTTTCATCAAAGAGGGTAATCAGCTACCCGATGAGTTTGTTGT
TATCGAAAGAAAGAAGCGGAGCTTGTCGACAAATACAAGTGATATTTCTGTAACAGCTACCAACGAC
AGTCGCCTCTATCCTGGAGCACTTCTCGTAGTGGATGAGACCTTGTTAGAGAATAATCCCACTCTTC
TTGCGGTTGATCGTGCTCCGATGACTTATAGTATTGATTTGCCTGGTTTGGCAAGTAGCGATAGCTT
TCTCCAAGTGGAAGACCCCAGCAATTCAAGTGTTCGCGGAGCGGTAAACGATTTGTTGGCTAAGTGG
CATCAAGATTATGGTCAGGTCAATAATGTCCCAGCTAGAATGCAGTATGAAAAAATAACGGCTCACA
GCATGGAACAACTCAAGGTCAAGTTTGGTTCTGACTTTGAAAAGACAGGGAATTCTCTTGATATTGA
TTTTAACTCTGTCCATTCAGGTGAAAAGCAGATTCAGATTGTTAATTTTAAGCAGATTTATTATACA
GTCAGCGTAGACGCTGTTAAAAATCCAGGAGATGTGTTTCAAGATACTGTAACGGTAGAGGATTTAA
AACAGAGAGGAATTTCTGCAGAGCGTCCTTTGGTCTATATTTCGAGTGTTGCTTATGGGCGCCAAGT
CTATCTCAAGTTGGAAACCACGAGTAAGAGTGATGAAGTAGAGGCTGCTTTTGAAGCTTTGATAAAA
GGAGTCAAGGTAGCTCCTCAGACAGAGTGGAAGCAGATTTTGGACAATACAGAAGTGAAGGCGGTTA
TTTTAGGGGGCGACCCAAGTTCGGGTGCCCGAGTTGTAACAGGCAAGGTGGATATGGTAGAGGACTT
GATTCAAGAAGGCAGTCGCTTTACAGCAGATCATCCAGGCTTGCCGATTTCCTATACAACTTCTTTT
TTACGTGACAATGTAGTTGCGACCTTTCAAAACAGTACAGACTATGTTGAGACTAAGGTTACAGCTT
ACAGAAACGGAGATTTACTGCTGGATCATAGTGGTGCCTATGTTGCCCAATATTATATTACTTGGGA
TGAATTATCCTATGATCATCAAGGTAAGGAAGTCTTGACTCCTAAGGCTTGGGACAGAAATGGGCAG
GATTTGACGGCTCACTTTACCACTAGTATTCCTTTAAAAGGGAATGTTCGTAATCTCTCTGTCAAAA
TTAGAGAGTGTACCGGGCTTGCCTTCGAATGGTGGCGTACGGTTTATGAAAAAACCGATTTGCCACT
AGTGCGTAAGCGGACGATTTCTATTTGGGGAACAACTCTCTATCCTCAGGTAGAGGATAAGGTAGAA
AATGACTAG
```

FIG. 70A

```
MANKAVNDFILAMNYDKKKLLTHQGESIENRFIKEGNQLPDEFVVIERKKRSLSTNTSDISVTATND
SRLYPGALLVVDETLLENNPTLLAVDRAPMTYSIDLPGLASSDSFLQVEDPSNSSVRGAVNDLLAKW
HQDYGQVNNVPARMQYEKITAHSMEQLKVKFGSDFEKTGNSLDIDFNSVHSGEKQIQIVNFKQIYYT
VSVDAVKNPGDVFQDTVTVEDLKQRGISAERPLVYISSVAYGRQVYLKLETTSKSDEVEAAFEALIK
GVKVAPQTEWKQILDNTEVKAVILGGDPSSGARVVTGKVDMVEDLIQEGSRFTADHPGLPISYTTSF
LRDNVVATFQNSTDYVETKVTAYRNGDLLLDHSGAYVAQYYITWDELSYNHQGKEVLTPKAWDRNGQ
DLTAHFTTSIPLKGNVRNLSVKIRECTGLAFEWWRTVYEKTDLPLVRKRTISIWGTTLYPQVEDKVE
ND*
```

FIG. 70B

```
atggcaaataaagcagtaaatgactttatCctGgctatgaattacgataaaaagaaactcttgaccc
atcagggTgaaagtattgaaaatcgtttcatcaaagagggtaatcagctGccGgatgagtttgttgt
tatcgaaCgTaagaagcgTagcttgtcgacaaatacaagtgatatttctgtaacagctaccaacgac
agtcgcctctatcctggTgcacttctcgtagtggatgagaccttgttagagaataatccGactcttc
ttgcggttgatcgtgctccgatgacttatagtattgatttgcctggtttggcaagtagcgatagctt
tctccaagtggaagacccGagcaattcaagtgttcgcggTgcggtaaacgatttgttggctaagtgg
catcaagattatggtcaggtcaataatgtcccagctCgTatgcagtatgaaaaaatCacggctcaca
gcatggaacaactcaaggtcaagtttggttctgactttgaaaagacagggaattctcttgatattga
ttttaactctgtccattcaggtgaaaagcagattcagattgttaattttaagcagatttattataca
gtcagcgtagacgctgttaaaaatccaggagatgtgtttcaagatactgtaacggtagaggatttaa
aacagCgTggaatttctgcagagcgtcctttggtctatatttcgagtgttgcttatgggcgccaagt
ctatctcaagttggaaaccacgagtaagagtgatgaagtagaggctgcttttgaagctttgatCaaa
ggTgtcaaggtagctcctcagacagagtggaagcagattttggacaatacagaagtgaaggcggtta
ttttaggggggcgacccaagttcgggtgcccgTgttgtaacaggcaaggtggatatggtagaggactt
gattcaagaaggcagtcgctttacagcagatcatccaggcttgccgatttcctatacaacttcttt
ttacgtgacaatgtagttgcgacctttcaaaacagtacagactatgttgagactaaggttacagctt
acCgTaacggagatttactgctggatcatagtggtgcctatgttgcccaatattatattacttggga
tgaattatcctatgatcatcaaggtaaggaagtcttgactcctaaggcttgggacCgTaatgggcag
gatttgacggctcactttaccactagtattcctttaaaagggaatgttcgtaatctctctgtcaaaa
ttCgTgagtgtaccgggcttgccttcgaatggtggcgtacggtttatgaaaaaccgatttgccact
GgtgcgtaagcgTacgatttctatttggggTacaactctctatcctcaggtagaggataaggtagaa
aatgactag
```

FIG. 71A

```
MANKAVNDFILAMNYDKKKLLTHQGESIENRFIKEGNQLPDEFVVIERKKRSLSTNTSDISVTATND
SRLYPGALLVVDETLLENNPTLLAVDRAPMTYSIDLPGLASSDSFLQVEDPSNSSVRGAVNDLLAKW
HQDYGQVNNVPARMQYEKITAHSMEQLKVKFGSDFEKTGNSLDIDFNSVHSGEKQIQIVNFKQIYYT
VSVDAVKNPGDVFQDTVTVEDLKQRGISAERPLVYISSVAYGRQVYLKLETTSKSDEVEAAFEALIK
GVKVAPQTEWKQILDNTEVKAVILGGDPSSGARVVTGKVDMVEDLIQEGSRFTADHPGLPISYTTSF
LRDNVVATFQNSTDYVETKVTAYRNGDLLLDHSGAYVAQYYITWDELSYNHQGKEVLTPKAWDRNGQ
DLTAHFTTSIPLKGNVRNLSVKIRECTGLAFEWWRTVYEKTDLPLVRKRTISIWGTTLYPQVEDKVE
ND*
```

FIG. 71B

Deletion of 2247 bp (*relA-12* to *relA2235/2235*) and inserted 2393 bp of *araC* P<sub>BAD</sub> *lacI* TT ΔrelA196::araC P<sub>BAD</sub> <u>AGGGTGGTGAAT</u> GTG-*lacI* TT
                              SD ΔrelA197::araC P<sub>BAD</sub> <u>AGGATGGTGAAT</u> ATG-*lacI* TT
                              SD ΔrelA198::araC P<sub>BAD</sub> <u>AGGATGGTGAAT</u> ATG-*lacI*\* TT
                              SD pYA4996  (pYA3342-PcsB-PsaA-StkP)

agcttggctgttttggcggatgagagaagattttcagcctgatacagattaaatcagaacgcagaagcggtctgataaaacagaatttgcctggcggcagt
agcgcggtggtcccacctgacccatgccgaactcagaagtgaaacgccgtagcgccgatggtagtgtggggtctcccatgcgagagtagggaact
gccaggcatcaaataaaacgaaaggctcagtcgaaagactgggcctttcgttttatctgttgtttgtcggtgaacgctctcctgagtaggacaaatccgccg
ggagcggatttgaacgttgcgaagcaacggcccggagggtggcgggcaggacgcccgccataaactgccaggcatcaaattaagcagaaggccatc
ctgacggatggccttttgcgtttctacaaactcttttgtttattttctaaatacattcaaatatgtatccgctcatgagacaataaccctgataaatgcttcaataa
tggaagatcttccaacatcacaggtaaacagaaacgtcgggtcgatcgggaaattcttccggacggcgcggggttgggcaagccgcaggcgcgtca
gtgcttttagcgggtgtcggggcgcagccatgacccagtcacgtagcgatagcggagtgtatactggcttaactatgcggcatcagagcagattgtactg
agagtgcaccatatgcggtgtgaaataccgcacagatgcgtaaggagaaaataccgcatcaggcgctcttccgcttcctcgctcactgactcgctgcgct
cggtcgttcggctgcggcgagcggtatcagctcactcaaaggcggtaatacggttatccacagaatcaggggataacgcaggaaagaacatgtgagca
aaaggccagcaaaaggccaggaaccgtaaaaaggccgcgttgctggcgtttttccataggctccgcccccctgacgagcatcacaaaaatcgacgctc
aagtcagaggtggcgaaacccgacaggactataaagataccaggcgtttccccctggaagctccctcgtgcgctctcctgttccgaccctgccgcttacc
ggatacctgtccgcctttctcccttcgggaagcgtggcgctttctcatagctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcgccactggcagc
agccactggtaacaggattagcagagcgaggtatgtaggcggtgctacagagttcttgaagtggtggcctaactacggctacactagaaggacagtattt
ggtatctgcgctctgctgaagccagttaccttcggaaaaagagttggtagctcttgatccggcaaacaaaccaccgctggtagcggtggtttttttgtttgca
agcagcagattacgcgcagaaaaaaaggatctcaagaagatcctttgatcttttctacggggtctgacgctcagtggaacgaaaactcacgttaagggatt
ttggtcatgagattatcaaaaaggatcttcacctagatccttttaaattaaaaatgaagttttaaatcaatctaaagtatatatgagtaaacttggtctgacagtct
agactaggccaactggcgcagcattcgacgcagcggctcggcggcgccccataacaactggtcgcctacggtaaacgccgacaagaactctggccc
catgttcagcttacgcagacgaccaaccggcgtagtcaacgtgccggtcaccgccgccggggttaattcgcgcatagtgatatcacgatcgttcggcac
cactttcgcccacggattatgtgccgccagcagttcttccaccgtcggaatggataccttttttcagcttgatggtgaacgcctggctgtgacagcgcagc
gcgccgacgcgcacacacaaaccatcaaccggaatcacagaggcagtattgagaatcttgttggtttccgcctggcctttccactcttcgcggctctggcc
gttatcgagctgtttgtcgatccaggggatcaggcttcccgccagcggtacgccaaagtatcaaccggcagctcgccgctgcgggtcaatgccgtaact
ttgcgttcaatatcaagaattgcggaagacggcgtcgccagttcatcggcgacatggccatacaactgacccatctgggttaacagctcgcgcatatggc
gcgcgccgccgccggaggcggcctgataggtcgcgacggataccagtcaacgagattatgggcaaagagaccgcccagcgacatcaacatcagg
ctaacggtacagttaccgcccacaaaggtcttcacgccattgttcaggccgtcggtaatcacgtcctggttgaccgggtcgagaataataatggcatcatct
ttcatgcgcagcgtagaagccgcatcaatccagtaaccctgccatccgctttcgcgcagctttggataaatttcgttggtataatcgccgccctggcaggtc
acgatgatatcgagcgcttttagcgcatccagatcaaaagcgtcctgtagcgtgccggtggaggtgtcgccgaaggtgggcgccgcctgtccaaactgg
gaggtagaaaagaaaacagggcgaatagcgtcgaaatcgcgctcctctaccatgcgttcatgagaacagagccgaccattccgcgccagccgataa
aaccaacattttcatagcgttttttcctgcaaagagatgtgcggatcttccggaagaccttccattctgaaatgagctgttgacaattaatcatccggctcgta
taatgtgtggaattgtgagcggataacaatttcacacaggaaacagaccatgaaaagatttggctggcgctggctggtatggttttagcttttagcgcctcg
gcagcacagatcagcgacgaattcgaaacgactgatgacaaaattgctgctcaagataataaaattagtaacttaacagcacaacaacaagaagcccaa
aaacaagttgaccaaattcaggagcaagtatcagctattcaagctgagcagtctaacttgcaagctgaaaatgatagattacaagcagaatctaagaaact
cgagggtgagattacagaactttctaaaaacattgtttctcgtaaccaatcgttggaaaaacaagctcgtagtgctcaaacaaatggagccgtaactagcta
tatcaataccattgtaaactcaaaatcaattacagaagctatttcacgtgttgctgcaatgagtgaaatcgtatctgcaaacaacaaaatgttagaacaacaaa
aggcagataaaaaagctatttctgaaaaacaagtagcaaataatgatgctatcaatactgtaattgctaatcaacaaaaattggctgatgatgctcaagcatt
gactacgaaacaggcagaactaaaagctgctgaattaagtcttgctgctgagaaagcgacagctgaaggggaaaaagcaagtctattagagcaaaaag
cagcagctgaggcagaggctcgtgcagctgcggtagcagaagcagcttataaagaaaaacgagctagccaacaacaatcagtacttgcttcagcaaac
actaacttaacagctcaagtgcaagcagtatctgaatctgcagcagcacctgtccgtgcaaaagttcgtccaacatacagtacaaacgcttcaagttatcca

FIG. 78A attggagaatgtacatggggagtaaaaacattggcaccttgggctggagactactggggtaatggagcacagtgggctacaagtgcagcagcagcagg
tttccgtacaggttcaacacctcaagttggagcaattgcatgttggaatgatggtggatatggtcacgtagcggttgttacagctgttgaatcaacaacacgt
atccaagtatcagaatcaaattatgcaggtaatcgtacaattggaaatcaccgtggatggttcaatccaacaacaacttctgaaggttttgttacatatatttat
gcagattaaccatgaaggaaacagaccAtgaaaaaattaggtacattactcgttctctttctttctgcaatcattcttgtagcatgtgctagcggaaaaaaag
atacaacttctggtcaaaaactaaaagttgttgctacaaactcaatcatcgctgatattactaaaaatattgctggtgacaaaattgaccttcatagtatcgttcc
gattgggcaagacccacacgaatacgaaccacttcctgaagacgttaagaaaacttctgaggctaatttgattttctataacggtatcaaccttgaaacaggt
ggcaatgcttggtttacaaaattggtagaaaatgccaagaaaactgaaaacaaagactacttcgcagtcagcgacggcgttgatgttatctaccttgaaggt
caaaatgaaaaaggaaaagaagacccacacgcttggcttaaccttgaaaacggtattattttttgctaaaaatatcgccaaacaattgagcgccaaagaccc
taacaataaagaattctatgaaaaaaatctcaaagaatatactgataagttagacaaacttgataaagaaagtaaggataaatttaataagatccctgctgaa
aagaaactcattgtaaccagcgaaggagcattcaaatacttctctaaagcctatggtgtcccaagtgcttacatctgggaaatcaatactgaagaagaagg
aactcctgaacaaatcaagaccttggttgaaaaacttcgccaaacaaaagttccatcactctttgtagaatcaagtgtggatgaccgtccaatgaaaactgtt
tctcaagacacaaacatcccaatctacgctcaaatctttactgactctatcgcagaacaaggtaaagaaggcgacagctactacagcatgatgaaatacaa
ccttgacaagattgctgaaggattggcaaaataaaggaaacagaccatgAAACAAAGCACTATTGCACTGGCACTGCTGC
CGCTGCTGTTTACCCCTGTGACCAAAGCCCGTACCCCAGAAATGAACaaagctactaaactggtactgggc
gcggtaatcctgggttctactctgctggcaggttgctccagcaagaattcctgatttgttggccagccttgtattggtggcagcttctcttatttggatactatc
cagaactcctgcaaccattgccattccagatgtggcaggtcagacagttgcagaggccaaggcaacgctcaaaaaagccaattttgagattggtgagga
gaagacagaggctagtgaaaaggtggaagaagggcggattatccgtacagatcctggcgctggaactggtcgaaaagaaggaacgaaaatcaatttg
gttgtctcatcaggcaagcaatctttccaaattagtaattatgtcggtcggaaatcctctgatgtcattgcggaattaaaagagaaaaaagttccagataatttg
attaaaattgaggaagaagagtcgaatgagagtgaggctggaacggtcctgaagcaaagtctaccagaaggtacgacctatgacttgagcaaggcaac
tcaaattgttttgacagtagctaaaaaagctacgacgattcaattagggaactatattggacggaactctacagaagtaatctcagaactcaagcagaagaa
ggttcctgagaatttgattaagatagaggaagaagagtccagcgaaagcgaaccaggaacgattatgaaacaaagtccaggtgccggaacgacttatga
tgtgagtaaacctactcaaattgtcttgacagtagctaaaaaagttacaagtgttgccatgccgagttacattggttctagcttggagtttactaagaacaattt
gattcaaattgttgggattaaggaagctaatatagaagttgtagaagtgacgacagcgcctgcaggtagtgcagaaggcatggttgttgaacaaagtccta
gagcaggtgaaaaggtagacctcaataagactagagtcaagatttcaatctacaaacctaaaacaacttcagctactccttaaccatgg PcsB:

TTDDKIAAQDNKISNLTAQQQEAQKQVDQIQEQVSAIQAEQSNLQAENDRLQAESKKLEGEITELSKNIV
SRNQSLEKQARSAQTNGAVTSYINTIVNSKSITEAISRVAAMSEIVSANNKMLEQQKADKKAISEKQVAN
NDAINTVIANQQKLADDAQALTTKQAELKAAELSLAAEKATAEGEKASLLEQKAAAEAEARAAAVAEA
AYKEKRASQQQSVLASANTNLTAQVQAVSESAAAPVRAKVRPTYSTNASSYPIGECTWGVKTLAPWAG
DYWGNGAQWATSAAAAGFRTGSTPQVGAIACWNDGGYGHVAVVTAVESTTRIQVSESNYAGNRTIGN
HRGWFNPTTTSEGFVTYIYAD

FIG. 78C

PsaA:

MKKLGTLLVLFLSAIILVACASGKKDTTSGQKLKVVATNSIIADITKNIAGDKIDLHSIVPIGQDPH
EYEPLPEDVKKTSEANLIFYNGINLETGGNAWFTKLVENAKKTENKDYFAVSDGVDVIYLEGQN
EKGKEDPHAWLNLENGIIFAKNIAKQLSAKDPNNKEFYEKNLKEYTDKLDKLDKESKDKFNKIP
AEKKLIVTSEGAFKYFSKAYGVPSAYIWEINTEEEGTPEQIKTLVEKLRQTKVPSLFVESSVDDRP
MKTVSQDTNIPIYAQIFTDSIAEQGKEGDSYYSMMKYNLDKIAEGLAK

FIG. 78D

StkP:

LILLASLVLVAASLIWILSRTPATIAIPDVAGQTVAEAKATLKKANFEIGEEKTEASEKVEEGRIIRT
DPGAGTGRKEGTKINLVVSSGKQSFQISNYVGRKSSDVIAELKEKKVPDNLIKIEEEESNESEAGT
VLKQSLPEGTTYDLSKATQIVLTVAKKATTIQLGNYIGRNSTEVISELKQKKVPENLIKIEEEESSE
SEPGTIMKQSPGAGTTYDVSKPTQIVLTVAKKVTSVAMPSYIGSSLEFTKNNLIQIVGIKEANIEVV
EVTTAPAGSAEGMVVEQSPRAGEKVDLNKTRVKIS

FIG. 78E pYA4901   (Pya4673-PcsB-PsaA-StkP)

agatctagcccgcctaatgagcgggcttttttttaattcgcaattccccgatgcataatgtgcctgtcaaatggacgaagcagggattctgcaaacccatgc
tactccgtcaagccgtcaattgtctgattcgttaccaattatgacaacttgacggctacatcattcactttttcttcacaaccggcacggaactcgctcgggctg
gcccggtgcattttttaaatacccgcgagaaatagagttgatcgtcaaaaccaacattgcgaccgacggtggcgataggcatccggtggtgctcaaaa
gcagcttcgcctggctgatacgttggtcctcgcgccagcttaagacgctaatccctaactgctggcggaaaagatgtgacagacgcgacggcgacaag
caaacatgctgtgcgacgctggcgatatcaaaattgctgtctgccaggtgatcgctgatgtactgacaagcctcgcgtacccgattatccatcggtggatg
gagcgactcgttaatcgcttccatgcgccgcagtaacaattgctcaagcagatttatcgccagcagctccgaatagcgcccttcccttgcccggcgttaat
gatttgcccaaacaggtcgctgaaatgcggctggtgcgcttcatccgggcgaaagaaccccgtattggcaaatattgacggccagttaagccattcatgc
cagtaggcgcgcggacgaaagtaaacccactggtgataccattcgcgagcctccggatgacgaccgtagtgatgaatctctcctggcgggaacagcaa
aatatcacccggtcggcaaacaaattctcgtccctgatttttcaccaccccctgaccgcgaatggtgagattgagaatataaacctttcattcccagcggtcgg
tcgataaaaaaatcgagataaccgttggcctcaatcggcgttaaacccgccaccagatgggcattaaacgagtatcccggcagcaggggatcattttgcg
cttcagccatactttcatactcccgccattcagagaagaaaccaattgtccatattgcatcagacattgccgtcactgcgtcttttactggctcttctcgctaac
caaaccggtaaccccgcttattaaaagcattctgtaacaaagcgggaccaaagccatgacaaaaacgcgtaacaaaagtgtctataatcacggcagaaa
agtccacattgattatttgcacggcgtcacactttgctatgccatagcattttttatccataagattagcggatcctacctgacgcttttatcgcaactctctactg
tttctccatacccgttttttttgggctagcgaattctgagaacaaactaaatggataaatttcgtgttcagggggccaacgaagctccagggcgaagtcacaattt
ccggcgctaaaaatgctgctctgcctatcctttttgccgcactactggcggaagaaccggtagagatccagaacgtcccgaaactgaaagacgtcgatac
atcaatgaagctgctaagccagctgggtgcgaaagtagaacgtaatggttctgtgcatattgatgcccgcgacgttaatgtattctgcgcaccttacgatct
ggttaaaaccatgcgtgcttctatctgggcgctggggccgctggtagcgcgctttggtcaggggcaagtttcactacctggcggttgtacgatcggtgcgc
gtccggttgatctacacattctggcctcgaacaattaggcgcgaccatcaaactggaagaaggttacgttaaagcttccgtcgatggtcgtttgaaaggtg
cacatatcgtgatggataaagtcagcgttggcgcaacggtgaccatcatgtgtgctgcaaccctggcggaaggcaccacgattattgaaaacgcagcgc
gtgaaccggaaatcgtcgataccgcgaacttcctgattacgctgggtgcgaaaattagcggtcagggcaccgatcgtatcgtcatcgaaggtgtggaac
gtttaggcggcggtgtctatcgcgttctgccggatcgtatcgaaaccggtactttcctggtggcggcggcgatttctcgcggcaaaattatctgccgtaacg
cgcagccagatactctcgacgccgtgctggcgaaactgcgtgacgctggagcggacatcgaagtcggcgaagactggattagcctggatatgcatggc
aaacgtccgaaggctgttaacgtacgtaccgcgccgcatccggcattcccgaccgatatgcaggcccagttcacgctgttgaacctggtggcagaagg
gaccgggtttatcaccgaaacggtctttgaaaaccgctttatgcatgtgccagagctgagccgtatgggcgcgcacgccgaaatcgaaagcaataccgtt
atttgtcacggtgttgaaaaactttctggcgcacaggttatggcaaccgatctgcgtgcatcagcaagcctggtgctggctggctgtattgcggaagggac
gacggtggttgatcgtatttatcacatcgatcgtggctacgaacgcattgaagacaaactgcgcgctttaggtgcaaatattgagcgtgtgaaaggcgaat
aagaattcaggaaaaaaacgctgtgaaaaatgttggttttatcggctggcgcggaatggtcggctctgttctcatgcaacgcatggtagaggagcgcgatt
tcgacgctattcgccctgttttcttttctacctcccagtttggacaggcggcgcccaccttcggcgacacctccaccggcacgctacaggacgcttttgatct
ggatgcgctaaaagcgctcgatatcatcgtgacctgccaggggcggcgattataccaacgaaatttatccaaagctgcgcgaaagcggatggcagggtta
ctggattgatgcggcttctacgctgcgcatgaaagatgatgccattattattctgacccggtcaaccaggacgtgattaccgacggcctgaacaatggcg
tgaagacctttgtgggcggtaactgtaccgttagcctgatgttgatgtcgctggcggtctctttgcccataatctcgttgactgggtatccgtcgcgacctat
caggccgcctccggcggcggcgcgccatatgcgcgagctgttaacccagatgggtcagttgtatggccatgtcgccgatgaactggcgacgccgt
cttccgcaattcttgatattgaacgcaaagttacggcattgacccgcagcggcgagctgccggttgataactttggcgtaccgctggcgggaagcctgatc
ccctggatcgacaaacagctcgataacggccagagccgcgaagagtggaaaggccaggcggaaaccaacaagattctcaatactgcctctgtgattcc
ggttgatggttttgtgtgtgcgcgtcggcgcgctgcgctgtcacagccaggcgttcaccatcaagctgaaaaaagaggtatccattccgacggtggaaga
actgctggcggcacataatccgtgggcgaaagtggtgccgaacgatcgtgatatcactatgcgcgaattaaccccggcggcggtgaccggcacgttga
ctacgccggttggtcgtctgcgtaagctgaacatggggccagagttcttgtcggcgtttaccgtaggcgaccagttgttatggggcgccgccgagccgct gcgtcgaatgctgcgccagttggcgtagtctagctgcacgataccgtcgacttgtacatagactcgctccgaaattaaagaacacttaaattatctactaaa
ggaatctttagtcaagtttatttaagatgacttaactatgaatacacaattgatgggtgagcgtaggagcatgcttatgcgaaaggccatcctgacggatggc
cttttggatcttccggaagaccttccattctgaaatgagctgttgacaattaatcatccggctcgtataatgtgtggaattgtgagcggataacaatttcacac
aggaaacagaccatgatgaaaaagatttggctggcgctggctggtatggttttagcttttagcgcctcggcagcacagatcagcgacgaattcgaaacga
ctgatgacaaaattgctgctcaagataataaaattagtaacttaacagcacaacaacaagaagcccaaaaacaagttgaccaaattcaggagcaagtatca
gctattcaagctgagcagtctaacttgcaagctgaaaatgatagattacaagcagaatctaagaaactcgagggtgagattacagaactttctaaaaacatt
gtttctcgtaaccaatcgttggaaaaacaagctcgtagtgctcaaacaaatggagccgtaactagctatatcaataccattgtaaactcaaaatcaattacag
aagctatttcacgtgttgctgcaatgagtgaaatcgtatctgcaaacaacaaaatgttagaacaacaaaaggcagataaaaaagctatttctgaaaaacaag
tagcaaataatgatgctatcaatactgtaattgctaatcaacaaaaattggctgatgatgctcaagcattgactacgaaacaggcagaactaaaagctgctg
aattaagtcttgctgctgagaaagcgacagctgaaggggaaaaagcaagtctattagagcaaaaagcagcagctgaggcagaggctcgtgcagctgc
ggtagcagaagcagcttataaagaaaaacgagctagccaacaacaatcagtacttgcttcagcaaacactaacttaacagctcaagtgcaagcagtatct
gaatctgcagcagcacctgtccgtgcaaaagttcgtccaacatacagtacaaacgcttcaagttatccaattggagaatgtacatgggagtaaaaacatt
ggcaccttgggctggagactactggggtaatggagcacagtgggctacaagtgcagcagcagcaggtttccgtacaggttcaacacctcaagttggag
caattgcatgttggaatgatggtggatatggtcacgtagcggttgttacagctgttgaatcaacaacacgtatccaagtatcagaatcaaattatgcaggtaa
tcgtacaattggaaatcaccgtggatggttcaatccaacaacaacttctgaaggttttgttacatatatttatgcagattaaaggaaacagaccatgaaagcta
ctaaactggtactgggcgcggtaatcctgggttctactctgctggcaggttgctccagcaagaattccttgtagcatgtgctagcggaaaaaaagatacaa
cttctggtcaaaaactaaaagttgttgctacaaaactcaatcatcgctgatattactaaaaatattgctggtgacaaaattgaccttcatagtatcgttccgattgg
gcaagacccacacgaatacgaaccacttcctgaagacgttaagaaaacttctgaggctaatttgattttctataacggtatcaaccttgaaacaggtggcaa
tgcttggtttacaaaattggtagaaaatgccaagaaaactgaaaacaaagactacttcgcagtcagcgacggcgttgatgttatctaccttgaaggtcaaaa
tgaaaaaggaaaagaagacccacacgcttggcttaaccttgaaaacggtattattttttgctaaaaatatcgccaaacaattgagcgccaaagaccctaaca
ataaagagttctatgaaaaaaatctcaaagaatatactgataagttagacaaacttgataaagaaagtaaggataaatttaataagatccctgctgaaaagaa
actcattgtaaccagcgaaggagcattcaaatacttctctaaagcctatggtgtcccaagtgcttacatctgggaaatcaatactgaagaagaaggaactcc
tgaacaaatcaagaccttggttgaaaaacttcgccaaacaaaagttccatcactctttgtagaatcaagtgtggatgaccgtccaatgaaaactgtttctcaa
gacacaaacatcccaatctacgctcaaatctttactgactctatcgcagaacaaggtaaagaaggcgacagctactacagcatgatgaaatacaaccttga
caagattgctgaaggattggcaaaataaataggagatatacccccatggcaaataaaggagtaaatgacttatcctggctatgaattacgataaaaagaaa
ctcttgacccatcagggtgaaagtattgaaaatcgtttcatcaaagagggtaatcagctgccggatgagtttgttgttatcgaacgtaagaagcgtagcttgt
cgacaaatacaagtgatatttcgtaacagctaccaacgacagtcgcctctatcctggtgcacttctcgtagtggatgagaccttgttagagaataatccgac
tcttcttgcggttgatcgtgctccgatgacttatagtattgatttgcctggttttggcaagtagcgatagcttctccaagtggaagacccgagcaattcaagtgt
tcgcggtgcggtaaacgatttgttggctaagtggcatcaagattatggtcaggtcaataatgtcccagctcgtatgcagtatgaaaaaatcacggctcacag
catggaacaactcaaggtcaagtttggttctgactttgaaaagacagggaattctcttgatattgattttaactctgtccattcaggtgaaaagcagattcagat
tgttaattttaagcagatttattatacagtcagcgtagacgctgttaaaaatccaggagatgtgtttcaagatactgtaacggtagaggatttaaaacagcgtg
gaatttctgcagagcgtccttggtctatatttcgagtgttgcttatgggcgccaagtctatctcaagttggaaaccacgagtaagagtgatgaagtagaggc
tgcttttgaagctttgatcaaaggtgtcaaggtagctcctcagacagagtggaagcagattttggacaatacagaagtgaaggcggttatttaggggcg
acccaagttcgggtgcccgtgttgtaacaggcaaggtggatatggtagaggacttgattcaagaaggcagtcgctttacagcagatcatccaggcttgcc
gatttcctatacaacttctttttacgtgacaatgtagttgcgacctttcaaaacagtacagactatgttgagactaaggttacagcttaccgtaacggagattta
ctgctggatcatagtggtgcctatgttgcccaatattatattacttgggatgaattatcctatgatcatcaaggtaaggaagtcttgactcctaaggcttgggac
cgtaatgggcaggatttgacggctcactttaccactagtattccttttaaaaagggaatgttcgtaatctctctgtcaaaattcgtgagtgtaccgggcttgccttc
gaatggtggcgtacggtttatgaaaaaaccgatttgccactggtgcgtaagcgtacgatttctatttggggtacaactctctatcctcaggtagaggataagg

FIG. 79B tagaaaatgactaatcccggggatccgtcgacctgcagccaagctcccaagcttggctgttttggcggatgagagaagattttcagcctgatacagattaa
atcagaacgcagaagcggtctgataaaacagaatttgcctggcggcagtagcgcggtggtcccacctgaccccatgccgaactcagaagtgaaacgcc
gtagcgccgatggtagtgtggggtctccccatgcgagagtagggaactgccaggcatcaaataaaacgaaaggctcagtcgaaagactgggcctttcg
ttttatctgttgtttgtcggtgaacgctctcctgagtaggacaaatccgccgggagcggatttgaacgttgcgaagcaacggcccggagggtggcgggca
ggacgcccgccataaactgccaggcatcaaattaagcagaaggccatcctgacggatggccttttttgcgtttctacaaactcttttgtttattttctaaataca
ttcaaatatgtatccgctcatgagacaataaccctgataaatgcttcaataatggaagatcttccaacatcacaggtaaacagaaacgtcgggtcgatcggg
aaattctttcccggacggcgcggggttgggcaagccgcaggcgcgtcagtgcttttagcgggtgtcggggcgcagccatgacccagtcacgtagcgat
agcggagtgtatactggcttaactatgcggcatcagagcagattgtactgagagtgcaccatatgcggtgtgaaataccgcacagatgcgtaaggagaa
aataccgcatcaggcgctcttccgcttcctcgctcactgactcgctgcgctcggtcgttcggctgcggcgagcggtatcagctcactcaaaggcggtaata
cggttatccacagaatcaggggataacgcaggaaagaacatgtgagcaaaaggccagcaaaaggccaggaaccgtaaaaaggccgcgttgctggcg
tttttccataggctccgcccccctgacgagcatcacaaaaatcgacgctcaagtcagaggtggcgaaacccgacaggactataaagataccaggcgtttc
ccccctggaagctccctcgtgcgctctcctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccgaccgctgcgccttatccggtaact
atcgtcttgagtccaacccggtaagacacgacttatcgccactggcagcagccactggtaacaggattagcagagcgaggtatgtaggcggtgctacag
agttcttgaagtggtggcctaactacggctacactagaaggacagtatttggtatctgcgctctgctgaagccagttaccttcggaaaaagagttggtagct
cttgatccggcaaacaaaccaccgctggtagcggtggtttttttgtttgcaagcagcagattacgcgcagaaaaaaaggatctcaagaagatcctttgatct
ttttctacggggtctgacgctcagtggaacgaaaactcacgttaagggattttggtcatgagattatcaaaaaggatcttcacctagatcctttaaattaaaaat
gaagttttaaatcaatctaaagtatatatgagtaaacttggtctgacagtctaga

FIG. 79C

PcsB:

TTDDKIAAQDNKISNLTAQQQEAQKQVDQIQEQVSAIQAEQSNLQAENDRLQAESKKLEGEITELSKNIV
SRNQSLEKQARSAQTNGAVTSYINTIVNSKSITEAISRVAAMSEIVSANNKMLEQQKADKKAISEKQVAN
NDAINTVIANQQKLADDAQALTTKQAELKAAELSLAAEKATAEGEKASLLEQKAAAEAEARAAAVAEA
AYKEKRASQQQSVLASANTNLTAQVQAVSESAAAPVRAKVRPTYSTNASSYPIGECTWGVKTLAPWAG
DYWGNGAQWATSAAAAGFRTGSTPQVGAIACWNDGGYGHVAVVTAVESTTRIQVSESNYAGNRTIGN
HRGWFNPTTTSEGFVTYIYAD

FIG. 79D

PsaA:

MKKLGTLLVLFLSAIILVACASGKKDTTSGQKLKVVATNSIIADITKNIAGDKIDLHSIVPIGQDPH
EYEPLPEDVKKTSEANLIFYNGINLETGGNAWFTKLVENAKKTENKDYFAVSDGVDVIYLEGQN
EKGKEDPHAWLNLENGIIFAKNIAKQLSAKDPNNKEFYEKNLKEYTDKLDKLDKESKDKFNKIP
AEKKLIVTSEGAFKYFSKAYGVPSAYIWEINTEEEGTPEQIKTLVEKLRQTKVPSLFVESSVDDRP
MKTVSQDTNIPIYAQIFTDSIAEQGKEGDSYYSMMKYNLDKIAEGLAK

FIG. 79E

Ply:

MANKGVNDFILAMNYDKKKLLTHQGESIENRFIKEGNQLPDEFVVIERKKRSLSTNTSDISVTAT
NDSRLYPGALLVVDETLLENNPTLLAVDRAPMTYSIDLPGLASSDSFLQVEDPSNSSVRGAVNDL
LAKWHQDYGQVNNVPARMQYEKITAHSMEQLKVKFGSDFEKTGNSLDIDFNSVHSGEKQIQIV
NFKQIYYTVSVDAVKNPGDVFQDTVTVEDLKQRGISAERPLVYISSVAYGRQVYLKLETTSKSDE
VEAAFEALIKGVKVAPQTEWKQILDNTEVKAVILGGDPSSGARVVTGKVDMVEDLIQEGSRFTA
DHPGLPISYTTSFLRDNVVATFQNSTDYVETKVTAYRNGDLLLDHSGAYVAQYYITWDELSYDH
QGKEVLTPKAWDRNGQDLTAHFTTSIPLKGNVRNLSVKIRECTGLAFEWWRTVYEKTDLPLVR
KRTISIWGTTLYPQVEDKVEND

FIG. 79F

RECOMBINANT BACTERIUM CAPABLE OF ELICITING AN IMMUNE RESPONSE AGAINST *STREPTOCOCCUS PNEUMONIAE*

CROSS REFERENCE TO RELATED APPLICATIONS

This application is a continuation-in-part of PCT Application PCT/US2009/061100, filed Oct. 16, 2009, which claims the priority of U.S. provisional application No. 61/106,367, filed Oct. 17, 2008, each of which is hereby incorporated by reference in its entirety.

GOVERNMENTAL RIGHTS

This invention was made with government support under RO1 AI056289 awarded by the National Institutes of Health. The government has certain rights in the invention.

FIELD OF THE INVENTION

The invention encompasses a recombinant bacterium capable of eliciting an immune response against *Streptococcus pneumoniae*, a vaccine comprising the bacterium, and methods of using the bacterium.

BACKGROUND OF THE INVENTION

The use of attenuated bacteria that are unable to cause disease triggers a self-limited infection that leads to the stimulation of protective immunity. Attenuated *Salmonella* vaccines induce cellular immune responses by limited replication in the host, which mimics natural infection and results in strong and long-lasting immunity. Oral vaccination with attenuated *Salmonella* induces mucosal immunity and prevents infection at the portal of entry for mucosal pathogens.

Avirulent strains of *Salmonella* can be genetically engineered to stably express, at high levels, colonization and virulence antigens from other bacterial, viral, parasitic, and fungal pathogens. When used for oral immunization, these live avirulent recombinant vaccine strains attach to, invade, and colonize the gut associated lymphoid tissue (GALT) and then pass to other lymphoid tissues, such as mesenteric lymph nodes, liver and spleen. In these lymphoid tissues, the live avirulent recombinant vaccine strains continue to synthesize the foreign colonization or virulence antigens. Since delivery of antigens to the gut associated lymphoid tissue stimulates a generalized secretory immune response, oral immunization with these vaccines stimulates mucosal immunity throughout the body. In addition, systemic and cellular immune responses are elicited against the foreign expressed antigens as well as against *Salmonella* antigens.

Achieving maximal immune responses to the foreign antigen is dependent upon the amount of the foreign antigen produced by the recombinant avirulent *Salmonella* and also upon the inherent immunogenic properties of the foreign antigen. Although data to indicate the importance or non importance of antigen location in recombinant avirulent *Salmonella* is by and large lacking, there are some reasons to believe that the time of onset, magnitude and/or duration, as well as the type of immune response might be influenced by antigen localization in the recombinant avirulent *Salmonella* vaccine.

*S. pneumoniae* is the world's foremost bacterial pathogen, causing high morbidity and mortality, even in regions where antibiotics are readily available. It is the single most common cause of community-acquired pneumonia, and has become the most common cause of meningitis in many regions. The pneumococcus is conservatively estimated to kill 1-2 million children under the age of 5 years each year in developing countries, accounting for 20-25% of all deaths in this age group. The problem of pneumococcal disease is being further exacerbated by the rate at which this organism is acquiring drug resistance and the rapid global spread of highly resistant clones. In developed countries this necessitates use of newer, more expensive antimicrobials, but this option is not available in the developing world. Antibodies to pneumococcal capsular polysaccharides can protect against fatal infection and capsule-based human vaccines have been developed. These vaccines provide serotype-specific protection, and the adult formulation contains a mixture of the 23 most common polysaccharides. However, there are over 90 distinct capsular serotypes of *S. pneumoniae*, and geographic differences in serotype prevalence have resulted in suboptimal protection in many countries. Moreover, this vaccine is not immunogenic in children under two years old who have the highest disease burden. A more immunogenic 7-valent protein-polysaccharide conjugate vaccine has recently been licensed for children that is quite effective against invasive disease and provides some protection against nasal carriage and otitis media. Unfortunately, it covers only 50-60% of pneumococcal infections in many developing countries. Alarmingly, trials of the conjugate vaccine have shown that although carriage of vaccine types was reduced, the vacated niche was promptly occupied by non-vaccine serotypes known to cause invasive disease. This "replacement carriage" has translated into a significant increase in cases of disease caused by non-vaccine serotypes in conjugate vaccine recipients. The remedy for this problem has been to add more capsular types to the conjugate vaccine. However, at its current cost of US$260/course the 7-valent vaccine is already too expensive for use in the developing countries. Thus, continued use of vaccines that simply alter the serotype distribution of pneumococcal disease are likely to have little long-term impact on pneumococcal disease, especially in the poorest countries where most of the disease occurs.

Consequently, there is a need in the art for an effective vaccine against *Streptococcus pneumoniae*.

SUMMARY OF THE INVENTION

One aspect of the present invention encompasses a recombinant *Salmonella* bacterium. The bacterium is capable of the regulated expression of at least one nucleic acid encoding a *Streptococcus pneumoniae* antigen. Additionally, the bacterium is capable of regulated attenuation. The bacterium further comprises at least one mutation that affects the persistence of the bacterium in a host, and at least one mutation that reduces fluid secretion in a host.

Another aspect of the invention encompasses a recombinant *Salmonella Typhi* bacterium. The bacterium is typically capable of the regulated expression of at least one nucleic acid encoding a *Streptococcus pneumoniae* antigen, wherein the bacterium comprises at least one of the mutations selected from the group consisting of ΔaroC1083, ΔaroD769, $\Delta P_{murA25}$::TT araC $P_{BAD}$ murA, and ΔasdA27::TT araC $P_{BAD}$ c2. The bacterium is also typically capable of regulated attenuation, wherein the bacterium comprises at least one of the mutations selected from the group consisting of Δpmi-2426, $\Delta P_{rfc174}$::TT araC $P_{BAD}$ rfc, $\Delta P_{fur81}$::TT araC $P_{BAD}$ fur, $\Delta P_{crp527}$::TT araC $P_{BAD}$ crp, and $\Delta P_{murA25}$::TT araC $P_{BAD}$ murA. Additionally, the bacterium comprises at least one mutation that effects the persistence of the bacterium selected from the group consisting of Δpmi-2426, $\Delta P_{rfc174}$::TT araC P$_{BAD}$ rfc, ΔP$_{fur81}$::TT araC P$_{BAD}$ fur, ΔP$_{crp527}$::TT araC P$_{BAD}$ crp, ΔsopB1925, ΔtviABCDE10, ΔP$_{murA25}$::TT araC P$_{BAD}$ murA, and ΔpagP81::P$_{lpp}$ IpxE., and at least one mutation that reduces fluid secretion in a host selected from the group consisting of ΔsopB1925 and ΔpagP81::P$_{lpp}$ IpxE.

Yet another aspect of the invention comprises a vaccine composition, the composition comprising a recombinant *Salmonella* bacterium.

Still another aspect of the invention comprises a method for eliciting an immune response against *Streptococcus pneumoniae* in a host. The method comprising administering a vaccine composition to the host comprising a recombinant *Salmonella* bacterium.

Other aspects and iterations of the invention are described more thoroughly below.

BRIEF DESCRIPTION OF THE FIGURES

FIG. 4 depicts (A-B) the sequence of wild-type gmd-fcl showing the deleted region and its flanking region (SEQ ID NO:47). The deleted region is bracketed [ ] and primers for PCR verification are bolded and underlined. (C) A schematic of the mutation. Primers for validating the presence of the Δ(gmd-fcl)-26 mutation are as follows: primer (wcaF-SmaI): 5'TCCCCCGGGCAAAATATTGTATCGCTGG 3'(SEQ ID NO:89) and Primer (gmm/wcaH-SphI): 5'GCACGCATGCT-CAGGCAGGCGTAAATCGCTCT 3' (SEQ ID NO:90). When the Δ(gmd-fcl)-26 mutation is present the expected PCR product length is 849 bp compared to 2940 bp for the wild-type sequence.

FIG. 5 depicts (A-B) the sequence of wild-type araE showing the deleted region and its flanking region ((SEQ ID NO:48 (nucleic acid sequence); SEQ ID NO:49 (amino acid sequence)). Deleted region is bracketed [ ] and primers for PCR verification are bolded and underlined. (C) A schematic of the mutation. Primers for validating the presence of the ΔaraE25 mutation are as follows: primer araE N-SphI: 5' GACTGCATGCATGGTGTTGGTACA 3'(SEQ ID NO:91) and primer araE C-BamHI: 5' CGGGATCCCATAGCGGTA-GATG 3'(SEQ ID NO:92). When the ΔaraE25 mutation is present the expected PCR product length is 774 bp compared to 2198 bp for the wild-type sequence.

FIG. 6 depicts (A-B) the sequence of the wild-type araBAD operon showing the deleted region and its flanking region (SEQ ID NO:50). The deleted region is bracketed [ ] and primers for PCR verification is bolded and underlined. (C) A schematic of the mutation. The primers for validating the presence of the ΔaraBAD23 mutation are as follows: primer araC-SphI: 5'ACATGCATGCGGACGATCGATAA 3'(SEQ ID NO:93) and primer araD-BamHI:5'CGGGATCCTGG-TAGGGAACGAC 3' (SEQ ID NO:94). When the Δara-BAD23 mutation is present the expected PCR product length is 847 bp compared to 4935 bp for the wild-type sequence.

FIG. 7 depicts (A-B) the sequence of wild-type sopB showing the deleted region and its flanking region. ((SEQ ID NO:51 (nucleic acid sequence); SEQ ID NO:52 (amino acid sequence)) The deleted region is bracketed [ ] and primers for PCR verification are bolded and underlined. (C) A schematic of the mutation. The primers for validating the presence of the ΔsopB1925 mutation are as follows: primer N-SphI: 5' ACATGCATGCGGCATACACACACCTGTATAACA 3'(SEQ ID NO:95) and primer C-XmaI: 5' TTC-CCCCGGGGCAGTATTGTCTGCGTCAGCG 3'(SEQ ID NO:96). When the ΔsopB1925 mutation is present the expected PCR product length is 593 bp compared to 2291 bp for the wild-type sequence.

FIG. 8 depicts (A-C) the sequence of the wild-type tviAB-DCE operon showing the deleted region and its flanking region (SEQ ID NO:53). The deleted region is bracketed [ ] and primers for PCR verification are bolded and underlined. (D) A schematic of the mutation. The primers for validating the presence of the ΔtviABCDE10 mutation are as follows: primer vexA-3 SphI: 5' ACATGCATGCGAACGGTAT-TACTGTCAGTCACAAG 3'(SEQ ID NO:97) and primer UtviA-5 SmaI: 5' TCCCCCGGGCAGAT-TATTTCAAATACGATTAGG 3'(SEQ ID NO:98). When the ΔtviABCDE10 mutation is present the expected PCR product length is 707 bp compared to 8111 bp for the wild-type sequence.

FIG. 11 depicts (A) the sequence of wild-type crp showing the deleted region and its flanking region ((SEQ ID NO:57 (nucleic acid sequence); SEQ ID NO:58 (amino acid sequence)). The deleted region is bracketed [ ] and primers for PCR verification are bolded and underlined. (B) A schematic of the mutation is depicted. The primers for validating the presence of the ΔP$_{crp527}$::TTaraCP$_{BAD}$crp mutation are as follows: primer Ucrp-N SphI: 5' ACAT GCATGCATCTCCATCGGA CTCGGCGCTTT 3'(SEQ ID NO:103) and primer crp C-SacI: 5' TGCGAGCTC CAGAATATCCGGGTTGACCTG 2'(SEQ ID NO:104).

When the ΔP$_{crp527}$::TT araC P$_{BAD}$ crp mutation is present the expected PCR product length is 2024 bp compared to 784 bp for the wild-type sequence.

FIG. 12 depicts (A-B) the chromosomal sequence after ΔP$_{crp527}$::TTaraCP$_{BAD}$crp deletion-insertion mutation.

Figure 13D:
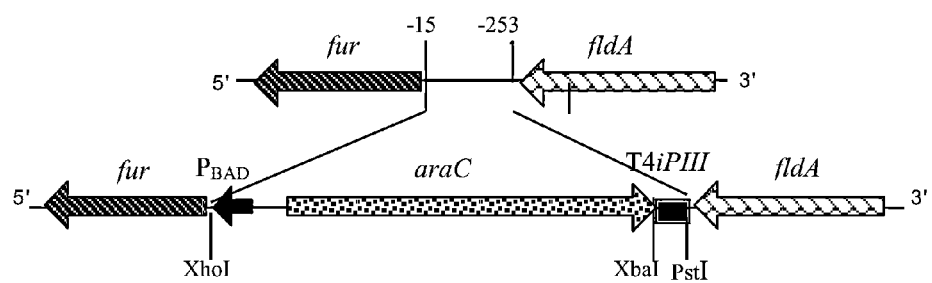

FIG. 13 depicts (A) the sequence of wild-type fur showing the deleted region and its flanking region ((SEQ ID NO:62 (nucleic acid sequence); SEQ ID NO:63 and SEQ ID NO:64 (amino acid sequences)). The wild-type SD region and start codon is: AGGA CAGATTCCGC ATG ACT GAC AAC AAT (SEQ ID NO:105), while the modified sequence for ΔP$_{fur81}$::TT araC P$_{BAD}$ fur is: AAGG CAGATTCCGC GTG ACT GAC AAC AAT (SEQ ID NO:106). The modifications are marked in bold. (B-C) The chromosomal sequence after ΔP$_{fur81}$::TTaraCP$_{BAD}$fur deletion-insertion mutation is depicted ((SEQ ID NO:65 (nucleic acid sequence); SEQ ID NO:66, SEQ ID NO:67, and SEQ ID NO:68 (amino acid sequences)). The deleted region is bracketed [ ] and primers for PCR verification are bolded and underlined. The primers for validating the presence of the ΔP$_{fur81}$::TTaraCP$_{BAD}$fur mutation are as follows: primer 1 (fldA-N SphI): 5'ACATG-CATGCTGTGACTGGGATGACTTCTTCCCG 3' (SEQ ID NO:107) and primer 2 (fur-XmaI): 5'TCCCCCGGGCACTTTTCCGCAATCAAGGCAG 3' (SEQ ID NO: 108). When the ΔP$_{fur81}$::TT araC P$_{BAD}$ fur mutation is present the expected PCR product length is 2035 bp compared to 939 bp for the wild-type sequence. (D) A schematic of the mutation is depicted. 239 bp of fur promoter region (−15 to −253; including Fur consensus, CRP binding, and OxyR binding site) is deleted and 1335 bp P$_{BAD}$ araC TT inserted. The SD and ATG starting codon is changed to AAGG (weaker SD) and GTG respectively.

FIG. 14 depicts (A-B) the sequence of wild-type relA showing the deleted region and its flanking region is depicted ((SEQ ID NO:69 (nucleic acid sequence); SEQ ID NO:70 (amino acid sequence)). The deleted region is bracketed [ ] and primers for PCR verification are bolded and underlined. When the DrelA198::araC P$_{BAD}$ lacl TT mutation is present, the expected PCR product lengths are as follows: 3,307 bp for primers 1 and 2; 1,592 bp for primers 1 and 3; and 1,727 bp for primers 2 and 4. For the wild-type sequence, the expected PCR product length with primers 1 and 2 is 3,125 bp. Note that the primers 3 and 4 are present only in the ΔrelA198 mutant since these primers are in the araC P$_{BAD}$ lacI TT insert. The primer sequences are as follows: primer 1(RelA N-HindIIISacI): 5'CCCAAGCTTGAGCTCGAGGGCGTTCCG-GCGCTGGTAGAA3'(SEQ ID NO: 109), primer 2(RelA C-KpnI): 5'CGGGTACCCCAGATATTTTCCAGATCT-TCAC 3'(SEQ ID NO: 110), primer 3(SD*-ATG lacl-NXhoI): 5'CCGCTCGAGAGGATGGTGAATATGAAAC-CAGTAACGTT3'(SEQ ID NO:111), and primer 4(P$_{BAD}$araC KpnI): 5' AGAGGTACCCTCGAGGCTAGC-CCAAAAAAACGGG 3'(SEQ ID NO: 112). (C) A schematic of the mutation is depicted. 2247 bp of relA (−12 to 2235/2235) is deleted and 2393 bp of TT araC P$_{BAD}$ ATG-lacI is inserted. (D-E) The chromosomal sequence after ΔrelA198::araCP$_{BAD}$lacITT deletion-insertion mutation is depicted (SEQ ID NO:71 and SEQ ID NO:72). The base pairs changed to optimize lacI are shown in bold.

Figure 15A:
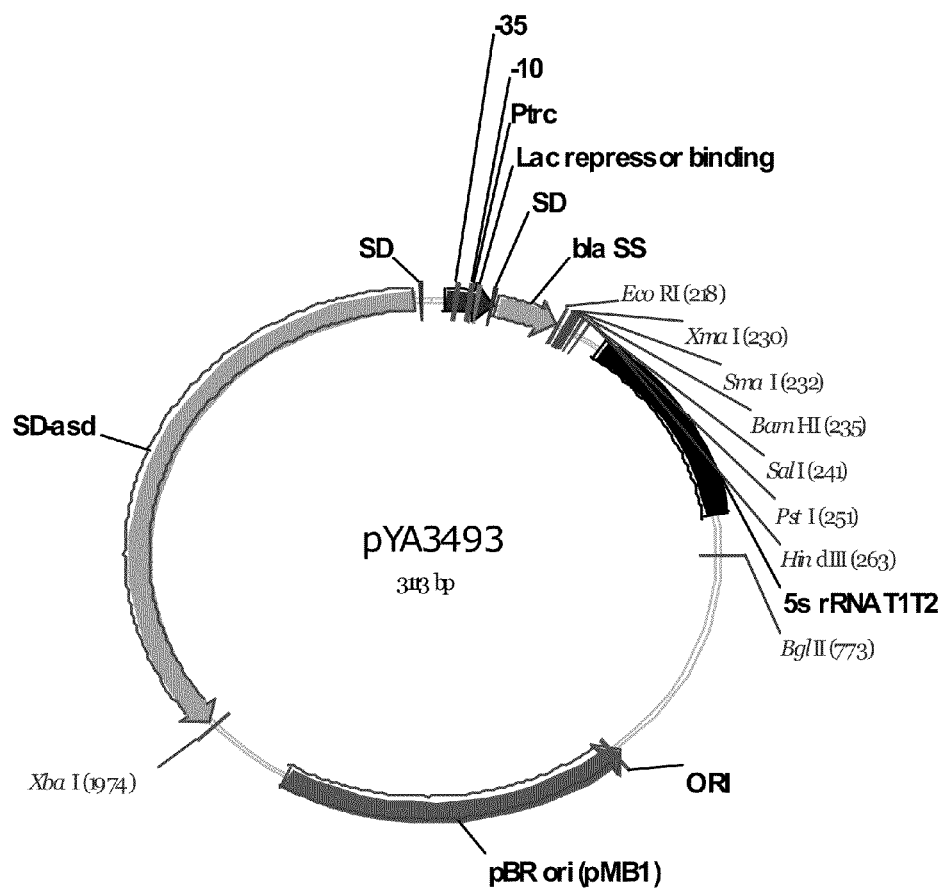

FIG. 15 depicts the pYA3493 nucleotide sequence (SEQ ID NO:76) (B) and plasmid map (A).

Figure 16A:
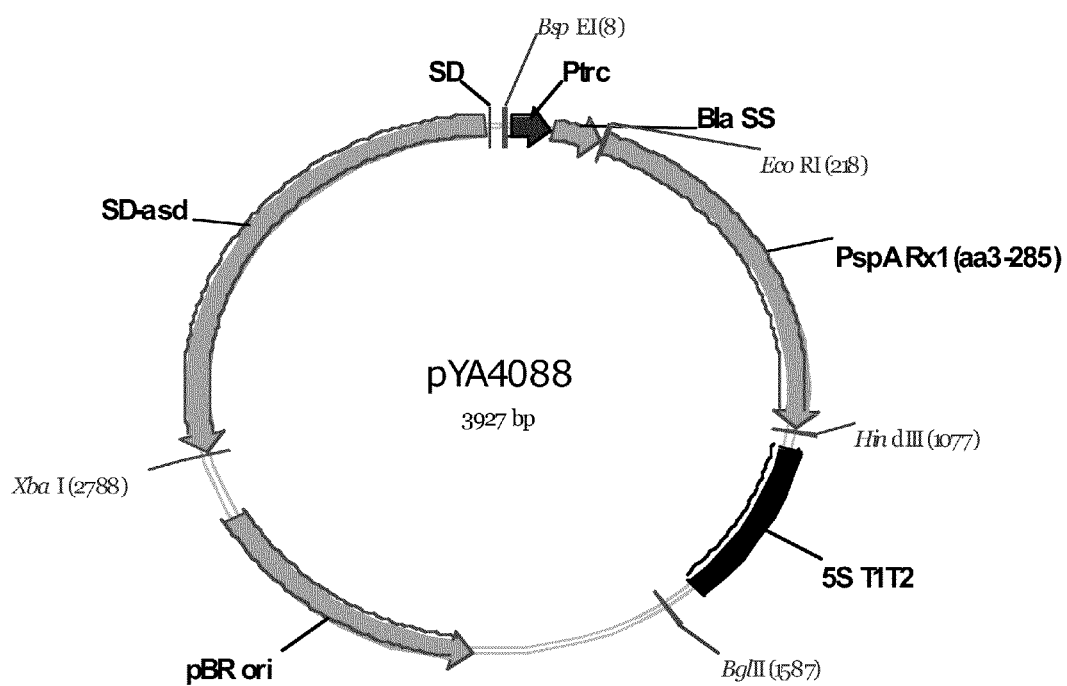

FIG. 16 depicts the pYA4088 nucleotide sequence (SEQ ID NO:77) (B-C) and plasmid map (A).

FIG. 17 depicts the amino acid sequence of PspA/Rx1(aa 3-285) with signal peptide in pYA4088. SEQ ID NO:78 is the amino acid sequence. SEQ ID NO:79 is the nucleotide sequence.

FIG. 18 depicts the nucleic acid sequence of PspA/Rx1(aa 3-285) with signal peptide in pYA4088 (SEQ ID NO:80).

FIG. 19 depicts PspA/Rx1(aa 3-285) without signal peptide in pYA4088 (nucleotide sequence) (SEQ ID NO:81).

FIG. 20 depicts PspA/Rx1 amino acid sequence with signal peptide (SEQ ID NO:82).

FIG. 21 depicts PspA/Rx1 amino acid sequence without signal peptide (SEQ ID NO:83).

FIG. 22 depicts the predicted hypothetical mature, secreted PspA/Rx1 protein (SEQ ID NO:84).

Figure 23A:
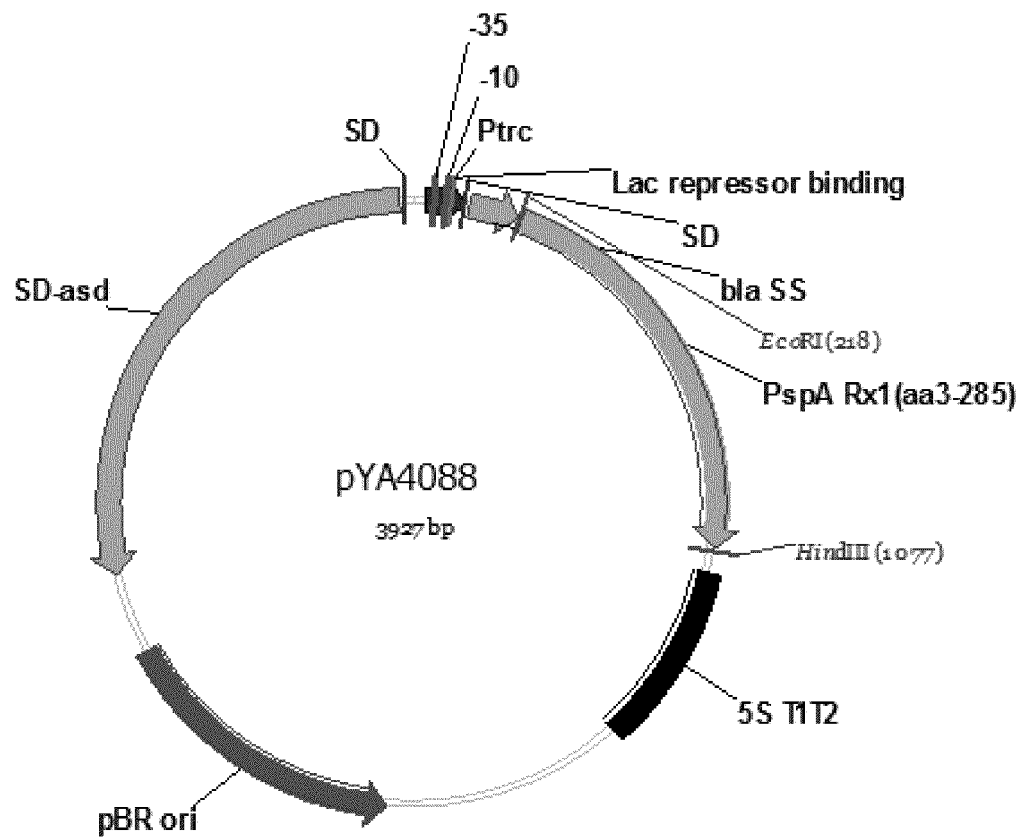
Figure 23B:
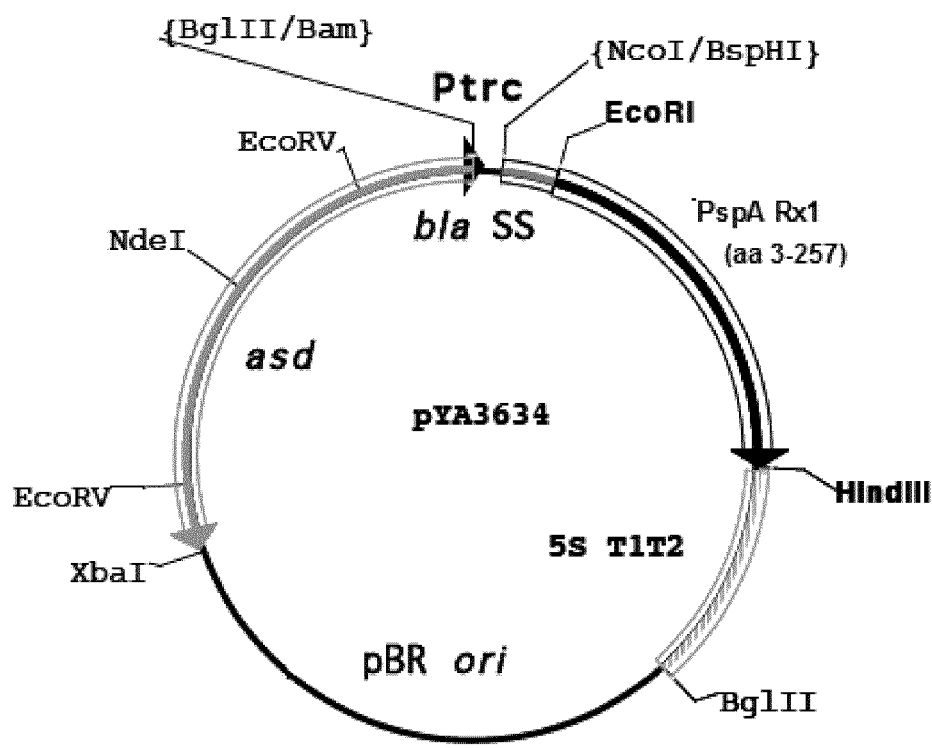
Figure 23C:
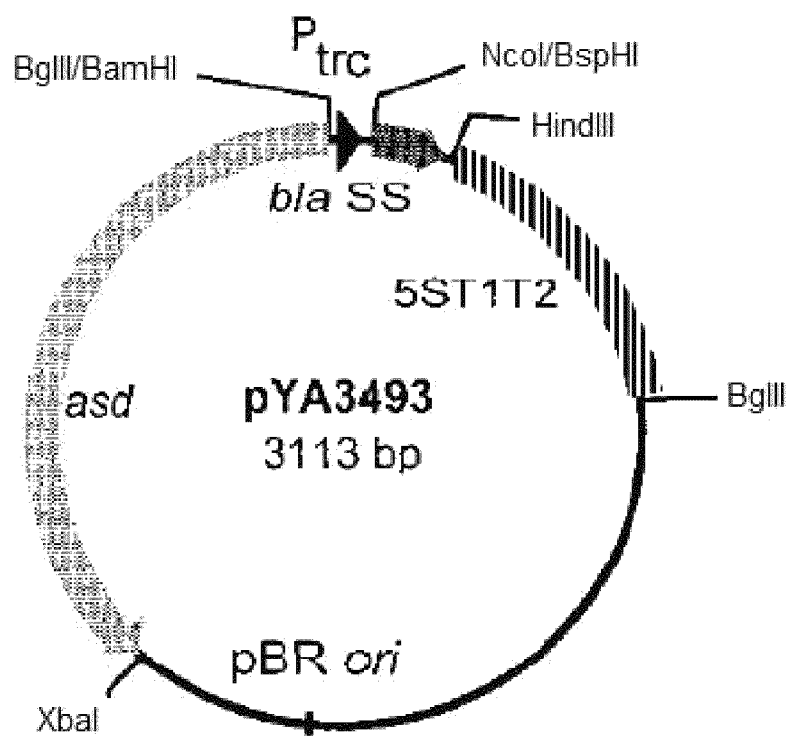

FIG. 23 depicts a schematic of PspA expression plasmids (A) pYA4088 and (B) pYA3634 with empty control vector (C) pYA3493.

Figure 24:
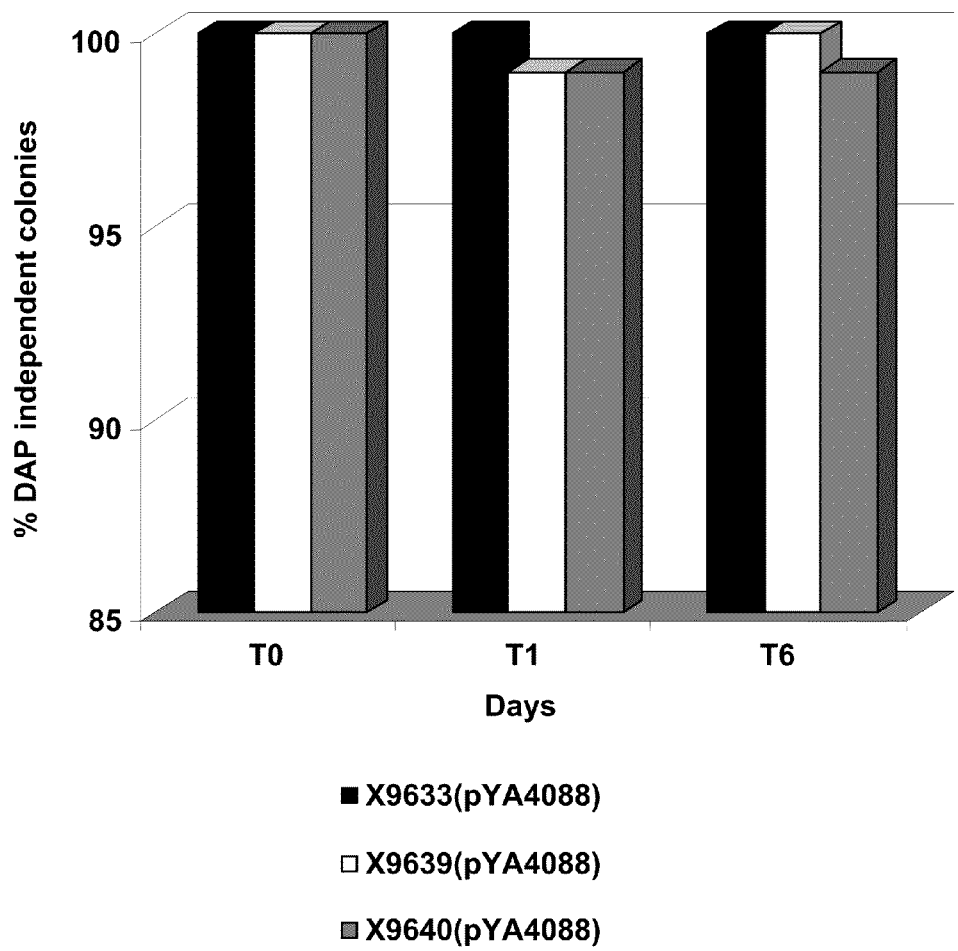

FIG. 24 depicts a graph showing the stability of PspA Asd+ plasmid pYA4088 in KT broth. Electrophoresis of plasmid extractions of isolates recovered after 50 generations of growth show that 100% of the retained plasmids were of the correct size and expressed the 37 kDA PspA protein.

Figure 25A:
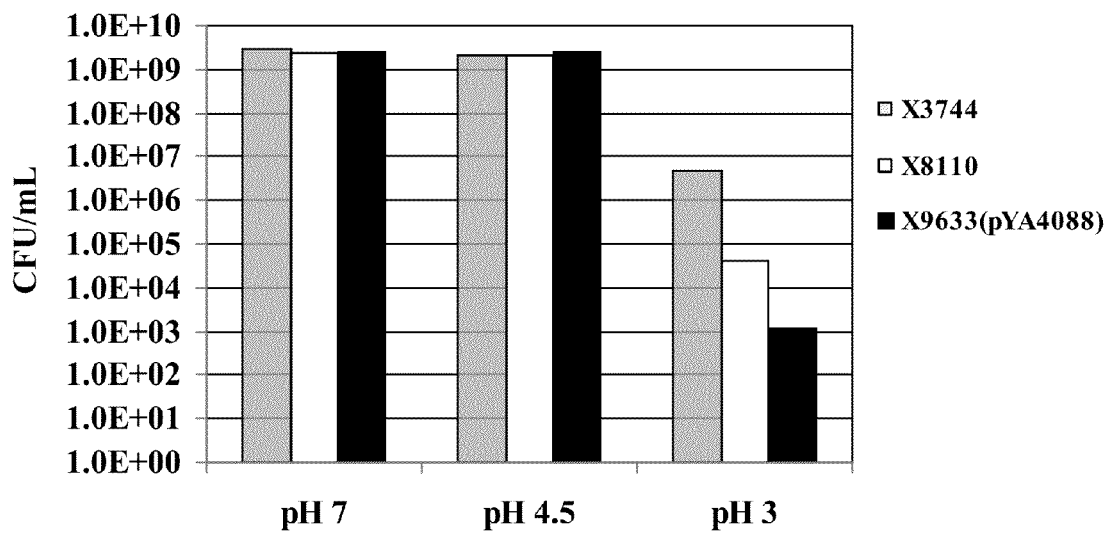
Figure 25B:
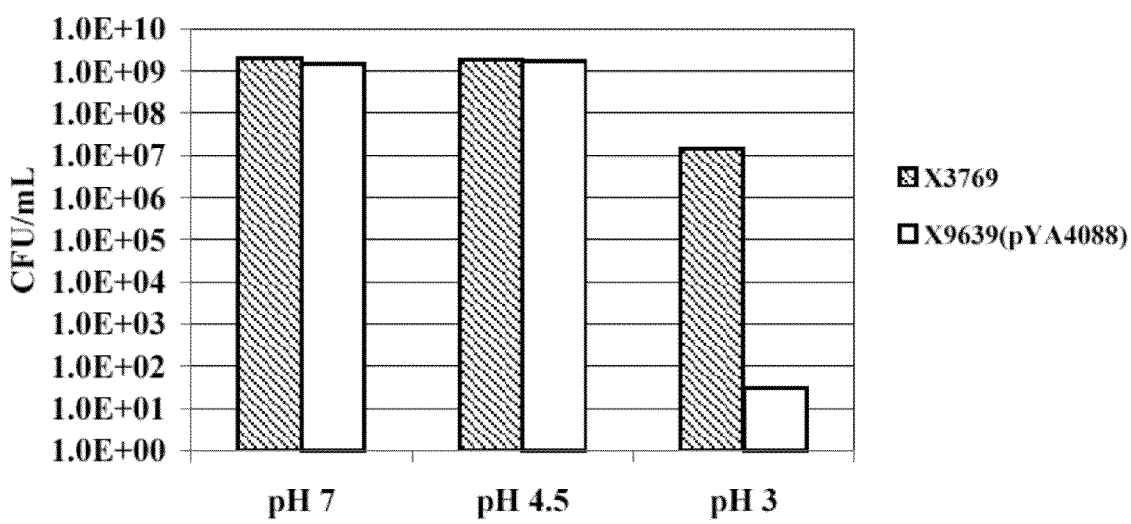
Figure 25C:
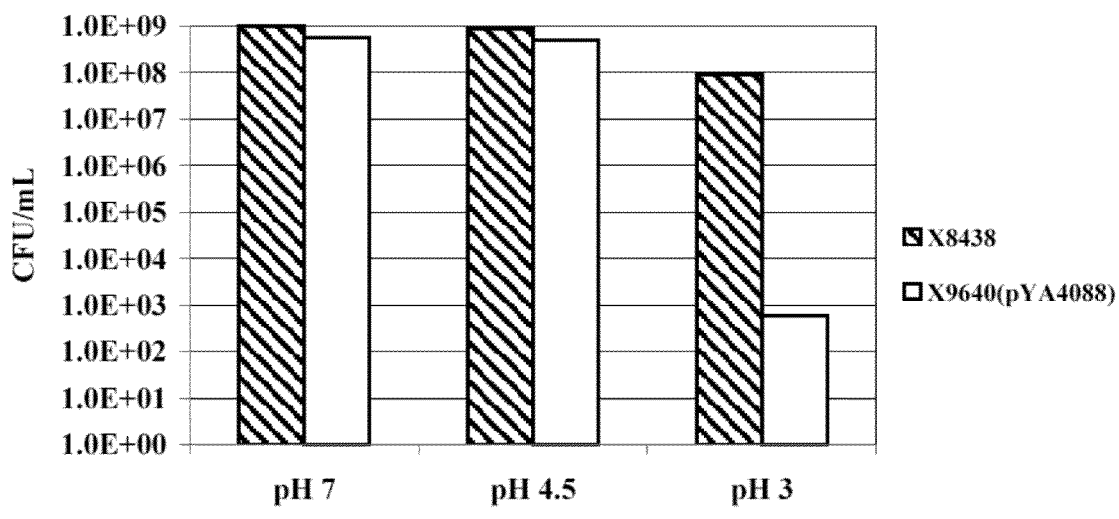

FIG. 25 depicts a series of graphs showing the sensitivity of (A) χ9633(pYA4088), (B) χ9639(pYA4088) and (C) χ9640 (pYA4088) RASV-Sp strains to low pH.

Figure 26:
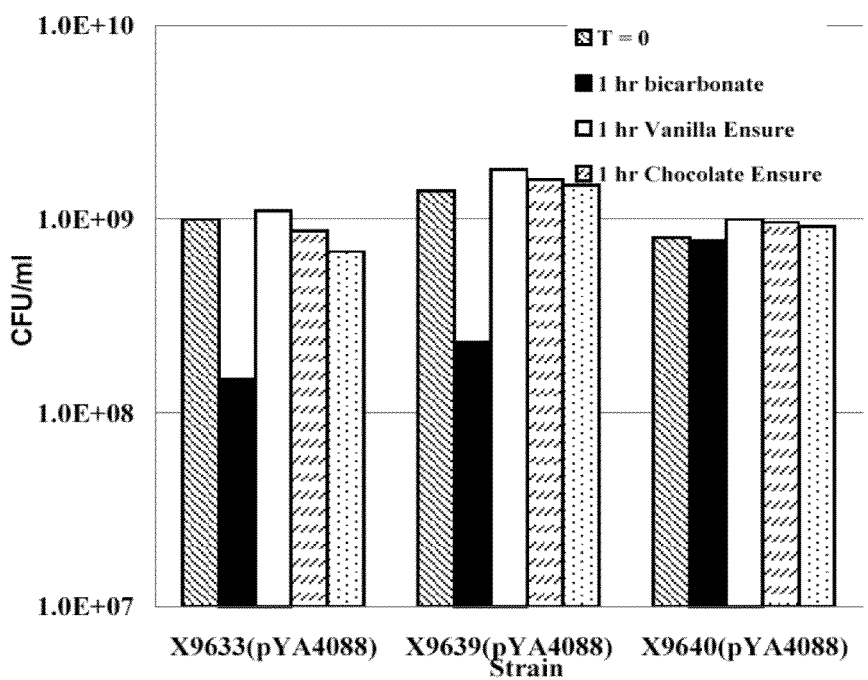

FIG. 26 depicts a graph showing the stability of RASV-Sp vaccine in Ensure nutrition shakes at 37° C.

Figure 27:
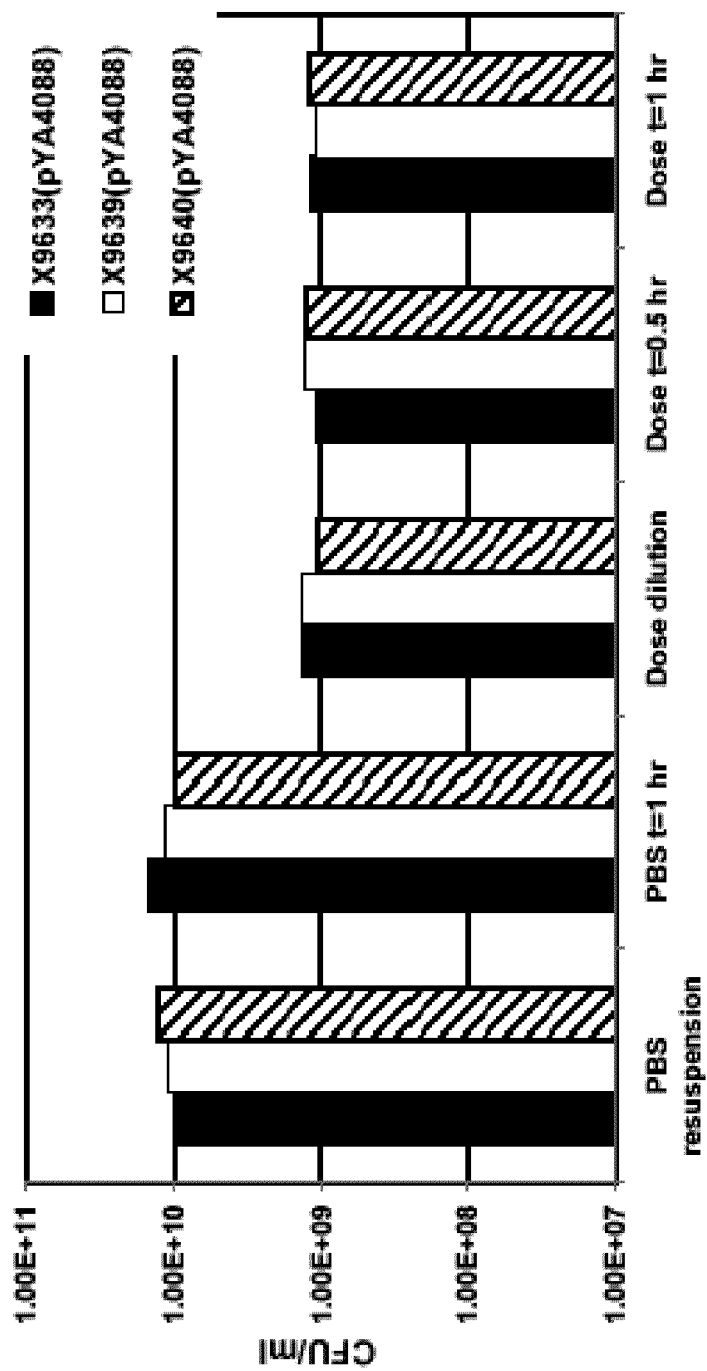

FIG. 27 depicts a graph showing the stability of RASV-Sp strains in PBS at room temperature.

Figure 28A:
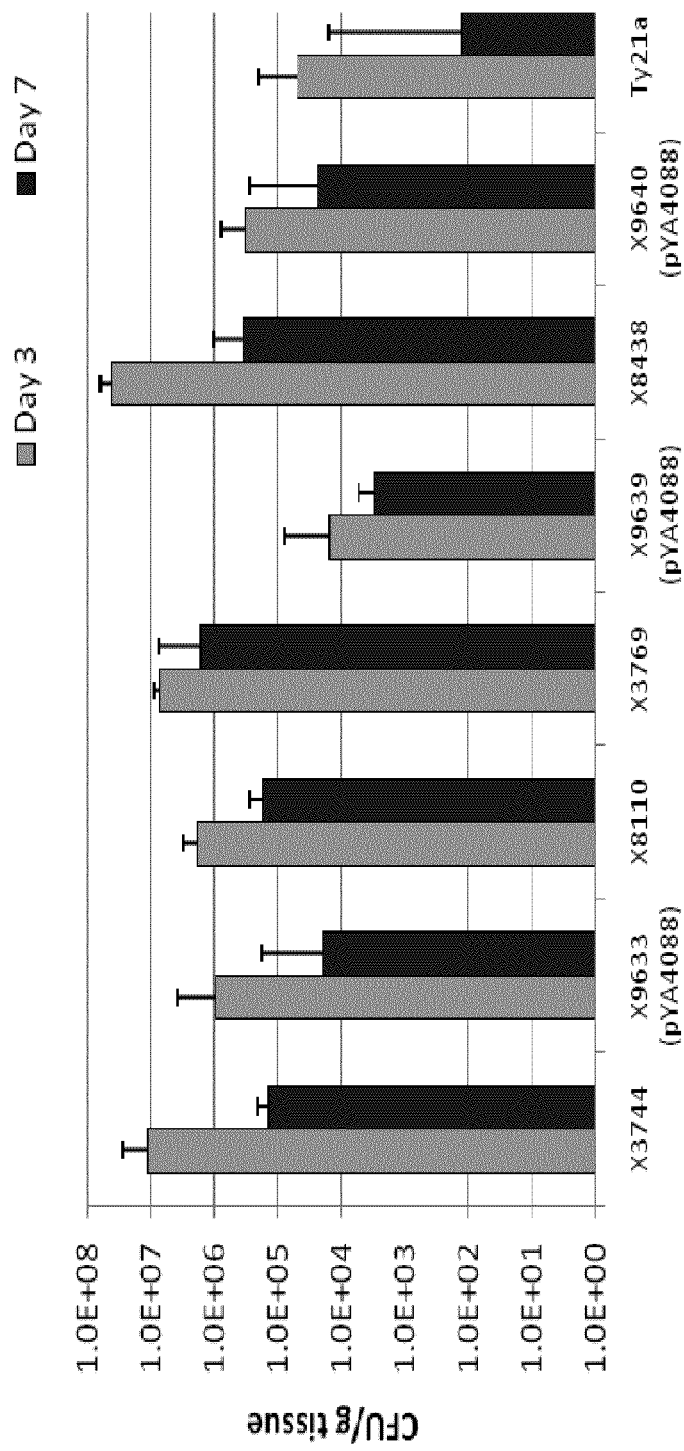
Figure 28B:
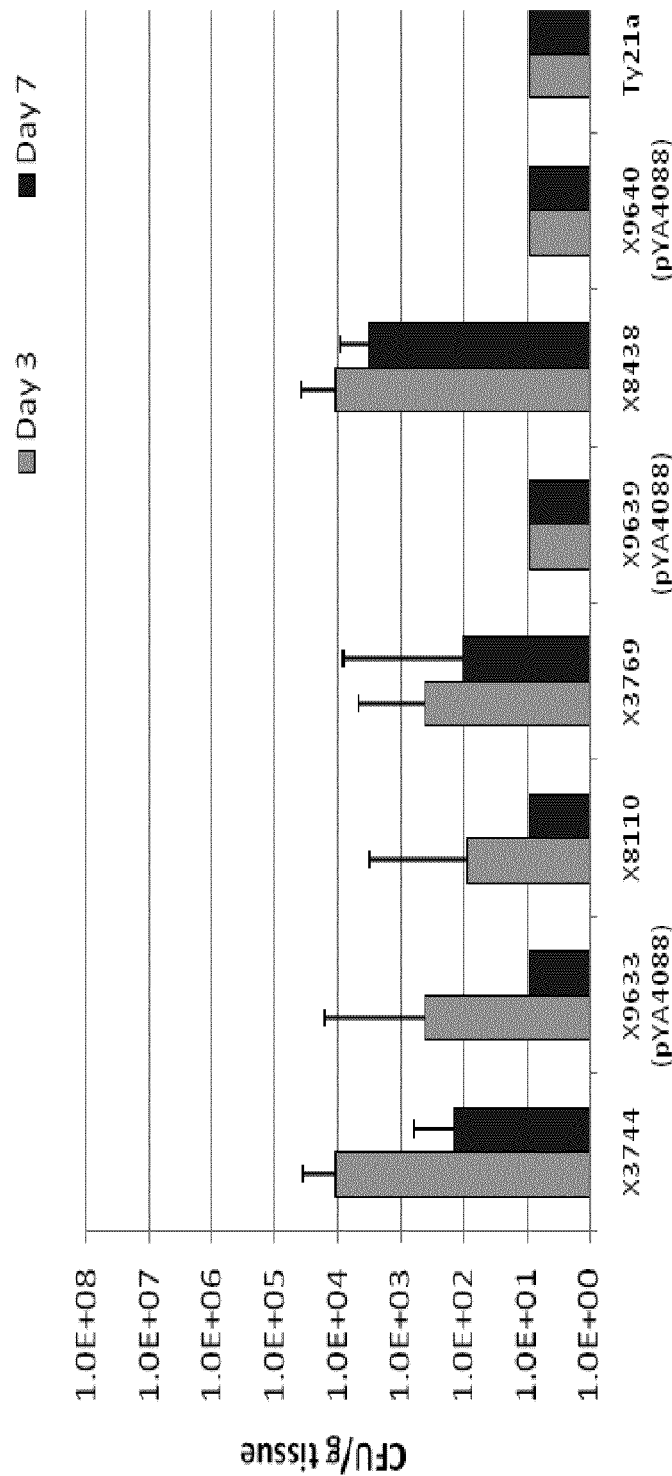
Figure 28C:
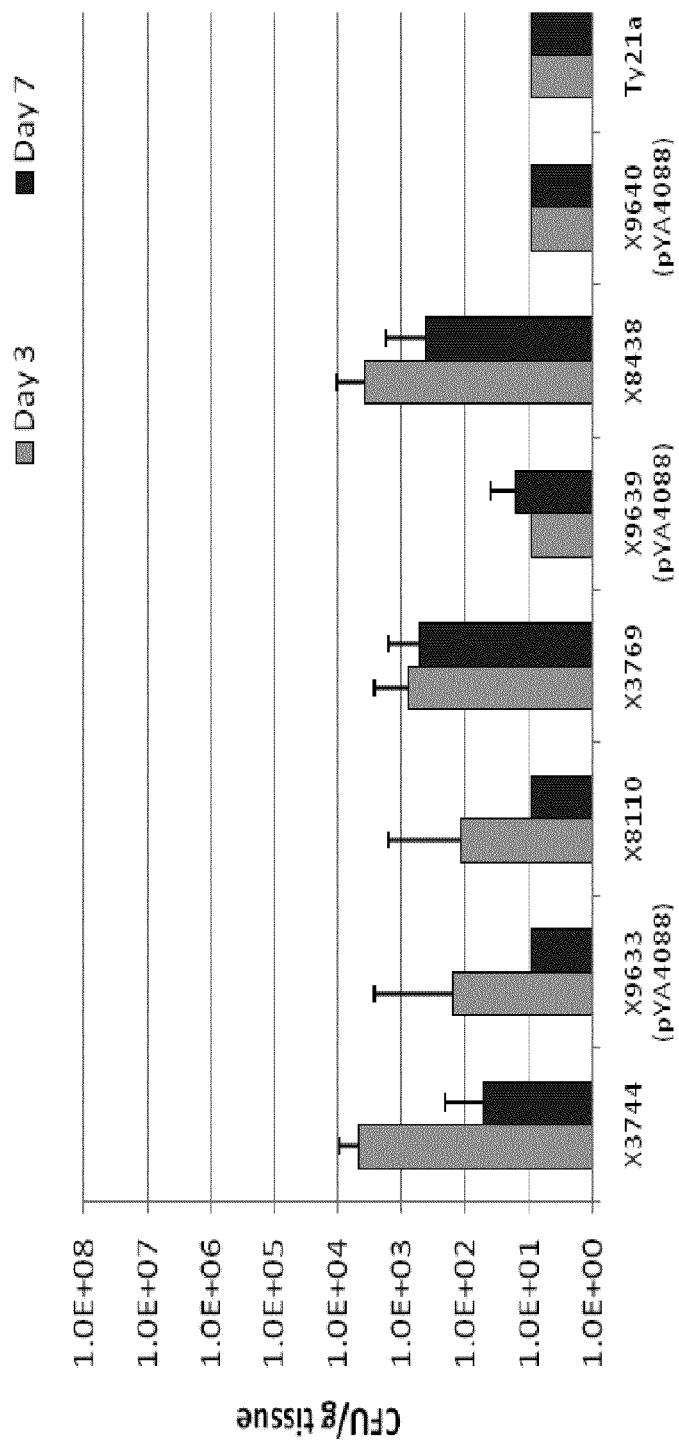

FIG. 28 depicts a series of graphs showing the colonization of the S. Typhi strains in (A) instestine, (B) spleen, and (C) liver of newborn mice.

Figure 29A:
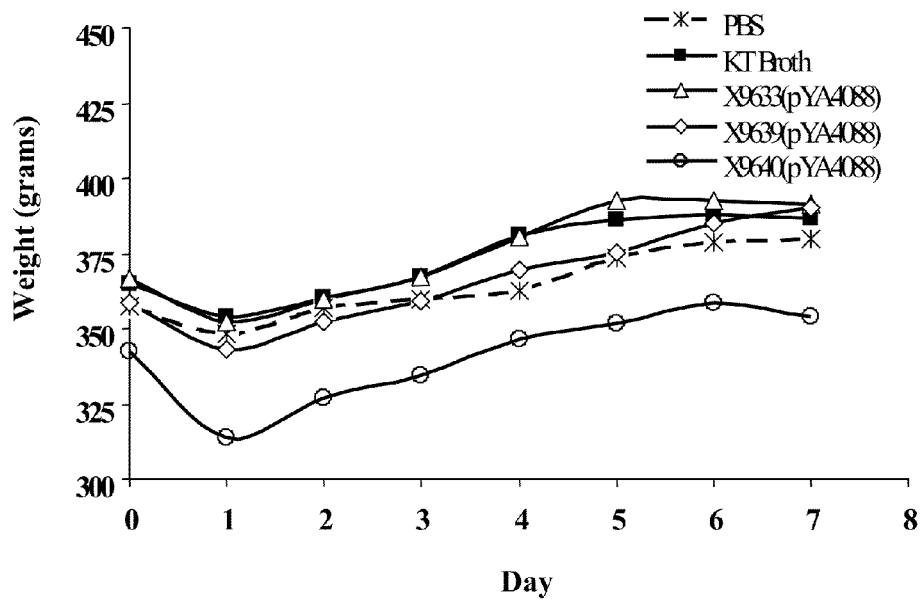
Figure 29B:
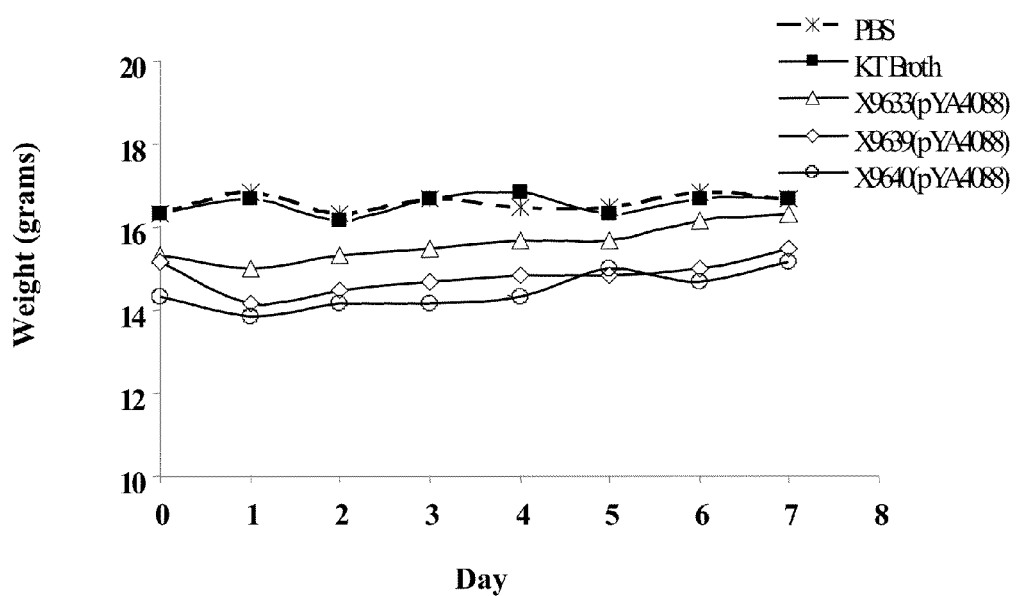

FIG. 29 depicts a series of graphs showing the (A) weights of guinea pigs administered sterile and cell-free PBS wash, and (B) weights of mice administered sterile and cell-free PBS wash.

Figure 30A:
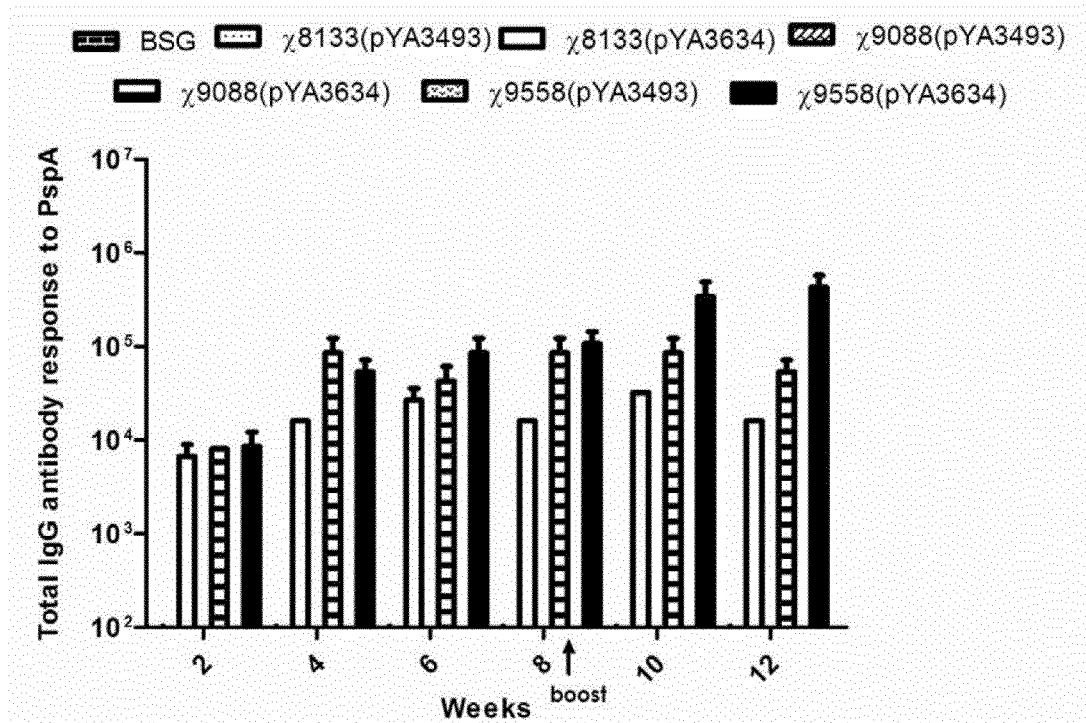
Figure 30B:
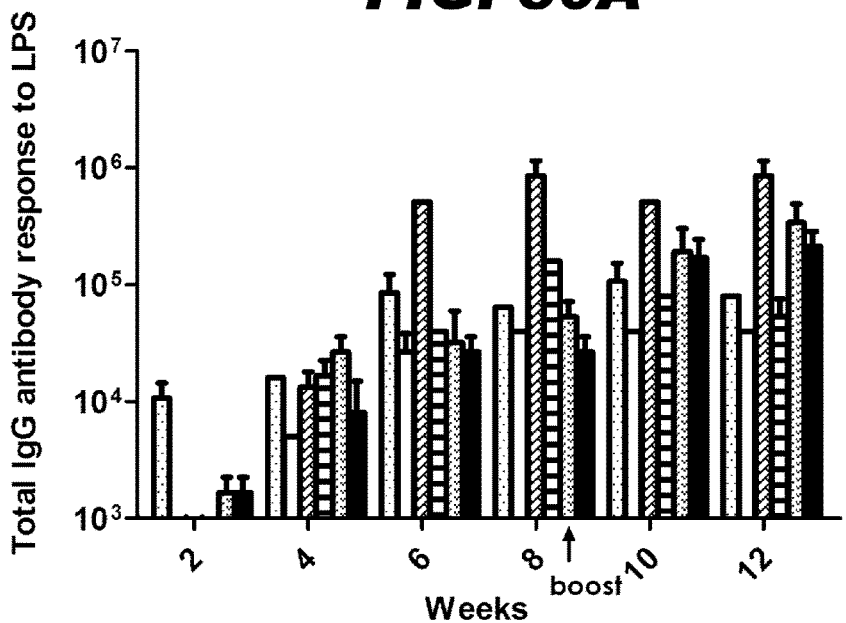

FIG. 30 depicts a series of graphs showing the total serum IgG from mice orally vaccinated with χ8133(pYA3634), χ9088(pYA3634) and χ9558(pYA3634) to (A) PspA and to (B) S. Typhimurium LPS.

Figure 31:
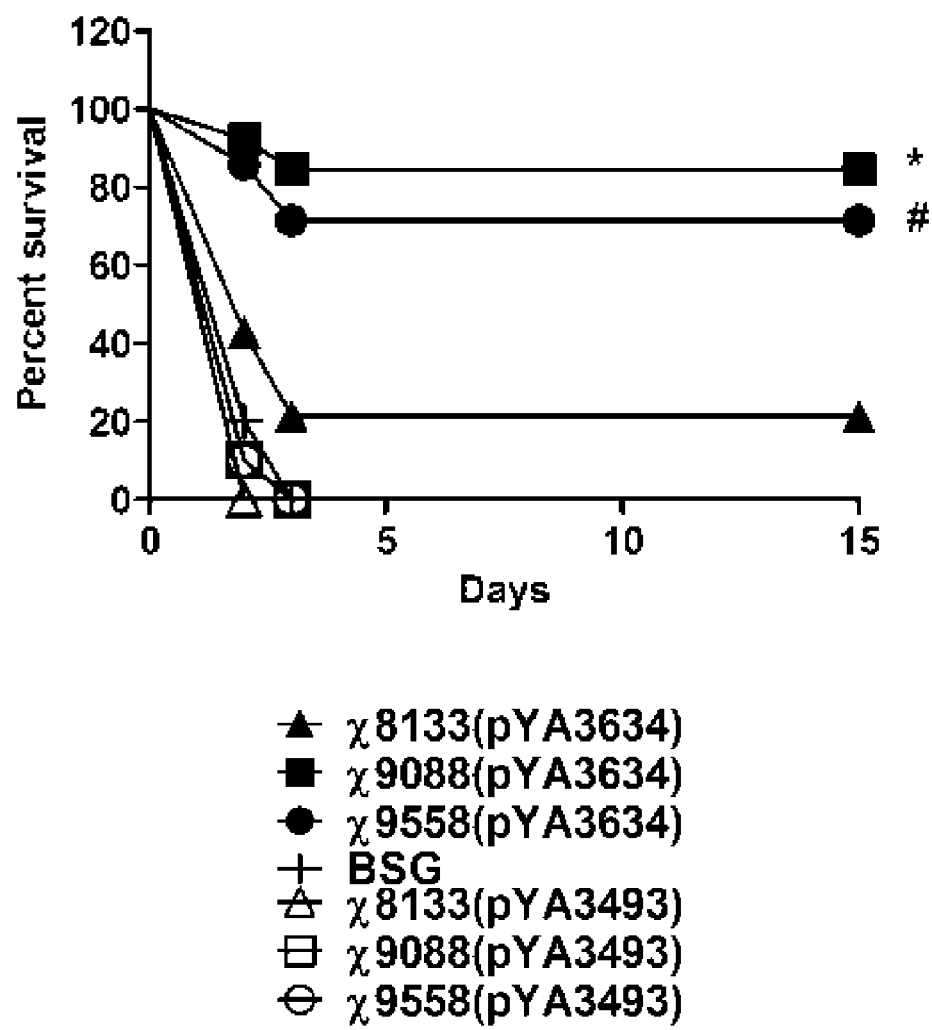

FIG. 31 depicts a graph showing immunization with χ9558 (pYA3634) protects mice against challenge with virulent S. pneumoniae strain WU2.

FIG. 32 depicts a series of graphs showing (A) the total IgG antibody response to PspA, (B) the total IgG antibody response to S. Typhi LPS, and (C) the total antibody response to S. Typhi outer membrane proteins.

Figure 33A:
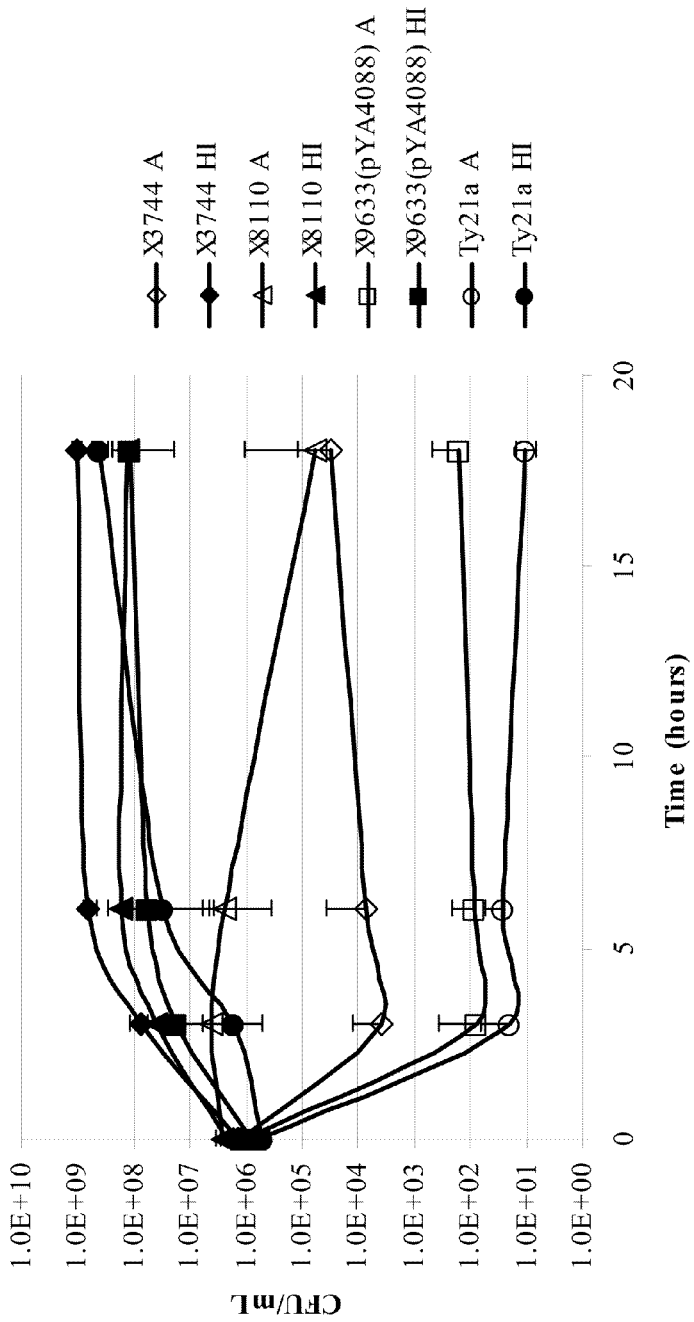
Figure 33B:
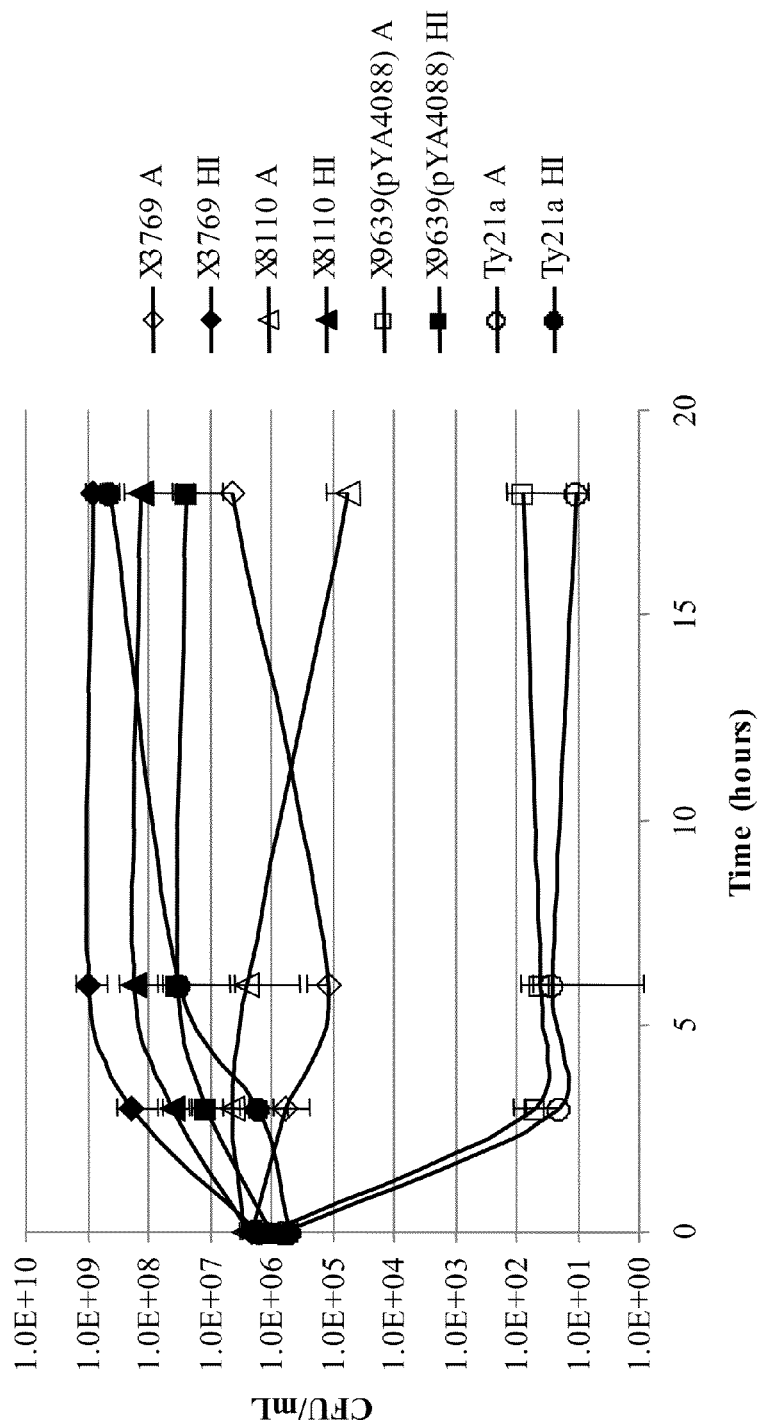
Figure 33C:
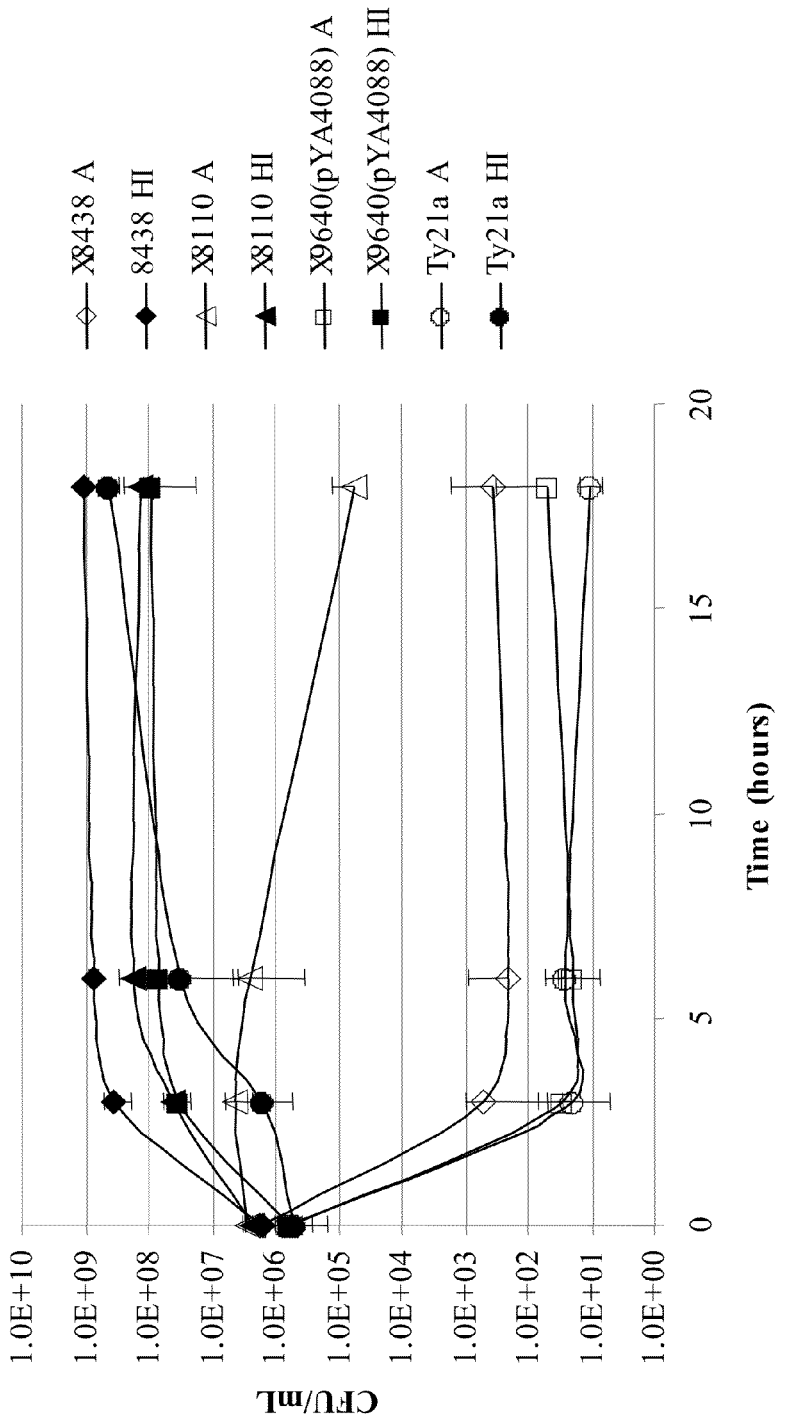

FIG. 33 depicts a series of graphs showing the survival of (A) S. Typhi ISP1820 derivatives, (B) Ty2 RpoS$^-$ derivatives, and (C) Ty2 RpoS$^+$ derivatives in active (A) and heat-inactivated (HI) whole human blood including χ8110 and Ty21a as controls.

Figure 34:
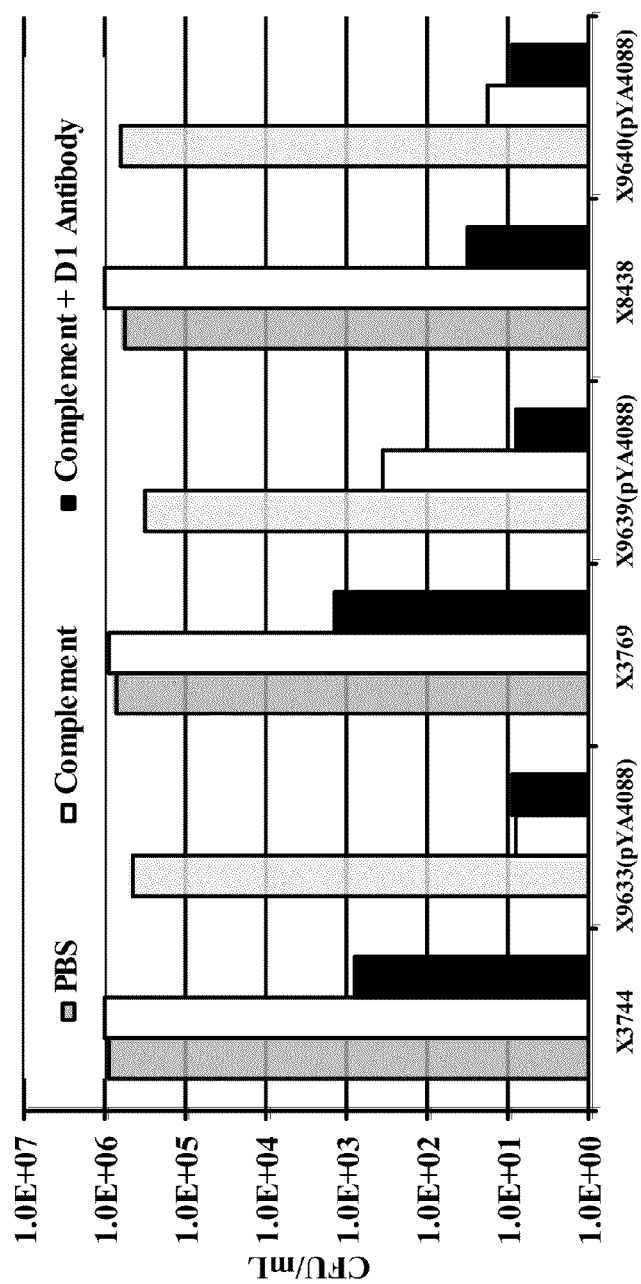

FIG. 34 depicts a graph showing the resistance of RASV-Sp strains compared to wild-type S. Typhi strains to guinea pig complement.

Figure 35A:
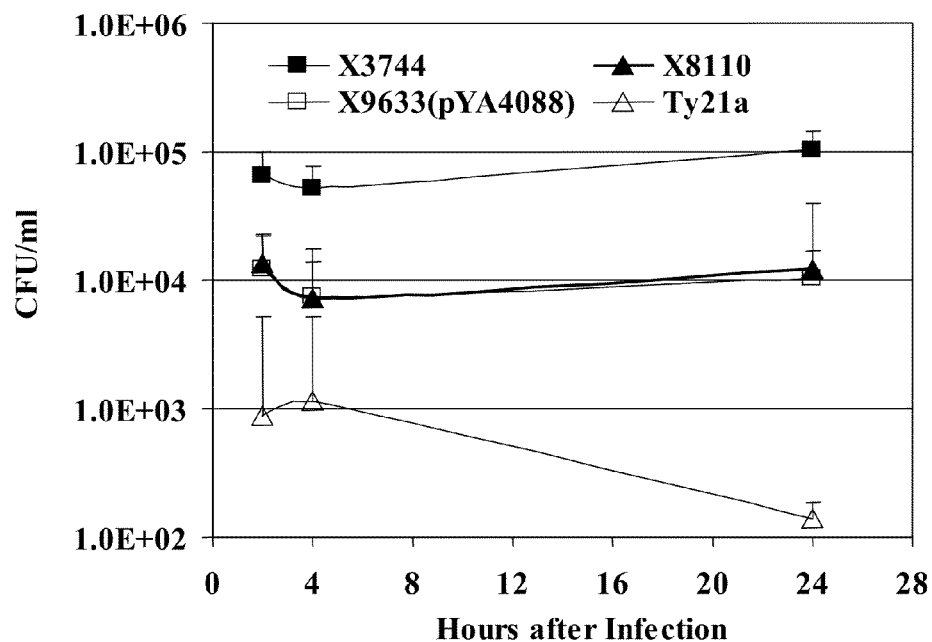
Figure 35B:
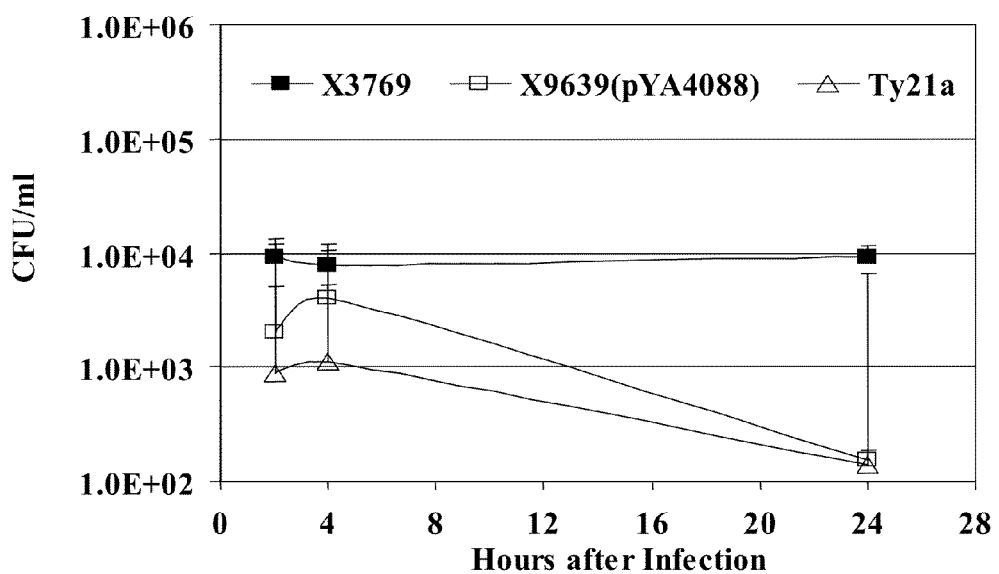
Figure 35C:
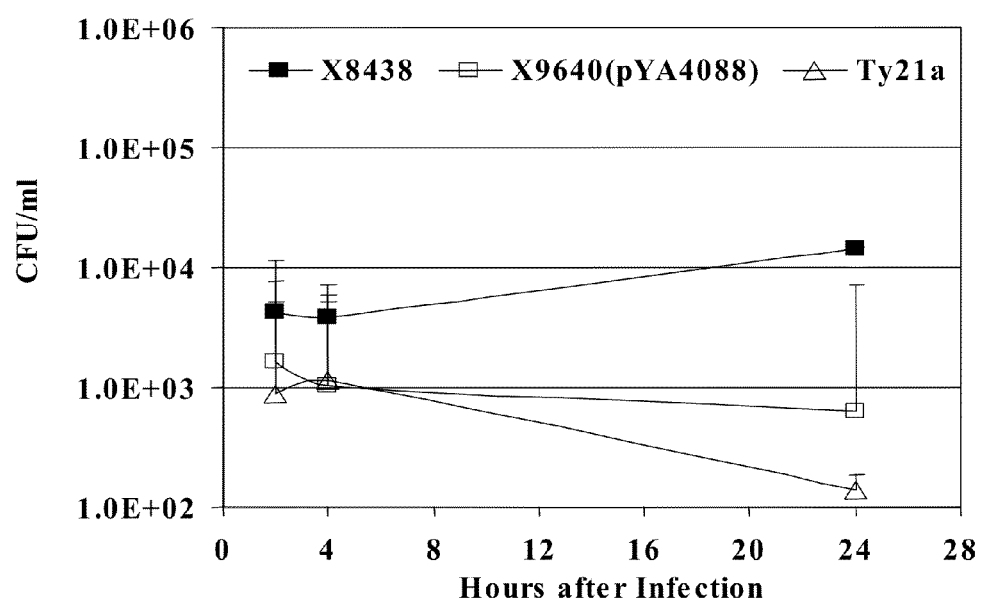

FIG. 35 depicts a series of graphs showing the survival of (A) S. Typhi ISP1820 derivatives, (B) Ty2 RpoS$^-$ derivatives, and (C) Ty2 RpoS$^+$ derivatives in peripheral blood mononuclear cells.

Figure 36:
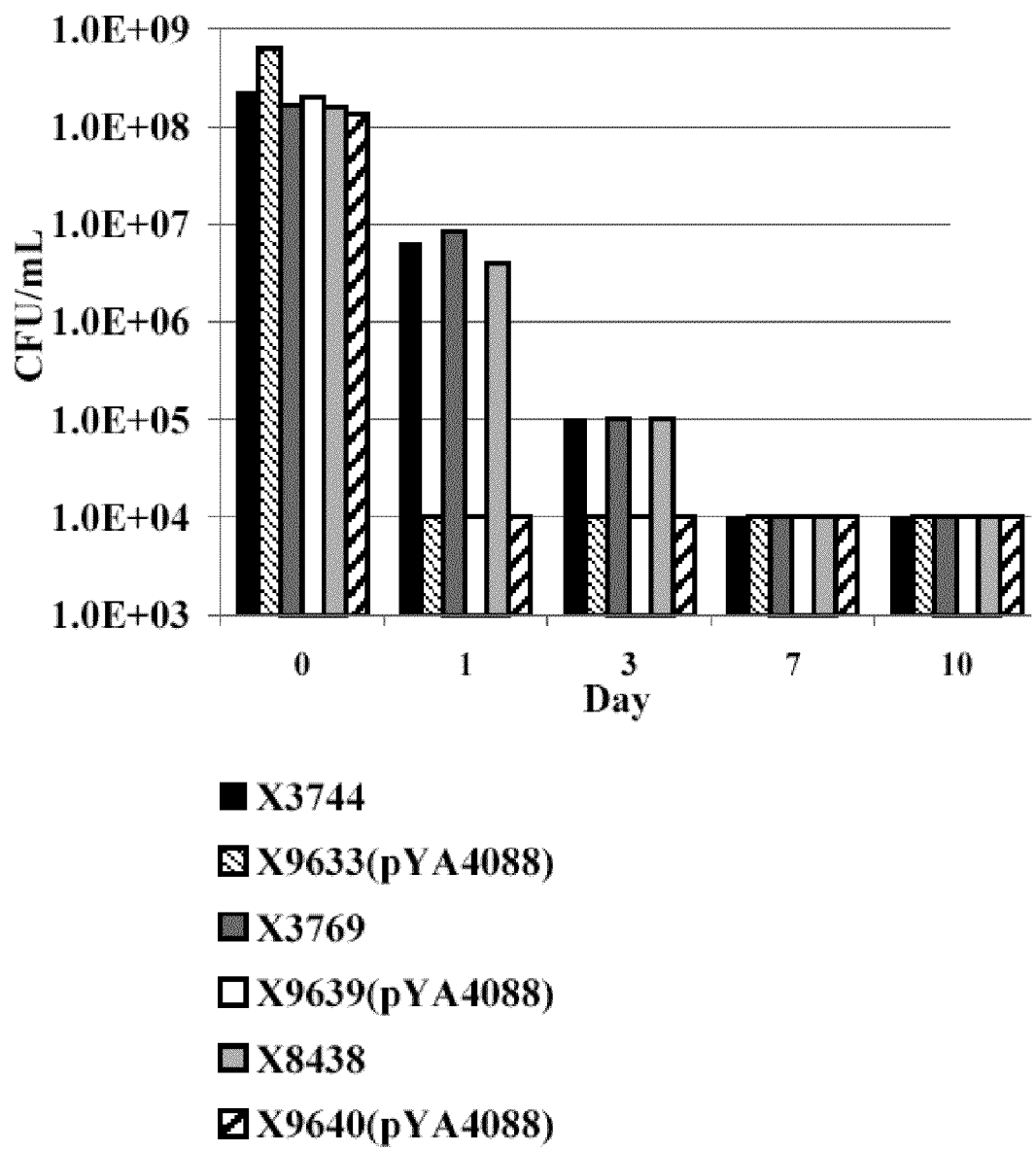

FIG. 36 depicts the survival of S. Typhi in human stool.

Figure 37A:
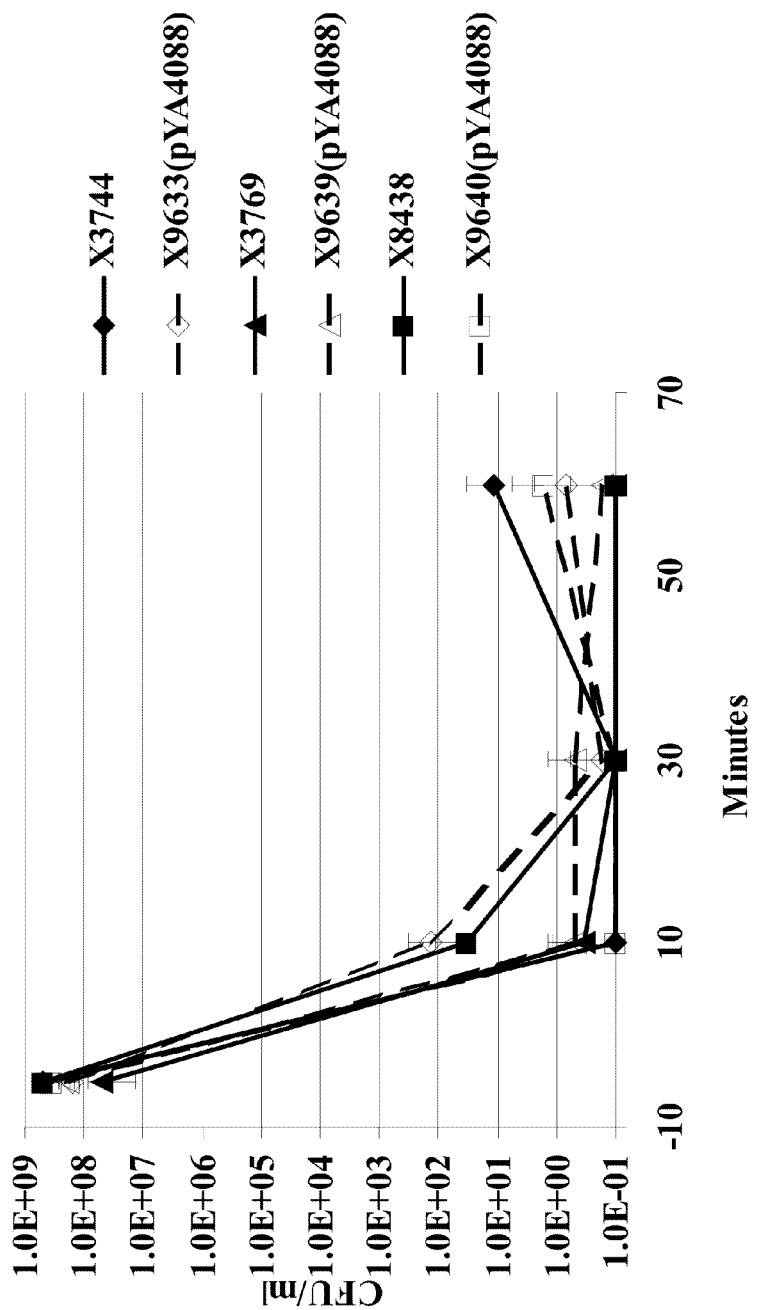
Figure 37B:
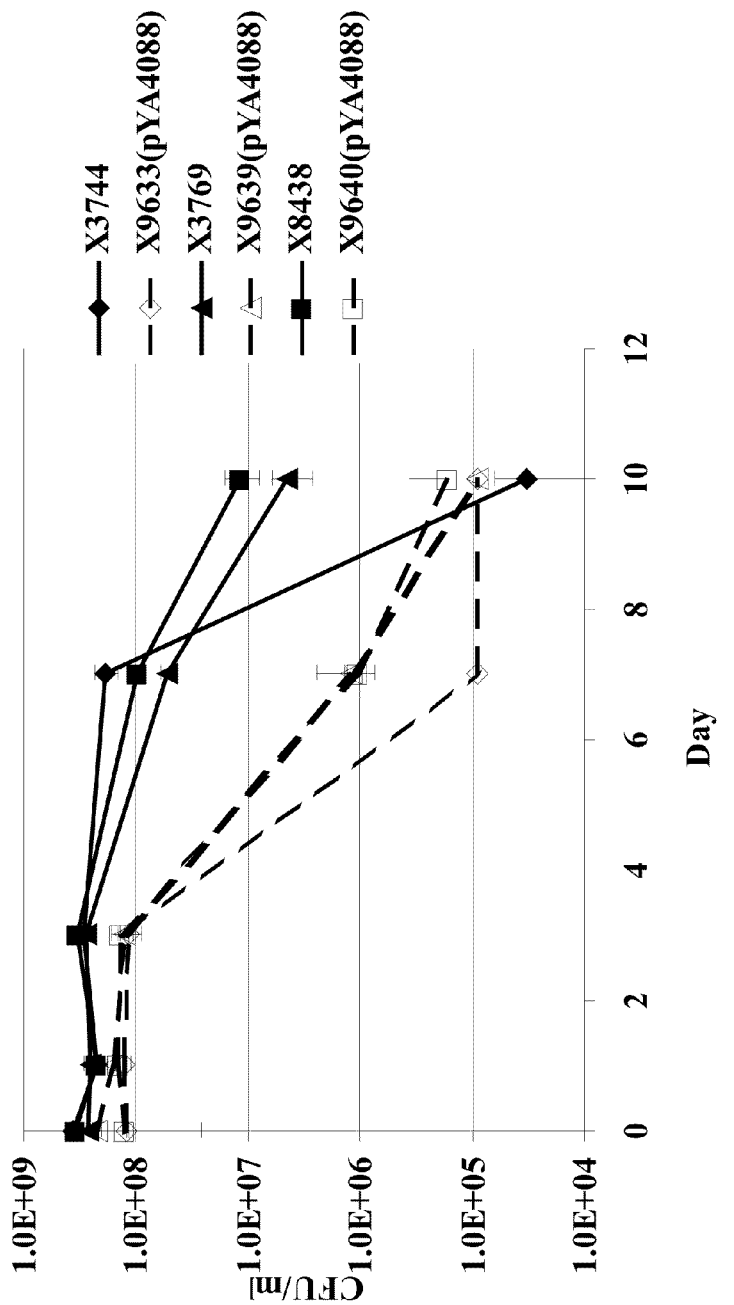
Figure 37C:
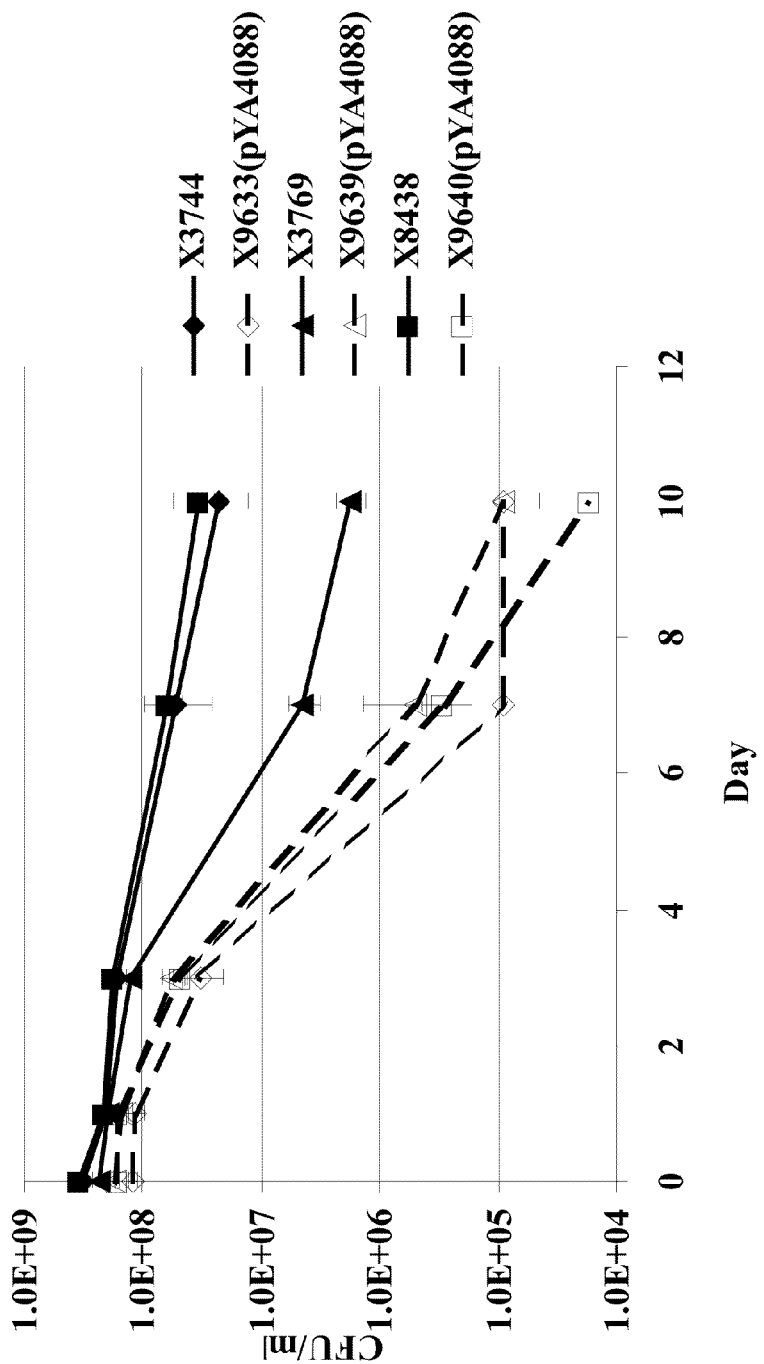

FIG. 37 depicts the survival of RASV-Sp strains and wild-type S. Typhi in (a) chlorinated water, (b) untreated canal water, and (c) raw sewage.

Figure 38A:
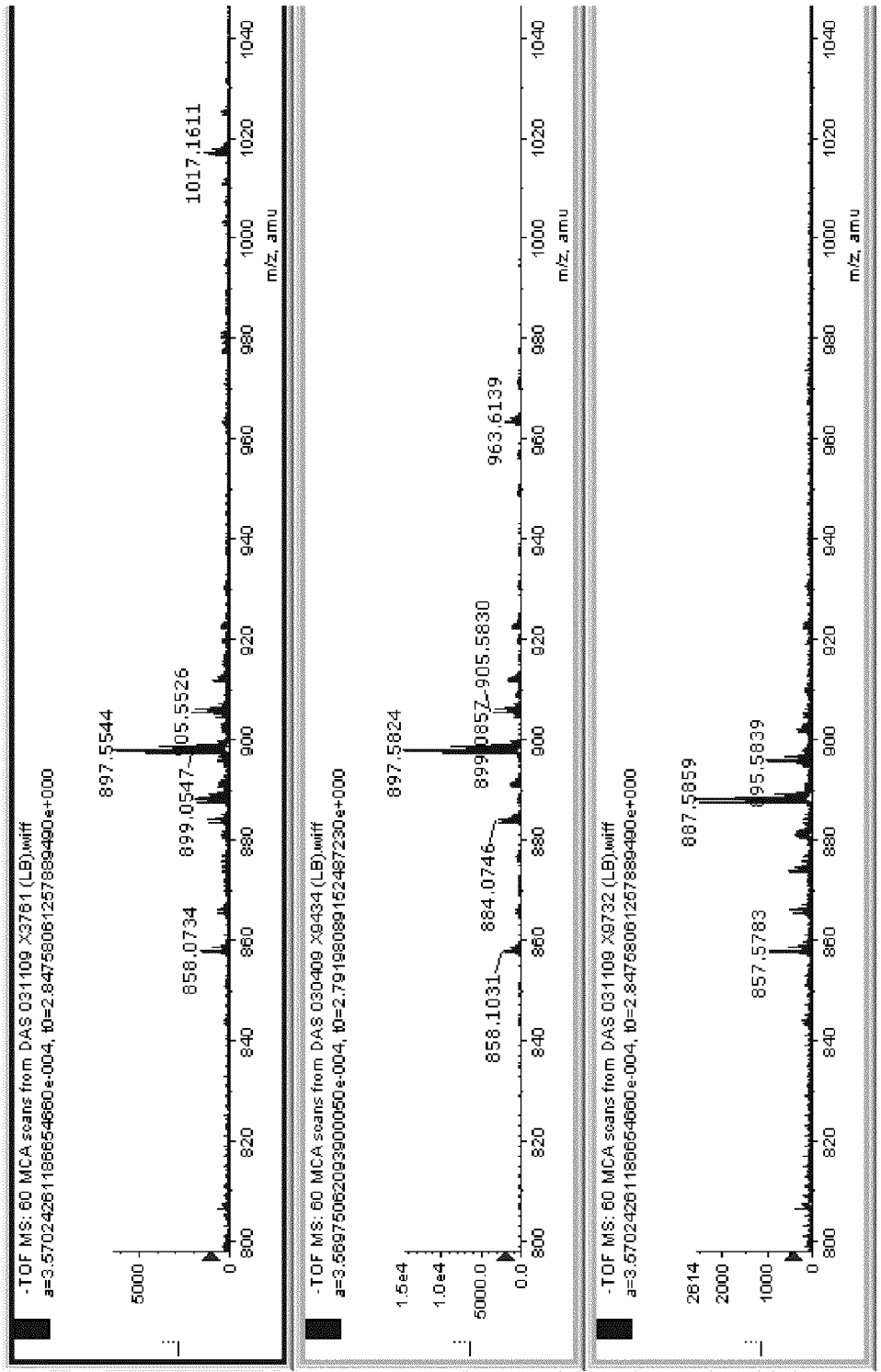
Figure 38B:
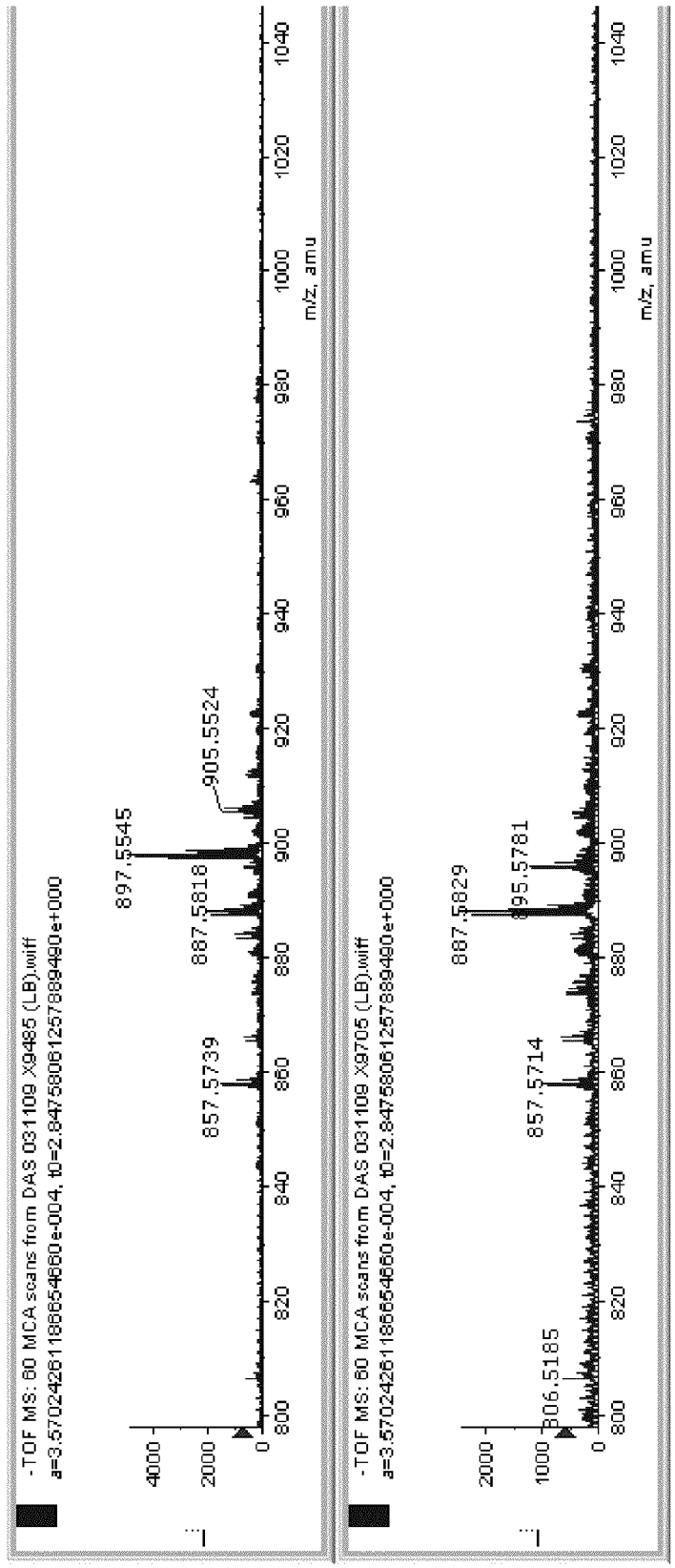
Figure 39A:
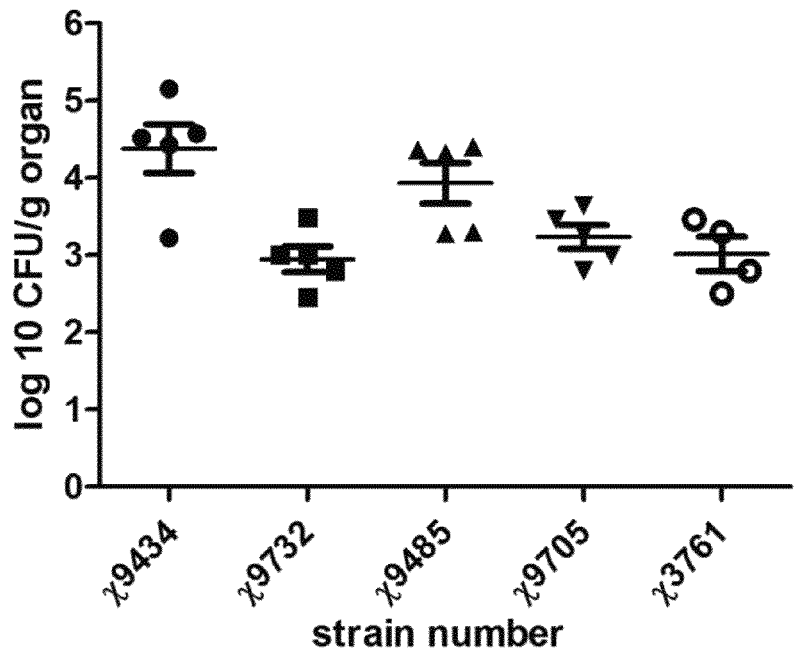
Figure 39B:
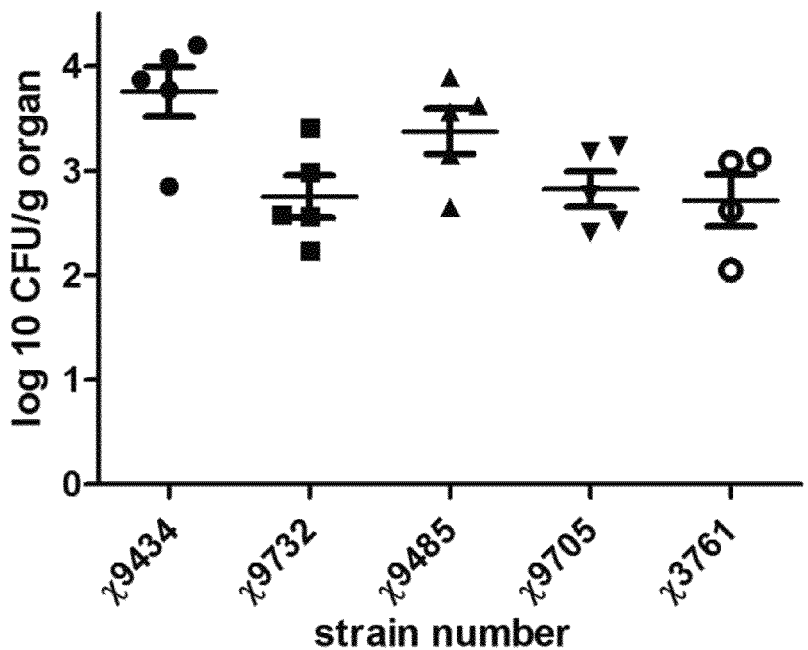
Figure 39C:
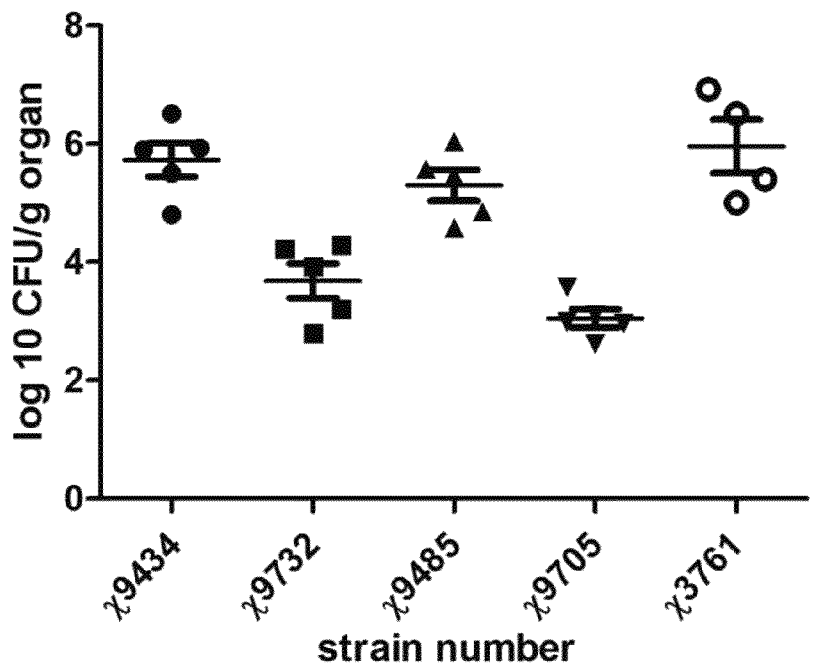
Figure 39D:
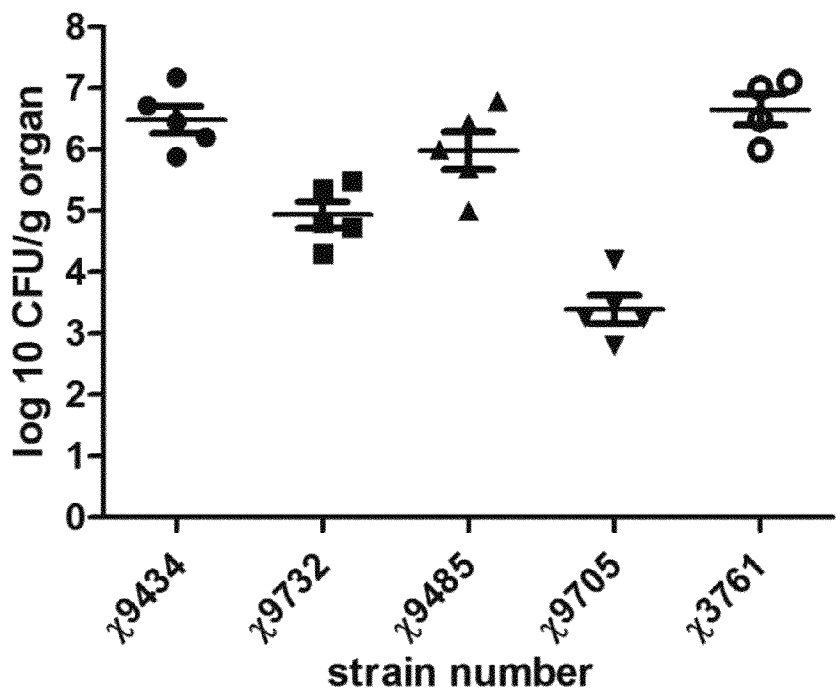
Figure 40A:
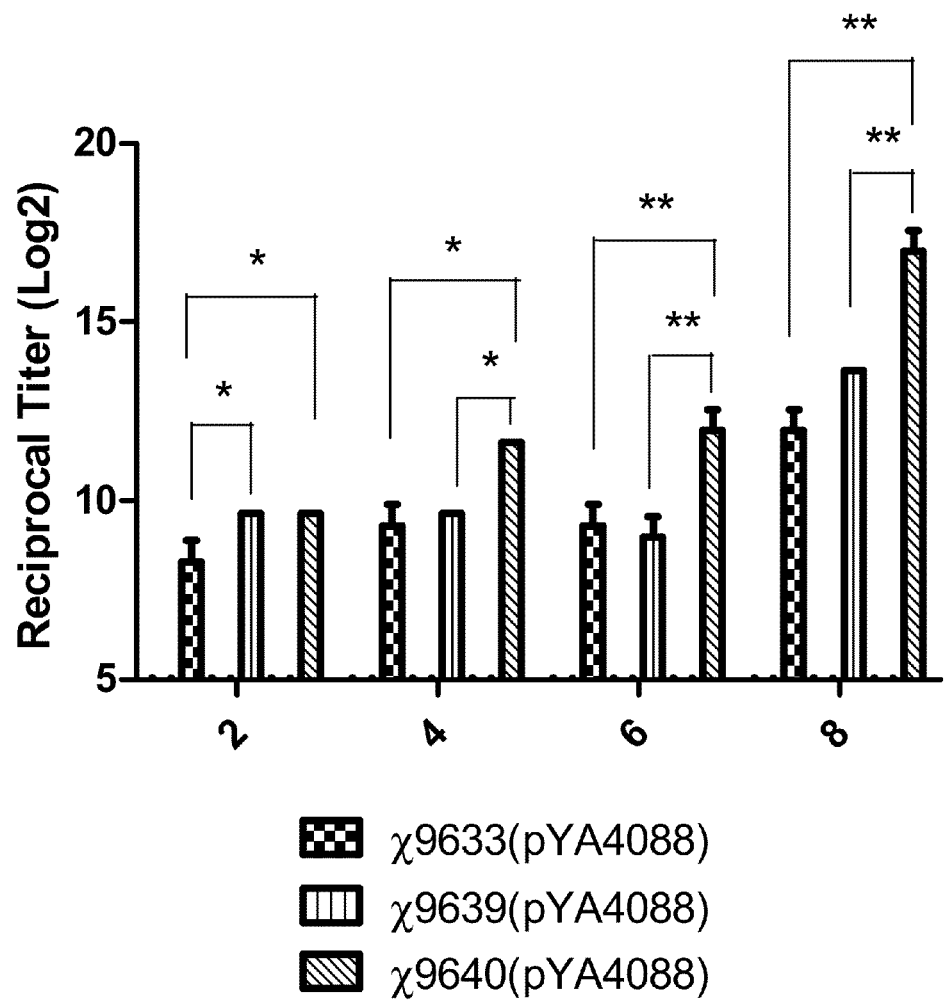
Figure 40B:
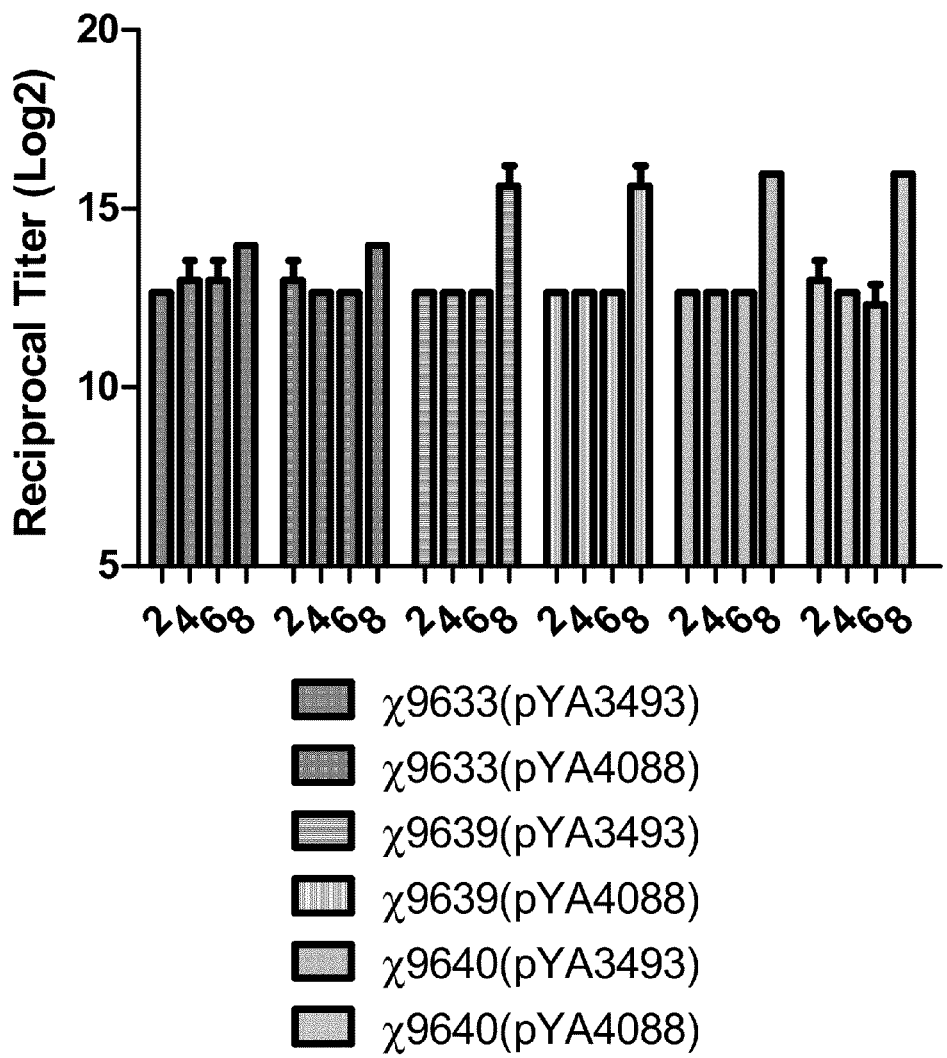
Figure 40C:
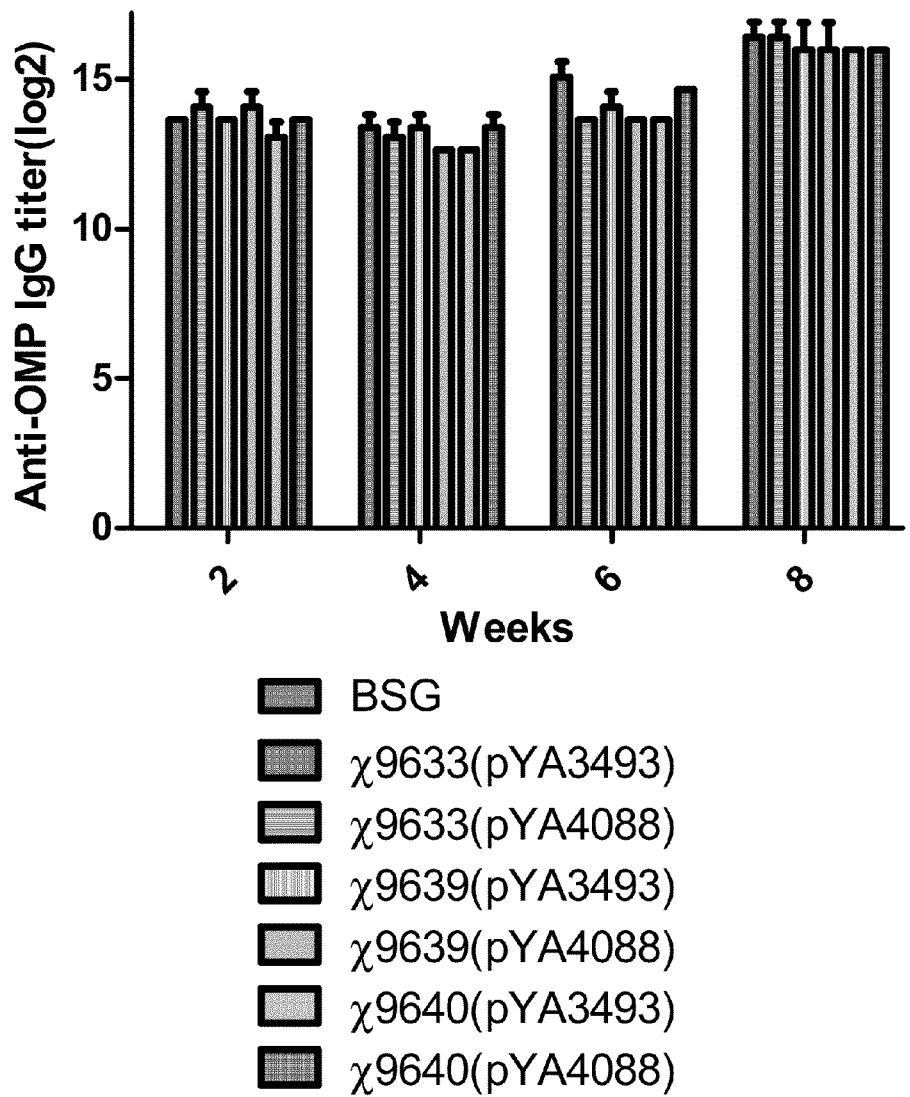
Figure 40D:
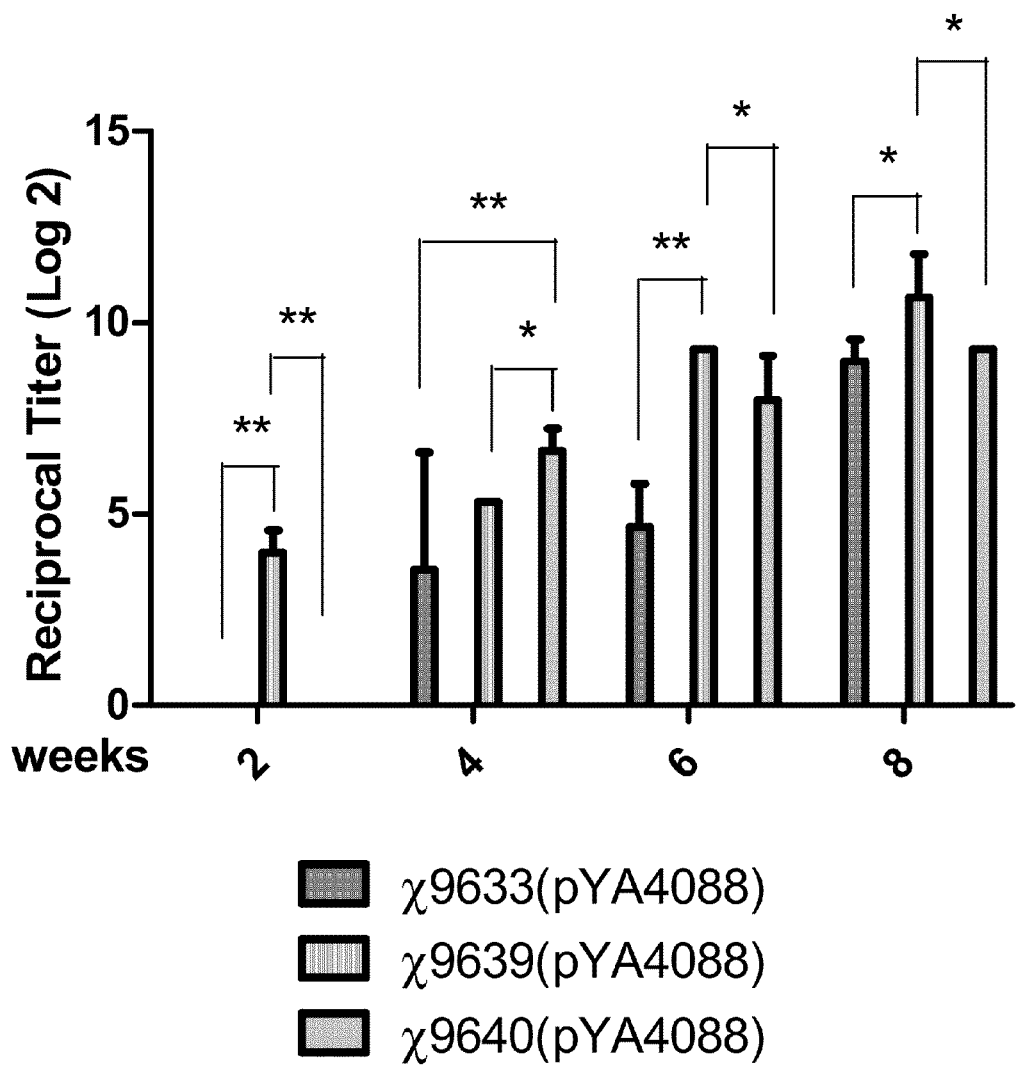

FIG. 38 depicts the ESI-MS profile of Salmonella lipid A extracted from wild-type strain χ3761 (A) and strains χ9434, (B), χ9732 (C), χ9485 (D) and χ9705 (E).

FIG. 39 depicts diagrams representing counts of bacteria recovered from liver and spleen of animals inoculated with Salmonella strains χ9434, χ9732, χ9705, and χ3761. (A) Bacterial count in liver 3 days post-inoculation. (B) Bacterial count in spleen 3 days post-inoculation. (C) Bacterial count in liver 6 days post-inoculation. (D) Bacterial count in spleen 6 days post-inoculation.

FIG. 40 depicts the serum IgG responses to rPspA (A), to S. Typhi LPS (B), to OMPs (C) and sIgA (D) in immunized mice. Serum IgG responses against rPspA (A) S. Typhi LPS (B), and SOMPS (C) and mucosal IgA responses to rPspA (D) were measured by ELISA using pooled sera from BALB/c mice intranasally immunized with the indicated strains carrying either plasmid pYA3493 (negative control) or pYA4088 (PspA). Error bars represent variation between triplicate wells. Mice were boosted at week 6. Statistical significance was determined at week 8. *, $P<0.05$; **, $P<0.01$ for $\chi 9633$(pYA4088), $\chi 9639$(pYA4088) and $\chi 9640$(pYA4088) were compared each other.

Figure 41:
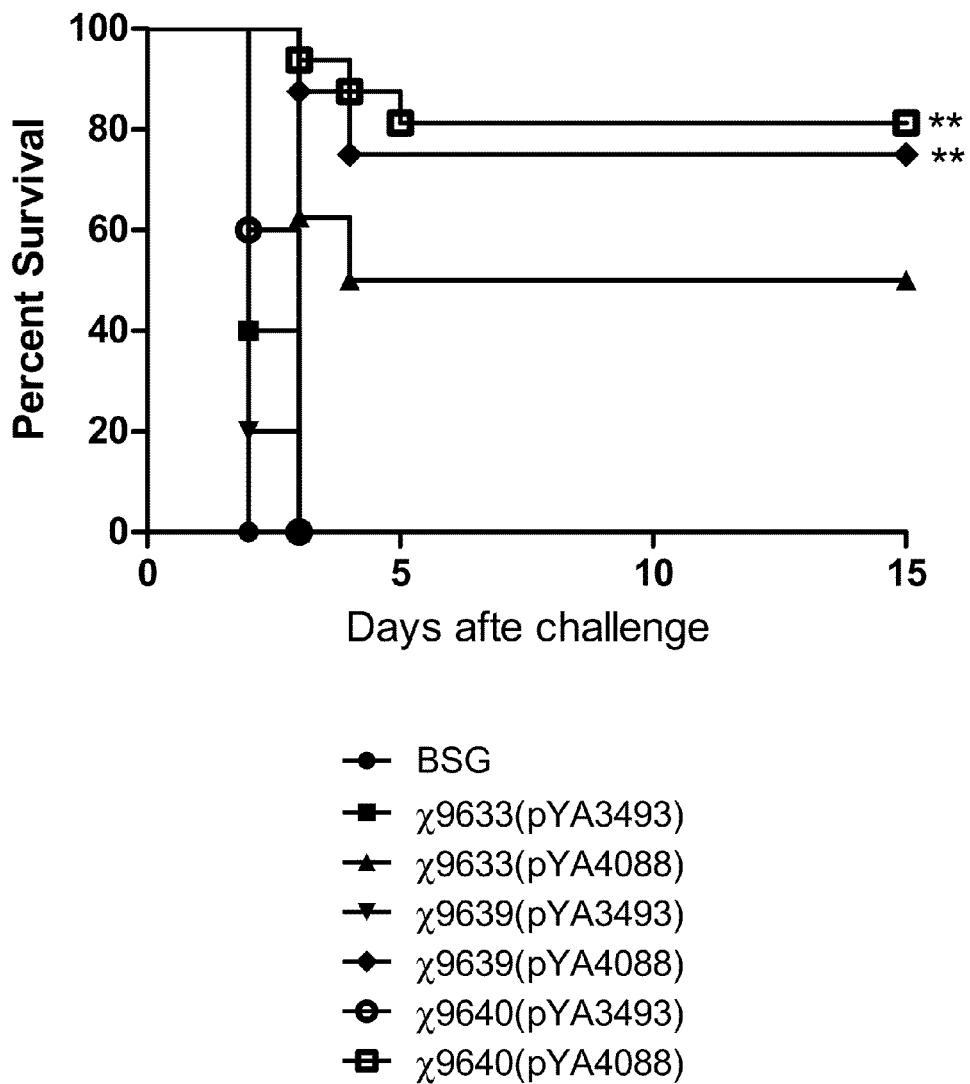

FIG. 41 depicts an evaluation of protective efficacy. Eight mice per group were intranasally immunized twice at 6-weeks intervals with the indicated strains and challenged intraperitoneally with $1\times 10^4$ CFU of S. pneumoniae WU2 4 weeks later. The experiment was performed twice. Both experiments gave similar results, and the data have been pooled. **, $P<0.01$ for vaccines compared with controls, and for survival of mice immunized with $\chi 9640$(pYA4088) compared with survival of mice immunized with $\chi 9633$ (pYA4088).

FIG. 42 depicts the distribution of S. Typhimurium strain $\chi 9558$(pYA4088) in tissues of newborn mice born from naïve or immunized mothers. Groups of pups were orally inoculated on the indicated day after birth with $5\times 10^8$ CFU of $\chi 9558$(pYA4088). In mice born to naïve mothers, the doses were $1.4\times 10^8$ for 0-day mice, $1.6\times 10^8$ for 2-day mice, $3.0\times 10^8$ for 4-day mice, and $3.5\times 10^8$ for 7-day mice. In mice born to immunized mother, the doses were $1.5\times 10^8$ for 0-day mice, $1.5\times 10^8$ for 2-day mice, $2.0\times 10^8$ for 4-day mice, $1.0\times 10^8$ for 7-day mice. Significant differences between results obtained from mice born to naïve or immunized mothers are indicated (*, $P<0.01$; **, $P<0.05$). Tissue samples were taken from 3 mice/group on days 3 and 7 after inoculation. The results from three experiments are summarized. (A) intestine; (B) liver; (C) spleen.

Figure 43A:
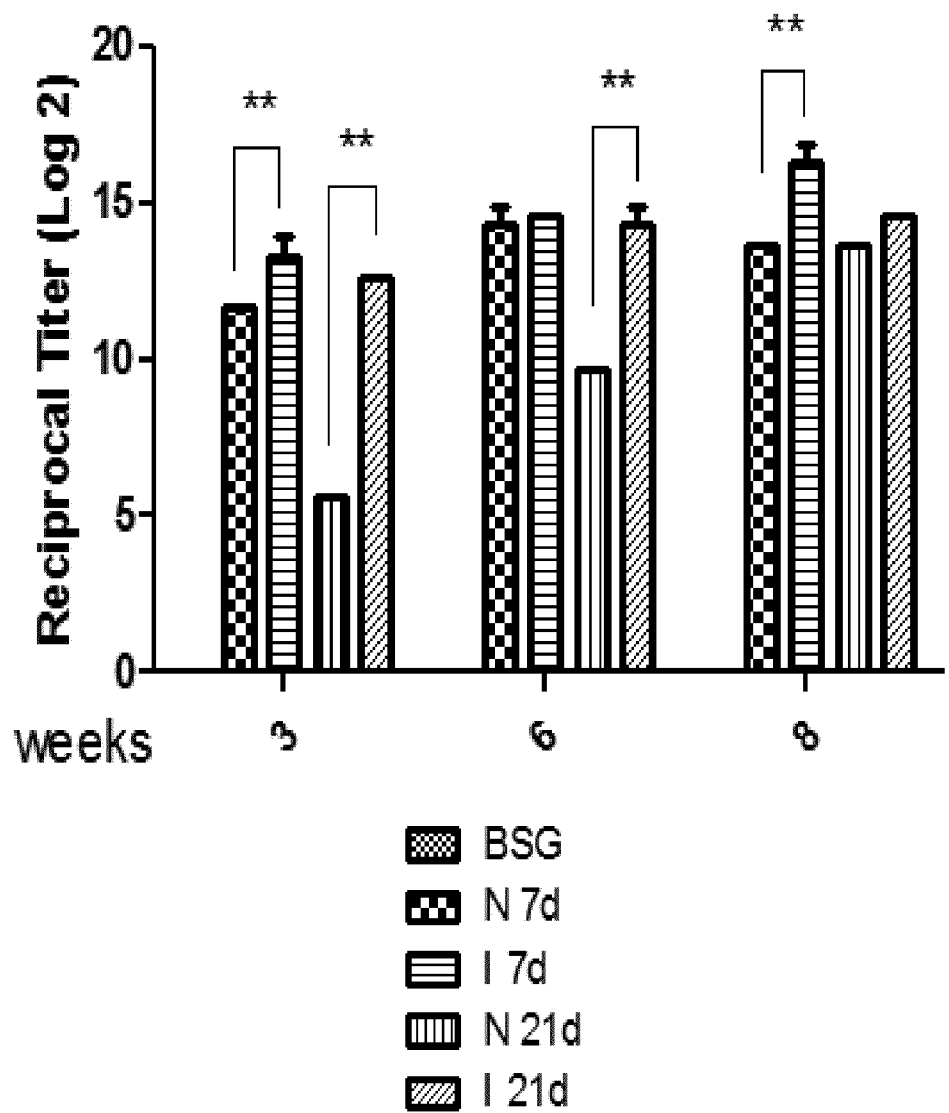
Figure 43B:
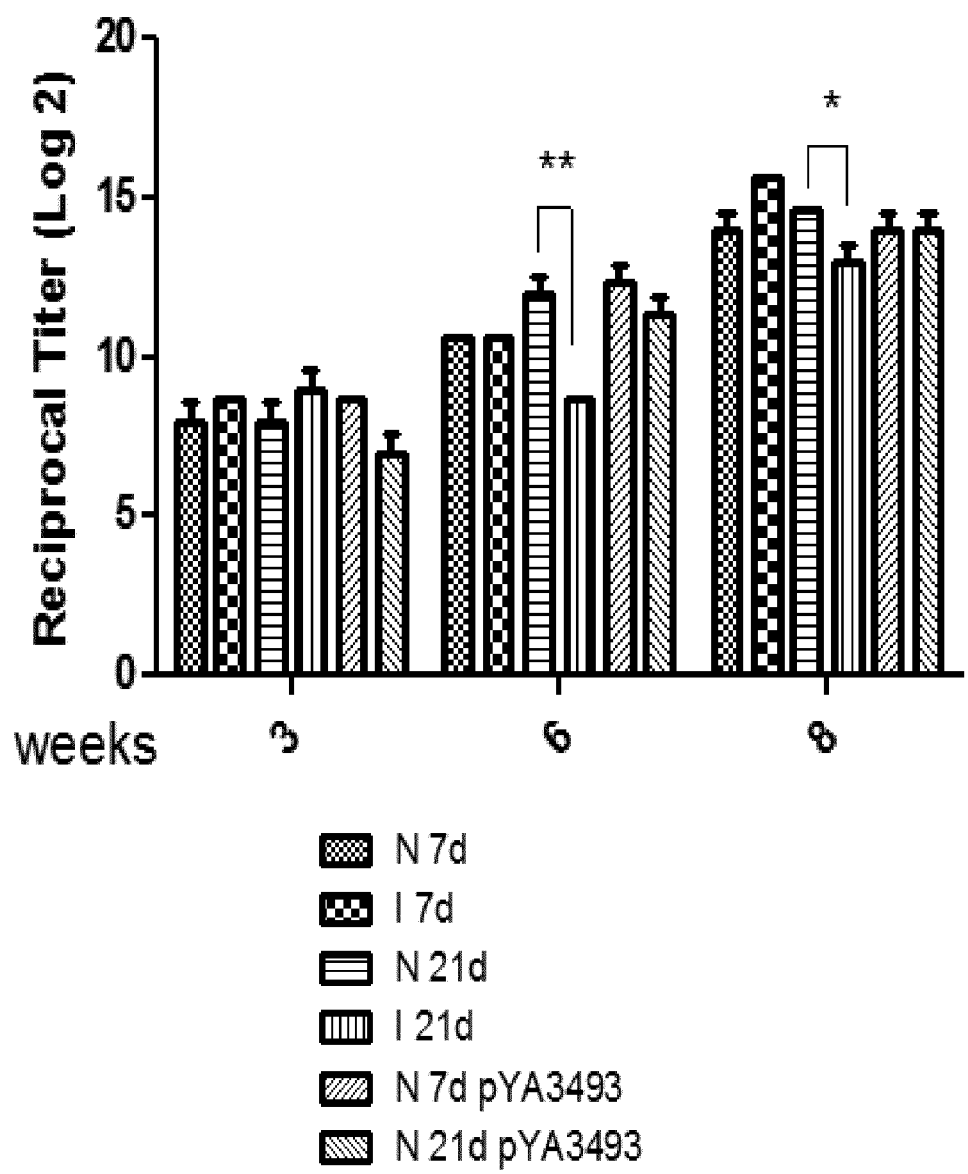

FIG. 43 depicts ELISA measurements of serum IgG and mucosal IgA responses in immunized mice. Serum IgG responses against rPspA (A) and S. Typhimunium LPS (B), were measured using pooled sera from neonates and infants born to either naïve (N) or immunized (I) mothers. Mucosal IgA responses against rPspA (C) were measured in pooled vaginal washes. Mice were immunized orally with either $\chi 9558$(pYA4088) (pspA), $\chi 9558$(pYA3493) (control) or mock immunized with BSG on either day 7 (7 d) or day 21 (21 d) after birth. Only mice from naïve mothers were inoculated with $\chi 9558$(pYA3493). Mice were boosted 3 and 6 weeks after the primary immunization. Error bars represent variation between triplicate wells. Significant differences between groups are indicated (*, $P<0.05$; **, $P<0.01$). No immune responses were detected to PspA in mice immunized with $\chi 9558$(pYA3493). No antibody to PspA or LPS was detected in mice inoculated with buffer only or in pre-immune sera from vaccinated mice (reciprocal titer <1:50).

Figure 44:
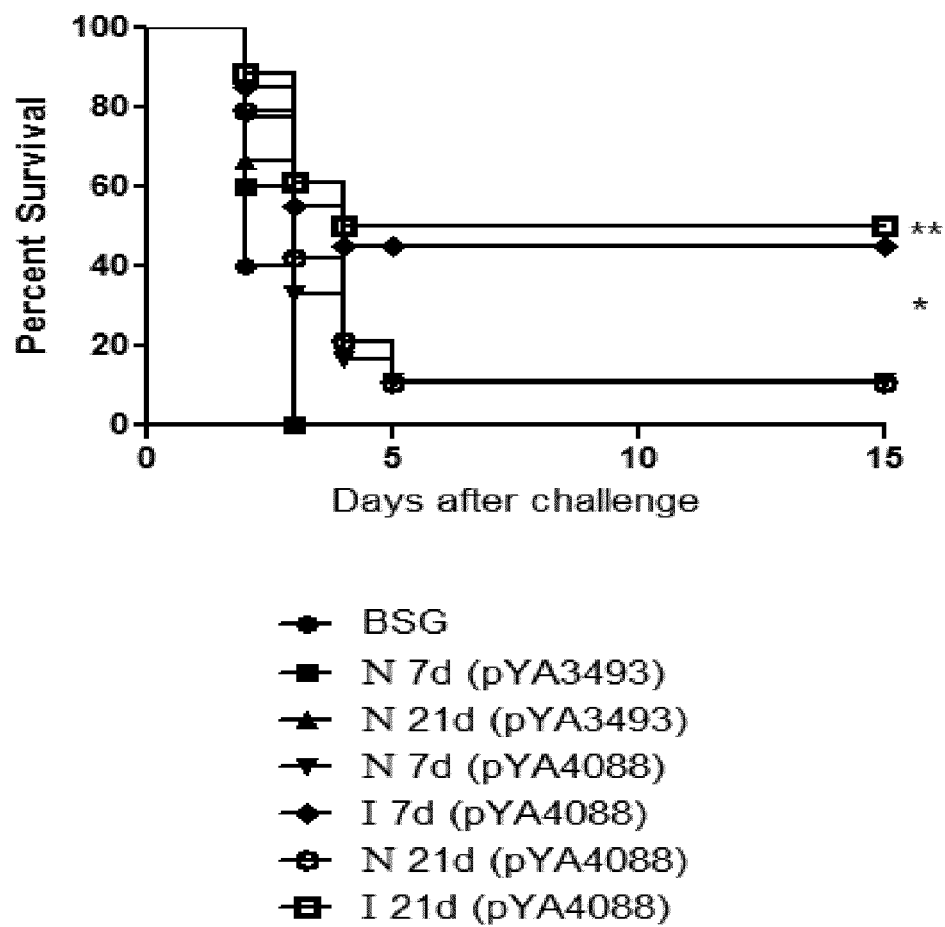

FIG. 44 depicts a graph showing that immunization with $\chi 9558$(pYA4088) protects BALB/c mice against i.p. challenge with S. pneumoniae WU2. Survival of orally-immunized or non-immunized mice after intraperitoneal challenge with $2\times 10^3$ CFU of S. pneumoniae WU2 4 weeks after the final immunization. N 7d mice and N 21 d mice: born to naïve mothers; I 7 d mice and I 21 d mice: born to immunized mothers. All vaccine groups were significantly different from the $\chi 9558$(pYA3493) (vector control) and PBS controls ($P<0.01$); **, $P<0.01$ for survival of infants born to naïve compared to infants born to immunized mothers, and *, $P<0.05$ for survival of neonates born to naïve mothers compared to neonates born to immunized mothers.

Figure 45:
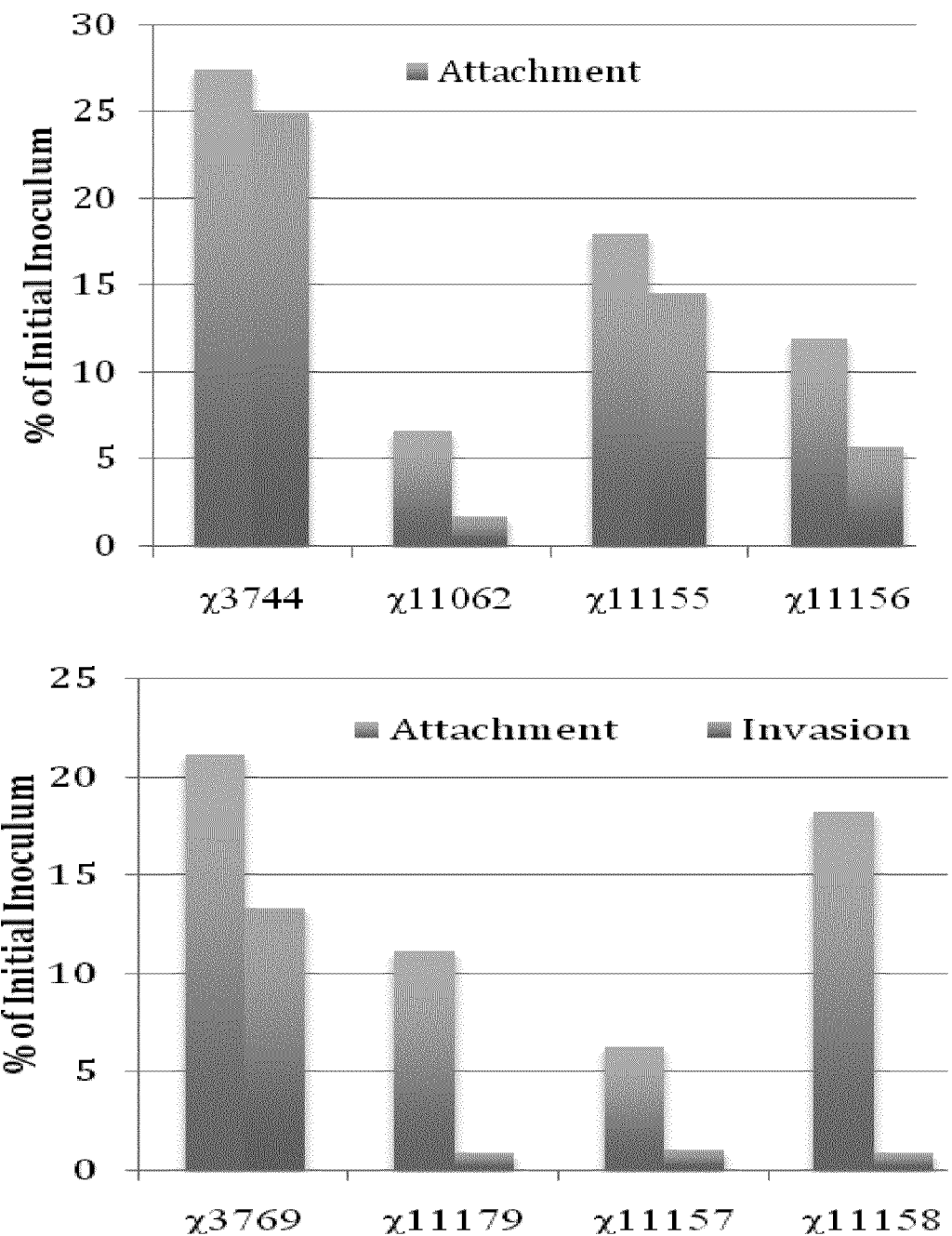

FIG. 45 depicts invasion of Human Epithelial Cells (INT-407) by S. Typhi. All strains of S. Typhi used were grown in LB with 0.3M NaCl, without glucose. Infections were done at an MOI of 1:1-1:2 for 1 hour at 37° C., then cells were washed and the number of adherent S. Typhi enumerated by plating. 100 µg/ml gentamicin was added for an additional hour, then the number of internal S. Typhi was enumerated by plating.

Figure 46:
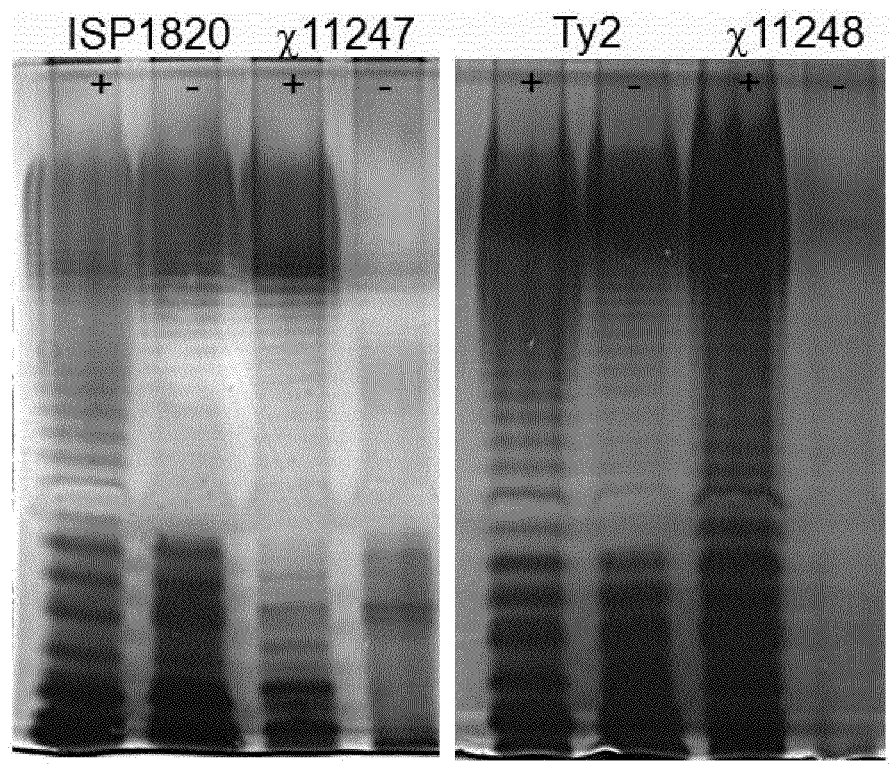

FIG. 46 depicts galactose-dependent O-antigen production in S. Typhi. Wild-type and Δ(galE-ybhC)-851 strains were grown to stationary phase in nutrient broth in the presence (+) or absence (−) of 0.05% galactose.

Figure 47:
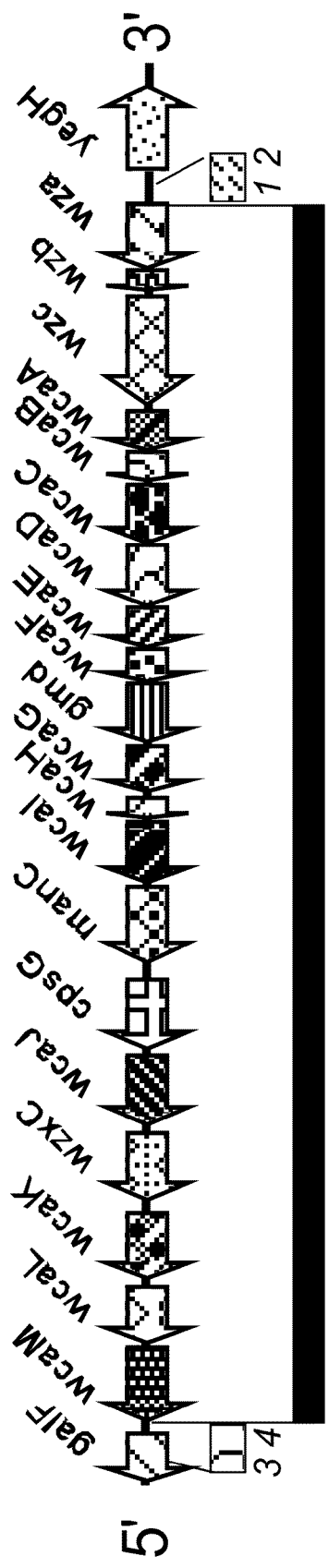

FIG. 47 depicts a diagram representing the genomic region and deletion of the Δ(wza-wcaM)-8 mutation.

Figure 48:
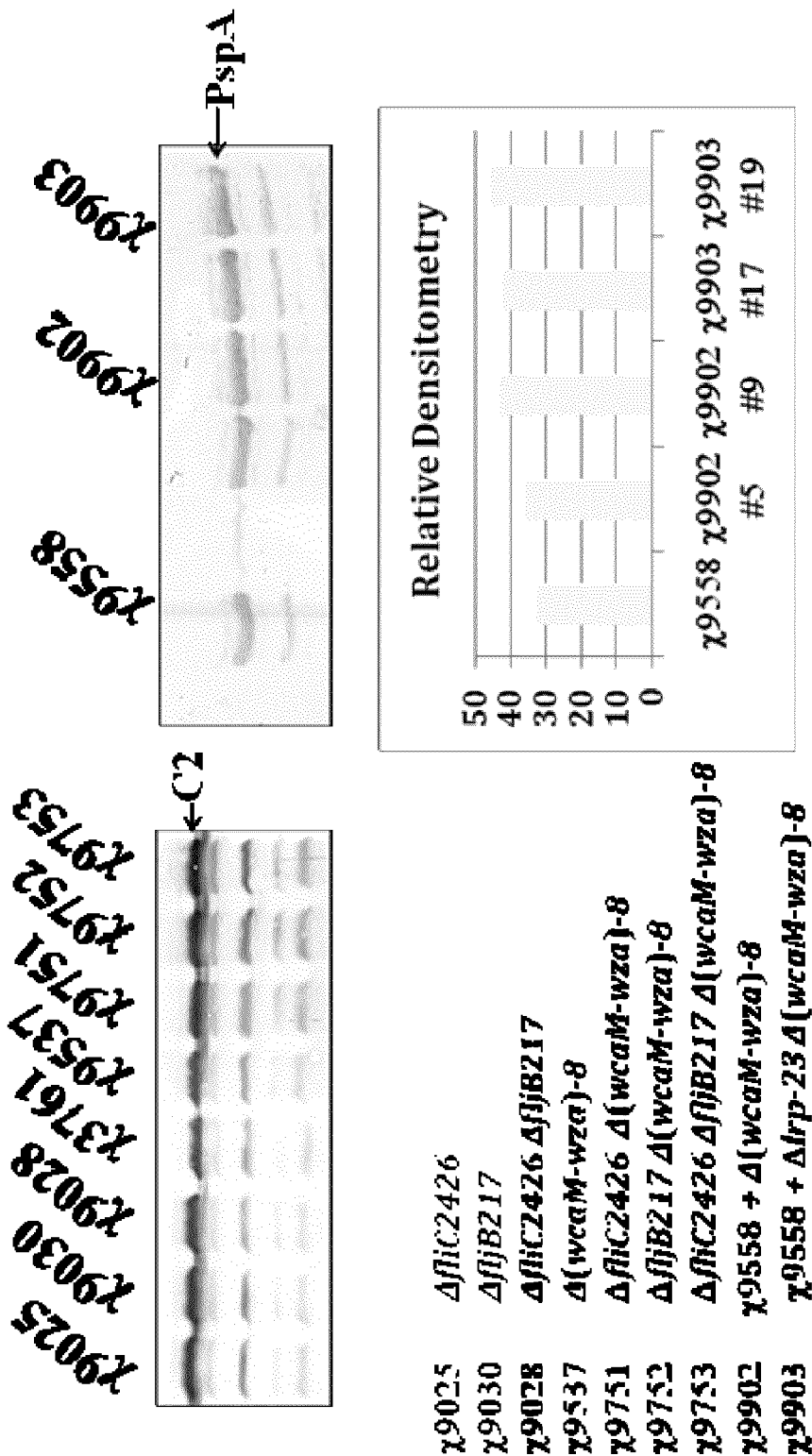

FIG. 48 depicts a photograph showing that strains harboring a Δ(wza-wcaM)-8 mutation can increase heterologous protein production. Strain $\chi 9558$ has Δ(gmd-fcl)-26, $\chi 9902$ has Δ(wza-wcaM)-8, while $\chi 9903$ has an additional Δrp-23 mutation. All strains were transformed with plasmid pYA4088, containing a sequence encoding S. pneumonia PspA. Similar numbers of cells were subjected to SDS-PAGE and then transferred onto nitrocellulose (NC) membrane. The PspA protein was detected using PspA antiserum followed by AP conjugate anti-rabbit secondary antiserum and then the color was developed by BCIP-NBT. The NC membrane were scanned and analysis by Quantity One software (Biorad). The densitometry shows that the band corresponding to PspA in strain $\chi 9902$ with Δ(wza-wcaM)-8 mutation increases PspA production compared with $\chi 9558$ with Δ(gmd-fcl)-26 mutation.

FIG. 49 depicts diagrams representing the genomic regions and deletions of the ΔfljB217 and ΔfliC2426 mutations.

FIG. 50 depicts diagrams representing the genomic regions and deletions of the ΔfliC180 and ΔfliC240 mutations.

Figure 51:
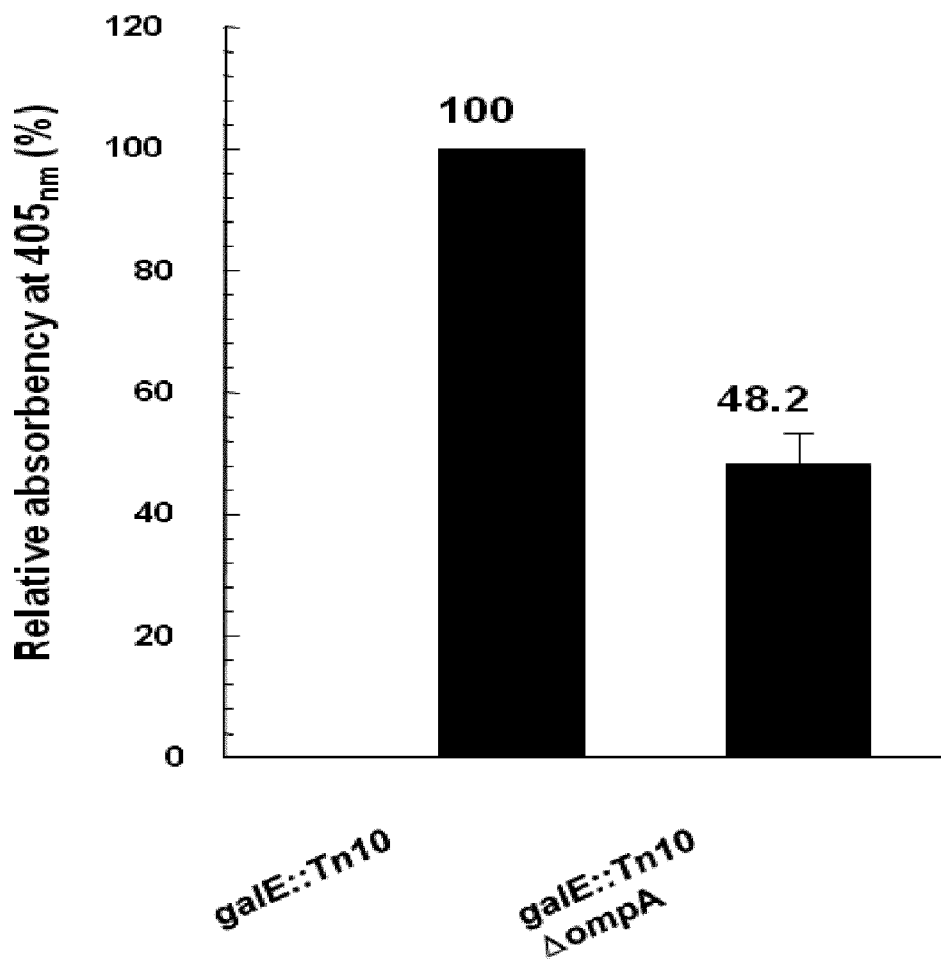

FIG. 51 depicts an illustration of the relative portion of anti-OmpA over anti-SOMPs using sera from mice orally immunized with S. Typhimurium UK-1.

Figure 52:
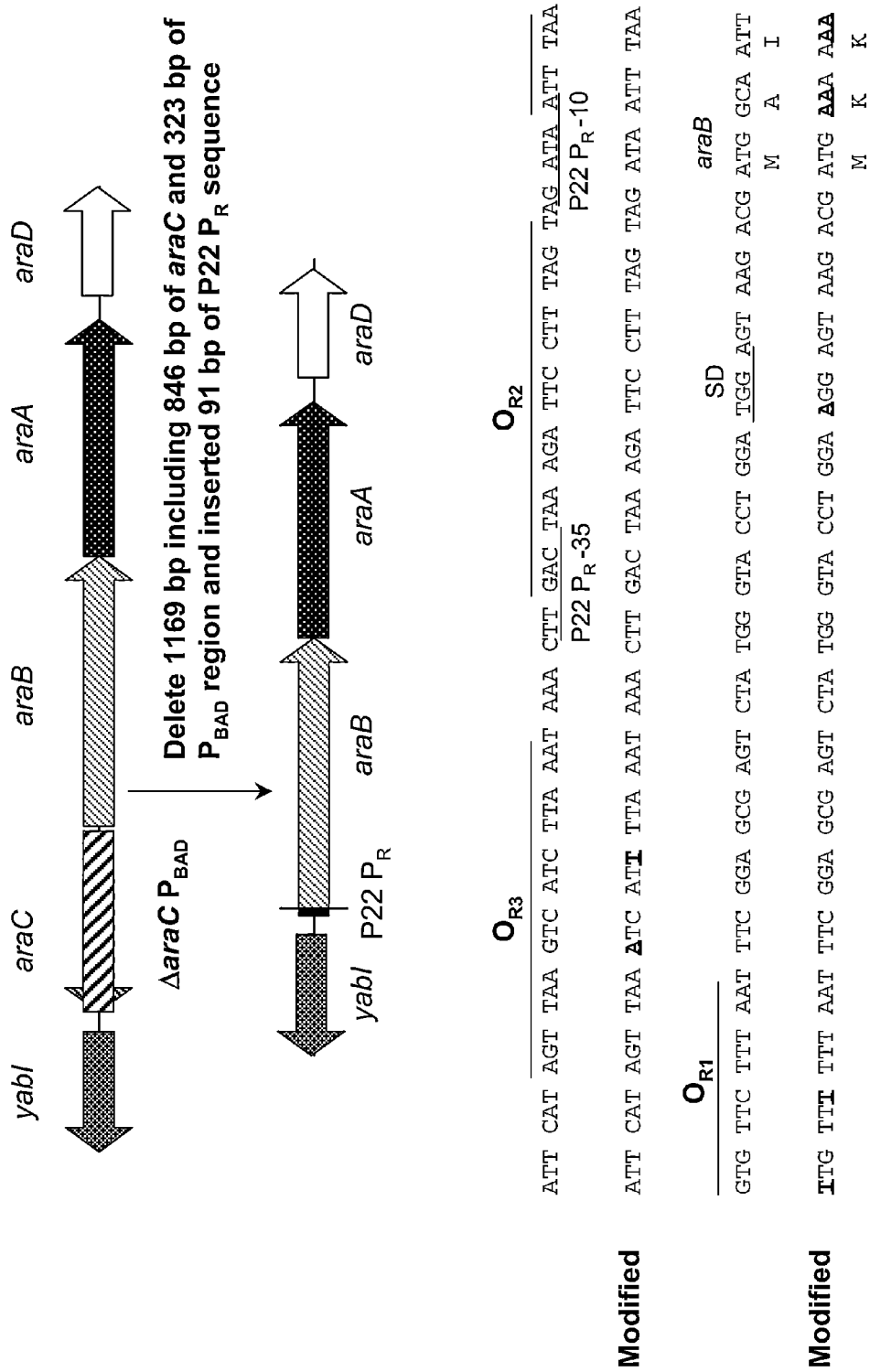

FIG. 52 depicts various modifications of Δ(araC $P_{BAD}$)-5:: P22 $P_R$ araBAD44. Original is SEQ ID NO:85 (first and third lines) and modified is SEQ ID NO:86 (second and fourth lines).

Figure 53A:
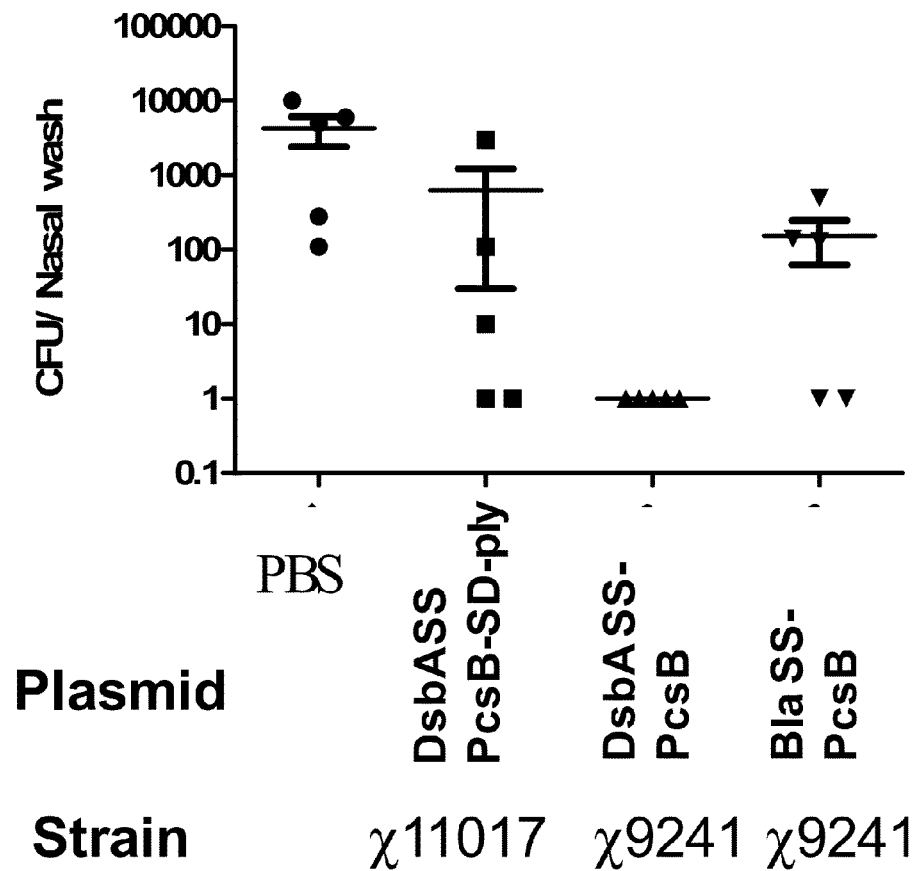
Figure 53B:
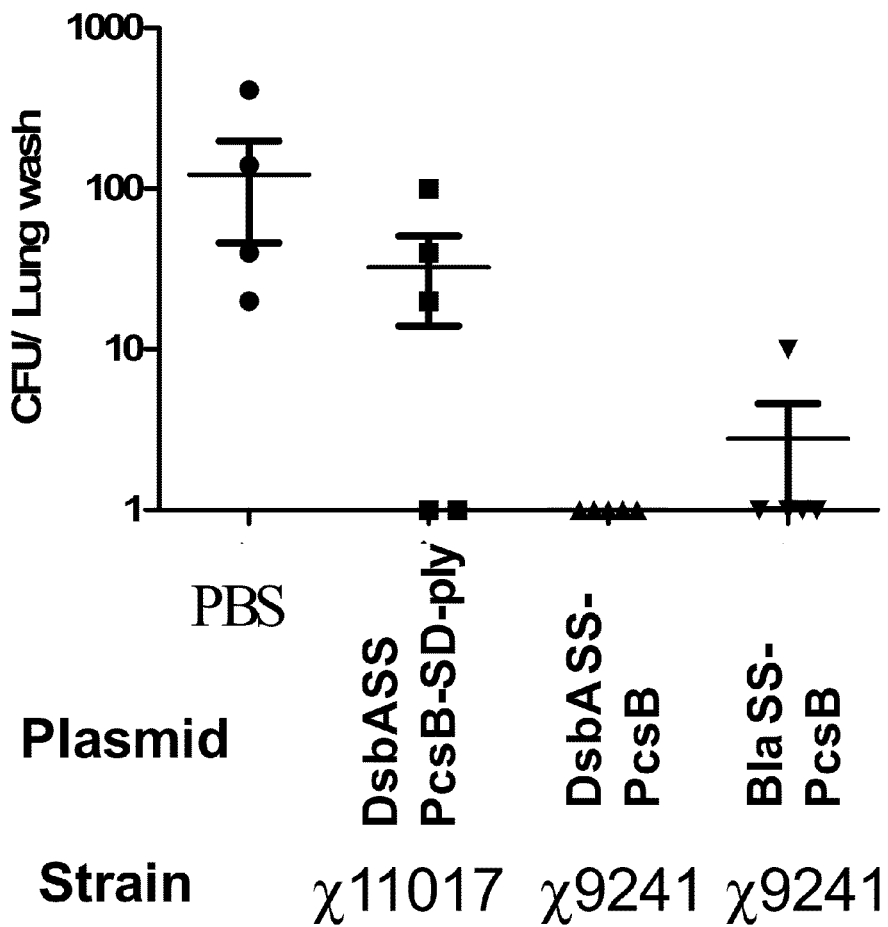

FIG. 53 depicts bacterial counts from nasal (A) and lung (B), of mice immunized with strain $\chi 11017$ and strains $\chi 9241$ harboring various forms of PcsB.

Figure 54A:
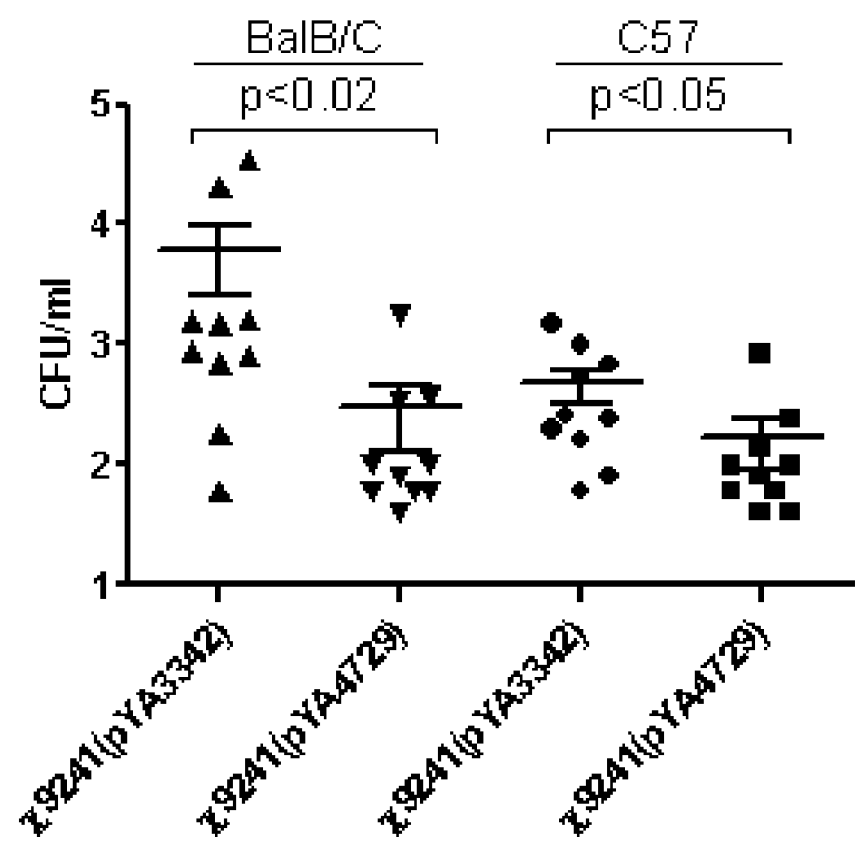
Figure 54B:
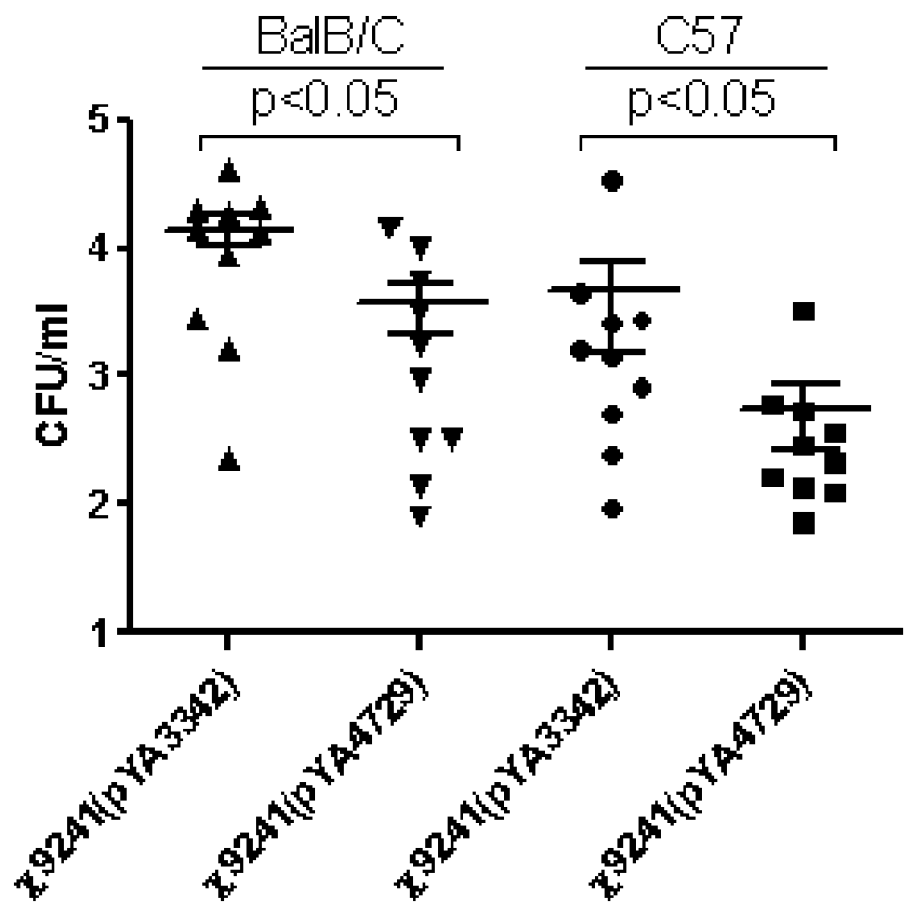

FIG. 54 depicts bacterial counts from nasal (A) and lung (B), of mice immunized with strain $\chi 11017$ and strains $\chi 9241$ harboring various forms of PcsB, and challenged with S. pneumoniae L82016.

Figure 55:
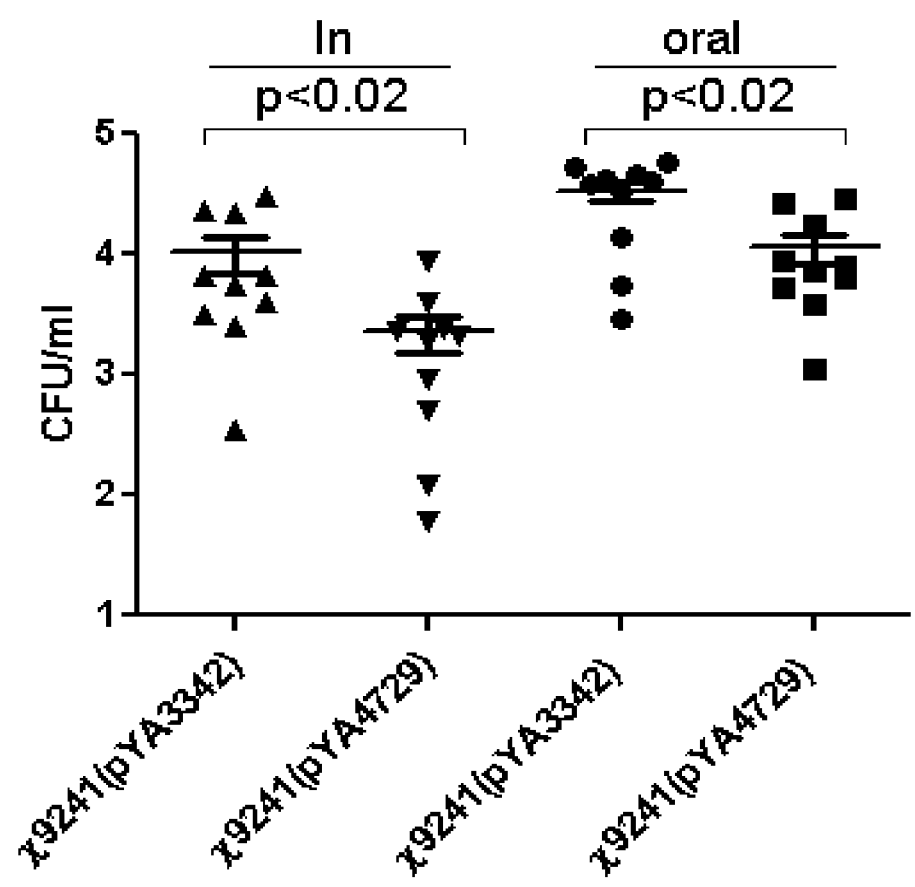

FIG. 55 depicts bacterial counts from mice administered $\chi 9241$(pYA4729) intranasally and orally and challenged with serotype 23 S. pneumoniae of E134.

Figure 56:
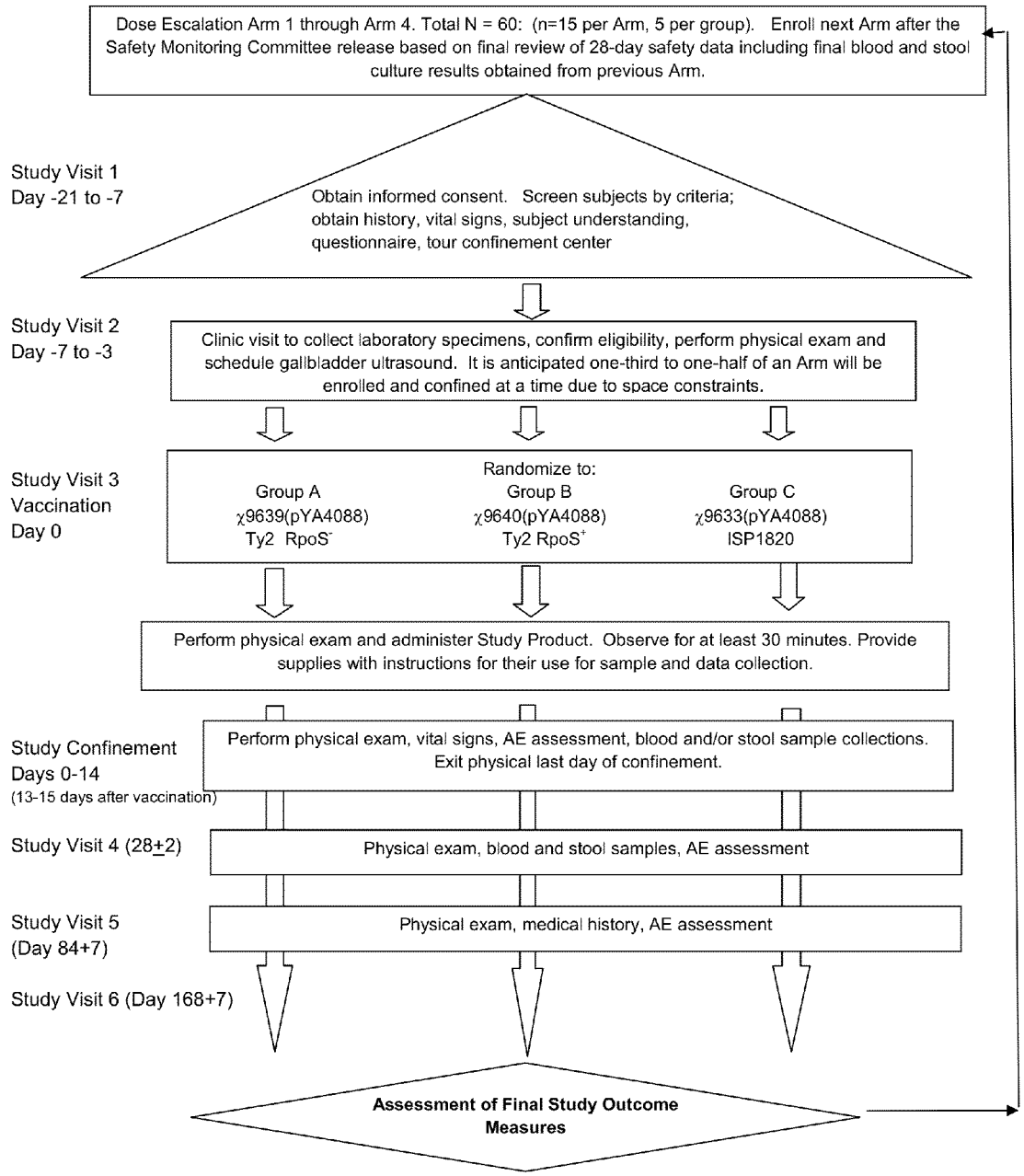

FIG. 56 depicts a schematic of the phase I safety and tolerability clinical study design.

FIG. 57 depicts (A-C) the sequence of codon optimized Rx1 aa 3-285. All the changed nucleotides are in red. "Ori" is original sequence and "opt" is codon optimized sequence. SEQ ID NO:1 is the original nucleic acid sequence, SEQ ID NO:2 is the original protein sequence, SEQ ID NO:3 is the optimized nucleic acid sequence, and SEQ ID NO:4 is the optimized protein sequence.

FIG. 58 (A-C) depicts the sequence of codon optimized Rx1 aa 3-257. All the changed nucleotides are in red. "Ori" is original sequence and "opt" is codon optimized sequence. SEQ ID NO:5 is the original nucleic acid sequence, SEQ ID NO:6 is the original protein sequence, SEQ ID NO:7 is the optimized nucleic acid sequence, and SEQ ID NO:8 is the optimized protein sequence.

FIG. 59 depicts (A-D) the sequence of codon optimized EF5668 aa 4-417. All the changed nucleotides are in red. "Ori" is original sequence and "opt" is codon optimized sequence. SEQ ID NO:9 is the original nucleic acid sequence, SEQ ID NO:10 is the original protein sequence, SEQ ID NO:11 is the optimized nucleic acid sequence, and SEQ ID NO:12 is the optimized protein sequence.

FIG. 60 depicts (A) the nucleic acid sequence of codon optimized PspA Fusion: Rx1 aa 3-285::EF5668 aa 4-417 (SEQ ID NO:13) and (B) the protein sequence (SEQ ID NO:14).

FIG. 61 depicts (A) the nucleic acid sequence of codon optimized PspA Fusion EF5668 aa 4-417::Rx1 aa 3-285 (SEQ ID NO:15) and (B) the protein sequence (SEQ ID NO:16).

FIG. 62 depicts (A-D) the sequence of codon optimized L81905 aa 4-404. All the changed nucleotides are in red. "Ori" is original sequence and "opt" is codon optimized sequence. SEQ ID NO:17 is the original nucleic acid sequence, SEQ ID NO:18 is the original protein sequence, SEQ ID NO:19 is the optimized nucleic acid sequence, and SEQ ID NO:20 is the optimized protein sequence.

FIG. 63 depicts (A-E) the sequence of codon optimized L81905 aa 4-444. All the changed nucleotides are in red. "Ori" is original sequence and "opt" is codon optimized sequence. SEQ ID NO:21 is the original nucleic acid sequence, SEQ ID NO:22 is the original protein sequence, SEQ ID NO:23 is the optimized nucleic acid sequence, and SEQ ID NO:24 is the optimized protein sequence.

FIG. 64 depicts (A-G) the sequence of codon optimized EF6796 aa 3-587. All the changed nucleotides are in red. "Ori" is original sequence and "opt" is codon optimized sequence. SEQ ID NO:25 is the original nucleic acid sequence, SEQ ID NO:26 is the original protein sequence, SEQ ID NO:27 is the optimized nucleic acid sequence, and SEQ ID NO:28 is the optimized protein sequence.

FIG. 65 depicts (A-B) the nucleic acid sequence of codon optimized PspC Fusion L81905 aa 4-404::EF6796-G54-G31 aa 1-590 (SEQ ID NO:29) and (C) the protein sequence (SEQ ID NO:30).

Figure 66B:
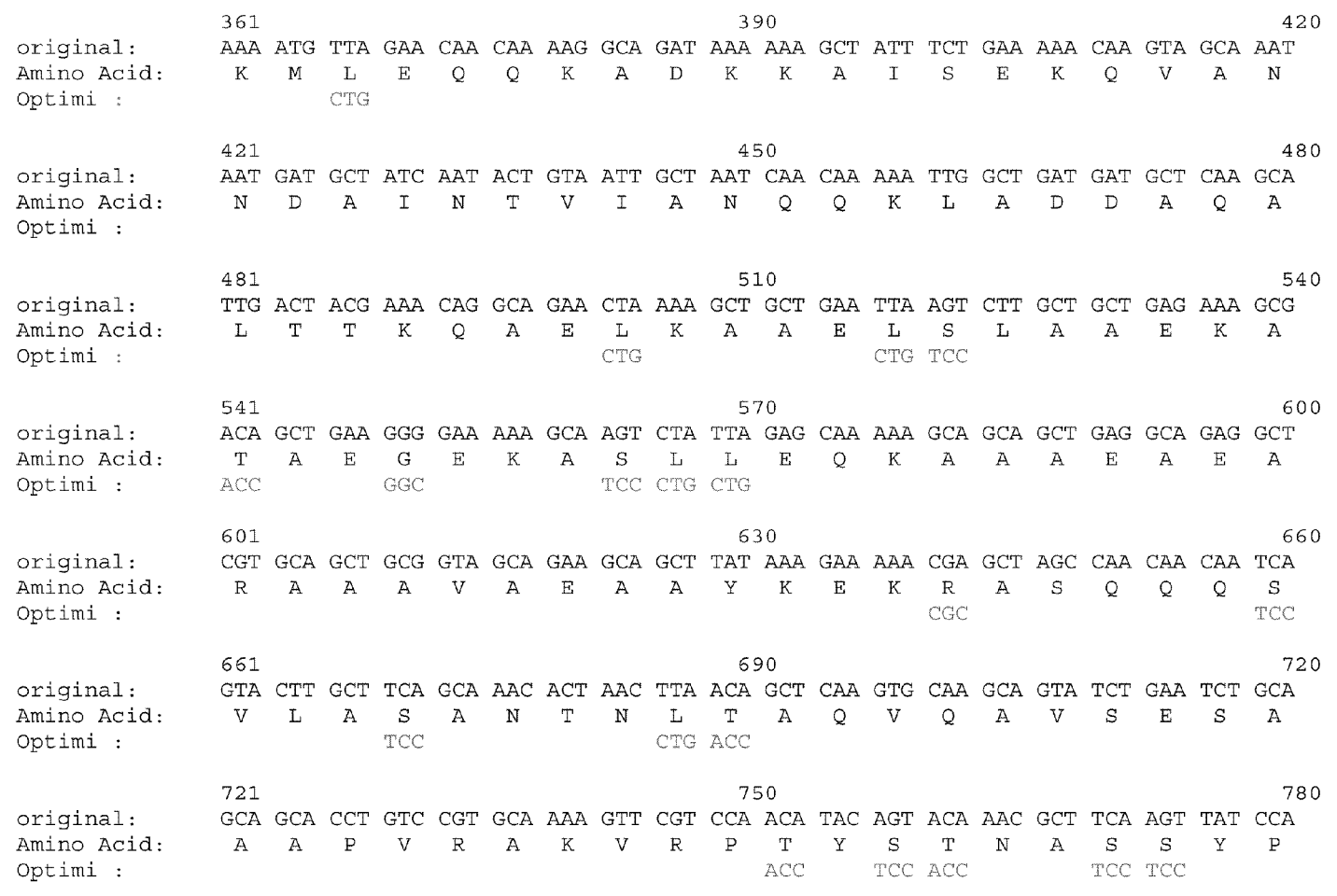

FIG. 66 depicts (A-C) the sequence of codon optimized Tigr 4 aa 1-364. All the changed nucleotides are in red. SEQ ID NO:31 is the original nucleic acid sequence, SEQ ID NO:32 is the original protein sequence, and SEQ ID NO:33 is the optimized nucleic acid sequence.

FIG. 67 depicts (A-E) the sequence of codon optimized Tigr 4 aa 1-648. All the changed nucleotides are in red. SEQ ID NO:34 is the original nucleic acid sequence, SEQ ID NO:35 is the original protein sequence, and SEQ ID NO:36 is the optimized nucleic acid sequence.

FIG. 68 depicts (A) the nucleic acid sequence of PsaA aa 1-288 (SEQ ID NO:37) and (B) the protein sequence (SEQ ID NO:38).

FIG. 69 depicts (A) the nucleic acid sequence of PsaA aa 1-309 (SEQ ID NO:39) and (B) the protein sequence (SEQ ID NO:40).

FIG. 70 depicts (A) the nucleic acid sequence of D39 Tweten mutant aa 8-471 (original, L460D) (SEQ ID NO:41) and (B) the protein sequence (SEQ ID NO:42).

FIG. 71 depicts (A) the nucleic acid sequence of D39 Double mutant aa 8-471 (codon optimized, D385N, W433F) (SEQ ID NO:43) and (B) the protein sequence (SEQ ID NO:44).

Figure 72:
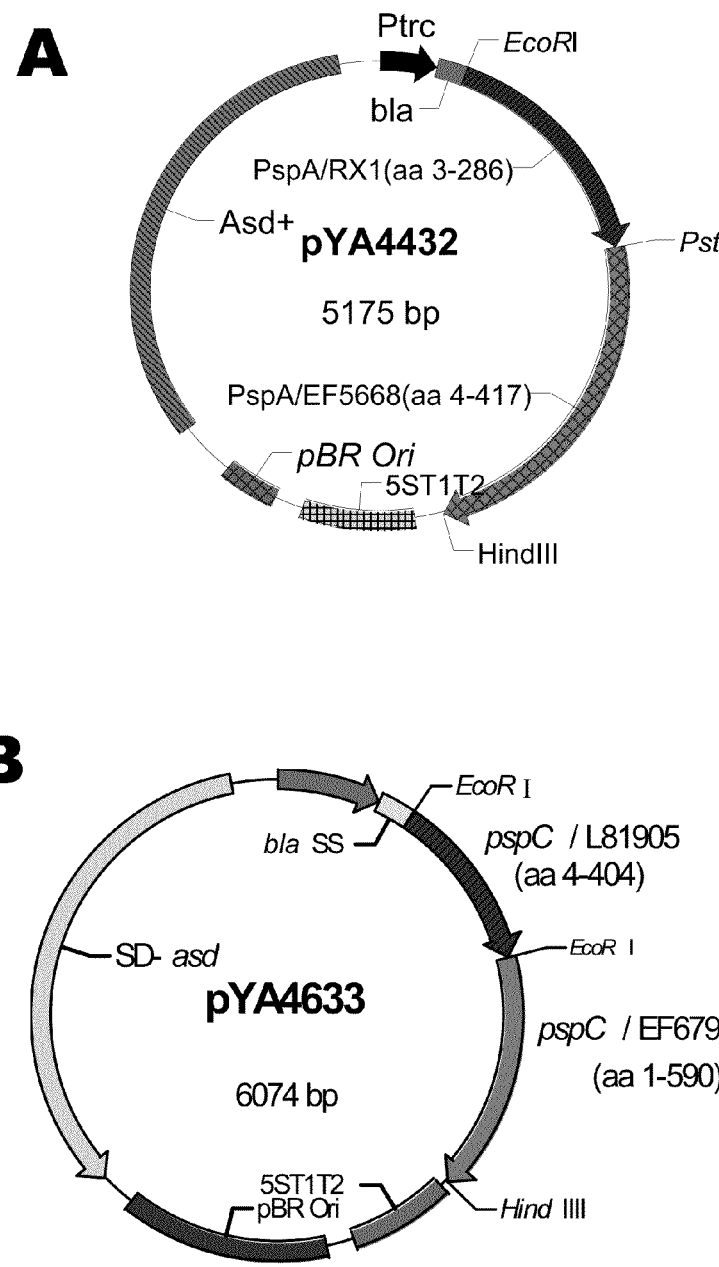
Figure 72C:
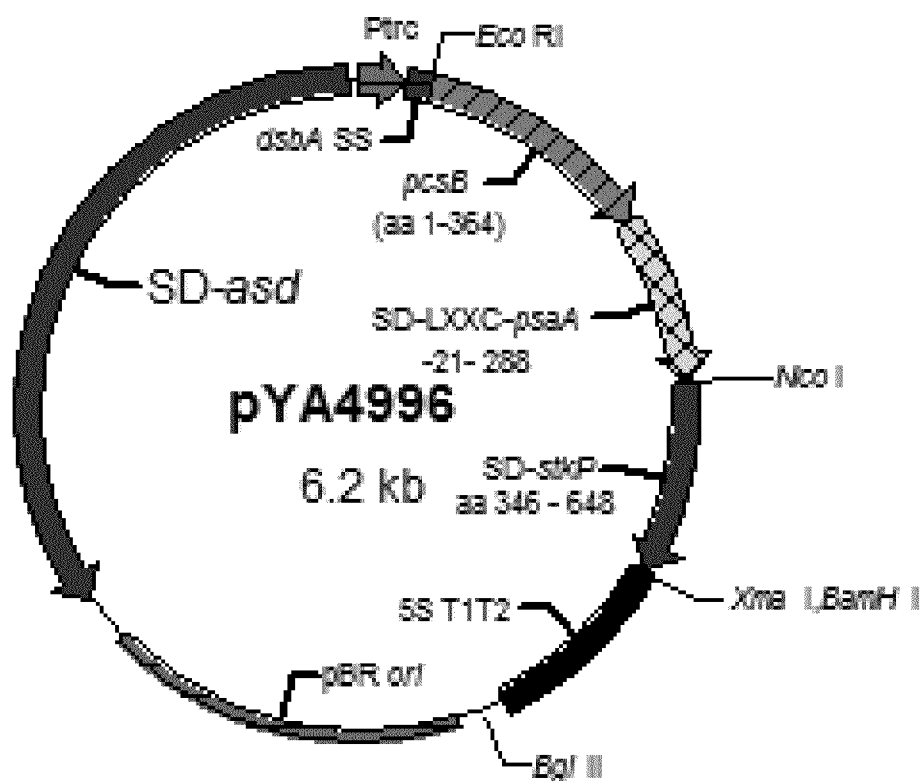

FIG. 72 depicts the pYA4901 (A), the pYA4633 (B) and the pYA4996 (C) plasmid maps.

Figure 73:
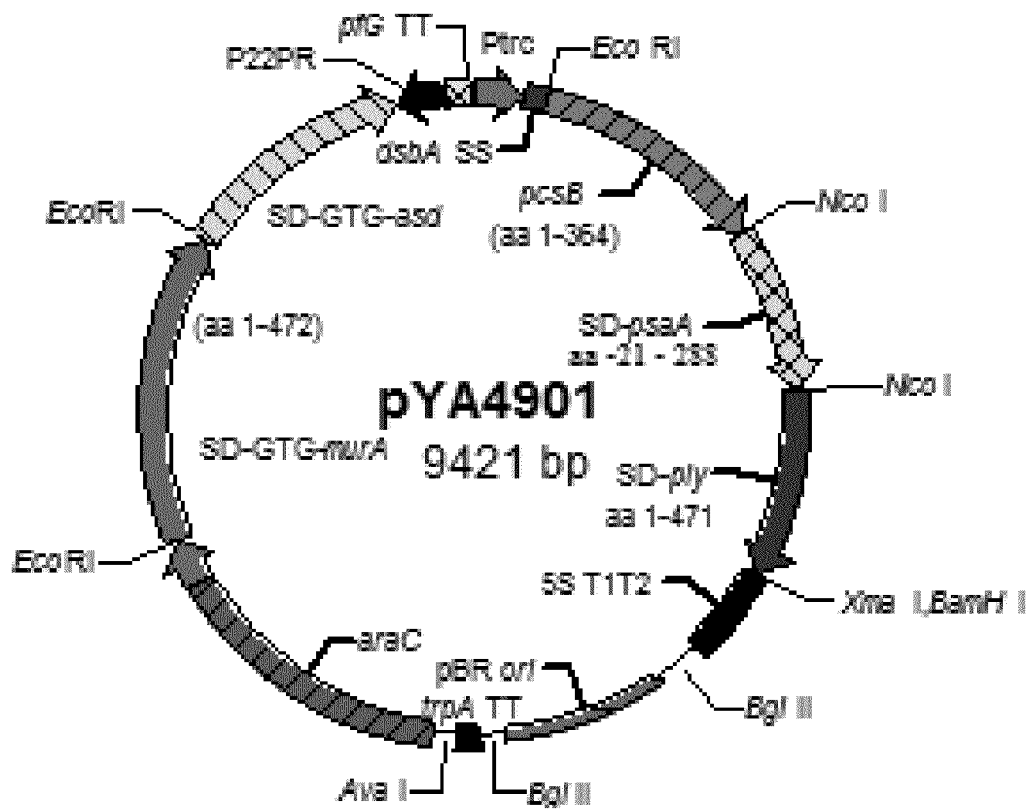

FIG. 73 depicts the pYA4901 plasmid map.

Figure 74:
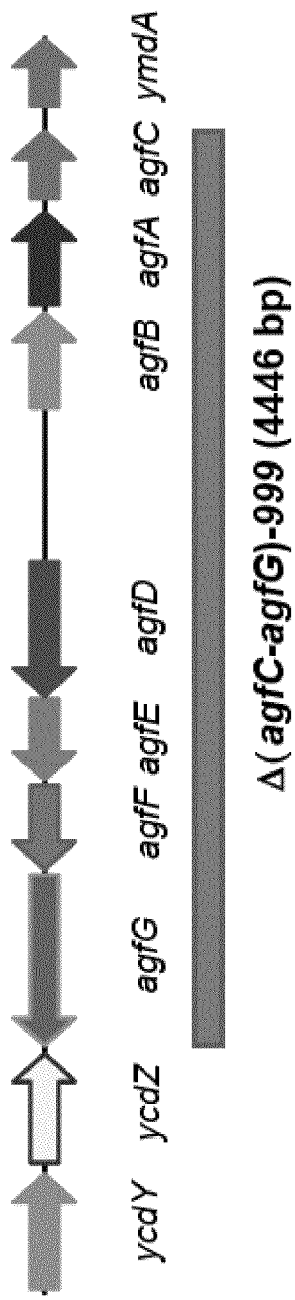

FIG. 74 depicts a schematic diagram of the Δ(agfC-agfG)-999 mutation which is an expansion of the existing Δagf-BAC811 mutation. 4454 bp of agfGFEDBAC (agfG$_{834/834}$ to agfC$_{+5}$) is deleted.

Figure 75:
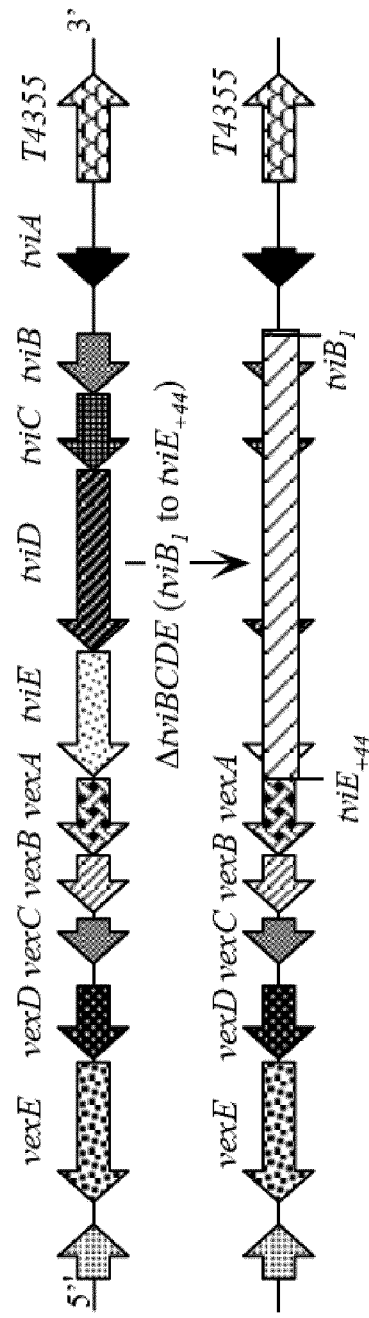

FIG. 75 depicts a schematic diagram of the ΔtviBCDE29 mutation which is an alternative to existent ΔtviABCDE10 mutation. 6625 bp of tviBCDE (tvi$_{B1}$ to tviE$_{+44}$) including 6571 bp of whole tviBCDE ORF is deleted.

Figure 76A:
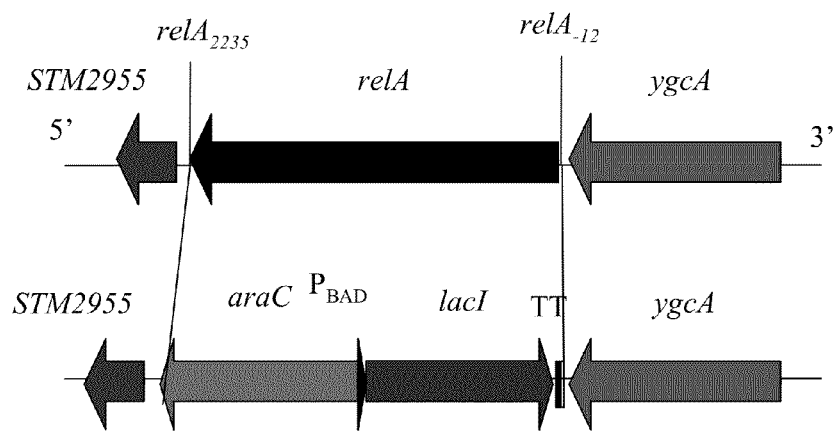
Figure 76B:
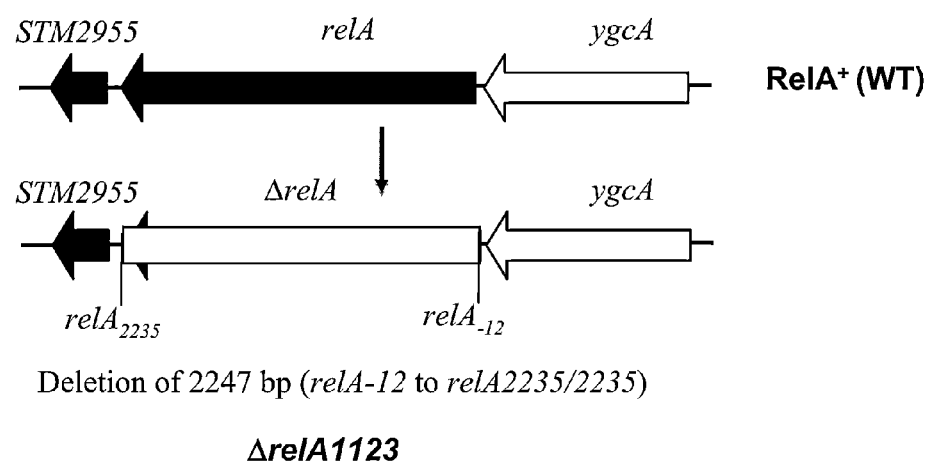

FIG. 76 depicts various modification diagrams (A) of the ΔrelA::araC P$_{BAD}$ lacI TT mutation which will replace the existing ΔrelA198::araC P$_{BAD}$ lacI TT mutation. 2247 bp of relA (−12 to 2235/2235) is deleted and 2393 bp of araC P$_{BAD}$ lacI TT is inserted. The ΔrelA196::araC P$_{BAD}$ lacI TT mutation includes the native Shine Dalgarno (SD) sequence and the GTG start codon of lacI, while in the ΔrelA197::araC P$_{BAD}$ lacI TT mutation, the SD sequence is modified to AGGA from AGGG and the starting codon to ATG from GTG (SEQ ID NOs: 138, 139, 140). Also depicts the diagram (B) of the ΔrelA1123 mutation that has the only relA deletion without the lacI insertion.

Figure 77:
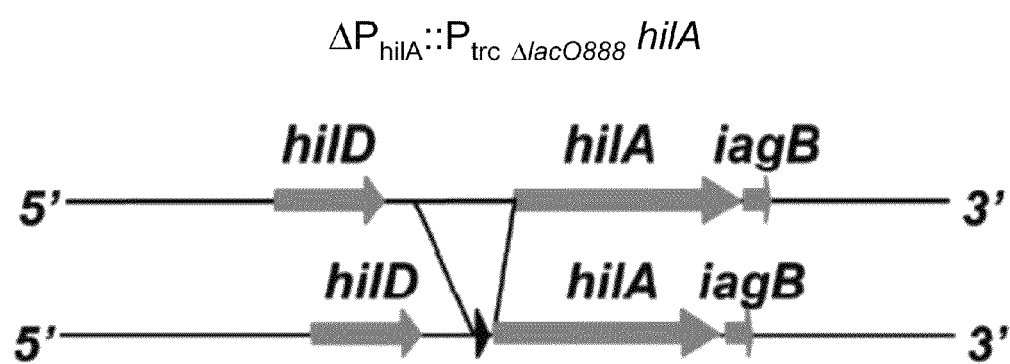

FIG. 77 depicts a schematic diagram of the ΔP$_{hilA}$::P$_{trc}$ Δ$_{lacO888}$ hilA mutation which removes 570 bp of the native hilA promoter and substitutes the P$_{trc}$ promoter. The lacO regulatory site of P$_{trc}$ has been removed in this construction.

FIG. 78 depicts (A-B) the nucleic acid sequence of the PYA4996 plasmid (SEQ ID NO:130) (C) the protein sequence (SEQ ID NO:131), (D) the protein sequence (SEQ ID NO:132) and (E) the protein sequence (SEQ ID NO:133).

FIG. 79 depicts (A-C) the nucleic acid sequence of the PYA4901 plasmid (SEQ ID NO:134) (D) the protein sequence (SEQ ID NO:135), (E) the protein sequence (SEQ ID NO:136) and (F) the protein sequence (SEQ ID NO:137).

DETAILED DESCRIPTION OF THE INVENTION

The present invention provides a recombinant *Salmonella* bacterium wherein the bacterium is capable of both the regulated expression of at least one nucleic acid encoding a *Strepococcus pneumoniae* antigen and capable of regulated attenuation. The bacterium further comprises at least one mutation that affects the persistence of the bacterium, and at least one mutation that reduces fluid secretion in a host. As used herein, "persistence" refers to the bacterium's ability to survive (i.e. live), whether within a host or in the environment. In an exemplary embodiment, the present invention provides a recombinant bacterium possessing the genetic characteristics of χ9639, χ9640, χ9633, or a derivative thereof. In another exemplary embodiment, a recombinant bacterium may comprise ten or more of the mutations selected from the group comprising Δpmi-2426, $\Delta P_{rfc174}$::TT araC $P_{BAD}$ rfc, Δ(wza-wcaM)-8, $\Delta P_{murA}$25::TT araC $P_{BAD}$ murA, ΔasdA27::TT araC $P_{BAD}$ c2$\Delta P_{fur81}$ araC $P_{BAD}$ fur, $\Delta P_{crp527}$::TT araC $P_{BAD}$ crp, ΔsopB1925, ΔtviABCDE10, ΔagfBAC811, ΔrelA198::araC $P_{BAD}$ lacl TT, ΔaraE25, ΔfliC181, ΔaroC1083, ΔaroD1299, and ΔpagP81::$P_{lpp}$ lpxE.

Additionally, the present invention provides a vaccine composition comprising a recombinant bacterium of the invention, and methods of eliciting an immune response against *S. pneumonia* using a bacterium of the invention.

Generally speaking, a recombinant bacterium of the invention is a species or subspecies of the *Salmonella* genera. For instance, the recombinant bacterium may be a *Salmonella enterica* serovar. Non-limiting examples of suitable serovars may include *S. Typhimurium, S. Typhi, S. Paratyphi, S. Enter-*

*itidis, S. Choleraesius,* or *S. Dublin.* In an exemplary embodiment, a recombinant bacterium of the invention is derived from *S. Typhi.* Such a bacterium may be RpoS+ or RpoS−.

I. Regulated Expression of at Least One Nucleic Acid Encoding a *Streptococcus pneumoniae* Antigen The present invention encompasses a recombinant bacterium capable of regulated expression of at least one nucleic acid sequence encoding a *S. pneumoniae* antigen. For instance, the bacterium may comprise a chromosomally integrated nucleic acid sequence encoding a repressor and a vector. Each is discussed in more detail below.

(a) Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA, ilvG or cysG nucleic acid sequences. Other suitable insertion sites can be readily identified by those with skill in the art.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

i. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

In some embodiments, the repressor is not derived from the same species of bacteria as the recombinant bacterium. For instance, the repressor may be derived from *E. coli* if the recombinant bacterium is from the genus *Salmonella.* Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

ii. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC araBAD system from *E. coli.* For example, there is homology at the amino acid sequence level between the *E. coli* and the *S. Typhimurium*AraC proteins, and less homology at the DNA level. However, there is high specificity in the activity of the AraC proteins. For example, the E. coli AraC protein activates only E. coli $P_{BAD}$ (in the presence of arabinose) and not S. Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the malT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rha}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xy/R-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

iii. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

iv. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

(b) Vector

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

i. Antigen

As used herein, "antigen" refers to a biomolecule capable of eliciting an immune response against *S. pneumoniae* in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with *S. pneumoniae*. The use of the term "protective" in this invention does not necessarily require that the host is completely protected from the effects of the pathogen.

In preferred embodiments, an antigen of interest will be conserved across many different pneumococcal strains. For instance, PspA may be an antigen of interest because >99.9% of pneumococcal strains express pspA. Similarly, PspC (found in >95% of pneumococcal strains), PsaA, PcsB, and Ply are also highly conserved across pneumococcal strains, and therefore may also be preferred antigens of interest. Generally speaking, a conserved antigen may be found in greater than 85, 86, 87, 88, 89, 90, 91, 92, 93, 94, 95, 96, 97, 98, or 99% of pneumococcal strains.

In certain embodiments, a conserved antigen of interest may be classified into one or more families based on sequence homology. For instance, there are three families of PspA sequences based on homology. In order to induce an immune response against as many different pneumococcal strains as possible, an antigen of interest may comprise a fusion protein that combines sequences from two or more antigen families. For example, a PspA antigen may comprise a fusion protein comprising sequence from a Family 1 PspA and a Family 2 PspA. Similarly, a PspC antigen may comprise a fusion protein comprising sequence from a group 2-3 hybrid and a group 1, 6, 7, hybrid.

In one embodiment, an antigen of interest may include PspA and/or PspC from *Streptococcus pneumoniae*. In another embodiment, the antigens of interest may include Ply, PcsB, PsaA, and StkP. In other embodiments, the antigens of interest may be selected from any of the antigens listed in Table A.

TABLE A

| Pneumococcal antigens | Description | SEQ ID NO:[1] |
|---|---|---|
| PspA | Rx1 aa 3-285 (codon optimized) | SEQ ID NOs: 1-4 |
| | Rx1 aa 3-257 (original and codon optimized) | SEQ ID NOs: 5-8 |
| | EF5668 aa 4-417 (original and codon optimized) | SEQ ID NOs: 9-12 |
| PspA Fusion | Rx1 aa 3-285::EF5668 aa 4-417 (codon optimized) | SEQ ID NOs: 13-14 |
| | EF5668 aa 4-417::Rx1 aa 3-285 (codon optimized) | SEQ ID NOs: 15-16 |
| PspC | L81905 aa 4-404 (original and codon optimized) | SEQ ID NOs: 17-20 |
| | L81905 aa 4-444 (original and codon optimized) | SEQ ID NOs: 21-24 |
| | EF6796 aa 3-587 (original and codon optimized) | SEQ ID NOs: 25-28 |
| PspC Fusion | L81905 aa 4-404 (codon optimized)::EF6796-G54-G31 aa 1-590 (original and codon optimized) | SEQ ID NOs: 29-30 |
| PcsB | Tigr 4 aa 1-364 (original and codon optimized) | SEQ ID NOs: 31-33 |
| StkP | Tigr 4 aa 1-648 (original and codon optimized) | SEQ ID NOs: 34-36 |
| PsaA | aa 1-288 (original) | SEQ ID NOs: 37-38 |
| | aa 1-309 (original) | SEQ ID NOs: 39-40 |
| Ply | D39 Tweten mutant aa 8-471 (original, L460D) | SEQ ID NOs: 41-42 |
| | D39 Double mutant aa 8-471 (codon optimized, D385N, W433F) | SEQ ID NOs: 43-44 |

[1] see figures for more details

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tetnus toxin fragment C, CT-B, LT-B and hepatitis virus B core are particularly useful for these purposes, although other epitope presentation systems are well known in the art.

In further embodiments, a nucleic acid sequence encoding an antigen of the invention may comprise a secretion signal. In other embodiments, an antigen of the invention may be toxic to the recombinant bacterium.

ii. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

iii. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art. For more details, see the examples.

(c) Crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(d) Attenuation

In each of the above embodiments, a recombinant bacterium of the invention capable of regulated expression may also be attenuated. "Attenuated" refers to the state of the bacterium wherein the bacterium has been weakened from its wild type fitness by some form of recombinant or physical manipulation. This includes altering the genotype of the bacterium to reduce its ability to cause disease. However, the bacterium's ability to colonize the gut (in the case of *Salmonella*) and induce immune responses is, preferably, not substantially compromised.

In an exemplary embodiment, a recombinant bacterium may be attenuated as described in section II below. In which case, both regulated attenuation and regulated expression of an antigen encoding sequence may be dependent upon an arabinose regulatable system. Consequently, the concentration of arabinose needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

II. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

(a) Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be a necessary component of the cell wall of the bacterium, such as the protein encoded by murA. In still other embodiments, the protein may be listed in Section I(d) above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

(b) Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, $\Delta P_{rfc}$::TT araC $P_{BAD}$ rfc or a combination thereof. (P stands for promoter and TT stands for transcription terminator). Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta$araBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as $\Delta$araBAD23, which prevents use of arabinose retained in the cell cytoplasm at the time of oral immunization, and/or $\Delta$araE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

(c) Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in Section I.

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments of the invention, the SD sequences and/or the start codons for the fur and/or the phoPQ virulence nucleic acid sequences may be altered so that the production levels of these nucleic acid products are optimal for regulated attenuation. For instance, in $\Delta P_{fur77}$::TT araC $P_{BAD}$ fur, the start codon may be changed from ATG to GTG, and in $\Delta P_{fur81}$::TT araC $P_{BAD}$ fur the SD sequence may be weakened as well as the start codon changed from ATG to GTG. Additionally, $\Delta P_{phoPQ173}$::TT araC $P_{BAD}$ phoPQ may have modifications to the start codon as well as the second codon, which may be changed from ATG to GTG. Similarly, $\Delta P_{phoPQ177}$::TT araC $P_{BAD}$ phoPQ, may have a SD sequence that has been changed to the weaker AAGG sequence, a modified start codon, and a modified second codon (from ATG to GTG).

In other exemplary embodiments of the invention, the SD sequences and/or start codons for the rfc virulence nucleic acid sequence may be altered so that the production levels of the nucleic acid product is optimal for regulated attenuation. For instance, nucleotides upstream from the rfc start codon may be replaced with araC $P_{BAD}$ and either a modified SD sequence, a modified start codon, or a combination or both. Non-limiting examples of modifcations to the rfc nucleic acid sequence may be found in Table B.

In certain embodiments, a bacterium of the invention may comprise a modified fur sequence in combination with one or more modifications selected from the group consisting of a modified phoPQ sequence and a modified rfc sequence. In an exemplary embodiment, a modified fur sequence may be used in combination with a modified rfc sequence.

TABLE B

| Mutant strains | Sequence | SEQ ID NO: |
|---|---|---|
| $\Delta P_{rfc173}$ | AGGA ctctatATG cttataatttc | SEQ ID NO: 113 |

TABLE B-continued

| Mutant strains | Sequence | SEQ ID NO: |
|---|---|---|
| ΔP$_{rfc174}$ | AGGA ctctatGTG cttataatttc | SEQ ID NO: 114 |
| ΔP$_{rfc175}$ | AAGG ctctatGTG cttataatttc | SEQ ID NO: 115 |

(d) Crp Cassette

In some embodiments, a recombinant bacterium of the invention may also comprise a ΔP$_{crp}$::TT araC P$_{BAD}$ crp deletion-insertion mutation, as described above. Since the araC P$_{BAD}$ cassette is dependent both on the presence of arabinose and the binding of the catabolite repressor protein Crp, a ΔP$_{crp}$::TT araC P$_{BAD}$ crp deletion-insertion mutation may be included as an additional control on the expression of the nucleic acid sequence encoding an attenuation protein.

Generally speaking, the activity of the Crp protein requires interaction with cAMP, but the addition of glucose, which may inhibit synthesis of cAMP, decreases the ability of the Crp protein to regulate transcription from the araC P$_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from P$_{BAD}$. This strategy may also be used in other systems responsive to Crp, such as the systems responsive to rhamnose and xylose described above (e) Regulated Expression In each of the above embodiments, a bacterium capable of regulated attenuation may also be capable of regulated expression of at least one nucleic acid encoding an antigen as detailed in section I above.

For instance, various embodiments of the present invention may encompass a recombinant pathogenic Enterobacteriaceae species comprising deletion-insertion insertion mutations conferring regulated attenuation and regulated expression of a nucleic acid sequence encoding an antigen. In some embodiments, the recombinant bacterium may further comprise at least one chromosomal nucleic acid sequence containing a mutation conferring a lethal phenotype. The mutated chromosomal nucleic acid sequence may be complemented by a plasmid vector containing a functional nucleic acid sequence corresponding to the mutated chromosomal nucleic acid sequence.

III. Balanced Host-Vector System

In some embodiments, a recombinant bacterium of the invention may comprise one or more balanced host-vector systems. In these embodiments, the recombinant bacterium comprises at least one chromosomally encoded essential nucleic acid sequence that is altered so that it is not expressed, and at least one extrachromosomal vector. Each is described in more detail below.

(a) Chromosomally Encoded Essential Nucleic Acid that is Altered so That it is not Expressed A recombinant bacterium of the invention comprises at least one chromosomally encoded essential nucleic acid sequence, wherein the essential nucleic acid sequence is altered so that it is not expressed. As described above, an essential nucleic acid is a native nucleic acid whose expression is necessary for cell viability or a metabolic activity essential for virulence. In some embodiments, an individual nucleic acid sequence is not essential, but the combination of one or more sequences, together, is essential. Stated another way, if the nucleic acid sequences in an essential combination are altered, so that they are not expressed, the cell is non-viable and/or avirulent.

A nucleic acid sequence that encodes a protein necessary for the formation of the peptidoglycan layer of the cell wall may be an essential nucleic acid. In one embodiment, an essential nucleic acid encodes a protein involved in D-alanine synthesis. For example, an essential nucleic acid may encode one or more alanine racemase proteins. In another embodiment, an essential nucleic acid may encode a protein involved in D-glutamate synthesis. In yet another embodiment, an essential nucleic acid may encode a protein involved in muramic acid synthesis. Such nucleic acid sequences are known in the art, and non-limiting examples may include asd, murA, murI, dap, alr, and dadB. In an alternative embodiment, a nucleic acid sequence that encodes a protein whose metabolic activity is essential for virulence may be an essential nucleic acid. Such nucleic acid sequences are also known in the art, and non-limiting examples may include aroA, aroC, aroD, aroE, ilvB, ilvC, ilvD or ilvE.

A recombinant bacterium of the invention may comprise more than one chromosomally encoded essential nucleic acid sequence that is altered so that it is not expressed. For instance, a recombinant bacterium may comprise two, three, four, five, or more than five different chromosomally encoded altered essential nucleic acid sequences.

Methods of making a recombinant bacterium comprising a chromosomally encoded essential nucleic acid sequence that is altered so that it is not expressed are known in the art and detailed in the examples. Non-limiting examples of suitable alterations are detailed below.

i. Essential Nucleic Acid Encoding a Protein Involved in D-Alanine Synthesis

In one embodiment, an essential nucleic acid may encode a protein involved in D-alanine synthesis, since D-alanine is a required constituent of the peptidoglycan layer of a bacterial cell wall. Gram-positive bacteria comprise only one alanine racemase, an enzyme necessary for D-alanine synthesis. Consequently, if the essential nucleic acid sequence encoding the Gram-positive alanine racemase is altered so that it is not expressed, the bacterium is non-viable. Gram-negative bacteria, however, comprise two alanine racemases. Consequently, it is the combination of both sequences that is essential, and the nucleic acid sequences encoding both alanine racemases need to be altered so that both sequences are not expressed. Suitable alterations may include deletion of the nucleic acid sequence encoding an alanine racemase. For instance, the combination of the deletions Δalr and ΔdadB will alter the essential combination such that neither racemase is expressed. Advantageously, an extrachromosomal vector need only encode one racemase to restore viability and/or virulence to the Gram-negative bacterium.

ii. Essential Nucleic Acid Encoding a Protein Involved in Muramic Acid Synthesis In another embodiment, an essential nucleic acid may encode a protein involved in muramic acid synthesis, as muramic acid is another required constituent of the peptidoglycan layer of the bacterial cell wall. For example, an essential nucleic acid may be murA. It is not possible to alter murA by deletion, however, because a ΔmurA mutation is lethal and can not be isolated. This is because the missing nutrient required for viability is a phosphorylated muramic acid that cannot be exogenously supplied because enteric bacteria cannot internalize it. Consequently, the murA nucleic acid sequence may be altered to make expression of murA dependent on a nutrient (e.g., arabinose) that can be supplied during the growth of the bacterium. For example, the alteration may comprise a $\Delta P_{murA}$::TT araC $P_{BAD}$ murA deletion-insertion mutation. During in vitro growth of the bacterium, this type of mutation makes synthesis of muramic acid dependent on the presence of arabinose in the growth medium. During growth of the bacterium in a host, however, arabinose is absent. Consequently, the bacterium is non-viable and/or avirulent in a host unless the bacterium further comprises at least one extrachromosomal vector comprising a nucleic acid sequence, that when expressed, substantially functions as murA. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to cell death due to cell wall-less lysing.

iii. Essential Protein Involved in D-Glutamate Synthesis

In yet another embodiment, an essential nucleic acid may encode a glutamate racemase, an enzyme essential for the synthesis of D-glutamic acid, which is another required constituent of the peptidoglycan layer of the bacterial cell wall. An essential nucleic acid encoding a glutamate racemase may be altered by deletion. For instance, the mutation Δmurl alters the nucleic acid sequence so that it is not expressed.

iv. Essential Protein Involved in DAP Synthesis

In still another embodiment, an essential nucleic acid may encode a protein involved in the synthesis of diaminopimelic acid (DAP). Various nucleic acid sequences are involved in the eventual synthesis of DAP, including dapA, dapB, dapC, dapD, dapE, dapF, and asd. Methods of altering an essential nucleic acid encoding a protein involved in the synthesis of DAP are known in the art. For instance, one of skill in the art may use the teachings of U.S. Pat. No. 6,872,547, hereby incorporated by reference in its entirety, for alterations that abolish DAP synthesis. In one example, the essential nucleic acid asdA may be altered by a ΔasdA mutation, so that asdA is not expressed. This eliminates the bacterium's ability to produce β-aspartate semialdehyde dehydrogenase, an enzyme essential for the synthesis of DAP.

v. More Than one Chromosomally Encoded Essential Nucleic Acid That is Altered

In exemplary embodiments of the invention, a recombinant bacterium may comprise more than one chromosomally encoded essential nucleic acid sequence that is altered so that it is not expressed and at least one extrachromosomal vector.

For instance, in one embodiment, a recombinant bacterium may comprise a first chromosomally encoded essential nucleic acid that is altered so that the first essential nucleic acid is not expressed, a second chromosomally encoded essential nucleic acid that is altered so that the second essential nucleic acid is not expressed, a first extrachromosomal vector, the vector comprising a nucleic acid comprising a nucleic acid sequence, that when expressed, substantially functions as the first essential nucleic acid sequence, and a second extrachromosomal vector, the vector comprising a nucleic acid sequence, that when expressed, substantially functions as the second essential nucleic acid sequence.

In another embodiment, a recombinant bacterium may comprise a first chromosomally encoded essential nucleic acid that is altered so that the first essential nucleic acid is not expressed, a second chromosomally encoded essential nucleic acid that is altered so that the second essential nucleic acid is not expressed, a third chromosomally encoded essential nucleic acid that is altered so that the third essential nucleic acid is not expressed, a first extrachromosomal vector, the vector comprising a nucleic acid comprising a nucleic acid sequence, that when expressed, substantially functions as the first essential nucleic acid sequence, a second extrachromosomal vector, the vector comprising a nucleic acid sequence, that when expressed, substantially functions as the second essential nucleic acid sequence, and a third extrachromosomal vector, the vector comprising a nucleic acid sequence, that when expressed, substantially functions as the third essential nucleic acid sequence.

In yet another embodiment, a recombinant bacterium may comprise a first chromosomally encoded essential nucleic acid that is altered so that the first essential nucleic acid is not expressed, a second chromosomally encoded essential nucleic acid that is altered so that the second essential nucleic acid is not expressed, a third chromosomally encoded essential nucleic acid that is altered so that the third essential nucleic acid is not expressed, a fourth chromosomally encoded essential nucleic acid that is altered so that the fourth essential nucleic acid is not expressed, a first extrachromosomal vector, the vector comprising a nucleic acid comprising a nucleic acid sequence, that when expressed, substantially functions as the first essential nucleic acid sequence, a second extrachromosomal vector, the vector comprising a nucleic acid sequence, that when expressed, substantially functions as the second essential nucleic acid sequence, a third extrachromosomal vector, the vector comprising a nucleic acid sequence, that when expressed, substantially functions as the third essential nucleic acid sequence, and a fourth extrachromosomal vector, the vector comprising a nucleic acid sequence, that when expressed, substantially functions as the fourth essential nucleic acid sequence.

In other embodiments, a recombinant bacterium may comprise more than four chromosomally encoded essential nucleic acid sequences that are each altered so that they are not expressed, and more than four corresponding extrachromosomal vectors. In each of the above embodiments, the extrachromosomal vectors may further comprise a nucleic acid sequence encoding one or more antigens, as detailed below.

By way of non-limiting example, suitable alterations in essential nucleic acid sequences may include an alteration selected from the group consisting of ΔasdA, any Δdap mutation, a ΔdadB mutation with a Δalr mutation, a $\Delta P_{murA}$::TT araC $P_{BAD}$ murA deletion-insertion mutation, a Δmurl mutation, a ΔaroA mutation, a ΔaroC mutation, a ΔaroD mutation, a ΔilvC mutation, and a ΔilvE mutation. For instance, a bacterium may comprise two, three, four, five, or more than five alterations in an essential nucleic acid sequence selected from the group consisting of ΔasdA, any Δdap mutation, a ΔdadB mutation with a Δalr mutation, a $\Delta P_{murA}$::TT araC $P_{BAD}$ murA deletion-insertion mutation, a Δmurl mutation, a ΔaroA mutation, a ΔaroC mutation, a ΔaroD mutation, a ΔilvC mutation, and a ΔilvE mutation.

(b) Extrachromosomal Vector

A recombinant bacterium of the invention also comprises an extrachromosomal vector. The vector comprises a nucleic acid sequence that when expressed, substantially functions as the chromosomally encoded essential nucleic acid that is not expressed. Furthermore, the vector typically also comprises a nucleic acid sequence that encodes at least one antigen. As used herein, "vector" refers to an autonomously replicating nucleic acid unit. The present invention may be practiced with any known type of vector, including viral, cosmid, phasmid, and plasmid vectors. The most preferred type of vector is a plasmid vector. The term "extrachromosomal," as used herein, refers to the fact that the vector is not contained within the bacterium's chromosomal DNA. The vector may comprise some sequences that are identical or similar to chromosomal sequences of the bacterium, however, the vectors used herein do not integrate with chromosomal sequences of the bacterium.

As is well known in the art, plasmids and other vectors may possess a wide array of promoters, multiple cloning sequences, transcription terminators, etc., and vectors may vary in copy number per bacterium. Selection of a vector may depend, in part, on the desired level of expression of the nucleic acid sequence substantially functioning as the essential nucleic acid. Additionally, the selection of a vector may depend, in part, on the level of expression of the nucleic acid sequence encoding a *S. pneumoniae* antigen of interest necessary to elicit an immune response.

For instance, in embodiments where the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori. In other cases, an intermediate copy number vector may be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori. In still other cases, a high copy number vector may be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the vector.

Vectors of the invention generally possess a multiple cloning site for insertion of a nucleic acid sequence that may be operably-linked to the promoter sequence and generally posses a transcription terminator (TT) sequence after a coding region. Preferably, vectors used herein do not comprise antibiotic resistance markers to select for maintenance of the vector.

i. Nucleic Acid that Substantially Functions as an Essential Nucleic Acid

An extrachromosomal vector of the invention comprises a nucleic acid, that when expressed, substantially functions as the essential nucleic acid that was chromosomally altered so that it is not expressed. The phrase “substantially functions,” as used herein, means that the expression of the nucleic acid sequence encoded by the vector restores viability and/or virulence to the recombinant bacterium comprising a chromosomally encoded essential nucleic acid sequence that was altered so that it was not expressed. The nucleic acid, that when expressed, substantially functions as the essential nucleic acid that was chromosomally altered, may, in some embodiments, be derived from the same strain of bacteria as the essential nucleic acid. In other embodiments, the nucleic acid, that when expressed, substantially functions as the essential nucleic acid that was chromosomally altered, may be derived from a different strain of bacteria as the essential nucleic acid.

As described above, if the chromosomally encoded essential nucleic acid that is not expressed encodes a protein such as Alr, DadB, Dap, MurA, MurI, Asd, AroA, AroC, AroD, IlvC, and IlvE, then the nucleic acid sequence encoded by the extrachromosomal vector will substantially function as a nucleic acid sequence encoding Alr, DadB, Dap, MurA, MurI, Asd, AroA, AroC, AroD, IlvC, and IlvE respectively.

An extrachromosomal vector of the invention vector may also comprise a promoter operably-linked to the nucleic acid sequence that substantially replaces the function of an essential nucleic acid sequence. This may depend, however, on the copy number of the vector. For instance, if the vector is a high copy number vector, the nucleic acid sequence that substantially replaces the function of an essential nucleic acid may not be operably-linked to a promoter but may instead only comprise a Shine-Dalgarno (SD) sequence. Alternatively, if the vector is a low copy number vector, the nucleic acid sequence that substantially replaces the function of an essential nucleic acid may be operably-linked to a promoter. Such a promoter may be a weak promoter, a strong promoter, a regulated promoter or a constitutive promoter, depending, in part, on the desired level of expression of the sequence that substantially replaces the function of an essential nucleic acid sequence. The “desired level,” as used herein, is at least the level necessary to render the bacterium viable and/or virulent.

In certain embodiments, the nucleic acid sequence encoded by the extrachromosomal vector may be modified to alter the level of transcription of the nucleic acid. For instance, such alterations may include modifying the SD sequence and or the sequence of the start codon.

ii. Nucleic Acid Sequence Encoding at Least One Antigen

A balanced host-vector system typically comprises an antigen. Suitable antigens are defined in section I(b)i. In an exemplary embodiment, the antigen elicits a protective immune response.

iii. Antigen Delivery System

In addition, the vectors may be designed for various types of antigen delivery systems. The system that is selected will depend, in part, on the immune response desired. For example, if an antibody response is desired, then a Type II secretion system may be used. Examples of Type II secretion systems are well-known in the art, for instance, the β-lactamase secretion system may be used. The use of a Type II secretion system with the signal sequence located at the N-terminus is useful for secretion of many antigens while a Type II secretion system that combines a signal sequence located at the N-terminus with a segment of the C-terminus portion of β-lactamase often improves secretion of the antigen encoded by the nucleic acid sequence between the N-terminus segment and the C-terminus segment. This may in turn improve the immune response to the antigen.

Alternatively, if a cytotoxic T lymphocyte (CTL) response is desired, then a Type III secretion system may be used. Type III secretion systems are known in the art. This type of antigen delivery system delivers the antigen to the cytoplasm of cells in the host to enhance induction of CTL responses.

Yet another type of antigen delivery strategy that may be used is regulated delayed lysis of a bacterium in vivo to release protein antigen(s) and/or viral proteins. The viral proteins may include viral core particles with or without epitope fusion. Regulated antigen delivery systems are known in the art. See, for example, U.S. Pat. No. 6,780,405, hereby incorporated by reference in its entirety.

(c) Inhibiting Recombination

Although extrachromosomal vectors, such as plasmids, may be designed with unique nucleotide sequences, there is some potential for vector-vector recombination to occur that might lead to deletion of and/or alterations in one or more nucleic acid sequences encoding an antigen of interest. This could potentially expose a host to unintended antigens. Accordingly, in some embodiments, a recombinant bacterium of the invention may be deficient in one or more of the enzymes that catalyzes recombination between extrachromosomal vectors. If a bacterium comprises only a single extrachromosomal vector, then such mutations are not necessary. If two or more extrachromosomal vectors are used, however, then the recombinant bacterium may be modified so that one or more recombination enzymes known to catalyze vector-vector recombination are rendered non-functional.

In certain embodiments, the recombination enzymes do not participate in recombinations involving chromosomal nucleic acid sequences. For instance, the recombinant bacterium may comprise a ΔrecF mutation. This mutation does not alter the virulence attributes of the recombinant bacterium, nor its ability to effectively colonize effector lymphoid tissues after immunization of a host. One of skill in the art will appreciate that other recombination enzymes known to catalyze vector-vector recombination but not to participate in recombinations involving chromosomal nucleic acid sequences may be targeted for deletion or mutation in addition to RecF.

Alternatively, the recombinant bacterium may be modified by introducing a ΔrecA mutation that prevents all recombination, whether between vectors or chromosomal nucleic acid sequences. A recombinant bacterium with a ΔrecA mutation is also attenuated. A ΔrecA mutation, however, may diminish a bacterium's ability to colonize effector lymphoid tissues after oral or intranasal immunization. To counter this, a recombinant bacterium may be constructed with a $\Delta P_{recA}$:: araC $P_{BAD}$ recA insertion-deletion mutation so that expression of the RecA recombination enzyme is dependent on the presence of arabinose in the growth medium. In this system, the recombinant bacterium with the $\Delta P_{recA}$:: araC $P_{BAD}$ recA mutation is grown in medium devoid of arabinose to preclude vector-vector recombination. Then, just prior to administration of the recombinant bacterium to a host, arabinose may be supplied to enable expression of the nucleic acid encoding the RecA enzyme. This allows the recombinant bacterium to efficiently colonize effector lymphoid tissues. However, since there is no arabinose present in animal or human host tissues, the RecA enzyme will be depleted by cell division and the absence of recombination in vivo can be restored. Such a strategy may be used in addition to, or in place of, using a ΔrecF mutation.

IV. Additional Mutations

In some embodiments, a recombinant bacterium of the invention may comprise additional mutations. Suitable mutations are described in more detail below and in the examples.

(a) Mutations That Reduce Fluid Secretion

In some embodiments, a recombinant bacterium of the invention may be modified so as to reduce fluid secretion in the host. For instance, the bacterium may comprise a mutation in sopB. By way of non-limiting example, the mutation may be a ΔsopB1925 mutation. Alternatively, the bacterium may comprise a mutation in msb. By way of non-limiting example, the mutation may be a ΔmsbB48 mutation. In yet another alternative, the bacterium may comprise a mutation in pagP. By way of non-limiting example, the mutation may be a ΔpagP81::$P_{lpp}$ lpxE mutation. For more details, see the Examples.

(b) Biological Containment

Under certain embodiments, a live recombinant bacterium may possess the potential to survive and multiply if excreted from a host. This leads to the possibility that individuals not electing to be immunized may be exposed to the recombinant bacterium. Consequently, in certain embodiments, a recombinant bacterium of the invention may comprise one or more mutations that decrease, if not preclude, the ability of *Salmonella* vaccines to persist in the GI tract of animals.

In another embodiment, a recombinant bacterium of the invention may comprise one or more of the Δ(gmd fcl)-26 or Δ(wcaL-wza)-7, ΔagfBAC811 or Δ($P_{agfD}$agfG)-4, Δbcs-ABZC2118 or ΔbcsEFG2319 and Δ(yshA-yihW)-157 mutations that block synthesis of colanic acid, thin aggregative fimbriae (i.e., curli), cellulose and extracellular polysaccharide, respectively, all of which contribute to biofilm formation. An expansion of the ΔagfBAC811 mutation may be made to Δ(agfC-agfG)-999, which would remove not only the curli structural subunits but also the curli export machinery and agfD (FIG. 74). AgfD upregulates the expression of numerous genes which aid in biofilm formation, cell aggregation and tissue colonization. Deletion of agfD will result in a more comprehensive down-regulation of the biofilm formation and bacterial persistence regulon. Since the LPS O-antigen also enables biofilm formation, a strain with the Δpmi-2426, $\Delta P_{rfc174}$::TT araC $P_{BAD}$ rfc, and Δ(galE-ybhC)-851 mutations with or without a Δ(gmd-fcl)-26 or Δ(wcaM-wza)-8 mutation would be expected to survive less well in nature because of a dependency on the availability of three sugars simultaneously, an unlikely occurrence. Such a strain would thus exhibit a rough phenotype making it less able to survive in soil or even in the intestinal environment. In another embodiment, mutations such as ΔyhiR36, that prevent use of DNA as a nutrient, may be used. Similarly, Δ(shdA-ratB)-64, ΔmisL2 and ΔbigA3 that encode four proteins that enable *Salmonella* to adhere to host extracellular matrix proteins and ΔackA233 that blocks use of acetate may be used.

A further anticipated benefit such mutations is the further stripping from the vaccine strain cell surface of macromolecules that might mask immunological surveillance of surface localized LPS core and cross reactive outer membrane antigens. Thus possibly allowing enhancement of levels of induced immune responses to expressed antigens. Indeed, vaccine strains with the Δ(wcaM-wza)-8 mutation synthesize five to ten percent more protective antigen and induce similarly higher antibody titers to this antigen. In exemplary embodiments, a recombinant bacterium comprising a biological containment mutation is not adversely effected in their virulence or the ability to colonize mice.

(c) Regulated Lysis

In some embodiments, a recombinant bacterium may comprise a method of regulated delayed lysis in vivo that prevents bacterial persistence in vivo and survival if excreted. Non-limiting examples of suitable mutations may include: Δ(gmd-fcl)-26 that precludes synthesis of colanic acid that can protect cells undergoing cell wall-less death from lysing completely and ΔagfBAC811 that blocks synthesis of thin aggregative fimbriae (curli) that are critical for biofilm formation to enable persistent colonization on bile stones in the gall bladder, ΔasdA27::TT araC $P_{BAD}$ c2 insertion-deletion mutation to impose a requirement for the peptidoglycan constituent DAP and $\Delta P_{murA12}$::TT araC $P_{BAD}$ murA insertion-deletion mutation as a conditional-lethal mutation blocking synthesis of the peptidoglycan constituent muramic acid. The latter two mutations are typically complemented by a regulated delayed lysis plasmid vector such as pYA3681 that has an arabinose-dependent expression of asdA and murA genes. A recombinant bacterium comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring biological containment.

(d) Modified Lipid A

A recombinant bacterium of the invention may also comprise a modified lipid A. Such modifications typically reduce the toxicity of lipid A. If a recombinant bacterium of the invention undergoes lysis in vivo, it may be advantageous to the host to reduce the toxicity of the lipid A released from the lysed bacterium. Suitable mutations that modify lipid A may include mutations in the acyltransferase PagP and/or the deacylases, PagL and LpxR. For instance, suitable mutations may include ΔpagP8, ΔpagP81::$P_{lpp}$ IpxE, ΔpagL7, ΔIpxR9 or combinations thereof. In one embodiment, a recombinant bacterium comprises the mutation ΔpagP81::$P_{lpp}$ IpxE.

(e) Flagellin Mutations

In various embodiments, a recombinant bacterium of the invention may comprise flagellin mutations. By way of non-limiting example, a bacterium may comprise a mutation in fljB or fliC. For instance, a bacterium may comprise a ΔfliC181, ΔfliC241, ΔfliC2426, or ΔfljB217 mutation. In one embodiment, a bacterium of the invention may comprise a ΔfliC181 mutation.

(f) Vi Antigen Mutations

In some embodiments, a recombinant bacterium of the invention may comprise a mutation that alters the synthesis of the Vi antigen. For instance, a bacterium may comprise a Δtvi mutation. To inactivate the expression of the *S. Typhi*-specific Vi capsular antigen, the genes tviA to tviE (ΔtviABCDE10) were deleted. However, tviA encodes a regulatory protein that plays a role in coordinating expression of Vi antigen, and a number of genes required for host invasion (Houng et al., 1992 J. Bacterio 174:5910; Pickard et al., 1994 Infect Immun 62:3984; Arricau et al., 1998 Mol Microbiol 29:835; Winter et al., 2008 Cell Microbiol 10:247). These include genes encoding flagella and T3SS-1, whose expression in *S. Typhi* is reduced by a TviA-mediated repression of the master regulator FlhDC (Winter et al., 2009 Mol Microbiol 74:175). The total numbers of genes regulated, directly or indirectly, by TviA remain unknown. Thus, a modification of the complete Vi antigen deletion, ΔtviABCDE10, may be made which leaves tviA intact in the chromosome (ΔtviBCDE29) (FIG. 75).

(g) Mutations Which Alter the Expression of Heterologous Antigen

In some embodiments, the ΔrelA198::araC $P_{BAD}$ lacI TT mutation may result in in vivo expression of heterologous antigen in inappropriate tissues or may delay expression past the optimal immunologic window. This mutation may be replaced with the ΔrelA196::araC $P_{BAD}$ lacI TT, ΔrelA197::araC $P_{BAD}$ lacI TT or ΔrelA1123 mutations in order to facilitate more rapid antigen expression. The ΔrelA196::araC $P_{BAD}$ lacI TT mutation contains a weak Shine-Dalgarno sequence (AGGG) and a suboptimal translation start codon (GTG) for lacI, which results in low levels of LacI synthesis and more rapid deregulation of antigen in vivo. The ΔrelA197::araC $P_{BAD}$ lacI TT mutation contains consensus Shine-Dalgarno (AGGA) and translation start codons (ATG) for lacI, which results in moderate levels of LacI synthesis and deregulation of antigen in vivo at an intermediate rate. In some instances, lacI regulation may not be desired at all, but the removal of the stringent response restrictions on translation of proteins may still be necessary. In such instances, the ΔrelA1123 mutation will be used (FIG. 76).

(h) Mutations Which Increase the Level of Eukaryotic Cell Invasion

In some embodiments, vaccines may exhibit sub-optimal levels of eukaryotic cell invasion. One of the major mechanisms of *S. Typhimurium* invasion of animal hosts is by entering and traversing the epithelial monolayer through microfold (M) cells. The hilA (hyper-invasion locus) regulator encodes an OmpR/ToxR family transcriptional regulator that activates expression of invasion genes in response to both environmental and genetic regulatory factors. To improve M cell-mediated *Salmonella* invasion, the Δ$P_{hilA}$::$P_{trc}$ ΔlacO888 hilA mutation will replace the native hilA promoter sequence (FIG. 77). This mutation places hilA under the control of a strong promoter ($P_{trc}$ promoter) which is not subject to regulation (the lacO binding site was removed from Ptrc) in order to enable constitutive synthesis of HilA.

V. Exemplary Recombinant Bacterium

An exemplary recombinant bacterium of the invention may express one or more than one protective antigen as detailed above. Specifically, in one embodiment, a recombinant bacterium may comprise a balanced-host vector system such that the chromosomally encoded essential nucleic acid sequence that is altered is aroC, and the extrachromosomal vector comprises a PspA fusion peptide. For instance, the aroC mutation may be ΔaroC1083, and the PspA fusion peptide may be a fusion between Rx1 and EF5668. In another embodiment, a recombinant bacterium may comprise a balanced-host vector system such that the chromosomally encoded essential nucleic acid sequence that is altered is aroD, and the extrachromosomal vector comprises a PspC fusion peptide. For instance, the aroD mutation may be ΔaroD769, and the PspC fusion peptide may be a fusion between L-81905 and EF6796-G54. In yet another embodiment, a recombinant bacterium may comprise both an aroC balanced-host vector system and an aroD balanced-host vector system. In such an embodiment, recombination between the extrachromosomal vectors of the balanced-host vector systems may be minimized by not including homologous sequences on the vectors.

A recombinant bacterium may also express one or more than one antigens using a regulated delayed lysis vector, as detailed in section IV(c) above. Specifically, in one embodiment, a bacterium may comprise a Δ$P_{murA}$::TT araC $P_{BAD}$ murA mutation, such as Δ$P_{murA15}$::TT araC $P_{BAD}$ murA or Δ$P_{murA25}$::TT araC $P_{BAD}$ murA, in conjunction with a ΔasdA27::TT araC $P_{BAD}$ c2 mutation. These mutations may be complemented with a vector that allows arabinose dependent expression of murA and asd. This vector may comprise one or more antigens. For instance, the vector may comprise a Ply antigen, a PcsB antigen, a PsaA antigen, or a combination thereof.

In an exemplary embodiment, a bacterium of the invention may express five different antigens by comprising the following mutations: ΔaroC1083 balanced by a vector encoding a PspA fusion peptide between Rx1 and EF5668, ΔaroD769 balanced by a vector encoding a PspC fusion peptide between L-81905 and EF6796-G54, and Δ$P_{murA25}$::TT araC $P_{BAD}$ murA, in conjunction with a ΔasdA27::TT araC $P_{BAD}$ c2, along with a vector encoding Ply, PsaA, and PcsB antigens.

An exemplary bacterium of the invention also comprises one or more than one mutation that attenuates the bacterium, including one or more mutations that allow regulated attenuation. For instance, in one embodiment a bacterium of the invention may comprise one or more than one of the following mutations: Δpmi-2426, $\Delta P_{rfc174}$::TT araC $P_{BAD}$ rfc, $\Delta P_{fur81}$::TT araC $P_{BAD}$ fur, $\Delta P_{crp527}$::TT araC $P_{BAD}$ crp, ΔsopB1925, ΔtviABCDE10, $\Delta P_{murA25}$::TT araC $P_{BAD}$ murA, and ΔpagP81::$P_{lpp}$ lpxE. In an exemplary embodiment, a bacterium may comprise two, three, four, five, six, seven, or eight mutations selected from the group comprising Δpmi-2426, $\Delta P_{rfc174}$::TT araC $P_{BAD}$ rfc, $\Delta P_{fur81}$::TT araC $P_{BAD}$ fur, $\Delta P_{crp527}$::TT araC $P_{BAD}$ crp, ΔsopB1925, ΔtviABCDE10, $\Delta P_{murA25}$::TT araC $P_{BAD}$ murA, and ΔpagP81::$P_{lpp}$ lpxE.

In further embodiments, an exemplary bacterium of the invention may comprise at least one mutation that affects the persistence of the bacterium. For instance, a bacterium may comprise one or more than one of the following mutations: Δpmi-2426, $\Delta P_{rfc174}$::TT araC $P_{BAD}$ rfc, Δ(wza-wcaM)-8, ΔagfBAC811, $\Delta P_{murA25}$::TT araC $P_{BAD}$ murA, and ΔasdA27::TT araC $P_{BAD}$ c2. In an exemplary embodiment, a bacterium may comprise two, three, four, five, or six mutations selected from the group comprising Δpmi-2426, $\Delta P_{rfc174}$::TT araC $P_{BAD}$ rfc, $\Delta P_{fur81}$::TT araC $P_{BAD}$ fur, $\Delta P_{crp527}$::TT araC $P_{BAD}$ crp, ΔsopB1925, ΔtviABCDE10, $\Delta P_{murA25}$::TT araC $P_{BAD}$ murA, and ΔpagP81::$P_{lpp}$ lpxE.

In certain embodiments, an exemplary bacterium of the invention may comprise at least one mutation that reduces fluid secretion in a host. For instance, a bacterium may comprise a sopB mutation such as ΔsopB1925.

In an especially exemplary embodiment, a recombinant bacterium of the invention may comprise one, two, three, four, five, six, seven, eight, nine, ten, eleven, twelve, thirteen, fourteen, fifteen, or sixteen mutations selected from the group comprising Δpmi-2426, $\Delta P_{rfc174}$::TT araC $P_{BAD}$ rfc, Δ(wza-wcaM)-8, $\Delta P_{murA25}$::TT araC $P_{BAD}$ murA, ΔasdA27::TT araC $P_{BAD}$ C2 $\Delta P_{fur81}$::TT araC $P_{BAD}$ fur, $\Delta P_{crp527}$::TT araC $P_{BAD}$ crp, ΔsopB1925, ΔtviABCDE10, ΔagfBAC811, ΔrelA198::araC $P_{BAD}$ lacI TT, ΔaraE25, ΔfliC181, ΔaroC1083, ΔaroD1299, and ΔpagP81::$P_{lpp}$ lpxE.

In one embodiment, a recombinant bacterium may comprise Δpmi-2426, $\Delta P_{rfc174}$::TT araC $P_{BAD}$ rfc, Δ(wza-wcaM)-8, $\Delta P_{murA25}$::TT araC $P_{BAD}$ murA, ΔasdA27::TT araC $P_{BAD}$ C2 $\Delta P_{fur81}$::TT araC $P_{BAD}$ fur, $\Delta P_{crp527}$::TT araC $P_{BAD}$ crp, ΔsopB1925, ΔtviABCDE10, ΔagfBAC811, ΔrelA198::araC $P_{BAD}$ lacI TT, ΔaraE25, ΔfliC181, ΔaroC1083, ΔaroD1299, and ΔpagP81::$P_{lpp}$ lpxE and may express one or more antigens selected from the group comprising Ply, PsaA, PcsB, PspC, and PspA antigens. In another embodiment, a recombinant bacterium of the invention may comprise Δpmi-2426, $\Delta P_{rfc174}$::TT araC $P_{BAD}$ rfc, Δ(wza-wcaM)-8, $\Delta P_{murA25}$::TT araC $P_{BAD}$ murA, ΔasdA27::TT araC $P_{BAD}$ C2 $\Delta P_{fur81}$::TT araC $P_{BAD}$ fur, $\Delta P_{crp527}$::TT araC $P_{BAD}$ crp, ΔsopB1925, ΔtviABCDE10, ΔagfBAC811, ΔrelA198::araC $P_{BAD}$ lacI TT, ΔaraE25, ΔfliC181, ΔaroC1083, ΔaroD1299, and ΔpagP81::$P_{lpp}$ lpxE and may express two, three, four or five antigens selected from the group comprising Ply, PsaA, PcsB, PspC, and PspA antigens. In still another embodiment, a recombinant bacterium of the invention may comprise Δpmi-2426, $\Delta P_{rfc174}$::TT araC $P_{BAD}$ rfc, Δ(wza-wcaM)-8, $\Delta P_{murA25}$::TT araC $P_{BAD}$ murA, ΔasdA27::TT araC $P_{BAD}$ C2 $\Delta P_{fur81}$::TT araC $P_{BAD}$ fur, $\Delta P_{crp527}$::TT araC $P_{BAD}$ crp, ΔsopB1925, ΔtviABCDE10, ΔagfBAC811, ΔrelA198::araC $P_{BAD}$ lacI TT, ΔaraE25, ΔfliC181, ΔaroC1083, ΔaroD1299, and ΔpagP81::$P_{lpp}$ lpxE and may express five antigens selected from the group comprising Ply, PsaA, PcsB, PspC, and PspA antigens.

A recombinant bacterium of the invention may be derived from, or posses the genetic characteristics of, a strain in Table C. Similarly, a recombinant bacterium of the invention may comprise a plasmid detailed in Table D.

TABLE C

| χ Number | Genotype and relevant characteristics |
|---|---|
| *Salmonella Typhimurium* UK-1 | |
| χ3761 | wild-type *S. Typhimurium* UK-1 |
| χ8133 | Δcya-27 Δcrp-27 ΔasdA16 |
| χ8477 | ΔaraE25 |
| χ8516 | ΔaraBAD1923 ΔaraE25 |
| χ8650 | Δpmi-2426 |
| χ8767 | ΔaraBAD23 |
| χ8831 | Δ(gmd-fcl)-26 |
| χ8868 | Δpmi-2426 Δ(gmd-fcl)-26 |
| χ8925 | $\Delta P_{sifA102}$::TT araC $P_{BAD}$ sifA |
| χ8958 | ΔasdA33 |
| χ8990 | ΔrelA196::araC $P_{BAD}$ lacI TT |
| χ9021 | $\Delta P_{crp527}$::TT araC $P_{BAD}$ crp |
| χ9088 | Δpmi-2426 Δ(gmd-fcl)-26 $\Delta P_{fur33}$::TT araC $P_{BAD}$ fur ΔasdA33 |
| χ9226 | ΔrelA198::araC $P_{BAD}$ lacI TT |
| χ9241 | ΔpabA 1516 ΔpabB232 ΔasdA16 ΔaraBAD23 ΔrelA198::araC $P_{BAD}$ lacI TT |
| χ9269 | $\Delta P_{fur81}$::TT araC $P_{BAD}$ fur |
| χ9434 | ΔpagP8 |
| χ9485 | ΔpagL7 ΔpagP8 ΔlpxR9 |
| χ9509 | ΔrelA198::araC $P_{BAD}$ lacI TT ΔaraBAD23 |
| χ9558 | Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 |
| χ9705 | ΔpagL7 ΔlpxR9 ΔpagP81::$P_{lpp}$ lpxE |
| χ9732 | ΔpagP81::$P_{lpp}$ lpxE |
| χ9845 | ΔpabA1516 ΔpabB232 ΔasdA16 ΔaraBAD23 ΔrelA198::araC $P_{BAD}$ lacI TT ΔpagP81::$P_{lpp}$ lpxE |
| χ9902 | Δpmi-2426 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 Δ(wza-wcaM)-8 |
| χ9903 | Δpmi-2426 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 Δlrp-23 Δ(wza-wcaM)-8 |
| χ9969 | Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 ΔompA11 |
| χ11017 | ΔasdA27::TT araC $P_{BAD}$ c2 ΔaraBAD23 Δ(gmd-fcl)-26 Δpmi-2426 ΔrelA198::araC $P_{BAD}$ lacI TT $\Delta P_{murA25}$::TT araC $P_{BAD}$ murA |
| χ11124 | ΔpabA1516 ΔpabB232 ΔasdA16 ΔaraBAD23 ΔrelA198::araC $P_{BAD}$ lacI TT ΔompA11 |
| *Salmonella Typhi* | |
| χ3744 | wild-type *S. Typhi* ISP1820, Cys⁻ Trp⁻ |
| χ3769 | wild-type *S. Typhi* Ty2, ATCC19430, Cys⁻ Trp⁻ RpoS⁻ |
| χ8110 | *S. Typhi* ISP1820 χ3744 Δcya-27 Δ(crp-pabA)-40 Δcfs |
| χ8438 | *S. Typhi* Ty2, ATCC202182, RpoS⁺ mutant of wild-type χ3769 |
| χ9603 | *S. Typhi* Ty2 RpoS⁻ $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔtviABCDE10 ΔagfBAC811 PhoP⁺ |
| Δ9604 | *S. Typhi* Ty2 RpoS⁺ $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔtviABCDE10 ΔagfBAC811 PhoP⁺ |
| χ9633 | *S. Typhi* ISP1820 $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔaraBAD23 ΔtviABCDE10 ΔagfBAC811 PhoP⁺ ΔasdA33 |
| χ9639 | *S. Typhi* Ty2 RpoS⁻ $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔtviABCDE10 ΔagfBAC811 PhoP⁺ ΔasdA33 |
| χ9640 | *S. Typhi* Ty2 RpoS⁺ $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔtviABCDE10 ΔagfBAC811 PhoP⁺ ΔasdA33 |
| χ11053 | *S. Typhi* Ty2 χ3769 ΔrecF126 |
| χ11159 | *S. Typhi* Ty2 χ3769 ΔrecA62 |
| χ11194 | *S. Typhi* Ty2 χ3769 ΔrecJ1315 |
| χ11247 | *S. Typhi* ISP1820 χ3744 Δ(galE-ybhC)-851 |
| χ11248 | *S. Typhi* Ty2 χ3769 Δ(galE-ybhC)-851 |

TABLE D

Suicide Vectors:
Genetic information

| pYA number | Description | Parent Vector | Host Strain | Marker |
|---|---|---|---|---|
| pYA3467 | rpoS | pMEG-375 | MGN654 | Cm, Amp |
| pYA3485 | ΔaroE25 | pMEG-375 | χ7213 | Cm, DAP |
| pYA3492 | ΔagfBAC811 | pDMS197 | χ7213 | Tet |
| pYA3546 | Δpmi-2426 | pDMS197 | χ7213 | Tet |
| pYA3548 | ΔfliB217 | pDMS197 | χ7213 | Tet |
| pYA3599 | ΔaraBAD23 | pMEG-375 | χ7213 | Cm, DAP |
| pYA3629 | Δ(gmd-fcl)-26 | pMEG-375 | χ7213 | Cm, DAP |
| pYA3702 | ΔfliC2426 | pRE112 | χ7213 | Cm, |
| pYA3721 | ΔfliC2426 | pRE112 | χ7213 | Cm, DAP |
| pYA3729 | ΔfliC180 | pRE112 | χ7213 | Cm, DAP |
| pYA3733 | ΔsopB1925 | pMEG-375 | χ7213 | Cm, DAP |
| pYA3736 | ΔasdA33 | pRE112 | χ7213 | Cm, DAP |
| pYA4009 | ΔtviABCDE10 | pRE112 | χ7213 | Cm, DAP |
| pYA4064 | ΔrelA araC $P_{BAD}$ lacI (ATG codon) | pRE112 | χ7213 | Cm, DAP |
| pYA4181 | $\Delta P_{fur81}$::TT araC $P_{BAD}$ fur | pRE112 | χ7213 | Cm, DAP |
| pYA4368 | ΔwcaM | pRE112 | χ7213 | Cm, DAP |

Cloning Vectors and Expression Plasmids

| Plasmid number | Parent Plasmid | Expressed Protein | Selective Marker | Replication Origin | Promoter | Signal sequence |
|---|---|---|---|---|---|---|
| pYA3193 | pYA3148 | PspA aa 1-470 | Asd | pBR | $P_{trc}$ | |
| pYA3342 | pYA3341 | none | Asd | pBR, | $P_{trc}$ | |
| pYA3493 | pYA3342 | none | Asd | pBR | $P_{trc}$ | bla SS |
| pYA3494 | pYA3493 | PspA aa 3-257 | Asd | pBR | $P_{trc}$ | bla SS |
| pYA3496 | pYA3342 | His-PspA aa 3-257 | Asd | pBR | $P_{trc}$ | |
| pYA3634 | pYA3494 | PspA aa 3-257 G insert | Asd | pBR | $P_{trc}$ | bla SS |
| pYA3635 | pYA3494 | PspA aa 3-257 Codon optimized | Asd | pBR | $P_{trc}$ | bla SS |
| pYA3822 | pMAL-p2X | malE SS-Esat-6 | Amp | | $P_{trc}$ | |
| pYA3681 | Lysis vector | | Asd | pBR | $P_{trc}$ | |
| pYA4088 | pYA3493 | PspA aa 3-285 Codon optimized | Asd | pBR | $P_{trc}$ | bla SS |
| pYA4729 | pYA3342 | PsaA aa 1-288 Codon optimized | Asd | pBR | $P_{trc}$ | lpp SS |
| pYA4901 | pYA3681 | DsbA SS-PcsB, aa 1-364 Lpp SS-PsaA, aa 1-288 Ply Tweten mutant aa 8-471(original, L460D) | Asd | pBR | $P_{trc}$ | DsbA SS lpp SS |
| pYA4902 | pYA4754 | PspA fusion Rx1(aa 3-285)-EF5668(aa 4-417) | AroD | pBR | $P_{lpp}$ | bla SS |
| pYA4903 | pYA4863 | PspC fusion L81905 (aa 4-404)-EF6796-G54-G31 (aa 1-590) | AroC | pBR | P22 $P_L$ | bla SS |

VI. Vaccine Compositions and Administration

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. In an exemplary embodiment, the host may be subject to infection by *S. pneumoniae*. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant, obviating the need for any additional adjuvants. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline (including buffered saline), Ringer's solution, dextrose solution, and the like.

VII. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

VIII. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by *S. pneumoniae* in a host. For certain pathogens, cultures or swabs taken as biological samples from a host may be used to monitor the existence or amount of pathogen in the individual.

In another embodiment, the invention provides a method for eliciting an immune response against *S. pneumoniae* in a host. The method comprises administering to the host an effective amount of a composition comprising a recombinant bacterium of the invention In still another embodiment, a recombinant bacterium of the invention may be used in a method for eliciting an immune response against *S. pneumoniae* in an individual in need thereof. The method comprises administrating to the host an effective amount of a composition comprising a recombinant bacterium as described herein. In a further embodiment, a recombinant bacterium described herein may be used in a method for ameliorating one or more symptoms of infection by *S. pneumoniae* in a host in need thereof. The method comprises administering an effective amount of a composition comprising a recombinant bacterium as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

*Salmonella Typhi* Vector Construction Description

Three live recombinant attenuated *Salmonella Typhi* vaccines (RASV) expressing *S. pneumoniae* surface protein PspA-Rx1 have been constructed. (see FIG. 1) Two are derived from the *S. Typhi* Ty2 parent wild type where one of the two vaccine constructs has the restored rpoS gene and is otherwise identical to the original RpoS$^-$ Ty2 vaccine derivative. The third vaccine construct is derived from the ISP1820 parent wild type. The three complete RASV are endowed with a plasmid, pYA4088, encoding the *S. pneumoniae* PspA-Rx1 antigen. PspA-Rx1 is fused to the β-lactamase export system and has been engineered to depend on the Asd$^+$ balanced-lethal system. For comparative purpose, a *S. Typhimurium* UK-1 was constructed, in parallel of the *S. Typhi* engineering, to enable safety and immunogenicity studies in the murine model. FIGS. 1 and 2 depict the genealogy of the *S. Typhi* and *S. Typhimurium* RASVs. The RASVs genotypic properties are described as follows:

*S. Typhi* Ty2 RpoS$^-$

A live recombinant attenuated $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacl TT ΔaraE25 ΔtviABCDE10 ΔagfBAC811 ΔasdA33, RpoS$^-$ *Salmonella Typhi* Ty2 χ9639 strain transformed with plasmid pYA4088 expressing *S. pneumoniae* PspA-Rx1 antigen to yield χ9639 (pYA4088).

*S. Typhi* Ty2 RpoS$^+$

A live recombinant attenuated $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacl TT ΔaraE25 ΔtviABCDE10 ΔagfBAC811 ΔasdA33, RpoS$^+$ *Salmonella Typhi* Ty2 strain χ9640 transformed with plasmid pYA4088 expressing *S. pneumoniae* PspA-Rx1 antigen to yield χ9640 (pYA4088).

*S. Typhi* ISP 1820

A live recombinant attenuated $\Delta P_{crp527}$::TT araC $P_{BAD}$ crp $\Delta P_{fur81}$::TT araC $P_{BAD}$ furΔpmi-2426 Δ(gmd-fcl)-26 ΔsopB1925 ΔrelA198::araC $P_{BAD}$ lacl TT ΔaraE25 ΔaraBAD23 ΔtviABCDE10 ΔagfBAC811 ΔasdA33, *Salmonella Typhi* ISP1820 strain χ9633 transformed with plasmid pYA4088 expressing *S. pneumoniae* PspA-Rx1 antigen to yield χ9633(pYA4088).

Description of all Mutations and Sequences

The following is a complete description of each deletion mutation engineered into the Ty2 and ISP1820 parent wild-type strains. In addition to the restoration of rpoS in the Ty2 derivative made by allelic exchange from the suicide vector pYA3467 containing the rpoS gene, there are eight deletion mutations incorporated into ISP1820 *S. Typhi*, seven deletion mutations incorporated into Ty2 RpoS$^-$ and Ty2 RpoS$^+$ and three deletion-insertion mutations incorporated into each Ty2 RpoS$^-$, Ty2 RpoS$^+$ and ISP1820 *S. Typhi* isotype. For comparative purposes, an *S. Typhimurium* UK-1 strain was constructed to enable safety and immunogenicity studies in a murine model.

Δpmi-2426 deletes the structural gene for phosphomannose isomerase (or mannose-6-phosphate isomerase) that interconverts fructose-6-phosphate and mannose-6-phosphate. (FIG. 3) The deletion encompasses 1,176 base pairs including the ATG start codon and the TAG stop codon. PCR analysis using oligonucleotide primers complementary to DNA sequences within the fumA and ydgA genes that flank the pmi locus generate a DNA fragment that is 1,176 bp shorter when using DNA from the mutant with the Δpmi-2426 mutation than DNA from the wild-type parent strain. Strains with the Δpmi-2426 mutation exhibit a reversible smooth-rough phenotype and will synthesize LPS O-antigen when grown in the presence of mannose. In vivo there is no free non-phosphorylated mannose so that LPS O-antigen synthesis ceases. This mutation results in attenuation of *S. Typhimurium* strains that possess it. pYA3546 is the suicide vector for introducing the Δpmi-2426 mutation into the chromosome.

Table 1 below shows the virulence of the Δpmi-2426 mutation, in an *S. Typhimurium* strain, in mice.

TABLE 1

Virulence and protection of *S. Typhimurium* with the Δpmi-2426 mutation in mice

| Strain | Oral dosage (CFU) | Survivors/ total | Oral challenge dose* (CFU) | Survivors/ total after Challenge |
|---|---|---|---|---|
| χ8650 | $1.5 \times 10^9$ | 3/8 | $8.0 \times 10^8$ | 3/3 |
| Δpmi-2426 | $1.5 \times 10^8$ | 7/8 | $8.0 \times 10^8$ | 4/4 |
| +0.5% mannose | $1.5 \times 10$ | 7/8 | $8.0 \times 10^8$ | 3/4 |
| | | | $8.0 \times 10^7$ | 3/3 |
| | $1.5 \times 10^6$ | 4/4 | $8.0 \times 10^7$ | 4/4 |
| | $1.5 \times 10^5$ | 4/4 | $8.0 \times 10^7$ | 4/4 |

*Challenge with wild-type *S. Typhimurium* UK-1 χ3761

To ensure that all mannose provided to the vaccine strain during growth prior to vaccination is directed at LPS O-antigen synthesis, we include the Δ(gmd-fcl)-26 mutation (FIG. 4) that deletes two genes that encode enzymes for conversion of GDP-mannose to GDP fucose. This mutation does not alter the attenuation (Table 2), tissue-colonizing ability or immunogenicity of a strain with the Δpmi-2426 mutation alone. The inability to synthesize colanic acid reduces ability of *S. Typhi* to form biofilms and thus confers some contribution to biological containment.

TABLE 2

Effect of other deletion mutations on virulence of *S. Typhimurium* in mice

| Strain | Oral dosage (CFU) | Survivors/ total |
|---|---|---|
| χ8868 | $1.1 \times 10^9$ | 5/5 |
| Δpmi-2426 | $1.1 \times 10^8$ | 4/5 |
| Δ(gmd-fcl)-26 | $1.5 \times 10^7$ | 5/5 |
| +0.5% mannose | $1.5 \times 10^6$ | 4/5 |
| χ8477 | $1.1 \times 10^8$ | 0/4 |
| ΔaraE25 | $1.1 \times 10^7$ | 1/4 |
| | $1.1 \times 10^6$ | 1/4 |
| | $1.1 \times 10^5$ | 2/4 |
| χ8767 | $9.2 \times 10^5$ | 4/5 |
| ΔaraBAD23 | $9.2 \times 10^4$ | 4/5 |
| | $9.2 \times 10^3$ | 5/5 |
| χ8516 | $7.0 \times 10^7$ | 1/4 |
| ΔaraBAD1923 | $7.0 \times 10^6$ | 2/4 |
| ΔaraE25 | $7.0 \times 10^5$ | 2/4 |
| | $7.0 \times 10^4$ | 2/4 |
| χ8831 | $5.9 \times 10^5$ | 1/4 |
| Δ(gmd-fcl)-26 | $5.9 \times 10^4$ | 4/4 |
| UK-1 | $5.9 \times 10^3$ | 4/4 |
| | $5.9 \times 10^2$ | 4/4 |
| χ8831 | $8.6 \times 10^6$ | 0/4 |
| Δ(gmd-fcl)-26 | $8.6 \times 10^5$ | 0/4 |
| UK-1 | $8.6 \times 10^4$ | 0/4 |
| | $8.6 \times 10^3$ | 1/4 |
| χ8958 | $6.4 \times 10^8$ | 5/5 |
| ΔasdA33 | | |
| UK-1 | | |
| χ8990 | $1.0 \times 10^5$ | 1/5 |
| re1A 196::araC | $1.0 \times 10^4$ | 4/5 |
| $P_{BAD}$ lacl (GTG) | $1.0 \times 10^3$ | 5/5 |
| TT | | |
| UK-1 | | |

Δ(gmd-fcl)-26 deletes two structural genes that encode GDP-mannose-4,6-dehydratase and GDP-fucose synthetase for conversion of GDP-Mannose to GDP-4-keto-6-deoxy-Mannose and GDP-4-keto-6-deoxy-Mannose to GDP-L-fucose, respectively, thus blocks colanic acid production. (FIG. 4) The mutation encompasses a 2,097 base pairs deletion including the ATG start codon of the gmd gene and including the TAG stop codon of the fcl gene. PCR analysis using oligonucleotide primers complementary to DNA sequences within the wacH and wacF genes that flank the gmd-fcl locus generates a DNA fragment that is 2,097 bp shorter when using DNA from the mutant with the Δ(gmd-fcl)-26 mutation than DNA from the wild-type parent strain. The inability to synthesize colanic acid reduces ability of S. Typhi to form biofilms and thus contributes to biological containment and lessens the likelihood for adherence to gallstones leading to persistence. The mutation does not alter virulence, which is the same as for the wild-type parent (Table 2). Additionally, this mutation does not alter the tissue-colonizing ability or immunogenicity of a strain with the Δpmi-2426 mutation alone. pYA3629 is the suicide vector for introducing the Δ(gmd-fcl)-26 mutation into the chromosome.

ΔaraE25 deletes the structural gene for the low-affinity L-arabinose transport system proton symport protein that promotes the internalization and externalization of the L-arabinose, thus enhancing retention of arabinose. (FIG. 5) The deletion encompasses 1,432 base pairs including the ATG start codon and including the TAG stop codon. PCR analysis using oligonucleotide primers complementary to DNA sequences within the ygeA and kduD genes that flank the araE locus generate a DNA fragment that is 1,432 bp shorter when using DNA from the mutant with the ΔaraE25 mutation than DNA from the wild-type parent strain. The ΔaraE25 mutation does not contribute to attenuation and *S. Typhimurium* strains with this mutation have the same virulence for mice as the wild-type parent. (Table 2) pYA3485 is the suicide vector for introducing the ΔaraE-25 mutation into the chromosome.

ΔaraBAD23 deletes the structural genes for L-ribulokinase, L-arabinose isomerase and L-ribulose-5-phosphate 4-epimerase, preventing use of arabinose retained in the cell cytoplasm at the time of oral immunization. (FIG. 6) The deletion encompasses 4,110 base pairs including the TG in the ATG start codon of the araB gene and including the TAA stop codon of the araD gene. The presence of the ΔaraBAD23 mutation does not appreciably alter the virulence of *S. Typhimurium* strains that possess it. (Table 2) pYA3599 is the suicide vector for introducing the ΔaraBAD23 mutation into the chromosome.

ΔsopB1925 deletes a gene for reduction of fluid secretion and neutrophil accumulation in the intestinal tract. (FIG. 7) This gene deletion also enhances immune responses. *S. Typhimurium* strains with the ΔsopB1925 mutation are slightly attenuated for mice. The mutation encompasses a 1,704 base pair deletion including the ATG start codon and the TGA stop codon. PCR analysis using oligonucleotide primers complementary to DNA sequences within the up stream (STM1092) and down stream (pipC) genes that flank the sopB gene generate a DNA fragment that is 1,704 bp shorter when using DNA from the ΔsopB mutant than DNA from the wild-type parent strain. pYA3733 is the suicide vector for introducing the ΔsopB1925 mutation into the chromosome.

ΔtviABCDE10 deletes the structural genes for synthesis of the Vi antigen, an external capsular polysaccharide and an essential virulence factor and protective antigen of *S. Typhi*. (FIG. 8) The deletion encompasses 7,410 base pairs including the ATG start codon of the tviA gene and including the TAG stop codon of the tviE gene. The Δtvi mutants of *S. Typhi* are attenuated in humans. PCR analysis using oligonucleotide primers complementary to DNA sequences within the up stream of viaA and vexA genes that flank the tviABCDE locus generate a DNA fragment that is 7,410 bp shorter when using DNA from the mutant with the ΔtviABCDE10 mutation than DNA from the wild-type parent strain. The mutant strain is unable to synthesize Vi antigen, revealed by rocket immune electrophoresis and by Vi-antisera negative agglutination, resistance to Vi-II phage infection and positive to the O-antisera agglutination assay in any stage of growth. Studies suggest that the Vi antigen protects the bacterial cell by masking the O antigens from the action of complement. pYA4009 is the suicide vector for introducing the ΔtviABCDE10 mutation into the chromosome.

ΔagfBAC811 deletes the structural genes for synthesis of thin aggregative fimbriae. (FIG. 9) The mutation encompasses a 1,714 base pair deletion including the ATG start codon of the agfB gene and including the TAG stop codon of the agfC gene. The inability to synthesize Agf fimbriae decreases biofilm formation on gallstones to establish persistent infections. The ΔagfBAC811 mutation does not alter the virulence of *S. Typhimurium* strains for mice. Agf fimbriae are also called curli. PCR analysis using oligonucleotide primers complementary to DNA sequences within the up stream of agfB and ymdA genes that flank the agfBAC locus generate a DNA fragment that is 1,714 bp shorter when using DNA from the mutant with the ΔagfBAC811 mutation than DNA from the wild-type parent strain. pYA3492 is the suicide vector for introducing the ΔagfBAC811 mutation into the chromosome.

ΔasdA33 deletes the gene coding for the enzyme aspartate β-semialdehyde dehydrogenase which is required for the synthesis of diaminopimelic acid (DAP), an essential component of peptidoglycan in gram-negative bacterial cell walls. (FIG. 10) Strains with Δasd mutations are totally avirulent. The mutation encompasses a 1,104 base pair deletion including the ATG start codon but not including the TAG stop codon. PCR analysis using oligonucleotide primers complementary to DNA sequences up-stream and down-stream of asd gene from *Salmonella Typhi* generate a DNA fragment that is 1,104 bp shorter when using DNA from the mutant than DNA from the wild-type parent strain. pYA3736 is the suicide vector for introducing the ΔasdA33 mutation into the chromosome. The asd mutation, if not complemented by an $Asd^+$ plasmid, is attenuating. (Table D)

$\Delta P_{crp527}$::TT araC $P_{BAD}$ crp deletes the promoter sequence of the crp gene and inserts the 1,335 bp TT araC $P_{BAD}$ cassette for arabinose regulated crp synthesis. (FIG. 11) The 95 bp deletion is from crp-109 to crp-15 leaving the Shine-Dalgarno (SD) ribosome binding site intact and generating a DNA fragment that is ~1,260 bp longer when using DNA from the mutant than DNA from the wild-type parent strain by PCR. (FIG. 12) A transcription terminator (TT) from T4 bacteriophage T4iPIII is inserted down-stream from the inserted araC gene to preclude continued transcription of the araC gene into adjacent genes that could alter their expression. The mutant strain expresses the crp gene when grown in the presence of arabinose and the Crp protein increases transcription from $P_{BAD}$ (the promoter for the missing araBAD genes). Crp is the cAMP receptor protein. In the absence of arabinose, which is not present in a non-phosphorylated form in vivo, transcription from $P_{BAD}$ ceases with cessation in the synthesis of the Crp protein. This acts to decrease transcription from all araC $P_{BAD}$ regulated genes present in the vaccine strain. The inclusion of this $\Delta P_{crp527}$::TT araC $P_{BAD}$ crp deletion-insertion mutation thus acts as a second shut-off, in addition to the absence of arabinose, in vivo of all araC $P_{BAD}$ regulated genes, This is an important safety feature. Absence of Crp attenuates *Salmonella*. (Table 3) pYA3822 is the suicide vector for introducing the $\Delta P_{crp527}$::TT araC $P_{BAD}$ crp mutation into the chromosome.

TABLE 3

Virulence and protection of *S. Typhimurium* with $\Delta P_{crp527}$::TT araC $P_{BAD}$ crp deletion-insertion mutation in mice

| Strain | % arabinose in media | Oral dosage (CFU) | Survivors/ total | Oral challenge dose* (CFU) | Survivors/ total after challenge |
|---|---|---|---|---|---|
| χ9021 | 0 | $1.5 \times 10^9$ | 5/5 | $3.1 \times 10^8$ | 5/5 |
| $\Delta P_{crp527}$::TT araC $P_{BAD}$crp | | $1.5 \times 10^8$ | 5/5 | $3.1 \times 10^8$ | 4/5 |
| | | $1.5 \times 10^7$ | 5/5 | $3.1 \times 10^8$ | 5/5 |
| | 0.05 | $1.6 \times 10^9$ | 5/5 | $3.1 \times 10^8$ | 5/5 |
| | | $1.6 \times 10^8$ | 5/5 | $3.1 \times 10^8$ | 5/5 |
| | | $1.6 \times 10^7$ | 5/5 | $3.1 \times 10^8$ | 5/5 |
| | 0.2 | $1.6 \times 10^9$ | 5/5 | $3.1 \times 10^8$ | 5/5 |
| | | $1.6 \times 10^8$ | 5/5 | $3.1 \times 10^8$ | 5/5 |
| | | $1.6 \times 10^7$ | 5/5 | $3.1 \times 10^8$ | 5/5 |

*Challenge with wild-type *S. Typhimurium* UK-1 χ3761

$\Delta P_{fur81}$::TT araC $P_{BAD}$ fur deletes the 239 bp promoter sequence of the fur gene and inserts the 1,335 bp TT araC $P_{BAD}$ cassette for arabinose regulated fur synthesis. (FIG. 13) The 239 bp deletion of the fur promoter (P) region is from fur-253 to fur-15 including the sites for OxyR binding, Crp binding and Fur binding consensus sites and generates a DNA fragment that is ~1,100 bp longer when using DNA from the mutant than DNA from the wild-type parent strain by PCR. The mutant strain turns off expression of the fur gene in the absence of arabinose. Fur is the ferric uptake regulator that is involved in iron metabolism, uptake, and transport. Absence of Fur attenuates *Salmonella*. In this construction, fur has a weak Shine-Dalgarno sequence (AAGG instead of AGGA) and the ATG start codon of the fur gene has been changed to GTG to reduce translation efficiency. Over expression of Fur in the vaccine strain during growth in the presence of arabinose prior to oral administration makes the vaccine strain somewhat more acid-sensitive and also starved for iron. Decreasing the level of Fur synthesis during cultivation in the presence of arabinose restores near wild-type abilities of acid tolerance and iron acquisition ability. (Table 4 and 5) The lower levels of Fur synthesis prior to immunization causes a more rapid complete absence of Fur in vivo as a consequence of cell division during the early stage of colonization of lymphoid tissues by the vaccine strain. pYA4181 is the suicide vector for introducing the $\Delta P_{fur81}$::TT araC $P_{BAD}$ fur mutation into the chromosome.

TABLE 4

Colonization of *S. Typhimurium* with altered $\Delta P_{fur81}$::TT araC $P_{BAD}$ fur deletion-insertion mutation in mice

| Strain | % arabinose in media | Day | Peyer's Patches (CFU/PP) | Spleen (CFU/g) | Liver (CFU/g) |
|---|---|---|---|---|---|
| χ9269 $\Delta P_{fur81}$::TT araC $P_{BAD}$fur | 0 | 3 | $1.9 \times 10^1$ | $3.5 \times 10^1$ | $3.2 \times 10^1$ |
| | | 7 | $1.4 \times 10^3$ | $4.2 \times 10^4$ | $4.8 \times 10^3$ |
| | 0.2 | 3 | $4.8 \times 10^2$ | $3.5 \times 10^2$ | $1.0 \times 10^0$ |
| | | 7 | $6.6 \times 10^1$ | $1.7 \times 10^5$ | $1.6 \times 10^4$ |

TABLE 5

Virulence and protection of *S. Typhimurium* with altered $\Delta P_{fur81}$::TT araC $P_{BAD}$ fur deletion-insertion mutation in mice

| Strain | % arabinose in media | Oral dosage (CFU) | Survivors/ total | Oral challenge dose* (CFU) | Survivors/ total after challenge |
|---|---|---|---|---|---|
| χ9269 | 0 | $1.4 \times 10^9$ | 5/5 | $1.7 \times 10^9$ | 5/5 |
| $\Delta P_{fur81}$::TT araC $P_{BAD}$fur | 0.2 | $2.2 \times 10^9$ | 5/5 | $1.7 \times 10^9$ | 5/5 |

Figure 1:
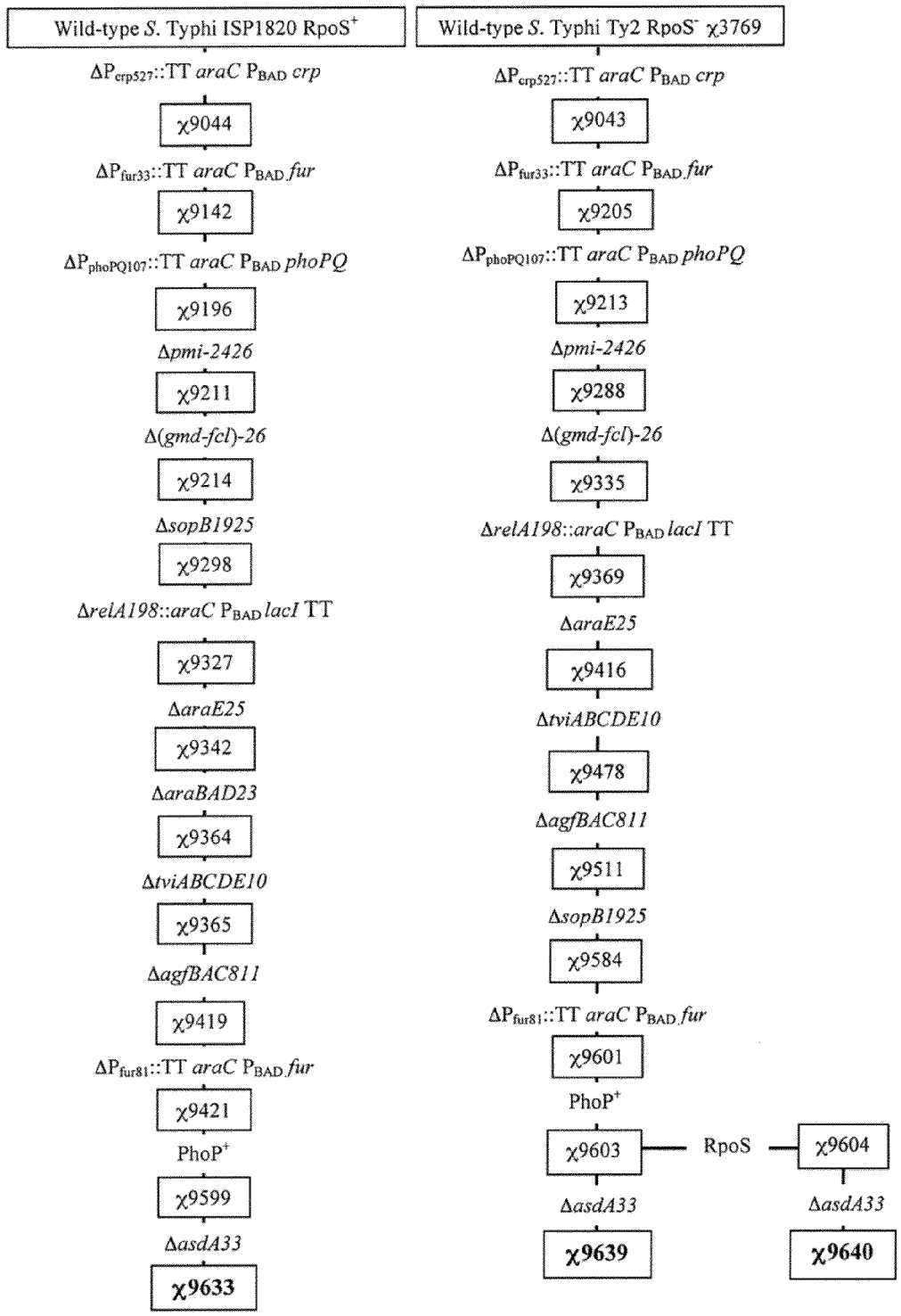
FIG. 1 depicts a diagram of the genealogy of the *S. Typhi* strains of the invention.
Figure 2:
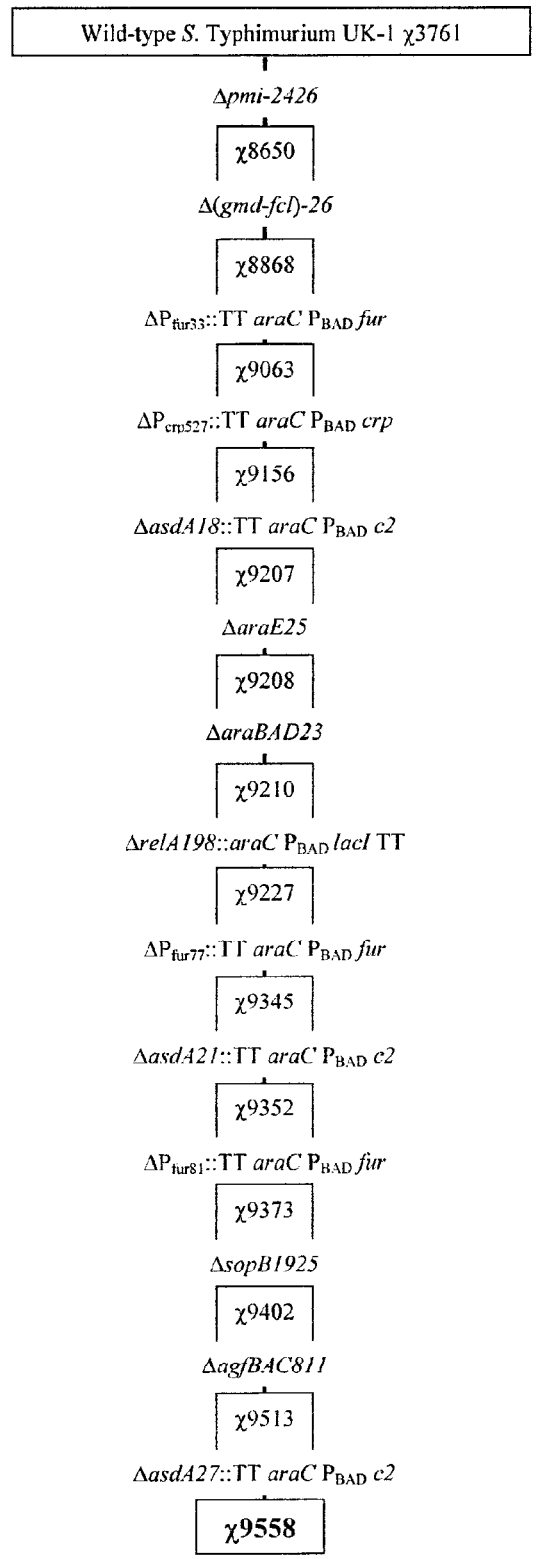
FIG. 2 depicts a diagram of the genealogy of an *S. Typhimurium* strain.
Figure 3B:
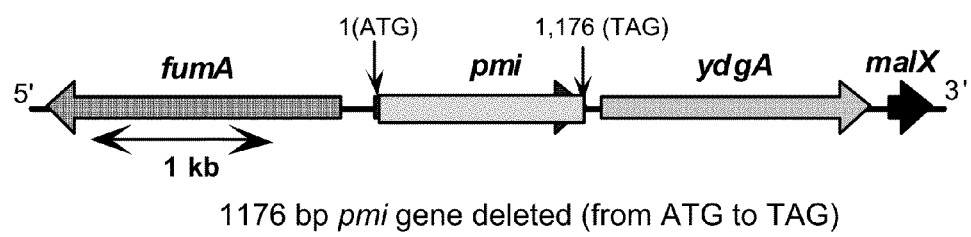
FIG. 3 depicts (A) the sequence of wild-type chromosomal sequence pmi showing the deleted region and its flanking region (SEQ ID NO:45 (nucleic acid sequence); SEQ ID NO:46 (amino acid sequence)). The deleted region is bracketed [ ] and primers for PCR verification are bolded and underlined. (B) A schematic of the mutation. The primers for validating the presence of the Δpmi-2426 mutation are as follows: Primer 1 (KpnI): 5' GGG GGTACCTTCGGCGACGGAA ACATGTTCGCT 3'(SEQ ID NO:87) and Primer 2 (SacI): 5' GGGGAGCTCGCC GCGCTGGTAGTTTTGATAACTTAA 3' (SEQ ID NO:88). When the Δpmi-2426 mutation is present the expected PCR product length is 613 bp compared to 1783 bp for the wild-type sequence.
Figure 9B:
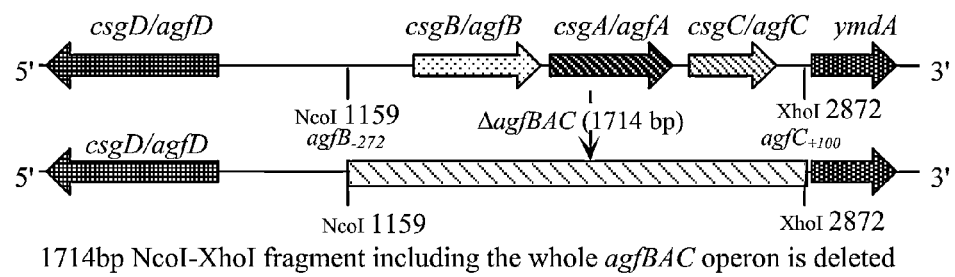
FIG. 9 depicts (A) the sequence of the wild-type agfBAC operon showing the deleted region and its flanking region (SEQ ID NO:54). The deleted region is bracketed [ ] and primers for PCR verification are bolded and underlined. (B) A schematic of the mutation. The primers for validating the presence of the ΔagfBAC811 mutation are as follows: primer UagfB: 5' GCACTGCTGTGGGTTGAAATAG 3'(SEQ ID NO:99) and primer ymdA: 5' CGGCGTGAGTA-GAAATATCG 3'(SEQ ID NO:100). When the ΔagfBAC811 mutation is present the expected PCR product length is 585 bp compared to 2299 bp for the wild-type sequence.
Figure 10B:
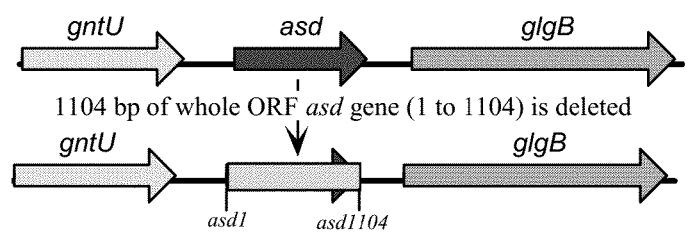
FIG. 10 depicts (A) the sequence of wild-type asd showing the deleted region and its flanking region ((SEQ ID NO:55 (nucleic acid sequence); SEQ ID NO:56 (amino acid sequence)). The deleted region is bracketed [ ] and primers for PCR verification are bolded and underlined. (B) A schematic of the mutation. The primers for validating the presence of the ΔasdA33 mutation are as follows: primer Uasd-N XbaI: 5' TGCTCTAGATGTGCATGGCAATCGCCCAAC 3'(SEQ ID NO:101) and primer asd-C XmaI: 5' TCC CCCGGGTATCTGCGTCGTCCTACCTTC 3'(SEQ ID NO:102). When the ΔasdA33 mutation is present the expected PCR product length is 633 bp compared to 1719 bp for the wild-type sequence.

*Challenge with wild-type *S. Typhimurium* UK-1 χ3761 rpoS conversion of *S. Typhi* Ty2. FIG. 1. Genealogy of *Salmonella Typhi* Strains shows the conversion of the RpoS⁻ *S. Typhi* Ty2 derivative to RpoS⁺. The suicide vector, pYA3467, which harbors the rpoS gene, was used to introduce the wild-type rpoS gene into the *S. Typhi* Ty2 chromosome of χ9603 bp an allele exchange with subsequent sucrose selection and screening for catalase-positive derivative χ9604.

$\Delta$relA198::araC $P_{BAD}$ lacI TT deletes the 2,247 bp of the relA gene including 12 bp of the SD sequence and 2235 bp of ORF and inserts 2,393 bp containing araC $P_{BAD}$ lacI TT sequence encoding for arabinose regulated lacI synthesis. (FIG. 14) The codon optimization of lacI and the starting codon GTG of the wild-type lacI gene is altered to ATG to increase LacI synthesis. In this construction, the TT is inserted after the codon-optimized lacI gene to preclude continued transcription into the adjacent ygcA gene that is transcribed in opposite direction. The relA mutation uncouples the occurrence of cell wall-less death from dependence on protein synthesis. PCR generates a ~2,400 bp longer product when using DNA from the mutant compared to DNA from the wild-type parent strain. pYA4064 is the suicide vector for introducing the $\Delta$relA198::araC $P_{BAD}$ lacI TT deletion-insertion mutation into the chromosome.

Example 2

Genetic Basis for Fluid Secretion and Means to Reduce Adverse Diarrheal Episodes in Vaccinees In studies with live attenuated *S. Typhi* strains in adults, mild diarrhea is observed in about 10 to 20 percent of volunteers. Since this might be a more common or severe problem in immunizing infants and children, we have evaluated fluid secretion by *S. Typhimurium* strains with specific mutations, including those to give a regulated delayed attenuation phenotype, using injection of strains into ileal loops of rabbits and measuring inflammatory symptoms histologically and accumulation of fluid. Strains with the $\Delta$sopB1925 mutation exhibit reduced symptoms with only slight attenuation (Table 6) or reduced ability to colonize lymphoid tissues after oral vaccination.

TABLE 6

Virulence of *S. Typhimurium* with $\Delta$sopB1925 mutation

| Strain | Oral dosage (CFU) | Survivors/total |
|---|---|---|
| χ8925 $\Delta$sopB1925 | $1.2 \times 10^7$ | 1/5 |
| | $1.2 \times 10^6$ | 2/5 |
| | $1.2 \times 10^5$ | 5/5 |
| | $1.2 \times 10^4$ | 5/5 |

Example 3

Impact of Acylation State of *Salmonella* Lipid A on Vaccine Immunogenicity and Efficacy

*Salmonella* lipid A is a mixture of closely related species that contain between 5-7 fatty acid moieties decorated with other small molecules (FIG. 38A). About 15% of *Salmonella* lipid A is hepta-acylated, while the most abundant species is hexa-acylated as in *E. coli* (Chan, 1994). The MPL isolated from *Salmonella* Minnesota R595 is a mixture of 3-6 fatty acid moieties with a single 4'-phosphate group (Baldrick, 2002). Recently it was shown that the acylation state significantly impacts vaccine immunogenicity and efficacy (Rallabhandi, 2008). *Salmonella* lipid A can be modified by the acyltransferase PagP and/or the deacylases, PagL and LpxR (references and unpublished data). The regulated expression of these genes in vivo could result in lipid A modifications that interfere with TLR4 activation (Raetz, 2007). To evaluate the effect of deleting these genes, in the presence or absence of IpxE, we constructed the following mutant strains: χ9434 (ΔpagP8) (FIG. 38B) and χ9732 (ΔpagP81::$P_{lpp}$ IpxE) (FIG. 38C), and triple mutant strains: χ9485 (ΔpagL7 ΔpagP8 ΔIpxR9) (FIG. 38D) and χ9705 (ΔpagL7 ΔpagP81::$P_{lpp}$ IpxE ΔIpxR9 (FIG. 38E). As expected, χ9434 and χ9485, which lack pagP also lack the palmitate-containing m/z 1016.7 peak seen in the wild-type strain χ3761 (FIG. 38A). Because LpxR and PagL are latent in normal laboratory growth conditions, no other differences are seen for χ9485 compared to χ3761. In χ9732(ΔpagP81::$P_{lpp}$ IpxE), the four major peaks detected are consistent with MPL (m/z 857.6), LpxO-modified MPL (m/z 865.5) and their acetate adducts (m/z 887.6 and 895.6, respectively) (FIGS. 38C and E). The lipid A structures in strains χ9485 and χ9705 are similar to those in strains χ9434 and χ9732, respectively. The small MPL peak (m/z 857.6) seen in strains χ3761, χ9434, and χ9485 (FIGS. 38A, B and D) is due to minor chemical 1-dephosphorylation as a result of the mild acid hydrolysis step employed to liberate free lipid A from the LPS (Zhou, 1999).

The role of the individual mutations in mouse virulence was determined (Table 7). The $LD_{50}$ of the wild-type strain, χ3761, ($1.0\times10^4$ CFU) was similar to that previously observed (Kong Q, Liu Q, Roland K L, Curtiss R 3rd. Infect Immun. 2009). The ΔpagP8 mutant strain χ9434 had the same oral $LD_{50}$ as wild-type, consistent with a previous report that a pagP mutant is unaltered for virulence when introduced by the intraperitoneal route (Belden, 1994). The $LD_{50}$ of χ9845 (ΔpagL7 ΔpagP8 ΔIpxR9) was increased 10-fold compared to χ3761 and χ9434. However, the $LD_{50}$ of χ9732 (ΔpagP81::$P_{lpp}$ IpxE) was approximately 105-fold greater than either χ3761 or χ9434, although at the highest doses we observed mild to severe clinical manifestations of disease (scruffy coat, lethargy, and death) from which some mice recovered. Strain χ9705 (ΔpagL7 ΔpagP81::$P_{lpp}$ IpxE ΔIpxR9) was completely avirulent, and no disease symptoms were observed even at the highest dose, suggesting a $LD_{50}$ value at least 105-fold greater than the wild-type strain.

TABLE 7

Survival after infection with different *Salmonella* strains

| | Survivors/Mice Challenged | | | | |
|---|---|---|---|---|---|
| Inocula | χ3761 | χ9434 | χ9732* | χ9485 | χ9705 |
| $1\times10^3$ CFU | 4/5 | 6/7 | — | 2/2 | — |
| $1\times10^4$ CFU | 2/5 | 3/7 | — | 6/7 | — |
| $1\times10^5$ CFU | 0/5 | 0/7 | — | 3/7 | — |
| $1\times10^6$ CFU | — | 0/2 | 2/2 | 0/7 | 2/2 |
| $1\times10^7$ CFU | — | — | 7/7 | — | 7/7 |
| $1\times10^8$ CFU | — | — | 6/7* | — | 7/7 |
| $1\times10^9$ CFU | — | — | 3/7** | — | 7/7 |

— Not determined

*Mice are sick and weight is lost, but they can recover after 3 weeks' inoculation, only one mouse was dead

**Mice are very sick and weight is lost, but 3 of 7 mice recovered after 3 weeks' inoculation, 4 mice were dead after 3 weeks.

The greatly attenuated phenotype for both χ9732 and χ9705 was not due to a general growth defect, as each mutant strains had a similar growth curve to χ3761 when grown in LB medium (data not shown). The ΔpagP81::$P_{lpp}$ IpxE strains, χ9732 and χ9705, exhibited an LPS profile similar to χ3761, although the O-antigen banding pattern was less distinct. In addition, χ9732 and χ9705 were slightly more sensitive to bile salts and SDS than other strains, which may affect their survival in the intestinal tract. Nevertheless, each mutant strain was able to colonize mouse lymphoid tissues. Similar numbers of bacteria were recovered from Peyer's patches, liver and spleen for each strain, 3 days post-inoculation (FIG. 39). Strain χ9434 (ΔpagP8) colonized more quickly than the other mutants, and more bacteria were recovered from the spleen and liver at 3 days post-infection. The bacterial numbers of strains χ9732 and χ9705 dropped by 6 days post infection, with significantly lower numbers than strains χ9434 and χ9485.

Surviving mice from the $LD_{50}$ experiment for strains χ9732 and χ9705 (inoculation from $1.0\times10^6$ to $1.0\times10^9$ CFU) were challenged orally with a lethal inoculum of the wild-type strain χ3761 ($1.0\times10^9$ CFU) thirty days after administration of the attenuated strains. All mice immunized with χ9732 or χ9705 were protected from challenge. Taken together, these data indicate the triple mutant χ9732 (ΔpagL7 ΔpagP81::$P_{lpp}$ IpxE ΔIpxR9) is completely attenuated, yet remains sufficiently immunogenic to give protection with wild-type challenge with a shift in $LD_{50}$ of $10^5$-fold.

Example 4

Enhanced Antigen Expression by Inclusion of Δ(wza-wcaM)-8 Mutation

The mutation Δ(wza-wcaM)-8 deletes twenty structural genes from wza to wcaM that encode colanic acid synthesis genes, thus blocking colanic acid production (FIG. 47). The mutation encompasses a 22,623 base pair deletion including the ATG start codon of the wza gene through the TAA stop codon of the wcaM gene. PCR using oligonucleotide primers (Table 8) complementary to DNA sequences that flank the wza-wcaM locus generates a DNA fragment that is 812 bp. The strain harboring the (wza-wcaM)-8 mutation can increase heterologous protein production as shown in (FIG. 48). The inability to synthesize colanic acid reduces the ability of *S. Typhi* to form biofilms and thus contributes to biological containment and lessens the likelihood for adherence to gallstones, thus reducing persistence. The mutation slightly increases virulence (Table 9). pYA4368 is the suicide vector for introducing the Δ(wza-wcaM)-8 mutation into the chromosome.

TABLE 8

| | | |
|---|---|---|
| Wza-u-BglII-s: (SEQ ID NO: 116) | 5' | CGCGAGATCTGATTATTTATCACTTTGGCAG 3' |
| Wza-u-SacI-a: (SEQ ID NO: 117) | 5' | ACGAGGAGCTCCTTGCCTGTCATTAGGTTAG 3' |
| WzaM-d-KpnI-s: (SEQ ID NO: 118) | 5' | GTGAAGGTACCAAGTTCATAAGAGGTGTCGAAGTG 3' |
| WzaM-d-BglII-a: (SEQ ID NO: 119) | 5' | CGCTGAGATCTGTACCGCTATTTTTACGAAAATTC 3' |

TABLE 9

Virulence of Δ(wcaM-wza)-8 mutants in orally inoculated BALB/c mice

| Strain | CFU/Dose | Survivors/Total | MDD |
|---|---|---|---|
| χ3761 | $0.9 \times 10^6$ | 0/5 | 6.75 |
| | $0.9 \times 10^5$ | 1/5 | 8.25 |
| | $0.9 \times 10^4$ | 0/5 | 15.4 |
| | $0.9 \times 10^3$ | 1/5 | 13.25 |
| χ9537 | $1.8 \times 10^6$ | 0/5 | 7.6 |
| Δ(wcaM-wza)-8 | $1.8 \times 10^5$ | 0/5 | 7.4 |
| | $1.8 \times 10^4$ | 1/5 | 7.75 |
| χ8868 | $0.76 \times 10^9$ | 0/5 | 14.2 |
| Δpmi-2426 | $0.76 \times 10^8$ | 4/5 | 9 |
| | $0.76 \times 10^7$ | 3/5 | 18.5 |
| χ9540 | $1.2 \times 10^9$ | 1/5 | 13.25 |
| Δ(wcaM-wza)-8 | $1.2 \times 10^8$ | 2/5 | 14.3 |
| Δpmi-2426 | $1.2 \times 10^7$ | 2/5 | 15.3 |

Example 5

The ΔP$_{rfc174}$::TT araC P$_{BAD}$ rfc when Added to Δpmi-2426 Confers Added Attenuation In Vivo The use of attenuated bacteria as vaccine delivery vehicles for heterologous antigens has been studied extensively in both animals and humans. Attenuated *Salmonella* is the best choice due its ability to, when given orally, stimulate both cell and humoral-mediated immunity against a heterologous antigen and thus provide protection against pathogen challenge. A good live oral *Salmonella* vaccine would retain its ability to colonize and invade host lymphoid tissues but would be completely avirulent after oral administration. The lipopolysaccharide of *Salmonella* is a recognized virulence determinant, and contributes to several stages of the infectious process, including swarming motility, intestinal colonization, serum resistance, invasion/intracellular replication, and resistance to killing by macrophages. Rough *Salmonella* strains that do not make the O-antigen side chains or outer core or inner core sugar were not able to survive the succession of stresses encountered in vivo and were less virulent than the smooth *Salmonella* strain. Therefore, structural rough mutants have been considered to be inappropriate live vaccine carriers. There are currently many other attenuating mutations being investigated by researchers involved in vaccine development, but it is a good choice to manipulate LPS synthesis gene to develop vaccine. Theoretically, a moderate decrease in the number and/or length of LPS chains can lead to attenuation paralleled by retained immunogenic potential to deliver the heterologous antigen.

Three *Salmonella Typhimurium* strains have apparently provided attenuation through modification of LPS. Two of these mutations, galE and pmi, are involved in synthesizing the sugars of LPS. GalE is a UDP-galactose epimerase that inter-converts UDP-glucose and UPD-galactose, an essential part of core sugar and O-antigen. This mutant synthesized core-defective LPS in the absence of galactose but made normal LPS when galactose was available in the growth media. The avirulence of this mutant in the murine model of Typhoid was thought to be due to the fact that the strains were susceptible to galactose-induced lysis. However, this same mutation, transferred to *S. Typhi*, was not attenuated and was poorly immunogenic in humans. Following a similar concept, a pmi knockout in *Salmonella Typhimurium* was constructed and evaluated in our lab. Pmi is a phosphomannose isomerase, which converts fructose-6-P to mannose-6-P, and, in vivo, the deletion mutant is unable to synthesize the O-antigen due to inavailability of mannose, which is a component of O-antigen. When the mutant is grown in the presence of mannose, the smooth LPS phenotype is exhibited. This mutant was attenuated but also showed high immunogenicity and efficacy in enhancing induction of high antibody titers to cross-protective OMPs, however, the pmi deletion in *Typhi* has not yet been evaluated in humans. Both galE and pmi mutant strains transiently express LPS before colonizing the GALT or organs. Another gene involved in LPS biosynthesis, rfaH, was evaluated in BALB/c mice. RfaH is a transcriptional anti-terminator, and is involved in the synthesis of many virulence determinants including O-antigen, core sugar, capsular polysaccharide, and Vi antigen. An rfaH deletion mutant, described as "gently rough", exhibited some deep-rough characteristics, i.e. lack of O-antigen and outer core, sufficient attenuation, susceptibility to detergents and to some antibiotics, but still proved to be immunogenic.

Rfc (Wzy) is a polymerase responsible for polymerizing the O-unit, and, in conjunction with Wzx (transporter), Wzz (length determinant) and WbaP (O-antigen synthesis initiation). synthesizing, assembling, and transporting the O antigen to the periplasm, where WaaL (Ligase) ligates O-antigen to lipid A to form complete LPS (Whitfield, 1995) (Raetz, 2002) (Tran, 2009). The mutant with an rfc deletion constitutively makes LPS with a single O-unit in each core molecule, which is designated as a semi-rough phenotype. *Salmonella* with an rfc mutation exhibited good colonization and immunogenic attributes against *Salmonella Typhimurium* when orally inoculated BALB/c mice. A tightly regulated araC P$_{BAD}$ activator-promoter has been used extensively in our lab to regulate gene expression. We replaced the rfc promoter with an araC P$_{BAD}$ promoter to create arabinose inducible production of Rfc and thus regulate rfc expression to mimic transient expression of smooth LPS; this is similar to the manner in which the galE or pmi phenotypes are controlled by the availability of, galactose or mannose. It is of interest to evaluate the ability of each mutant to deliver heterologous antigen to the host immune system and the strain's ability to protect the host against subsequent challenge.

Example 6

Mutations that Increase Reusability of the Vector System in the Host

ΔfljB217 deletes the flagella gene encoding Phase 2 flagella antigen in *S. Typhimurium*, which does not exist in *S. Typhi*. The deletion encompasses 1,247 base pairs from fljB300 to fljB+26 (FIG. 49). PCR using oligonucleotide primers complementary to DNA sequences up-stream and down-stream of that flanking region the fljB locus generate a DNA fragment that is 1,247 bp shorter when using DNA from the mutant with the ΔfljB217 mutation than DNA from the wild-type parent strain. The ΔfljB217 mutation does not contribute to attenuation and *S. Typhimurium* strains with this mutation have the same virulence for mice as the wild-type parent. pYA3548 is the suicide vector for introducing the ΔfljB217 mutation into the chromosome.

ΔfliC2426 deletes the flagella gene encoding Phase 1 flagella antigen. The deletion encompasses 1,488 base pairs including the ATG start codon and including the TAA stop codon (FIG. 49). PCR using oligonucleotide primers complementary to DNA sequences up-stream and down-stream of the flanking region of the fliC gene generates a DNA fragment that is 1,488 bp shorter when using DNA from the mutant with the ΔfliC2426 mutation than DNA from the wild-type parent strain. The ΔfliC2426 mutation does not contribute to attenuation and *S. Typhimurium* strains with this mutation have the same virulence for mice as the wild-type parent. pYA3702 is the suicide vector for introducing the ΔfliC2426 mutation into the chromosome.

ΔfliC180 deletes the part of flagella gene encoding Phase 1 flagella antigen. The deletion encompasses 540 base pairs encoding flagella antigen from amino acid 181 to amino acid 360 (FIG. 50). PCR using oligonucleotide primers complementary to DNA sequences up-stream and down-stream of the deletion region generates a DNA fragment that is 540 bp shorter when using DNA from the mutant with the ΔfliC180 mutation than DNA from the wild-type parent strain. The ΔfliC180 mutation does not contribute to attenuation and *S. Typhimurium* strains with this mutation have the same virulence for mice as the wild-type parent. pYA3729 is the suicide vector for introducing the ΔfliC180 mutation into the chromosome.

ΔfliC240 deletes the part of flagella gene encoding Phase 1 flagella antigen. The deletion encompasses 720 base pairs encoding flagella antigen from amino acid 181 to amino acid 420 (FIG. 50). PCR analysis using oligonucleotide primers complementary to DNA sequences up-stream and down-stream of the deletion region generates a DNA fragment that is 720 bp shorter when using DNA from the mutant with the ΔfliC240 mutation than DNA from the wild-type parent strain. The ΔfliC180 mutation does not contribute to attenuation and *S. Typhimurium* strains with this mutation have the same virulence for mice as the wild-type parent. pYA3721 is the suicide vector for introducing the ΔfliC240 mutation into the chromosome.

ΔompA deletion encompasses 1050 base pairs encoding ompA antigen starting from ATG start codon to TAA stop codon. PCR using oligonucleotide primers complementary to DNA sequences up-stream and down-stream of that flank the ompA gene generate a DNA fragment that is 1050 bp shorter when using DNA from the mutant with the ΔompA mutation than DNA from the wild-type parent strain. The ompA 11 mutation does not contribute to attenuation and *S. Typhimurium* strains with this mutation have the same virulence for mice as the wild-type parent (Table 10). The *S. Typhimurium* with ΔompA reduces the ability of the bacterium to synthesize dominant surface antigens, diminishes immune response to dominant *Salmonella* antigen (FIG. 51), and reduces the ability of intranasally administered *Salmonella* to access the brain of mice (7-day-old mice) (Table 11).

TABLE 10

$LD_{50}$ of ompA mutants in BALB/c mice

| Strains | Genotype | Inoculated dose (CFU) | Survival/Total |
|---|---|---|---|
| CK43 | ΔompA11 in UK-1 | $6.1 \times 10^6$ | 1/5 |
|  |  | $6.1 \times 10^5$ | 2/5 |
|  |  | $6.1 \times 10^4$ | 3/5 |
| CK43 | ΔompA11 in UK-1 | $0.6 \times 10^6$ | 0/5 |
|  |  | $0.6 \times 10^5$ | 0/5 |
|  |  | $0.6 \times 10^4$ | 0/5 |

TABLE 11

The impact of the ΔompA11 mutation in χ9241 and χ9558 background on brain colonization of 7-day-old mice after intranasal inoculation

| Strains | Dose of inoculation (CFU) | Mice No. | MacConkey (CFU/Gram) | LB Agar (CFU/Gram) | Selenite broth | Result |
|---|---|---|---|---|---|---|
| χ11124(pYA4088) (χ9241 ΔompA11) | $2.1 \times 10^8$ | 1 | 0 | 67 | + | + |
|  | $2.1 \times 10^8$ | 2 | 786 | 1500 | + | + |
|  | $2.1 \times 10^8$ | 3 | 640 | 727 | + | + |
|  | $2.1 \times 10^8$ | 4~10 | 0 | 0 | − | 0 |
| χ9241(pYA4088) | $3.2 \times 10^8$ | 1 | 720 | 760 | + | + |
|  | $3.2 \times 10^8$ | 2 | 3100 | 3100 | + | + |
|  | $3.2 \times 10^8$ | 3 | 0 | 34 | + | + |
|  | $3.2 \times 10^8$ | 4~10 | 0 | 0 | − | 0 |
| χ9969(pYA4088) (χ9558 ΔompA11) | $3.8~9 \times 10^8$ | 1 | 344 | 538 | + | + |
|  | $3.8~9 \times 10^8$ | 2~20 | 0 | 0 | − | 0 |
| χ9558(pYA4088) | $1.6 \times 10^8$ | 1 | 9 | 21 | + | + |
|  | $1.6 \times 10^8$ | 2 | 157 | 200 | + | + |
|  | $1.6 \times 10^8$ | 3 | 460 | 480 | + | + |
|  | $1.6 \times 10^8$ | 4 | 270 | 278 | + | + |
|  | $1.6 \times 10^8$ | 5 | 28 | 50 | + | + |
|  | $1.6 \times 10^8$ | 6 | 480 | 485 | + | + |
|  | $1.6 \times 10^8$ | 7 | 56 | 60 | + | + |
|  | $1.6 \times 10^8$ | 8 | 430 | 420 | + | + |
|  | $1.6 \times 10^8$ | 9 | 8 | 10 | + | + |
|  | $1.6 \times 10^8$ | 10~20 | 0 | 0 | − | 0 |

Example 7

Description of Δ(araC P$_{BAD}$)-5::P22 P$_R$ araBAD44 Modifications

Various mutations are described below and shown in FIG. 52.

Δ(araC P$_{BAD}$)-5::P$_R$ araBAD44: Changed original TGGA to AGGA and the second and the third codon to K (lysine) from A, to enhance the expression of araB.

Δ(araC P$_{BAD}$)-5::P$_{R13}$ araBAD44: Addition to the modification in the araB region, further modification in the OR1 region by changing G and C bases to T and T (underlined and bolded) to reduce the binding of the repressor C2.

Δ(araC P$_{BAD}$)-5::P$_{R14}$ araBAD44: Addition to the modification in the araB region, further modification in the OR3 region by changing G and C bases to A and T (underlined and bolded) to reduce the binding of the repressor C2.

Δ(araC P$_{BAD}$)-5::P$_{R15}$ araBAD44: Addition to the modification in the araB region, further modifications in the OR1 and OR3 region by changing G and C bases to T, T and A, T (underlined and bolded) to reduce the binding of the repressor C2.

Example 8

Construction of Recombinant Plasmid Containing PspA/Rx1 pYA3494 (PspA/Rx1 aa 3-257)

The mature PspA/Rx1 protein (588 amino acids) contains a highly immunogenic a-helical region that spans amino acids 3-257. This immunogenic region of PspA/Rx1 (255 amino acids; 765 base pairs) was selected for use as a test antigen.

For overexpression of PspA/Rx1 fused to the β-lactamase signal sequence, the fragment of the pspA/Rx1 gene specifying the immunogenic α-helical region (amino acids 3-257) was cloned into the pYA3493 vector (FIG. 15). The 765 bp DNA fragment encoding the a-helical region of PspA/Rx1 was PCR amplified from template pYA3193 DNA using the primers:

```
N-terminal,
                                     (SEQ ID NO: 120)
5'CCGGAATTCTCTCCCGTAGCCAGTCAGTCT3'

C-terminal,
                                     (SEQ ID NO: 121)
5'GGGAAGCTTCTATTATTCTACTATTATTGTT3'
```

The N-terminal primer contains an EcoRI site (underlined). The C-terminal primer specifies two consecutive stop codons (TAA TAG; boldface) followed by a HindIII site (underlined). The amplified PCR product was digested with EcoRI and HindIII enzymes, and then cloned into the EcoRI and HindIII sites of pYA3493, resulting in pYA3494. The in-frame fusion of PspA/Rx1 with the 3-lactamase signal sequence was confirmed by nucleotide sequencing. The nucleotide sequencing data showed that one base pair G is missing at position 703 causing the frameshift after amino acid 233.

For overexpression of His$_6$-tagged PspA/Rx1, the fragment of the pspA/Rx1 gene specifying the immunogenic α-helical region (amino acids 3-257) was cloned into the pYA3342 vector. The 765 bp DNA fragment was PCR amplified from template pYA3193 DNA using the primers:

```
N-terminal,
                                     (SEQ ID NO: 122)
5'CCGGAATTCATCACCATCACCATCACTCTCCCGTAGCCAGTCAGT3'

C terminal,
                                     (SEQ ID NO: 123)
5'GGGAAGCTTCTATTATTCTACTATTATTGTT3'
```

The N-terminal primer contains an EcoRI site (underlined) and six consecutive histidine codons (alternate use of CAT and CAC; boldface) for His$_6$ tagging at the N-terminus. The C-terminal primer specifies two consecutive stop codons (TAA TAG; boldface) followed by a HindIII site (underlined). The amplified gene fragment, digested with EcoRI and HindIII enzymes, was then cloned into the pYA3342 vector using the EcoRI and HindIII sites of pYA3342, resulting in pYA3496. The in-frame fusion of PspA/Rx1 to the His$_6$ tag was confirmed by nucleotide sequencing.

pYA3635 (Codon Optimization of PspA/Rx1 aa 3-257)

In order to optimize PspA expression, the following nine rare codons contained in the pspA/Rx1 gene of pYA3494 were altered: 2nd CCC to CCG, 57th CTA to CTG, 77th CTA to CTG, 95th ATA to ATC, 113th CGA to CGT, 144th CTA to CTG, 185th AGA to CGT, 186th CTA to CTG, 221st CTA to CTG. All codon changes were designed to introduce the optimal codon used by *Salmonella* without altering the amino acid sequence of PspA. Additionally, a G was inserted at position 703. Mutations were introduced into the gene sequence by PCR. Primers containing the altered codon sequence were used to amplify different fragments harboring the optimal codons. These fragments were then used as template to run a second round of amplification in order to assemble the final sequence containing all the altered codons. The optimized gene sequence was cloned into pYA3493 using the EcoRI and HindIII sites to generate pYA3635. After cloning, an additional two codons in pYA3635 were altered by the same PCR method: 23rd GCG to GCT and 124th GCT to GCG. The nucleotide sequence of the codon optimized pspA/Rx1 was verified by sequencing and restriction enzyme digestion.

pYA4088 (PspA/Rx1 aa 3-285) (FIG. 16)

The pspA/Rx1 gene was extended to include amino acids 258-285 bp three rounds of PCR amplification. In the first amplification, the pspA/Rx1 gene was amplified from the DNA template pYA3635 using the primers:

```
N-terminal,
                                     (SEQ ID NO: 124)
5'-TCTCCGGTAGCCAGTCAGTCTAAAGCTGAG-3'

C-terminal,
                                     (SEQ ID NO: 125)
5'-CTAATTCAGCTTTTTTAGCAGCAATAGTTTTCTCTAAACCTTCTTT

AAAGTAGTCTTCTACATTATTGTTTTCTTC-3'
```

The 820 bp gene fragment generated from the first reaction was used as the template for the second PCR amplification with the primers:

```
N-terminal,
                                     (SEQ ID NO: 126)
5'-TCTCCGGTAGCCAGTCAGTCTAAAGCTGAG-3'

C-terminal,
                                     (SEQ ID NO: 127)
5'-TGCTTTCTTAAGGTCAGCTTCAGTTTTTTCTAATTCAGCTTTTTTA

GCAGCAATAGTTTTCTC-3'
```

The 849 bp PCR fragment produced in the second step was used as the template for the third and final amplification with primers:

```
N-terminal,
                                   (SEQ ID NO: 128)
5'-GGAATTCTCTCCGGTAGCCAGTCAGTCT-3'

C-terminal,
                                   (SEQ ID NO: 129)
5'-TTCAAGCTTATTATGCTTTCTTAAGGTCAGCTTC-3'
```

This reaction produced an 869 bp gene fragment which was cloned into pYA3493 using the EcoRI and HindIII restriction sites. The resulting plasmid was pYA4088. In-frame cloning was verified by sequencing and enzyme digestion.

FIG. 15 depicts the pYA3493 nucleotide sequence and plasmid map. FIG. 16 depicts the pYA4088 nucleotide sequence and plasmid map. FIG. 17 depicts the nucleotide and amino acid sequence of PspA/Rx1(aa 3-285) with a signal peptide in pYA4088. FIG. 18 depicts the nucleotide sequence of PspA/Rx1(aa 3-285) with a signal peptide in pYA4088, and FIG. 19 without signal peptide. FIG. 20 depicts the PspA/Rx1 amino acid sequence with a signal peptide, and FIG. 21 depicts the sequence without a signal peptide. FIG. 22 depicts the predicted hypothetical mature, secreted PspA/Rx1 protein. FIG. 23 depicts a schematic of PspA expression plasmids pYA4088 and pYA3634 with empty control vector pYA3493.

Example 9

Improvements in Induction of Enhanced Immune Responses to Expressed Recombinant *S. pneumoniae* PspA Antigens by Using the 6-Lactamase Type II-Like Secretion Pathway We have expressed the α-helical domain of the *S. pneumoniae* Rx1 to PspA protective antigen as a fusion to the 3-lactamase signal sequence. Half of the protein was secreted with an equal apportionment to the periplasm and to the cell exterior without cell lysis. The antibody titers induced to PspA were significantly higher than to *S. Typhimurium* LPS and OMP antigens.

The DNA sequence encoding the fusion of the α-helical domain of PspA from strain Rx1 to the β-lactamase export system (bla SS) has been engineered to depend on the Asd$^+$ balanced-lethal system.

The plasmid pYA4088, shown in FIG. 16, possesses a 852-bp DNA sequence encoding 283 amino acids (aa 3-285) from the α-helical domain of PspA from strain Rx1.
In Vivo Expression Technologies Using araC $P_{BAD}$ lacI Constructions.

Over-expression of protective antigens by RASV strains can be deleterious, reducing colonizing ability and thus immunogenicity. On the other hand, high-level expression of recombinant protective antigens is very important to induce significant protective mucosal and systemic antibody responses. The $P_{trc}$ that we have used is constitutive under most environments but actually is more transcriptionally active both anaerobically and aerobically than other promoters selected for in vivo activity. For this reason, we have generated the ΔrelA198::TT araC $P_{BAD}$ lacI TT deletion-insertion mutation so that vaccine strains growing in culture in the presence of 0.2 percent arabinose synthesize the LacI repressor at high level to repress transcription from $P_{trc}$ on the Asd$^+$ plasmid vectors until after vaccination when the vaccine strain is already colonizing internal lymphoid tissues. This has been achieved by increasing the expression of the lacI gene by changing the SD sequence from AGGG to AGGA, the lacI start codon from GTG to ATG and optimizing all codons for high-level expression of lacI in *Salmonella*. Strains with the ΔrelA196::TT araC $P_{BAD}$ lacI TT deletion-insertion mutation present in χ9226 and χ9226 are unaltered in virulence. The presence of the ΔaraBAD23 deletion, which further increases the amount of LacI synthesized, also has no appreciable effect on virulence (χ9509 Table 12).

TABLE 12

Virulence of *S. Typhimurium* with ΔrelA198::TT araC $P_{BAD}$ lacI TT deletion-insertion mutation.

| Strain | Oral dosage (CFU) | Survivors/ total |
| --- | --- | --- |
| χ9226 | $0.92 \times 10^6$ | 0/5 |
| ΔrelA198::araC $P_{BAD}$ lacI TT | $0.92 \times 10^5$ | 1/5 |
| UK-1 | $0.92 \times 10^4$ | 1/5 |
| χ9509 | $1.3 \times 10^6$ | 0/3 |
| ΔrelA198::araC $P_{BAD}$ lacI TT | $1.3 \times 10^5$ | 0/3 |
| ΔaraBAD23 | $1.3 \times 10^4$ | 3/3 |
| UK-1 | $2.5 \times 10^5$ | 5/5 |
|  | $2.5 \times 10^4$ | 5/5 |
|  | $2.5 \times 10^3$ | 5/5 |

Example 10

Plasmid pYA4088 Stability in RASV-Sp Derivatives of *S. Typhi* ISP1820 and Ty2

The stability of the Asd$^+$ PspA plasmid pYA4088 was evaluated in strains χ9633(pYA4088), χ9639(pYA4088) and χ9640(pYA4088) grown in broth medium without DAP to simulate the same conditions to be used in the clinical trial. The stability of pYA4088 in each Asd$^-$ bacterial host was subsequently determined by growing the strain in the broth media with DAP for approximately 50 generations which was accomplished by a succession of subcultures over a 6-day period. At the end of approximately 50 generations of growth, 100 colonies each from the Working Seed, from the 1$^{st}$ and from the 5$^{th}$ passages were analyzed for the requirement for diaminopimelic acid (DAP). Representative colonies were further tested for the presence of the 3927 bp plasmid and the expression of the PspA protein. FIG. 24 shows that the plasmid pYA4088 was retained nearly 100% by the RASV-Sp strains over approximately 50 generations of growth.

Example 11

Preparation of Vaccine Product

Master seed and working seed banks of each vaccine organism in separate vials have been prepared for frozen storage in vegetable-based cryopreservative. Purity of the seed banks was established following standard operating procedures Full characterization of the seed banks includes phenotypic evaluation on selective media, PCR, antigenic agglutination, colorimetric assays, LPS gel analysis, production of catalase to reveal the RpoS phenotype and demonstrated to reflect the correct and anticipated phenotype and genotype of the three vaccine strains. Antibiotic sensitivity testing has confirmed that these strains are sensitive to ciprofloxacin, ampicillin, ceftriaxone, trimethoprim/sulfamethoxazole (Table 13). Ampicillin, ciprofloxacin, ceftriaxone and trimethoprim/sulfamethoxazole are typically tested for minimum inhibitory concentrations (MICs) for *Salmonella*.

TABLE 13

Minimum inhibitory concentrations of antibiotics for RASV-Sp strains.

| Antibiotic | *Salmonella Typhi* strain (µg/ml) | | |
|---|---|---|---|
| | χ9633(pYA4088) | χ9639(pYA4088) | χ9640(pYA4088) |
| ampicillin | <2 | <2 | <2 |
| ciprofloxacin | <0.25 | <0.25 | <0.25 |
| ceftriaxone | <0.25 | <1 | <1 |
| trimethroprim-sulfamethoxazole | <20 | <20 | <20 |

The vials of vaccine Working Seed are maintained frozen in designated boxes and entered into the freezers' inventory logs. The Working Seed vials are stored in duplicate freezers maintained between −65° and −75° C. Vaccine stability is determined by titration of representative vials of each of the RASV-Sp Master and Working Seed banks at 0, 3, 6, 12, 24 months and every 6 months thereafter. Table 14 shows the stability of the RASV-Sp Master Seed and Working Seed stocks as determined by quarterly viable titration.

TABLE 14

Stability of RASV-Sp Master Seed (MS) and Working Seed (WS) banks

| Date of | χ9633(pYA4088) CFU/ml | | χ9639(pYA4088) CFU/ml | | χ9640(pYA4088) CFU/ml | |
|---|---|---|---|---|---|---|
| Titer | MS | WS | MS | WS | MS | WS |
| Nov. 17, 2007 | $1.95 \times 10^{10}$ | $3.20 \times 10^{10}$ | $1.60 \times 10^{10}$ | $2.63 \times 10^{10}$ | $1.76 \times 10^{10}$ | $3.00 \times 10^{10}$ |
| Feb. 22, 2008 | $1.98 \times 10^{10}$ | $3.40 \times 10^{10}$ | $1.66 \times 10^{10}$ | $3.20 \times 10^{10}$ | $1.69 \times 10^{10}$ | $3.53 \times 10^{10}$ |
| May 17, 2008 | $1.62 \times 10^{10}$ | $4.23 \times 10^{10}$ | $1.58 \times 10^{10}$ | $3.08 \times 10^{10}$ | $1.54 \times 10^{10}$ | $3.01 \times 10^{10}$ |
| Sep. 8, 2008 | $1.44 \times 10^{10}$ | $2.70 \times 10^{10}$ | $1.11 \times 10^{10}$ | $3.55 \times 10^{10}$ | $1.43 \times 10^{10}$ | $1.30 \times 10^{10}$ |

Live, whole bacteria constitute the unformulated active immunogenic substance that when fermented in permissive conditions will be formulated with sterile PBS pH 7.4 to produce the final vaccine product.

The final vaccine products will be prepared on the day of administration to the volunteers in the clinical trial to optimize immunogenicity and fitness of the strains.

Briefly, a 37° C. overnight culture of each vaccine strain is prepared from a frozen vial of RASV-Sp Working Seed. The next morning, the cultures are subcultured 1:20 into fresh, prewarmed media and shaken gently at 37° C. to an optical density (OD) at 600 nm ideally between 2.0-2.3. The cells are harvested by centrifugation and resuspended gently in sterile PBS to the final dosage prescribed. Data collected from production runs of the vaccine dosages conducted prior to the start of the clinical trial will be used to correlate the $OD_{600}$ of the final PBS cell suspension to CFU/ml (GCGH-ASU-SOP-096-00, see CMC section of the IND application). This data will be used to confirm the target range of the final dosage prior to releasing the vaccine dosages to the clinic.

Table 15 shows the production record of three consecutive dosages of the RASV-Sp inocula for producing 10-ml final liquid dosages of live vaccine for oral administration to adult volunteers. The data provide assurance that the RASV-Sp vaccine inocula can be consistently produced within the target range of the dosage required on the start date of the clinical trial.

TABLE 15

RASV-Sp final dosage preparation record

| Production date | RASV-Sp Strain | Harvest $OD_{600}$ | Hours to culture harvest | Vaccine Dosage/ 10 ml[1] |
|---|---|---|---|---|
| Aug. 11, 2008 | χ9633(pYA4088) | 2.83 | 4 h 37 min | $2.14 \times 10^7$ |
| | χ9639(pYA4088) | 2.20 | 4 h 24 min | $3.04 \times 10^7$ |
| | χ9640(pYA4088) | 2.38 | 4 h | $2.30 \times 10^7$ |
| Aug. 19, 2008 | χ9633(pYA4088) | 2.11 | 3 h 58 min | $1.14 \times 10^7$ |
| | χ9639(pYA4088) | 2.08 | 4 h 40 min | $2.22 \times 10^7$ |
| | χ9640(pYA4088) | 2.14 | 3 h 57 min | $1.29 \times 10^7$ |
| Aug. 21, 2008 | χ9633(pYA4088) | 2.15 | 3 h 48 min | $1.37 \times 10^7$ |
| | χ9639(pYA4088) | 2.01 | 4 h 30 min | $2.09 \times 10^7$ |
| | χ9640(pYA4088) | 2.14 | 3 h 42 min | $1.51 \times 10^7$ |

[1]Each lot produced passed purity and identity testing following standard operating procedures.

Formulation

The human fasting stomach can reach pH levels as low as 1.5. Low pH tolerance of the RASV-Sp strains was tested after suspending cells in medium at pH 7, 4.5 or 3 for 1 hour at 37° C. Viability of the samples after incubation was assessed by plate counts. Data shown are the average number of CFU/ml recovered. In these studies, we included the parental wild-type *S. Typhi* strains χ3744 (ISP1820), χ3769 (Ty2) and χ8438 (Ty2 $RpoS^+$). We also included an attenuated *S. Typhi* ISP1820 strain (χ8110) that had been used in a previous trial in which reactogenicity was observed. In all cases, the vaccine constructions χ9633(pYA4088), χ9639(pYA4088) and χ9640(pYA4088) were more acid sensitive than their wild-type parents or than the attenuated ISP1820 strain χ8110 (FIG. 25).

The PBS used as the diluent is unlikely to provide sufficient buffering activity. Since the stomach pH rises dramatically upon ingestion of food, we plan to increase the stomach pH of volunteers by administering Ensure nutrition shakes prior to administering the vaccine dosages. FIG. 26 shows the stability after one hour of the RASV-Sp vaccines suspended in three different flavors of Ensure® nutrition shake.

Stability of RASV-Sp Strains

The RASV-Sp vaccine dosages maintain a stable titer suspended in the PBS at room temperature for a period of less than 2 hours. FIG. 27 shows that the initial cell suspensions hold titers near $1 \times 10^{10}$ CFU for up to an hour and then maintain stably after dilution in PBS for an additional hour. The RASV-Sp final dosages will be administered to volunteers within two hours of resuspension in PBS to ensure optimal immunogenicity.

Example 12

Nonclinical Studies

It should be noted that *S. Typhi* is an obligate human pathogen and no animal models are available for a full evaluation of the *S. Typhi*-based vaccines. Inoculation of newborn mice with high doses of wild-type virulent strains of *S. Typhi*, even when modified to express the *S. Typhimurium* virulence plasmid needed by *S. Typhimurium* to cause disseminated disease in mice, fails to infect or cause any signs of disease or any weight loss. We constructed, in parallel of the engineering of *S. Typhi, S. Typhimurium* strains bearing essentially identical mutations as the *S. Typhi*-based vaccines for pre-clinical safety and immunogenicity evaluation in mice.

Safety of *S. Typhimurium* χ9558(pYA4088) in Newborn Mice.

A relevant safety test was to evaluate the safety in newborn and infant mice of *S. Typhimurium* strain χ9558(pYA4088) [(Δpmi-2426 Δ(gmd-fcl)-26 ΔP$^{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198::araC P$_{BAD}$ lacI TT ΔsopB1925 ΔagfBAC811], which carries mutations nearly identical to the *S. Typhi* vaccine strains and the same plasmid to enable PspA expression. Newborn mice are highly suscep- The levels of colonization of the intestinal tract by *S. Typhimurium* χ9558(pYA4088) were quite good. In this regard, it should be noted that isolation of Peyer's patch tissue in these infant mice to determine *Salmonella* titers is not feasible. Titers in liver and spleen were lower than expected but this was interpreted as an indication of the safety of χ9558 (pYA4088) for newborn and infant mice.

These data in Table 14 and Table 15 show that the attenuated *S. Typhimurium* vaccine strain with mutations nearly identical to the *S. Typhi* vaccine strains is safe for newborn and infant mice. Therefore, it can be extrapolated from these data that these mutations provide an equivalent level of safety to the *S. Typhi* vaccines.

TABLE 17

Colonization data of χ9558(pYA4088) in tissues (CFU/gram) 3 and 7 days post inoculation in infant mice

| Age of Mice (day) | Oral dosage (CFU) | Number of mice | Spleen (CFU/g) Day 3 | Spleen (CFU/g) Day 7 | Liver (CFU/g) Day 3 | Liver (CFU/g) Day 7 | Intestine* (CFU/g) Day 3 | Intestine* (CFU/g) Day 7 |
|---|---|---|---|---|---|---|---|---|
| 0 | $1.0 \times 10^8$ | 1 | <10 | $5.9 \times 10^3$ | <10 | $6.8 \times 10^3$ | $2.7 \times 10^6$ | $6.3 \times 10^4$ |
|   |   | 2 | <10 | $7.3 \times 10^3$ | <10 | $5.0 \times 10^4$ | $5.9 \times 10^5$ | $3.1 \times 10^5$ |
|   |   | 3 | <10 | $2.4 \times 10^3$ | $3.0 \times 10^3$ | $2.5 \times 10^4$ | $1.6 \times 10^6$ | $2.4 \times 10^5$ |
| 2 | $1.2 \times 10^8$ | 1 | 0 << 10 | $1.1 \times 10^3$ | $2.9 \times 10^3$ | $1.1 \times 10^3$ | $6.1 \times 10^5$ | $5.0 \times 10^5$ |
|   |   | 2 | 0 << 10 | $1.4 \times 10^3$ | $5.9 \times 10^2$ | $1.7 \times 10^3$ | $2.3 \times 10^5$ | $5.4 \times 10^3$ |
|   |   | 3 | $2.5 \times 10^3$ | $1.7 \times 10^3$ | $5.7 \times 10^3$ | $3.3 \times 10^3$ | $2.7 \times 10^6$ | $3.1 \times 10^5$ |
| 4 | $3.0 \times 10^8$ | 1 | $3.3 \times 10^3$ | <10 | $5.2 \times 10^3$ | <10 | $1.1 \times 10^8$ | $5.4 \times 10^6$ |
|   |   | 2 | <10 | $8.5 \times 10^3$ | $2.4 \times 10^3$ | $8.0 \times 10^3$ | $1.1 \times 10^8$ | $1.8 \times 10^7$ |
|   |   | 3 | $8.1 \times 10^4$ | $2.7 \times 10^3$ | $1.2 \times 10^4$ | $2.1 \times 10^4$ | $7.1 \times 10^6$ | $2.8 \times 10^7$ |
| 7 | $3.5 \times 10^8$ | 1 | <10 | <10 | $2.4 \times 10^2$ | <10 | $7.0 \times 10^6$ | $1.5 \times 10^7$ |
|   |   | 2 | <10 | <10 | $5.0 \times 10^2$ | <10 | $1.1 \times 10^7$ | $6.0 \times 10^6$ |
|   |   | 3 | <10 | <10 | $3.2 \times 10^2$ | <10 | $1.8 \times 10^7$ | $3.9 \times 10^6$ |

*Entire small intestine and contents tible to wild-type *S. Typhimurium* infection and succumb at oral doses lower than 100 CFU.

Newborn and infant mice were orally inoculated with 5 μl containing 1-3×10$^8$ CFU of the strain χ9558(pYA4088) at 0, 2, 4 or 7 days of age. Table 16 shows the health status and survivors over a 10-week period. No disease symptoms or death occurred in any of the mice at any time after oral inoculation with over 10$^6$ times the wild-type LD$_{50}$.

TABLE 16

Safety of χ9558(pYA4088) in newborn/infant BALB/c mice

| Age of mice (days) | Oral dosage CFU | Health status 10 weeks post-vaccination | Survivors/ total |
|---|---|---|---|
| 0 | $1.0 \times 10^8$ | Healthy | 9/9 |
| 2 | $1.2 \times 10^8$ | Healthy | 12/12 |
| 4 | $3.0 \times 10^8$ | Healthy | 11/11 |
| 7 | $3.5 \times 10^8$ | Healthy | 13/13 |

The oral LD$_{50}$ for the wild-type parent strain χ3761 is less than 100 CFU.

Distribution of *S. Typhimurium* χ9558(pYA4088) in Tissues of Newborn Mice

Colonization of tissues from newborn and infant mice was evaluated 3 and 7 days after oral inoculation with the *S. Typhimurium* strain χ9558(pYA4088). Homogenized tissue samples from euthanized mice were spread onto agar plates and CFU/g enumerated. In addition, samples of homogenized tissues were also subjected to enrichment culture to reveal presence or absence of *Salmonella*. Table 17 shows the tissue distribution of the attenuated *S. Typhimurium* strain χ9558 (pYA4088) in newborn mice to 7 days of age.

Evaluation of Safety of *S. Typhi* Vaccine Strains in Young Mice.

Newborn mice (<24 h) were each orally inoculated with 10 μl containing 1×10$^9$ CFU of each of the *S. Typhi* vaccine strains. Table 18 shows the health status and survivors over a six-week period. No disease symptoms or death occurred in any of the mice at any time after oral inoculation.

TABLE 18

Safety of *S. Typhi* χ9633(pYA4088), χ9639(pYA4088) and χ9640(pYA4088) in newborn mice

| Strain | Oral dosage (CFU) | Health status 6-weeks post-inoculation | Survivors/ total |
|---|---|---|---|
| χ9633(pYA4088) | $1.2 \times 10^9$ | healthy | 3/3 |
| χ9639(pYA4088) | $6.0 \times 10^8$ | healthy | 3/3 |
| χ9640(pYA4088) | $7.5 \times 10^8$ | healthy | 3/3 |

Distribution of *S. Typhi* Strains in Tissues of Newborn Mice.

Although *S. Typhi* can invade murine cells with low efficiency (compared to *S. Typhimurium*), they do not survive well or multiply and quickly decline in titer following oral administration. For this reason, the ability of *S. Typhi* to colonize (or not colonize) murine tissues is not necessarily indicative of the ability of the strain to colonize human tissue. However, the distribution of *S. Typhi* cells in tissues from newborn mice was evaluated as an addition to the data from the *S. Typhimurium* RASV-Sp strain χ9558(pYA4088) (see Table 17).

Colonization was assessed 3 and 7 days after oral inoculation with the *S. Typhi* vaccine and wild-type strains. The attenuated ISP1820 strain used in a previous trial (χ8110) and the typhoid vaccine strain Ty21a were also included for comparative purposes. Homogenized tissue samples from euthanized mice were spread onto agar plates and CFU/g enumerated. In addition, samples of homogenized tissues were also subjected to enrichment culture to reveal the presence or absence of *Salmonella*. FIG. 28 shows the distribution of the *S. Typhi* vaccine and wild-type strains in the intestine, spleen and liver tissues 3 and 7 days after inoculation. Data shown are the geometric means+standard deviations of two separate colonization experiments.

These data demonstrate that the mutant vaccine candidate *S. Typhi* strains colonize mouse tissues no better than the wild-type parental strains. The additional strains Ty21a and χ8110 showed similarly poor levels of colonization. These results were not unexpected, since mice are unable to support an infection with *S. Typhi* strains even when infected soon after birth.

Reactogenicity of PBS Diluent With and Without *S. Typhi*

The general safety test as directed in 21 CFR 610.11 was performed to address concerns raised of the possibility that residual media components might be reactogenic in volunteers.

The RASV-Sp PBS cell suspensions were filter-sterilized and these cell-free solutions, along with sterile PBS and sterile growth medium were injected intraperitonneally into mice and guinea pigs. The weight, health and general well-being of study animals were monitored daily for 7 days. At the conclusion of the study, animals were euthanized and necropsied, and observable differences of the internal organs (including alterations in size, shape, coloration and vascularization) were photographed for comparative analysis.

All animals survived for the duration of the general safety test (7 days after injection). No unexpected or nonspecific responses were observed with any of the RASV-Sp strains as compared to the PBS controls. The average weights for each group throughout the course of the study are shown in FIGS. 29(*a*) and (*b*). For each group, the animals weigh the same or more on Day 7 than they did on the day of injection.

No diminishment of the health and general well-being, and no change in the character of internal organs of mice and guinea pigs were noted.

These data provide evidence to support the conclusion that the trace amount of residual media components present in the final vaccine preparation is unlikely to be reactogenic in human volunteers.

Immunogenicity Assessment of *S. pneumoniae* Antigen

The immunogenicity of the PspA antigen of *S. pneumoniae* was assessed using the Asd+ plasmid vector pYA3634. The pYA3634 plasmid is a precursor of pYA4088 and encodes aa 3-257 of the PspA-Rx1 protein (pYA4088 spans aa 3-285) (See FIG. 23). Cultures of the RASV-Sp strains grown in the presence of arabinose synthesize the LacI repressor at high levels to repress transcription from $P_{trc}$ on the Asd+ plasmid vector pYA3634 to minimize synthesis of PspA until after immunization when the vaccine strain is already colonizing internal lymphoid tissues. 0.05% arabinose and 0.2% mannose were used to prepare *S. Typhimurium* χ9558(pYA3634) (Δpmi-2426 Δ(gmd-fcl)-26 $ΔP_{fur81}$::TT araC $P_{BAD}$ fur $ΔP_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811) to evaluate relative IgG response to PspA-Rx1 expressed from χ9558(pYA3634) in BALB/c mice compared to χ9088(pYA3634) ($ΔP_{fur33}$::TT araC $P_{BAD}$ furΔpmi-2426 Δ(gmd-fcl)-26 ΔasdA33) and χ8133 (pYA3634) (Δcya-27 Δcrp-27 ΔasdA16). Groups of 7-week-old female BALB/c mice were orally administered approximately $10^9$ CFU of each strain and boosted with the same dose at 8 weeks. Blood was obtained by mandibular vein puncture with heparinized capillary tubes at biweekly intervals. ELISA was performed to determine IgG antibody titers to PspA, *S. Typhimurium* LPS. FIG. 30 shows total serum IgG titers to the PspA protein and to *S. Typhimurium* LPS.

Four weeks after the second oral immunization, mice were challenged in two experiments with approximately $5×10^4$CFU of *S. pneumoniae* WU2. Both experiments gave similar results, and the data have been pooled for presentation and analysis. This challenge dose resulted in the deaths of 100% of the unvaccinated mice, with a mean time to death of 2-3 days.

The percent protection rate and the number of days of survival after challenge with virulent *S. pneumoniae* strain WU2 are shown in FIG. 31. Seventy-one percent of the mice immunized with χ9558(pYA3634) were protected from pneumococcal challenge. This is significantly higher than the level of protection observed for the Δcya Δcrp strain χ8133 (pYA3634) (p=0.0063).

Passive Transfer of Pneumococcal Immunity.

An experiment to demonstrate passive-antibody transfer of protective immunity to pneumococcal challenge was conducted in mice. Mice were orally inoculated with $1×10^9$ CFU of a RASV-Sp strain containing either the empty vector pYA3493 or the vector pYA3634 and boosted with the same strain and dose 8 weeks after primary immunization. At week 12, sera from immunized mice were collected and pooled.

Naïve, syngeneic BALB/c mice received 100 μl in the tail vein of undiluted serum from pooled serum of immunized mice. All groups were challenged intraperitoneally 12 h later with *S. pneumoniae* WU2. The percent survival of mice receiving pooled serum was assessed 15 days after challenge with *S. pneumoniae* WU2. Table 19 shows the percent survival of mice that were protected by passive-antibody transfer from challenge with more than 250 $LD_{50}$ doses of the virulent *S. pneumoniae* WU2.

Sera from mice immunized with *S. Typhimurium* χ9558 (pYA3634) passively protected 100% of mice challenged with over 250 $LD_{50}$ doses of the virulent *S. pneumoniae* WU2.

TABLE 19

Passive transfer of pneumococcal immunity by serum from donors immunized with *S. Typhimurium* vaccines expressing PspA

| Donors immunized with vaccine strain | Strain expresses PspA | No. of mice | Volume of the donor serum (μl) administered IV | % survival of pooled serum recipients[1] |
|---|---|---|---|---|
| Saline control | — | 5 | 100 | 0 |
| χ8133(pYA3493) Δcya-27 Δcrp-27 ΔasdA16 | No | 5 | 100 | 0 |
| χ9088(pYA3493) Δpmi-2426 Δ(gmd-fcl)-26 $ΔP_{fur81}$::TT araC $P_{BAD}$ fur ΔasdA33 | No | 5 | 100 | 0 |
| χ9558(pYA3493) Δpmi-2426 Δ(gmd-fcl)-26 $ΔP_{fur33}$::TT araC $P_{BAD}$ fur $ΔP_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 | No | 5 | 100 | 0 |
| χ8133(pYA3634) | Yes | 5 | 100 | 80 |

TABLE 19-continued Passive transfer of pneumococcal immunity by serum from donors immunized with S. Typhimurium vaccines expressing PspA

| Donors immunized with vaccine strain | Strain expresses PspA | No. of mice | Volume of the donor serum (μl) administered IV | % survival of pooled serum recipients[1] |
|---|---|---|---|---|
| χ9088(pYA3634) | Yes | 5 | 100 | 100 |
| χ9558(pYA3634) | Yes | 5 | 100 | 100 |

[1] Mice were challenged IP 12 h after receiving donor immune serum with >250 $LD_{50}$ doses of S. pneumoniae WU2

Immunogenicity of χ9633(pYA4088), χ9639(pYA4088), and χ9640(pYA4088) in Female 6- to 7-Week-Old BALB/c Mice.

The ability of the S. Typhi RASV-Sp strains administered intranasally to BALB/c to induce serum antibody titers to PspA was assessed (GCGH-ASU-SOP-074-00, see CMC section of the IND application). Mice were inoculated intranasally with 10 μl of approximately $10^9$ CFU of a RASV strain with either the empty vector pYA3493 or the PspA$^+$ vector pYA4088. Sera were collected 2, 4, 6 and 8 weeks after vaccination and anti-PspA, -LPS and -OMP IgG titers determined by ELISA.

Figure 32A:
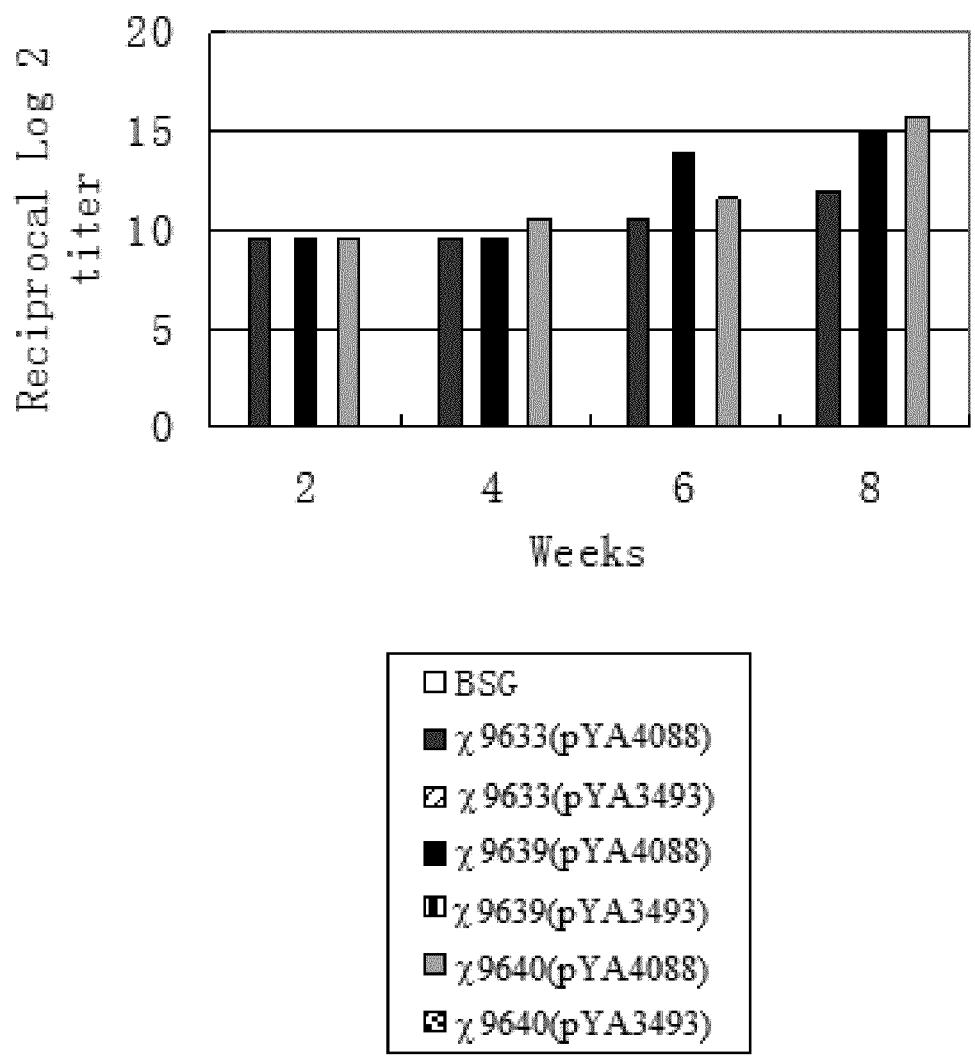
Figure 32B:
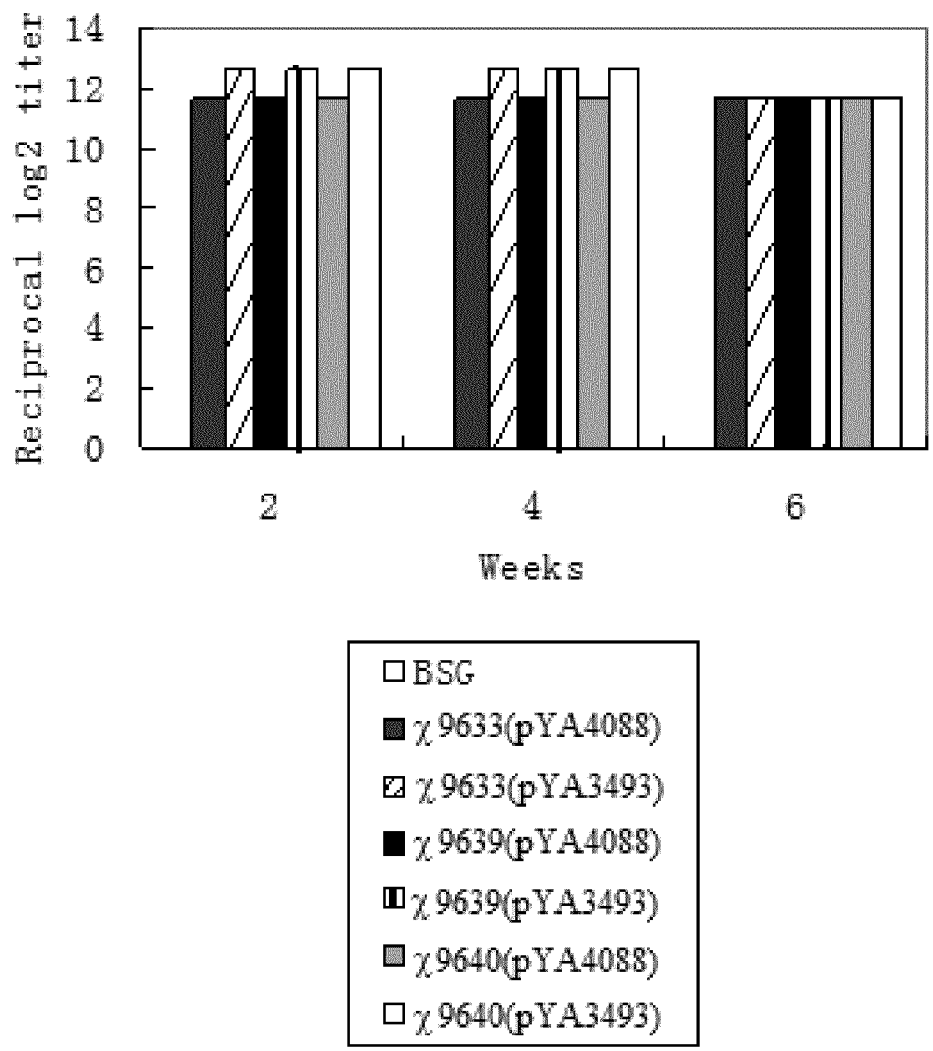
Figure 32C:
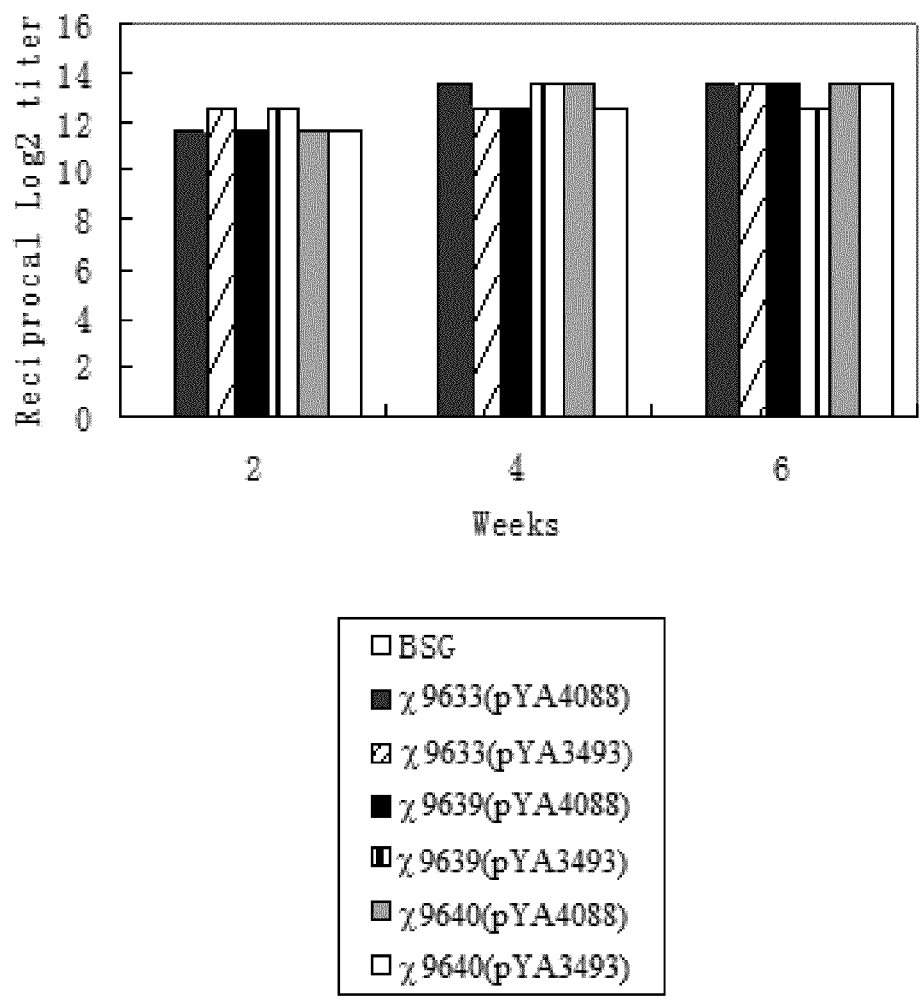

It should be noted that this type of immunogenicity assay has been used by others even though we believe it is of marginal value. This is because S. Typhi (wild-type or mutant) is unable to successfully invade and persist in murine cells or lymphoid tissues as is S. Typhimurium. FIGS. 32(a)-(c) show the total IgG response to PspA, LPS and OMP from sera collected over an 8-week period after intranasal administration of the RASV strains with the PspA plasmid pYA4088 or the empty vector pYA3493. All RASV strains harboring either pYA3493 or pYA4088 equally induced significant anti-LPS and anti-OMP IgG titers as soon as two weeks post-inoculation. PspA IgG titers gradually increased over the eight-week period from mice administered the RASV-Sp strains. Although the group size was small, the RASV-Sp Ty2 RpoS$^+$ strain χ9640(pYA4088) induced a slightly higher anti-PspA IgG titer than the ISP1820 derivative χ9633(pYA4088).

Complement Deposition Assay and Passive Protection of Mice Using Serum from Human Vaccine Volunteers.

Sera from the vaccine volunteers which test positive for PspA will be evaluated for their ability to passively protect mice from pneumococcal infection. Passive transfer of protective immunity to pneumococcal challenge will be demonstrated by transfer of pre- and post-immune serum and the antibodies it contains to naive unimmunized mice followed by intravenous challenge with virulent S. pneumoniae.

As an additional measure of the protective capacity of the anti-PspA response in volunteers, sera may be further evaluated by the complement deposition assay. This test will quantitatively evaluate the ability of antibody in pre- and post-immune sera to facilitate deposition of complement C3 onto S. pneumoniae. Immunization of humans with PspA has been shown to lead to elevated levels of antibody to PspA, increases in the ability of the sera to mediate complement deposition on S. pneumoniae, and increases in the ability of human sera to protect mice from fatal pneumococcal infection. The deposition of complement on S. pneumoniae has been shown to correlate inversely with the ability of S. pneumoniae to cause invasive disease.

Example 13

Non-Clinical Assessment of Safety

Additional safety tests were conducted to address concerns raised regarding the apparent lack of adequate safety data for the ISP1820 derivative strain χ9633(pYA4088). Another ISP1820 derivative, χ8110 χcfs), (χcya-27 χcrp-pabA-40 Δcfs), was shown to be safe in Phase I clinical trials. To bridge the previous human data with χ8110 to the present vaccine candidate χ9633(pYA4088), additional safety data were generated to demonstrate that χ9633(pYA4088) is equivalent to or more attenuated than χ8110 as evaluated by survival in human blood and peripheral blood monocytes. Comparisons to the Ty21a vaccine Vivotif® which is the gold standard for live Salmonella vaccine safety were also included in the following non-clinical assessment of safety.

Survival of RASV-Sp Strains in Human Blood

The bactericidal effects of heat-treated and untreated whole blood were compared by incubating the RASV-Sp strains and wild-type S. Typhi counterparts in the presence of normal whole blood (GCGH-ASU-SOP-081-01, see CMC section of the IND application).

Approximately $1 \times 10^6$ CFU of each RASV-Sp strain, χ8110, Ty21a and their wild-type counterparts were added to duplicate 1.5 ml blood aliquots from volunteers. Blood was collected in accordance with the ASU human use protocol #0804002872. Survival of the Salmonella strains was assayed in blood that had been heat inactivated (HI) by incubation at 55° C. for one hour prior to inoculation, or in untreated, active (A) blood. Viability of the Salmonella strains was measured by plating samples on permissive media 0, 3, 6 and 18 hours after inoculation. FIG. 33 shows the geometric mean of the CFU recovered of at least 3 trials±the standard deviation.

The RASV-Sp candidates are severely attenuated in their ability to survive in whole human blood as compared to wild-type S. Typhi and χ8110. Vaccine strain levels drop below the threshold of detection within 3 hours and the strains did not regrow at the later timepoints of the assay. This is in contrast to χ3744, χ3769 and χ8110, which are not only present at significantly higher levels, but also replicate in the blood at the later timepoints of the assay. The RASV-Sp candidates, including the ISP1820 derivative χ9633 (pYA4088), are as attenuated as Ty21a and more attenuated than the ISP1820 RASV χ8110 used in a previous clinical trial.

Sensitivity of RASV-Sp Strains to Native Guinea Pig Serum Complement.

The bactericidal properties of guinea pig serum complement were determined for the RASV-Sp strains and their wild-type counterparts. Guinea pig complement was used for this assay because of its high level of bacteriocidal activity.

The S. Typhi strains χ3744 (wild-type ISP1820), χ3769 (wild-type Ty2), χ8438 (RpoS$^+$ wild-type Ty2), χ9633 (pYA4088), χ9639(pYA4088) and χ9640(pYA4088) were prepared following GCGH-ASU-SOP-062-01 Preparation of RASV-Sp dosages for adult volunteers. The sensitivity of the cells to complement was assayed following GCGH-ASU-SOP-091-00 Resistance of RASV-Sp strains to guinea pig complement. Strains were assayed in PBS only, complement (purified from guinea pig serum) only, and complement with anti-S. Typhi O-antigen $D_1$ opsonizing antibody. Reactions were incubated for 3 hours at 37° C., and then the viability of the Salmonella strains was measured by plating on permissive media. Data shown in FIG. 34 represent the average CFU/ml.

Both the wild-type Salmonella Typhi strains and the RASV-Sp strains are sensitive to killing by complement in the presence of Salmonella Typhi O-antigen specific $D_1$ antibody. The vaccine strains are killed to a moderately higher degree than the wild-type strains. In the absence of S. Typhi-specific antibody, the wild-type strains are resistant to complement-mediated killing. However, the RASV-Sp strains exhibit a high level of sensitivity to complement-mediated killing even in the absence of opsonizing antibody.

Survival of RASV-Sp Strains in Peripheral Human Mononuclear Cells.

Rubin et al. demonstrated that in patients with typhoid fever, circulating S. Typhi cells are associated with mononuclear cell-platelet fraction of whole blood. Because this serovar does not typically cause disease in mice or other animals, the development of rapid ex-vivo assays using freshly elutriated peripheral blood mononuclear cells (PBMCs) have been demonstrated as reliable tools for determining attenuation of S. Typhi for vaccine research and development.

Figure 42A:
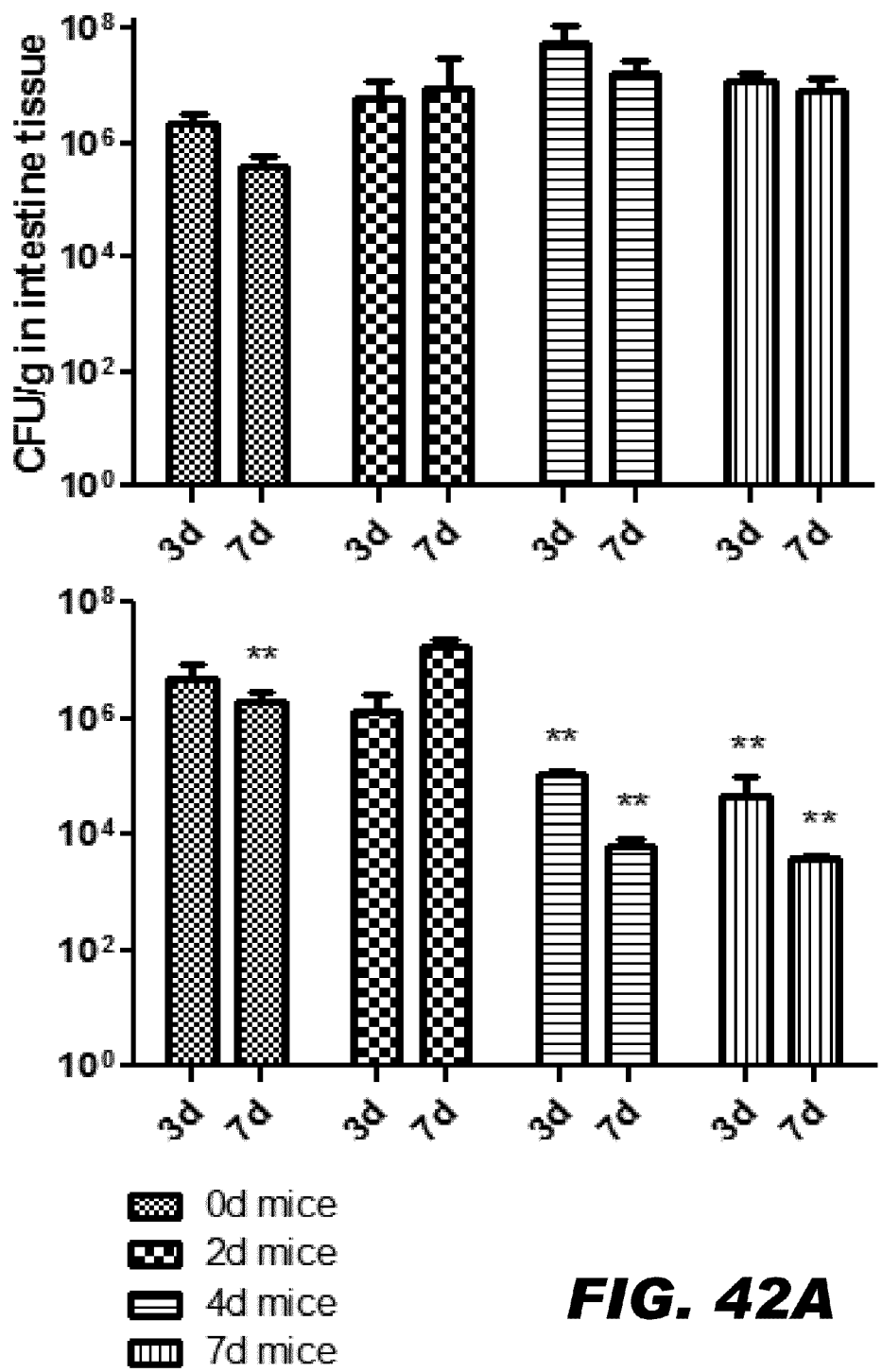
Figure 42B:
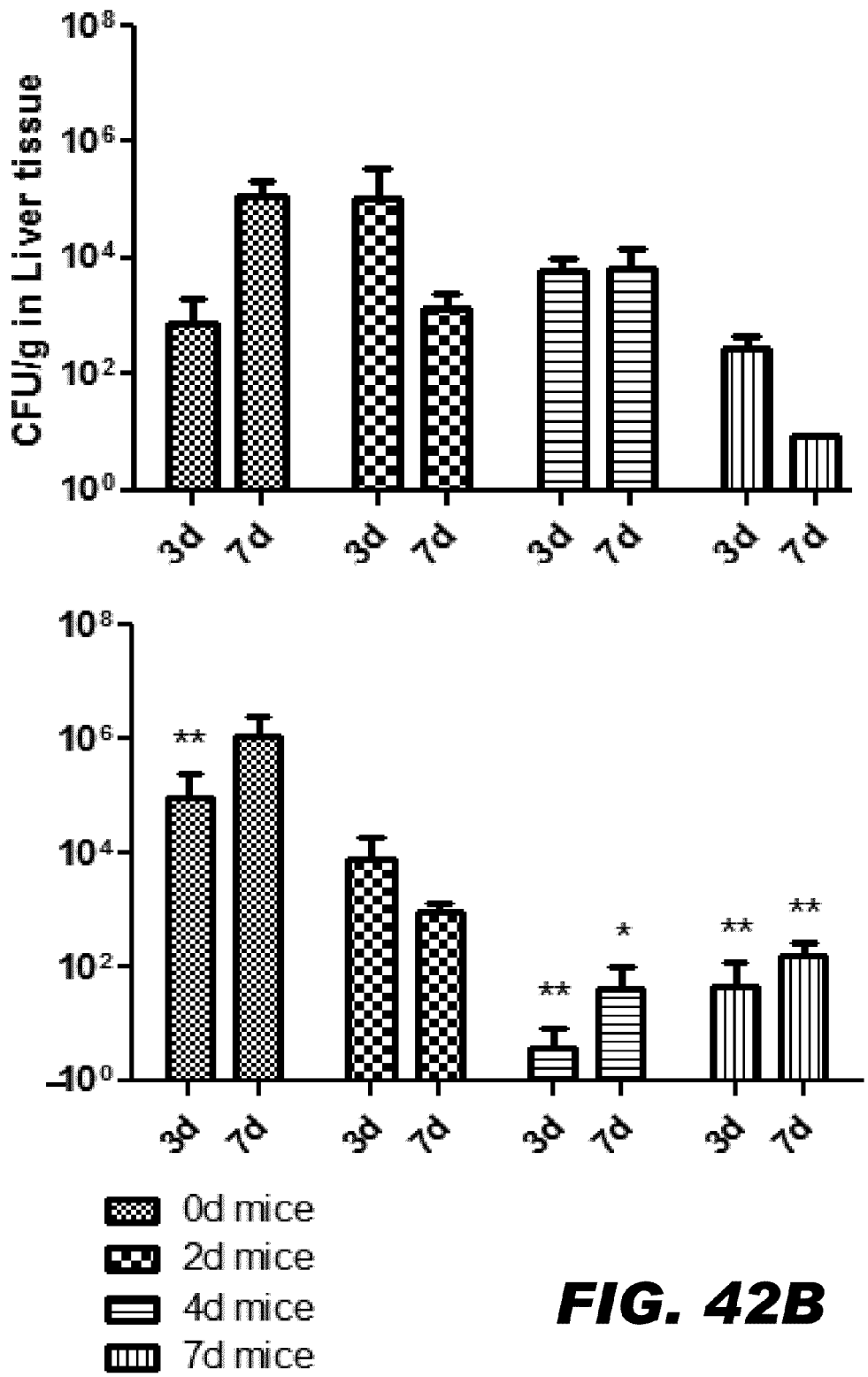
Figure 42C:
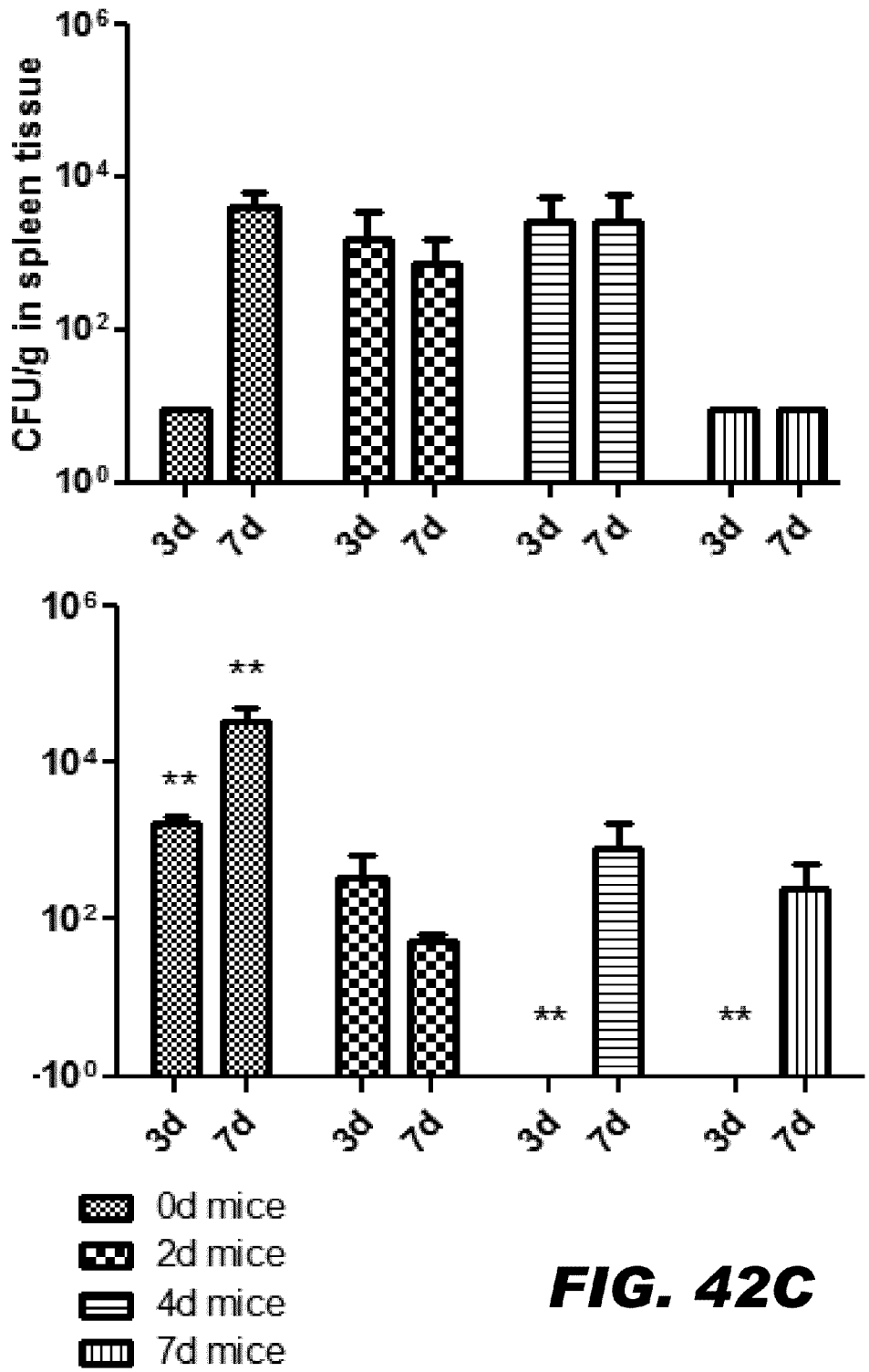

PBMCs derived from blood of 3 different volunteers were elutriated following GCGH-ASU-SOP-082-01 Survival of RASV-Sp strains in peripheral human mononuclear cells. After incubation of PBMCs and bacteria in 24-well culture plates for 1, 3 and 23 additional hours, PBMCs were lysed and cell lysates were plated onto permissive media to determine viable CFU. Survivability of the RASV-Sp strains χ9633 (pYA4088), χ9639(pYA4088) and χ9640(pYA4088) compared to χ8110 (ISP1820 Δcya-27 Δcrp-pabA-40 Δcfs), Ty21a and to wild-type *S. Typhi* χ3744 (wild-type ISP1820), χ3769 (wild-type Ty2), χ8438 ($RpoS^+$ wild-type Ty2) are shown in FIG. 35(*a.-c.*). The data shown are the geometric means+standard deviations of three separate assays.

The peripheral blood mononuclear cell assay used to measure the invasion and persistence of the *S. Typhi* strains readily distinguished between virulent *S. Typhi* and the attenuated RASV-Sp strains and Ty21a, known to survive poorly both in vitro and in vivo. The wild-type Ty2 and ISP1820 strains invaded and persisted at a significantly higher rate than the RASV-Sp strains and Ty21a ($p<0.05$).

Both χ9639(pYA4088) and Ty21a were the least fit to survive and persist in PBMCs compared to the wild-type Ty2 $RpoS^-$ strain (p=0.0022 and 0.0022 at 24 hours, respectively), which may be a consequence of possessing the rpoS mutation. These results are consistent with the $RpoS^-$ phenotype in that null mutants are susceptible to killing by macrophage and exhibit increased sensitivity to environmental stress.

The ISP1820 derivative χ9633(pYA4088) was equivalent to χ8110 in surviving within PBMCs at 2, 4 and 24 hours (p=1.00, 0.505 and 0.878, respectively) and both strains were significantly reduced in their ability to invade and persist within PBMCs compared to the wild-type ISP1820 at all timepoints.

Together these data demonstrate further safety of the RASV-Sp strains. Additionally the ability of the ISP1820 derivative χ9633(pYA4088) to invade to a lesser degree than the wild-type ISP1820 but persist at a low level in PBMCs demonstrates that this strain is not compromised to reach host target cells to deliver the PspA for antigen processing.

Taken collectively, the RASV-Sp strains are adequately attenuated due to their extreme sensitivity to complement-mediated killing, their poor survival in whole human blood and in fresh elutriated peripheral blood mononuclear cells. The ISP1820 derivative χ9633(pYA4088), although sufficiently attenuated by the data presented here, may display the best attributes for antigen presentation to the appropriate antigen-presenting cells of the host immune system.

RASV-Sp Shedding and Survival in Human Stool

A consequence of oral administration of live *Salmonella* vaccine organisms is that they can be shed transiently in the stool of vaccine recipients. An important aspect of the potential impact of environmental release of a live vaccine is to evaluate the duration, rate of shedding and the survival rate. Endeavors to develop live vaccines that reduce shedding have been met with variable success. The licensed live oral typhoid vaccine, serovar *Typhi* Ty21a, is shed at low rates in the stools of most vaccinees for 1 to 4 days. Ideally, it is desirable to limit the number of genetically modified microorganisms entering the environment, without decreasing vaccine immunogenicity or efficacy.

An initial assessment of the duration of shedding following oral inoculation was conducted in 6-week old adult mice. The *S. Typhi* RASV-Sp strains χ9633(pYA4088), χ9639 (pYA4088), and χ9640(pYA4088), the *S. Typhimurium* RASV-Sp counterpart χ9558(pYA4088) and the *S. Typhi* wild-type strains χ3744, χ3769 and χ8438 were grown. Approximately $1\times10^9$ CFU of each strain was administered orally to groups of 3 mice. Shedding was monitored for 6 days after inoculation by homogenizing fecal pellets and plating on selectively differential media. The data shown in Table 20 represent the average number of CFU/ml detected for each group. None of the *S. Typhi* strains (wild-type or RASV-Sp) were detected more than 3 hours following the inoculation. The *S. Typhimurium* RASV-Sp strain χ9558(pYA4088) was also not detected after the initial day of inoculation. These data indicate that significant levels of vaccine organism shedding are confined to the initial day of immunization. Low-level shedding (less than $10^3$ CFU/ml) may occur for a slightly longer period.

TABLE 20

Fecal shedding of RASV-Sp strains and *S. Typhi* wild-type strains following oral inoculation of mice.

| Strain | 3 Hours (CFU/ml) | 18 Hours (CFU/ml) | Day 2 (CFU/ml) | Day 4 (CFU/ml) | Day 6 (CFU/ml) |
|---|---|---|---|---|---|
| χ9558(pYA4088) | $1.7\times10^7$ | $<10^3$ | $<10^3$ | $<10^3$ | $<10^3$ |
| χ3744 | $1.7\times10^7$ | $<10^3$ | $<10^3$ | $<10^3$ | $<10^3$ |
| χ9633(pYA4088) | $8.0\times10^6$ | $<10^3$ | $<10^3$ | $<10^3$ | $<10^3$ |
| χ3769 | $1.0\times10^7$ | $<10^3$ | $<10^3$ | $<10^3$ | $<10^3$ |
| χ9639(pYA4088) | $1.6\times10^7$ | $<10^3$ | $<10^3$ | $<10^3$ | $<10^3$ |
| χ8438 | $1.8\times10^7$ | $<10^3$ | $<10^3$ | $<10^3$ | $<10^3$ |
| χ9640(pYA4088) | $1.6\times10^6$ | $<10^3$ | $<10^3$ | $<10^3$ | $<10^3$ |

Limit of detection for this assay was $10^3$ CFU/ml

Since *S. Typhi* is unable to efficiently attach to and invade to the intestinal epithelial cells of mice, the results of the previous study may not accurately represent the duration of shedding from a human host. In order to gather data about the competitive fitness of the strains in the human intestinal environment, the RASV-Sp and wild-type *S. Typhi* strains were evaluated in anaerobic human stool samples. Viability of the *S. Typhi* strains was assessed by plating dilutions onto selective media 1, 3, 7 and 10 days after inoculation of fresh stool suspensions with approximately $1\times10^8$ CFU/ml. Inoculated samples were incubated at 37° C. in an anaerobic environment. The limit of detection for recovering the *S. Typhi* strains was $10^4$ CFU/ml.

FIG. 36 shows the survival of the *S. Typhi* wild-type χ3744 (wild-type ISP1820), χ3769 (wild-type Ty2), χ8438 ($RpoS^+$ wild-type Ty2) and RASV-Sp strains χ9633(pYA4088), χ9639(pYA4088) and χ9640(pYA4088) in human stool over the 10-day period of evaluation. The RASV-Sp strains were not recoverable 24 hours after inoculation of the stool samples and remained below the threshold of detection ($10^4$ CFU) throughout the remainder of the study. The wild-type strains, however, persisted through day 3 at measurable titers above $10^4$ CFU and then fell below the level of detection through day 10 of the study.

These data represent the worst case scenario as the RASV-Sp strains were prepared in this study to allow the regulated-delayed expression of the near wild-type attributes that would endow the strains with characteristics that would make them most fit for survival. In reality, once ingested by volunteers, the strains will eventually lose and no longer display these protective attributes due to the absence of exogenous arabinose and mannose and would rapidly succumb to the harsh and competitive environment present in stool.

Survival of *S. Typhi* in Canal Water, Chlorinated Water and Sewage

The aim of this study was to compare the survivability of the RASV-Sp strains and *S. Typhi* wild-type counterparts in several conditions that mimic the environment and to address concerns regarding the impact of releasing live attenuated, genetically-modified organisms into the environment.

Three environmental conditions were prepared to serve as test material for assessing survivability of the *S. Typhi* strains. Chlorinated water was prepared to contain approximately 3 to 5 ppm chlorine. The *S. Typhi* test strains were washed twice to remove residual media and approximately $1\times10^8$ CFU of each strain were added to triplicate tubes containing the test solution. Raw sewage was retrieved from a local waste water treatment plant in Phoenix, Ariz. Untreated canal water was collected from the Phoenix metropolitan area. Viability of the *S. Typhi* strains was assessed by plating dilutions onto selective media 1, 3, 7 and 10 days after inoculation of the triplicate test solutions with approximately $1\times10^8$ CFU/ml. The limit of detection for recovering the *S. Typhi* strains was $10^4$ CFU/ml.

FIG. 37(*a*)-(*c*) shows the survival of the *S. Typhi* wild-type χ3744 (wild-type ISP1820), χ3769 (wild-type Ty2), χ8438 ($RpoS^+$ wild-type Ty2) and RASV-Sp strains χ9633 (pYA4088), χ9639(pYA4088) and χ9640(pYA4088) in the environmental test solutions. The RASV-Sp and wild-type strains were extremely sensitive to chlorinated water experiencing several logs of killing after a 30-minute exposure (FIG. 37(*a*)). The RASV-Sp strains were less fit than the wild-type strains to persist in canal water decreasing more than 3 logs in titer over the 10-day evaluation period (FIG. 37(*b*)). Titers of the RASV-Sp strains in raw sewage dropped steadily decreasing more than 3 logs in titer over the 10-day period (FIG. 37(*c*)). These data show that the RASV-Sp strains did not display any enhanced attributes to survive in these environmental test solutions over the Ty2 or ISP1820 wild-type strains.

In summary, the data show that the RASV-Sp strains do not have a competitive advantage in chlorinated water, untreated surface water or sewage over naturally-occurring organisms and are no more likely to persist in these conditions than the wild-type *Salmonella Typhi.*

Example 14

Response to *S. Typhi* Vaccines in Adult Mice Immunized by Intranasal Response Immune Response to *S. Typhi* Vaccines in Adult Mice Immunized by Intranasal Response.

Adult BALB/c mice (7 weeks) were inoculated intranasally with approximately $1\times10^9$ CFU of RAStyV strains carrying either rPspA expression plasmid pYA4088 or control plasmid pYA3493 in 10 μl, and boosted with the same dose of the same strain six weeks later. Sera were collected 2, 4, 6 and 8 weeks after vaccination and serum IgG responses to rPspA, *S. Typhi* LPS and *S. Typhi* OMPs were measured by ELISA. This experiment was performed twice, with each group (8 mice) receiving approximately the same dose of vaccine. Sera from all mice in a group were pooled for analysis. Absorbance levels of a secondary anti-mouse antibody conjugated to HRP was recorded at 405 nm using an automated ELISA plate reader (model EL311SX; Biotek, Winooski, Vt.). Absorbance readings that were 0.1 higher than PBS control values were considered positive. The results from both experiments were similar and have been pooled for analysis.

Results: All mice immunized with strains expressing pspA developed anti-PspA antibodies (FIG. 40*a*). Anti-PspA titers were boosted after the second immunization at 6 weeks. Strain χ9640(pYA4088) (Ty2 $RpoS^+$) induced a significantly higher anti-rPspA IgG titer in mice than those of either the ISP1820 derivative χ9633(pYA4088), or the Ty2 derivative χ9639(pYA4088) at all time points ($P<0.01$). After boosting, the anti-rPspA IgG antibody levels in χ9639(pYA4088) immunized mice were significantly higher than the mice immunized with χ9633(pYA4088) ($P<0.05$). No anti-PspA IgG was detected in mice immunized with PBS or strains carrying pYA3493.

All RAStyV strains induced significant anti-LPS titers (FIG. 40*b*) and OMPs (FIG. 40*c*) as early as two weeks post inoculation. After the second immunization, significant boosting of serum antibody responses to LPS and OMPs was observed ($P<0.01$).

Mucosal IgA anti-PspA responses were slow to develop, but reached high titers after boosting (FIG. 40*d*).

Protection of Adult Mice Immunized with *S. Typhi* Vaccines Against Challenge with Virulent *S. Pneumoniae.*

Method: At week 10, mice were challenged by intraperitoneal injection with $1.0\times10^4$ CFU of *S. pneumoniae* WU2 (50 $LD_{50}$) in 100 μl BSG. Challenged mice were monitored daily for 30 days.

Result: All mice immunized with three *S. Typhi* vaccine strains expressing pspA were significantly protected compared with controls (FIG. 41). The protection afforded by the Ty2 derivatives, χ9639 (pYA4088) and χ9640 (pYA4088) was significantly greater than that the protective effects of χ9633 (pYA4088) (**, $P<0.01$).

Example 15

Colonization of χ9558 (pYA4088) in Neonatal Mice Either from Naïve or Immunized Mothers Method: For colonization studies, 0, 2, 4 and 7 day-old pups (6/group) born from either naïve or immunized mothers were orally inoculated with 5 μl containing approximately $5\times10^8$ CFU of χ9558 (pYA4088). Mice were euthanized on days 3 and 7 post-infection and samples of the upper intestinal tract (ileum, jejunum and duodenum), spleen and liver were collected. Tissues were weighed and homogenized in a total volume of 1 ml BSG. Serial dilutions were plated onto MacConkey agar plates containing 1% lactose, 0.05% arabinose and 0.2% mannose to determine the number of viable bacteria. Plates were incubated at 37° C. for at least 18 h. Also, 900 μl of homogenized tissues were inoculated into 5 ml selenite broth (Difco) for *Salmonella* enrichment. Samples that were negative by direct plating and positive by enrichment were recorded as 10 CFU/g. Samples that were negative by both direct plating and enrichment were recorded as 0 CFU/g.

Result: The ability of χ9558 (pYA4088) to colonize intestine, liver, and spleen was examined when administered to pups 0, 2, 4 or 7 days of age born from either naïve or immunized mothers. Overall, immunization of the mother had the greatest effect on inhibiting colonization in pups inoculated at 4 and 7 days of age, but had no negative effect on pups inoculated at 0 or 2 days of age (FIG. 42). Strain χ9558

(pYA4088) colonized intestinal tissues to high numbers in all groups (FIG. 42a). Despite the high level of intestinal colonization in the group of mice inoculated at day 7 from naïve mothers, colonization of the spleen and liver were somewhat lower than in the other groups of mice from naïve mothers. Intestinal colonization was inhibited in pups immunized at 4 or 7 days of age who were born to immune mothers (P<0.01) and colonization was increased in pups from immunized mothers who themselves were immunized at day 0 (when bacteria were enumerated on day 7). The effect of maternal immunization had a more profound effect on colonization levels of liver and spleen (FIG. 42b, 42c). As with intestinal colonization, there was no negative effect of maternal immunity in pups inoculated at 0 or 2 days of age and for pups immunized on day 0, maternal immunity enhanced colonization at some time points. In the case of liver colonization of pups inoculated at 4 days of age, colonization was inhibited in pups from immunized mothers compared to pups from naïve mothers at both time points examined (FIG. 42b). For mice inoculated at day 0, maternal immunization resulted in higher numbers of χ9558 (pYA4088) in the spleen on day 3 and day 7 (P<0.01) (FIG. 42c). No vaccine was recovered from spleens of pups from immune mothers three days after inoculation when they were inoculated at 4 or 7 days of age. However, by day 7 post-inoculation, spleen colonization in these groups was similar to spleen colonization in mice from naïve mothers (FIG. 42c) (P <0.05).

Example 16

Strain χ9558 (pYA4088) is Immunogenic in Infant and Neonatal Mice Born to Naïve or Immunized Mothers Method: To assess the immune responses to rPspA after immunization in early life, 18-24 neonatal (7-day-old), and infant (21-day-old) mice per group from naïve or immunized mothers were orally immunized with approximately $5 \times 10^8$ CFU of χ9558 (pYA4088) or strain χ9558 harboring the control plasmid pYA3493. For convenience, these groups will be referred to as N 7 d (naïve mother, pups immunized at day 7), I 7 d (immunized mother, pups immunized at day 7), N 21 d (naïve mother, pups immunized at day 21) and I 21 d (immunized mother, pups immunized on day 21). Mice were immunized again 3 and 6 weeks following the first dose. Age-matched control mice were given sterile BSG to serve as non-immunized controls. Serum IgG antibody responses to rPspA and *Salmonella* LPS and mucosal IgA responses to PspA were measured. This experiment was performed twice with similar results, which have been pooled for analysis.

Result: The anti-PspA serum titers in mice from immunized mothers were higher at three weeks post-primary immunization than the responses in mice born from naïve mothers (FIG. 43a) (P <0.01). The differences in IgG responses between the pups from naïve and immunized mothers were greatest for the pups immunized at 21 days. The anti-PspA titers in pups from naïve mothers were slower to develop than titers from immune mothers, although by week 8 there was no significant difference between the two groups. Among the pups immunized at day 7, pups from immunized mothers developed significantly higher titers than pups from naïve mothers by week 8. Overall, maternal immunity did not play a significant role in development of serum anti-LPS IgG (FIG. 43b), except for the group from immune mothers that were first immunized at day 21, which had significantly lower titers than the other groups (P<0.01 at 6 weeks; P<0.05 at 8 weeks).

Figure 43C:
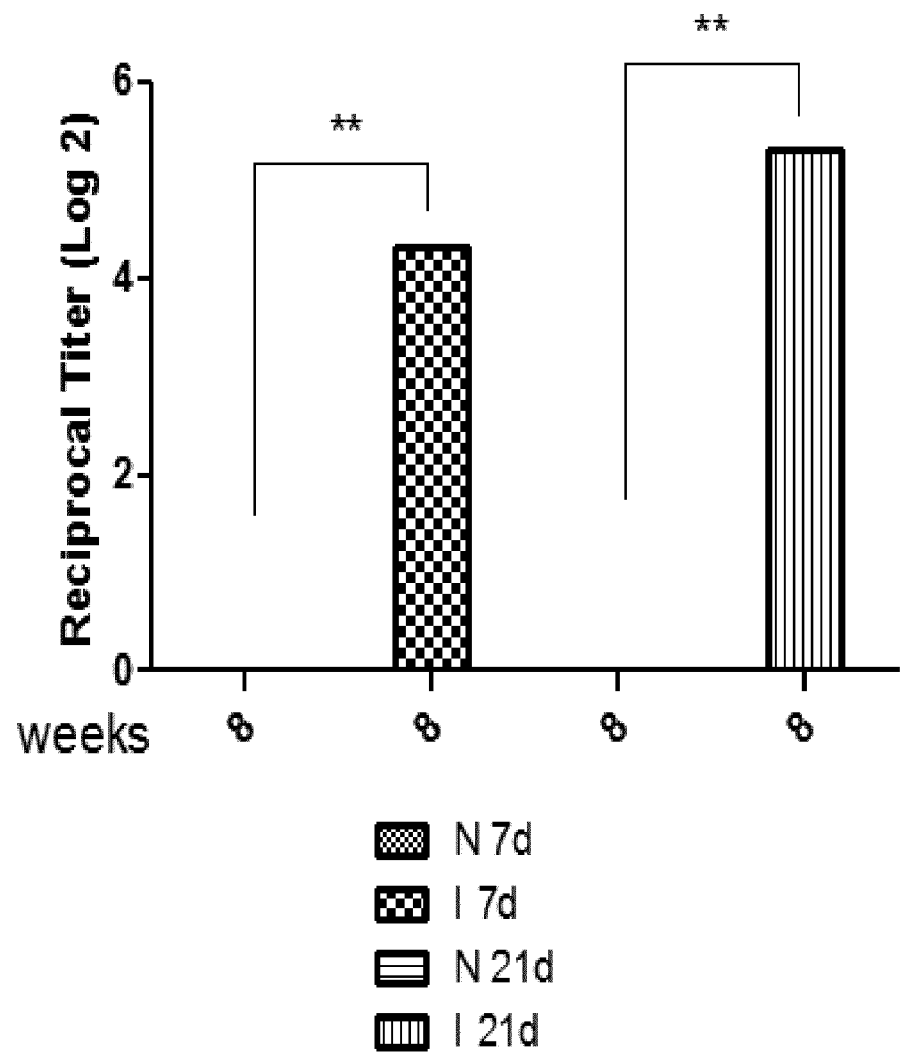

Vaginal washes were used to evaluate mucosal responses. This also allowed us to keep the mice alive for challenge studies. At week 8 vaginal washes were collected and evaluated in the 12-17 female mice per group. No mucosal samples were taken from the remaining male mice. Development of mucosal IgA responses was dramatically and significantly enhanced by maternal immunity (FIG. 43c). There was no detectable anti-PspA IgA in either group of mice from naïve mothers, while mice from immune mothers developed a detectable IgA response (P<0.01).

Example 17

Evaluation of Protective Immunity for χ9558(pYA4088)

Method: To evaluate the capacity of χ9558(pYA4088) to protect mice immunized as neonates or infants, immunized mice (18-24 mice per group) were challenged intraperitoneally with $2 \times 10^3$ CFU (10 $LD_{50}$) of *S. pneumoniae* WU2 four weeks after the final boost (≥11 weeks of age).

Result: All mice inoculated with χ9558(pYA3493), a *Salmonella* strain that does not express pspA, or with BSG, succumbed to the infection within 3 days (FIG. 44). All groups of mice immunized with χ9558(pYA4088) were significantly protected from challenge compared to controls (P<0.05). Protection in the I 21 d group was significantly greater than in the N 21 d groups (P<0.01) and protection in the I 7 d group was significantly greater than in the N 7 d group (P<0.05), indicating that maternal immunization enhances the protective efficacy of χ9558(pYA4088).

Example 18

Comparison of Final Product Vaccine Mutations in *S. Typhimurium* and *S. Typhi*

Although *S. Typhimurium* serves as a model for *S. Typhi*, the two organisms differ in many respects. For that reason, the effect(s) of the proposed second generation mutations on the phenotype of *S. Typhi* were compared to *S. Typhimurium* to ensure that all improvements to the vaccine would have the desired effect. Many mutations resulted in a phenotype not significantly different from *S. Typhimurium* and will not be described in this section. Three examples of mutations that differed between *S. Typhi* and *S. Typhimurium* are described below. Please refer to Table 21 for a list of all strains evaluated.

TABLE 21

*S. Typhi* Strains Constructed for the Evaluation of 2$^{nd}$ Generation Mutations

| Mutation | Ty2 χ Number | ISP1820 χ Number |
|---|---|---|
| ΔrecF126 | χ11053 | |
| ΔrecA62 | χ11159 | |
| ΔrecJ1315 | χ11194 | |
| ΔrecF1074 | χ11134 | χ11133 |
| ΔfliC181 | χ11157 | χ11155 |
| ΔfliC241 | χ11158 | χ11156 |
| ΔfliC2426 | χ11179 | χ11062 |
| Δlrp-23 | χ11031 | χ9998 |
| ΔpagP81::P$_{lpp}$ lpxE | χ11196 | χ11195 |
| Δ(galE-ybhC)-851 | χ11248 | χ11247 |
| ΔP$_{rfc174}$::TT araC P$_{BAD}$ rfc | χ11120 | χ11121 |
| Δpmi-2426 ΔP$_{rfc174}$::TT araC P$_{BAD}$ rfc | χ11170 | χ11171 |
| Δ(yshA-yihW)-207 | χ11058 | χ11032 |

TABLE 21-continued

S. Typhi Strains Constructed for the Evaluation of 2nd Generation Mutations

| Mutation | Ty2 χ Number | ISP1820 χ Number |
|---|---|---|
| Δ(wza-wcaM)-8 | χ11181 | χ11180 |
| ΔbcsABZC2118 | | χ11249 |

Plasmid Recombination in ΔrecF S. Typhi Strains

Deletion of the recF gene in S. Typhimurium has been shown to substantially reduce the frequency of recombination between plasmids within a cell. This allows stable carriage of multiple plasmids. However, a Ty2 ΔrecF126 S. Typhi strain (χ11053) carrying two plasmids with homologous sequences has the same frequency of interplasmid recombination as the wildtype Ty2 (Table 22). Deletion of other rec genes, such as recA (known to reduce interplasmid recombination in *S. Typhimurium*) and recJ (known to reduce interplasmid recombination in *E. coli*) has no impact on the frequency of interplasmid recombination in *S. Typhi*. The deletion of recF in *S. Typhi* is able to reduce the frequency of intraplasmid recombination (recombination between homologous sequences on the same plasmid), which was not observed in *S. Typhimurium*.

TABLE 22

Plasmid recombination in *S. Typhi* Ty2

| | | Intraplasmid | | |
|---|---|---|---|---|
| Strain | Genotype | Direct repeats | Unlinked repeats | Interplasmid |
| χ3769 | *S. Typhi* Ty2 | $5.33 \times 10^{-3}$ | $10.38 \times 10^{-3}$ | $4.90 \times 10^{-3}$ |
| χ11053 | χ3769ΔrecF126 | $5.11 \times 10^{-4}$ | $5.63 \times 10^{-4}$ | $7.22 \times 10^{-3}$ |
| χ11159 | χ3769ΔrecA62 | $1.18 \times 10^{-3}$ | $4.90 \times 10^{-4}$ | $3.25 \times 10^{-3}$ |
| χ11194 | χ3769ΔrecJ1315 | $1.68 \times 10^{-3}$ | $4.70 \times 10^{-3}$ | $9.13 \times 10^{-3}$ |

Invasion of Human Cells by *S. Typhi* with Flagellar Truncations

Large internal deletions in the flagellin protein frequently reduce the motility of strains, but in *S. Typhimurium*, the lack of motility presents no obstacle to epithelial cell invasion or to strain virulence. In *S. Typhi*, clinical observations of typhoid patients have indicated that there is a correlation between reduced motility, reduced cell invasion and strain attenuation. These same studies also indicate that internal deletions in the flagellin protein can reduce the likelihood of disease complications such as meningitis.

Two internal deletions of the flagellin protein were evaluated—ΔfliC181 (deletion of the 180 aa comprising the variable domain of flagellin) and ΔfliC241 (deletion of 240 aa comprising the variable domain and the TLR5 binding site)—as well as a complete deletion of the flagellin protein (ΔfliC2426). In both Ty2 and ISP1820, all mutations in the flagellin protein resulted in severely decreased motility on 0.3% BactoAgar (Table 23). However, a decrease in motility correlated with a decrease in cellular invasion only for strains derived from Ty2 (FIG. 45). Strains derived from ISP1820 that contained internal flagellin deletions were still able to enter epithelial cells, although to a lesser degree than the wild type (FIG. 45). For the invasion assays, all strains of *S. Typhi* were grown to stationary phase in LB with 0.3M NaCl without glucose. Human epithelial cells (INT-407) were infected at an MOI of 1:1-1:2 for one hour, then washed and treated with gentamicin to assess the number of internal *S. Typhi* cells. While it is unlikely that a mutation that renders *S. Typhi* non-invasive would be useful in a live attenuated vaccine, the internal flagellin deletions in ISP1820 which reduce invasion might be able to reduce the occurrence of complications following vaccination.

TABLE 23

Motility of *S. Typhi* Strains Containing Internal Flagellin Deletions.

| Strain | Chi number | Diameter (mm) | Strain | Chi number | Diameter (mm) |
|---|---|---|---|---|---|
| ISP1820 | 3744 | 16 | Ty2 | 3769 | 18 |
| ISP1820 ΔfliC2426 | 11062 | 6.5 | Ty2ΔfliC2426 | 11179 | 6 |
| ISP1820 ΔfliC181 | 11155 | 8 | Ty2 ΔfliC181 | 11157 | 7 |
| ISP1820 ΔfliC241 | 11156 | 7 | Ty2 ΔfliC241 | 11158 | 8 |

Strains were spotted onto 0.3% motility agar and incubated at 37° C. for 16 hours.

LPS O-Antigen Production by Δ(galE-ybhC)-851 *S. Typhi* Strains

The Δ(galE-ybhC)-851 deletion was created to render O-antigen production dependent on the presence of galactose, thus contributing to the delayed attenuation of the strain as well as its biological containment. This deletion was introduced into the ISP1820 and Ty2 wild-type *S. Typhi* strains (generating χ11247 and χ11248, respectively). LPS O-antigen production was assayed by growing strains in nutrient broth, then subculturing in nutrient broth in the presence or absence of 0.05% galactose and growing to stationary phase. LPS present on cells was analyzed by SDS-PAGE (FIG. 46) In the absence of galactose, both *Typhi* Δ(galE-ybhC)-851 strains exhibited the complete absence of O-antigen side chains. This differs from the *S. Typhimurium* mutant, in which small amounts of O-antigen are still produced. An additional difference noted was that the ISP1820-derived strain (χ11247) was much less sensitive to the presence of galactose than the *Typhimurium* or Ty2-derived strain. These findings may allow greater use of the Δ(galE-ybhC)-851 deletion in *S. Typhi* than in *S. Typhimurium.*

Example 19

PcsB Significantly Decreases Nasal and Lung Colonization of *S. pneumoniae* in Mice Methods: Mice were immunized orally with $1.0\times10^{9}$ CFU *Salmonella* on day 0, day 7, and day 42. On day 56, mice were challenged intranasally with $5\times10^{6}$ CFU *S. pneumoniae* EF3030 in 10 μl PBS. After five days, 200 μl of PBS was flushed through the trachea, out the nose, and collected. One hundred microliters of PBS was slowly injected into the lung and slowly suctioned out.

Results: Mice immunized with χ9241 harboring the plasmid containing PcsB fused to the signal sequence of DsbA showed higher immune responses and had significantly lower nasal colonization of *S. pneumoniae* EF3030 (FIG. 53). The PcsB gene was also codon-optimized to increase the expression and secretion of PcsB in *Salmonella*. Fusing the DsbA signal sequence to the PcsB gene significantly increased the secretion of the protein to the periplasm while the change due to codon optimization of the third codon AAA increased expression.

The same strategy may also be used to increase the expression and secretion of StkP in *Salmonella*.

Example 20

PsaA Significantly Decreases Nasal and Lung Colonization of *S. pneumoniae* in Mice An experiment to demonstrate protective immunity to pneumococcal challenge was conducted in C57BL/6 and Balb/C mice. Plasmid pYA4729 encodes the full length PsaA from *S. pneumonia* strain Tigr4. This plasmid and pYA3342 were transformed into χ9241. RASV strains χ9241 (pYA4729) and χ9241 (pYA3342) were grown statically overnight in Luria broth (LB) with 0.05% arabinose at 37° C. and then subcultured 1:100 into fresh warm LB with 0.05% arabinose with aeration at 37° C. to an optical density at 600 nm of 0.8 to 0.9. Cells were harvested by centrifugation at room temperature (6,000×g for 15 min), and the pellet resuspended in buffered saline with gelatin (BSG). Serial dilutions of the RASV strains were plated onto MacConkey agar supplemented with 1% lactose to determine titer. Mice were intranasally or orally inoculated with 10 or 20 μl of BSG containing $1\times10^9$ CFU of the RASV strain. At week 6, the mice were boosted with the same strain at $10^9$ CFU/mouse. At week 10, mice were challenged intranasally with $5\times10^6$ CFU *S. pneumoniae* strain L82016 or E134. Nasal washes were performed using 1 ml of saline after 5-6 days. Serial dilutions of the samples were plated in duplicate on blood agar containing 4 mg/ml gentamicin. Alpha-hemolytic colonies were counted after incubation of the plates for 24 h at 37° C. The detection limit was 20 CFU/ml. For representation in the graphic and statistical analysis $\log_{10}$ was applied to the values and recovery of 0 CFU was considered 20 CFU.

In C57BL/6 mice challenged with *S. pneumoniae* serotype 6B strain L82016, there is significant reduction of *S. pneumoniae* nasal colonization in the χ9241(pYA4729) by intranasal and oral immunization compared to the control animals that received χ9241(pYA3342) (P<0.05 for intranasal immunization and P<0.05 for oral immunization) (FIG. 54). The results were similar in Balb/C mice. Administration of χ9241 (pYA4729) led to significant reduction of *S. pneumoniae* L82016 colonization compared with the χ9241(pYA3342) group by intranasal and oral immunization (P<0.02 for intranasal immunization and P<0.05 for oral immunization in BALB/c mice) (FIG. 54).

Administration of χ9241(pYA4729) induced significant reduction of serotype 23 *S. pneumonia* of E134 colonization compared with the χ9241(pYA3342) group by intranasal and oral immunization (P<0.02 for intranasal immunization and P<0.02 for oral immunization in BALB/c mice) (FIG. 55).

Example 21

Delivery of Multiple Pneumococcal Protective Antigens Encoded on Plasmids Specifying Synthesis of a PspA Fusion, a PspC Fusion and PcsB, PsaA and StkP or PcsB, PsaA and Non-Toxic Ply Construction of a RASV conferring maximal protective immunity to diverse pneumococcal strains will be best achieved by delivery of multiple protective antigens. Since the protective PspA antigen has multiple B-cell epitopes, we have constructed a fusion that represents the diversity found among pneumococcal strains representing PspA Family 1 and PspA Family 2. FIG. 60 contains the DNA and protein sequences of the fusion protein encoded by pYA4432 diagrammed in FIG. 72A. Since the protective PspC antigen also has multiple B-cell epitopes, we have constructed a fusion that represents the PspC diversity found among pneumococcal strains. FIG. 65 contains the DNA and protein sequences of the fusion protein encoded by pYA4633 diagrammed in FIG. 72B. We also will deliver three conserved protective antigens PcsB, PsaA and StkP specified by the plasmid pYA4996 diagrammed in FIG. 72C and with the DNA and protein sequence given in FIG. 78. Alternatively, a non-toxic pneumolysin (Ply) encoded by DNA and protein sequences in either FIG. 70 or 71 can be substituted for the sequence encoding the StkP antigen as diagrammed in pYA4901 as diagrammed in FIG. 73 and with the DNA and protein sequences given in FIG. 79. The delivery of all these protective antigens is expected to induce a very broad immune response to the diversity of pneumococcal strains encountered throughout the world, especially when delivered by *S. Typhi* strains derived from χ9640 with substitutions for some of the mutations depicted and described in Example 22 below.

Example 22

Comparative Phase I Protocol to Test Safety and Immunogenicity in Adult Volunteers of Three Recombinant Attenuated *Salmonella Typhi* Vaccine Vectors Producing *Streptococcus pneumoniae* Surface Protein Antigen PspA This trial was conducted in compliance with the protocol, International Conference on Harmonisation Good Clinical Practice E6 (ICH-GCP) and the applicable Food and Drug Administration and other Department of Health and Human Services regulatory requirements. Study design is summarized below and in FIG. 56.

Objectives:

Objective 1. To evaluate maximum safe tolerable single dose levels of the three recombinant attenuated *S. Typhi* vaccine vectors (χ9639(pYA4088) *S. Typhi* Ty2 $RpoS^-$, χ9640 (pYA4088) *S. Typhi* Ty2 $RpoS^+$ and χ9633(pYA4088) *S. Typhi* ISP1820) using dose escalation studies in healthy adult volunteers.

Objective 2. To evaluate immunogenicity of the three recombinant attenuated *S. Typhi* vaccine vectors [χ9639 (pYA4088) *S. Typhi* Ty2 $RpoS^-$, χ9640(pYA4088) *S. Typhi* Ty2 $RpoS^+$ and χ9633(pYA4088) *S. Typhi* ISP1820] with regard to their abilities to induce mucosal and systemic antibody and cellular immune responses to the *S. pneumoniae* PspA antigen and to *Salmonella* LPS and outer membrane protein (OMP) antigens.

Study Outcome Measures

Primary Outcome Measures: Safety and tolerability will be measured by assessment of reactogenicity and Adverse Events following vaccination. Escalation to the next dose level will occur only after review of the safety data from day 28 post-inoculation of the previous Arm.

Secondary Outcome Measures: Immunogenicity testing will include antibody and/or cellular responses to vaccine at Days 0, 7, 28, 84 and 168.

Hypotheses Tested

The recombinant attenuated χ9639(pYA4088) *S. Typhi* Ty2 $RpoS^-$, χ9640(pYA4088) *S. Typhi* Ty2 $RpoS^+$ and χ9633

(pYA4088) *S. Typhi* ISP1820 vaccine vectors will be safe when given orally to healthy adult human volunteers.

The χ9640(pYA4088) *S. Typhi* Ty2 RpoS⁺ recombinant attenuated vaccine vector will induce higher titers of antibodies to the *Streptococcus pneumoniae* PspA antigen than will the parental χ9639(pYA4088) *S. Typhi* Ty2 RpoS⁻ vector.

The χ9633(pYA4088) *S. Typhi* ISP1820 recombinant attenuated vaccine vector will induce higher titers of antibodies to the *Streptococcus pneumoniae* PspA antigen than will either the parental χ9639(pYA4088) *S. Typhi* Ty2 RpoS⁻ or χ9640(pYA4088) *S. Typhi* Ty2 RpoS⁺ vaccine.

Study Design

The study was a dose escalating study divided into four Arms (1-4). Each Arm will consist of 3 groups (A-C) of 5 healthy young adults 18-40 years of age and each group (A-C) will be administered one of three different vaccine vectors. Each subject will receive an oral dose of vaccine on day 0 and be followed closely to determine the safety, tolerability and immunogenicity of the vector. The vaccine vector found to be both safe and immunogenic with maximum immunogenicity and ease of genetic manipulation will be selected as the parent for second generation vaccine vectors to deliver multiple *S. pneumoniae* protective antigens.

Arm 1 will evaluate the attenuated strains of χ9639 (pYA4088) *S. Typhi* Ty2 RpoS⁻, χ9640(pYA4088) *S. Typhi* Ty2 RpoS⁺ and χ9633(pYA4088) *S. Typhi* ISP1820 in an initial single oral dose ($10^7$ CFU), evaluating safety and immunogenicity of the recombinant attenuated strains. An escalation in dose will proceed only after demonstrating the safety and tolerability of the lower vaccine dose through Day 28.

Arm 2 will evaluate an escalation of dose ($10^8$ CFU) for safety and immunogenicity in 3 groups of 5 new volunteers. An escalation dose will proceed only after demonstrating the safety and tolerability of the lower vaccine dose through Day 28.

Arm 3 will evaluate an escalation of dose ($10^9$ CFU) for safety and immunogenicity in 3 groups of 5 new volunteers. An escalation dose will proceed only after demonstrating the safety and tolerability of the lower vaccine dose through Day 28.

Arm 4 will evaluate an escalation of dose ($10^{10}$ CFU) for safety and immunogenicity in 3 groups of 5 new volunteers. This is the highest dose to be tested The dose escalation schedule is provided below:

TABLE 24

| | Vaccination Schedule Vaccine Groups and Dose | | |
|---|---|---|---|
| | A | B | C |
| (n = 5/group) | χ9639(pYA4088) Ty2 RpoS⁻ | χ9640(pYA4088) Ty2 RpoS⁺ | χ9633(pYA4088) ISP1820 |
| Arm 1 | $10^7$ CFU | $10^7$ CFU | $10^7$ CFU |
| Arm 2 | $10^8$ CFU | $10^8$ CFU | $10^8$ CFU |
| Arm 3 | $10^9$ CFU | $10^9$ CFU | $10^9$ CFU |
| Arm 4 | $10^{10}$ CFU | $10^{10}$ CFU | $10^{10}$ CFU |

The study will enroll Arms 1 through Arms 4 in succession as data are reviewed following each Arm and the Safety Monitoring Committee (SMC) authorizes the next Arm to enroll based on review of 28-day safety data including final blood and stool culture results obtained from previous Arm. This review cycle allows for an interval of a minimum of 35 days of review of all data from the current Arm, after enrollment of the last subjects in the current Arm, before proceeding to the next higher dosage Arm of the study.

Maximum Limit of Tolerability and Dose Escalation of a Specific Strain

Escalation to the next dose level of any of the three vaccine vectors will occur only if the safety data in the preceding dose level cohort for a specific vaccine are acceptable to the SMC and the PI. Escalation to higher dose levels for each of the three vaccines shall proceed in this manner until the highest dose level is reached, or dose-limiting toxicity (maximum limit of tolerability) prevents further dose escalation. Dose escalation of a specific strain shall not proceed in the event that: 3 or more individuals within 1 dose level develop the same severe laboratory abnormality and the abnormality is deemed medically significant by the SMC and is determined to be associated with vaccine; or if 2 or more individuals develop a severe systemic reaction that is determined to be associated with the vaccine; or if 1 individual develops an SAE determined to be associated with vaccine.

Subject Selection Criteria

Volunteers will be healthy 18-40 year old male or non-pregnant female adults who fully understand the purpose and details of the study. Subject exclusion criteria include history of *Salmonella* infection or vaccination, and a history of pneumococcal vaccine.

What is claimed is:

1. A recombinant *Salmonella enterica* serovar *Typhi* bacterium, comprising
   (a) regulated expression of at least one nucleic acid encoding at least two *Streptococcus pneumoniae* antigens and comprises
      (i) at least one nucleic acid sequence encoding a repressor operably linked to a regulatable promoter, wherein the repressor is selected from the group consisting of Lacl, C2, and C1, and the regulatable promoter is selected from the group consisting of PBAD, a promoter regulated by maltose, a promoter regulated by rhamnose, and a promoter regulated by xylose, and (ii) at least one nucleic acid sequence encoding at least two *S. pneumoniae* antigens operably linked to a promoter regulated by the repressor such that the expression of the nucleic acid sequence encoding the *S. pneumoniae* antigens is repressed during in vitro growth of the recombinant bacterium, but the recombinant bacterium is capable of high level expression of the nucleic acid sequence encoding the *S. pneumoniae* antigens in vivo;

(b) regulated attenuation and comprises (i) a first mutation selected from the group consisting of a crp mutation, a fur mutation, and phoPQ mutation such that expression of the nucleic acid sequence encoding crp, fur, or phoPQ is repressed during in vivo growth but the recombinant bacterium is capable of high level expression of the nucleic acid in vitro, and (ii) a second mutation selected from the group consisting of an rfc mutation such that LPS O-antigen synthesis is greater during in vitro growth compared to in vivo growth of the recombinant bacterium, a pmi mutation that results in lack of function of the pmi gene product, and a galE mutation that results in lack of function of the galE gene product;

(c) decreased persistence in the gastrointestinal tract of a host and comprises a mutation selected from the group consisting of a Vi capsular antigen mutation that reduces synthesis of the Vi capsular antigen, a mutation that reduces synthesis of colanic acid, a mutation that reduces synthesis of thin aggregative fimbriae, a mutation that reduces synthesis of cellulose, a mutation that reduces synthesis of extracellular polysaccharide, or a combination thereof; and (d) reduced fluid secretion in the gastrointestinal tract of a host and comprises a mutation selected from the group consisting of a sopB mutation that reduces synthesis of SopB and a pagP mutation that reduces synthesis of PagP.

2. The recombinant bacterium of claim 1, further comprising a RpoS-mutation.

3. The recombinant bacterium of claim 1, wherein the bacterium comprises a first mutation conferring regulated attenuation selected from the group consisting of a $\Delta P_{crp}$::TT araC $P_{BAD}$ crp mutation, a $\Delta P_{fur}$::TT araC $P_{BAD}$ fur mutation, and a $\Delta P_{phoPQ}$::TT araC $P_{BAD}$ phoPQ mutation, and a second mutation conferring regulated attenuation selected from the group consisting of a $\Delta P_{rfc}$::TT araC $P_{BAD}$ rfc mutation, a Δpmi mutation, and a ΔgalE mutation.

4. The recombinant bacterium of claim 1, wherein the bacterium comprises a Vi capsular antigen mutation that reduces synthesis of the Vi capsular antigen, and at least one mutation selected from the group consisting of a mutation that reduces synthesis of colanic acid, a mutation that reduces synthesis of thin aggregative fimbriae, a mutation that reduces synthesis of cellulose, a mutation that reduces synthesis of extracellular polysaccharide.

5. The recombinant bacterium of claim 1, wherein the bacterium comprises a ΔpagP::$P_{ipp}$ IpxE mutation or a ΔsopB mutation.

6. The recombinant bacterium of claim 1, wherein the bacterium comprises (a) a ΔrelA::araC $P_{BAD}$ lacl TT mutation and at least one nucleic acid sequence encoding at least two *S. pneumoniae* antigens operably linked to a promoter regulated by Lacl;

(b) a first mutation conferring regulated attenuation selected from the group consisting of a $\Delta P_{crp}$::TT araC $P_{BAD}$ crp mutation, a $\Delta P_{fur}$::TT araC $P_{BAD}$ fur mutation, and a $\Delta P_{phoPQ}$)::TT araC $P_{BAD}$ phoPQ mutation, and a second mutation conferring regulated attenuation selected from the group consisting of a $\Delta P_{rfc}$::TT araC $P_{BAD}$ rfc mutation, a Δpmi mutation, and a ΔgalE mutation;

(c) at least one mutation selected from the group consisting of a ΔtviABCDE mutation, a ΔtviBCDE mutation, a Δ(gmd-fcl) mutation, a Δ(wza-wcaM) mutation, a ΔagfBAC mutation, a Δ(agfC-agfG) mutation, a ΔbcsABZC mutation, a ΔbcsEFG mutation, and a Δ(yshA-yihW) mutation; and (d) at least one mutation selected from the group consisting of a ΔsopB mutation and a ΔpagP::P$_{lpp}$ lpxE mutation.

7. A vaccine composition, the composition comprising a bacterium of claim 1.

8. The recombinant bacterium of claim 1, wherein the bacterium comprises (i) a mutation selected from the group consisting of a ΔtviABCDE mutation, a ΔtviBCDE mutation, a Δ(gmd-fcl) mutation, and a Δ(wza-wcaM) mutation, and (ii) a mutation selected from the group consisting of a ΔagfBAC mutation, a Δ(agfC-agfG) mutation, a ΔbcsABZC mutation, a ΔbcsEFG mutation, and a Δ(yshA-yihW) mutation.

9. The recombinant bacterium of claim 1, wherein the bacterium is derived from an RpoS-strain and has a restored rpoS gene.

10. The recombinant bacterium of claim 1, wherein the at least two *S. pneumoniae* antigens are independently selected from the group consisting of PspA, PspC, Ply, PcsB, PsaA, StkP, a PspA fusion, and a PspC fusion, wherein the PspA fusion comprises sequences from two or more PspA antigen families and the PspC fusion comprises sequences from two or more PspC antigen families.

\* \* \* \* \*

SEQUENCE LISTING

```
<160> NUMBER OF SEQ ID NOS: 140

<210> SEQ ID NO 1
<211> LENGTH: 852
<212> TYPE: DNA
<213> ORGANISM: Streptococcus pneumoniae

<400> SEQUENCE: 1
tctcccgtag ccagtcagtc taaagctgag aaagactatg atgcagcgaa gaaagatgct      60
aagaatgcga aaaaagcagt agaagatgct caaaaggctt tagatgatgc aaaagctgct     120
cagaaaaaat atgacgagga tcagaagaaa actgaggaga aagccgcgct agaaaaagca     180
gcgtctgaag agatggataa ggcagtggca gcagttcaac aagcgaatct ggcctatcaa     240
caagctacag acaaagccgc aaaagacgca gcagataaga tgatagatga agctaagaaa     300
cgcgaagaag aggcaaaaac taaatttaat actgttcgag caatggtagt tcctgagcca     360
```

```
gagcagttgg ctgagactaa gaaaaaatca gaagaagcta acaaaaagc accagaactt    420 actaaaaaac tagaagaagc taaagcaaaa ttagaagagg ctgagaaaaa agctactgaa    480
gccaaacaaa aagtggatgc tgaagaagtc gctcctcaag ctaaaatcgc tgaattggaa    540
aatcaagttc atagactaga acaagagctc aaagagattg atgagtctga atcagaagat    600
tatgctaaag aaggtttccg tgctcctctt caatctaaat tggatgccaa aaaagctaaa    660
ctatcaaaac ttgaagagtt aagtgataag attgatgagt tagacgctga aattgcaaaa    720
cttgaagatc aacttaaagc tgctgaagaa aacaataatg tagaagacta ctttaaagaa    780
ggtttagaga aaactattgc tgctaaaaaa gctgaattag aaaaaactga agctgacctt    840
aagaaagcat aa    852
```

<210> SEQ ID NO 2
<211> LENGTH: 283
<212> TYPE: PRT
<213> ORGANISM: Streptococcus pneumoniae

<400> SEQUENCE: 2

```
Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys
            20                  25                  30

Ala Leu Asp Asp Ala Lys Ala Ala Gln Lys Lys Tyr Asp Glu Asp Gln
        35                  40                  45

Lys Lys Thr Glu Glu Lys Ala Ala Leu Glu Lys Ala Ala Ser Glu Glu
    50                  55                  60

Met Asp Lys Ala Val Ala Ala Val Gln Gln Ala Asn Leu Ala Tyr Gln
65                  70                  75                  80

Gln Ala Thr Asp Lys Ala Lys Asp Ala Ala Asp Lys Met Ile Asp
                85                  90                  95

Glu Ala Lys Lys Arg Glu Glu Glu Ala Lys Thr Lys Phe Asn Thr Val
            100                 105                 110

Arg Ala Met Val Val Pro Glu Pro Glu Gln Leu Ala Glu Thr Lys Lys
        115                 120                 125

Lys Ser Glu Glu Ala Lys Gln Lys Ala Pro Glu Leu Thr Lys Lys Leu
    130                 135                 140

Glu Glu Ala Lys Ala Lys Leu Glu Glu Ala Glu Lys Lys Ala Thr Glu
145                 150                 155                 160

Ala Lys Gln Lys Val Asp Ala Glu Glu Val Ala Pro Gln Ala Lys Ile
                165                 170                 175

Ala Glu Leu Glu Asn Gln Val His Arg Leu Glu Gln Glu Leu Lys Glu
            180                 185                 190

Ile Asp Glu Ser Glu Ser Glu Asp Tyr Ala Lys Glu Gly Phe Arg Ala
        195                 200                 205

Pro Leu Gln Ser Lys Leu Asp Ala Lys Lys Ala Lys Leu Ser Lys Leu
    210                 215                 220

Glu Glu Leu Ser Asp Lys Ile Asp Glu Leu Asp Ala Glu Ile Ala Lys
225                 230                 235                 240

Leu Glu Asp Gln Leu Lys Ala Ala Glu Glu Asn Asn Asn Val Glu Asp
                245                 250                 255

Tyr Phe Lys Glu Gly Leu Glu Lys Thr Ile Ala Ala Lys Lys Ala Glu
            260                 265                 270

Leu Glu Lys Thr Glu Ala Asp Leu Lys Lys Ala
        275                 280
```

<210> SEQ ID NO 3
<211> LENGTH: 852
<212> TYPE: DNA
<213> ORGANISM: Streptococcus pneumoniae

<400> SEQUENCE: 3

```
tctccggtag ccagtcagtc taaagctgag aaagactatg atgcagcgaa gaaagatgct    60
aagaatgcta aaaagcagt  agaagatgct caaaaggctt tagatgatgc aaaagctgct   120
cagaaaaaat atgacgagga tcagaagaaa actgaggaga aagccgcgct ggaaaaagca   180
gcgtctgaag agatggataa ggcagtggca gcagttcaac aagcgtatct ggcctatcaa   240
caagctacag acaaagccgc aaaagacgca gcagataaga tgatcgatga agctaagaaa   300
cgcgaagaag aggcaaaaac taaatttaat actgttcgtg caatggtagt tcctgagcca   360
gagcagttgg cggagactaa gaaaaaatca gaagaagcta acaaaaagc  accagaactt   420
actaaaaaac tggaagaagc taaagcaaaa ttagaagagg ctgagaaaaa agctactgaa   480
gccaaacaaa aagtggatgc tgaagaagtc gctcctcaag ctaaaatcgc tgaattggaa   540
aatcaagttc atcgtctgga acaagagctc aaagagattg atgagtctga atcagaagat   600
tatgctaaag aaggtttccg tgctcctctt caatctaaat tggatgccaa aaaagctaaa   660
ctgtcaaaac ttgaagagtt aagtgataag attgatgagt tagacgctga aattgcaaaa   720
cttgaagatc aacttaaagc tgctgaagaa aacaataatg tagaagacta ctttaaagaa   780
ggtttagaga aaactattgc tgctaaaaaa gctgaattag aaaaaactga agctgacctt   840
aagaaagcat aa                                                        852
```

<210> SEQ ID NO 4
<211> LENGTH: 283
<212> TYPE: PRT
<213> ORGANISM: Streptococcus pneumoniae

<400> SEQUENCE: 4

Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys
            20                  25                  30

Ala Leu Asp Asp Ala Lys Ala Ala Gln Lys Lys Tyr Asp Glu Asp Gln
        35                  40                  45

Lys Lys Thr Glu Glu Lys Ala Ala Leu Glu Lys Ala Ala Ser Glu Glu
    50                  55                  60

Met Asp Lys Ala Val Ala Ala Val Gln Gln Ala Tyr Leu Ala Tyr Gln
65                  70                  75                  80

Gln Ala Thr Asp Lys Ala Ala Lys Asp Ala Ala Asp Lys Met Ile Asp
                85                  90                  95

Glu Ala Lys Lys Arg Glu Glu Glu Ala Lys Thr Lys Phe Asn Thr Val
            100                 105                 110

Arg Ala Met Val Val Pro Glu Pro Glu Gln Leu Ala Glu Thr Lys Lys
        115                 120                 125

Lys Ser Glu Glu Ala Lys Gln Lys Ala Pro Glu Leu Thr Lys Lys Leu
    130                 135                 140

Glu Glu Ala Lys Ala Lys Leu Glu Glu Ala Glu Lys Lys Ala Thr Glu
145                 150                 155                 160

Ala Lys Gln Lys Val Asp Ala Glu Glu Val Ala Pro Gln Ala Lys Ile
                165                 170                 175

```
Ala Glu Leu Glu Asn Gln Val His Arg Leu Glu Gln Glu Leu Lys Glu
            180                 185                 190

Ile Asp Glu Ser Glu Ser Glu Asp Tyr Ala Lys Glu Gly Phe Arg Ala
            195                 200                 205

Pro Leu Gln Ser Lys Leu Asp Ala Lys Lys Ala Lys Leu Ser Lys Leu
            210                 215                 220

Glu Glu Leu Ser Asp Lys Ile Asp Glu Leu Asp Ala Glu Ile Ala Lys
225                 230                 235                 240

Leu Glu Asp Gln Leu Lys Ala Ala Glu Glu Asn Asn Val Glu Asp
                245                 250                 255

Tyr Phe Lys Glu Gly Leu Glu Lys Thr Ile Ala Ala Lys Lys Ala Glu
            260                 265                 270

Leu Glu Lys Thr Glu Ala Asp Leu Lys Lys Ala
            275                 280

<210> SEQ ID NO 5
<211> LENGTH: 765
<212> TYPE: DNA
<213> ORGANISM: Streptococcus pneumoniae

<400> SEQUENCE: 5
tctcccgtag ccagtcagtc taaagctgag aaagactatg atgcagcgaa gaaagatgct      60
aagaatgcga aaaaagcagt agaagatgct caaaaggctt tagatgatgc aaaagctgct     120
cagaaaaaat atgacgagga tcagaagaaa actgaggaga agccgcgcgt agaaaaagca     180
gcgtctgaag agatggataa ggcagtggca gcagttcaac aagcgaatct ggcctatcaa     240
caagctacag acaaagccgc aaaagacgca gcagataaga tgatagatga agctaagaaa     300
cgcgaagaag aggcaaaaac taaatttaat actgttcgag caatggtagt tcctgagcca     360
gagcagttgg ctgagactaa gaaaaaatca gaagaagcta acaaaaagc accagaactt      420 actaaaaaac tagaagaagc taaagcaaaa ttagaagagg ctgagaaaaa agctactgaa     480
gccaaacaaa aagtggatgc tgaagaagtc gctcctcaag ctaaaatcgc tgaattggaa     540
aatcaagttc atagactaga acaagagctc aaagagattg atgagtctga atcagaagat     600
tatgctaaag aaggtttccg tgctcctctt caatctaaat tggatgccaa aaagctaaa      660 ctatcaaaac ttgaagagtt aagtgataag attgatgagt tagacgctga aattgcaaaa     720
cttgaagatc aacttaaagc tgctgaagaa acaataatg tagaa                      765

<210> SEQ ID NO 6
<211> LENGTH: 255
<212> TYPE: PRT
<213> ORGANISM: Streptococcus pneumoniae

<400> SEQUENCE: 6

Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys
                20                  25                  30

Ala Leu Asp Asp Ala Lys Ala Ala Gln Lys Lys Tyr Asp Glu Asp Gln
            35                  40                  45

Lys Lys Thr Glu Glu Lys Ala Ala Leu Glu Lys Ala Ala Ser Glu Glu
        50                  55                  60

Met Asp Lys Ala Val Ala Ala Val Gln Gln Ala Asn Leu Ala Tyr Gln
65                  70                  75                  80
```

Gln Ala Thr Asp Lys Ala Ala Lys Asp Ala Asp Lys Met Ile Asp
            85                  90                  95

Glu Ala Lys Lys Arg Glu Glu Ala Lys Thr Lys Phe Asn Thr Val
        100                 105                 110

Arg Ala Met Val Val Pro Glu Pro Glu Gln Leu Ala Glu Thr Lys Lys
        115                 120                 125

Lys Ser Glu Glu Ala Lys Gln Lys Ala Pro Glu Leu Thr Lys Lys Leu
    130                 135                 140

Glu Glu Ala Lys Ala Lys Leu Glu Glu Ala Glu Lys Lys Ala Thr Glu
145                 150                 155                 160

Ala Lys Gln Lys Val Asp Ala Glu Val Ala Pro Gln Ala Lys Ile
            165                 170                 175

Ala Glu Leu Glu Asn Gln Val His Arg Leu Glu Gln Glu Leu Lys Glu
        180                 185                 190

Ile Asp Glu Ser Glu Ser Glu Asp Tyr Ala Lys Glu Gly Phe Arg Ala
        195                 200                 205

Pro Leu Gln Ser Lys Leu Asp Ala Lys Lys Ala Lys Leu Ser Lys Leu
        210                 215                 220

Glu Glu Leu Ser Asp Lys Ile Asp Glu Leu Asp Ala Glu Ile Ala Lys
225                 230                 235                 240

Leu Glu Asp Gln Leu Lys Ala Ala Glu Glu Asn Asn Asn Val Glu
            245                 250                 255

<210> SEQ ID NO 7
<211> LENGTH: 765
<212> TYPE: DNA
<213> ORGANISM: Streptococcus pneumoniae

<400> SEQUENCE: 7
tctccggtag ccagtcagtc taaagctgag aaagactatg atgcagcgaa gaaagatgct      60
aagaatgcta aaaagcagt agaagatgct caaaaggctt tagatgatgc aaaagctgct     120
cagaaaaaat atgacgagga tcagaagaaa actgaggaga aagccgcgct ggaaaaagca     180
gcgtctgaag agatggataa ggcagtggca gcagttcaac aagcgtatct ggcctatcaa     240
caagctacag acaaagccgc aaaagacgca gcagataaga tgatcgatga agctaagaaa     300
cgcgaagaag aggcaaaaac taaatttaat actgttcgtg caatggtagt tcctgagcca     360
gagcagttgg cggagactaa gaaaaaatca gaagaagcta acaaaaaagc accagaactt     420
actaaaaaac tggaagaagc taaagcaaaa ttagaagagg ctgagaaaaa agctactgaa     480
gccaaacaaa aagtggatgc tgaagaagtc gctcctcaag ctaaaatcgc tgaattggaa     540
aatcaagttc atcgtctgga acaagagctc aaagagattg atgagtctga atcagaagat     600
tatgctaaag aaggtttccg tgctcctctt caatctaaat tggatgccaa aaaagctaaa     660
ctgtcaaaac ttgaagagtt aagtgataag attgatgagt tagacgctga aattgcaaaa     720
cttgaagatc aacttaaagc tgctgaagaa aacaataatg tagaa                     765

<210> SEQ ID NO 8
<211> LENGTH: 255
<212> TYPE: PRT
<213> ORGANISM: Streptococcus pneumoniae

<400> SEQUENCE: 8

Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys

|   |   |   |   | 20 |   |   |   |   | 25 |   |   |   |   | 30 |   |

Ala Leu Asp Asp Ala Lys Ala Ala Gln Lys Lys Tyr Asp Glu Asp Gln
                35                  40                  45

Lys Lys Thr Glu Glu Lys Ala Ala Leu Glu Lys Ala Ala Ser Glu Glu
         50                  55                  60

Met Asp Lys Ala Val Ala Val Gln Gln Ala Tyr Leu Ala Tyr Gln
 65              70                  75                  80

Gln Ala Thr Asp Lys Ala Ala Lys Asp Ala Asp Lys Met Ile Asp
                 85                  90                  95

Glu Ala Lys Lys Arg Glu Glu Ala Lys Thr Lys Phe Asn Thr Val
                100                 105                 110

Arg Ala Met Val Val Pro Glu Pro Glu Gln Leu Ala Glu Thr Lys Lys
            115                 120                 125

Lys Ser Glu Glu Ala Lys Gln Lys Ala Pro Glu Leu Thr Lys Lys Leu
        130                 135                 140

Glu Glu Ala Lys Ala Lys Leu Glu Glu Ala Glu Lys Lys Ala Thr Glu
145                 150                 155                 160

Ala Lys Gln Lys Val Asp Ala Glu Glu Val Ala Pro Gln Ala Lys Ile
                165                 170                 175

Ala Glu Leu Glu Asn Gln Val His Arg Leu Glu Gln Glu Leu Lys Glu
            180                 185                 190

Ile Asp Glu Ser Glu Ser Glu Asp Tyr Ala Lys Glu Gly Phe Arg Ala
        195                 200                 205

Pro Leu Gln Ser Lys Leu Asp Ala Lys Lys Ala Lys Leu Ser Lys Leu
    210                 215                 220

Glu Glu Leu Ser Asp Lys Ile Asp Leu Asp Ala Glu Ile Ala Lys
225                 230                 235                 240

Leu Glu Asp Gln Leu Lys Ala Ala Glu Glu Asn Asn Asn Val Glu
                245                 250                 255

<210> SEQ ID NO 9
<211> LENGTH: 1256
<212> TYPE: DNA
<213> ORGANISM: Streptococcus pneumoniae

<400> SEQUENCE: 9

| aaccagtcta | aagctgagaa | agactatgat | gcagcagtga | aaaaatctga | agctgctaag | 60 |
| aaagattacg | aaacggctaa | aaagaaagca | gaagacgctc | agaagaaata | tgatgaggat | 120 |
| cagaagaaaa | ctgaggcaaa | agcggaaaaa | gaacgtaaag | cttctgaaaa | gatcgctgag | 180 |
| gcaacaaaag | aagttcaaca | agcgtaccta | gcttatctac | aagctagcaa | cgaaagtcag | 240 |
| cgtaaagagg | cagataagaa | gatcaaagaa | gctacgcaac | gcaaagatga | ggcggaagct | 300 |
| gcatttgcta | ctattcgtac | aacaattgta | gttcctgaac | caagtgagtt | agctgagact | 360 |
| aagaaaaaag | cagaagaggc | aacaaaagaa | gcagaagtag | ctaagaaaaa | atctgaagag | 420 |
| gcagctaaag | aggtagaagt | agagaaaaat | aaaatccttg | aacaagatgc | tgaaaacgaa | 480 |
| aagaaaattg | acgtacttca | aaacaaagtc | gctgatttag | aaaaaggaat | tgctccttat | 540 |
| caaaacgaag | tcgctgaatt | aaataaagaa | attgctcgtc | ttcaaagcga | tttaaaagat | 600 |
| gctgaagaaa | ataatgtaga | agactacatt | aagaaggtt | tagagcaagc | tatcactaat | 660 |
| aaaaaagctg | aattagctac | aactcaacaa | aacatcgata | aactcaaaaa | agatttagag | 720 |
| gatgctgaat | tagaacttga | aaaagtatta | gctacattag | cccctgaagg | taaaactcaa | 780 |
| gatgaattag | ataaagaagc | tgctgaagct | gagttgaatg | aaaaagttga | agctcttcaa | 840 |

```
aaccaagttg ctgaattaga agaagaactt tcaaaacttg aagataatct taaagatgct      900
gaaacaaaca acgttgaaga ctacattaaa gaaggtttag aagaagctat cgcgactaaa      960
aaagctgaat tggaaaaaac tcaaaaagaa ttagatgcag ctcttaatga gttaggccct     1020
gatggagatg aagaagagac tccagcgccg gctcctcaac cagaaaaacc agctgaagag     1080
cctgagaatc cagctccagc accaaaacca gagaagtcag cagatcaaca agctgaagaa     1140
gactatgctc gtagatcaga agaagaatat aatcgcttga cccaacagca accgccaaaa     1200
gcagaaaaac cagctcctgc accacaacca gagcaaccag ctcctgcacc aataat         1256

<210> SEQ ID NO 10
<211> LENGTH: 418
<212> TYPE: PRT
<213> ORGANISM: Streptococcus pneumoniae

<400> SEQUENCE: 10
```

| Asn | Gln | Ser | Lys | Ala | Glu | Lys | Asp | Tyr | Asp | Ala | Ala | Val | Lys | Lys | Ser |
|---|---|---|---|---|---|---|---|---|---|---|---|---|---|---|---|
| 1 | | | | 5 | | | | | 10 | | | | | 15 | |

| Glu | Ala | Ala | Lys | Lys | Asp | Tyr | Glu | Thr | Ala | Lys | Lys | Ala | Glu | Asp |
|---|---|---|---|---|---|---|---|---|---|---|---|---|---|---|
| | | | 20 | | | | | 25 | | | | | 30 | |

| Ala | Gln | Lys | Lys | Tyr | Asp | Glu | Asp | Gln | Lys | Lys | Thr | Glu | Ala | Lys | Ala |
|---|---|---|---|---|---|---|---|---|---|---|---|---|---|---|---|
| | | 35 | | | | | 40 | | | | | 45 | | | |

| Glu | Lys | Glu | Arg | Lys | Ala | Ser | Glu | Lys | Ile | Ala | Glu | Ala | Thr | Lys | Glu |
|---|---|---|---|---|---|---|---|---|---|---|---|---|---|---|---|
| 50 | | | | | 55 | | | | | 60 | | | | | |

| Val | Gln | Gln | Ala | Tyr | Leu | Ala | Tyr | Leu | Gln | Ala | Ser | Asn | Glu | Ser | Gln |
|---|---|---|---|---|---|---|---|---|---|---|---|---|---|---|---|
| 65 | | | | 70 | | | | | 75 | | | | | 80 | |

| Arg | Lys | Glu | Ala | Asp | Lys | Lys | Ile | Lys | Glu | Ala | Thr | Gln | Arg | Lys | Asp |
|---|---|---|---|---|---|---|---|---|---|---|---|---|---|---|---|
| | | | | 85 | | | | | 90 | | | | | 95 | |

| Glu | Ala | Glu | Ala | Ala | Phe | Ala | Thr | Ile | Arg | Thr | Thr | Ile | Val | Val | Pro |
|---|---|---|---|---|---|---|---|---|---|---|---|---|---|---|---|
| | 100 | | | | | 105 | | | | | 110 | | | | |

| Glu | Pro | Ser | Glu | Leu | Ala | Glu | Thr | Lys | Lys | Lys | Ala | Glu | Glu | Ala | Thr |
|---|---|---|---|---|---|---|---|---|---|---|---|---|---|---|---|
| | | 115 | | | | | 120 | | | | | 125 | | | |

| Lys | Glu | Ala | Glu | Val | Ala | Lys | Lys | Ser | Glu | Glu | Ala | Ala | Lys | Glu |
|---|---|---|---|---|---|---|---|---|---|---|---|---|---|---|
| 130 | | | | | 135 | | | | | 140 | | | | |

| Val | Glu | Val | Glu | Lys | Asn | Lys | Ile | Leu | Glu | Gln | Asp | Ala | Glu | Asn | Glu |
|---|---|---|---|---|---|---|---|---|---|---|---|---|---|---|---|
| 145 | | | | | 150 | | | | | 155 | | | | | 160 |

| Lys | Lys | Ile | Asp | Val | Leu | Gln | Asn | Lys | Val | Ala | Asp | Leu | Glu | Lys | Gly |
|---|---|---|---|---|---|---|---|---|---|---|---|---|---|---|---|
| | | | | 165 | | | | | 170 | | | | | 175 | |

| Ile | Ala | Pro | Tyr | Gln | Asn | Glu | Val | Ala | Glu | Leu | Asn | Lys | Glu | Ile | Ala |
|---|---|---|---|---|---|---|---|---|---|---|---|---|---|---|---|
| | | | 180 | | | | | 185 | | | | | 190 | | |

| Arg | Leu | Gln | Ser | Asp | Leu | Lys | Asp | Ala | Glu | Glu | Asn | Val | Glu | Asp |
|---|---|---|---|---|---|---|---|---|---|---|---|---|---|---|
| | | 195 | | | | | 200 | | | | | 205 | | |

| Tyr | Ile | Lys | Glu | Gly | Leu | Glu | Gln | Ala | Ile | Thr | Asn | Lys | Lys | Ala | Glu |
|---|---|---|---|---|---|---|---|---|---|---|---|---|---|---|---|
| | 210 | | | | | 215 | | | | | 220 | | | | |

| Leu | Ala | Thr | Thr | Gln | Gln | Asn | Ile | Asp | Lys | Thr | Gln | Lys | Asp | Leu | Glu |
|---|---|---|---|---|---|---|---|---|---|---|---|---|---|---|---|
| 225 | | | | | 230 | | | | | 235 | | | | | 240 |

| Asp | Ala | Glu | Leu | Glu | Leu | Glu | Lys | Val | Leu | Ala | Thr | Leu | Asp | Pro | Glu |
|---|---|---|---|---|---|---|---|---|---|---|---|---|---|---|---|
| | | | | 245 | | | | | 250 | | | | | 255 | |

| Gly | Lys | Thr | Gln | Asp | Glu | Leu | Asp | Lys | Glu | Ala | Ala | Glu | Ala | Glu | Leu |
|---|---|---|---|---|---|---|---|---|---|---|---|---|---|---|---|
| | | | 260 | | | | | 265 | | | | | 270 | | |

| Asn | Glu | Lys | Val | Glu | Ala | Leu | Gln | Asn | Gln | Val | Ala | Glu | Leu | Glu | Glu |
|---|---|---|---|---|---|---|---|---|---|---|---|---|---|---|---|
| | | 275 | | | | | 280 | | | | | 285 | | | |

| Glu | Leu | Ser | Lys | Leu | Glu | Asp | Asn | Leu | Lys | Asp | Ala | Glu | Thr | Asn | Asn |
|---|---|---|---|---|---|---|---|---|---|---|---|---|---|---|---|
| | 290 | | | | | 295 | | | | | 300 | | | | |

Val Glu Asp Tyr Ile Lys Glu Gly Leu Glu Glu Ala Ile Ala Thr Lys
305                 310                 315                 320

Lys Ala Glu Leu Glu Lys Thr Gln Lys Glu Leu Asp Ala Ala Leu Asn
            325                 330                 335

Glu Leu Gly Pro Asp Gly Asp Glu Glu Thr Pro Ala Pro Ala Pro
        340                 345                 350

Gln Pro Glu Lys Pro Ala Glu Glu Pro Glu Asn Pro Ala Pro Ala Pro
            355                 360                 365

Lys Pro Glu Lys Ser Ala Asp Gln Gln Ala Glu Glu Asp Tyr Ala Arg
        370                 375                 380

Arg Ser Glu Glu Glu Tyr Asn Arg Leu Thr Gln Gln Pro Pro Lys
385                 390                 395                 400

Ala Glu Lys Pro Ala Pro Ala Pro Gln Pro Glu Gln Pro Ala Pro Ala
                405                 410                 415

Pro Ile

```
<210> SEQ ID NO 11
<211> LENGTH: 1251
<212> TYPE: DNA
<213> ORGANISM: Streptococcus pneumoniae

<400> SEQUENCE: 11
aaccagtcta aagctgagaa agactatgat gcagcagtga aaaaatctga agctgctaag      60
aaagattacg aaacggctaa aagaaagca gaagacgctc agaagaaata tgatgaggat     120
cagaagaaaa ctgaggcaaa agcggaaaaa gaaagaaaag cttctgaaaa gatagctgag     180
gcaacaaaag aagttcaaca agcgtaccta gcttatctac aagctagcaa cgaaagtcag     240
agaaaagagg cagataagaa gataaaagaa gctacgcaac gcaaagatga ggcggaagct     300
gcatttgcta ctattcgaac aacaattgta gttcctgaac caagtgagtt agctgagact     360
aagaaaaaag cagaagaggc aacaaagaa gcagaagtag ctaagaaaaa atctgaagag     420
gcagctaaag aggtagaagt agagaaaaat aaaatacttg aacaagatgc tgaaaacgaa     480
aagaaaattg acgtacttca aaacaaagtc gctgatttag aaaaaggaat tgctccttat     540
caaaacgaag tcgctgaatt aaataaagaa attgctagac ttcaaagcga tttaaaagat     600
gctgaagaaa ataatgtaga agactacatt aagaaaggtt tagagcaagc tatcactaat     660
aaaaaagctg aattagctac aactcaacaa acatagata aaactcaaaa agatttagag     720
gatgctgaat tagaacttga aaagtatta gctacattag ccctgaagg taaaactcaa     780 gatgaattag ataaagaagc tgctgaagct gagttgaatg aaaaagttga agctcttcaa     840
aaccaagttg ctgaattaga agaagaactt tcaaaacttg aagataatct taaagatgct     900
gaaacaaaca acgttgaaga ctacattaaa gaaggttag aagaagctat cgcgactaaa     960
aaagctgaat tggaaaaaac tcaaaaagaa ttagatgcag ctcttaatga gttaggccct    1020
gatggagatg aagaagagac tccagcgccg gctcctcaac cagaaaaacc agctgaagag    1080
cctgagaatc cagctccagc accaaaacca gagaagtcag cagatcaaca agctgaagaa    1140
gactatgctc gtagatcaga agaagaatat aatcgcttga cccaacagca accgccaaaa    1200
gcagaaaaac cagctcctgc accacaacca gagcaaccag ctcctgcacc a            1251

<210> SEQ ID NO 12
<211> LENGTH: 417
<212> TYPE: PRT
<213> ORGANISM: Streptococcus pneumoniae
```

<400> SEQUENCE: 12

```
Asn Gln Ser Lys Ala Glu Lys Asp Tyr Asp Ala Ala Val Lys Lys Ser
1               5                   10                  15
Glu Ala Ala Lys Lys Asp Tyr Glu Thr Ala Lys Lys Ala Glu Lys Asp
                20                  25                  30
Ala Gln Lys Lys Tyr Asp Glu Asp Gln Lys Lys Thr Glu Ala Lys Ala
                35                  40                  45
Glu Lys Glu Arg Lys Ala Ser Glu Lys Ile Ala Glu Ala Thr Lys Glu
            50                  55                  60
Val Gln Gln Ala Tyr Leu Ala Tyr Leu Gln Ala Ser Asn Glu Ser Gln
65                  70                  75                  80
Arg Lys Glu Ala Asp Lys Lys Ile Lys Glu Ala Thr Gln Arg Lys Asp
                85                  90                  95
Glu Ala Glu Ala Ala Phe Ala Thr Ile Arg Thr Thr Ile Val Val Pro
                100                 105                 110
Glu Pro Ser Glu Leu Ala Glu Thr Lys Lys Ala Glu Glu Ala Thr
                115                 120                 125
Lys Glu Ala Glu Val Ala Lys Lys Ser Glu Glu Ala Ala Lys Glu
130                 135                 140
Val Glu Val Glu Lys Asn Lys Ile Leu Glu Gln Asp Ala Glu Asn Glu
145                 150                 155                 160
Lys Lys Ile Asp Val Leu Gln Asn Lys Val Ala Asp Leu Glu Lys Gly
                165                 170                 175
Ile Ala Pro Tyr Gln Asn Glu Val Ala Glu Leu Asn Lys Glu Ile Ala
                180                 185                 190
Arg Leu Gln Ser Asp Leu Lys Asp Ala Glu Glu Asn Asn Val Glu Asp
                195                 200                 205
Tyr Ile Lys Glu Gly Leu Glu Gln Ala Ile Thr Asn Lys Lys Ala Glu
                210                 215                 220
Leu Ala Thr Thr Gln Gln Asn Ile Asp Lys Thr Gln Lys Asp Leu Glu
225                 230                 235                 240
Asp Ala Glu Leu Glu Leu Glu Lys Val Leu Ala Thr Leu Asp Pro Glu
                245                 250                 255
Gly Lys Thr Gln Asp Glu Leu Asp Lys Glu Ala Ala Glu Ala Glu Leu
                260                 265                 270
Asn Glu Lys Val Glu Ala Leu Gln Asn Gln Val Ala Glu Leu Glu Glu
                275                 280                 285
Glu Leu Ser Lys Leu Glu Asp Asn Leu Lys Asp Ala Glu Thr Asn Asn
                290                 295                 300
Val Glu Asp Tyr Ile Lys Glu Gly Leu Glu Glu Ala Ile Ala Thr Lys
305                 310                 315                 320
Lys Ala Glu Leu Glu Lys Thr Gln Lys Glu Leu Asp Ala Ala Leu Asn
                325                 330                 335
Glu Leu Gly Pro Asp Gly Asp Glu Glu Thr Pro Ala Pro Ala Pro
                340                 345                 350
Gln Pro Glu Lys Pro Ala Glu Glu Pro Glu Asn Pro Ala Pro Ala Pro
                355                 360                 365
Lys Pro Glu Lys Ser Ala Asp Gln Gln Ala Glu Asp Tyr Ala Arg
                370                 375                 380
Arg Ser Glu Glu Glu Tyr Asn Arg Leu Thr Gln Gln Pro Pro Lys
385                 390                 395                 400
Ala Glu Lys Pro Ala Pro Ala Pro Gln Pro Glu Gln Pro Ala Pro Ala
```

Pro

<210> SEQ ID NO 13
<211> LENGTH: 2117
<212> TYPE: DNA
<213> ORGANISM: Streptococcus pneumoniae

<400> SEQUENCE: 13

```
gaattctctc cggtagccag tcagtctaaa gctgagaaag actatgatgc agcgaagaaa      60
gatgctaaga atgctaaaaa agcagtagaa gatgctcaaa aggctttaga tgatgcaaaa     120
gctgctcaga aaaatatga cgaggatcag aagaaaactg aggagaaagc cgcgctggaa     180
aaagcagcgt ctgaagagat ggataaggca gtggcagcag ttcaacaagc gtatctggcc     240
tatcaacaag ctacagacaa agccgcaaaa gacgcagcag ataagatgat cgatgaagct     300
aagaaacgcg aagaagaggc aaaaactaaa tttaatactg ttcgtgcaat ggtagttcct     360
gagccagagc agttggcgga gactaagaaa aaatcagaag aagctaaaca aaaagcacca     420
gaacttacta aaaaactgga gaagctaaa gcaaaattag aagaggctga gaaaaagct     480
actgaagcca acaaaaagt ggatgctgaa gaagtcgctc ctcaagctaa atcgctgaa     540
ttggaaaatc aagttcatcg tctggaacaa gagctcaaag agattgatga gtctgaatca     600
gaagattatg ctaaagaagg ttccgtgct cctcttcaat ctaaattgga tgccaaaaaa     660
gctaaactgt caaaacttga agagttaagt gataagattg atgagttaga cgctgaaatt     720
gcaaaacttg aagatcaact taaagctgct gaagaaaaca ataatgtaga agactacttt     780
aaagaaggtt tagagaaaac tattgctgct aaaaaagctg aattagaaaa aactgaagct     840
gaccttaaga agcactgca gaaccagtct aaagctgaga agactatga tgcagcagtg     900
aaaaaatctg aagctgctaa gaaagattac gaaacggcta aaagaaagc agaagacgct     960
cagaagaaat atgatgagga tcagaagaaa actgaggcaa aagcggaaaa agaacgtaaa    1020
gcttctgaaa gatcgctga ggcaacaaaa gaagttcaac aagcgtacct agcttatcta    1080
caagctagca acgaaagtca gcgtaaagag gcagataaga gatcaaaga agctacgcaa    1140
cgcaaagatg aggcggaagc tgcatttgct actattcgta caacaattgt agttcctgaa    1200
ccaagtgagt tagctgagac taagaaaaaa gcagaagagg caacaaaaga agcagaagta    1260
gctaagaaaa aatctgaaga ggcagctaaa gaggtagaag tagagaaaaa taaaatcctt    1320
gaacaagatg ctgaaaacga aaagaaaatt gacgtacttc aaaacaaagt cgctgattta    1380
gaaaaggaa ttgctcctta tcaaaacgaa gtcgctgaat aaataaaga aattgctcgt    1440
cttcaaagcg atttaaaaga tgctgaagaa aataatgtag aagactacat taagaaggt    1500
ttagagcaag ctatcactaa taaaaaagct gaattagcta caactcaaca aacatcgat    1560
aaaactcaaa aagatttaga ggatgctgaa ttagaacttg aaaaagtatt agctacatta    1620
gaccctgaag gtaaaactca agatgaatta gataaagaag ctgctgaagc tgagttgaat    1680
gaaaaagttg aagctcttca aaaccaagtt gctgaattag aagaagaact ttcaaaactt    1740
gaagataatc ttaaagatgc tgaaacaaac aacgttgaag actacattaa agaaggttta    1800
gaagaagcta tcgcgactaa aaaagctgaa ttggaaaaaa ctcaaaaaga attagatgca    1860
gctcttaatg agttaggccc tgatggagat gaagaagaga ctccagcgcc ggctcctcaa    1920
ccagaaaaac cagctgaaga gcctgagaat ccagctccag caccaaaacc agagaagtca    1980
gcagatcaac aagctgaaga agactatgct cgtagatcag aagaagaata taatcgcttg    2040
```

```
                                      -continued acccaacagc aaccgccaaa agcagaaaaa ccagctcctg caccacaacc agagcaacca     2100
gctcctgcac caataat                                                    2117

<210> SEQ ID NO 14
<211> LENGTH: 697
<212> TYPE: PRT
<213> ORGANISM: Streptococcus pneumoniae

<400> SEQUENCE: 14

Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys
                20                  25                  30

Ala Leu Asp Asp Ala Lys Ala Ala Gln Lys Lys Tyr Asp Glu Asp Gln
            35                  40                  45

Lys Lys Thr Glu Glu Lys Ala Ala Leu Glu Lys Ala Ala Ser Glu Glu
        50                  55                  60

Met Asp Lys Ala Val Ala Ala Val Gln Gln Ala Tyr Leu Ala Tyr Gln
65                  70                  75                  80

Gln Ala Thr Asp Lys Ala Ala Lys Asp Ala Ala Asp Lys Met Ile Asp
                85                  90                  95

Glu Ala Lys Lys Arg Glu Glu Glu Ala Lys Thr Lys Phe Asn Thr Val
            100                 105                 110

Arg Ala Met Val Val Pro Glu Pro Glu Gln Leu Ala Glu Thr Lys Lys
        115                 120                 125

Lys Ser Glu Glu Ala Lys Gln Lys Ala Pro Glu Leu Thr Lys Lys Leu
    130                 135                 140

Glu Glu Ala Lys Ala Lys Leu Glu Glu Ala Lys Lys Ala Thr Glu
145                 150                 155                 160

Ala Lys Gln Lys Val Asp Ala Glu Glu Val Ala Pro Gln Ala Lys Ile
                165                 170                 175

Ala Glu Leu Glu Asn Gln Val His Arg Leu Glu Gln Glu Leu Lys Glu
            180                 185                 190

Ile Asp Glu Ser Glu Ser Glu Asp Tyr Ala Lys Glu Gly Phe Arg Ala
        195                 200                 205

Pro Leu Gln Ser Lys Leu Asp Ala Lys Lys Ala Lys Leu Ser Lys Leu
    210                 215                 220

Glu Glu Leu Ser Asp Lys Ile Asp Glu Leu Asp Ala Glu Ile Ala Lys
225                 230                 235                 240

Leu Glu Asp Gln Leu Lys Ala Ala Glu Asn Asn Asn Val Glu Asp
                245                 250                 255

Tyr Phe Lys Glu Gly Leu Glu Lys Thr Ile Ala Ala Lys Lys Ala Glu
            260                 265                 270

Leu Glu Lys Thr Glu Ala Asp Leu Lys Lys Ala Lys Ala Glu Lys Asp
        275                 280                 285

Tyr Asp Ala Ala Val Lys Lys Ser Glu Ala Ala Lys Lys Asp Tyr Glu
    290                 295                 300

Thr Ala Lys Lys Lys Ala Glu Asp Ala Gln Lys Lys Tyr Asp Glu Asp
305                 310                 315                 320

Gln Lys Lys Thr Glu Ala Lys Ala Lys Glu Arg Lys Ala Ser Glu
                325                 330                 335

Lys Ile Ala Glu Ala Thr Lys Val Gln Gln Ala Tyr Leu Ala Tyr
            340                 345                 350
```

| | | | | | | | | | | | |
|---|---|---|---|---|---|---|---|---|---|---|---|
|Leu|Gln|Ala|Ser|Asn|Glu|Ser|Gln|Arg|Lys|Glu|Ala|Asp|Lys|Lys|Ile|
| | |355| | | |360| | | |365| |
|Lys|Glu|Ala|Thr|Gln|Arg|Lys|Asp|Glu|Ala|Ala|Ala|Phe|Ala|Thr|
|370| | | | |375| | | | |380| |
|Ile|Arg|Thr|Thr|Ile|Val|Val|Pro|Glu|Pro|Ser|Glu|Leu|Ala|Glu|Thr|
|385| | | | |390| | | | |395| | | | |400|
|Lys|Lys|Lys|Ala|Glu|Glu|Ala|Thr|Lys|Glu|Ala|Val|Ala|Lys|Lys|
| | | | |405| | | | |410| | | | |415|
|Lys|Ser|Glu|Glu|Ala|Ala|Lys|Glu|Val|Glu|Val|Glu|Lys|Asn|Lys|Ile|
| | | |420| | | | |425| | | | |430| |
|Leu|Glu|Gln|Asp|Ala|Glu|Asn|Glu|Lys|Lys|Ile|Asp|Val|Leu|Gln|Asn|
| | |435| | | | |440| | | | |445| | |
|Lys|Val|Ala|Asp|Leu|Glu|Lys|Gly|Ile|Ala|Pro|Tyr|Gln|Asn|Glu|Val|
| |450| | | | |455| | | | |460| | | | |
|Ala|Glu|Leu|Asn|Lys|Glu|Ile|Ala|Arg|Leu|Gln|Ser|Asp|Leu|Lys|Asp|
|465| | | | |470| | | | |475| | | | |480|
|Ala|Glu|Glu|Asn|Asn|Val|Glu|Asp|Tyr|Ile|Lys|Glu|Gly|Leu|Glu|Gln|
| | | | |485| | | | |490| | | | |495| |
|Ala|Ile|Thr|Asn|Lys|Lys|Ala|Glu|Leu|Ala|Thr|Thr|Gln|Gln|Asn|Ile|
| | | |500| | | | |505| | | | |510| | |
|Asp|Lys|Thr|Gln|Lys|Asp|Leu|Glu|Asp|Ala|Glu|Leu|Glu|Leu|Glu|Lys|
| | |515| | | | |520| | | | |525| | | |
|Val|Leu|Ala|Thr|Leu|Asp|Pro|Glu|Gly|Lys|Thr|Gln|Asp|Glu|Leu|Asp|
| |530| | | | |535| | | | |540| | | | |
|Lys|Glu|Ala|Ala|Glu|Ala|Glu|Leu|Asn|Glu|Lys|Val|Glu|Ala|Leu|Gln|
|545| | | | |550| | | | |555| | | | |560|
|Asn|Gln|Val|Ala|Glu|Leu|Glu|Glu|Leu|Ser|Lys|Leu|Glu|Asp|Asn|
| | | | |565| | | | |570| | | | |575|
|Leu|Lys|Asp|Ala|Glu|Thr|Asn|Asn|Val|Glu|Asp|Tyr|Ile|Lys|Glu|Gly|
| | | |580| | | | |585| | | | |590| | |
|Leu|Glu|Glu|Ala|Ile|Ala|Thr|Lys|Lys|Ala|Glu|Leu|Glu|Lys|Thr|Gln|
| | | |595| | | | |600| | | | |605| | |
|Lys|Glu|Leu|Asp|Ala|Ala|Leu|Asn|Glu|Leu|Gly|Pro|Asp|Gly|Asp|Glu|
| |610| | | | |615| | | | |620| | | | |
|Glu|Glu|Thr|Pro|Ala|Pro|Ala|Pro|Gln|Pro|Glu|Lys|Pro|Ala|Glu|Glu|
|625| | | | |630| | | | |635| | | | |640|
|Pro|Glu|Asn|Pro|Ala|Pro|Ala|Pro|Lys|Pro|Glu|Lys|Ser|Ala|Asp|Gln|
| | | |645| | | | |650| | | | |655| | |
|Gln|Ala|Glu|Glu|Asp|Tyr|Ala|Arg|Arg|Ser|Glu|Glu|Tyr|Asn|Arg|
| | | |660| | | | |665| | | | |670| | |
|Leu|Thr|Gln|Gln|Pro|Pro|Lys|Ala|Glu|Lys|Pro|Ala|Pro|Ala|Pro|
| | | |675| | | | |680| | | | |685| | |
|Gln|Pro|Glu|Gln|Pro|Ala|Pro|Ala|Pro|
| | |690| | | | |695| |

<210> SEQ ID NO 15
<211> LENGTH: 2117
<212> TYPE: DNA
<213> ORGANISM: Streptococcus pneumoniae

<400> SEQUENCE: 15

```
gaattcaacc agtctaaagc tgagaaagac tatgatgcag cagtgaaaaa atctgaagct      60
gctaagaaag attacgaaac ggctaaaaag aaagcagaag acgctcagaa gaaatatgat     120
gaggatcaga agaaaactga ggcaaaagcg gaaaagaaac gtaaagcttc tgaaaagatc     180
```

```
gctgaggcaa caaaagaagt tcaacaagcg tacctagctt atctacaagc tagcaacgaa       240
agtcagcgta aagaggcaga taagaagatc aagaagctca cgcaacgcaa agatgaggcg       300
gaagctgcat ttgctactat tcgtacaaca attgtagttc ctgaaccaag tgagttagct       360
gagactaaga aaaagcaga agaggcaaca aaagaagcag aagtagctaa gaaaaaatct        420
gaagaggcag ctaaagaggt agaagtagag aaaaataaaa tccttgaaca agatgctgaa      480
aacgaaaaga aaattgacgt acttcaaaac aaagtcgctg atttagaaaa aggaattgct      540
ccttatcaaa acgaagtcgc tgaattaaat aaagaaattg ctcgtcttca aagcgattta     600
aaagatgctg aagaaaataa tgtagaagac tacattaaag aaggtttaga gcaagctatc     660
actaataaaa aagctgaatt agctacaact caacaaaaca tcgataaaac tcaaaaagat    720
ttagaggatg ctgaattaga acttgaaaaa gtattagcta cattagaccc tgaaggtaaa    780
actcaagatg aattagataa agaagctgct gaagctgagt tgaatgaaaa agttgaagct    840
cttcaaaacc aagttgctga attagaagaa gaacttcaa aacttgaaga taatcttaaa     900
gatgctgaaa caaacaacgt tgaagactac attaagaag gtttagaaga agctatcgcg     960 actaaaaag ctgaattgga aaaaactcaa aagaattag atgcagctct taatgagtta    1020
ggccctgatg gagatgaaga agagactcca gcgccggctc ctcaaccaga aaaccagct    1080 gaagagcctg agaatccagc tccagcacca aaaccagaga agtcagcaga tcaacaagct    1140
gaagaagact atgctcgtag atcagaagaa gaatataatc gcttgaccca acagcaaccg   1200
ccaaaagcag aaaaaccagc tcctgcacca caaccagagc aaccagctcc tgcaccaaga   1260
attctctccg gtagccagtc agtctaaagc tgagaaagac tatgatgcag cgaagaaaga   1320
tgctaagaat gctaaaaaag cagtagaaga tgctcaaaag gctttagatg atgcaaaagc   1380
tgctcagaaa aaatatgacg aggatcagaa gaaaactgag gagaaagccg cgctggaaaa   1440
agcagcgtct gaagagatgg ataaggcagt ggcagcagtt caacaagcgt atctggccta   1500
tcaacaagct acagacaaag ccgcaaaaga cgcagcagat aagatgatcg atgaagctaa   1560
gaaacgcgaa aagagggcaa aaactaaatt taatactgtt cgtgcaatgg tagttcctga   1620
gccagagcag ttggcggaga ctaagaaaaa atcagaagaa gctaaacaaa aagcaccaga   1680
acttactaaa aaactggaag aagctaaagc aaaattagaa gaggctgaga aaaaagctac   1740
tgaagccaaa caaaagtgg atgctgaaga agtcgctcct caagctaaaa tcgctgaatt   1800
ggaaaatcaa gttcatcgtc tggaacaaga gctcaaagag attgatgagt ctgaatcaga   1860
agattatgct aaagaaggtt tccgtgctcc tcttcaatct aaattggatg ccaaaaaagc   1920
taaactgtca aaacttgaag agttaagtga taagattgat gagttagacg ctgaaattgc   1980
aaaacttgaa gatcaactta agctgctga agaaaacaat aatgtagaag actactttaa   2040
agaaggttta gagaaaacta ttgctgctaa aaaagctgaa ttagaaaaaa ctgaagctga   2100
ccttaagaaa gcataat                                                    2117
```

<210> SEQ ID NO 16
<211> LENGTH: 697
<212> TYPE: PRT
<213> ORGANISM: Streptococcus pneumoniae

<400> SEQUENCE: 16

Lys Ala Glu Lys Asp Tyr Asp Ala Ala Val Lys Lys Ser Glu Ala Ala
1               5                   10                  15

Lys Lys Asp Tyr Glu Thr Ala Lys Lys Lys Ala Glu Asp Ala Gln Lys

```
            20                  25                  30
Lys Tyr Asp Glu Asp Gln Lys Lys Thr Glu Ala Lys Ala Glu Lys Glu
        35                  40                  45
Arg Lys Ala Ser Glu Lys Ile Ala Glu Ala Thr Lys Glu Val Gln Gln
        50                  55                  60
Ala Tyr Leu Ala Tyr Leu Gln Ala Ser Asn Glu Ser Gln Arg Lys Glu
65                  70                  75                  80
Ala Asp Lys Lys Ile Lys Glu Ala Thr Gln Arg Lys Asp Glu Ala Glu
                85                  90                  95
Ala Ala Phe Ala Thr Ile Arg Thr Thr Ile Val Val Pro Glu Pro Ser
            100                 105                 110
Glu Leu Ala Glu Thr Lys Lys Lys Ala Glu Glu Ala Thr Lys Glu Ala
        115                 120                 125
Glu Val Ala Lys Lys Ser Glu Glu Ala Ala Lys Glu Val Glu Val
        130                 135                 140
Glu Lys Asn Lys Ile Leu Glu Gln Asp Ala Glu Asn Glu Lys Lys Ile
145                 150                 155                 160
Asp Val Leu Gln Asn Lys Val Ala Asp Leu Glu Lys Gly Ile Ala Pro
                165                 170                 175
Tyr Gln Asn Glu Val Ala Glu Leu Asn Lys Glu Ile Ala Arg Leu Gln
            180                 185                 190
Ser Asp Leu Lys Asp Ala Glu Glu Asn Asn Val Glu Asp Tyr Ile Lys
        195                 200                 205
Glu Gly Leu Glu Gln Ala Ile Thr Asn Lys Lys Ala Glu Leu Ala Thr
        210                 215                 220
Thr Gln Gln Asn Ile Asp Lys Thr Gln Lys Asp Leu Glu Asp Ala Glu
225                 230                 235                 240
Leu Glu Leu Glu Lys Val Leu Ala Thr Leu Asp Pro Glu Gly Lys Thr
                245                 250                 255
Gln Asp Glu Leu Asp Lys Glu Ala Ala Glu Ala Glu Leu Asn Glu Lys
            260                 265                 270
Val Glu Ala Leu Gln Asn Gln Val Ala Glu Leu Glu Glu Leu Ser
        275                 280                 285
Lys Leu Glu Asp Asn Leu Lys Asp Ala Glu Thr Asn Asn Val Glu Asp
        290                 295                 300
Tyr Ile Lys Glu Gly Leu Glu Glu Ala Ile Ala Thr Lys Lys Ala Glu
305                 310                 315                 320
Leu Glu Lys Thr Gln Lys Glu Leu Asp Ala Ala Leu Asn Glu Leu Gly
                325                 330                 335
Pro Asp Gly Asp Glu Glu Thr Pro Ala Pro Ala Pro Gln Pro Glu
            340                 345                 350
Lys Pro Ala Glu Glu Pro Glu Asn Pro Ala Pro Ala Lys Pro Glu
        355                 360                 365
Lys Ser Ala Asp Gln Gln Ala Glu Glu Asp Tyr Ala Arg Arg Ser Glu
        370                 375                 380
Glu Glu Tyr Asn Arg Leu Thr Gln Gln Gln Pro Lys Ala Glu Lys
385                 390                 395                 400
Pro Ala Pro Ala Pro Gln Pro Glu Gln Pro Ala Pro Ala Pro Ser Pro
                405                 410                 415
Val Ala Ser Gln Ser Lys Ala Glu Lys Asp Tyr Asp Ala Ala Lys Lys
            420                 425                 430
Asp Ala Lys Asn Ala Lys Lys Ala Val Glu Asp Ala Gln Lys Ala Leu
        435                 440                 445
```

```
Asp Asp Ala Lys Ala Ala Gln Lys Lys Tyr Asp Glu Asp Gln Lys Lys
         450                 455                 460

Thr Glu Glu Lys Ala Ala Leu Glu Lys Ala Ala Ser Glu Glu Met Asp
465                 470                 475                 480

Lys Ala Val Ala Ala Val Gln Gln Ala Tyr Leu Ala Tyr Gln Gln Ala
                485                 490                 495

Thr Asp Lys Ala Ala Lys Asp Ala Ala Asp Lys Met Ile Asp Glu Ala
                500                 505                 510

Lys Lys Arg Glu Glu Glu Ala Lys Thr Lys Phe Asn Thr Val Arg Ala
            515                 520                 525

Met Val Val Pro Glu Pro Glu Gln Leu Ala Glu Thr Lys Lys Lys Ser
            530                 535                 540

Glu Glu Ala Lys Gln Lys Ala Pro Glu Leu Thr Lys Lys Leu Glu Glu
545                 550                 555                 560

Ala Lys Ala Lys Leu Glu Glu Ala Glu Lys Lys Ala Thr Glu Ala Lys
                565                 570                 575

Gln Lys Val Asp Ala Glu Glu Val Ala Pro Gln Ala Lys Ile Ala Glu
                580                 585                 590

Leu Glu Asn Gln Val His Arg Leu Glu Gln Glu Leu Lys Glu Ile Asp
            595                 600                 605

Glu Ser Glu Ser Glu Asp Tyr Ala Lys Glu Gly Phe Arg Ala Pro Leu
610                 615                 620

Gln Ser Lys Leu Asp Ala Lys Ala Lys Leu Ser Lys Leu Glu Glu
625                 630                 635                 640

Leu Ser Asp Lys Ile Asp Glu Leu Asp Ala Glu Ile Ala Lys Leu Glu
                645                 650                 655

Asp Gln Leu Lys Ala Ala Glu Glu Asn Asn Asn Val Glu Asp Tyr Phe
            660                 665                 670

Lys Glu Gly Leu Glu Lys Thr Ile Ala Ala Lys Lys Ala Glu Leu Glu
            675                 680                 685

Lys Thr Glu Ala Asp Leu Lys Lys Ala
690                 695

<210> SEQ ID NO 17
<211> LENGTH: 1215
<212> TYPE: DNA
<213> ORGANISM: Streptococcus pneumoniae

<400> SEQUENCE: 17
gagaacgaag gcctgccaag taccacttct tctaatcgcg caaatgaaag tcaggcagaa      60
caaggcgaac aacctaaaaa actcgattca gaacgcgata aggcacgcaa agaggtcgag     120
gaatatgtaa aaaaaatcgt gggtgagagc tatgcaaaat caactaaaaa gcgccataca     180
attactgtag ctctggttaa cgagttgaac aacattaaga acgagtattt gaataaaatc     240
gttgaatcaa cctcagaaag ccaactacag atcctgatga tggagagtcg ctcaaaagta     300
gatgaagctg tgtctaagtt tgaaaaggac tcatcttctt cgtcaagttc agactcttcc     360
actaaaccgg aagcttcaga tacagcgaag ccaaacaagc cgacagaacc aggcgaaaag     420
gtagcagaag ctaagaagaa ggttgaagaa gctgagaaaa agccaaggga tcaaaaagaa     480
gaagatcgtc gtaactaccc aaccattact tacaaaacgc ttgaacttga aattgctgag     540
tccgatgtgg aagttaaaaa agcggagctt gaactagtaa aagtgaaagc taacgaacct     600
cgcgacgagc aaaaaattaa gcaagcagaa gcggaagttg agagtaaaca agctgaggct     660
```

```
acacgcttaa aaaaaatcaa gacagatcgt gaagaagcag aagaagaagc taaacgccgc      720
gcagatgcta aagagcaagg taaaccaaag gggcgcgcaa aacgcggagt tcctggcgag      780
ctggcaacac ctgataaaaa agaaaatgat gcgaagtctt cagattctag cgtaggtgaa      840
gaaactcttc caagcccatc cctgaaacca gaaaaaaagg tagcagaagc tgagaagaag      900
gttgaagaag ctaagaaaaa agccgaggat caaaagaag aagatcgccg taactaccca      960
accaatactt acaaaacgct tgaacttgaa attgctgagt ccgatgtgga agttaaaaaa      1020
gcggagcttg aactggtaaa agaggaagct aaggaacctc gcaacgagga aaaagttaag      1080
caagcaaaag cggaagttga gagtaaaaaa gctgaggcta ctcgcttaga aaaaatcaag      1140
acagatcgta aaaagcaga agaagaagct aaacgcaaag cagcagaaga agataaagtt      1200
aaagaaaaac cagct                                                       1215
```

<210> SEQ ID NO 18
<211> LENGTH: 405
<212> TYPE: PRT
<213> ORGANISM: Streptococcus pneumoniae

<400> SEQUENCE: 18

```
Glu Asn Glu Gly Leu Pro Ser Thr Thr Ser Ser Asn Arg Ala Asn Glu
1               5                   10                  15

Ser Gln Ala Glu Gln Gly Glu Gln Pro Lys Lys Leu Asp Ser Glu Arg
            20                  25                  30

Asp Lys Ala Arg Lys Glu Val Glu Glu Tyr Val Lys Ile Val Gly
        35                  40                  45

Glu Ser Tyr Ala Lys Ser Thr Lys Lys Arg His Thr Ile Thr Val Ala
50                  55                  60

Leu Val Asn Glu Leu Asn Asn Ile Lys Asn Glu Tyr Leu Asn Lys Ile
65                  70                  75                  80

Val Glu Ser Thr Ser Glu Ser Gln Leu Gln Ile Leu Met Met Glu Ser
                85                  90                  95

Arg Ser Lys Val Asp Glu Ala Val Ser Lys Phe Glu Lys Asp Ser Ser
            100                 105                 110

Ser Ser Ser Ser Ser Asp Ser Ser Thr Lys Pro Glu Ala Ser Asp Thr
        115                 120                 125

Ala Lys Pro Asn Lys Pro Thr Glu Pro Gly Glu Lys Val Ala Glu Ala
    130                 135                 140

Lys Lys Lys Val Glu Glu Ala Glu Lys Ala Lys Asp Gln Lys Glu
145                 150                 155                 160

Glu Asp Arg Arg Asn Tyr Pro Thr Ile Thr Tyr Lys Thr Leu Glu Leu
                165                 170                 175

Glu Ile Ala Glu Ser Asp Val Val Lys Lys Ala Glu Leu Glu Leu
            180                 185                 190

Val Lys Val Lys Ala Asn Glu Pro Arg Asp Glu Gln Lys Ile Lys Gln
        195                 200                 205

Ala Glu Ala Glu Val Glu Ser Lys Gln Ala Glu Ala Thr Arg Leu Lys
    210                 215                 220

Lys Ile Lys Thr Asp Arg Glu Glu Ala Glu Glu Ala Lys Arg Arg
225                 230                 235                 240

Ala Asp Ala Lys Glu Gln Gly Lys Pro Lys Gly Arg Ala Lys Arg Gly
                245                 250                 255

Val Pro Gly Glu Leu Ala Thr Pro Asp Lys Lys Glu Asn Asp Ala Lys
            260                 265                 270
```

```
Ser Ser Asp Ser Ser Val Gly Glu Glu Thr Leu Pro Ser Pro Ser Leu
            275                 280                 285

Lys Pro Glu Lys Lys Val Ala Glu Ala Glu Lys Lys Val Glu Glu Ala
290                 295                 300

Lys Lys Lys Ala Glu Asp Gln Lys Glu Glu Asp Arg Arg Asn Tyr Pro
305                 310                 315                 320

Thr Asn Thr Tyr Lys Thr Leu Glu Leu Glu Ile Ala Glu Ser Asp Val
                325                 330                 335

Glu Val Lys Lys Ala Glu Leu Glu Leu Val Lys Glu Ala Lys Glu
                340                 345                 350

Pro Arg Asn Glu Glu Lys Val Lys Gln Ala Lys Ala Glu Val Glu Ser
            355                 360                 365

Lys Lys Ala Glu Ala Thr Arg Leu Glu Lys Ile Lys Thr Asp Arg Lys
370                 375                 380

Lys Ala Glu Glu Glu Ala Lys Arg Lys Ala Ala Glu Glu Asp Lys Val
385                 390                 395                 400

Lys Glu Lys Pro Ala
            405

<210> SEQ ID NO 19
<211> LENGTH: 1215
<212> TYPE: DNA
<213> ORGANISM: Streptococcus pneumoniae

<400> SEQUENCE: 19
gagaacgaag gactaccaag taccacttct tctaataggg caaatgaaag tcaggcagaa      60
caaggagaac aacctaaaaa actcgattca gaacgagata aggcaaggaa agaggtcgag     120
gaatatgtaa aaaaaatagt gggtgagagc tatgcaaaat caactaaaaa gcgacataca     180
attactgtag ctctagttaa cgagttgaac aacattaaga acgagtattt gaataaaata     240
gttgaatcaa cctcagaaag ccaactacag atactgatga tggagagtcg atcaaaagta     300
gatgaagctg tgtctaagtt tgaaaaggac tcatcttctt cgtcaagttc agactcttcc     360
actaaaccgg aagcttcaga tacagcgaag ccaaacaagc cgacagaacc aggagaaaag     420
gtagcagaag ctaagaagaa ggttgaagaa gctgagaaaa agccaaggaa tcaaaaagaa     480
gaagatcgtc gtaactaccc aaccattact tacaaaacgc ttgaacttga aattgctgag     540
tccgatgtgg aagttaaaaa agcggagctt gaactagtaa aagtgaaagc taacgaacct     600
cgagacgagc aaaaaattaa gcaagcagaa gcggaagttg agagtaaaca agctgaggct     660
acaaggttaa aaaaaatcaa gacagatcgt gaagaagcag aagaagaagc taaacgaaga     720
gcagatgcta agagcaagg taaccaaag gggcgggcaa aacgaggagt tcctggagag     780
ctagcaacac ctgataaaaa agaaaatgat gcgaagtctt cagattctag cgtaggtgaa     840
gaaactcttc caagcccatc cctgaaacca gaaaaaaagg tagcagaagc tgagaagaag     900
gttgaagaag ctaagaaaaa agccgaggat caaaagaag aagatcgccg taactaccca     960
accaatactt acaaaacgct tgaacttgaa attgctgagt ccgatgtgga agttaaaaaa    1020
gcggagcttg aactagtaaa agaggaagct aaggaacctc gaaacgagga aaaagttaag    1080
caagcaaaag cggaagttga gagtaaaaaa gctgaggcta ctaggttaga aaaaatcaag    1140
acagatcgta aaaagcaga agaagaagct aaacgaaaag cagcagaaga agataaagtt    1200
aaagaaaaac cagct                                                     1215

<210> SEQ ID NO 20
```

```
<211> LENGTH: 405
<212> TYPE: PRT
<213> ORGANISM: Streptococcus pneumoniae

<400> SEQUENCE: 20
```

| | | | | | | | | | | | | | | |
|---|---|---|---|---|---|---|---|---|---|---|---|---|---|---|
| Glu | Asn | Glu | Gly | Leu | Pro | Ser | Thr | Thr | Ser | Ser | Asn | Arg | Ala | Asn | Glu |
| 1 | | | | 5 | | | | | 10 | | | | | 15 |

Ser Gln Ala Glu Gln Gly Glu Gln Pro Lys Lys Leu Asp Ser Glu Arg
            20                  25                  30

Asp Lys Ala Arg Lys Glu Val Glu Tyr Val Lys Lys Ile Val Gly
     35                  40                  45

Glu Ser Tyr Ala Lys Ser Thr Lys Lys Arg His Thr Ile Thr Val Ala
 50                  55                  60

Leu Val Asn Glu Leu Asn Asn Ile Lys Asn Glu Tyr Leu Asn Lys Ile
 65                  70                  75                  80

Val Glu Ser Thr Ser Glu Ser Gln Leu Gln Ile Leu Met Met Glu Ser
                 85                  90                  95

Arg Ser Lys Val Asp Glu Ala Val Ser Lys Phe Glu Lys Asp Ser Ser
             100                 105                 110

Ser Ser Ser Ser Ser Asp Ser Ser Thr Lys Pro Glu Ala Ser Asp Thr
         115                 120                 125

Ala Lys Pro Asn Lys Pro Thr Glu Pro Gly Glu Lys Val Ala Glu Ala
130                 135                 140

Lys Lys Lys Val Glu Glu Ala Lys Lys Ala Lys Asp Gln Lys Glu
145                 150                 155                 160

Glu Asp Arg Arg Asn Tyr Pro Thr Ile Thr Tyr Lys Thr Leu Glu Leu
                165                 170                 175

Glu Ile Ala Glu Ser Asp Val Glu Val Lys Lys Ala Glu Leu Glu Leu
             180                 185                 190

Val Lys Val Lys Ala Asn Glu Pro Arg Asp Glu Gln Lys Ile Lys Gln
         195                 200                 205

Ala Glu Ala Glu Val Glu Ser Lys Gln Ala Glu Ala Thr Arg Leu Lys
210                 215                 220

Lys Ile Lys Thr Asp Arg Glu Glu Ala Glu Glu Ala Lys Arg Arg
225                 230                 235                 240

Ala Asp Ala Lys Glu Gln Gly Lys Pro Lys Gly Arg Ala Lys Arg Gly
                245                 250                 255

Val Pro Gly Glu Leu Ala Thr Pro Asp Lys Lys Glu Asn Asp Ala Lys
             260                 265                 270

Ser Ser Asp Ser Ser Val Gly Glu Glu Thr Leu Pro Ser Pro Ser Leu
         275                 280                 285

Lys Pro Glu Lys Lys Val Ala Glu Ala Glu Lys Lys Val Glu Glu Ala
290                 295                 300

Lys Lys Lys Ala Glu Asp Gln Lys Glu Glu Asp Arg Arg Asn Tyr Pro
305                 310                 315                 320

Thr Asn Thr Tyr Lys Thr Leu Glu Leu Glu Ile Ala Glu Ser Asp Val
                325                 330                 335

Glu Val Lys Lys Ala Glu Leu Glu Leu Val Lys Glu Ala Lys Glu
             340                 345                 350

Pro Arg Asn Glu Glu Lys Val Lys Gln Ala Lys Ala Glu Val Glu Ser
         355                 360                 365

Lys Lys Ala Glu Ala Thr Arg Leu Glu Lys Ile Lys Thr Asp Arg Lys
370                 375                 380

Lys Ala Glu Glu Glu Ala Lys Arg Lys Ala Ala Glu Glu Asp Lys Val

Lys Glu Lys Pro Ala
            405

<210> SEQ ID NO 21
<211> LENGTH: 1433
<212> TYPE: DNA
<213> ORGANISM: Streptococcus pneumoniae

<400> SEQUENCE: 21

| | | |
|---|---|---|
| gagaacgaag gcctgccaag taccacttct tctaatcgcg caaatgaaag tcaggcagaa | 60 |
| caaggcgaac aacctaaaaa actcgattca gaacgcgata aggcacgcaa agaggtcgag | 120 |
| gaatatgtaa aaaaaatcgt gggtgagagc tatgcaaaat caactaaaaa gcgccataca | 180 |
| attactgtag ctctggttaa cgagttgaac aacattaaga acgagtattt gaataaaatc | 240 |
| gttgaatcaa cctcagaaag ccaactacag atcctgatga tggagagtcg ctcaaaagta | 300 |
| gatgaagctg tgtctaagtt tgaaaaggac tcatcttctt cgtcaagttc agactcttcc | 360 |
| actaaaccgg aagcttcaga tacagcgaag ccaaacaagc cgacagaacc aggcgaaaag | 420 |
| gtagcagaag ctaagaagaa ggttgaagaa gctgagaaaa agccaaggat caaaaagaa | 480 |
| gaagatcgtc gtaactaccc aaccattact tacaaaacgc ttgaacttga aattgctgag | 540 |
| tccgatgtgg aagttaaaaa agcggagctt gaactagtaa aagtgaaagc taacgaacct | 600 |
| cgcgacgagc aaaaaattaa gcaagcagaa gcggaagttg agagtaaaca agctgaggct | 660 |
| acacgcttaa aaaaaatcaa gacagatcgt gaagaagcag aagaagagc taaacgccgc | 720 |
| gcagatgcta agagcaagg taaccaaag gggcgcgcaa acgcggagt tcctggcgag | 780 |
| ctggcaacac tgataaaaa agaaaatgat gcgaagtctt cagattctag cgtaggtgaa | 840 |
| gaaactcttc caagcccatc cctgaaacca gaaaaaaagg tagcagaagc tgagaagaag | 900 |
| gttgaagaag ctaagaaaaa agccgaggat caaaaagaag aagatcgccg taactaccca | 960 |
| accaatactt acaaaacgct tgaacttgaa attgctgagt ccgatgtgga agttaaaaaa | 1020 |
| gcggagcttg aactggtaaa agaggaagct aaggaacctc gcaacgagga aaaagttaag | 1080 |
| caagcaaaag cggaagttga gagtaaaaaa gctgaggcta ctcgcttaga aaaaatcaag | 1140 |
| acagatcgta aaaagcaga agaagaagct aaacgcaaag cagcagaaga agataaagtt | 1200 |
| aaagaaaaac cagctgaaca accacaacca gcgccggctc caaaagcaga aaaaccagct | 1260 |
| ccagctccaa aaccagagaa tccagctgaa caaccaaaag cagaaaaacc agctgatcaa | 1320 |
| caagctgaag aagagtatgc tcgtagatca gaagaagaat ataatcgctt gactctacag | 1380 |
| caaccgccaa aaactgaaaa accagcacaa ccatctactc aaaaacaaa tac | 1433 |

<210> SEQ ID NO 22
<211> LENGTH: 477
<212> TYPE: PRT
<213> ORGANISM: Streptococcus pneumoniae

<400> SEQUENCE: 22

Glu Asn Glu Gly Leu Pro Ser Thr Thr Ser Ser Asn Arg Ala Asn Glu
1               5                   10                  15

Ser Gln Ala Glu Gln Gly Glu Gln Pro Lys Lys Leu Asp Ser Glu Arg
            20                  25                  30

Asp Lys Ala Arg Lys Glu Val Glu Glu Tyr Val Lys Lys Ile Val Gly
        35                  40                  45

Glu Ser Tyr Ala Lys Ser Thr Lys Lys Arg His Thr Ile Thr Val Ala

```
                50                  55                  60
Leu Val Asn Glu Leu Asn Asn Ile Lys Asn Glu Tyr Leu Asn Lys Ile
 65                  70                  75                  80

Val Glu Ser Thr Ser Glu Ser Gln Leu Gln Ile Leu Met Met Glu Ser
                     85                  90                  95

Arg Ser Lys Val Asp Glu Ala Val Ser Lys Phe Glu Lys Asp Ser Ser
                100                 105                 110

Ser Ser Ser Ser Ser Asp Ser Ser Thr Lys Pro Glu Ala Ser Asp Thr
                115                 120                 125

Ala Lys Pro Asn Lys Pro Thr Glu Pro Gly Glu Lys Val Ala Glu Ala
130                 135                 140

Lys Lys Lys Val Glu Glu Ala Glu Lys Lys Ala Lys Asp Gln Lys Glu
145                 150                 155                 160

Glu Asp Arg Arg Asn Tyr Pro Thr Ile Thr Tyr Lys Thr Leu Glu Leu
                165                 170                 175

Glu Ile Ala Glu Ser Asp Val Glu Val Lys Lys Ala Glu Leu Glu Leu
                180                 185                 190

Val Lys Val Lys Ala Asn Glu Pro Arg Asp Glu Gln Lys Ile Lys Gln
                195                 200                 205

Ala Glu Ala Glu Val Glu Ser Lys Gln Ala Glu Ala Thr Arg Leu Lys
210                 215                 220

Lys Ile Lys Thr Asp Arg Glu Glu Ala Glu Glu Ala Lys Arg Arg
225                 230                 235                 240

Ala Asp Ala Lys Glu Gln Gly Lys Pro Lys Gly Arg Ala Lys Arg Gly
                245                 250                 255

Val Pro Gly Glu Leu Ala Thr Pro Asp Lys Lys Glu Asn Asp Ala Lys
                260                 265                 270

Ser Ser Asp Ser Ser Val Gly Glu Thr Leu Pro Ser Pro Ser Leu
                275                 280                 285

Lys Pro Glu Lys Lys Val Ala Glu Ala Glu Lys Lys Val Glu Glu Ala
290                 295                 300

Lys Lys Lys Ala Glu Asp Gln Lys Glu Glu Asp Arg Arg Asn Tyr Pro
305                 310                 315                 320

Thr Asn Thr Tyr Lys Thr Leu Glu Leu Glu Ile Ala Glu Ser Asp Val
                325                 330                 335

Glu Val Lys Lys Ala Glu Leu Glu Leu Val Lys Glu Glu Ala Lys Glu
                340                 345                 350

Pro Arg Asn Glu Glu Lys Val Lys Gln Ala Lys Ala Glu Val Glu Ser
                355                 360                 365

Lys Lys Ala Glu Ala Thr Arg Leu Glu Lys Ile Lys Thr Asp Arg Lys
370                 375                 380

Lys Ala Glu Glu Glu Ala Lys Arg Lys Ala Ala Glu Glu Asp Lys Val
385                 390                 395                 400

Lys Glu Lys Pro Ala Glu Gln Pro Gln Pro Ala Pro Ala Pro Lys Ala
                405                 410                 415

Glu Lys Pro Ala Pro Ala Pro Lys Pro Glu Asn Pro Ala Glu Gln Pro
                420                 425                 430

Lys Ala Glu Lys Pro Ala Asp Gln Gln Ala Glu Glu Tyr Ala Arg
                435                 440                 445

Arg Ser Glu Glu Glu Tyr Asn Arg Leu Thr Leu Gln Gln Pro Pro Lys
                450                 455                 460

Thr Glu Lys Pro Ala Gln Pro Ser Thr Pro Lys Thr Asn
465                 470                 475
```

<210> SEQ ID NO 23
<211> LENGTH: 1433
<212> TYPE: DNA
<213> ORGANISM: Streptococcus pneumoniae

<400> SEQUENCE: 23

```
gagaacgaag gactaccaag taccacttct tctaataggg caaatgaaag tcaggcagaa      60
caaggagaac aacctaaaaa actcgattca gaacgagata aggcaaggaa agaggtcgag     120
gaatatgtaa aaaaaatagt gggtgagagc tatgcaaaat caactaaaaa gcgacataca     180
attactgtag ctctagttaa cgagttgaac aacattaaga acgagtattt gaataaaata     240
gttgaatcaa cctcagaaag ccaactacag atactgatga tggagagtcg atcaaaagta     300
gatgaagctg tgtctaagtt tgaaaaggac tcatcttctt cgtcaagttc agactcttcc     360
actaaaccgg aagcttcaga tacagcgaag ccaaacaagc cgacagaacc aggagaaaag     420
gtagcagaag ctaagaagaa ggttgaagaa gctgagaaaa agccaaggga tcaaaaagaa     480
gaagatcgtc gtaactaccc aaccattact tacaaaacgc ttgaacttga aattgctgag     540
tccgatgtgg aagttaaaaa agcggagctt gaactagtaa aagtgaaagc taacgaacct     600
cgagacgagc aaaaaattaa gcaagcagaa gcggaagttg agagtaaaca agctgaggct     660
acaaggttaa aaaaaatcaa gacagatcgt gaagaagcag aagaagaagc taaacgaaga     720
gcagatgcta agagcaagg taaccaaag gggcgggcaa acgaggagt tcctggagag     780
ctagcaacac ctgataaaaa agaaaatgat gcgaagtctt cagattctag cgtaggtgaa     840
gaaactcttc caagcccatc cctgaaacca gaaaaaaagg tagcagaagc tgagaagaag     900
gttgaagaag ctaagaaaaa agccgaggat caaaagaag aagatcgccg taactaccca     960
accaatactt acaaaacgct tgaacttgaa attgctgagt ccgatgtgga agttaaaaaa    1020
gcggagcttg aactagtaaa agaggaagct aaggaacctc gaaacgagga aaaagttaag    1080
caagcaaaag cggaagttga gagtaaaaaa gctgaggcta ctaggttaga aaaaatcaag    1140
acagatcgta aaaagcaga gaagaagct aaacgaaaag cagcagaaga agataaagtt    1200
aaagaaaaac cagctgaaca accacaacca gcgccggctc caaaagcaga aaaaccagct    1260
ccagctccaa aaccagagaa tccagctgaa caaccaaaag cagaaaaacc agctgatcaa    1320
caagctgaag aagagtatgc tcgtagatca gaagaagaat ataatcgctt gactctacag    1380
caaccgccaa aaactgaaaa accagcacaa ccatctactc aaaaacaaa tac            1433
```

<210> SEQ ID NO 24
<211> LENGTH: 477
<212> TYPE: PRT
<213> ORGANISM: Streptococcus pneumoniae

<400> SEQUENCE: 24

```
Glu Asn Glu Gly Leu Pro Ser Thr Thr Ser Ser Asn Arg Ala Asn Glu
1               5                   10                  15

Ser Gln Ala Glu Gln Gly Glu Gln Pro Lys Lys Leu Asp Ser Glu Arg
            20                  25                  30

Asp Lys Ala Arg Lys Glu Val Glu Glu Tyr Val Lys Lys Ile Val Gly
        35                  40                  45

Glu Ser Tyr Ala Lys Ser Thr Lys Lys Arg His Thr Ile Thr Val Ala
    50                  55                  60

Leu Val Asn Glu Leu Asn Asn Ile Lys Asn Glu Tyr Leu Asn Lys Ile
65                  70                  75                  80
```

Val Glu Ser Thr Ser Glu Ser Gln Leu Gln Ile Leu Met Met Glu Ser
            85                  90                  95

Arg Ser Lys Val Asp Glu Ala Val Ser Lys Phe Glu Lys Asp Ser Ser
            100                 105                 110

Ser Ser Ser Ser Asp Ser Ser Thr Lys Pro Glu Ala Ser Asp Thr
        115                 120                 125

Ala Lys Pro Asn Lys Pro Thr Glu Pro Gly Glu Lys Val Ala Glu Ala
130                 135                 140

Lys Lys Val Glu Glu Ala Glu Lys Ala Lys Asp Gln Lys Glu
145                 150                 155                 160

Glu Asp Arg Arg Asn Tyr Pro Thr Ile Thr Tyr Lys Thr Leu Glu Leu
                165                 170                 175

Glu Ile Ala Glu Ser Asp Val Glu Val Lys Lys Ala Glu Leu Glu Leu
            180                 185                 190

Val Lys Val Lys Ala Asn Glu Pro Arg Asp Glu Gln Lys Ile Lys Gln
            195                 200                 205

Ala Glu Ala Glu Val Glu Ser Lys Gln Ala Glu Ala Thr Arg Leu Lys
210                 215                 220

Lys Ile Lys Thr Asp Arg Glu Glu Ala Glu Glu Ala Lys Arg Arg
225                 230                 235                 240

Ala Asp Ala Lys Glu Gln Gly Lys Pro Lys Gly Arg Ala Lys Arg Gly
                245                 250                 255

Val Pro Gly Glu Leu Ala Thr Pro Asp Lys Lys Glu Asn Asp Ala Lys
            260                 265                 270

Ser Ser Asp Ser Ser Val Gly Glu Thr Leu Pro Ser Pro Ser Leu
        275                 280                 285

Lys Pro Glu Lys Val Ala Glu Ala Glu Lys Lys Val Glu Glu Ala
290                 295                 300

Lys Lys Lys Ala Glu Asp Gln Lys Glu Glu Asp Arg Arg Asn Tyr Pro
305                 310                 315                 320

Thr Asn Thr Tyr Lys Thr Leu Glu Leu Glu Ile Ala Glu Ser Asp Val
                325                 330                 335

Glu Val Lys Lys Ala Glu Leu Glu Leu Val Lys Glu Glu Ala Lys Glu
            340                 345                 350

Pro Arg Asn Glu Glu Lys Val Lys Gln Ala Lys Ala Glu Val Glu Ser
            355                 360                 365

Lys Lys Ala Glu Ala Thr Arg Leu Glu Lys Ile Lys Thr Asp Arg Lys
370                 375                 380

Lys Ala Glu Glu Glu Ala Lys Arg Lys Ala Ala Glu Glu Asp Lys Val
385                 390                 395                 400

Lys Glu Lys Pro Ala Glu Gln Pro Gln Pro Ala Pro Ala Pro Lys Ala
                405                 410                 415

Glu Lys Pro Ala Pro Ala Pro Lys Pro Glu Asn Pro Ala Glu Gln Pro
            420                 425                 430

Lys Ala Glu Lys Pro Ala Asp Gln Gln Ala Glu Glu Tyr Ala Arg
        435                 440                 445

Arg Ser Glu Glu Glu Tyr Asn Arg Leu Thr Leu Gln Gln Pro Pro Lys
450                 455                 460

Thr Glu Lys Pro Ala Gln Pro Ser Thr Pro Lys Thr Asn
465                 470                 475

<210> SEQ ID NO 25
<211> LENGTH: 2070

<212> TYPE: DNA
<213> ORGANISM: Streptococcus pneumoniae

<400> SEQUENCE: 25

```
gtccatgcag aagggggttag aagtgggaat aacctcacgg ttacatctag tgggcaagat      60
atatcgaaga agtatgctga tgaagtcgag tcgcatctag aaagtatatt gaaggatgtc     120
aaaaaaatt tgaaaaagt tcaacatacc caaaatgtcg gcttaattac aaagttgagc       180
gaaattaaaa agaagtattt gtatgactta aagttaatg ttttatcgga agctgagttg      240
acgtcaaaaa caaagaaac aaaagaaaag ttaaccgcaa cttttgagca gtttaaaaaa      300
gatacattac caacgaacc agaaaaaaag gtagcagaag ctcagaagaa ggttgaagaa      360
gctaagaaaa aagccgagga tcaaaagaa aaagatcgcc gtaactaccc aaccattact      420
tacaaaacgc ttgaacttga aattgctgag tccgatgtgg aagttaaaaa agcggagctt      480
gaactagtaa aagtgaaagc taaggaatct caagacgagg aaaaaattaa gcaagcagaa      540
gcggaagttg agagtaaaca agctgaggct acaaggttaa aaaaatcaa gacagatcgt      600
gaagaagcta acgaaaagc agatgctaag ttgaaggaag ctgttgaaaa gaatgtagcg      660
acttcagagc aagataaacc aaagaggcgg gcaaaacgag gagtttctgg agagctagca      720
acacctgata aaaagaaaa tgatgcgaag tcttcagatt ctagcgtagg tgaagaaact      780
cttccaagcc catcccttaa tatggcaaat gaaagtcaga cagaacatag gaaagatgtc      840
gatgaatata taaaaaaaat gttgagtgag atccaattag atagaagaaa acatacccaa      900
aatgtcaact aaacataaa gttgagcgca attaaaacga agtatttgta tgaattaagt      960
gttttaaaag agaactcgaa aaagaagag ttgacgtcaa aaaccaaagc agagttaacc     1020
gcagcttttg agcagtttaa aaaagataca ttgaaaccag aaaaaaaggt agcagaagct     1080
gagaagaagg ttgaagaagc taagaaaaaa gccaaggatc aaaaagaaga gatcgccgt     1140
aactacccaa ccaatactta caaaacgctt gaacttgaaa ttgctgagtc cgatgtgaaa     1200
gttaagaag cggagcttga actagtaaaa gaggaagcta acgaatctcg aaacgaggaa     1260
aaaattaagc aagcaaaaga gaagttgag agtaaaaaag ctgaggctac aaggttagaa     1320
aaaatcaaga cagatcgtaa aaaagcagaa gaagaagcta acgaaaagc agaagaatct     1380
gagaaaaaag ctgctgaagc caaacaaaaa gtggatgctg aagaatatgc tcttgaagct     1440
aaaatcgctg agttggaata tgaagttcag agactagaaa aagagctcaa agagattgat     1500
gagtctgact cagaagatta tcttaaagaa ggcctccgtg ctcctcttca atctaaattg     1560
gataccaaaa aagctaaact atcaaaactt gaagagttga gtgataagat tgatgagtta     1620
gacgctgaaa ttgcaaaact tgaagttcaa cttaaagatg ctgaaggaaa caataatgta     1680
gaagcctact ttaagaagg tttagagaaa actactgctg agaaaaaagc tgaattagaa     1740
aaagctgaag ctgaccttaa gaaagcagtt gatgagccag aaactccagc tccggctcct     1800
caaccagctc cagctccaga aaaaccagct gaaaaaccag ctccagctcc agaaaaacca     1860
gctccagctc cagaaaaacc agctccagct ccagaaaaac cagctccagc tccagaaaaa     1920
ccagctccag ctccagaaaaa accagctcca actccagaaa ctccaaaaac aggctggaaa     1980
caagaaaacg gtatgtggta cttctacaat actgatggtt caatggcaac aggctggctc     2040
caaaacaatg gctcatggta ctacctcaac                                       2070
```

<210> SEQ ID NO 26
<211> LENGTH: 690
<212> TYPE: PRT

<213> ORGANISM: Streptococcus pneumoniae

<400> SEQUENCE: 26

```
Val His Ala Glu Gly Val Arg Ser Gly Asn Leu Thr Val Thr Ser
1               5                   10                  15

Ser Gly Gln Asp Ile Ser Lys Lys Tyr Ala Asp Glu Val Glu Ser His
            20                  25                  30

Leu Glu Ser Ile Leu Lys Asp Val Lys Lys Asn Leu Lys Lys Val Gln
        35                  40                  45

His Thr Gln Asn Val Gly Leu Ile Thr Lys Leu Ser Glu Ile Lys Lys
    50                  55                  60

Lys Tyr Leu Tyr Asp Leu Lys Val Asn Val Leu Ser Glu Ala Glu Leu
65                  70                  75                  80

Thr Ser Lys Thr Lys Glu Thr Lys Glu Lys Leu Thr Ala Thr Phe Glu
                85                  90                  95

Gln Phe Lys Lys Asp Thr Leu Pro Thr Glu Pro Glu Lys Lys Val Ala
            100                 105                 110

Glu Ala Gln Lys Lys Val Glu Glu Ala Lys Lys Lys Ala Glu Asp Gln
        115                 120                 125

Lys Glu Lys Asp Arg Arg Asn Tyr Pro Thr Ile Thr Tyr Lys Thr Leu
    130                 135                 140

Glu Leu Glu Ile Ala Glu Ser Asp Val Glu Val Lys Lys Ala Glu Leu
145                 150                 155                 160

Glu Leu Val Lys Val Lys Ala Lys Glu Ser Gln Asp Glu Glu Lys Ile
                165                 170                 175

Lys Gln Ala Glu Ala Glu Val Glu Ser Lys Gln Ala Glu Ala Thr Arg
            180                 185                 190

Leu Lys Lys Ile Lys Thr Asp Arg Glu Glu Ala Lys Arg Lys Ala Asp
        195                 200                 205

Ala Lys Leu Lys Glu Ala Val Glu Lys Asn Val Ala Thr Ser Glu Gln
    210                 215                 220

Asp Lys Pro Lys Arg Arg Ala Lys Arg Gly Val Ser Gly Glu Leu Ala
225                 230                 235                 240

Thr Pro Asp Lys Lys Glu Asn Asp Ala Lys Ser Ser Asp Ser Ser Val
                245                 250                 255

Gly Glu Glu Thr Leu Pro Ser Pro Ser Leu Asn Met Ala Asn Glu Ser
            260                 265                 270

Gln Thr Glu His Arg Lys Asp Val Asp Glu Tyr Ile Lys Lys Met Leu
        275                 280                 285

Ser Glu Ile Gln Leu Asp Arg Arg Lys His Thr Gln Asn Val Asn Leu
    290                 295                 300

Asn Ile Lys Leu Ser Ala Ile Lys Thr Lys Tyr Leu Tyr Glu Leu Ser
305                 310                 315                 320

Val Leu Lys Glu Asn Ser Lys Lys Glu Leu Thr Ser Lys Thr Lys
                325                 330                 335

Ala Glu Leu Thr Ala Ala Phe Glu Gln Phe Lys Lys Asp Thr Leu Lys
            340                 345                 350

Pro Glu Lys Lys Val Ala Glu Ala Glu Lys Lys Val Glu Glu Ala Lys
        355                 360                 365

Lys Lys Ala Lys Asp Gln Lys Glu Glu Asp Arg Arg Asn Tyr Pro Thr
    370                 375                 380

Asn Thr Tyr Lys Thr Leu Glu Leu Glu Ile Ala Glu Ser Asp Val Lys
385                 390                 395                 400
```

Val Lys Glu Ala Glu Leu Glu Leu Val Lys Glu Ala Asn Glu Ser
            405                 410                 415

Arg Asn Glu Glu Lys Ile Lys Gln Ala Lys Lys Val Glu Ser Lys
            420                 425                 430

Lys Ala Glu Ala Thr Arg Leu Glu Lys Ile Lys Thr Asp Arg Lys Lys
            435                 440                 445

Ala Glu Glu Glu Ala Lys Arg Lys Ala Glu Glu Ser Glu Lys Lys Ala
    450                 455                 460

Ala Glu Ala Lys Gln Lys Val Asp Ala Glu Glu Tyr Ala Leu Glu Ala
465                 470                 475                 480

Lys Ile Ala Glu Leu Glu Tyr Glu Val Gln Arg Leu Glu Lys Glu Leu
            485                 490                 495

Lys Glu Ile Asp Glu Ser Asp Ser Glu Asp Tyr Leu Lys Glu Gly Leu
            500                 505                 510

Arg Ala Pro Leu Gln Ser Lys Leu Asp Thr Lys Lys Ala Lys Leu Ser
            515                 520                 525

Lys Leu Glu Glu Leu Ser Asp Lys Ile Asp Glu Leu Asp Ala Glu Ile
            530                 535                 540

Ala Lys Leu Glu Val Gln Leu Lys Asp Ala Glu Gly Asn Asn Asn Val
545                 550                 555                 560

Glu Ala Tyr Phe Lys Glu Gly Leu Glu Lys Thr Thr Ala Glu Lys Lys
            565                 570                 575

Ala Glu Leu Glu Lys Ala Glu Ala Asp Leu Lys Lys Ala Val Asp Glu
            580                 585                 590

Pro Glu Thr Pro Ala Pro Ala Pro Gln Pro Ala Pro Ala Pro Glu Lys
            595                 600                 605

Pro Ala Glu Lys Pro Ala Pro Ala Pro Glu Lys Pro Ala Pro Ala Pro
610                 615                 620

Glu Lys Pro Ala Pro Ala Pro Glu Lys Pro Ala Pro Ala Pro Glu Lys
625                 630                 635                 640

Pro Ala Pro Ala Pro Glu Lys Pro Ala Pro Thr Pro Glu Thr Pro Lys
            645                 650                 655

Thr Gly Trp Lys Gln Glu Asn Gly Met Trp Tyr Phe Tyr Asn Thr Asp
            660                 665                 670

Gly Ser Met Ala Thr Gly Trp Leu Gln Asn Asn Gly Ser Trp Tyr Tyr
            675                 680                 685

Leu Asn
    690

<210> SEQ ID NO 27
<211> LENGTH: 2067
<212> TYPE: DNA
<213> ORGANISM: Streptococcus pneumoniae

<400> SEQUENCE: 27
gtccatgcag aagggttcg cagtgggaat aacctcacgg ttacatctag tgggcaagat     60
atctcgaaga agtatgctga tgaagtcgag tcgcatctgg aaagtatctt gaaggatgtc    120
aaaaaaaatt tgaaaaaagt tcaacatacc caaaatgtcg gcttaattac aaagttgagc    180
gaaattaaaa agaagtattt gtatgactta aagttaatgt ttttatcgga agctgagttg    240
acgtcaaaaa caaagaaac aaaagaaaag ttaaccgcaa cttttgagca gtttaaaaaa    300
gatacattac caacagaacc agaaaaaaag gtagcagaag ctcagaagaa ggttgaagaa    360
gctaagaaaa aagccgagga tcaaaaagaa aaagatcgcc gtaactaccc aaccattact    420

```
tacaaaacgc ttgaacttga aattgctgag tccgatgtgg aagttaaaaa agcggagctt      480
gaactggtaa aagtgaaagc taaggaatct caagacgagg aaaaaattaa gcaagcagaa      540
gcggaagttg agagtaaaca agctgaggct acacgcttaa aaaaaatcaa gacagatcgt      600
gaagctaaac gcaaagcaga tgctaagttg aaggaagctg ttgaaaagaa tgtagcgact      660
tcagagcaag ataaaccaaa gcggcgcgca aaacgcggcg tttctggcga gctggcaaca      720
cctgataaaa aagaaaatga tgcgaagtct tcagattcta gcgtaggtga agaaactctt      780
ccaagcccat cccttaatat ggcaaatgaa agtcagacag aacatcggaa agatgtcgat      840
gaatatatca aaaaaatgtt gagtgagatc caattagatc gccgcaaaca tacccaaaat      900
gtcaacttaa acatcaagtt gagcgcaatt aaaacgaagt atttgtatga attaagtgtt      960
ttaaaagaga actcgaaaaa agaagagttg acgtcaaaaa ccaaagcaga gttaaccgca     1020
gcttttgagc agtttaaaaa agatacattg aaaccagaaa aaaaggtagc agaagctgag     1080
aagaaggttg aagaagctaa gaaaaaagcc aaggatcaaa agaagaaga tcgccgtaac     1140
tacccaacca atacttacaa aacgcttgaa cttgaaattg ctgagtccga tgtgaaagtt     1200
aaagaagcgg agctcgaact agtaaaagag gaagctaacg aatctcgcaa cgaggaaaaa     1260
attaagcaag caaagagaa agttgagagt aaaaaagctg aggctacacg cttagaaaaa     1320
atcaagacag atcgtaaaaa agcagaagaa gaagctaaac gcaaagcaga gaatctgag     1380
aaaaagctg ctgaagccaa acaaaagtg gatgctgaag aatatgctct tgaagctaaa     1440
atcgctgagt tggaatatga agttcagcgc ctggaaaaag agctcaaaga gattgatgag     1500
tctgactcag aagattatct taagaaggc ctccgtgctc ctcttcaatc taaattggat     1560
accaaaaaag ctaaactgtc aaaacttgaa gagttgagtg ataagattga tgagttagac     1620
gctgaaattg caaaacttga agttcaactt aaagatgctg aaggaaacaa taatgtagaa     1680
gcctactta aagaaggttt agagaaaact actgctgaga aaaaagctga attagaaaaa     1740
gctgaagctg accttaagaa agcagttgat gagccagaaa ctccagctcc ggctcctcaa     1800
ccagctccag ctccagaaaa accagctgaa aaaccagctc agctccaga aaaaccagct     1860
ccagctccag aaaaaccagc tccagctcca gaaaaaccag ctccagctcc agaaaaacca     1920
gctccagctc cagaaaaacc agctccaact ccagaaactc aaaaacagg ctggaaacaa     1980
gaaaacggta tgtggtactt ctacaatact gatggttcaa tggcaacagg ctggctccaa     2040
aacaatggct catggtacta cctcaac                                         2067
```

<210> SEQ ID NO 28
<211> LENGTH: 673
<212> TYPE: PRT
<213> ORGANISM: Streptococcus pneumoniae

<400> SEQUENCE: 28

```
Val His Ala Glu Gly Val Arg Ser Gly Asn Asn Leu Thr Val Thr Ser
1               5                   10                  15

Ser Gly Gln Asp Ile Ser Lys Lys Tyr Ala Asp Glu Val Glu Ser His
            20                  25                  30

Leu Glu Ser Ile Leu Lys Asp Val Lys Lys Asn Leu Lys Lys Val Gln
        35                  40                  45

His Thr Gln Asn Val Gly Leu Ile Thr Lys Leu Ser Glu Ile Lys Lys
    50                  55                  60

Lys Tyr Leu Tyr Asp Leu Lys Val Asn Val Leu Ser Glu Ala Glu Leu
65                  70                  75                  80
```

```
Thr Ser Lys Thr Lys Glu Thr Lys Glu Lys Leu Thr Ala Thr Phe Glu
            85                  90                  95
Gln Phe Lys Lys Asp Thr Leu Pro Thr Glu Pro Glu Lys Lys Val Ala
                100                 105                 110
Glu Ala Gln Lys Lys Val Glu Glu Ala Lys Lys Lys Ala Glu Asp Gln
            115                 120                 125
Lys Glu Lys Asp Arg Arg Asn Tyr Pro Thr Ile Thr Tyr Lys Thr Leu
            130                 135                 140
Glu Leu Glu Ile Ala Glu Ser Asp Val Glu Val Lys Lys Ala Glu Leu
145                 150                 155                 160
Glu Leu Val Lys Val Lys Ala Lys Glu Ser Gln Asp Glu Glu Lys Ile
                165                 170                 175
Lys Gln Ala Glu Ala Glu Val Glu Ser Lys Gln Ala Glu Ala Thr Arg
            180                 185                 190
Leu Lys Lys Ile Lys Thr Asp Arg Ala Lys Arg Lys Ala Asp Ala Lys
            195                 200                 205
Leu Lys Glu Ala Val Glu Lys Asn Val Ala Thr Ser Glu Gln Asp Lys
            210                 215                 220
Pro Lys Arg Arg Ala Lys Arg Gly Val Ser Gly Glu Leu Ala Thr Pro
225                 230                 235                 240
Asp Lys Lys Glu Asn Asp Ala Lys Ser Ser Asp Ser Ser Val Gly Glu
                245                 250                 255
Glu Thr Leu Pro Ser Pro Ser Leu Asn Met Ala Asn Glu Ser Gln Thr
            260                 265                 270
Glu His Arg Lys Asp Val Asp Glu Tyr Ile Lys Lys Met Leu Ser Glu
            275                 280                 285
Ile Gln Leu Asp Arg Arg Lys His Thr Gln Asn Val Asn Leu Asn Ile
            290                 295                 300
Lys Leu Ser Ala Ile Lys Thr Lys Tyr Leu Tyr Glu Leu Ser Val Leu
305                 310                 315                 320
Lys Glu Asn Ser Lys Lys Glu Glu Leu Thr Ser Lys Thr Lys Ala Glu
                325                 330                 335
Leu Thr Ala Ala Phe Glu Gln Phe Lys Lys Asp Thr Leu Lys Pro Glu
            340                 345                 350
Lys Lys Val Ala Glu Ala Glu Lys Lys Val Glu Glu Ala Lys Lys Lys
            355                 360                 365
Ala Lys Asp Gln Lys Glu Glu Asp Arg Arg Asn Tyr Pro Thr Asn Thr
            370                 375                 380
Tyr Lys Thr Leu Glu Leu Glu Ile Ala Glu Ser Asp Val Lys Val Lys
385                 390                 395                 400
Glu Ala Glu Lys Ile Lys Gln Ala Lys Glu Lys Val Glu Ser Lys Lys
                405                 410                 415
Ala Glu Ala Thr Arg Leu Glu Lys Ile Lys Thr Asp Arg Lys Lys Ala
            420                 425                 430
Glu Glu Glu Ala Lys Arg Lys Ala Glu Glu Ser Glu Lys Lys Ala Ala
            435                 440                 445
Glu Ala Lys Gln Lys Val Asp Ala Glu Tyr Ala Leu Glu Ala Lys
            450                 455                 460
Ile Ala Glu Leu Glu Tyr Glu Val Gln Arg Leu Glu Lys Glu Leu Lys
465                 470                 475                 480
Glu Ile Asp Glu Ser Asp Ser Glu Asp Tyr Leu Lys Glu Gly Leu Arg
                485                 490                 495
Ala Pro Leu Gln Ser Lys Leu Asp Thr Lys Lys Ala Lys Leu Ser Lys
```

-continued

```
                500           505           510
Leu Glu Glu Leu Ser Asp Lys Ile Asp Glu Leu Asp Ala Glu Ile Ala
            515                   520                   525

Lys Leu Glu Val Gln Leu Lys Asp Ala Glu Gly Asn Asn Val Glu
530                     535                     540

Ala Tyr Phe Lys Glu Gly Leu Glu Lys Thr Thr Ala Glu Lys Lys Ala
545                     550                     555                     560

Glu Leu Glu Lys Ala Glu Ala Asp Leu Lys Lys Ala Val Asp Glu Pro
            565                     570                     575

Glu Thr Pro Ala Pro Ala Pro Gln Pro Ala Pro Ala Pro Glu Lys Pro
            580                     585                     590

Ala Glu Lys Pro Ala Pro Ala Pro Glu Lys Pro Ala Pro Ala Pro Glu
            595                     600                     605

Lys Pro Ala Pro Ala Pro Glu Lys Pro Ala Pro Ala Pro Glu Lys Pro
            610                     615                     620

Ala Pro Ala Pro Glu Lys Pro Ala Pro Thr Pro Glu Thr Pro Lys Thr
625                     630                     635                     640

Gly Trp Lys Gln Glu Asn Gly Met Trp Tyr Phe Tyr Asn Thr Asp Gly
            645                     650                     655

Ser Met Ala Thr Gly Trp Leu Gln Asn Asn Gly Ser Trp Tyr Tyr Leu
            660                     665                     670

Asn

<210> SEQ ID NO 29
<211> LENGTH: 3228
<212> TYPE: DNA
<213> ORGANISM: Streptococcus pneumoniae

<400> SEQUENCE: 29
gaattcgaga acgaaggcct gccaagtacc acttcttcta atcgcgcaaa tgaaagtcag      60
gcagaacaag gcgaacaacc taaaaaactc gattcagaac gcgataaggc acgcaaagag     120
gtcgaggaat atgtaaaaaa aatcgtgggt gagagctatg caaaatcaac taaaaagcgc     180
catacaatta ctgtagctct ggttaacgag ttgaacaaca ttaagaacga gtatttgaat     240
aaaatcgttg aatcaaccct agaaagccaa ctacagatcc tgatgatgga gagtcgctca     300
aaagtagatg aagctgtgtc taagtttgaa aaggactcat cttcttcgtc aagttcagac     360
tcttccacta accggaagc ttcagataca gcgaagccaa acaagccgac agaaccaggc     420
gaaaaggtag cagaagctaa gaagaaggtt gaagaagctg agaaaaaagc caaggatcaa     480
aaagaagaag atcgtcgtaa ctacccaacc attacttaca aaacgcttga acttgaaatt     540
gctgagtccg atgtggaagt taaaaaagcg agcttgaac tagtaaaagt gaaagctaac     600
gaacctcgcg acgagcaaaa aattaagcaa gcagaagcgg aagttgagag taaacaagct     660
gaggctacac gcttaaaaaa aatcaagaca gatcgtgaag aagcagaaga agaagctaaa     720
cgccgcgcag atgctaaaga gcaaggtaaa ccaaaggggc gcgcaaaacg cggagttcct     780
ggcgagctgg caacacctga taaaaaagaa aatgatgcga agtcttcaga ttctagcgta     840
ggtgaagaaa ctcttccaag cccatccctg aaaccagaaa aaaggtagc agaagctgag     900 aagaaggttg aagaagctaa gaaaaaagcc gaggatcaaa agaagaaga tcgccgtaac     960 tacccaacca atacttacaa aacgcttgaa cttgaaattg ctgagtccga tgtggaagtt    1020
aaaaaagcga gcttgaact ggtaaaagag gaagctaagg aacctcgcaa cgaggaaaaa    1080
gttaagcaag caaaagcgga agttgagagt aaaaagctg aggctactcg cttagaaaaa    1140
```

```
atcaagacag atcgtaaaaa agcagaagaa gaagctaaac gcaaagcagc agaagaagat    1200
aaagttaaag aaaaaccagc tgaacaacca caaccagcgc cggctccaaa agcagaaaaa    1260
ccagctccag ctccaaaacc agagaatcca gctgaacaac caaaagcaga aaaaccagct    1320
gatcaacaag ctgaagaaga gtatgctcgt agatcagaag aagaatataa tcgcttgact    1380
ctacagcaac cgccaaaaac tgaaaaacca gcacaaccat ctactccaaa aacactgcag    1440
gttcgcagtg ggaataacct cacggttaca tctagtgggc aagatatctc gaagaagtat    1500
gctgatgaag tcgagtcgca tctggaaagt atcttgaagg atgtcaaaaa aaatttgaaa    1560
aaagttcaac atacccaaaa tgtcggctta attacaaagt gagcgaaat  taaaaagaag    1620
tatttgtatg acttaaaagt taatgtttta tcggaagctg agttgacgtc aaaaacaaaa    1680
gaaacaaaag aaaagttaac cgcaacttttt gagcagttta aaaagatac  attaccaaca    1740
gaaactaccc aagcacccac ttcttctaat aggggaaatg aaagtcaggc agaacaacgt    1800
agagaactcg atttagaacg agataaggta agaaagagg  tcagggaata taagaaaaa     1860
aaagtgaaag agctctattc aaaatcaact aaaagtcgac ataagaagac tgtagatata    1920
gttaacaagt tgcaaaacat taataacgag tatttgaata aaataattca atcaacctca    1980
acatacgaag aactgcagaa actgatgatg gagagtcaat cccttaatat ggcaaatgaa    2040
agtcagacag aacatcggaa agatgtcgat gaatatatca aaaaaatgtt gagtgagatc    2100
caattagatc gccgcaaaca tacccaaaat gtcaacttaa acatcaagtt gagcgcaatt    2160
aaaacgaagt atttgtatga attaagtgtt ttaaaagaga actcgaaaaa agaagagttg    2220
acgtcaaaaa ccaaagcaga gttaaccgca gcttttgagc agtttaaaaa agatgattat    2280
tttgaaaaag acttccgtcc agctttcaat aaaaaccggc agatggtagc cattcaagaa    2340
tccttgaaca aactagatgg tgaaacaaaa actgttccag atgggctaa  actcacagga    2400
gaagctggaa atgcctataa tgaggtcaga gattatgcaa taaagttgt  ttctgaaaac    2460
aagaaacttc tatcacagac agcagtgaca atggatgaac tggcaatgca attaaccaaa    2520
ttgaacgatg ccatgtctaa attgagagag gctaaagcga aattggtaaa agaaaaagat    2580
cgccgtaact acccaaccat tacttacaaa acgaaagctg ctgaagccaa acaaaaagtg    2640
gatgctgaag aatatgctct tgaagctaaa atcgctgagt tggaatatga agttcagcgc    2700
ctggaaaaag agctcaaaga gattgatgag tctgactcag aagattatct taagaaggc    2760
ctccgtgctc ctcttcaatc taaattggat accaaaaaag ctaaactgtc aaaacttgaa    2820
gagttgagtg ataagattga tgagttagac gctgaaattg caaaacttga agttcaactt    2880
aaagatgctg aaggaaacaa taatgtagaa gcctacttta agaaggtt  t agagaaaact    2940
actgctgaga aaaagctga  attagaaaaa gctgaagctg accttaagaa agcagttgat    3000
gagccagaaa ctccagctcc ggctcctcaa ccagctccag ctccagaaaa accagctgaa    3060
aaaccagctc cagctccaga aaaccagct ccagctccaa aaaaccagc  tccagctcca    3120
gaaaaaccag ctccagctcc agaaaaacca gctccagctc cagaaaaacc agctccaact    3180
ccagaaactc aaaaacagg ctggaaacaa gaaaacggta tgaagctt               3228
```

<210> SEQ ID NO 30
<211> LENGTH: 1063
<212> TYPE: PRT
<213> ORGANISM: Streptococcus pneumoniae

<400> SEQUENCE: 30

```
Glu Gly Leu Pro Ser Thr Thr Ser Ser Asn Arg Ala Asn Glu Ser Gln
1               5                   10                  15

Ala Glu Gln Gly Glu Gln Pro Lys Lys Leu Asp Ser Glu Arg Asp Lys
            20                  25                  30

Ala Arg Lys Glu Val Glu Glu Tyr Val Lys Lys Ile Val Gly Glu Ser
            35                  40                  45

Tyr Ala Lys Ser Thr Lys Lys Arg His Thr Ile Thr Val Ala Leu Val
        50                  55                  60

Asn Glu Leu Asn Asn Ile Lys Asn Glu Tyr Leu Asn Lys Ile Val Glu
65                  70                  75                  80

Ser Thr Ser Glu Ser Gln Leu Gln Ile Leu Met Met Glu Ser Arg Ser
                85                  90                  95

Lys Val Asp Glu Ala Val Ser Lys Phe Glu Lys Asp Ser Ser Ser Ser
                100                 105                 110

Ser Ser Ser Asp Ser Ser Thr Lys Pro Glu Ala Ser Asp Thr Ala Lys
            115                 120                 125

Pro Asn Lys Pro Thr Glu Pro Gly Glu Lys Val Ala Glu Ala Lys Lys
        130                 135                 140

Lys Val Glu Glu Ala Glu Lys Lys Ala Lys Asp Gln Lys Glu Glu Asp
145                 150                 155                 160

Arg Arg Asn Tyr Pro Thr Ile Thr Tyr Lys Thr Leu Glu Leu Glu Ile
                165                 170                 175

Ala Glu Ser Asp Val Glu Val Lys Lys Ala Glu Leu Glu Leu Val Lys
            180                 185                 190

Val Lys Ala Asn Glu Pro Arg Asp Glu Gln Lys Ile Lys Gln Ala Glu
        195                 200                 205

Ala Glu Val Glu Ser Lys Gln Ala Glu Ala Thr Arg Leu Lys Lys Ile
        210                 215                 220

Lys Thr Asp Arg Glu Glu Ala Glu Glu Ala Lys Arg Arg Ala Asp
225                 230                 235                 240

Ala Lys Glu Gln Gly Lys Pro Lys Gly Arg Ala Lys Arg Gly Val Pro
            245                 250                 255

Gly Glu Leu Ala Thr Pro Asp Lys Lys Glu Asn Asp Ala Lys Ser Ser
            260                 265                 270

Asp Ser Ser Val Gly Glu Glu Thr Leu Pro Ser Pro Ser Leu Lys Pro
        275                 280                 285

Glu Lys Lys Val Ala Glu Ala Glu Lys Lys Val Glu Glu Ala Lys Lys
        290                 295                 300

Lys Ala Glu Asp Gln Lys Glu Glu Asp Arg Arg Asn Tyr Pro Thr Asn
305                 310                 315                 320

Thr Tyr Lys Thr Leu Glu Leu Glu Ile Ala Glu Ser Asp Val Glu Val
            325                 330                 335

Lys Lys Ala Glu Leu Glu Leu Val Lys Glu Glu Ala Lys Glu Pro Arg
            340                 345                 350

Asn Glu Glu Lys Val Lys Gln Ala Lys Ala Glu Val Glu Ser Lys Lys
                355                 360                 365

Ala Glu Ala Thr Arg Leu Glu Lys Ile Lys Thr Asp Arg Lys Lys Ala
        370                 375                 380

Glu Glu Glu Ala Lys Arg Lys Ala Ala Glu Glu Asp Lys Val Lys Glu
385                 390                 395                 400

Lys Pro Ala Glu Gln Pro Gln Pro Ala Pro Ala Pro Lys Ala Glu Lys
                405                 410                 415

Pro Ala Pro Ala Pro Lys Pro Glu Asn Pro Ala Glu Gln Pro Lys Ala
```

```
              420             425             430
Glu Lys Pro Ala Asp Gln Gln Ala Glu Glu Tyr Ala Arg Arg Ser
        435             440             445
Glu Glu Glu Tyr Asn Arg Leu Thr Leu Gln Gln Pro Pro Lys Thr Glu
    450             455             460
Lys Pro Ala Gln Pro Ser Thr Pro Lys Thr Leu Gln Val Arg Ser Gly
465             470             475             480
Asn Asn Leu Thr Val Thr Ser Ser Gly Gln Asp Ile Ser Lys Lys Tyr
            485             490             495
Ala Asp Glu Val Glu Ser His Leu Glu Ser Ile Leu Lys Asp Val Lys
        500             505             510
Lys Asn Leu Lys Lys Val Gln His Thr Gln Asn Val Gly Leu Ile Thr
    515             520             525
Lys Leu Ser Glu Ile Lys Lys Lys Tyr Leu Tyr Asp Leu Lys Val Asn
    530             535             540
Val Leu Ser Glu Ala Glu Leu Thr Ser Lys Thr Lys Glu Thr Lys Glu
545             550             555             560
Lys Leu Thr Ala Thr Phe Glu Gln Phe Lys Lys Asp Thr Leu Pro Thr
            565             570             575
Glu Thr Thr Gln Ala Pro Thr Ser Ser Asn Arg Gly Asn Glu Ser Gln
            580             585             590
Ala Glu Gln Arg Arg Glu Leu Asp Leu Glu Arg Asp Lys Val Lys Lys
        595             600             605
Glu Val Arg Glu Tyr Lys Glu Lys Val Lys Glu Leu Tyr Ser Lys
    610             615             620
Ser Thr Lys Ser Arg His Lys Lys Thr Val Asp Ile Val Asn Lys Leu
625             630             635             640
Gln Asn Ile Asn Asn Glu Tyr Leu Asn Lys Ile Ile Gln Ser Thr Ser
            645             650             655
Thr Tyr Glu Glu Leu Gln Lys Leu Met Met Glu Ser Gln Ser Leu Asn
            660             665             670
Met Ala Asn Glu Ser Gln Thr Glu His Arg Lys Asp Val Asp Glu Tyr
        675             680             685
Ile Lys Lys Met Leu Ser Glu Ile Gln Leu Asp Arg Arg Lys His Thr
    690             695             700
Gln Asn Val Asn Leu Asn Ile Lys Leu Ser Ala Ile Lys Thr Lys Tyr
705             710             715             720
Leu Tyr Glu Leu Ser Val Leu Lys Glu Asn Ser Lys Lys Glu Glu Leu
            725             730             735
Thr Ser Lys Thr Lys Ala Glu Leu Thr Ala Ala Phe Glu Gln Phe Lys
            740             745             750
Lys Asp Asp Tyr Phe Glu Lys Asp Phe Arg Pro Ala Phe Asn Lys Asn
        755             760             765
Arg Gln Met Val Ala Ile Gln Glu Ser Leu Asn Lys Leu Asp Gly Glu
    770             775             780
Thr Lys Thr Val Pro Asp Gly Ala Lys Leu Thr Gly Glu Ala Gly Asn
785             790             795             800
Ala Tyr Asn Glu Val Arg Asp Tyr Ala Ile Lys Val Val Ser Glu Asn
            805             810             815
Lys Lys Leu Leu Ser Gln Thr Ala Val Thr Met Asp Glu Leu Ala Met
        820             825             830
Gln Leu Thr Lys Leu Asn Asp Ala Met Ser Lys Leu Arg Glu Ala Lys
    835             840             845
```

```
Ala Lys Leu Val Lys Glu Lys Asp Arg Arg Asn Tyr Pro Thr Ile Thr
        850                 855                 860

Tyr Lys Thr Lys Ala Ala Glu Ala Lys Gln Lys Val Asp Ala Glu Glu
865                 870                 875                 880

Tyr Ala Leu Glu Ala Lys Ile Ala Glu Leu Tyr Glu Val Gln Arg
                885                 890                 895

Leu Glu Lys Glu Leu Lys Glu Ile Asp Glu Ser Asp Ser Glu Asp Tyr
            900                 905                 910

Leu Lys Glu Gly Leu Arg Ala Pro Leu Gln Ser Lys Leu Asp Thr Lys
        915                 920                 925

Lys Ala Lys Leu Ser Lys Leu Glu Glu Leu Ser Asp Lys Ile Asp Glu
    930                 935                 940

Leu Asp Ala Glu Ile Ala Lys Leu Glu Val Gln Leu Lys Asp Ala Glu
945                 950                 955                 960

Gly Asn Asn Val Glu Ala Tyr Phe Lys Glu Gly Leu Glu Lys Thr
                965                 970                 975

Thr Ala Glu Lys Lys Ala Glu Leu Glu Lys Ala Glu Ala Asp Leu Lys
            980                 985                 990

Lys Ala Val Asp Glu Pro Glu Thr  Pro Ala Pro Ala Pro Gln Pro Ala
        995                 1000                1005

Pro Ala  Pro Glu Lys Pro Ala  Glu Lys Pro Ala Pro  Ala Pro Glu
    1010                1015                1020

Lys Pro  Ala Pro Ala Pro Glu  Lys Pro Ala Pro Ala  Pro Glu Lys
    1025                1030                1035

Pro Ala  Pro Ala Pro Glu Lys  Pro Ala Pro Ala Pro  Glu Lys Pro
    1040                1045                1050

Ala Pro  Thr Pro Glu Thr Pro  Lys Thr Gly
    1055                1060
```

<210> SEQ ID NO 31
<211> LENGTH: 1095
<212> TYPE: DNA
<213> ORGANISM: Streptococcus pneumoniae

<400> SEQUENCE: 31

```
acgactgatg acaaaattgc tgctcaagat aataaaatta gtaacttaac agcacaacaa    60
caagaagccc aaaaacaagt tgaccaaatt caggagcaag tatcagctat tcaagctgag   120
cagtctaact tgcaagctga aaatgataga ttacaagcag aatctaagaa actcgagggt   180
gagattacag aactttctaa aaacattgtt tctcgtaacc aatcgttgga aaaacaagct   240
cgtagtgctc aaacaaatgg agccgtaact agctatatca ataccattgt aaactcaaaa   300
tcaattacag aagctatttc acgtgttgct gcaatgagtg aaatcgtatc tgcaaacaac   360
aaaatgttag aacaacaaaa ggcagataaa aaagctattt ctgaaaaaca gtagcaaat   420 aatgatgcta tcaatactgt aattgctaat caacaaaaat ggctgatga tgctcaagca   480 ttgactacga aacaggcaga actaaaagct gctgaattaa gtcttgctgc tgagaaagcg   540
acagctgaag gggaaaaagc aagtctatta gagcaaaaag cagcagctga ggcagaggct   600
cgtgcagctg cggtagcaga agcagcttat aagaaaaac gagctagcca acaacaatca   660
gtacttgctt cagcaaacac taacttaaca gctcaagtgc aagcagtatc tgaatctgca   720
gcagcacctg tccgtgcaaa agttcgtcca acatacagta caaacgcttc aagttatcca   780
attggagaat gtacatgggg agtaaaaaca ttggcaccct gggctggaga ctactgggt    840
```

-continued

```
aatggagcac agtgggctac aagtgcagca gcagcaggtt tccgtacagg ttcaacacct      900
caagttggag caattgcatg ttggaatgat ggtggatatg gtcacgtagc ggttgttaca      960
gctgttgaat caacaacacg tatccaagta tcagaatcaa attatgcagg taatcgtaca     1020
attggaaatc accgtggatg gttcaatcca acaacaactt ctgaaggttt tgttacatat     1080
atttatgcag attaa                                                      1095
```

<210> SEQ ID NO 32
<211> LENGTH: 364
<212> TYPE: PRT
<213> ORGANISM: Streptococcus pneumoniae

<400> SEQUENCE: 32

```
Thr Thr Asp Asp Lys Ile Ala Ala Gln Asp Asn Lys Ile Ser Asn Leu
1               5                   10                  15

Thr Ala Gln Gln Glu Ala Gln Lys Gln Val Asp Gln Ile Gln Glu
            20                  25                  30

Gln Val Ser Ala Ile Gln Ala Glu Gln Ser Asn Leu Gln Ala Glu Asn
        35                  40                  45

Asp Arg Leu Gln Ala Glu Ser Lys Lys Leu Glu Gly Glu Ile Thr Glu
    50                  55                  60

Leu Ser Lys Asn Ile Val Ser Arg Asn Gln Ser Leu Glu Lys Gln Ala
65                  70                  75                  80

Arg Ser Ala Gln Thr Asn Gly Ala Val Thr Ser Tyr Ile Asn Thr Ile
                85                  90                  95

Val Asn Ser Lys Ser Ile Thr Glu Ala Ile Ser Arg Val Ala Ala Met
            100                 105                 110

Ser Glu Ile Val Ser Ala Asn Asn Lys Met Leu Glu Gln Gln Lys Ala
        115                 120                 125

Asp Lys Lys Ala Ile Ser Glu Lys Gln Val Ala Asn Asn Asp Ala Ile
    130                 135                 140

Asn Thr Val Ile Ala Asn Gln Gln Lys Leu Ala Asp Asp Ala Gln Ala
145                 150                 155                 160

Leu Thr Thr Lys Gln Ala Glu Leu Lys Ala Ala Glu Leu Ser Leu Ala
                165                 170                 175

Ala Glu Lys Ala Thr Ala Glu Gly Glu Lys Ala Ser Leu Leu Glu Gln
            180                 185                 190

Lys Ala Ala Glu Ala Glu Ala Arg Ala Ala Ala Val Ala Glu Ala
        195                 200                 205

Ala Tyr Lys Glu Lys Arg Ala Ser Gln Gln Ser Val Leu Ala Ser
    210                 215                 220

Ala Asn Thr Asn Leu Thr Ala Gln Val Gln Ala Val Ser Glu Ser Ala
225                 230                 235                 240

Ala Ala Pro Val Arg Ala Lys Val Arg Pro Thr Tyr Ser Thr Asn Ala
                245                 250                 255

Ser Ser Tyr Pro Ile Gly Glu Cys Thr Trp Gly Val Lys Thr Leu Ala
            260                 265                 270

Pro Trp Ala Gly Asp Tyr Trp Gly Asn Gly Ala Gln Trp Ala Thr Ser
        275                 280                 285

Ala Ala Ala Gly Phe Arg Thr Gly Ser Thr Pro Gln Val Gly Ala
    290                 295                 300

Ile Ala Cys Trp Asn Asp Gly Gly Tyr Gly His Val Ala Val Val Thr
305                 310                 315                 320

Ala Val Glu Ser Thr Thr Arg Ile Gln Val Ser Glu Ser Asn Tyr Ala
```

325                 330                 335
Gly Asn Arg Thr Ile Gly Asn His Arg Gly Trp Phe Asn Pro Thr Thr
            340                 345                 350
Thr Ser Glu Gly Phe Val Thr Tyr Ile Tyr Ala Asp
            355                 360

<210> SEQ ID NO 33
<211> LENGTH: 1095
<212> TYPE: DNA
<213> ORGANISM: Streptococcus pneumoniae

<400> SEQUENCE: 33
acgactgatg acaaaattgc tgctcaagat aataaaattt ccaacctgac cgcacaacaa      60
caagaagccc aaaaacaagt tgaccaaatt caggagcaag tatccgctat tcaagctgag     120
cagtctaact tgcaagctga aaatgatcgc ctgcaagcag aatctaagaa actcgagggt     180
gagattaccg aactttctaa aaacattgtt tctcgtaacc aatcgttgga aaaacaagct     240
cgttccgctc aaaccaatgg cgccgtaact agctatatca ataccattgt aaactccaaa     300
tccattaccg aagctatttc ccgtgttgct gcaatgtccg aaatcgtatc tgcaaacaac     360
aaaatgctgg aacaacaaaa ggcagataaa aaagctattt ctgaaaaaca gtagcaaat     420 aatgatgcta tcaatactgt aattgctaat caacaaaaat tggctgatga tgctcaagca     480
ttgactacga acaggcaga actgaaagct gctgaactgt cccttgctgc tgagaaagcg     540
accgctgaag gcgaaaaagc atccctgctg agcaaaaag cagcagctga ggcagaggct     600
cgtgcagctg cggtagcaga agcagcttat aagaaaaac gcgctagcca acaacaatcc     660
gtacttgctt ccgcaaacac taacctgacc gctcaagtgc aagcagtatc tgaatctgca     720
gcagcacctg tccgtgcaaa agttcgtcca acctactcca ccaacgcttc ctcctatcca     780
attggcgaat gtacctgggg cgtaaaaacc ttggcacctt gggctggcga ctactggggt     840
aatggcgcac agtgggctac ctccgcagca gcagcaggtt tccgtaccgg ttccacccct     900
caagttggcg caattgcatg ttggaatgat ggtggctatg gtcacgtagc ggttgttacc     960
gctgttgaat ccaccacccg tatccaagta tccgaatcca attatgcagg taatcgtacc    1020
attggcaatc accgtggctg gttcaatcca accaccactt ctgaaggttt tgttacctat    1080
atttatgcag attaa                                                    1095

<210> SEQ ID NO 34
<211> LENGTH: 1980
<212> TYPE: DNA
<213> ORGANISM: Streptococcus pneumoniae

<400> SEQUENCE: 34
atgatccaaa tcggcaagat ttttgccgga cgctatcgga ttgtcaaaca gattggtcga      60
ggaggtatgg cggatgtcta cctagccaaa gacttaatct tagatgggga agaagtggca     120
gtgaaggttc tgaggaccaa ctaccagacg gacccgatag ctgtagctcg ttttcagcgt     180
gaagcgagag ctatggcaga tctagaccat cctcatatcg ttcggataac agatattggc     240
gaggaagacg tcaacagta cctagctatg gagtatgtgg ctggactgga cctcaaacgc     300
tatatcaagg aacattatcc tctttctaat gaagaagcag tccgtatcat gggacaaatt     360
ctcttggcta tgcgcttggc ccatactcga ggaattgttc acagggactt gaaacctcaa     420 aatatccctct tgcaccaga tgggactgcc aaggtcacag actttgggat tgctgtagcc     480
tttgcagaga caagtctgac ccagactaac tcgatgttgg gctcagttca ttacttgtca     540

```
ccagagcagg cgcgtggttc gaaggcgact gtgcagagtg atatctatgc catgggatt    600 attttctatg agatgctgac aggccatatc ccttatgacg gggatagcgc ggtgaccatt    660
gccctccagc atttccagaa acccctgccg tccgttattg cagaaaatcc atctgtacct    720
caggctttag aaaatgttat tatcaaggca actgctaaaa agttgaccaa tcgctaccgc    780
tcggtttcag agatgtatgt ggacttgtct agtagcttgt cctacaatcg tagaaatgaa    840
agtaagttaa tctttgatga acgagcaag gcagatacca agaccttgcc gaaggtttct    900
cagagtacct tgacatctat tcctaaggtt caagcgcaaa cagaacacaa atcaatcaaa    960
aacccaagcc aggctgtgac agaggaaact taccaaccac aagcaccgaa aaaacataga    1020
tttaagatgc gttacctgat tttgttggcc agccttgtat tggtggcagc ttctcttatt    1080
tggatactat ccagaactcc tgcaaccatt gccattccag atgtggcagg tcagacagtt    1140
gcagaggcca aggcaacgct caaaaaagcc aattttgaga ttggtgagga agacagag    1200 gctagtgaaa aggtggaaga agggcggatt atccgtacag atcctggcgc tggaactggt    1260
cgaaaagaag gaacgaaaat caatttggtt gtctcatcag gcaagcaatc tttccaaatt    1320
agtaattatg tcggtcggaa atcctctgat gtcattgcgg aattaaaaga gaaaaaagtt    1380
ccagataatt tgattaaaat tgaggaagaa gagtcgaatg agagtgaggc tggaacggtc    1440
ctgaagcaaa gtctaccaga aggtacgacc tatgacttga gcaaggcaac tcaaattgtt    1500
ttgacagtag ctaaaaaagc tacgacgatt caattaggga actatattgg acggaactct    1560
acagaagtaa tctcagaact caagcagaag aaggttcctg agaatttgat taagatagag    1620
gaagaagagt ccagcgaaag cgaaccagga acgattatga acaaagtcc aggtgccgga    1680 acgacttatg atgtgagtaa acctactcaa attgtcttga cagtagctaa aaaagttaca    1740
agtgttgcca tgccgagtta cattggttct agcttggagt ttactaagaa caattgatt    1800 caaattgttg ggattaagga agctaatata gaagttgtag aagtgacgac agcgcctgca    1860
ggtagtgcag aaggcatggt tgttgaacaa gtcctagag caggtgaaaa ggtagacctc    1920
aataagacta gagtcaagat ttcaatctac aaacctaaaa caacttcagc tactccttaa    1980
```

<210> SEQ ID NO 35
<211> LENGTH: 659
<212> TYPE: PRT
<213> ORGANISM: Streptococcus pneumoniae

<400> SEQUENCE: 35

Met Ile Gln Ile Gly Lys Ile Phe Ala Gly Arg Tyr Arg Ile Val Lys
1               5                   10                  15

Gln Ile Gly Arg Gly Gly Met Ala Asp Val Tyr Leu Ala Lys Asp Leu
            20                  25                  30

Ile Leu Asp Gly Glu Glu Val Ala Val Lys Val Leu Arg Thr Asn Tyr
        35                  40                  45

Gln Thr Asp Pro Ile Ala Val Ala Arg Phe Gln Arg Glu Ala Arg Ala
    50                  55                  60

Met Ala Asp Leu Asp His Pro His Ile Val Arg Ile Thr Asp Ile Gly
65                  70                  75                  80

Glu Glu Asp Gly Gln Gln Tyr Leu Ala Met Glu Tyr Val Ala Gly Leu
                85                  90                  95

Asp Leu Lys Arg Tyr Ile Lys Glu His Tyr Pro Leu Ser Asn Glu Glu
            100                 105                 110

Ala Val Arg Ile Met Gly Gln Ile Leu Leu Ala Met Arg Leu Ala His

-continued

```
                115                 120                 125
Thr Arg Gly Ile Val His Arg Asp Leu Lys Pro Gln Asn Ile Leu Leu
130                 135                 140

Thr Pro Asp Gly Thr Ala Lys Val Thr Asp Phe Gly Ile Ala Val Ala
145                 150                 155                 160

Phe Ala Glu Thr Ser Leu Thr Gln Thr Asn Ser Met Leu Gly Ser Val
                165                 170                 175

His Tyr Leu Ser Pro Glu Gln Ala Arg Gly Ser Lys Ala Thr Val Gln
                180                 185                 190

Ser Asp Ile Tyr Ala Met Gly Ile Ile Phe Tyr Glu Met Leu Thr Gly
                195                 200                 205

His Ile Pro Tyr Asp Gly Asp Ser Ala Val Thr Ile Ala Leu Gln His
210                 215                 220

Phe Gln Lys Pro Leu Pro Ser Val Ile Ala Glu Asn Pro Ser Val Pro
225                 230                 235                 240

Gln Ala Leu Glu Asn Val Ile Ile Lys Ala Thr Ala Lys Lys Leu Thr
                245                 250                 255

Asn Arg Tyr Arg Ser Val Ser Glu Met Tyr Val Asp Leu Ser Ser Ser
                260                 265                 270

Leu Ser Tyr Asn Arg Arg Asn Glu Ser Lys Leu Ile Phe Asp Glu Thr
                275                 280                 285

Ser Lys Ala Asp Thr Lys Thr Leu Pro Lys Val Ser Gln Ser Thr Leu
290                 295                 300

Thr Ser Ile Pro Lys Val Gln Ala Gln Thr Glu His Lys Ser Ile Lys
305                 310                 315                 320

Asn Pro Ser Gln Ala Val Thr Glu Glu Thr Tyr Gln Pro Gln Ala Pro
                325                 330                 335

Lys Lys His Arg Phe Lys Met Arg Tyr Leu Ile Leu Leu Ala Ser Leu
                340                 345                 350

Val Leu Val Ala Ala Ser Leu Ile Trp Ile Leu Ser Arg Thr Pro Ala
                355                 360                 365

Thr Ile Ala Ile Pro Asp Val Ala Gly Gln Thr Val Ala Glu Ala Lys
370                 375                 380

Ala Thr Leu Lys Lys Ala Asn Phe Glu Ile Gly Glu Glu Lys Thr Glu
385                 390                 395                 400

Ala Ser Glu Lys Val Glu Glu Gly Arg Ile Ile Arg Thr Asp Pro Gly
                405                 410                 415

Ala Gly Thr Gly Arg Lys Glu Gly Thr Lys Ile Asn Leu Val Val Ser
                420                 425                 430

Ser Gly Lys Gln Ser Phe Gln Ile Ser Asn Tyr Val Gly Arg Lys Ser
                435                 440                 445

Ser Asp Val Ile Ala Glu Leu Lys Glu Lys Val Pro Asp Asn Leu
450                 455                 460

Ile Lys Ile Glu Glu Glu Ser Asn Glu Ser Glu Ala Gly Thr Val
465                 470                 475                 480

Leu Lys Gln Ser Leu Pro Glu Gly Thr Thr Tyr Asp Leu Ser Lys Ala
                485                 490                 495

Thr Gln Ile Val Leu Thr Val Ala Lys Lys Ala Thr Thr Ile Gln Leu
                500                 505                 510

Gly Asn Tyr Ile Gly Arg Asn Ser Thr Glu Val Ile Ser Glu Leu Lys
                515                 520                 525

Gln Lys Lys Val Pro Glu Asn Leu Ile Lys Ile Glu Glu Glu Glu Ser
530                 535                 540
```

Ser Glu Ser Glu Pro Gly Thr Ile Met Lys Gln Ser Pro Gly Ala Gly
545                 550                 555                 560

Thr Thr Tyr Asp Val Ser Lys Pro Thr Gln Ile Val Leu Thr Val Ala
            565                 570                 575

Lys Lys Val Thr Ser Val Ala Met Pro Ser Tyr Ile Gly Ser Ser Leu
        580                 585                 590

Glu Phe Thr Lys Asn Asn Leu Ile Gln Ile Val Gly Ile Lys Glu Ala
            595                 600                 605

Asn Ile Glu Val Val Glu Val Thr Thr Ala Pro Ala Gly Ser Ala Glu
610                 615                 620

Gly Met Val Val Glu Gln Ser Pro Arg Ala Gly Glu Lys Val Asp Leu
625                 630                 635                 640

Asn Lys Thr Arg Val Lys Ile Ser Ile Tyr Lys Pro Lys Thr Thr Ser
            645                 650                 655

Ala Thr Pro

<210> SEQ ID NO 36
<211> LENGTH: 1980
<212> TYPE: DNA
<213> ORGANISM: Streptococcus pneumoniae

<400> SEQUENCE: 36
atgatccaaa tcggcaagat ttttgccggt cgctatcgta ttgtcaaaca gattggtcgt     60
ggtggtatgg cggatgtcta cctggccaaa gacctgatcc tggatggtga agaagtggca    120
gtgaaggttc tgcgtaccaa ctaccagacg gacccgatcg ctgtagctcg ttttcagcgt    180
gaagcgcgtg ctatggcaga tctggaccat cctcatatcg ttcgtatcac cgatattggc    240
gaggaagacg tcaacagta cctggctatg gagtatgtgg ctggtctgga cctcaaacgc    300
tatatcaagg aacattatcc tctttctaat gaagaagcag tccgtatcat gggtcaaatt    360
ctcttggcta tgcgcttggc ccatactcgt ggtattgttc accgtgactt gaaacctcaa    420
aatatcctct gaccccaga tggtactgcc aaggtcaccg actttggtat tgctgtagcc    480
tttgcagaga cctctctgac ccagactaac tcgatgttgg gctctgttca ttacttgtct    540
ccagagcagg cgcgtggttc gaaggcgact gtgcagtctg atatctatgc catgggtatt    600
attttctatg agatgctgac cggccatatc ccttatgacg tgatagcgc ggtgaccatt    660 gccctccagc atttccagaa accgctgccg tccgttattg cagaaaatcc atctgtacct    720
caggctctgg aaaatgttat tatcaaggca actgctaaaa agttgaccaa tcgctaccgc    780
tcggtttctg agatgtatgt ggacttgtct tctagcttgt cctacaatcg tcgtaatgaa    840
tctaagctga tctttgatga acgagcaag gcagatacca agaccttgcc gaaggtttct    900
cagtctacct tgacctctat tcctaaggtt caagcgcaaa ccgaacacaa atctatcaaa    960
aacccaagcc aggctgtgac cgaggaaact taccaaccac aagcaccgaa aaaacatcgt   1020
tttaagatgc gttacctgat tttgttggcc agccttgtat ggtggcagc ttctcttatt   1080 tggatcctgt cccgtactcc tgcaaccatt gccattccag atgtggcagg tcagaccgtt   1140
gcagaggcca aggcaacgct caaaaaagcc aattttgaga ttggtgagga agaccgag   1200 gcttctgaaa aggtggaaga aggtcgtatt atccgtaccg atcctggcgc tggtactggt   1260
cgtaaagaag gtacgaaaat caatttggtt gtctcttctg gcaagcaatc tttccaaatt   1320
tctaattatg tcggtcgtaa atcctctgat gtcattgcgg aactgaaaga gaaaaagtt   1380 ccagataatt tgattaaaat tgaggaagaa gagtcgaatg agtctgaggc tggtacggtc   1440

```
ctgaagcaat ctctgccaga aggtacgacc tatgacttga gcaaggcaac tcaaattgtt    1500
ttgaccgtag ctaaaaaagc tacgacgatt caactgggta actatattgg tcgtaactct    1560
accgaagtaa tctctgaact caagcagaag aaggttcctg agaatttgat taagatcgag    1620
gaagaagagt ccagcgaaag cgaaccaggt acgattatga acaatctcc aggtgccggt     1680 acgacttatg atgtgtctaa acctactcaa attgtcttga ccgtagctaa aaaagttacc    1740
tctgttgcca tgccgtctta cattggttct agcttggagt ttactaagaa caatttgatt    1800
caaattgttg gtattaagga agctaatatc gaagttgtag aagtgacgac cgcgcctgca    1860
ggttctgcag aaggcatggt tgttgaacaa tctcctcgtg caggtgaaaa ggtagacctc    1920
aataagactc gtgtcaagat ttctatctac aaacctaaaa ccacttctgc tactccttaa    1980
```

<210> SEQ ID NO 37
<211> LENGTH: 867
<212> TYPE: DNA
<213> ORGANISM: Streptococcus pneumoniae

<400> SEQUENCE: 37

```
agcggaaaaa aagatacaac ttctggtcaa aaactaaaag ttgttgctac aaactcaatc      60
atcgctgata ttactaaaaa tattgctggt gacaaaattg accttcatag tatcgttccg     120
attgggcaag accacacga atacgaacca cttcctgaag acgttaagaa aacttctgag      180
gctaatttga ttttctataa cggtatcaac cttgaaacag gtggcaatgc ttggtttaca    240
aaattggtag aaaatgccaa gaaaactgaa aacaaagact acttcgcagt cagcgacggc    300
gttgatgtta tctaccttga aggtcaaaat gaaaaggaa aagaagaccc acacgcttgg     360
cttaaccttg aaaacggtat tatttttgct aaaaatatcg ccaaacaatt gagcgccaaa    420
gaccctaaca ataaagaatt ctatgaaaaa aatctcaaag aatatactga taagttagac    480
aaacttgata agaaagtaa ggataaattt aataagatcc ctgctgaaaa gaaactcatt    540
gtaaccagcg aaggagcatt caaatacttc tctaaagcct atggtgtccc aagtgcttac    600
atctgggaaa tcaatactga agaagaagga actcctgaac aaatcaagac cttggttgaa    660
aaacttcgcc aaacaaaagt tccatcactc tttgtagaat caagtgtgga tgaccgtcca    720
atgaaaactg tttctcaaga cacaaacatc ccaatctacg ctcaaatctt tactgactct    780
atcgcagaac aaggtaaaga aggcgacagc tactacagca tgatgaaata caaccttgac    840
aagattgctg aaggattggc aaaataa                                        867
```

<210> SEQ ID NO 38
<211> LENGTH: 288
<212> TYPE: PRT
<213> ORGANISM: Streptococcus pneumoniae

<400> SEQUENCE: 38

```
Ser Gly Lys Lys Asp Thr Thr Ser Gly Gln Lys Leu Lys Val Val Ala
1               5                   10                  15

Thr Asn Ser Ile Ile Ala Asp Ile Thr Lys Asn Ile Ala Gly Asp Lys
            20                  25                  30

Ile Asp Leu His Ser Ile Val Pro Ile Gly Gln Asp Pro His Glu Tyr
        35                  40                  45

Glu Pro Leu Pro Glu Asp Val Lys Lys Thr Ser Glu Ala Asn Leu Ile
    50                  55                  60

Phe Tyr Asn Gly Ile Asn Leu Glu Thr Gly Gly Asn Ala Trp Phe Thr
65                  70                  75                  80
```

Lys Leu Val Glu Asn Ala Lys Lys Thr Glu Asn Lys Asp Tyr Phe Ala
                85                  90                  95

Val Ser Asp Gly Val Asp Val Ile Tyr Leu Glu Gly Gln Asn Glu Lys
            100                 105                 110

Gly Lys Glu Asp Pro His Ala Trp Leu Asn Leu Glu Asn Gly Ile Ile
        115                 120                 125

Phe Ala Lys Asn Ile Ala Lys Gln Leu Ser Ala Lys Asp Pro Asn Asn
    130                 135                 140

Lys Glu Phe Tyr Glu Lys Asn Leu Lys Glu Tyr Thr Asp Lys Leu Asp
145                 150                 155                 160

Lys Leu Asp Lys Glu Ser Lys Asp Lys Phe Asn Lys Ile Pro Ala Glu
                165                 170                 175

Lys Lys Leu Ile Val Thr Ser Glu Gly Ala Phe Lys Tyr Phe Ser Lys
            180                 185                 190

Ala Tyr Gly Val Pro Ser Ala Tyr Ile Trp Glu Ile Asn Thr Glu Glu
        195                 200                 205

Glu Gly Thr Pro Glu Gln Ile Lys Thr Leu Val Glu Lys Leu Arg Gln
    210                 215                 220

Thr Lys Val Pro Ser Leu Phe Val Glu Ser Ser Val Asp Asp Arg Pro
225                 230                 235                 240

Met Lys Thr Val Ser Gln Asp Thr Asn Ile Pro Ile Tyr Ala Gln Ile
                245                 250                 255

Phe Thr Asp Ser Ile Ala Glu Gln Gly Lys Glu Gly Asp Ser Tyr Tyr
            260                 265                 270

Ser Met Met Lys Tyr Asn Leu Asp Lys Ile Ala Glu Gly Leu Ala Lys
        275                 280                 285

<210> SEQ ID NO 39
<211> LENGTH: 930
<212> TYPE: DNA
<213> ORGANISM: Streptococcus pneumoniae

<400> SEQUENCE: 39
atgaaaaaat taggtacatt actcgttctc tttctttctg caatcattct tgtagcatgt      60
gctagcggaa aaaagatac aacttctggt caaaaactaa agttgttgc tacaaactca      120 atcatcgctg atattactaa aaatattgct ggtgacaaaa ttgaccttca tagtatcgtt      180
ccgattgggc aagacccaca cgaatacgaa ccacttcctg aagacgttaa gaaaacttct      240
gaggctaatt tgattttcta taacggtatc aaccttgaaa caggtggcaa tgcttggttt      300
acaaaattgg tagaaaatgc caagaaaact gaaaacaaag actacttcgc agtcagcgac      360
ggcgttgatg ttatctacct tgaaggtcaa aatgaaaaag aaaagaaga cccacacgct      420 tggcttaacc ttgaaaacgg tattattttt gctaaaaata tcgccaaaca attgagcgcc      480
aaagacccta acaataaaga attctatgaa aaaaatctca agaatatac tgataagtta      540 gacaaacttg ataaagaaag taaggataaa tttaataaga tccctgctga aaagaaactc      600
attgtaacca gcgaaggagc attcaaatac ttctctaaag cctatggtgt cccaagtgct      660
tacatctggg aaatcaatac tgaagaagaa ggaactcctg aacaaatcaa gaccttggtt      720
gaaaaacttc gccaaacaaa agttccatca ctctttgtag aatcaagtgt ggatgaccgt      780
ccaatgaaaa ctgtttctca agacacaaac atcccaatct acgctcaaat ctttactgac      840
tctatcgcag aacaaggtaa agaaggcgac agctactaca gcatgatgaa atacaacctt      900
gacaagattg ctgaaggatt ggcaaaataa                                       930

<210> SEQ ID NO 40
<211> LENGTH: 309
<212> TYPE: PRT
<213> ORGANISM: Streptococcus pneumoniae

<400> SEQUENCE: 40

```
Met Lys Lys Leu Gly Thr Leu Val Leu Phe Leu Ser Ala Ile Ile
1               5                   10                  15

Leu Val Ala Cys Ala Ser Gly Lys Lys Asp Thr Thr Ser Gly Gln Lys
                20                  25                  30

Leu Lys Val Val Ala Thr Asn Ser Ile Ile Ala Asp Ile Thr Lys Asn
                35                  40                  45

Ile Ala Gly Asp Lys Ile Asp Leu His Ser Ile Val Pro Ile Gly Gln
        50                  55                  60

Asp Pro His Glu Tyr Glu Pro Leu Pro Glu Asp Val Lys Lys Thr Ser
65                  70                  75                  80

Glu Ala Asn Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
                100                 105                 110

Lys Asp Tyr Phe Ala Val Ser Asp Gly Val Asp Val Ile Tyr Leu Glu
                115                 120                 125

Gly Gln Asn Glu Lys Gly Lys Glu Asp Pro His Ala Trp Leu Asn Leu
        130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
                180                 185                 190

Lys Ile Pro Ala Glu Lys Lys Leu Ile Val Thr Ser Glu Gly Ala Phe
                195                 200                 205

Lys Tyr Phe Ser Lys Ala Tyr Gly Val Pro Ser Ala Tyr Ile Trp Glu
        210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
                260                 265                 270

Ile Tyr Ala Gln Ile Phe Thr Asp Ser Ile Ala Glu Gln Gly Lys Glu
                275                 280                 285

Gly Asp Ser Tyr Tyr Ser Met Met Lys Tyr Asn Leu Asp Lys Ile Ala
        290                 295                 300

Glu Gly Leu Ala Lys
305
```

<210> SEQ ID NO 41
<211> LENGTH: 1416
<212> TYPE: DNA
<213> ORGANISM: Streptococcus pneumoniae

<400> SEQUENCE: 41

```
atggcaaata aagcagtaaa tgactttata ctagctatga attacgataa aaagaaactc    60
```

```
ttgacccatc agggagaaag tattgaaaat cgtttcatca agagggtaa tcagctaccc      120
gatgagtttg ttgttatcga agaaagaag cggagcttgt cgacaaatac aagtgatatt      180
tctgtaacag ctaccaacga cagtcgcctc tatcctggag cacttctcgt agtggatgag      240
accttgttag agaataatcc cactcttctt gcggttgatc gtgctccgat gacttatagt      300
attgatttgc ctggtttggc aagtagcgat agctttctcc aagtggaaga ccccagcaat      360
tcaagtgttc gcggagcggt aaacgatttg ttggctaagt ggcatcaaga ttatggtcag      420
gtcaataatg tcccagctag aatgcagtat gaaaaaataa cggctcacag catggaacaa      480
ctcaaggtca agtttggttc tgactttgaa aagacaggga attctcttga tattgatttt      540
aactctgtcc attcaggtga aaagcagatt cagattgtta attttaagca gatttattat      600
acagtcagcg tagacgctgt taaaaatcca ggagatgtgt ttcaagatac tgtaacggta      660
gaggatttaa acagagagg aatttctgca gagcgtcctt tggtctatat ttcgagtgtt      720
gcttatgggc gccaagtcta tctcaagttg gaaaccacga gtaagagtga tgaagtagag      780
gctgcttttg aagctttgat aaaaggagtc aaggtagctc ctcagacaga gtggaagcag      840
attttggaca atacagaagt gaaggcggtt attttagggg gcgacccaag ttcgggtgcc      900
cgagttgtaa caggcaaggt ggatatggta gaggacttga ttcaagaagg cagtcgcttt      960
acagcagatc atccaggctt gccgatttcc tatacaactt cttttttacg tgacaatgta     1020
gttgcgacct tcaaaacag tacagactat gttgagacta aggttacagc ttacagaaac     1080
ggagattttac tgctggatca tagtggtgcc tatgttgccc aatattatat tacttgggat     1140
gaattatcct atgatcatca aggtaaggaa gtcttgactc ctaaggcttg ggacagaaat     1200
gggcaggatt tgacggctca ctttaccact agtattcctt taaaagggaa tgttcgtaat     1260
ctctctgtca aaattagaga gtgtaccggg cttgccttcg aatggtggcg tacggtttat     1320
gaaaaaaccg atttgccact agtgcgtaag cggacgattt ctatttgggg aacaactctc     1380
tatcctcagg tagaggataa ggtagaaaat gactag                               1416
```

<210> SEQ ID NO 42
<211> LENGTH: 471
<212> TYPE: PRT
<213> ORGANISM: Streptococcus pneumoniae

<400> SEQUENCE: 42

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
```

|  |  | 130 |  |  |  | 135 |  |  |  | 140 |  |

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Lys Gln Ile Gln Ile
        180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Asp His Ser
        355                 360                 365

Gly Ala Tyr Val Ala Gln Tyr Tyr Ile Thr Trp Asp Glu Leu Ser Tyr
370                 375                 380

Asn His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Phe Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 43
<211> LENGTH: 1416
<212> TYPE: DNA
<213> ORGANISM: Streptococcus pneumoniae

<400> SEQUENCE: 43
atggcaaata aagcagtaaa tgactttatc ctggctatga attacgataa aagaaaactc     60
ttgacccatc agggtgaaag tattgaaaat cgtttcatca agagggtaa tcagctgccg    120 gatgagtttg ttgttatcga acgtaagaag cgtagcttgt cgacaaatac aagtgatatt    180

-continued

| | |
|---|---|
| tctgtaacag ctaccaacga cagtcgcctc tatcctggtg cacttctcgt agtggatgag | 240 |
| accttgttag agaataatcc gactcttctt gcggttgatc gtgctccgat gacttatagt | 300 |
| attgatttgc ctggtttggc aagtagcgat agctttctcc aagtggaaga cccgagcaat | 360 |
| tcaagtgttc gcggtgcggt aaacgatttg ttggctaagt ggcatcaaga ttatggtcag | 420 |
| gtcaataatg tcccagctcg tatgcagtat gaaaaaatca cggctcacag catggaacaa | 480 |
| ctcaaggtca agtttggttc tgactttgaa aagacaggga attctcttga tattgatttt | 540 |
| aactctgtcc attcaggtga aaagcagatt cagattgtta attttaagca gatttattat | 600 |
| acagtcagcg tagacgctgt taaaaatcca ggagatgtgt ttcaagatac tgtaacggta | 660 |
| gaggatttaa acagcgtgg aatttctgca gagcgtcctt tggtctatat ttcgagtgtt | 720 |
| gcttatgggc gccaagtcta tctcaagttg gaaaccacga gtaagagtga tgaagtagag | 780 |
| gctgcttttg aagctttgat caaaggtgtc aaggtagctc ctcagacaga gtggaagcag | 840 |
| attttggaca atacagaagt gaaggcggtt attttagggg gcgacccaag ttcgggtgcc | 900 |
| cgtgttgtaa caggcaaggt ggatatggta gaggacttga ttcaagaagg cagtcgcttt | 960 |
| acagcagatc atccaggctt gccgatttcc tatacaactt cttttttacg tgacaatgta | 1020 |
| gttgcgacct ttcaaaacag tacagactat gttgagacta aggttacagc ttaccgtaac | 1080 |
| ggagatttac tgctggatca tagtggtgcc tatgttgccc aatattatat tacttgggat | 1140 |
| gaattatcct atgatcatca aggtaaggaa gtcttgactc ctaaggcttg ggaccgtaat | 1200 |
| gggcaggatt tgacggctca ctttaccact agtattcctt taaagggaa tgttcgtaat | 1260 |
| ctctctgtca aaattcgtga gtgtaccggg cttgccttcg aatggtggcg tacggtttat | 1320 |
| gaaaaaaccg atttgccact ggtgcgtaag cgtacgattt ctatttgggg tacaactctc | 1380 |
| tatcctcagg tagaggataa ggtagaaaat gactag | 1416 |

<210> SEQ ID NO 44
<211> LENGTH: 471
<212> TYPE: PRT
<213> ORGANISM: Streptococcus pneumoniae

<400> SEQUENCE: 44

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
            210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
            325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
            370                 375                 380

Asn His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Phe Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 45
<211> LENGTH: 1848
<212> TYPE: DNA
<213> ORGANISM: Salmonella typhi

<400> SEQUENCE: 45
gttagcgctt ccggcgcgac tttcaggatc tcttgtcctt cgaattcggc gacggaaaca      60
tgttcgctgg tcaacaagta gtactcggta tcgtcctttt tgaggggaaa agggtcttga     120
taaaagaagg gtttgtttga cattgtgctc tcacttaccg ctcggtatgg ttattctctg     180
ggcaggtgtt ccattgcccg actcaaagcg agtaacacta tcctacacaa ttttttaaca     240
aaaactgaga caagtacgac ttttacgcc cggaggttac ttcatgcggg tttcttggtt      300

-continued

| | |
|---|---|
| taatacctcc cattgatctc cacattgaaa cagggcttga taatgcaaaa actcattaac | 360 |
| tcagtgcaaa actatgcctg gggaagtaaa actgcgttaa cggaacttta tggcatcgcc | 420 |
| aatccgcagc agcagccaat ggctgaactc tggatgggcg cgcatcccaa aagcagctcg | 480 |
| cgaatcacca ccgccaacgg cgaaaccgtc tccctgcgtg acgccatcga aaagaataaa | 540 |
| accgccatgc tgggcgaagc ggtagccaac cgtttcggcg aactgccgtt tctgtttaaa | 600 |
| gtactgtgcg ccgcacaacc gctctctatt caggtgcacc cgaataaacg caactccgaa | 660 |
| atcggtttcg cgaaagaaaa tgcggcgggt atccccatgg atgccgcaga gcggaactat | 720 |
| aaagatccta accataaacc agagctggtt tttgccctga cgcctttcct ggcgatgaac | 780 |
| gcgttccgcg aatttttctga cattgtctct ttactgcaac ctgtcgccgg cgcgcattcc | 840 |
| gctatcgccc acttttttgca ggtgccgaat gctgaacgtc tgagccagct tttcgccagc | 900 |
| ctgttgaata tgcaaggcga agaaaaatcc cgcgcgttag ccgtactcaa agcggcgctt | 960 |
| aacagccagc aaggcgaacc gtggcaaacg atccgcgtga tttcagagta ttatcctgac | 1020 |
| gacagcgggc ttttctctcc tttgttgctg aatgtggtca aactgaatcc cggcgaggcg | 1080 |
| atgttcctgt ttgctgaaac gcctcatgct tatctgcagg gcgttgcgct ggaagtcatg | 1140 |
| gcgaactccg ataacgttct gcgcgctggc cttacgccaa aatatatcga catccctgag | 1200 |
| ctggtcgcga acgtgaagtt cgaacctaag cctgccggcg agttgctgac tgccccggtg | 1260 |
| aaaagcggcg cggagctgga cttcccaatt ccggttgacg attttgcttt ttcactgcac | 1320 |
| gacctggcgc ttcaggagac gagcatcggc caacacagcg ccgcgattct gttctgcgtt | 1380 |
| gagggtgagg cggtgttacg taaagatgaa cagcgtctgg tactgaagcc gggtgaatct | 1440 |
| gcctttatcg gcgcggatga gtctccggtt aacgccagcg gcacgggccg tttagcgcgt | 1500 |
| gtttataaca agctgtagca acgtactgaa ttttttaaca actcttgcta agcttataac | 1560 |
| agacgtaaaa ctcctccagg cggtttaatc cgcctggttt cattttttatg gacaattgat | 1620 |
| atgaaaaaaa cactggtagc tgcaggtgta gtaattgcac ttggcatcgt ctggacaggc | 1680 |
| ggcgcctggt atacggggaa aaagctggag aaccatcttg cagaaatggt gactcaggcc | 1740 |
| aatgaacagc tcaagcgtac tgcgccgagc gccggtgtcg aattaagtta tcaaaactac | 1800 |
| cagcgcggcg tgttcagtag ccatctgcaa ctggttgtca aaccggtt | 1848 |

<210> SEQ ID NO 46
<211> LENGTH: 391
<212> TYPE: PRT
<213> ORGANISM: Salmonella typhi

<400> SEQUENCE: 46

Met Gln Lys Leu Ile Asn Ser Val Gln Asn Tyr Ala Trp Gly Ser Lys
1               5                   10                  15

Thr Ala Leu Thr Glu Leu Tyr Gly Ile Ala Asn Pro Gln Gln Gln Pro
            20                  25                  30

Met Ala Glu Leu Trp Met Gly Ala His Pro Lys Ser Ser Ser Arg Ile
        35                  40                  45

Thr Thr Ala Asn Gly Glu Thr Val Ser Leu Arg Asp Ala Ile Glu Lys
    50                  55                  60

Asn Lys Thr Ala Met Leu Gly Glu Ala Val Ala Asn Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys Arg Asn Ser Glu Ile Gly Phe Ala Lys Glu

|   |   | 100 |   |   |   | 105 |   |   |   | 110 |   |
|---|---|---|---|---|---|---|---|---|---|---|---|

Asn Ala Ala Gly Ile Pro Met Asp Ala Ala Glu Arg Asn Tyr Lys Asp
            115                  120                  125

Pro Asn His Lys Pro Glu Leu Val Phe Ala Leu Thr Pro Phe Leu Ala
   130                  135                  140

Met Asn Ala Phe Arg Glu Phe Ser Asp Ile Val Ser Leu Leu Gln Pro
145                 150                  155                  160

Val Ala Gly Ala His Ser Ala Ile Ala His Phe Leu Gln Val Pro Asn
            165                  170                  175

Ala Glu Arg Leu Ser Gln Leu Phe Ala Ser Leu Leu Asn Met Gln Gly
   180                  185                  190

Glu Glu Lys Ser Arg Ala Leu Ala Val Leu Lys Ala Ala Leu Asn Ser
            195                  200                  205

Gln Gln Gly Glu Pro Trp Gln Thr Ile Arg Val Ile Ser Glu Tyr Tyr
   210                  215                  220

Pro Asp Asp Ser Gly Leu Phe Ser Pro Leu Leu Leu Asn Val Val Lys
225                 230                  235                  240

Leu Asn Pro Gly Glu Ala Met Phe Leu Phe Ala Glu Thr Pro His Ala
            245                  250                  255

Tyr Leu Gln Gly Val Ala Leu Glu Val Met Ala Asn Ser Asp Asn Val
   260                  265                  270

Leu Arg Ala Gly Leu Thr Pro Lys Tyr Ile Asp Ile Pro Glu Leu Val
            275                  280                  285

Ala Asn Val Lys Phe Glu Pro Lys Pro Ala Gly Glu Leu Leu Thr Ala
   290                  295                  300

Pro Val Lys Ser Gly Ala Glu Leu Asp Phe Pro Ile Pro Val Asp Asp
305                 310                  315                  320

Phe Ala Phe Ser Leu His Asp Leu Ala Leu Gln Glu Thr Ser Ile Gly
            325                  330                  335

Gln His Ser Ala Ala Ile Leu Phe Cys Val Glu Gly Glu Ala Val Leu
            340                  345                  350

Arg Lys Asp Glu Gln Arg Leu Val Leu Lys Pro Gly Glu Ser Ala Phe
            355                  360                  365

Ile Gly Ala Asp Glu Ser Pro Val Asn Ala Ser Gly Thr Gly Arg Leu
   370                  375                  380

Ala Arg Val Tyr Asn Lys Leu
385                 390

<210> SEQ ID NO 47
<211> LENGTH: 2997
<212> TYPE: DNA
<213> ORGANISM: Salmonella typhi

<400> SEQUENCE: 47

```
ggcggtacag gcgacattat tcgccgggtc gccgcaaata ttgtatcgct ggcgagcctt      60
tttgctgcgt ctgtttggcg ccaaaattgg aaagaatgtg ttattcgac cgtcagtaaa     120 aattacctat ccgtggaaat taaccgtcgg cgattatgcc tgggtaggcg acgacgctgt     180
gttatatacg ttgggtgaaa ttaatattgg cgcacatgcg ttatttcac aaaaagggta     240 tttgtgtacc ggtagccatg attataccag cgcccatttc gatattaatg ccgcgccgat     300
tgttattggc gaaaaatgtt ggctggcgac cgatgttttt gtcgcgcccg gcgtgacgat     360
aggtcatggc accgtcgtcg gcgcgcgcag cagcgtattt aaatcattac cggcaaatgc     420
gatttgtcgg ggcaatcccg cagtggtaac gcgccagcgc gttcagaaag ttactcccta     480
```

```
acgggactat tgaggaaat gaaaatgtca aaagtcgctc tcattactgg cgtaaccgga    540
caggatgggt cttacctggc agaatttctg ctggaaaaag ggtatgaggt gcatggtatc   600
aagcgccgcg cgtcatcgtt taataccgag cgcgtggacc atatttatca ggacccgcac   660
agctgcaacc cgaaatttca tctgcattat ggcgacctga ccgacgcctc caacctgacc   720
cgcattttac aggaagtgca gccggatgag gtctacaacc tgggcgcgat gagccatgtg   780
gcggtgtcgt tgagtcgcc ggaatatacc gccgatgtgg atgcgatggg cacgctgcgc    840
ctgctggagg cgatccgctt cctcggtctt gaaagaaaa cgcggttcta ccaggcctcc    900
acctctgaac tgtacgggct ggtgcaggag atcccgcaga agagaccac gccgttctac     960
ccgcgttccc cctatgcggt ggcgaaactg tacgcctact ggatcaccgt taactaccgt   1020
gaatcctacg gtatttacgc ctgtaacggc attctgttta accacgagtc cccgcgtcgc   1080
ggcgaaacct tcgtcacccg taagatcacc cgcgccatcg ccaatatcgc ccagggacta   1140
gagtcctgcc tgtatctcgg caacatggac tcgctgcgcg actggggtca tgcgaaagat   1200
tacgtgcgga tgcagtggat gatgttacag caggagcagc cggaagattt cgtgattgcc   1260
accggcgtgc agtattccgt acgccagttt gtggagctgg cagcggcgca actggggata   1320
aaactgcgct ttgaaggcga aggcattaat gagaaaggga tcgtggtatc cgttaccgga   1380
cacgatgcgc cgggcgtgaa accggggat gtgattgtgg ccgttgatcc gcgttatttc    1440
cgtccggcgg aagtggaaac cctgctgggc gacccgtcca aagcgcatga gaaactgggc   1500
tggaaaccgg aaatcaccct gtcggagatg gtctccgaga tggtggcgaa cgatctggag   1560
gccgcgaaaa acactcact gttgaaatct cacggttatg aggtggccat cgcgctggag    1620
tcctgagaat gaataagcaa cgaattttg tggcggccca tcgcggaatg gtgggctccg    1680
ccattgtacg gcagcttgcg cagcgcggcg acgtggaact ggtactgcgc acccgcgatg   1740
agctggatct gctcgacggg cgcgcggtac aggcgttctt tgccggggcg ggtatcgacc   1800
aggtttatct ggcggcggcg aaagtgggcg gcattgtcgc caacaacacg tatccggcgg   1860
attttatta tgaaaacatg atgatagaga gcaacattat tcacgccgcg cacctgcaca   1920
acgtgaacaa actgctgttt ctcggttcgt cctgtatcta tccgaaactg gcaaggcagc   1980
cgatggcgga aagcgagctg ctgcaggga cgctggagcc gaccaacgag ccgtacgcca    2040
tcgccaagat cgccgggatt aaactgtgcg agtcctacaa ccggcagtac ggtcgcgact   2100
accgttcggt gatgccaacc aacctgtacg gcccgcatga taatttccac ccggacaatt   2160
cacatgtgat cccggcgctg ctgcgtcgct ttcatgaggc tgcgcagagc cacgcgccgg   2220
aggtggtggt gtggggcagc ggcacgccga tgcgtgaatt tctgcacgtt gacgatatgg   2280
cggcggccag tattcacgtg atggagctgg cgcgcgaagt gtggcaggag aacactgccc   2340
cgatgctgtc gcacattaac gtcggcactg gcgtggactg caccatccgc gagctggcgc   2400
agaccatcgc aaaggtggtg ggttaccagg gccgggtggt gttcgatgcc gcgaagccgg   2460
acggcacgcc gcgtaaattg ctcgacgtca cgcgcctgca tcagcttggc tggtatcacg   2520
aaatttcact ggaggcaggg cttgccggta cttaccagtg gttccttgag aatcagcaac   2580
ggttccgggg gtgacaatgt ttttacgtca ggaagatttc gccgccgtgg tgcggccacg   2640
ccctcatct ccctcgattt catcgtggaa acggccaggg gggaaatttt actgggccag    2700
cgtctcaacc gtccggcgca gggctactgg tttgtgccgg ggggcgggt gtgcaaagac    2760
gaaacgctgg aggccgcctt tgcacgcctg acgcaggcgg aactgggcgt gcgtctgccg   2820
```

| | |
|---|---:|
| ctggcggcag ggacgtttta tgcgtctgg cagcacttct atgacgacaa cttttccggt | 2880 |
| gaggattttt caactcacta catcgtgctc ggctttcgtc tgcgcgtggc ggagagcgat | 2940 |
| ttacgcctgc ctgatgccca gcatggcagt taccgctggc tgacgccgga acagctt | 2997 |

```
<210> SEQ ID NO 48
<211> LENGTH: 2220
<212> TYPE: DNA
<213> ORGANISM: Salmonella typhi

<400> SEQUENCE: 48
```

| | |
|---|---:|
| tgattatatt aacggctata ccatagcggt agatggcggt tggctggcgc gttaatccgc | 60 |
| tactgacaaa tgcgtttctg ggaaaatcga cgctttggcc gaaaaaactg ataaagccct | 120 |
| gtcctcgtac agggttttt tatgatctca ttagcatagt ccatattgtg ggtttaactt | 180 |
| aatccatata ttgttaaata atagctatga tcaatgcttt aattcattga atatattggtg | 240 |
| gtttaaaaaa atacccggca acggcgttaa atttaaaaag tgtaatatcc atcacatatc | 300 |
| gctatagcgt agccatttaa tccatatttta tgccgtttcc agcctgacac ttgaggaaga | 360 |
| gtatcccgta ctttcaggct atgtcttact ctgttgtggc aggaaaatat ggtctctatt | 420 |
| aatcatgact ctgctttaac gccgcgttcg cttcgcgaca cacgacgtat gaatatgttt | 480 |
| gtttcggttt ctgcagcggt agcgggactg ttatttggtc tggatatcgg cgttatcgcc | 540 |
| ggggcgctgc cttttattac cgaccatttc gtactgacca gccggctgca ggaatgggtc | 600 |
| gtcagcagca tgatgcttgg cgcggcaatt ggcgcattat taacggctg ctttcattc | 660 |
| cggctggggc gtaagtatag cctgatggct ggcgcgattt tgttcgtgct cggctcgctg | 720 |
| gggtcggcgt ttgcttccag cgtggaagta ttgattggcg cccgcgtgat actgggcgta | 780 |
| gcagtaggga ttgcctccta taccgcgccg ctttatctct ctgaaatggc aagtgaaaat | 840 |
| gttcgcggca aaatgatcag tatgtatcaa ctgatggtga cgttaggcat tgtgctggct | 900 |
| tttttatccg atacggcatt cagctacagc ggcaactggc gcgcgatgtt gggcgtgctg | 960 |
| gcgctgcctg cggtgttgct cattattctg gtggtattcc tgccgaatag tccgcgttgg | 1020 |
| ctggcgcaaa aaggtcgcca tattgaagcg aagaggtgc tgcgtatgct gcgcgatacc | 1080 |
| tcggaaaaag cccgtgatga actgaatgag attcgggaaa gcctcaaact caagcaggga | 1140 |
| gggtgggcat tatttaaagc taaccgcaat gttcgccgcg ccgtgttcct cggtatgctg | 1200 |
| ctacaggcaa tgcagcagtt caccggcatg aacatcatta tgtactatgc gccgcgcatt | 1260 |
| tttaaaatgg ccggctttac caccacgaa cagcaaatga tcgccacgct ggtggtcgga | 1320 |
| ctgacttta tgttcgcgac gtttatcgcc gtctttacgg tcgataaggc cgggcgtaaa | 1380 |
| ccggcgttaa aaatcggttt cagcgtaatg gcgttaggga cattggtgtt gggctactgc | 1440 |
| ctgatgcagt ttgataacgg tacggcatca agcggtctct cctggctttc cgttgggatg | 1500 |
| acgatgatgt gtatcgccgg ttacgcgatg agcgccgctc cggtggtgtg gatactgtgt | 1560 |
| tcggaaatcc agccgctgaa atgccgtgat tttggcatta cctgttcaac cacgacaaac | 1620 |
| tgggtatcga acatgatcat cggcgcgaca ttcctgacac tgttggacag cattggcgcg | 1680 |
| gcaggtacat tctggctcta caccgcgctg aatatcgctt ttatcggcat cacttttctgg | 1740 |
| ctgattccgg aaaccaaaaa tgtcaccctg agcacatcg aacgcaagct gatggcgggc | 1800 |
| gagaagctaa gaatattgg cgtgtaatcc ccctcccat gccggatgac gcctgttatc | 1860 |
| cggcatgatg aaaaatagac tggaaacgga tgtgtaagtt tgcttcactg ccataatgct | 1920 |
| ttacaaaaag gagagcgcag tgaaaacgat cggactgttg gggggatga gctgggaatc | 1980 |

```
gactatccct tattaccgtt taatcaatga aggtattaaa cagcagttgg gaggcctgca    2040
ctcggcgagc ttactgctgc atagcgtaga tttccacgat attgaagtat gtcaacgccg    2100
cgacgagtgg gataaagcgg gcgatatcct ggcgcaggcc gcccatgggt tacagcaggc    2160
gggcgcagaa ggcattgtgc tgtgtaccaa caccatgcat aaaatcgcgc acgttattga    2220
```

<210> SEQ ID NO 49
<211> LENGTH: 472
<212> TYPE: PRT
<213> ORGANISM: Salmonella typhi

<400> SEQUENCE: 49

```
Met Val Ser Ile Asn His Asp Ser Ala Leu Thr Pro Arg Ser Leu Arg
1               5                   10                  15

Asp Thr Arg Arg Met Asn Met Phe Val Ser Val Ser Ala Ala Val Ala
            20                  25                  30

Gly Leu Leu Phe Gly Leu Asp Ile Gly Val Ile Ala Gly Ala Leu Pro
        35                  40                  45

Phe Ile Thr Asp His Phe Val Leu Thr Ser Arg Leu Gln Glu Trp Val
    50                  55                  60

Val Ser Ser Met Met Leu Gly Ala Ala Ile Gly Ala Leu Phe Asn Gly
65                  70                  75                  80

Trp Leu Ser Phe Arg Leu Gly Arg Lys Tyr Ser Leu Met Ala Gly Ala
                85                  90                  95

Ile Leu Phe Val Leu Gly Ser Leu Gly Ser Ala Phe Ala Ser Ser Val
            100                 105                 110

Glu Val Leu Ile Gly Ala Arg Val Ile Leu Gly Val Ala Val Gly Ile
        115                 120                 125

Ala Ser Tyr Thr Ala Pro Leu Tyr Leu Ser Glu Met Ala Ser Glu Asn
    130                 135                 140

Val Arg Gly Lys Met Ile Ser Met Tyr Gln Leu Met Val Thr Leu Gly
145                 150                 155                 160

Ile Val Leu Ala Phe Leu Ser Asp Thr Ala Phe Ser Tyr Ser Gly Asn
                165                 170                 175

Trp Arg Ala Met Leu Gly Val Leu Ala Leu Pro Ala Val Leu Leu Ile
            180                 185                 190

Ile Leu Val Val Phe Leu Pro Asn Ser Pro Arg Trp Leu Ala Gln Lys
        195                 200                 205

Gly Arg His Ile Glu Ala Glu Glu Val Leu Arg Met Leu Arg Asp Thr
    210                 215                 220

Ser Glu Lys Ala Arg Asp Glu Leu Asn Glu Ile Arg Glu Ser Leu Lys
225                 230                 235                 240

Leu Lys Gln Gly Gly Trp Ala Leu Phe Lys Ala Asn Arg Asn Val Arg
                245                 250                 255

Arg Ala Val Phe Leu Gly Met Leu Leu Gln Ala Met Gln Gln Phe Thr
            260                 265                 270

Gly Met Asn Ile Ile Met Tyr Tyr Ala Pro Arg Ile Phe Lys Met Ala
        275                 280                 285

Gly Phe Thr Thr Thr Glu Gln Gln Met Ile Ala Thr Leu Val Val Gly
    290                 295                 300

Leu Thr Phe Met Phe Ala Thr Phe Ile Ala Val Phe Thr Val Asp Lys
305                 310                 315                 320

Ala Gly Arg Lys Pro Ala Leu Lys Ile Gly Phe Ser Val Met Ala Leu
                325                 330                 335
```

```
Gly Thr Leu Val Leu Gly Tyr Cys Leu Met Gln Phe Asp Asn Gly Thr
                340                 345                 350

Ala Ser Ser Gly Leu Ser Trp Leu Ser Val Gly Met Thr Met Met Cys
            355                 360                 365

Ile Ala Gly Tyr Ala Met Ser Ala Ala Pro Val Val Trp Ile Leu Cys
        370                 375                 380

Ser Glu Ile Gln Pro Leu Lys Cys Arg Asp Phe Gly Ile Thr Cys Ser
385                 390                 395                 400

Thr Thr Thr Asn Trp Val Ser Asn Met Ile Ile Gly Ala Thr Phe Leu
                405                 410                 415

Thr Leu Leu Asp Ser Ile Gly Ala Gly Thr Phe Trp Leu Tyr Thr
                420                 425                 430

Ala Leu Asn Ile Ala Phe Ile Gly Ile Thr Phe Trp Leu Ile Pro Glu
            435                 440                 445

Thr Lys Asn Val Thr Leu Glu His Ile Glu Arg Lys Leu Met Ala Gly
        450                 455                 460

Glu Lys Leu Arg Asn Ile Gly Val
465                 470

<210> SEQ ID NO 50
<211> LENGTH: 4938
<212> TYPE: DNA
<213> ORGANISM: Salmonella typhimurium

<400> SEQUENCE: 50
aacggacgat cgataaaaaa atccagatat ccattcgctt caattggcgt cagcccggcg      60
accagatggg cattaaatga atatcccggc aatagcggat cattttgcgt ttcagccatg     120
atttctctac cccccgatgt tcagagaaga aacaaattgt ccatatcgac caggacgaca     180
gagcttccgt ctccgcaaga ctttgcgctt gatgaaagca cgtatcaacc ccgcttgtga     240
aaagcgcttt gtaacaaaag cgtacagttc aggcgataaa attaagtaac agaagtgtct     300
ataactatgg ctggaatgtc cacattgaat atttgcacag cgtcacactt tgcaaagcat     360
tagcattttt gtcccataaga ttagcggatc ctgcctgacg ttttttgccg cgactctcta     420
ctgtttctcc ataccctgttt ttctggatgg agtaagacga tggcaattgc aattggcctc     480
gattttggca gtgattcagt gcgcgctctg gcagtggact gcgccaccgg cgacgagatc     540
gccaccagcg tagagtggta tccgcgctgg caagaaggcc gttattgcga cggcccgaac     600
aaccagttcc gtcatcatcc gcgcgactac atggagtcaa tggaggccgc gctgaaagcc     660
gttctggcac aattaagcgc cgcgcaacgc gcaaatgtcg ttggcattgg cgttgacagc     720
accggctcta cgccagcgcc gattgacgcc gacggtaacg tcctggcgct cgtccagag     780 ttcgccgaga acccgaatgc gatgtttgtg ctgtggaaag atcacaccgc cgtggaagag     840
gccgacgaaa tcactcgtct gtgccataag ccaggcaagg tcgactactc ccgctatatt     900
ggcggcattt actccagcga atggtcttgg gcgaagattc tgcacgtcac ccggcaggat     960
agcgccgtcg cgcaggccgc cgtctcgtgg attgagctgt gcgactgggt gccggcgctg    1020
ctttccggca ccactcgccc gcaggatatc cgcgtggcc gctgcagcgc cgggcacaaa    1080
acgctgtggc atgaaagctg gggcggtctg ccgcccgcga gcttctttga tgaactcgat    1140
ccgtgcatta accgtcatct gcgctacccg ttatttagcg aaaccttcac cgccgatctg    1200
cccgtgggca ccctgtgcgc cgaatgggcg cagcgcctcg acttgccgga aagcgtagtg    1260
atttccggcg gcgcgttcga ctgtcacatg ggcgcggtcg gcgcgggcgc acagcccaat    1320
```

-continued

```
acgctggtga aagtcatcgg cacgtctacc tgcgacattc tgattgcgga taaacagagc    1380 gtcgggatc  gcgccgtgaa aggcatttgc ggtcaggttg acggcagcgt ggtgccgaac    1440
tttatcggtc tggaagcggg gcaatctgct ttcggcgata tctacgcctg gtttagccgc    1500
gtgttgagct ggccgctgga gcaacttgcc gcgcagcacc cggaactgaa accccagatt    1560
aacgccagcc agaagcagct actgccagcg ctcaccgacg cctgggcgaa aaatccgtcc    1620
ctggatcacc tgccggtggt gctcgactgg tttaacggtc gccgcacgcc aaacgctaat    1680
cagcgtctga aaggcgtcat taccgatctc aatctcgcca ccgacgcgcc agcgctgttt    1740
ggcggtctgt tcgcttcgac cgccttcggc gcgcgcgcca ttcaggagtg ttttaccgat    1800
cagggtatcg cggtcaataa cgtgatggcg cttggcggca tcgcccgtaa aaatcaggtc    1860
attatgcagg tctgctgcga cgtactgaat cgtccgttgc agatcgtcgc ttccgaccag    1920
tgttgcgcat taggcgccgc tatctttgcc gccgtcgctg cgaaagtcca tgccgacatt    1980
ccagccgccc agcaaagcat ggcgagcgcg gtagaacgca ctctgcgccc ccaccctgaa    2040
caggcgcaac gcttcgaaca gctttaccgc cgctaccagc agtgggcgct aagcgcagaa    2100
caacattatc ttccgactgc cgcgccggcg ccaacgaccc cggccaatca ggcaatcctg    2160
actcattaag gacacgacaa tgacgatttt tgataattat gaagtatggt tgtgattgg     2220 cagccagcat ttgtatggcg cagaaaccct gcgtcaggtc acccaacatg ccgagcatgt    2280
ggtcaacgcg ctgaataccg aagccaaact gccatgtaaa ctggtattaa accgctggg    2340 cacctcgccg gatgagatta ccgccatttg tcgtgacgcc aattatgacg atcgctgcgc    2400
agggctggtg gtctggctgc acaccttctc cccggccaaa atgtggatca acgggctgag    2460
tatccttaac aaaccactac tgcaattcca tacccaattt aacgccgccc tgccgtggga    2520
cagcattgat atggactta  tgaacctgaa ccagactgcg cacggcggtc gtgagttcgg    2580
ttttatcggc gcgcggatgc gccagcagca cgcggtcgtc accggtcact ggcaggataa    2640
agaggcccat acgcgtatcg gtgcctggat gcgccaggcg gtctctaaac aggatacccg    2700
ccagctaaaa gtctgccgct tcggcgacaa tatgcgtgaa gtcgcagtga ctgacggtga    2760
taaagtggcc gcgcaaatca aatttggctt ttcggtcaat acctgggcgg tcggcgatct    2820
ggtgcaggtg gtgaattcta tcggcgacgg cgatatcaac gctctgattg acgagtatga    2880
aagcagctat accctgacgc ccgccaccca aatccacggc gataaacgcc agaacgtgcg    2940
ggaggcggcg cgtattgaac tcggtatgaa gcgtttcctg aacagggcg  gcttccacgc    3000 attcactact acctttgaag atttacacgg tctgaaacag cttccgggtc tggccgtaca    3060
gcgtctgatg cagcaaggct acggctttgc gggcgaaggc gactggaaaa ccgccgctct    3120
gcttcgcatt atgaaagtga tgtcaaccgg tctgcagggc ggcacctcat ttatggagga    3180
ttacacctac cacttcgaga aaggcaacga tctggtgctc ggctcgcaca tgctggaagt    3240
gtgtccgtcc atcgcggtgg aagagaaacc gatcctcgac gtccagcacc tcggcattgg    3300
cggcaaggaa gatccggcgc gtttgatttt caatacccaa accggcccgg cgatcgtcgc    3360
cagcctgatc gacctcggcg atcgttatcg cctgctggtc aactgcattg acaccgtaaa    3420
aacgccgcac tccctgccga aactgccggt ggctaacgcg ctgtggaagg cgcagccgga    3480
tctgccgacc gcctccgaag cgtggattct ggctggcggc gcgcaccata ccgtcttcag    3540
ccacgcgctg gatctgaacg atatgcgcca gtttgcagaa atacacgata tcgaaatcgc    3600
ggtgattgat aacgatacc  atctgccggc ctttaaggac gcgctgcgct ggaacgaggt    3660
```

| | |
|---|---:|
| gtattacggg ttcaaacgtt aattggtgaa acggattgcc cggtggcact gcgtttaccg | 3720 |
| ggcctacggt cctgtaggcc gaataaggca tttatgtcgc catccggcac accgtcgctc | 3780 |
| gtaggccgga taagcgaagc gccatccggc agggagaaaa caatgttaga agatctcaaa | 3840 |
| cgccaggtac tggaagctaa tctggcgctg ccaaaacaca acctggtcac ccttacctgg | 3900 |
| ggtaacgtta gcgccgtcga tcgcgaacgc ggcgtactgg tgattaagcc gtccggcgtc | 3960 |
| gattatagcg tcatgaccgc tgacgatatg gtggtggtca gcctggagag cggtgaagtc | 4020 |
| gttgaaggtc ataagaaacc gtcgtccgat acgccaaccc accgtctgtt gtaccaggca | 4080 |
| tttccgacta tcggcggcat cgtacacacc cattcgcgcc acgcgactat ctgggcgcag | 4140 |
| gcgggtcagc caattccggc gacgggaacc acccatgccg actatttcta cggtacgatt | 4200 |
| ccctgcactc gcaaaatgac cgaggcgaaa attaatggcg agtatgaatg ggaaacgggc | 4260 |
| aatgtcattg ttgaaacctt tgaaaaacaa ggcattgacg ccgctcaaat gcccggcgtg | 4320 |
| cttgtccatt cgcacggccc gtttgcctgg ggtaaaaatg ccgaggatgc agtgcataac | 4380 |
| gccatcgtgc tggaagaagt ggcctatatg gggatcttct gccgcagct tgcgccgcag | 4440 |
| ttgcccgaca tgcagcaatc cctgctggat aaacactatc tacgcaaaca cggcgcaaaa | 4500 |
| gcctattacg ggcagtaatg cctctaaaaa cgcgtcccat gggggggcgcg ttgatgaatc | 4560 |
| tggtcggtga tatattcagc aaatgcgctt tgatagacgt aatgatcaga actcacatat | 4620 |
| tcaataatat tgtcataatg tccctgccac gcttttcctt ccagcgcatg gaagaaaata | 4680 |
| taatcttcga ttgttgactg ccagcgttgc ccatttaaca gatagttaat aatggtatcc | 4740 |
| cgatgtccgt tttttctgtc gtgtccttgc cagtgaaaaa aagcattgcc gttttcaata | 4800 |
| atctcggtac gccaaatctg ttctgtccat gttttatact caaaaaatcg actcacggtt | 4860 |
| tttatggaag ggttagcgcg ttgagtattg acgaaaagat aacggtcgtt ccctaccaga | 4920 |
| cgcgcctgca tactcaca | 4938 |

<210> SEQ ID NO 51
<211> LENGTH: 2280
<212> TYPE: DNA
<213> ORGANISM: Salmonella typhi

<400> SEQUENCE: 51

| | |
|---|---:|
| ggcatacaca cacctgtata acatttgatg taacgccgtt actttacgca ggagtaaatc | 60 |
| ggtgaatttg atctgagtca agaaggtggg ttttcaataa aagttgtgcc ataaattgtg | 120 |
| aagtttgtag attttatgaa catttgatgt accgatctcc cccatgatcg ccactacgta | 180 |
| tggacgtcag gatgcctccc cgcctgatca gaagcgtttc ctcattaaaa aggacatttt | 240 |
| tttaaagttc ctggtgcata aaagtcacat ccttttaaag ggttgttaac cctgttgaat | 300 |
| gttcccactc ccctattcag gaatattaaa aacgctatgc aaatacagag cttctatcac | 360 |
| tcagcttcac taaaaaccca ggaggctttt aaaagcctac aaaaaacctt atacaacgga | 420 |
| atgcagattc tctcaggcca gggcaaagcg ccggctaaag cgcccgacgc tcgcccggaa | 480 |
| attattgtcc tgcgagaacc cggcgcgaca tgggggaatt atctacagca tcagaaggcg | 540 |
| tctaaccact cgctgcataa cctctataac ttacagcgcg atcttcttac cgtcgcggca | 600 |
| accgttctgg gtaaacaaga cccggttcta acgtcaatgg caaaccaaat ggagttagcc | 660 |
| aaagttaaag cggaccggcc agcaacaaaa caagaagaag ccgcggcaaa agcattgaag | 720 |
| aaaaatctta tcgaacttat tgcagcacgc actcagcagc aggatggctt acctgcaaaa | 780 |
| gaagctcatc gctttgcggc agtagcgttt agagatgctc aggtcaagca gcttaataac | 840 |

-continued

```
cagccctggc aaaccataaa aaatacactc acgcataacg ggcatcacta taccaacacg    900
cagctccctg cagcagagat gaaaatcggc gcaaaagata tctttcccag tgcttatgag    960
ggaaagggcg tatgcagttg ggataccaag aatattcatc acgccaataa tttgtggatg   1020
tccacggtga gtgtgcatga ggacggtaaa gataaaacgc ttttttgcgg gatacgtcat   1080
ggcgtgcttt ccccctatca tgaaaagat ccgcttctgc gtcacgtcgg cgctgaaaac    1140
aaagccaaag aagtattaac tgcggcactt tttagtaaac ctgagttgct taacaaagcc   1200
ttagcgggcg aggcggtaag cctgaaactg gtatccgtcg ggttactcac cgcgtcgaat   1260
attttcggca agagggaac gatggtcgag gaccaaatgc gcgcatggca atcgttgacc    1320
cagccgggaa aaatgattca tttaaaaatc cgcaataaag atggcgatct acagacggta   1380
aaaataaaac cggacgtcgc cgcatttaat gtgggtgtta atgagctggc gctcaagctc   1440
ggctttggcc ttaaggcatc ggatagctat aatgccgagg cgctacatca gttattaggc   1500
aatgatttac gccctgaagc cagaccaggt ggctgggttg gcgaatggct ggcgcaatac   1560
ccggataatt atgaggtcgt caatacatta gcgcgccaga ttaaggatat atggaaaaat   1620
aaccaacatc ataaagatgg cggcgaaccc tataaactcg cacaacgcct tgccatgtta   1680
gcccatgaaa ttgacgcggt acccgcctgg aattgtaaaa gcggcaaaga tcgtacaggg   1740
atgatggatt cagaaatcaa gcgagagatc atttccttac atcagaccca tatgttaagt   1800
gcgcctggta gtcttccgga tagcggtgga cagaaaattt tccaaaaagt attactgaat   1860
agcggtaacc tggagattca gaacaaaat acgggcgggg cgggaaacaa agtaatgaaa    1920
aatttatcgc cagaggtgct caatctttcc tatcaaaaac gagttgggga tgaaaatatt   1980
tggcagtcag taaaaggcat ttcttcatta atcacatctt gagtcttgag gtaactatat   2040
ggaaagtcta ttaaatcgtt tatatgacgc gttaggcctg gatgcgccag aagatgagcc   2100
actgcttatc attgatgatg ggatacaggt ttatttaat gaatccgatc atacactgga    2160
aatgtgctgt ccctttatgc cattgcctga cgacatcctg actttgcagc attttttacg   2220
tctgaactac accagcgccg tcactatcgg cgctgacgca gacaatactg ctttagtggc   2280
```

<210> SEQ ID NO 52
<211> LENGTH: 561
<212> TYPE: PRT
<213> ORGANISM: Salmonella typhi

<400> SEQUENCE: 52

Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
    50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Glu Ala Ala Ala Lys Ala Leu Lys

-continued

```
            115                 120                 125
Lys Asn Leu Ile Glu Leu Ile Ala Ala Arg Thr Gln Gln Asp Gly
        130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
                165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
        195                 200                 205

Gly Lys Gly Val Cys Ser Trp Asp Thr Lys Asn Ile His His Ala Asn
    210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
    290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
        355                 360                 365

Gly Phe Gly Leu Lys Ala Ser Asp Ser Tyr Asn Ala Glu Ala Leu His
    370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
                405                 410                 415

Thr Leu Ala Arg Gln Ile Lys Asp Ile Trp Lys Asn Asn Gln His His
            420                 425                 430

Lys Asp Gly Gly Glu Pro Tyr Lys Leu Ala Gln Arg Leu Ala Met Leu
        435                 440                 445

Ala His Glu Ile Asp Ala Val Pro Ala Trp Asn Cys Lys Ser Gly Lys
    450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
                485                 490                 495

Gly Gly Gln Lys Ile Phe Gln Lys Val Leu Leu Asn Ser Gly Asn Leu
            500                 505                 510

Glu Ile Gln Lys Gln Asn Thr Gly Gly Ala Gly Asn Lys Val Met Lys
        515                 520                 525

Asn Leu Ser Pro Glu Val Leu Asn Leu Ser Tyr Gln Lys Arg Val Gly
    530                 535                 540
```

Asp Glu Asn Ile Trp Gln Ser Val Lys Gly Ile Ser Ser Leu Ile Thr
545                 550                 555                 560

Ser

<210> SEQ ID NO 53
<211> LENGTH: 8160
<212> TYPE: DNA
<213> ORGANISM: Salmonella typhi

<400> SEQUENCE: 53

| | | | | | |
|---|---|---|---|---|---|
| agcctgtgat | tctgtacagt | taaggtttaa | ccccaaaggt | gcaaacaatt | aaatttgtaa | 60 |
| cagattattt | caaatacgat | taggaatatt | cttattttga | ggaatggctt | agcattttt | 120 |
| atggtcgcca | ggattaaaaa | atacgcccta | tccaaacaat | ttagcataat | ttatcattcg | 180 |
| atttctaga | ctaaataaga | tttttgata | ggtacaaaca | atgaattgtg | caggtttgac | 240 |
| atcaattctc | tgttgtgtaa | aaatcccgtt | taggccgtta | gtactattaa | aattagggta | 300 |
| ataatttat | tgttagttaa | ttgttaacag | gagcaaagaa | ttagatattg | cttgtacctt | 360 |
| ttctatggat | gaaattaggt | tatttcagca | taaggagact | tcatgaggtt | tcatcatttc | 420 |
| tggcctccga | atgatatcta | tttcggggtt | ggagctgctg | gcattattga | agaagtgtca | 480 |
| ctgataacaa | atgacagaaa | ttatttgttt | gtgaacctaa | atcgctacag | cctgttaaat | 540 |
| gccctgaatt | ttttcacgcg | aatgagtgat | attaataaaa | taatcgttat | catttcaagt | 600 |
| tcgcgactaa | tgccccttgc | acgttttttgg | ttgacagagt | gcaaaaatgt | tattgctgtt | 660 |
| ttcgatgcgg | caacatcagt | ccaggatatt | atcagaaatg | tcagtcaaca | ccaaagtggt | 720 |
| gaaaagatct | tgacggagca | gagagattat | cgtttcagaa | ttaaccgtaa | ggatatagta | 780 |
| aagatgaaat | atttcctttc | ggaaagtggt | atggaagagc | ttcaggatag | atttatgaac | 840 |
| tcatcatcga | ctatgtatcg | ctggagaaaa | gaattggcag | taaaatttgg | agtacgtgag | 900 |
| ccgcgctatc | tgttattgcc | ggattcagtt | actttactgt | aatgcggtaa | ttttattga | 960 |
| gtaaaacacg | gacaagtatt | tcgtttcagc | acaaaattat | tttcgttact | cattggcgtt | 1020 |
| aatacatata | ttctcagcga | cttctgttct | attcaagtaa | gaaagggta | cggttatacg | 1080 |
| ttttcattaa | ccatactggc | tgctacggcc | aggggcggta | gcgtatctga | ataaacacct | 1140 |
| agaattaact | ttgtaaatat | aaaatttag | taaggatta | ataagagtgt | tcggtataga | 1200 |
| cgaggtaaaa | atcgcgatta | ttgggctggg | atatgttggg | cttcctctgg | cagttgaatt | 1260 |
| tgcaaatct | cgtcaggttg | ttggcttcga | cgttaataaa | aagcgtattc | ttgaattaaa | 1320 |
| gaatggggtg | gatgtcaatc | tggaaaccac | tgaagaagaa | ttacgtgagg | ctcgttatct | 1380 |
| gaaatttact | tccagattg | agaagatcaa | agaatgtaat | ttttacatca | tcaccgtccc | 1440 |
| gacgccgata | aatacctaca | agcaaccaga | cctcacccca | ctaatcaagg | cgagtgaaac | 1500 |
| cgttggtaca | gtgctgaatc | ggggagatat | tgtggtatat | gaatctacgg | tatatccggg | 1560 |
| atgtaccgaa | gaagaatgcg | tgccgatcct | tgctcgtatg | tccggaatga | ctttcaacca | 1620 |
| ggatttctat | gtcggttata | gcccggaaag | gatcaatccc | ggtgataaaa | agcaccgttt | 1680 |
| aaccaacatc | aagaaaatca | cctccggttc | aaccgcacag | atcgccgaac | ttatcgatga | 1740 |
| agtatatcag | cagatcatca | gcgcaggtac | atataaagca | gagagcatca | agttgctga | 1800 |
| ggcagcgaag | gtgattgaaa | atacgcaacg | cgatctgaat | attgccttgg | tcaatgagct | 1860 |
| ggcgattatt | tttaatcgtt | taaatatcga | tactgaagcc | gtgctacgtg | ccgctggcag | 1920 |
| caaatggaat | ttcctgccat | tccgtccggg | actggtcggt | ggtcactgta | ttggcgtaga | 1980 |

```
tccctattat ctgacacata aatctcaggg cattggctat tatccagaaa tcatacttgc    2040
aggacgccgc ctgaacgaca acatgggcaa ctatgtctcc gagcagttga tcaaagcaat    2100
gatcaaaaaa ggaattaacg ttgagggttc cagcgtgctg attctcggct ttaccfttaa    2160 agaaaactgt ccgacatca gaaatacacg cattattgat gtggtaaagg aactcggtaa    2220
atatagttgt aaagtggata tttttgatcc atgggtggat gccgaagagg taagacgaga    2280
gtatggcatt atcccggtat cggaagtcaa atcaagccac tacgatgcga tcattgttgc    2340
agtaggacat cagcaattta aacagatggg aagtgaggat attcgcggct cggaaaaga    2400 taaacatgta ctttatgatt tgaagtatgt tcttccggct gagcagtcag atgtgagatt    2460
gtaatcatga cggcttacga agaactacgg accaaactgg ttctggcacc aaagcgctgg    2520
ctgatcactg gcgtagcagg ctttattggc tccggcttat tagaagaatt actctttctc    2580
aaccagactg tcattggact ggataacttt tccaccggtt atcagcataa tctagacgac    2640
gttcgcacgt ccgtcagtga ggagcaatgg tcgcgattta ttttattca gggtgacatc    2700 aggaaattta ctgactgtca gaaagcgtgt aagaacgttg actatgttct ccaccaagcc    2760
gcgctaggaa gcgtgccacg ttccctaaag gatcccatcg cgactaatag cgccaatatt    2820
gatggttttt taaatatgtt gacggcggcg agagatgctc atgtctctag tttcacctac    2880
gccgcaagca gtagcaccta tggagaccat cccgatttac ctaaaattga ggaacggatc    2940
ggtcgaccac tcagcccgta tgcggtaaca aaatacgtca atgaattgta cgctgatgtg    3000
tttgcacgta gctatgaatt taacgctatt ggcctacgct actttaatgt ctttggtcgc    3060
cgccaaaatc ctaacggagc gtactcggca gttattcctc gctggatact atcgcttctt    3120
aaagatgaac caatttatat caatggcgat ggctcaacaa gcagggattt ttgctatata    3180
gagaatgtga ttcaggccaa tctattatca gcaacaacta atgatttagc ctctaaaaat    3240
aaggtctata atgtggcagt tggagataga acttcgttaa atgagcttta ttatctaatt    3300
cgcgatgggc ttaatttatg gcggaacgaa caaagtagag ctgaaccaat ttataaagat    3360
tttcgtgacg gtgacgttaa gcatagccag gcagatatta ccaaaataaa aacatttctt    3420
tcatatgagc ctgaatttga tatcaaagaa ggacttaagc agactctaaa atggtatatc    3480
gataaacatt ctactttgta ttcctcggta taactactca cttcctttc acgtggatga    3540 atttaatgaa atcgtcaggg atgtttacgc ttacagccat ggcagttgc cgtattgtga    3600 gtccggtaaa acgagctcag ccttatttta atttcaggc aaactttaag agaatatatg    3660
gttttacgca tacgagcagc gaggcattac agcagattcg gttatttttg ggcttgatag    3720
acattcctga aaaggtccga ccatttattt ttagacctaa tgtaaactat tcaaacaccg    3780
acgtacatag tcgttctgat ttctatatca ttgagatttc aagtcagaag aagattatgg    3840
cctatgggtt ctgcttacaa ataaattatt taactcgtca tttctatgaa ttttttagcc    3900
aaacagagcg ggcgtgcatg tactggtcgt tggccacgca aggaaatcga cacaaactgc    3960
tggcctatct caaagacgat ccctgttttg ccggaatgtc ggaagacgat cgtgccttat    4020
taagcaatat caatgtcgag cagatggatg agcatgctat cgaacaggat atgatggaaa    4080
tcgttcagct tcttggtcgc gatcgcgtta tgtttatgac acatgttgat gccgtgactc    4140
gtgctggaac cgtcattcta tcccgtagtc ggttgattaa aaatgtcgac accatcgccg    4200
ccaggatgga tattccctgc gttaacccga caaatttgat ggaaagtgg gggcagaaac    4260 gagccctgga aaaaaatggc gacgatctta ctcattatac cgatatgttt ggtgacgcga    4320
```

| | |
|---|---|
| tcgttgcggc tattttttaag ggagtgatca ataatactaa tcatcatctt gatgaggggc | 4380 |
| gacaagagaa acaggaccaa atacgtgaga ttaccttatc gatcactaag cagcttgcag | 4440 |
| atggcgacat tattgctgca tcacaacaac tttttgccgc attaagaaat cagcagcaag | 4500 |
| atcccgttct aatccaactt cggtccgtaa tcttcagcca tttaggttat tatgaacagg | 4560 |
| cttatcagga tattagtgat gttgagaaaa ttatcggtac gactgacagt acattacgtt | 4620 |
| gtcggctgag gtctctacat ggattagcgc gttggcggga agccttatcg acggcagaga | 4680 |
| tgatgctttc caatgaaatt gaagatgaag aagtccttac cgttgccgcc ggctcagccg | 4740 |
| atgctttaca gctgtttgat aagtcatatc attattggaa acgtgtacta ttattgaatc | 4800 |
| ctgaaactca aagcggatgg gttaatttcc tgagcagcac gcaatatttc aatgatggca | 4860 |
| acgcattctc tgaagctttc catgccggca ttcaatcgca gcgcctaaat gatacgttta | 4920 |
| tggaaacggc gttatctttg gcaatcaaat tcagtgatga attgattttc atgcatgcgc | 4980 |
| tcgagcagct actccgccat gagtcagaat ttgcgctgac ggtattgtcg acgattcatg | 5040 |
| ataccggtct cgttatccgc acagcttttct gcatcaagaa tatgagctat catcaagcgc | 5100 |
| ttcgcacctc gtataaagat aaaatccacg acgtttttga ggcatggaac aataccgcgc | 5160 |
| tgtcgctaca ttcggttgat gattttgtct cactgagtac ttcgctagcc tatagctact | 5220 |
| ctgcatttat ggtttatccc cattcacgta tttctcgctt taataatgaa gttaaaatgg | 5280 |
| catgcgcga taaattaaga gaaatgtatg agcgtgagga ttatgaaaat atcctggcag | 5340 |
| gggcgaaaat agtgtggcca cttctgaagt ttgatcccgt tggcaccgta tattgtgcaa | 5400 |
| gaacgctggt gaatcttggt gcctggaaag acgcgtgcac gttggcccac atgaccttga | 5460 |
| ttcgtaactc gaacattacc agcctgcagt cgattatgtt acgcagcata cgtcatatta | 5520 |
| acaacattcc gttcctcatt gatttgattg ctaacgtcat gagcattact ctatcattcc | 5580 |
| agaatgcctc aatgaacaag ttgtttgaga aagagtgtcg caatgttgca accagagccc | 5640 |
| ttaaatatgt acgccagaag aaaactgaag ggcgtctgga tgaagcattg tctgtattga | 5700 |
| ttagcctgaa acgaattgag cctgatgttt ctcgtctgat gcgtgaatat aagcaaatta | 5760 |
| tcagattatt taatgagtca cggaaggatg gcggtagcac tatcacgtct tatgaacatc | 5820 |
| tagactatgc gaaaaaatta ctcgtttttg atagcgaaaa tgcctatgcc ttgaaatatg | 5880 |
| ccgcattaaa tgcaatgcat ttacgcgact acacgcaggc tttgcagtat ggcagcgac | 5940 |
| tggagaaagt gaatggacca acggagccgg tgacaaggca gatctcgacc tgcataaccg | 6000 |
| cattacaaaa aaatacatca gggaagtcgt aatgattacg caggaagaaa agttagctgc | 6060 |
| actaggaaaa acgtgtttaa cattaaaaca agagaagaag cttgcgcaag ctgttgcgtt | 6120 |
| aattgacagt gaattaccga ctgaggcttt aacttcatta gcgatgctaa aaaaagcaga | 6180 |
| gtttcttcat gatgtcaatg aaacggagcg tgcatacgcg ctctacgaaa cgctgattgc | 6240 |
| acaaaacaat gatgaagcac gttatgagta tgcacgtcgt ttatataata cggggctagc | 6300 |
| caaagatgct cagctaattc ttaaaaaggt tagcaatggt gtgcagaaaa aatataacaa | 6360 |
| ttatttaggc aaaataaata agatctgtga tttgcttgaa cgccttgaag ggaaagcgat | 6420 |
| ccctgtgggg accaacacct gtattattgc aatgaagcat gccatcttgt tctatagaaa | 6480 |
| tcgtcaaccc aggcagcttc ccgtcgggtc tttcggtcgt cttgcgctct gtactggctc | 6540 |
| gctaggtagc ggtggtgcag agcgtcagat ttccaggctg gctatcgaaa tcgccagaaa | 6600 |
| atatcggcaa aaggggaaaa ttggcggcct gaaagtagaa gaaccggtag aactaattat | 6660 |
| tcgctccctg acaccggaac tcaggcaaga cttttttcctg aaagaagtgc tggaagaaca | 6720 |

```
ggtcgaggtt cttgaaatcg cgaagattac cggaaacttg tttgacgatg cgacaataga      6780
atctccagag ttgcgcttat tgctatcgca tctaccgccg gtgtgtaaat acggcatcaa      6840
gcatctggtc ccccatttat gcgagcgcaa gctggattat ctctccgttt ggcaggatgg      6900
cgcttgtctg atgattgcgc ttgcagcatt gattgctggc gtgcccagaa ttcaactggg      6960
attacgtggg ttaccgccgg tggttagaaa gcgtctgttc aagccggaat atgagcctct      7020
ctaccaggcg ctggcggtcg tgcctggcgt tgatttatg agtaacaacc attgtgtgac      7080
tcgccattat gccgactggc tgaagttgga ggcgaagcac ttccaggttg tatataacgg      7140
cgtcttaccg ccatctactg aaccctcttc tgaggtgcca cataaaatct ggcagcagtt      7200
tacgcaaaaa acccaggatg cggacacgac tattggtggc gttttccgct tgtaggcga      7260 taagaaccct tttgcatgga ttgattttgc agcacgctat ttacaacacc ccccgccac       7320 gcgctttgtg ctggtaggcg atggtgattt acgcgctgaa gcgcagaaac gcgccgaaca      7380 gttaggggatt ctggagagaa tactattcgt tggcgcctcg cgtgacgtag ggtattggct     7440
gcaaaaaatg aatgtattca ttttgttttc gcgttatgaa gggctaccta atgtgcttat      7500
tgaagcacaa atggtcgggg tgccggtgat ttcaaccccct gcaggtggat cggcagaatg    7560
ctttattgag ggtgtttcgg gtttcattct tgatgatgca cagacggtca atcttgacca      7620
ggcttgccgc tatgcagaaa agttggtcaa tttatggcgc agcagaaccg gtatttgcca     7680
acagacgcag tcatttttac aagaacgctt caccgtggaa catatggtgg aacgtttgt      7740 aaaaaccatt gcctctcagc ctcgttaatt aatgggcatc attttttcagc tatttcattt     7800 ataaaataag ttatgaaaaa aatcatcata ttactaacga cattttttcct gctttcggga    7860 tgcactattc ccagggcggt atttaaatcc agccttatta atcaggacga tcctcgttat      7920
aatctggtcg aagtcacgcc gacattaaaa ctaagcgctc ccgatactgt gccgaaaact      7980
attgtcgatc cggttttttgc cgcaaataac tggcactgga catctttggc taaaggcgat    8040
gtgctgcata tcactatttt atcctcgggc ggggctggat atttatccaa taacgcgagc    8100
ggcgaccgtg cggatttttga aaatattctt gtgactgaca gtaataccgt tcaggtgcct    8160
```

<210> SEQ ID NO 54
<211> LENGTH: 2640
<212> TYPE: DNA
<213> ORGANISM: Salmonella typhi

<400> SEQUENCE: 54

```
aataatgttt ttatattatt gttttttgcgg cttaaattat cctgccaata gtggataagc      60
ttcttatccg cttccatcat atccattaaa acaatgcaac cggccgagat atcttccaga     120
gaacgttgaa tattatgcag ttttccggtt atggccagcg attgctttaa atgttgcaat      180
aatgccgtag cttgcagaga tggctttgtg atcaacaata gtgtgtgacc atgactacta     240
tggacttcat taaacatgat gaaactccac ttttttttaat cgcacatctg acagctgccc     300
ccataaaata aaggcaccag aagtactgac agatgttgca ctgctgtggg ttgaaatagc     360
ccattatcca gaaagagaaa aatatttacg aaaatacttt taactgtttt caatctagcc     420
attacaaatc ttaaagcaag tgttaaactt gtaaccaaat gtaaaatat atattaaaat     480 gttgttttttg ggtttttttg aagtttagat ttgatagtaa agttgtacat ttcgctgtta      540
ttgcatagat ttaaaaaatc atacaaatta taataattca ttgatttta atcattttaa       600 ttattatatg ttatgttttg attttatttt ttcttaaaat ttgagacgtg gcattaaccct      660
```

| | |
|---|---|
| ggacagcaca aagacaaaaa aaacgaagtg tgtcacgtct tgtgcgtatt gccccacatg | 720 |
| ggaagcataa gaacatcccc atggcggcat aacacacacc aacacttcat tttttaggtg | 780 |
| cgcgatacac tatcttctgt ggccaaaaat caattataaa aaatcacatg ctatcgttt | 840 |
| tattagcact ttggtatgag cttaaataac aaaataccac gcgtgggtga gttattaaaa | 900 |
| atgtttccac ggacatactc ttcatcgtaa cgacgcgtta acaaaaaacg catgtcgcta | 960 |
| acaaggtaat agataatttt cgctatgtac gaccaggtcc agggtgacag catgaaaaac | 1020 |
| aaattgttat ttatgatgtt gacaatactg ggtgcgcctg ggattgcaac cgcgacaaat | 1080 |
| tatgatctgg ctcgttcaga gtataatttt gcggtaaatg aattaagcaa gtcttcattt | 1140 |
| aatcaggcgg ccattattgg tcaagtcggc acggataata gtgccagagt acgccaggaa | 1200 |
| ggatcaaaac tattgtccgt tatttcacaa gaaggaggaa ataatcgggc gaaagtcgac | 1260 |
| caggcaggga attataactt tgcgtatatt gagcaaacgg gcaatgccaa cgatgccagt | 1320 |
| atatcgcaaa gcgcttacgg taatagtgcg gctattatcc agaaaggttc tggaaataag | 1380 |
| gccaatatta cccagtacgg tacgcagaaa acagcagttg tagtgcagaa acagtcgcat | 1440 |
| atggctattc gcgtcaccca acgctaatac cgttacgact tttaaatcaa tccgatgggg | 1500 |
| gttttaccat gaaactttta aaagtggcag cattcgcagc aatcgtagtt tctggcagtg | 1560 |
| ctctggctgg cgtcgttcca caatggggcg gcggcggtaa tcataacggc ggcggcaata | 1620 |
| gttccggccc ggattccacg ttgagcattt atcagtacgg ttccgctaac gctgcgcttg | 1680 |
| ctctgcaaag cgatgcccgt aaatctgaaa cgaccattac ccagagcggt tatggtaacg | 1740 |
| gcgccgatgt aggccagggt gcggataaca gtactattga actgactcag aatggtttca | 1800 |
| gaaacaatgc caccatcgac cagtggaacg ctaaaaactc cgatattact gtcggtcaat | 1860 |
| acggcggtaa taacgccgcg ctggttaatc agaccgcatc tgattccagc gtaatggtgc | 1920 |
| gtcaggttgg ttttggcaac aacgccacgg ctaaccagta ttaatttagc gtctgcgcta | 1980 |
| ataaaaaaac agggcataag ccctgttttt tttcgggagg aaattatgca tactttattg | 2040 |
| ctccttgccg cactttcaaa tcagattacg tttaccacga ctcagcaagg cgatatttac | 2100 |
| acggtgatcc ctcaggtcac attaaacgaa ccctgcgtct gtcaggtgca aattctctct | 2160 |
| gtgcgcgacg gcgtcggggg acaaagccat acacagcaaa acaaacgct atctttacct | 2220 |
| gctaatcaac cgattgagtt gtctcgtctt agtgtaaata tatcttcaga ggactcggtt | 2280 |
| aaaattattg ttactgtttc ggacggacaa tcactgcatt tatcacaaca atggccgcct | 2340 |
| tctgcacagt agtttttgat ggtggcggaa atggattggc tgacctgggt ataaagaggc | 2400 |
| gataaaagcg tctcatcgtc tcggcatgtc gctataaggt aacgccgaac cctcgaggat | 2460 |
| gactaatcat tgaggagtta acatgtccgt aatcaagaaa aatatccctg ccataggcct | 2520 |
| gtgtatctgc gctttttta tccattctgc ggtagggcaa caaacggtac agggcggcgt | 2580 |
| tatccatttt cgcggcgcga ttgttgagcc actgtgcgat atttctactc acgccgaaaa | 2640 |

<210> SEQ ID NO 55
<211> LENGTH: 1800
<212> TYPE: DNA
<213> ORGANISM: Salmonella typhi

<400> SEQUENCE: 55

| | |
|---|---|
| cgggcacata tcgataccgt aagccgggta aggcgtaatc gctaccggt ttttttattg | 60 |
| aggtgtgcat ggcaatcgcc caacgacatt ttgcctcgcc atgtttcagt acgcgcataa | 120 |
| aagcaggcaa atttctacgc tgatccataa ttaggatcaa taaaacagcg acggaaatga | 180 |

```
ttcccttcct aacgcaaatt ccctgataat cgccactgga ctttctgctt gcgcggtaag      240
gcaggataag tcgcattact gatggcttcg ctatcattga ttaatttcac ttgcgacttt      300
ggctgctttt tgtatggtga aggatgcgcc acaggatact ggcgcgcata cacagcacat      360
ctctttgcag gaaaaaacgc tatgaaaaat gttggtttta tcggctggcg cggaatggtc      420
ggctctgttc tcatgcaacg catggtagag gagcgcgatt tcgacgctat tcgccctgtt      480
ttcttttcta cctcccagtt tggacaggcg cgcccacct tcggcgacac ctccaccggc       540
acgctacagg acgcttttga tctggatgcg ctaaaagcgc tcgatatcat cgtgacctgc      600
cagggcggcg attataccaa cgaaatttat ccaaagctgc gcgaaagcgg atggcagggt      660
tactggattg acgcggcttc tacgctgcgc atgaaagatg atgccattat tattctcgac      720
ccggtcaacc aggacgtgat taccgacgga ctgaacaatg gcgtgaagac ctttgtgggc      780
ggtaactgta ccgttagcct gatgttgatg tcgctgggcg gtctctttgc ccataatctc      840
gttgactggg tatccgtcgc gacctatcag gccgcctccg gcggcggcgc gcgccatatg      900
cgcgagctgt taacccaaat ggggcagttg tatggccatg tcgccgatga actggcgacg      960
ccgtcttccg caattcttga tattgaacgc aaagttacgg cattgacccg cagcggcgag     1020
ctgccggtgg ataactttgg cgtaccgctg gcgggaagcc tgatcccctg gatcgacaaa     1080
cagcttgata acgccaaag ccgcgaagag tggaaaggcc aggcggaaac caacaagatc      1140
ctcaatactg cctctgtgat cccggttgat ggtttgtgcg tgcgcgtcgg cgcgctgcgc     1200
tgtcacagcc aggcgttcac cattaagctg aaaaaagagg tatccattcc gacggtggaa     1260
gaactgctgg cggcacataa tccgtgggcg aaagtggtgc cgaacgatcg tgatatcact     1320
atgcgcgaat aaccccggc ggcggtgacc ggcacgttga ctacgccggt tggtcgtctg      1380
cgtaagctga acatggggcc agagttcttg tcggcgttta ccgtaggcga ccagttgtta     1440
tggggcgccg ccgagccgct gcgtcgaatg ctgcgccagt tggcgtagtg gctattgcag     1500
cgcttatcgg gcctgcgtgt ggttctgtag gccggataag gcgtgtcagc gccgccatcc     1560
ggcaatatcc gccagataag gcgtagtcgg caagcagacg tcagattgat atgtagggtg     1620
catcgtcacc tttttttgcg taatacagga gtaaacgcag atgtttcatt tttatcagga     1680
gttaagcaga gcattggcta ttcttttaagg gtagcttaat cccacgggta ttaagcctaa     1740
cctgaaggta ggacgacgca gataggatgc acagtgtgct gcgccgttca ggtcaaagaa     1800
```

<210> SEQ ID NO 56
<211> LENGTH: 368
<212> TYPE: PRT
<213> ORGANISM: Salmonella typhi

<400> SEQUENCE: 56

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Phe Gly Gln Ala Ala Pro Thr Phe Gly
        35                  40                  45

Asp Thr Ser Thr Gly Thr Leu Gln Asp Ala Phe Asp Leu Asp Ala Leu
    50                  55                  60

Lys Ala Leu Asp Ile Ile Val Thr Cys Gln Gly Gly Asp Tyr Thr Asn
65                  70                  75                  80

Glu Ile Tyr Pro Lys Leu Arg Glu Ser Gly Trp Gln Gly Tyr Trp Ile

```
                         85                  90                  95
Asp Ala Ala Ser Thr Leu Arg Met Lys Asp Ala Ile Ile Ile Leu
                    100                 105                 110

Asp Pro Val Asn Gln Asp Val Ile Thr Asp Gly Leu Asn Asn Gly Val
                115                 120                 125

Lys Thr Phe Val Gly Gly Asn Cys Thr Val Ser Leu Met Leu Met Ser
            130                 135                 140

Leu Gly Gly Leu Phe Ala His Asn Leu Val Asp Trp Val Ser Val Ala
145                 150                 155                 160

Thr Tyr Gln Ala Ala Ser Gly Gly Ala Arg His Met Arg Glu Leu
                165                 170                 175

Leu Thr Gln Met Gly Gln Leu Tyr Gly His Val Ala Asp Glu Leu Ala
                180                 185                 190

Thr Pro Ser Ser Ala Ile Leu Asp Ile Glu Arg Lys Val Thr Ala Leu
                195                 200                 205

Thr Arg Ser Gly Glu Leu Pro Val Asp Asn Phe Gly Val Pro Leu Ala
210                 215                 220

Gly Ser Leu Ile Pro Trp Ile Asp Lys Gln Leu Asp Asn Gly Gln Ser
225                 230                 235                 240

Arg Glu Glu Trp Lys Gly Gln Ala Glu Thr Asn Lys Ile Leu Asn Thr
                245                 250                 255

Ala Ser Val Ile Pro Val Asp Gly Leu Cys Val Arg Val Gly Ala Leu
                260                 265                 270

Arg Cys His Ser Gln Ala Phe Thr Ile Lys Leu Lys Lys Glu Val Ser
                275                 280                 285

Ile Pro Thr Val Glu Glu Leu Leu Ala Ala His Asn Pro Trp Ala Lys
                290                 295                 300

Val Val Pro Asn Asp Arg Asp Ile Thr Met Arg Glu Leu Thr Pro Ala
305                 310                 315                 320

Ala Val Thr Gly Thr Leu Thr Thr Pro Val Gly Arg Leu Arg Lys Leu
                325                 330                 335

Asn Met Gly Pro Glu Phe Leu Ser Ala Phe Thr Val Gly Asp Gln Leu
                340                 345                 350

Leu Trp Gly Ala Ala Glu Pro Leu Arg Arg Met Leu Arg Gln Leu Ala
                355                 360                 365

<210> SEQ ID NO 57
<211> LENGTH: 840
<212> TYPE: DNA
<213> ORGANISM: Salmonella typhi

<400> SEQUENCE: 57
ctacatccgc cagccgccat aataccatc tccatcggac tcggcgcttt gtcaccggag      60
ttgccatcca ttaaaatctg gtggccggag gaggactctc cgaggaacgt gagcccttca    120
acccacttta cacgcgcttg catatttcgt aactccaatg tttcaatttt cctgaaagat    180
tacgcgcata acaaaaagt cgcaatggaa ggcgacctgg gtcatgctga agcgagacac     240
caggagacac acggcgaaag ctatgctaaa acagacaaga tgctacagta atacattgac    300
gtactgcatg tatgcagagg acatcacatt acaggctaca atctattttc gtagccccct    360
tcccaggtag cgggaagtat attttttgcaa ccccagagac agtgccgttt tctggctctg    420
gagacagctt ataacagagg ataaccgcgc atggtgcttg caaaccgca aacagacccg     480 actcttgaat ggttcttgtc tcattgccac attcataagt acccgtcaaa gagcacgctg    540
```

```
attcaccagg gtgaaaaagc agaaacgctg tactacatcg ttaaaggctc cgtggcagtg      600
ctgatcaaag atgaagaagg gaaagaaatg atcctttctt atctgaatca gggtgatttt      660
attggtgaac tgggcctgtt tgaagaaggc caggaacgca gcgcctgggt acgtgcgaaa      720
accgcatgtg aggtcgctga aatttcctac aaaaaatttc gccaattaat ccaggtcaac      780
ccggatattc tgatgcgcct ctcttcccag atggctcgtc gcttacaagt cacctctgaa      840
```

<210> SEQ ID NO 58
<211> LENGTH: 130
<212> TYPE: PRT
<213> ORGANISM: Salmonella typhi

<400> SEQUENCE: 58

```
Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ser Gln Met Ala Arg Arg Leu Gln Val Thr
        115                 120                 125

Ser Glu
    130
```

<210> SEQ ID NO 59
<211> LENGTH: 3039
<212> TYPE: DNA
<213> ORGANISM: Salmonella typhi

<400> SEQUENCE: 59

```
tacatccgcc agccgccatt aataccatct ccatcggact cggcgctttg tcaccggagt       60
tgccatccat taaatctggt tggccggagg aggactctcc gaggaacgtg agcccttcaa      120
cccactttac acgcgcttgc atatttcgta actccaatgt ttcaattttc ctgaaagatt      180
acgcgcatac aacaaaagtc gcaatggaag gcgacctggg tcatgctgaa gcgagacacc      240
aggagacaca cggcgaaagc tatgctaaaa cagacaagat gctacagtaa tacattgacg      300
tactgcatgt atgcagagga catcacatta caggctacaa ctgcagagat cttttattat      360
tctatcctag aattgtgata atatattcac aattctagga gttgtaaact gcttttattt      420
atctagagtc aagccgtcaa ttgtctgatt cgttaccaat tatgacaact tgacggctac      480
tagatctcag ttcggcagtt aacagactaa gcaatggtta atactgttga actgccgatg      540
atcattcact ttttcttcac aaccggcacg aaactcgctc gggctggccc cggtgcattt      600
tagtaagtga aaaagaagtg ttggccgtgc tttgagcgag cccgaccggg gccacgtaaa      660
tttaaatact cgcgagaaat agagttgatc gtcaaaacca acattgcgac cgacggtggc      720
aaatttatga gcgctcttta tctcaactag cagttttggt tgtaacgctg gctgccaccg      780
```

```
gataggcatc cgggtagtgc tcaaaagcag cttcgcctga ctaatgcgtt ggtcctcgcg    840
ctatccgtag gcccatcacg agttttcgtc gaagcggact gattacgcaa ccaggagcgc    900
ccagcttaag acgctaatcc ctaactgctg gcggaaaaga tgtgacagac gcgacggcga    960
ggtcgaattc tgcgattagg gattgacgac cgccttttct acactgtctg cgctgccgct   1020
caagcaaaca tgctgtgcga cgctggcgat atcaaaattg ctgtctgcca ggtgatcgct   1080
gttcgtttgt acgacacgct gcgaccgcta tagttttaac gacagacggt ccactagcga   1140
gatgtactga caagcctcgc gtacccgatt atccatcggt ggatggagcg actcgttaat   1200
ctacatgact gttcggagcg catgggctaa taggtagcca cctacctcgc tgagcaatta   1260
cgcttccatg cgccgcagta acaattgctc aagcagattt atcgccagca gctccgaata   1320
gcgaaggtac gcggcgtcat tgttaacgag ttcgtctaaa tagcggtcgt cgaggcttat   1380
gcgcccttcc ccttgcccgg cgttaatgat ttgcccaaac aggtcgctga aatgcggctg   1440
cgcgggaagg ggaacgggcc gcaattacta aacgggtttg tccagcgact ttacgccgac   1500
gtgcgcttca tccgggcgaa agaaacccgt attggcaaat attgacggcc agttaagcca   1560
cacgcgaagt aggcccgctt tcttgggca taaccgttta taactgccgg tcaattcggt   1620
ttcatgccag taggcgcgcg gacgaaagta aacccactgg tgataccatt cgcgagcctc   1680
aagtacggtc atccgcgcgc ctgctttcat ttgggtgacc actatggtaa gcgctcggag   1740
cggatgacga ccgtagtgat gaatctctcc tggcgggaac agcaaaatat cacccggtcg   1800
gcctactgct ggcatcacta cttagagagg accgcccttg tcgttttata gtgggccagc   1860
gcagacaaat tctcgtccct gattttcac cacccctga ccgcgaatgg tgagattgag    1920
cgtctgttta agagcaggga ctaaaagtg gtggggact ggcgcttacc actctaactc    1980
aatataacct ttcattccca gcggtcggtc gataaaaaaa tcgagataac cgttggcctc   2040
ttatattgga aagtaagggt cgccagccag ctatttttt agctctattg caaccggag    2100
aatcggcgtt aaacccgcca ccagatgggc gttaaacgag tatcccggca gcggggatc    2160
ttagccgcaa tttgggcggt ggtctacccg caatttgctc atagggccgt cgtcccctag   2220
attttgcgct tcagccatac ttttcatact cccaccattc agagaagaaa ccaattgtcc   2280
taaaacgcga agtcggtatg aaaagtatga gggtggtaag tctcttcttt ggttaacagg   2340
atattgcatc agacattgcc gtcactgcgt cttttactgg ctcttctcgc taacccaacc   2400
ggtaaccccg cttattaaaa gcattctgta acaaagcggg accaaagcca tgacaaaaac   2460
gcgtaacaaa agtgtctata atcacggcag aaaagtccac attgattatt tgcacggcgt   2520
cacactttgc tatgccatag catttttatc cataagatta gcggatccta cctgacgctt   2580
tttatcgcaa ctctctactg tttctccata cccgtttttt tgggctagcc tcgaggagga   2640
taaccgcgca tggtgcttgg caaaccgcaa acagacccga ctcttgaatg gttcttgtct   2700
cattgccaca ttcataagta cccgtcaaag agcacgctga ttcaccaggg tgaaaaagca   2760
gaaacgctgt actacatcgt taaaggctcc gtggcagtgc tgatcaaaga tgaagaaggg   2820
aaagaaatga tcctttctta tctgaatcag ggtgatttta ttggtgaact gggcctgttt   2880
gaagaaggcc aggaacgcag cgcctgggta cgtgcgaaaa ccgcatgtga ggtcgctgaa   2940
atttcctaca aaaatttcg ccaattaatc caggtcaacc cggatattct gatgcgcctc    3000
tcttcccaga tggctcgtcg cttacaagtc acctctgaa                          3039
```

<210> SEQ ID NO 60
<211> LENGTH: 292

<212> TYPE: PRT
<213> ORGANISM: Salmonella typhi

<400> SEQUENCE: 60

Ser Leu Lys Val Ala Val Asp Asn Val Lys Glu Glu Cys Gly Ala Arg
1               5                   10                  15

Phe Glu Ser Pro Ser Ala Gly Thr Cys Lys Lys Phe Val Arg Ser Phe
            20                  25                  30

Tyr Leu Gln Asp Asp Phe Gly Val Asn Arg Gly Val Thr Ala Ile Pro
        35                  40                  45

Met Arg Thr Thr Ser Leu Leu Leu Lys Ala Gln Ser Ile Arg Gln Asp
    50                  55                  60

Glu Arg Trp Ser Leu Val Ser Ile Gly Leu Gln Gln Arg Phe Leu His
65                  70                  75                  80

Ser Leu Arg Ser Pro Ser Leu Cys Val His Gln Ala Val Ser Ala Ile
                85                  90                  95

Asp Phe Asn Ser Asp Ala Leu His Asp Ser Ile Tyr Gln Cys Ala Glu
            100                 105                 110

Arg Val Arg Asn Asp Met Pro Pro His Leu Ser Glu Asn Ile Ala Glu
        115                 120                 125

Met Arg Arg Leu Leu Leu Gln Glu Leu Leu Asn Ile Ala Leu Leu Glu
    130                 135                 140

Ser Tyr Arg Gly Glu Gly Gln Gly Ala Asn Ile Ile Gln Gly Phe Leu
145                 150                 155                 160

Asp Ser Phe His Pro Gln His Ala Glu Asp Pro Arg Phe Phe Gly Thr
                165                 170                 175

Asn Ala Phe Ile Ser Pro Trp Asn Leu Trp Glu His Trp Tyr Ala Arg
            180                 185                 190

Pro Arg Phe Tyr Val Trp Gln His Tyr Trp Glu Arg Ala Glu Pro His
        195                 200                 205

Arg Gly Tyr His His Ile Glu Gly Pro Pro Phe Leu Leu Ile Asp Gly
    210                 215                 220

Pro Arg Cys Val Phe Glu Arg Gly Gln Asn Lys Val Val Gly Gln Gly
225                 230                 235                 240

Arg Ile Thr Leu Asn Leu Ile Tyr Gly Lys Met Gly Leu Pro Arg Asp
                245                 250                 255

Ile Phe Phe Asp Leu Tyr Gly Asn Ala Glu Ile Pro Thr Leu Gly Ala
            260                 265                 270

Val Leu His Ala Asn Phe Ser Tyr Gly Pro Leu Leu Pro Asp Asn Gln
        275                 280                 285

Ala Glu Ala Met
    290

<210> SEQ ID NO 61
<211> LENGTH: 130
<212> TYPE: PRT
<213> ORGANISM: Salmonella typhi

<400> SEQUENCE: 61

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

```
Ala Val Leu Ile Lys Asp Glu Glu Gly Lys Glu Met Ile Leu Ser Tyr
        50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ser Gln Met Ala Arg Arg Leu Gln Val Thr
            115                 120                 125

Ser Glu
    130

<210> SEQ ID NO 62
<211> LENGTH: 1130
<212> TYPE: DNA
<213> ORGANISM: Salmonella typhi

<400> SEQUENCE: 62
gaagcgcaat gtgactggga tgacttcttc ccgactctcg aagagattga ctttaacggt      60
aagctggtgg cgctgtttgg ctgtggcgat caggaagact acgcggaata cttctgtgat     120
gcgctgggca cgattcgcga cattattgag ccgcgcggcg ccacgattgt gggtcactgg     180
ccaaccgcag gctatcattt tgaagcctct aaaggtctgg ctgacgacga tcattttgtc     240
ggcctggcga ttgacgaaga ccgtcagcct gaactgaccg ccgagcgtgt tgaaaaatgg     300
gttaagcaag tttcggctga attgcacctc ggcgacatcc tcaacgccta atcttatgcg     360
gcgcagcgtt atatctgcgc cgcatcaata gacaagacca atcaaaataa ttgctacaaa     420
tttgtaactt tcgcacccat ccctgtacaa tgtccgggtg taatcaggtg cgccagaat      480
ttgcaggcaa aaccacagtt ttattaacat ctgcgagaga cttgcggttt tcatttcggc     540
atggcagtcc tataatgata cgcattatct tgagtgcaat ttctgtcact tctctaatga     600
agtgaatcgt ttagcaacag gacagattcc gcatgactga caacaatacc gcattaaaga     660
aggctggcct gaaagtaacg cttcctcgtt taaaaattct ggaagttctt caggaaccag     720
ataaccatca cgtcagtgcg gaagatttat acaaacgcct gatcgacatg ggtgaagaaa     780
tcggtctggc aaccgtatac cgtgtgctga accagtttga cgatgccggt atcgtgaccc     840
gccataactt tgaaggcggt aaatccgttt ttgaactgac gcaacagcat catcacgacc     900
atcttatctg ccttgactgc ggaaaagtga ttgaatttag tgatgactct attgaagcgc     960
gccagcgtga aattgcggcg aaacacggta ttcgtttaac taatcacagc ctctatcttt    1020
acggccactg cgctgaaggc gactgccgcg aagacgagca cgcgcacgat gacgcgacta    1080
aataagtgta atctttcga agagccaacc gcccggttgg ctttttttata               1130

<210> SEQ ID NO 63
<211> LENGTH: 116
<212> TYPE: PRT
<213> ORGANISM: Salmonella typhi

<400> SEQUENCE: 63

Glu Ala Gln Cys Asp Trp Asp Asp Phe Phe Pro Thr Leu Glu Glu Ile
 1               5                  10                  15

Asp Phe Asn Gly Lys Leu Val Ala Leu Phe Gly Cys Gly Asp Gln Glu
                 20                  25                  30

Asp Tyr Ala Glu Tyr Phe Cys Asp Ala Leu Gly Thr Ile Arg Asp Ile
```

```
                    35                  40                  45
Ile Glu Pro Arg Gly Ala Thr Ile Val Gly His Trp Pro Thr Ala Gly
            50                  55                  60
Tyr His Phe Glu Ala Ser Lys Gly Leu Ala Asp Asp His Phe Val
65                  70                  75                  80
Gly Leu Ala Ile Asp Glu Asp Arg Gln Pro Glu Leu Thr Ala Glu Arg
                85                  90                  95
Val Glu Lys Trp Val Lys Gln Val Ser Ala Glu Leu His Leu Gly Asp
            100                 105                 110
Ile Leu Asn Ala
        115

<210> SEQ ID NO 64
<211> LENGTH: 150
<212> TYPE: PRT
<213> ORGANISM: Salmonella typhi

<400> SEQUENCE: 64

Met Thr Asp Asn Asn Thr Ala Leu Lys Lys Ala Gly Leu Lys Val Thr
1               5                   10                  15
Leu Pro Arg Leu Lys Ile Leu Glu Val Leu Gln Glu Pro Asp Asn His
            20                  25                  30
His Val Ser Ala Glu Asp Leu Tyr Lys Arg Leu Ile Asp Met Gly Glu
        35                  40                  45
Glu Ile Gly Leu Ala Thr Val Tyr Arg Val Leu Asn Gln Phe Asp Asp
    50                  55                  60
Ala Gly Ile Val Thr Arg His Asn Phe Glu Gly Gly Lys Ser Val Phe
65                  70                  75                  80
Glu Leu Thr Gln Gln His His His Asp His Leu Ile Cys Leu Asp Cys
                85                  90                  95
Gly Lys Val Ile Glu Phe Ser Asp Asp Ser Ile Glu Ala Arg Gln Arg
            100                 105                 110
Glu Ile Ala Ala Lys His Gly Ile Arg Leu Thr Asn His Ser Leu Tyr
        115                 120                 125
Leu Tyr Gly His Cys Ala Glu Gly Asp Cys Arg Glu Asp Glu His Ala
    130                 135                 140
His Asp Asp Ala Thr Lys
145                 150

<210> SEQ ID NO 65
<211> LENGTH: 3093
<212> TYPE: DNA
<213> ORGANISM: Salmonella typhi

<400> SEQUENCE: 65
gaagcgcaat gtgactggga tgacttcttc ccgactctcg aagagattga ctttaacggt     60
aagctggtgg cgctgtttgg ctgtggcgat caggaagact acgcggaata cttctgtgat    120
gcgctgggca cgattcgcga cattattgag ccgcgcggcg ccacgattgt gggtcactgg    180
ccaaccgcag gctatcattt tgaagcctct aaaggtctgg ctgacgacga tcattttgtc    240
ggcctggcga ttgacgaaga ccgtcagcct gaactgaccg ccgagcgtgt tgaaaaatgg    300
gttaagcaag tttcggctga attgcacctc ggcgacatcc tcaacgccta atcttatgcg    360
gcgcagcgtt atatctgcgc tgcagagatc ttttattatt ctatcctaga attgtgataa    420
tatattcaca attctaggag ttgtaaactg cttttattta tctagagtca agccgtcaat    480
```

```
tgtctgattc gttaccaatt atgacaactt gacggctaca tcattcactt tttcttcaca    540
acagactaag caatggttaa tactgttgaa ctgccgatgt agtaagtgaa aagaagtgt     600
accggcacga aactcgctcg ggctggcccc ggtgcatttt ttaaatactc gcgagaaata    660
tggccgtgct ttgagcgagc ccgaccgggg ccacgtaaaa aatttatgag cgctctttat    720
gagttgatcg tcaaaaccaa cattgcgacc gacggtggcg ataggcatcc gggtagtgct    780
ctcaactagc agttttggtt gtaacgctgg ctgccaccgc tatccgtagg cccatcacga    840
caaaagcagc ttcgcctgac taatgcgttg gtcctcgcgc cagcttaaga cgctaatccc    900
gttttcgtcg aagcggactg attacgcaac caggagcgcg gtcgaattct gcgattaggg    960
taactgctgg cggaaaagat gtgacagacg cgacggcgac aagcaaacat gctgtgcgac   1020
attgacgacc gccttttcta cactgtctgc gctgccgctg ttcgtttgta cgacacgctg   1080
gctggcgata tcaaaattgc tgtctgccag gtgatcgctg atgtactgac aagcctcgcg   1140
cgaccgctat agttttaacg acagacggtc cactagcgac tacatgactg ttcggagcgc   1200
tacccgatta tccatcggtg gatggagcga ctcgttaatc gcttccatgc gccgcagtaa   1260
atgggctaat aggtagccac ctacctcgct gagcaattag cgaaggtacg cggcgtcatt   1320
caattgctca agcagattta tcgccagcag ctccgaatag cgcccttccc cttgcccggc   1380
gttaacgagt tcgtctaaat agcggtcgtc gaggcttatc gcgggaaggg aacgggccg    1440
gttaatgatt tgcccaaaca ggtcgctgaa atgcggctgg tgcgcttcat ccgggcgaaa   1500
caattactaa cgggtttgt ccagcgactt tacgccgacc acgcgaagta ggcccgcttt    1560
gaaacccgta ttggcaaata ttgacggcca gttaagccat tcatgccagt aggcgcgcgg   1620
ctttgggcat aaccgtttat aactgccggt caattcggta agtacggtca tccgcgcgcc   1680
acgaaagtaa acccactggt gataccattc gcgagcctcc ggatgacgac cgtagtgatg   1740
tgctttcatt tgggtgacca ctatggtaag cgctcggagg cctactgctg gcatcactac   1800
aatctctcct ggcgggaaca gcaaaatatc acccggtcgg cagacaaatt ctcgtccctg   1860
ttagagagga ccgcccttgt cgttttatag tgggccagcc gtctgtttaa gagcagggac   1920
attttttcacc acccccctgac cgcgaatggt gagattgaga atataacctt tcattcccag   1980
taaaaagtgg tgggggactg gcgcttacca ctctaactct tatattggaa agtaagggtc   2040
cggtcggtcg ataaaaaaat cgagataacc gttggcctca atcggcgtta aacccgccac   2100
gccagccagc tatttttta gctctattgg caaccggagt tagccgcaat ttgggcggtg    2160
cagatgggcg ttaaacgagt atcccggcag caggggatca ttttgcgctt cagccatact   2220
gtctacccgc aatttgctca tagggccgtc gtcccctagt aaaacgcgaa gtcggtatga   2280
tttcatactc ccaccattca gagaagaaac caattgtcca tattgcatca gacattgccg   2340
tcactgcgtc ttttactggc tcttctcgct aacccaaccg gtaaccccgc ttattaaaag   2400
cattctgtaa caaagcggga ccaaagccat gacaaaaacg cgtaacaaaa gtgtctataa   2460
tcacggcaga aaagtccaca ttgattattt gcacggcgtc acactttgct atgccatagc   2520
atttttatcc ataagattag cggatcctac ctgacgcttt ttatcgcaac tctctactgt   2580
ttctccatac ccgttttttt gggctagcct cgagaaggca gattccgcgt gactgacaac   2640
aataccgcat taagaaggc tggcctgaaa gtaacgcttc ctcgttttaaa aattctggaa   2700
gttcttcagg aaccagataa ccatcacgtc agtgcggaag atttatacaa acgcctgatc   2760
gacatggggtg aagaaatcgg tctggcaacc gtataccgtg tgctgaacca gtttgacgat   2820
gccggtatcg tgacccgcca taacttgaa ggcggtaaat ccgttttttga actgacgcaa   2880
```

```
cagcatcatc acgaccatct tatctgcctt gactgcggaa aagtgattga atttagtgat    2940
gactctattg aagcgcgcca gcgtgaaatt gcggcgaaac acggtattcg tttaactaat    3000
cacagcctct atctttacgg ccactgcgct gaaggcgact gccgcgaaga cgagcacgcg    3060
cacgatgacg cgactaaata atgagctctc ccg                                 3093
```

```
<210> SEQ ID NO 66
<211> LENGTH: 116
<212> TYPE: PRT
<213> ORGANISM: Salmonella typhi

<400> SEQUENCE: 66

Glu Ala Gln Cys Asp Trp Asp Asp Phe Phe Pro Thr Leu Glu Glu Ile
1               5                   10                  15

Asp Phe Asn Gly Lys Leu Val Ala Leu Phe Gly Cys Gly Asp Gln Glu
            20                  25                  30

Asp Tyr Ala Glu Tyr Phe Cys Asp Ala Leu Gly Thr Ile Arg Asp Ile
        35                  40                  45

Ile Glu Pro Arg Gly Ala Thr Ile Val Gly His Trp Pro Thr Ala Gly
50                  55                  60

Tyr His Phe Glu Ala Ser Lys Gly Leu Ala Asp Asp His Phe Val
65                  70                  75                  80

Gly Leu Ala Ile Asp Glu Asp Arg Gln Pro Glu Leu Thr Ala Glu Arg
                85                  90                  95

Val Glu Lys Trp Val Lys Gln Val Ser Ala Glu Leu His Leu Gly Asp
            100                 105                 110

Ile Leu Asn Ala
        115

<210> SEQ ID NO 67
<211> LENGTH: 292
<212> TYPE: PRT
<213> ORGANISM: Salmonella typhi

<400> SEQUENCE: 67

Ser Leu Lys Val Ala Val Asp Asn Val Lys Glu Glu Cys Gly Ala Arg
1               5                   10                  15

Phe Glu Ser Pro Ser Ala Gly Thr Cys Lys Lys Phe Val Arg Ser Phe
            20                  25                  30

Tyr Leu Gln Asp Asp Phe Gly Val Asn Arg Gly Val Thr Ala Ile Pro
        35                  40                  45

Met Arg Thr Thr Ser Leu Leu Leu Lys Ala Gln Ser Ile Arg Gln Asp
50                  55                  60

Glu Arg Trp Ser Leu Val Ser Ile Gly Leu Gln Gln Arg Phe Leu His
65                  70                  75                  80

Ser Leu Arg Ser Pro Ser Leu Cys Val His Gln Ala Val Ser Ala Ile
                85                  90                  95

Asp Phe Asn Ser Asp Ala Leu His Asp Ser Ile Tyr Gln Cys Ala Glu
            100                 105                 110

Arg Val Arg Asn Asp Met Pro Pro His Leu Ser Glu Asn Ile Ala Glu
        115                 120                 125

Met Arg Arg Leu Leu Leu Gln Glu Leu Leu Asn Ile Ala Leu Leu Glu
130                 135                 140

Ser Tyr Arg Gly Glu Gly Gln Gly Ala Asn Ile Ile Gln Gly Phe Leu
145                 150                 155                 160
```

Asp Ser Phe His Pro Gln His Ala Glu Asp Pro Arg Phe Phe Gly Thr
                165                 170                 175

Asn Ala Phe Ile Ser Pro Trp Asn Leu Trp Glu His Trp Tyr Ala Arg
            180                 185                 190

Pro Arg Phe Tyr Val Trp Gln His Tyr Trp Glu Arg Ala Glu Pro His
        195                 200                 205

Arg Gly Tyr His His Ile Glu Gly Pro Pro Phe Leu Leu Ile Asp Gly
    210                 215                 220

Pro Arg Cys Val Phe Glu Arg Gly Gln Asn Lys Val Val Gly Gln Gly
225                 230                 235                 240

Arg Ile Thr Leu Asn Leu Ile Tyr Gly Lys Met Gly Leu Pro Arg Asp
                245                 250                 255

Ile Phe Phe Asp Leu Tyr Gly Asn Ala Glu Ile Pro Thr Leu Gly Ala
            260                 265                 270

Val Leu His Ala Asn Phe Ser Tyr Gly Pro Leu Leu Pro Asp Asn Gln
        275                 280                 285

Ala Glu Ala Met
    290

<210> SEQ ID NO 68
<211> LENGTH: 150
<212> TYPE: PRT
<213> ORGANISM: Salmonella typhi

<400> SEQUENCE: 68

Met Thr Asp Asn Asn Thr Ala Leu Lys Lys Ala Gly Leu Lys Val Thr
1               5                   10                  15

Leu Pro Arg Leu Lys Ile Leu Glu Val Leu Gln Glu Pro Asp Asn His
            20                  25                  30

His Val Ser Ala Glu Asp Leu Tyr Lys Arg Leu Ile Asp Met Gly Glu
        35                  40                  45

Glu Ile Gly Leu Ala Thr Val Tyr Arg Val Leu Asn Gln Phe Asp Asp
    50                  55                  60

Ala Gly Ile Val Thr Arg His Asn Phe Glu Gly Gly Lys Ser Val Phe
65                  70                  75                  80

Glu Leu Thr Gln Gln His His His Asp His Leu Ile Cys Leu Asp Cys
                85                  90                  95

Gly Lys Val Ile Glu Phe Ser Asp Ser Ile Glu Ala Arg Gln Arg
            100                 105                 110

Glu Ile Ala Ala Lys His Gly Ile Arg Leu Thr Asn His Ser Leu Tyr
        115                 120                 125

Leu Tyr Gly His Cys Ala Glu Gly Asp Cys Arg Glu Asp Glu His Ala
    130                 135                 140

His Asp Asp Ala Thr Lys
145                 150

<210> SEQ ID NO 69
<211> LENGTH: 3180
<212> TYPE: DNA
<213> ORGANISM: Salmonella typhimurium

<400> SEQUENCE: 69
gcaagcgtga ttggggttga gggcgttccg gcgctggtag aaaaaggccg tgaaaacgcc      60
atccgcaatg gtttacataa tgtgacattc ttccatgaga acctggagga agatgtcacg     120
aagcagccgt gggcgaaaaa cggctttgac aaagtcttac tcgatcctgc gcgtgcgggg     180

-continued

```
gctacaggag tgatgcgaca tattataaaa ttaaaaccta ttcgcattgt ttatgtatcc      240
tgtaacccgg cgacgctggc gcgcgatagt gaagcgctgg tcaatgcggg atatgaggtt      300
acgcgtttag cgatgctcga catgttcccg cacacaggac atctggaatc aatggttctg      360
ttcgagcgca tgtaatgatt accggcttac cgacttcggt aggcctggtc ccttaaggag      420
aggacgatgg tcgcggtaag aagtgcacat attaataaag ctggtgaatt tgatccgaag      480
aagtggatcg caagcctggg aatttccagc cagcagtcgt gtgagcgctt agccgaaacc      540
tgggcgtatt gcctgcaaca gacacaagga catccggatg cggatctgtt gctgtggcgt      600
ggcgtggaga tggtagaaat tctttccacg ctgagtatgg atatcgacac gctgcgggcg      660
gcgctactgt tccctctggc cgacgccaac gtagtcagcg aagatgtact gcgcgaaagc      720
gtcggcaaat ctatcgttac cctgattcat ggcgtgcgcg atatggcggc gatccgtcag      780
ctaaacgcca ctcataacga ctctgtttct tcggagcagg ttgataacgt ccgtcgaatg      840
ttattggcga tggtggatga tttccgctgc gtggtgatca aactggccga gcgaatcgct      900
catttgcgcg aagtgaaaga ggcgccggaa gatgagcgcg tgctggcggc gaagaatgt       960 accaacatct atgcgccgct cgccaatcgt ctgggcatcg gcaactgaa gtgggaactg      1020 gaagactact gtttccgcta cctgcatccg gcggaataca aacgcatcgc caaactgctg      1080
catgagcgcc gtctcgatcg cgaacattac atcgaagagt ttgttggaca tctgcgcgcc      1140
gaaatgaaaa acgaaggcgt gcaggcggag gtctacggac gaccaaaaca tatttatagc      1200
atctggcgca aaatgcagaa aaagcatctg gcgtttgatg aactctttga cgtgcgcgcc      1260
gtgcgtattg tcgctgaacg tctgcaggac tgctacgccg cgttgggat agtgcatacg       1320 cactatcgtc acctgccgga tgaattcgat gattatgtcg ctaacccgaa accgaacggt      1380
taccagtcta tccacaccgt ggtcctggga ccgggcggta aaaccgttga gatccagatc      1440
cgtaccaaac agatgcatga agacgccgaa ctgggcgtgg cggcacactg gaagtataaa      1500
gaaggcgccg cgtccggcgg cgtgcgctcc ggtcatgaag acagaattgc gtggctgcgt      1560
aagctgatcg cctggcagga agagatggcc gattccggcg aaatgctgga tgaagtgcgc      1620
agccaggtgt tgacgatcg ggtctacgtt tttacgccaa aaggcgacgt ggttgacttg       1680
cctgccggat ctacgccgct cgatttgct taccacatcc acagcgatgt tgggcaccgc       1740
tgcattggcg ctaaaatcgg cggccgtatt gtgccattca cctatcagtt gcagatgggt      1800
gatcaaattg aaattatcac tcagaagcag ccgaatccca gccgcgactg gctgaatcca      1860
aacctgggct atgtgacgac cagccgcgga cgctcgaaaa ttcacgcctg gttccgcaag      1920
caggatcgtg acaaaaatat ccaggctgga cggcagatcc tcgacgatga gctggcgcat      1980
ttggggatta gcctgaaaga ggccgaaaaa catctgctgc cgcgctacaa ctttaatgag      2040
ctggaagagt tgctggcggc gataggcggc ggcgatatcc gtcttaatca gatggtgaat      2100
ttcctgcaat cacagttcaa taagccgagt gcagaggagc aggatgcagc ggcgctgaaa      2160
cagcttcagc aaaaaacata cgcgccgcaa aatcgtcgta agacgacgg gcgcgtggtg       2220 gtagaaggcg tgggtaattt gatgcaccac atcgcccgct gctgccagcc gattccgggg      2280
gatgaaattg tcggcttcat tactcaaggg cgagggattt ccgtgcaccg gccgactgc       2340 gaacagctgg cggaactgcg ctcccatgcg ccggagcgga tcgtagaggc ggtatgggc       2400 gagagctact cggcgggata ttcgctggtg gtgcgcgtcc aggccaacga tcgcagcggc      2460
ttgctacgcg atatcaccac cattctggct aacgaaaaag tcaacgtgct gggcgtcgcc      2520
agccgcagcg acattaaaca gcagatcgcc accattgata tgaccatcga gatctacaac      2580
```

-continued

```
ctgcaggtgc tgggccgggt gctcggtaag ctgaaccagg tgccggatgt gattgatgca    2640
cggcgactgc acgggggta  accccagac  agtaatcatg tagcggcttt gctactcgtt    2700
cagcaaagcc gcattagcaa ccccataagc atgagatatg gggtatgttt ttgacgtaca    2760
tttcatttcc ggtgtactct tatgtaagat ttatacttac agtggaggct gttatggcca    2820
gaacaatgac cgttgatctt ggcgatgaac tgcgcgagtt tattgaatcg ctcatagaat    2880
caggtgatta cagaacacaa agtgaagtga tcagagagtc tcttcgtctg ctgagggaaa    2940
aacaggccga gtcacgactt caggcgttac gtgaacttct ggctgaaggt ctgaacagcg    3000
gagagccgca ggcctgggaa aaggatgcct ttttacggaa ggtcaaaaca gggatgatca    3060
aacccgatga gaatggtaaa attaacgcca aaggccagtg aagatctgga aaatatctgg    3120
cattacggct ggcagcattt tggcgaaata caggccgatc gatatattaa tcatctatca    3180
```

<210> SEQ ID NO 70
<211> LENGTH: 744
<212> TYPE: PRT
<213> ORGANISM: Salmonella typhimurium

<400> SEQUENCE: 70

```
Met Val Ala Val Arg Ser Ala His Ile Asn Lys Ala Gly Glu Phe Asp
1               5                   10                  15

Pro Lys Lys Trp Ile Ala Ser Leu Gly Ile Ser Ser Gln Gln Ser Cys
            20                  25                  30

Glu Arg Leu Ala Glu Thr Trp Ala Tyr Cys Leu Gln Gln Thr Gln Gly
        35                  40                  45

His Pro Asp Ala Asp Leu Leu Leu Trp Arg Gly Val Glu Met Val Glu
    50                  55                  60

Ile Leu Ser Thr Leu Ser Met Asp Ile Asp Thr Leu Arg Ala Ala Leu
65                  70                  75                  80

Leu Phe Pro Leu Ala Asp Ala Asn Val Val Ser Glu Asp Val Leu Arg
                85                  90                  95

Glu Ser Val Gly Lys Ser Ile Val Thr Leu Ile His Gly Val Arg Asp
            100                 105                 110

Met Ala Ala Ile Arg Gln Leu Asn Ala Thr His Asn Asp Ser Val Ser
        115                 120                 125

Ser Glu Gln Val Asp Asn Val Arg Arg Met Leu Leu Ala Met Val Asp
    130                 135                 140

Asp Phe Arg Cys Val Val Ile Lys Leu Ala Glu Arg Ile Ala His Leu
145                 150                 155                 160

Arg Glu Val Lys Glu Ala Pro Glu Asp Glu Arg Val Leu Ala Ala Lys
                165                 170                 175

Glu Cys Thr Asn Ile Tyr Ala Pro Leu Ala Asn Arg Leu Gly Ile Gly
            180                 185                 190

Gln Leu Lys Trp Glu Leu Glu Asp Tyr Cys Phe Arg Tyr Leu His Pro
        195                 200                 205

Ala Glu Tyr Lys Arg Ile Ala Lys Leu Leu His Glu Arg Arg Leu Asp
    210                 215                 220

Arg Glu His Tyr Ile Glu Glu Phe Val Gly His Leu Arg Ala Glu Met
225                 230                 235                 240

Lys Asn Glu Gly Val Gln Ala Glu Val Tyr Gly Arg Pro Lys His Ile
                245                 250                 255

Tyr Ser Ile Trp Arg Lys Met Gln Lys Lys His Leu Ala Phe Asp Glu
            260                 265                 270
```

```
Leu Phe Asp Val Arg Ala Val Arg Ile Val Ala Glu Arg Leu Gln Asp
            275                 280                 285

Cys Tyr Ala Ala Leu Gly Ile Val His Thr His Tyr Arg His Leu Pro
290                 295                 300

Asp Glu Phe Asp Asp Tyr Val Ala Asn Pro Lys Pro Asn Gly Tyr Gln
305                 310                 315                 320

Ser Ile His Thr Val Val Leu Gly Pro Gly Lys Thr Val Glu Ile
            325                 330                 335

Gln Ile Arg Thr Lys Gln Met His Glu Asp Ala Glu Leu Gly Val Ala
            340                 345                 350

Ala His Trp Lys Tyr Lys Glu Gly Ala Ala Ser Gly Gly Val Arg Ser
            355                 360                 365

Gly His Glu Asp Arg Ile Ala Trp Leu Arg Lys Leu Ile Ala Trp Gln
370                 375                 380

Glu Glu Met Ala Asp Ser Gly Glu Met Leu Asp Glu Val Arg Ser Gln
385                 390                 395                 400

Val Phe Asp Asp Arg Val Tyr Val Phe Thr Pro Lys Gly Asp Val Val
                405                 410                 415

Asp Leu Pro Ala Gly Ser Thr Pro Leu Asp Phe Ala Tyr His Ile His
            420                 425                 430

Ser Asp Val Gly His Arg Cys Ile Gly Ala Lys Ile Gly Arg Ile
            435                 440                 445

Val Pro Phe Thr Tyr Gln Leu Gln Met Gly Asp Gln Ile Glu Ile Ile
            450                 455                 460

Thr Gln Lys Gln Pro Asn Pro Ser Arg Asp Trp Leu Asn Pro Asn Leu
465                 470                 475                 480

Gly Tyr Val Thr Thr Ser Arg Gly Arg Ser Lys Ile His Ala Trp Phe
            485                 490                 495

Arg Lys Gln Asp Arg Asp Lys Asn Ile Gln Ala Gly Arg Gln Ile Leu
            500                 505                 510

Asp Asp Glu Leu Ala His Leu Gly Ile Ser Leu Lys Glu Ala Glu Lys
            515                 520                 525

His Leu Leu Pro Arg Tyr Asn Phe Asn Glu Leu Glu Glu Leu Leu Ala
            530                 535                 540

Ala Ile Gly Gly Gly Asp Ile Arg Leu Asn Gln Met Val Asn Phe Leu
545                 550                 555                 560

Gln Ser Gln Phe Asn Lys Pro Ser Ala Glu Glu Gln Asp Ala Ala Ala
                565                 570                 575

Leu Lys Gln Leu Gln Gln Lys Thr Tyr Ala Pro Gln Asn Arg Arg Lys
            580                 585                 590

Asp Asp Gly Arg Val Val Glu Gly Val Gly Asn Leu Met His His
            595                 600                 605

Ile Ala Arg Cys Cys Gln Pro Ile Pro Gly Asp Glu Ile Val Gly Phe
610                 615                 620

Ile Thr Gln Gly Arg Gly Ile Ser Val His Arg Ala Asp Cys Glu Gln
625                 630                 635                 640

Leu Ala Glu Leu Arg Ser His Ala Pro Glu Arg Ile Val Glu Ala Val
                645                 650                 655

Trp Gly Glu Ser Tyr Ser Ala Gly Tyr Ser Leu Val Val Arg Val Gln
            660                 665                 670

Ala Asn Asp Arg Ser Gly Leu Leu Arg Asp Ile Thr Thr Ile Leu Ala
            675                 680                 685
```

Asn Glu Lys Val Asn Val Leu Gly Val Ala Ser Arg Ser Asp Ile Lys
    690                 695                 700
Gln Gln Ile Ala Thr Ile Asp Met Thr Ile Glu Ile Tyr Asn Leu Gln
705                 710                 715                 720
Val Leu Gly Arg Val Leu Gly Lys Leu Asn Gln Val Pro Asp Val Ile
            725                 730                 735
Asp Ala Arg Arg Leu His Gly Gly
            740

<210> SEQ ID NO 71
<211> LENGTH: 1620
<212> TYPE: DNA
<213> ORGANISM: Salmonella typhimurium

<400> SEQUENCE: 71

| | | | | | |
|---|---|---|---|---|---|
| gagctcgagg | gcgttccggc | gctggtagaa | aaaggccgtg | aaaacgccat | ccgcaatggt | 60 |
| ttacataatg | tgacattctt | ccatgagaac | ctggaggaag | atgtcacgaa | gcagccgtgg | 120 |
| gcgaaaaacg | gctttgacaa | agtcttactc | gatcctgcgc | gtgcggggc | tacaggagtg | 180 |
| atgcgacata | ttataaaatt | aaaacctatt | cgcattgttt | atgtatcctg | taacccggcg | 240 |
| acgctggcgc | gcgatagtga | agcgctggtc | aatgcgggat | atgaggttac | gcgtttagcg | 300 |
| atgctcgaca | tgttcccgca | cacaggacat | ctggaatcaa | tggttctgtt | cgagcgcatg | 360 |
| taatgattac | cggcttaccg | acttcggtag | gcctggtccc | ttagatcttt | tattattcta | 420 |
| tcctagaatt | gtgataatat | attcacaatt | ctaggagttg | taaactgctt | ttatttatct | 480 |
| agatcactgc | ccgcttttcca | gacgggaaac | ctgacgtgcc | agctgcatta | atgaatcggc | 540 |
| caacgcgcgc | ggagaggcgg | tttgcgtatt | cggcgccagg | gtggttttac | gtttcaccag | 600 |
| tgagaccgga | acagctgat | tgcccttcac | cgcctggccc | tgagagagtt | gcagcaagcg | 660 |
| gtccacgctg | gtttgcccca | gcaggcgaaa | atcctgtttg | atggtggtta | acggcgggat | 720 |
| ataacatgag | ctgtcttcgg | tatcgtcgta | acccactacc | gagatatccg | caccaacgcg | 780 |
| cagcccggac | tcggtaatgg | cgcgcattgc | gcccagcgcc | atctgatcgt | tggcaaccag | 840 |
| catcgcagtc | ggaacgatgc | cctcattcag | catttgcatg | gtttgttgaa | aaccggacat | 900 |
| ggcactccag | tcgccttcac | gttccgcgat | cggctgaatt | tgattgcgag | tgagatattt | 960 |
| atgccagcca | gccagacgca | gacgcgccga | gacagaactt | aatgggcccg | ctaacagcgc | 1020 |
| gatttgctgg | tgacccaatg | cgaccagatg | ctccacgccc | agacgcgtac | cgtcttcatg | 1080 |
| ggagaaaata | atactgttga | tcggtgtctg | gtcagagaca | tcaagaaata | acgccggaac | 1140 |
| attagtgcag | gcagcttcca | cagcaatggc | atcctggtca | tccagcggat | agttaatgat | 1200 |
| cagcccactg | acgcgttgcg | cgagaagatt | gtgcaccgcc | gctttacagg | cttcgacgcc | 1260 |
| gctacgttct | accatcgaca | ccaccacgct | ggcacccagt | tgatcggcgc | gagatttaat | 1320 |
| cgccgcgaca | atttgcgacg | gcgcgtgcag | ggccagactg | gaggtggcaa | cgccaatcag | 1380 |
| caacgactgt | ttgcccgcca | gttgttgtgc | cacgcggttc | ggaatgtaat | tcagctccgc | 1440 |
| catcgccgct | tccacttttt | cacgcgtttt | cgcagaaacg | tggctggcct | ggttcaccac | 1500 |
| gcgggaaacg | gtctgataag | agacaccggc | atactctgcg | acatcgtata | acgttactgg | 1560 |
| tttcatattc | accatcctct | cgaggctagc | ccaaaaaaac | gggtatggag | aaacagtaga | 1620 |

<210> SEQ ID NO 72
<211> LENGTH: 1435
<212> TYPE: DNA
<213> ORGANISM: Salmonella typhimurium

<400> SEQUENCE: 72

```
tctagtgacg ggcgaaaggt ctgcccttg gactgcacgg tcgacgtaat tacttagccg      60
gttgcgcgcg cctctccgcc aaacgcataa gccgcggtcc caccaaaatg caaagtggtc     120
actctggccg ttgtcgacta acgggaagtg gcggaccggg actctctcaa cgtcgttcgc    180
caggtgcgac caaacggggt cgtccgcttt taggacaaac taccaccaat gccgccta      240
tattgtactc gacagaagcc atagcagcat gggtgatgg ctctataggc gtggttgcgc     300
gtcgggcctg agccattacc gcgcgtaacg cgggtcgcgg tagactagca accgttggtc    360
gtagcgtcag ccttgctacg ggagtaagtc gtaaacgtac caaacaactt ttggcctgta   420
ccgtgaggtc agcggaagtg caaggcgcta gccgacttaa actaacgctc actctataaa   480
tacggtcggt cggtctgcgt ctgcgcggct ctgtcttgaa ttacccgggc gattgtcgcg   540
ctaaacgacc actgggttac gctggtctac gaggtgcggg tctgcgcatg cagaagtac    600
cctcttttat tatgacaact agccacagac cagtctctgt agttctttat tgcggccttg   660
taatcacgtc cgtcgaaggt gtcgttaccg taggaccagt aggtcgccta tcaattacta   720
gtcgggtgac tgcgcaacgc gctcttctaa cacgtggcgg cgaaatgtcc gaagctgcgg   780
cgatgcaaga tggtagctgt ggtggtgcga ccgtgggtca actagccgcg ctctaaatta   840
gcggcgctgt taaacgctgc cgcgcacgtc ccggtctgac ctccaccgtt gcggttagtc   900
gttgctgaca acgggcggt caacaacacg gtgcgccaag ccttacatta agtcgaggcg   960
gtagcggcga aggtgaaaaa gtgcgcaaaa gcgtctttgc accgaccgga ccaagtggtg  1020
cgcccttttgc cagactattc tctgtggccg tatgagacgc tgtagcatat tgcaatgacc  1080
aaagtataag tggtaggaga gctccgatcg ggttttttg cccataccctc ttttgtcatct  1140
gagttgcgat aaaaagcgtc aggtaggatc cgctaatctt atggataaaa atgctatggc  1200
atagcaaagt gtgacgccgt gcaaataatc aatgtggact tttctgccgt gattatagac  1260
acttttgtta cgcgtttttg tcatggcttt ggtcccgctt tgttacagaa tgcttttaat  1320
aagcggggtt accggttggg ttagcgagaa gagccagtaa aagacgcagt gacggcaatg  1380
tctgatgcaa tatggacaat tggtttcttc tctgaatggt gggagtatga aaagt        1435
```

<210> SEQ ID NO 73
<211> LENGTH: 360
<212> TYPE: PRT
<213> ORGANISM: Salmonella typhimurium

<400> SEQUENCE: 73

```
Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110
```

```
Asn Leu Leu Ala Gln Arg Val Ser Gly Leu Ile Ile Asn Tyr Pro Leu
            115                 120                 125
Asp Asp Gln Asp Ala Ile Ala Val Glu Ala Ala Cys Thr Asn Val Pro
        130                 135                 140
Ala Leu Phe Leu Asp Val Ser Asp Gln Thr Pro Ile Asn Ser Ile Ile
145                 150                 155                 160
Phe Ser His Glu Asp Gly Thr Arg Leu Gly Val Glu His Leu Val Ala
                165                 170                 175
Leu Gly His Gln Gln Ile Ala Leu Leu Ala Gly Pro Leu Ser Ser Val
            180                 185                 190
Ser Ala Arg Leu Arg Leu Ala Gly Trp His Lys Tyr Leu Thr Arg Asn
        195                 200                 205
Gln Ile Gln Pro Ile Ala Glu Arg Glu Gly Asp Trp Ser Ala Met Ser
    210                 215                 220
Gly Phe Gln Gln Thr Met Gln Met Leu Asn Glu Gly Ile Val Pro Thr
225                 230                 235                 240
Ala Met Leu Val Ala Asn Asp Gln Met Ala Leu Gly Ala Met Arg Ala
                245                 250                 255
Ile Thr Glu Ser Gly Leu Arg Val Gly Ala Asp Ile Ser Val Val Gly
            260                 265                 270
Tyr Asp Asp Thr Glu Asp Ser Ser Cys Tyr Ile Pro Pro Leu Thr Thr
        275                 280                 285
Ile Lys Gln Asp Phe Arg Leu Leu Gly Gln Thr Ser Val Asp Arg Leu
    290                 295                 300
Leu Gln Leu Ser Gln Gly Gln Ala Val Lys Gly Asn Gln Leu Leu Pro
305                 310                 315                 320
Val Ser Leu Val Lys Arg Lys Thr Thr Leu Ala Pro Asn Thr Gln Thr
                325                 330                 335
Ala Ser Pro Arg Ala Leu Ala Asp Ser Leu Met Gln Leu Ala Arg Gln
            340                 345                 350
Val Ser Arg Leu Glu Ser Gly Gln
        355                 360

<210> SEQ ID NO 74
<211> LENGTH: 1385
<212> TYPE: DNA
<213> ORGANISM: Salmonella typhimurium

<400> SEQUENCE: 74
atggctgaag cgcaaaatga tcccctgctg ccgggatact cgtttaacgc ccatctggtg      60
gcgggtttaa cgccgattga ggccaacggt tatctcgatt tttttatcga ccgaccgctg     120
ggaatgaaag gttatattct caatctcacc attcgcggtc agggggtggt gaaaaatcag     180
ggacgagaat ttgtctgccg accgggtgat attttgctgt cccgccagg agagattcat      240 cactacggtc gtcatccgga ggctcgcgaa tggtatcacc agtgggttta ctttcgtccg     300
cgcgcctact ggcatgaatg gcttaactgg ccgtcaatat ttgccaatac gggtttcttt     360
cgcccggatg aagcgcacca gccgcatttc agcgacctgt tgggcaaat cattaacgcc      420 gggcaagggg aagggcgcta tcggagctg ctggcgataa atctgcttga gcaattgtta      480
ctgcggcgca tggaagcgat aacgagtcg ctccatccac cgatggataa tcgggtacgc      540
gaggcttgtc agtacatcag cgatcacctg cagacagca attttgatat cgccagcgtc     600
gcacagcatg tttgcttgtc gccgtcgcgt ctgtcacatc ttttccgcca gcagttaggg     660
```

-continued

```
attagcgtct taagctggcg cgaggaccaa cgcattagtc aggcgaagct gcttttgagc    720 actaccogga tgcctatcgc caccgtcggt cgcaatgttg gttttgacga tcaactctat    780
ttctcgcgag tatttaaaaa atgcaccggg gccagcccga gcgagtttcg tgccggttgt    840
gaagaaaaag tgaatgatgt agccgtcaag ttgtcataat tggtaacgaa tcagacaatt    900
gacggcttga ctcggaattc accccagaca gtaatcatgt agcggctttg ctactcgttc    960
agcaaagccg cattagcaac cccataagca tgagatatgg ggtatgtttt tgacgtacat   1020
ttcatttccg gtgtactctt atgtaagatt tatacttaca gtggaggctg ttatggccag   1080
aacaatgacc gttgatcttg gcgatgaact gcgcgagttt attgaatcgc tcatagaatc   1140
aggtgattac agaacacaaa gtgaagtgat cagagagtct cttcgtctgc tgagggaaaa   1200
acaggccgag tcacgacttc aggcgttacg tgaacttctg gctgaaggtc tgaacagcgg   1260
agagccgcag gcctgggaaa aggatgcctt tttacggaag gtcaaaacag ggatgatcaa   1320
acccgatgag aatggtaaaa ttaacgccaa aggccagtga agatctggaa aatatctggg   1380
gtacc                                                               1385
```

<210> SEQ ID NO 75
<211> LENGTH: 292
<212> TYPE: PRT
<213> ORGANISM: Salmonella typhimurium

<400> SEQUENCE: 75

```
Met Ala Glu Ala Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
            20                  25                  30

Asp Phe Phe Ile Asp Arg Pro Leu Gly Met Lys Gly Tyr Ile Leu Asn
        35                  40                  45

Leu Thr Ile Arg Gly Gln Gly Val Val Lys Asn Gln Gly Arg Glu Phe
    50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro
        115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
        195                 200                 205

Ser Arg Leu Ser His Leu Phe Arg Gln Gln Leu Gly Ile Ser Val Leu
    210                 215                 220

Ser Trp Arg Glu Asp Gln Arg Ile Ser Gln Ala Lys Leu Leu Leu Ser
225                 230                 235                 240
```

```
Thr Thr Arg Met Pro Ile Ala Thr Val Gly Arg Asn Val Gly Phe Asp
            245                 250                 255

Asp Gln Leu Tyr Phe Ser Arg Val Phe Lys Cys Thr Gly Ala Ser
        260                 265                 270

Pro Ser Glu Phe Arg Ala Gly Cys Glu Glu Lys Val Asn Asp Val Ala
        275                 280                 285

Val Lys Leu Ser
        290

<210> SEQ ID NO 76
<211> LENGTH: 3113
<212> TYPE: DNA
<213> ORGANISM: Artificial Sequence
<220> FEATURE:
<223> OTHER INFORMATION: based on Salmonella

<400> SEQUENCE: 76
```

| | | | | | |
|---|---|---|---|---|---|
| ggatcttccg | gaagaccttc | cattctgaaa | tgagctgttg | acaattaatc | atccggctcg | 60 |
| tataatgtgt | ggaattgtga | gcggataaca | atttcacaca | ggaaacagac | catgagtatt | 120 |
| caacatttcc | gtgtcgccct | tattcccttt | tttgcggcat | tttgccttcc | tgttttttgct | 180 |
| cacccagaaa | cgctggtgaa | agtaaaagat | gctgaagaat | cgcaattccc | ggggatccg | 240 |
| tcgacctgca | gccaagctcc | caagcttggc | tgttttggcg | gatgagagaa | gattttcagc | 300 |
| ctgatacaga | ttaaatcaga | acgcagaagc | ggtctgataa | aacagaattt | gcctggcggc | 360 |
| agtagcgcgg | tggtcccacc | tgaccccatg | ccgaactcag | aagtgaaacg | ccgtagcgcc | 420 |
| gatggtagtg | tggggtctcc | ccatgcgaga | gtagggaact | gccaggcatc | aaataaaacg | 480 |
| aaaggctcag | tcgaaagact | gggcctttcg | ttttatctgt | tgtttgtcgg | tgaacgctct | 540 |
| cctgagtagg | acaaatccgc | cgggagcgga | tttgaacgtt | gcgaagcaac | ggcccggagg | 600 |
| gtggcgggca | ggacgcccgc | cataaactgc | caggcatcaa | attaagcaga | aggccatcct | 660 |
| gacggatggc | cttttttgcgt | ttctacaaac | tcttttgttt | attttttctaa | atacattcaa | 720 |
| atatgtatcc | gctcatgaga | caataaccct | gataaatgct | tcaataatgg | aagatcttcc | 780 |
| aacatcacag | gtaaacagaa | acgtcgggtc | gatcgggaaa | ttctttcccg | gacgcgcgg | 840 |
| ggttgggcaa | gccgcaggcg | cgtcagtgct | tttagcgggt | gtcggggcgc | agccatgacc | 900 |
| cagtcacgta | gcgatagcgg | agtgtatact | ggcttaacta | tgcggcatca | gagcagattg | 960 |
| tactgagagt | gcaccatatg | cggtgtgaaa | taccgcacag | atgcgtaagg | agaaaatacc | 1020 |
| gcatcaggcg | ctcttccgct | tcctcgctca | ctgactcgct | gcgctcggtc | gttcggctgc | 1080 |
| ggcgagcggt | atcagctcac | tcaaaggcgg | taatacggtt | atccacagaa | tcaggggata | 1140 |
| acgcaggaaa | gaacatgtga | gcaaaaggcc | agcaaaaggc | caggaaccgt | aaaaaggccg | 1200 |
| cgttgctggc | gtttttccat | aggctccgcc | ccctgacga | gcatcacaaa | aatcgacgct | 1260 |
| caagtcagag | gtggcgaaac | ccgacaggac | tataaagata | ccaggcgttt | ccccctggaa | 1320 |
| gctccctcgt | gcgctctcct | gttccgaccc | tgccgcttac | cggatacctg | tccgcctttc | 1380 |
| tcccttcggg | aagcgtggcg | ctttctcata | gctcacgctg | taggtatctc | agttcggtgt | 1440 |
| aggtcgttcg | ctccaagctg | ggctgtgtgc | acgaaccccc | cgttcagccc | gaccgctgcg | 1500 |
| ccttatccgg | taactatcgt | cttgagtcca | acccggtaag | acacgactta | tcgccactgg | 1560 |
| cagcagccac | tggtaacagg | attagcagag | cgaggtatgt | aggcggtgct | acagagttct | 1620 |
| tgaagtggtg | gcctaactac | ggctacacta | gaaggacagt | atttggtatc | tgcgctctgc | 1680 |
| tgaagccagt | taccttcgga | aaaagagttg | gtagctcttg | atccggcaaa | caaaccaccg | 1740 |

```
ctggtagcgg tggttttttt gtttgcaagc agcagattac gcgcagaaaa aaaggatctc    1800
aagaagatcc tttgatcttt tctacggggt ctgacgctca gtggaacgaa aactcacgtt    1860
aagggatttt ggtcatgaga ttatcaaaaa ggatcttcac ctagatcctt ttaaattaaa    1920
aatgaagttt taaatcaatc taaagtatat atgagtaaac ttggtctgac agtctagact    1980
aggccaactg gcgcagcatt cgacgcagcg gctcggcggc gccccataac aactggtcgc    2040
ctacggtaaa cgccgacaag aactctggcc ccatgttcag cttacgcaga cgaccaaccg    2100
gcgtagtcaa cgtgccggtc accgccgccg gggttaattc gcgcatagtg atatcacgat    2160
cgttcggcac cactttcgcc cacgattat gtgccgccag cagttcttcc accgtcggaa    2220
tggataccct ttttttcagc ttgatggtga acgcctggct gtgacagcgc agcgcgccga    2280
cgcgcacaca caaaccatca accggaatca cagaggcagt attgagaatc ttgttggttt    2340
ccgcctggcc tttccactct tcgcggctct ggccgttatc gagctgtttg tcgatccagg    2400
ggatcaggct tcccgccagc ggtacgccaa agttatcaac cggcagctcg ccgctgcggg    2460
tcaatgccgt aactttgcgt tcaatatcaa gaattgcgga agacggcgtc gccagttcat    2520
cggcgacatg gccatacaac tgacccatct gggttaacag ctcgcgcata tggcgcgcgc    2580
cgccgccgga ggcggcctga taggtcgcga cggataccca gtcaacgaga ttatgggcaa    2640
agagaccgcc cagcgacatc aacatcaggc taacggtaca gttaccgccc acaaaggtct    2700
tcacgccatt gttcaggccg tcggtaatca cgtcctggtt gaccgggtcg agaataataa    2760
tggcatcatc tttcatgcgc agcgtagaag ccgcatcaat ccagtaaccc tgccatccgc    2820
tttcgcgcag ctttggataa atttcgttgg tataatcgcc gccctggcag gtcacgatga    2880
tatcgagcgc ttttagcgca tccagatcaa aagcgtcctg tagcgtgccg gtggaggtgt    2940
cgccgaaggt gggcgccgcc tgtccaaact gggaggtaga aaagaaaaca gggcgaatag    3000
cgtcgaaatc gcgctcctct accatgcgtt gcatgagaac agagccgacc attccgcgcc    3060
agccgataaa accaacattt ttcatagcgt ttttttcctg caaagagatg tgc           3113
```

<210> SEQ ID NO 77
<211> LENGTH: 3927
<212> TYPE: DNA
<213> ORGANISM: Artificial Sequence
<220> FEATURE:
<223> OTHER INFORMATION: based on Salmonella

<400> SEQUENCE: 77

```
ggatcttccg gaagaccttc cattctgaaa tgagctgttg acaattaatc atccggctcg     60
tataatgtgt ggaattgtga gcggataaca atttcacaca ggaaacagac catgagtatt    120
caacatttcc gtgtcgccct tattcccttt tttgcggcat tttgccttcc tgttttttgct  180 cacccagaaa cgctggtgaa agtaaaagat gctgaagaat tctctccggt agccagtcag    240
tctaaagctg agaagactta tgatgcagcg aagaaagatg ctaagaatgc taaaaaagca    300
gtagaagatg ctcaaaaggc tttagatgat gcaaagctg ctcagaaaaa atatgacgag    360
gatcagaaga aaactgagga gaagccgcg ctggaaaaag cagcgtctga agagatggat    420
aaggcagtgg cagcagttca acaagcgtat ctggcctatc aacaagctac agacaaagcc    480
gcaaaagacg cagcagataa gatgatcgat gaagctaaga acgcgaaga agaggcaaaa    540 actaaattta atactgttcg tgcaatggta gttcctgagc cagagcagtt ggcggagact    600
aagaaaaaat cagaagaagc taaacaaaaa gcaccagaac ttactaaaaa actggaagaa    660
```

```
gctaaagcaa aattagaaga ggctgagaaa aaagctactg aagccaaaca aaaagtggat    720
gctgaagaag tcgctcctca agctaaaatc gctgaattgg aaaatcaagt tcatcgtctg    780
gaacaagagc tcaaagagat tgatgagtct gaatcagaag attatgctaa agaaggtttc    840
cgtgctcctc ttcaatctaa attggatgcc aaaaaagcta actgtcaaa acttgaagag    900 ttaagtgata agattgatga gttagacgct gaaattgcaa aacttgaaga tcaacttaaa    960
gctgctgaag aaaacaataa tgtagaagac tactttaaag aaggtttaga gaaaactatt   1020
gctgctaaaa aagctgaatt agaaaaaact gaagctgacc ttaagaaagc ataataagct   1080
tggctgtttt ggcggatgag agaagatttt cagcctgata cagattaaat cagaacgcag   1140
aagcggtctg ataaaacaga atttgcctgg cggcagtagc gcggtggtcc cacctgaccc   1200
catgccgaac tcagaagtga aacgccgtag cgccgatggt agtgtggggt ctccccatgc   1260
gagagtaggg aactgccagg catcaaataa acgaaaggc tcagtcgaaa gactgggcct   1320
ttcgttttat ctgttgtttg tcggtgaacg ctctcctgag taggacaaat ccgccgggag   1380
cggatttgaa cgttgcgaag caacggcccg gagggtggcg gcaggacgc cgccataaa   1440 ctgccaggca tcaaattaag cagaaggcca tcctgacgga tggccttttt gcgtttctac   1500
aaactctttt gtttattttt ctaaatacat tcaaatatgt atccgctcat gagacaataa   1560
ccctgataaa tgcttcaata atggaagatc ttccaacatc acaggtaaac agaaacgtcg   1620
ggtcgatcgg gaaattcttt ccggacggc gcggggttgg gcaagccgca ggcgcgtcag   1680
tgcttttagc gggtgtcggg gcgcagccat gacccagtca cgtagcgata gcggagtgta   1740
tactggctta actatgcggc atcagagcag attgtactga gagtgcacca tatgcggtgt   1800
gaaataccgc acagatgcgt aaggagaaaa taccgcatca ggcgctcttc cgcttcctcg   1860
ctcactgact cgctgcgctc ggtcgttcgg ctgcggcgag cggtatcagc tcactcaaag   1920
gcggtaatac ggttatccac agaatcaggg gataacgcag gaaagaacat gtgagcaaaa   1980
ggccagcaaa aggccaggaa ccgtaaaaag gccgcgttgc tggcgttttt ccataggctc   2040 cgccccctg acgagcatca caaaaatcga cgctcaagtc agaggtggcg aaacccgaca   2100
ggactataaa gataccaggc gtttccccct ggaagctccc tcgtgcgctc tcctgttccg   2160
accctgccgc ttaccggata cctgtccgcc tttctccctt cgggaagcgt ggcgctttct   2220
catagctcac gctgtaggta tctcagttcg gtgtaggtcg ttcgctccaa gctgggctgt   2280
gtgcacgaac cccccgttca gcccgaccgc tgcgccttat ccggtaacta tcgtcttgag   2340
tccaacccgg taagacacga cttatcgcca ctggcagcag ccactggtaa caggattagc   2400
agagcgaggt atgtaggcgg tgctacagag ttcttgaagt ggtggcctaa ctacggctac   2460
actagaagga cagtatttgg tatctgcgct ctgctgaagc cagttacctt cggaaaaaga   2520
gttggtagct cttgatccgg caaacaaacc accgctggta gcggtggttt ttttgtttgc   2580
aagcagcaga ttacgcgcag aaaaaaagga tctcaagaag atcctttgat cttttctacg   2640
gggtctgacg ctcagtggaa cgaaaactca cgttaaggga ttttggtcat gagattatca   2700
aaaaggatct tcacctagat ccttttaaat taaaaatgaa gttttaaatc aatctaaagt   2760
atatatgagt aaacttggtc tgacagtcta gactaggcca actggcgcag cattcgacgc   2820
agcggctcgg cggcgcccca taacaactgg tcgcctacgg taaacgccga caagaactct   2880
ggccccatgt tcagcttacg cagacgacca accggcgtag tcaacgtgcc ggtcaccgcc   2940 gccgggtta attcgcgcat agtgatatca cgatcgttcg gcaccacttt cgcccacgga   3000
ttatgtgccg ccagcagttc ttccaccgtc ggaatggata cctctttttt cagcttgatg   3060
```

```
gtgaacgcct ggctgtgaca gcgcagcgcg ccgacgcgca cacacaaacc atcaaccgga    3120
atcacagagg cagtattgag aatcttgttg gtttccgcct ggcctttcca ctcttcgcgg    3180
ctctggccgt tatcgagctg tttgtcgatc caggggatca ggcttccgc cagcggtacg    3240 ccaaagttat caaccggcag ctcgccgctg cgggtcaatg ccgtaacttt gcgttcaata    3300
tcaagaattg cggaagacgg cgtcgccagt tcatcggcga catggccata caactgaccc    3360
atctgggtta acagctcgcg catatggcgc gcgccgccgc cggaggcggc ctgataggtc    3420
gcgacggata cccagtcaac gagattatgg gcaaagagac cgcccagcga catcaacatc    3480
aggctaacgg tacagttacc gcccacaaag gtcttcacgc cattgttcag gccgtcggta    3540
atcacgtcct ggttgaccgg gtcgagaata ataatggcat catctttcat gcgcagcgta    3600
gaagccgcat caatccagta accctgccat ccgctttcgc gcagctttgg ataaatttcg    3660
ttggtataat cgccgccctg gcaggtcacg atgatatcga gcgcttttag cgcatccaga    3720
tcaaaagcgt cctgtagcgt gccggtggag gtgtcgccga aggtgggcgc cgcctgtcca    3780
aactgggagg tagaaaagaa acagggcga atagcgtcga aatcgcgctc ctctaccatg    3840
cgttgcatga aacagagcc gaccattccg cgccagccga taaaaccaac attttcata    3900 gcgtttttt cctgcaaaga gatgtgc                                        3927
```

<210> SEQ ID NO 78
<211> LENGTH: 320
<212> TYPE: PRT
<213> ORGANISM: Streptococcus pneumoniae

<400> SEQUENCE: 78

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Glu Phe Ser Pro Val Ala Ser Gln Ser Lys Ala Glu Lys
        35                  40                  45

Asp Tyr Asp Ala Ala Lys Lys Asp Ala Lys Asn Ala Lys Lys Ala Val
    50                  55                  60

Glu Asp Ala Gln Lys Ala Leu Asp Asp Ala Lys Ala Ala Gln Lys Lys
65                  70                  75                  80

Tyr Asp Glu Asp Gln Lys Lys Thr Glu Glu Lys Ala Ala Leu Glu Lys
                85                  90                  95

Ala Ala Ser Glu Glu Met Asp Lys Ala Val Ala Ala Val Gln Gln Ala
            100                 105                 110

Tyr Leu Ala Tyr Gln Gln Ala Thr Asp Lys Ala Ala Lys Asp Ala Ala
        115                 120                 125

Asp Lys Met Ile Asp Glu Ala Lys Lys Arg Glu Glu Ala Lys Thr
    130                 135                 140

Lys Phe Asn Thr Val Arg Ala Met Val Val Pro Glu Pro Glu Gln Leu
145                 150                 155                 160

Ala Glu Thr Lys Lys Lys Ser Glu Glu Ala Lys Gln Lys Ala Pro Glu
                165                 170                 175

Leu Thr Lys Lys Leu Glu Glu Ala Lys Ala Lys Leu Glu Glu Ala Glu
            180                 185                 190

Lys Lys Ala Thr Glu Ala Lys Gln Lys Val Asp Ala Glu Glu Val Ala
        195                 200                 205

Pro Gln Ala Lys Ile Ala Glu Leu Glu Asn Gln Val His Arg Leu Glu
```

```
                  210                 215                 220

Gln Glu Leu Lys Glu Ile Asp Glu Ser Glu Ser Asp Tyr Ala Lys
225                 230                 235                 240

Glu Gly Phe Arg Ala Pro Leu Gln Ser Lys Leu Asp Ala Lys Lys Ala
                245                 250                 255

Lys Leu Ser Lys Leu Glu Glu Leu Ser Asp Lys Ile Asp Glu Leu Asp
                260                 265                 270

Ala Glu Ile Ala Lys Leu Glu Asp Gln Leu Lys Ala Ala Glu Glu Asn
                275                 280                 285

Asn Asn Val Glu Asp Tyr Phe Lys Glu Gly Leu Glu Lys Thr Ile Ala
        290                 295                 300

Ala Lys Lys Ala Glu Leu Glu Lys Thr Glu Ala Asp Leu Lys Lys Ala
305                 310                 315                 320
```

<210> SEQ ID NO 79
<211> LENGTH: 963
<212> TYPE: DNA
<213> ORGANISM: Streptococcus pneumoniae

<400> SEQUENCE: 79

```
atgagtattc aacatttccg tgtcgccctt attcccttttt tgcggcatt ttgccttcct    60
gtttttgctc acccagaaac gctggtgaaa gtaaagatg ctgaagaatt ctctccggta   120
gccagtcagt ctaaagctga aaagactat gatgcagcga agaaagatgc taagaatgct   180
aaaaaagcag tagaagatgc tcaaaaggct ttagatgatg caaaagctgc tcagaaaaaa   240
tatgacgagg atcagaagaa aactgaggag aaagccgcgc tggaaaaagc agcgtctgaa   300
gagatggata aggcagtggc agcagttcaa caagcgtatc tggcctatca acaagctaca   360
gacaaagccg caaaagacgc agcagataag atgatcgatg aagctaagaa acgcgaagaa   420
gaggcaaaaa ctaaatttaa tactgttcgt gcaatggtag ttcctgagcc agagcagttg   480
gcggagacta gaaaaaaatc agaagaagct aaacaaaaag caccagaact tactaaaaaa   540
ctggaagaag ctaaagcaaa attagaagag gctgagaaaa aagctactga agccaaacaa   600
aaagtggatg ctgaagaagt cgctcctcaa gctaaaatcg ctgaattgga aaatcaagtt   660
catcgtctgg aacaagagct caaagagatt gatgagtctg aatcagaaga ttatgctaaa   720
gaaggtttcc gtgctcctct tcaatctaaa ttggatgcca aaaaagctaa actgtcaaaa   780
cttgaagagt taagtgataa gattgatgag ttagacgctg aaattgcaaa acttgaagat   840
caacttaaag ctgctgaaga aaacaataat gtagaagact actttaaaga aggtttagag   900
aaaactattg ctgctaaaaa agctgaatta gaaaaaactg aagctgacct taagaaagca   960
taa                                                                 963
```

<210> SEQ ID NO 80
<211> LENGTH: 963
<212> TYPE: DNA
<213> ORGANISM: Streptococcus pneumoniae

<400> SEQUENCE: 80

```
atgagtattc aacatttccg tgtcgccctt attcccttttt tgcggcatt ttgccttcct    60
gtttttgctc acccagaaac gctggtgaaa gtaaagatg ctgaagaatt ctctccggta   120
gccagtcagt ctaaagctga aaagactat gatgcagcga agaaagatgc taagaatgct   180
aaaaaagcag tagaagatgc tcaaaaggct ttagatgatg caaaagctgc tcagaaaaaa   240
tatgacgagg atcagaagaa aactgaggag aaagccgcgc tggaaaaagc agcgtctgaa   300
```

```
gagatggata aggcagtggc agcagttcaa caagcgtatc tggcctatca acaagctaca    360
gacaaagccg caaagacgc agcagataag atgatcgatg aagctaagaa acgcgaagaa    420
gaggcaaaaa ctaaatttaa tactgttcgt gcaatggtag ttcctgagcc agagcagttg    480
gcggagacta agaaaaaatc agaagaagct aaacaaaaag caccagaact tactaaaaaa    540
ctggaagaag ctaaagcaaa attagaagag gctgagaaaa aagctactga agccaaacaa    600
aaagtggatg ctgaagaagt cgctcctcaa gctaaaatcg ctgaattgga aaatcaagtt    660
catcgtctgg aacaagagct caaagagatt gatgagtctg aatcagaaga ttatgctaaa    720
gaaggtttcc gtgctcctct tcaatctaaa ttggatgcca aaaagctaa actgtcaaaa    780 cttgaagagt taagtgataa gattgatgag ttagacgctg aaattgcaaa acttgaagat    840
caacttaaag ctgctgaaga aacaataat gtagaagact actttaaaga aggtttagag    900
aaaactattg ctgctaaaaa agctgaatta gaaaaaactg aagctgaccct taagaaagca    960 taa                                                                  963
```

<210> SEQ ID NO 81
<211> LENGTH: 852
<212> TYPE: DNA
<213> ORGANISM: Streptococcus pneumoniae

<400> SEQUENCE: 81

```
tctccggtag ccagtcagtc taaagctgag aaagactatg atgcagcgaa gaaagatgct    60
aagaatgcta aaaagcagt agaagatgct caaaaggctt tagatgatgc aaaagctgct   120
cagaaaaaat atgacgagga tcagaagaaa actgaggaga agccgcgct ggaaaagca   180 gcgtctgaag agatggataa ggcagtggca gcagttcaac aagcgtatct ggcctatcaa   240
caagctacag acaaagccgc aaaagacgca gcagataaga tgatcgatga agctaagaaa   300
cgcgaagaag aggcaaaaac taaatttaat actgttcgtg caatggtagt tcctgagcca   360
gagcagttgg cggagactaa gaaaaaatca gaagaagcta aacaaaaagc accagaactt   420
actaaaaaac tggaagaagc taaagcaaaa ttagaagagg ctgagaaaaa agctactgaa   480
gccaaacaaa aagtggatgc tgaagaagtc gctcctcaag ctaaaatcgc tgaattggaa   540
aatcaagttc atcgtctgga acaagagctc aaagagattg atgagtctga atcagaagat   600
tatgctaaag aaggtttccg tgctcctctt caatctaaat tggatgccaa aaagctaaa   660 ctgtcaaaac ttgaagagtt aagtgataag attgatgagt tagacgctga aattgcaaaa   720
cttgaagatc aacttaaagc tgctgaagaa acaataatg tagaagacta ctttaaagaa   780
ggtttagaga aaactattgc tgctaaaaaa gctgaattag aaaaaactga agctgacctt   840
aagaaagcat aa                                                       852
```

<210> SEQ ID NO 82
<211> LENGTH: 320
<212> TYPE: PRT
<213> ORGANISM: Streptococcus pneumoniae

<400> SEQUENCE: 82

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Glu Phe Ser Pro Val Ala Ser Gln Ser Lys Ala Glu Lys
        35                  40                  45
```

Asp Tyr Asp Ala Ala Lys Lys Asp Ala Lys Asn Ala Lys Lys Ala Val
        50                  55                  60

Glu Asp Ala Gln Lys Ala Leu Asp Asp Ala Lys Ala Ala Gln Lys Lys
65                  70                  75                  80

Tyr Asp Glu Asp Gln Lys Lys Thr Glu Glu Lys Ala Ala Leu Glu Lys
                85                  90                  95

Ala Ala Ser Glu Glu Met Asp Lys Ala Val Ala Val Gln Gln Ala
            100                 105                 110

Tyr Leu Ala Tyr Gln Gln Ala Thr Asp Lys Ala Ala Lys Asp Ala Ala
            115                 120                 125

Asp Lys Met Ile Asp Glu Ala Lys Lys Arg Glu Glu Ala Lys Thr
        130                 135                 140

Lys Phe Asn Thr Val Arg Ala Met Val Val Pro Glu Pro Gln Leu
145                 150                 155                 160

Ala Glu Thr Lys Lys Lys Ser Glu Glu Ala Lys Gln Lys Ala Pro Glu
                165                 170                 175

Leu Thr Lys Lys Leu Glu Glu Ala Lys Ala Lys Leu Glu Glu Ala Glu
            180                 185                 190

Lys Lys Ala Thr Glu Ala Lys Gln Lys Val Asp Ala Glu Glu Val Ala
            195                 200                 205

Pro Gln Ala Lys Ile Ala Glu Leu Glu Asn Gln Val His Arg Leu Glu
        210                 215                 220

Gln Glu Leu Lys Glu Ile Asp Glu Ser Glu Ser Glu Asp Tyr Ala Lys
225                 230                 235                 240

Glu Gly Phe Arg Ala Pro Leu Gln Ser Lys Leu Asp Ala Lys Lys Ala
                245                 250                 255

Lys Leu Ser Lys Leu Glu Glu Leu Ser Asp Lys Ile Asp Glu Leu Asp
            260                 265                 270

Ala Glu Ile Ala Lys Leu Glu Asp Gln Leu Lys Ala Ala Glu Glu Asn
        275                 280                 285

Asn Asn Val Glu Asp Tyr Phe Lys Glu Gly Leu Glu Lys Thr Ile Ala
        290                 295                 300

Ala Lys Lys Ala Glu Leu Glu Lys Thr Glu Ala Asp Leu Lys Lys Ala
305                 310                 315                 320

<210> SEQ ID NO 83
<211> LENGTH: 283
<212> TYPE: PRT
<213> ORGANISM: Streptococcus pneumoniae

<400> SEQUENCE: 83

Ser Pro Val Ala Ser Gln Ser Lys Ala Glu Lys Asp Tyr Asp Ala Ala
1               5                   10                  15

Lys Lys Asp Ala Lys Asn Ala Lys Lys Ala Val Glu Asp Ala Gln Lys
            20                  25                  30

Ala Leu Asp Asp Ala Lys Ala Ala Gln Lys Lys Tyr Asp Glu Asp Gln
        35                  40                  45

Lys Lys Thr Glu Glu Lys Ala Ala Leu Glu Lys Ala Ala Ser Glu Glu
    50                  55                  60

Met Asp Lys Ala Val Ala Val Gln Gln Ala Tyr Leu Ala Tyr Gln
65                  70                  75                  80

Gln Ala Thr Asp Lys Ala Ala Lys Asp Ala Ala Asp Lys Met Ile Asp
                85                  90                  95

Glu Ala Lys Lys Arg Glu Glu Glu Ala Lys Thr Lys Phe Asn Thr Val

```
                100             105             110
Arg Ala Met Val Val Pro Glu Pro Glu Gln Leu Ala Glu Thr Lys Lys
            115             120             125

Lys Ser Glu Glu Ala Lys Gln Lys Ala Pro Glu Leu Thr Lys Lys Leu
            130             135             140

Glu Glu Ala Lys Ala Lys Leu Glu Glu Ala Lys Lys Ala Thr Glu
145             150             155             160

Ala Lys Gln Lys Val Asp Ala Glu Val Ala Pro Gln Ala Lys Ile
                165             170             175

Ala Glu Leu Glu Asn Gln Val His Arg Leu Glu Gln Glu Leu Lys Glu
            180             185             190

Ile Asp Glu Ser Glu Ser Glu Asp Tyr Ala Lys Glu Gly Phe Arg Ala
            195             200             205

Pro Leu Gln Ser Lys Leu Asp Ala Lys Lys Ala Lys Leu Ser Lys Leu
            210             215             220

Glu Glu Leu Ser Asp Lys Ile Asp Glu Leu Asp Ala Glu Ile Ala Lys
225             230             235             240

Leu Glu Asp Gln Leu Lys Ala Ala Glu Glu Asn Asn Asn Val Glu Asp
            245             250             255

Tyr Phe Lys Glu Gly Leu Glu Lys Thr Ile Ala Ala Lys Lys Ala Glu
            260             265             270

Leu Glu Lys Thr Glu Ala Asp Leu Lys Lys Ala
            275             280

<210> SEQ ID NO 84
<211> LENGTH: 297
<212> TYPE: PRT
<213> ORGANISM: Streptococcus pneumoniae

<400> SEQUENCE: 84

His Pro Glu Thr Leu Val Lys Val Lys Asp Ala Glu Glu Phe Ser Pro
1               5               10              15

Val Ala Ser Gln Ser Lys Ala Glu Lys Asp Tyr Asp Ala Ala Lys Lys
            20              25              30

Asp Ala Lys Asn Ala Lys Lys Ala Val Glu Asp Ala Gln Lys Ala Leu
            35              40              45

Asp Asp Ala Lys Ala Ala Gln Lys Lys Tyr Asp Glu Asp Gln Lys Lys
        50              55              60

Thr Glu Glu Lys Ala Ala Leu Glu Lys Ala Ala Ser Glu Glu Met Asp
65              70              75              80

Lys Ala Val Ala Ala Val Gln Gln Ala Tyr Leu Ala Tyr Gln Gln Ala
            85              90              95

Thr Asp Lys Ala Ala Lys Asp Ala Ala Asp Lys Met Ile Asp Glu Ala
            100             105             110

Lys Lys Arg Glu Glu Glu Ala Lys Thr Lys Phe Asn Thr Val Arg Ala
            115             120             125

Met Val Val Pro Glu Pro Glu Gln Leu Ala Glu Thr Lys Lys Lys Ser
            130             135             140

Glu Glu Ala Lys Gln Lys Ala Pro Glu Leu Thr Lys Lys Leu Glu Glu
145             150             155             160

Ala Lys Ala Lys Leu Glu Glu Ala Lys Lys Ala Thr Glu Ala Lys
            165             170             175

Gln Lys Val Asp Ala Glu Val Ala Pro Gln Ala Lys Ile Ala Glu
            180             185             190
```

```
Leu Glu Asn Gln Val His Arg Leu Glu Gln Glu Leu Lys Glu Ile Asp
            195                 200                 205

Glu Ser Glu Ser Glu Asp Tyr Ala Lys Glu Gly Phe Arg Ala Pro Leu
        210                 215                 220

Gln Ser Lys Leu Asp Ala Lys Ala Lys Leu Ser Lys Leu Glu Glu
225                 230                 235                 240

Leu Ser Asp Lys Ile Asp Glu Leu Asp Ala Glu Ile Ala Lys Leu Glu
                245                 250                 255

Asp Gln Leu Lys Ala Ala Glu Glu Asn Asn Val Glu Asp Tyr Phe
            260                 265                 270

Lys Glu Gly Leu Glu Lys Thr Ile Ala Ala Lys Lys Ala Glu Leu Glu
        275                 280                 285

Lys Thr Glu Ala Asp Leu Lys Lys Ala
    290                 295

<210> SEQ ID NO 85
<211> LENGTH: 120
<212> TYPE: DNA
<213> ORGANISM: Salmonella typhi

<400> SEQUENCE: 85
attcatagtt aagtcatctt aaataaactt gactaaagat tcctttagta gataatttaa     60
gtgttcttta atttcggagc gagtctatgg gtacctggat ggagtaagac gatggcaatt    120

<210> SEQ ID NO 86
<211> LENGTH: 120
<212> TYPE: DNA
<213> ORGANISM: Salmonella typhi

<400> SEQUENCE: 86
attcatagtt aaatcatttt aaataaactt gactaaagat tcctttagta gataatttaa     60
ttgtttttta atttcggagc gagtctatgg gtacctggaa ggagtaagac gatgaaaaaa    120

<210> SEQ ID NO 87
<211> LENGTH: 33
<212> TYPE: DNA
<213> ORGANISM: Streptococcus pneumoniae

<400> SEQUENCE: 87
gggggtacct tcggcgacgg aaacatgttc gct                                  33

<210> SEQ ID NO 88
<211> LENGTH: 36
<212> TYPE: DNA
<213> ORGANISM: Streptococcus pneumoniae

<400> SEQUENCE: 88
ggggagctcg ccgcgctggt agttttgata acttaa                               36

<210> SEQ ID NO 89
<211> LENGTH: 28
<212> TYPE: DNA
<213> ORGANISM: Streptococcus pneumoniae

<400> SEQUENCE: 89
tcccccgggc aaaatattgt atcgctgg                                        28

<210> SEQ ID NO 90
<211> LENGTH: 32
<212> TYPE: DNA
```

<213> ORGANISM: Streptococcus pneumoniae

<400> SEQUENCE: 90
gcacgcatgc tcaggcaggc gtaaatcgct ct    32

<210> SEQ ID NO 91
<211> LENGTH: 24
<212> TYPE: DNA
<213> ORGANISM: Streptococcus pneumoniae

<400> SEQUENCE: 91
gactgcatgc atggtgttgg taca    24

<210> SEQ ID NO 92
<211> LENGTH: 22
<212> TYPE: DNA
<213> ORGANISM: Streptococcus pneumoniae

<400> SEQUENCE: 92
cgggatccca tagcggtaga tg    22

<210> SEQ ID NO 93
<211> LENGTH: 23
<212> TYPE: DNA
<213> ORGANISM: Streptococcus pneumoniae

<400> SEQUENCE: 93
acatgcatgc ggacgatcga taa    23

<210> SEQ ID NO 94
<211> LENGTH: 22
<212> TYPE: DNA
<213> ORGANISM: Streptococcus pneumoniae

<400> SEQUENCE: 94
cgggatcctg gtagggaacg ac    22

<210> SEQ ID NO 95
<211> LENGTH: 33
<212> TYPE: DNA
<213> ORGANISM: Streptococcus pneumoniae

<400> SEQUENCE: 95
acatgcatgc ggcatacaca cacctgtata aca    33

<210> SEQ ID NO 96
<211> LENGTH: 31
<212> TYPE: DNA
<213> ORGANISM: Streptococcus pneumoniae

<400> SEQUENCE: 96
ttcccccggg gcagtattgt ctgcgtcagc g    31

<210> SEQ ID NO 97
<211> LENGTH: 35
<212> TYPE: DNA
<213> ORGANISM: Streptococcus pneumoniae

<400> SEQUENCE: 97
acatgcatgc gaacggtatt actgtcagtc acaag    35

<210> SEQ ID NO 98
<211> LENGTH: 33

```
<212> TYPE: DNA
<213> ORGANISM: Streptococcus pneumoniae

<400> SEQUENCE: 98
tcccccgggc agattatttc aaatacgatt agg                            33

<210> SEQ ID NO 99
<211> LENGTH: 22
<212> TYPE: DNA
<213> ORGANISM: Streptococcus pneumoniae

<400> SEQUENCE: 99
gcactgctgt gggttgaaat ag                                        22

<210> SEQ ID NO 100
<211> LENGTH: 20
<212> TYPE: DNA
<213> ORGANISM: Streptococcus pneumoniae

<400> SEQUENCE: 100
cggcgtgagt agaaatatcg                                           20

<210> SEQ ID NO 101
<211> LENGTH: 30
<212> TYPE: DNA
<213> ORGANISM: Streptococcus pneumoniae

<400> SEQUENCE: 101
tgctctagat gtgcatggca atcgcccaac                                30

<210> SEQ ID NO 102
<211> LENGTH: 30
<212> TYPE: DNA
<213> ORGANISM: Streptococcus pneumoniae

<400> SEQUENCE: 102
tcccccgggt atctgcgtcg tcctaccttc                                30

<210> SEQ ID NO 103
<211> LENGTH: 33
<212> TYPE: DNA
<213> ORGANISM: Streptococcus pneumoniae

<400> SEQUENCE: 103
acatgcatgc atctccatcg gactcggcgc ttt                            33

<210> SEQ ID NO 104
<211> LENGTH: 30
<212> TYPE: DNA
<213> ORGANISM: Streptococcus pneumoniae

<400> SEQUENCE: 104
tgcgagctcc agaatatccg ggttgacctg                                30

<210> SEQ ID NO 105
<211> LENGTH: 29
<212> TYPE: DNA
<213> ORGANISM: Streptococcus pneumoniae

<400> SEQUENCE: 105
aggacagatt ccgcatgact gacaacaat                                 29

<210> SEQ ID NO 106
```

```
<211> LENGTH: 29
<212> TYPE: DNA
<213> ORGANISM: Streptococcus pneumoniae

<400> SEQUENCE: 106
aaggcagatt ccgcgtgact gacaacaat                                            29

<210> SEQ ID NO 107
<211> LENGTH: 34
<212> TYPE: DNA
<213> ORGANISM: Streptococcus pneumoniae

<400> SEQUENCE: 107
acatgcatgc tgtgactggg atgacttctt cccg                                      34

<210> SEQ ID NO 108
<211> LENGTH: 31
<212> TYPE: DNA
<213> ORGANISM: Streptococcus pneumoniae

<400> SEQUENCE: 108
tcccccgggc actttccgc aatcaaggca g                                          31

<210> SEQ ID NO 109
<211> LENGTH: 39
<212> TYPE: DNA
<213> ORGANISM: Streptococcus pneumoniae

<400> SEQUENCE: 109
cccaagcttg agctcgaggg cgttccggcg ctggtagaa                                 39

<210> SEQ ID NO 110
<211> LENGTH: 31
<212> TYPE: DNA
<213> ORGANISM: Streptococcus pneumoniae

<400> SEQUENCE: 110
cgggtacccc agatattttc cagatcttca c                                         31

<210> SEQ ID NO 111
<211> LENGTH: 38
<212> TYPE: DNA
<213> ORGANISM: Streptococcus pneumoniae

<400> SEQUENCE: 111
ccgctcgaga ggatggtgaa tatgaaacca gtaacgtt                                  38

<210> SEQ ID NO 112
<211> LENGTH: 34
<212> TYPE: DNA
<213> ORGANISM: Streptococcus pneumoniae

<400> SEQUENCE: 112
agaggtaccc tcgaggctag cccaaaaaaa cggg                                      34

<210> SEQ ID NO 113
<211> LENGTH: 24
<212> TYPE: DNA
<213> ORGANISM: Streptococcus pneumoniae

<400> SEQUENCE: 113
aggactctat atgcttataa tttc                                                 24
```

```
<210> SEQ ID NO 114
<211> LENGTH: 24
<212> TYPE: DNA
<213> ORGANISM: Streptococcus pneumoniae

<400> SEQUENCE: 114
aggactctat gtgcttataa tttc                                          24

<210> SEQ ID NO 115
<211> LENGTH: 24
<212> TYPE: DNA
<213> ORGANISM: Streptococcus pneumoniae

<400> SEQUENCE: 115
aaggctctat gtgcttataa tttc                                          24

<210> SEQ ID NO 116
<211> LENGTH: 31
<212> TYPE: DNA
<213> ORGANISM: Streptococcus pneumoniae

<400> SEQUENCE: 116
cgcgagatct gattatttat cactttggca g                                  31

<210> SEQ ID NO 117
<211> LENGTH: 31
<212> TYPE: DNA
<213> ORGANISM: Streptococcus pneumoniae

<400> SEQUENCE: 117
acgaggagct ccttgcctgt cattaggtta g                                  31

<210> SEQ ID NO 118
<211> LENGTH: 35
<212> TYPE: DNA
<213> ORGANISM: Streptococcus pneumoniae

<400> SEQUENCE: 118
gtgaaggtac caagttcata agaggtgtcg aagtg                              35

<210> SEQ ID NO 119
<211> LENGTH: 35
<212> TYPE: DNA
<213> ORGANISM: Streptococcus pneumoniae

<400> SEQUENCE: 119
cgctgagatc tgtaccgcta tttttacgaa aattc                              35

<210> SEQ ID NO 120
<211> LENGTH: 30
<212> TYPE: DNA
<213> ORGANISM: Streptococcus pneumoniae

<400> SEQUENCE: 120
ccggaattct ctcccgtagc cagtcagtct                                    30

<210> SEQ ID NO 121
<211> LENGTH: 31
<212> TYPE: DNA
<213> ORGANISM: Streptococcus pneumoniae

<400> SEQUENCE: 121
gggaagcttc tattattcta ctattattgt t                                  31
```

```
<210> SEQ ID NO 122
<211> LENGTH: 45
<212> TYPE: DNA
<213> ORGANISM: Streptococcus pneumoniae

<400> SEQUENCE: 122
ccggaattca tcaccatcac catcactctc ccgtagccag tcagt            45

<210> SEQ ID NO 123
<211> LENGTH: 31
<212> TYPE: DNA
<213> ORGANISM: Streptococcus pneumoniae

<400> SEQUENCE: 123
gggaagcttc tattattcta ctattattgt t                           31

<210> SEQ ID NO 124
<211> LENGTH: 30
<212> TYPE: DNA
<213> ORGANISM: Streptococcus pneumoniae

<400> SEQUENCE: 124
tctccggtag ccagtcagtc taaagctgag                             30

<210> SEQ ID NO 125
<211> LENGTH: 76
<212> TYPE: DNA
<213> ORGANISM: Streptococcus pneumoniae

<400> SEQUENCE: 125
ctaattcagc tttttagca gcaatagttt tctctaaacc ttctttaaag tagtcttcta  60
cattattgtt ttcttc                                            76

<210> SEQ ID NO 126
<211> LENGTH: 30
<212> TYPE: DNA
<213> ORGANISM: Streptococcus pneumoniae

<400> SEQUENCE: 126
tctccggtag ccagtcagtc taaagctgag                             30

<210> SEQ ID NO 127
<211> LENGTH: 63
<212> TYPE: DNA
<213> ORGANISM: Streptococcus pneumoniae

<400> SEQUENCE: 127
tgctttctta aggtcagctt cagttttttc taattcagct tttttagcag caatagtttt  60
ctc                                                          63

<210> SEQ ID NO 128
<211> LENGTH: 28
<212> TYPE: DNA
<213> ORGANISM: Streptococcus pneumoniae

<400> SEQUENCE: 128
ggaattctct ccggtagcca gtcagtct                               28

<210> SEQ ID NO 129
<211> LENGTH: 34
<212> TYPE: DNA
<213> ORGANISM: Streptococcus pneumoniae
```

```
<400> SEQUENCE: 129
ttcaagctta ttatgctttc ttaaggtcag cttc                                    34

<210> SEQ ID NO 130
<211> LENGTH: 6204
<212> TYPE: DNA
<213> ORGANISM: Artificial Sequence
<220> FEATURE:
<223> OTHER INFORMATION: based on pneumococcus

<400> SEQUENCE: 130
agcttggctg ttttggcgga tgagagaaga ttttcagcct gatacagatt aaatcagaac        60
gcagaagcgg tctgataaaa cagaatttgc ctggcggcag tagcgcggtg gtcccacctg       120
accccatgcc gaactcagaa gtgaaacgcc gtagcgccga tggtagtgtg gggtctcccc       180
atgcgagagt agggaactgc caggcatcaa ataaaacgaa aggctcagtc gaaagactgg       240
gcctttcgtt ttatctgttg tttgtcggtg aacgctctcc tgagtaggac aaatccgccg       300
ggagcggatt tgaacgttgc gaagcaacgg cccggagggt ggcgggcagg acgcccgcca       360
taaactgcca ggcatcaaat taagcagaag gccatcctga cggatggcct ttttgcgttt       420
ctacaaactc ttttgtttat ttttctaaat acattcaaat atgtatccgc tcatgagaca       480
ataaccctga taaatgcttc aataatggaa gatcttccaa catcacaggt aaacagaaac       540
gtcgggtcga tcgggaaatt cttcccggaa cggcgcgggg ttgggcaagc cgcaggcgcg       600
tcagtgcttt tagcgggtgt cggggcgcag ccatgaccca gtcacgtagc gatagcggag       660
tgtatactgg cttaactatg cggcatcaga gcagattgta ctgagagtgc accatatgcg       720
gtgtgaaata ccgcacagat gcgtaaggag aaaataccgc atcaggcgct cttccgcttc       780
ctcgctcact gactcgctgc gctcggtcgt tcggctgcgg cgagcggtat cagctcactc       840
aaaggcggta atacggttat ccacagaatc aggggataac gcaggaaaga acatgtgagc       900
aaaaggccag caaaaggcca ggaaccgtaa aaaggccgcg ttgctggcgt ttttccatag       960
gctccgcccc cctgacgagc atcacaaaaa tcgacgctca agtcagaggt ggcgaaaccc      1020
gacaggacta taaagatacc aggcgtttcc ccctggaagc tccctcgtgc gctctcctgt      1080
tccgaccctg ccgcttaccg gatacctgtc cgcctttctc ccttcgggaa gcgtggcgct      1140
ttctcatagc tcacgctgta ggtatctcag ttcggtgtag tcgttcgct ccaagctggg      1200
ctgtgtgcac gaacccccg ttcagcccga ccgctgcgcc ttatccggta actatcgtct      1260
tgagtccaac ccggtaagac acgacttatc gccactggca gcagccactg gtaacaggat      1320
tagcagagcg aggtatgtag gcggtgctac agagttcttg aagtggtggc ctaactacgg      1380
ctacactaga aggacagtat ttggtatctg cgctctgctg aagccagtta ccttcggaaa      1440
aagagttggt agctcttgat ccggcaaaca aaccaccgct ggtagcggtg ttttttgt       1500
ttgcaagcag cagattacgc gcagaaaaaa aggatctcaa gaagatcctt tgatcttttc      1560
tacgggtct gacgctcagt ggaacgaaaa ctcacgttaa gggattttgg tcatgagatt      1620
atcaaaaagg atcttcacct agatcctttt aaattaaaaa tgaagtttta aatcaatcta      1680
aagtatatat gagtaaactt ggtctgacag tctagactag ccaactggc gcagcattcg      1740
acgcagcggc tcggcggcgc cccataacaa ctggtcgcct acggtaaacg ccgacaagaa      1800
ctctggcccc atgttcagct tacgcagacg accaaccggc gtagtcaacg tgccggtcac      1860
cgccgccggg gttaattcgc gcatagtgat atcacgatcg ttcggcacca ctttcgccca      1920
```

```
cggattatgt gccgccagca gttcttccac cgtcggaatg gatacctctt tttcagctt    1980 gatggtgaac gcctggctgt gacagcgcag gcgccgacg cgcacacaca aaccatcaac    2040
cggaatcaca gaggcagtat tgagaatctt gttggtttcc gcctggcctt ccactcttc    2100 gcggctctgg ccgttatcga gctgtttgtc gatccagggg atcaggcttc ccgccagcgg    2160
tacgccaaag ttatcaaccg gcagctcgcc gctgcgggtc aatgccgtaa ctttgcgttc    2220
aatatcaaga attgcggaag acggcgtcgc cagttcatcg gcgacatggc catacaactg    2280
acccatctgg gttaacagct cgcgcatatg gcgcgcgccg ccgccggagg cggcctgata    2340
ggtcgcgacg gatacccagt caacgagatt atgggcaaag agaccgccca gcgacatcaa    2400
catcaggcta acggtacagt taccgcccac aaaggtcttc acgccattgt tcaggccgtc    2460
ggtaatcacg tcctggttga ccgggtcgag aataataatg gcatcatctt tcatgcgcag    2520
cgtagaagcc gcatcaatcc agtaaccctg ccatccgctt cgcgcagct ttggataaat    2580 ttcgttggta taatcgccgc cctggcaggt cacgatgata tcgagcgctt ttagcgcatc    2640
cagatcaaaa gcgtcctgta gcgtgccggt ggaggtgtcg ccgaaggtgg gcgccgcctg    2700
tccaaactgg gaggtagaaa agaaaacagg gcgaatagcg tcgaaatcgc gctcctctac    2760
catgcgttgc atgagaacag agccgaccat tccgcgccag ccgataaaac caacattttt    2820
catagcgttt ttttcctgca aagagatgtg cggatcttcc ggaagacctt ccattctgaa    2880
atgagctgtt gacaattaat catccggctc gtataatgtg tggaattgtg agcggataac    2940
aatttcacac aggaaacaga ccatgaaaaa gatttggctg cgctggctg gtatggtttt    3000 agcttttagc gcctcggcag cacagatcag cgacgaattc gaaacgactg atgacaaaat    3060
tgctgctcaa gataataaaa ttagtaactt aacagcacaa caacaagaag cccaaaaaca    3120
agttgaccaa attcaggagc aagtatcagc tattcaagct gagcagtcta acttgcaagc    3180 tgaaatgat agattacaag cagaatctaa gaaactcgag ggtgagatta cagaactttc    3240 taaaacatt gtttctcgta accaatcgtt ggaaaaacaa gctcgtagtg ctcaaacaaa    3300
tggagccgta actagctata tcaataccat tgtaaactca aaatcaatta cagaagctat    3360
ttcacgtgtt gctgcaatga gtgaaatcgt atctgcaaac aacaaaatgt tagaacaaca    3420
aaaggcagat aaaaaagcta tttctgaaaa acaagtagca aataatgatg ctatcaatac    3480
tgtaattgct aatcaacaaa aattggctga tgatgctcaa gcattgacta cgaaacaggc    3540
agaactaaaa gctgctgaat taagtcttgc tgctgagaaa gcgacagctg aaggggaaaa    3600
agcaagtcta ttagagcaaa aagcagcagc tgaggcagag gctcgtgcag ctgcggtagc    3660
agaagcagct tataaagaaa aacgagctag ccaacaacaa tcagtacttg cttcagcaaa    3720
cactaactta acagctcaag tgcaagcagt atctgaatct gcagcagcac ctgtccgtgc    3780
aaaagttcgt ccaacataca gtacaaacgc ttcaagttat ccaattggag aatgtacatg    3840
gggagtaaaa acattggcac cttgggctgg agactactgg ggtaatggag cacagtgggc    3900
tacaagtgca gcagcagcag gtttccgtac aggttcaaca cctcaagttg gagcaattgc    3960
atgttggaat gatggtggat atggtcacgt agccgttgtt acagctgttg aatcaacaac    4020
acgtatccaa gtatcagaat caaattatgc aggtaatcgt acaattggaa atcaccgtgg    4080
atggttcaat ccaacaacaa cttctgaagg ttttgttaca tatatttatg cagattaacc    4140
atgaaggaaa cagaccatga aaaaattagg tacattactc gttctctttc tttctgcaat    4200
cattcttgta gcatgtgcta gcggaaaaaa agatacaact tctggtcaaa aactaaaagt    4260
tgttgctaca aactcaatca tcgctgatat tactaaaaat attgctggtg acaaaattga    4320
```

```
ccttcatagt atcgttccga ttgggcaaga cccacacgaa tacgaaccac ttcctgaaga    4380
cgttaagaaa acttctgagg ctaatttgat tttctataac ggtatcaacc ttgaaacagg    4440
tggcaatgct tggtttacaa aattggtaga aaatgccaag aaaactgaaa acaaagacta    4500
cttcgcagtc agcgacggcg ttgatgttat ctaccttgaa ggtcaaaatg aaaaaggaaa    4560
agaagaccca cacgcttggc ttaaccttga aacggtatt attttttgcta aaaatatcgc    4620 caaacaattg agcgccaaag accctaacaa taaagaattc tatgaaaaaa atctcaaaga    4680
atatactgat aagttagaca aacttgataa agaaagtaag gataaattta ataagatccc    4740
tgctgaaaag aaaactcattg taaccagcga aggagcattc aaatacttct ctaaagccta    4800
tggtgtccca agtgcttaca tctgggaaat caatactgaa gaagaaggaa ctcctgaaca    4860
aatcaagacc ttggttgaaa aacttcgcca acaaaagtt ccatcactct ttgtagaatc    4920
aagtgtggat gaccgtccaa tgaaaactgt ttctcaagac acaaacatcc caatctacgc    4980
tcaaatcttt actgactcta tcgcagaaca aggtaaagaa ggcgacagct actacagcat    5040
gatgaaatac aaccttgaca agattgctga aggattggca aaataaagga aacagaccat    5100
gaaacaaagc actattgcac tggcactgct gccgctgctg tttacccctg tgaccaaagc    5160
ccgtacccca gaaatgaaca agctactaa actggtactg ggcgcggtaa tcctgggttc    5220
tactctgctg gcaggttgct ccagcaagaa ttcctgattt tgttggccag ccttgtattg    5280
gtggcagctt ctcttatttg gatactatcc agaactcctg caaccattgc cattccagat    5340
gtggcaggtc agacagttgc agaggccaag gcaacgctca aaaagccaa ttttgagatt    5400 ggtgaggaga agacagaggc tagtgaaaag gtggaagaag ggcggattat ccgtacagat    5460
cctggcgctg gaactggtcg aaaagaagga acgaaaatca atttggttgt ctcatcaggc    5520
aagcaatctt tccaaattag taattatgtc ggtcggaaat cctctgatgt cattgcggaa    5580
ttaaaagaga aaaagttcc agataatttg attaaaattg aggaagaaga gtcgaatgag    5640
agtgaggctg aacggtcct gaagcaaagt ctaccagaag gtacgaccta tgacttgagc    5700
aaggcaactc aaattgtttt gacagtagct aaaaaagcta cgacgattca attagggaac    5760
tatattggac ggaactctac agaagtaatc tcagaactca agcagaagaa ggttcctgag    5820
aatttgatta agatagagga agaagagtcc agcgaaagcg aaccaggaac gattatgaaa    5880
caaagtccag gtgccggaac gacttatgat gtgagtaaac ctactcaaat tgtcttgaca    5940
gtagctaaaa aagttacaag tgttgccatg ccgagttaca ttggttctag cttggagttt    6000
actaagaaca atttgattca aattgttggg attaaggaag ctaatataga agttgtagaa    6060
gtgacgacag cgcctgcagg tagtgcagaa ggcatggttg ttgaacaaag tcctagagca    6120
ggtgaaaagg tagacctcaa taagactaga gtcaagattt caatctacaa acctaaaaca    6180
acttcagcta ctccttaacc atgg                                          6204
```

<210> SEQ ID NO 131
<211> LENGTH: 364
<212> TYPE: PRT
<213> ORGANISM: Artificial Sequence
<220> FEATURE:
<223> OTHER INFORMATION: based on pneumococcus

<400> SEQUENCE: 131

Thr Thr Asp Asp Lys Ile Ala Ala Gln Asp Asn Lys Ile Ser Asn Leu
1               5                   10                  15

Thr Ala Gln Gln Gln Glu Ala Gln Lys Gln Val Asp Gln Ile Gln Glu

```
            20                  25                  30
    Gln Val Ser Ala Ile Gln Ala Glu Gln Ser Asn Leu Gln Ala Glu Asn
             35                  40                  45

Asp Arg Leu Gln Ala Glu Ser Lys Lys Leu Glu Gly Glu Ile Thr Glu
         50                  55                  60

Leu Ser Lys Asn Ile Val Ser Arg Asn Gln Ser Leu Glu Lys Gln Ala
    65                  70                  75                  80

Arg Ser Ala Gln Thr Asn Gly Ala Val Thr Ser Tyr Ile Asn Thr Ile
                     85                  90                  95

Val Asn Ser Lys Ser Ile Thr Glu Ala Ile Ser Arg Val Ala Ala Met
                    100                 105                 110

Ser Glu Ile Val Ser Ala Asn Asn Lys Met Leu Glu Gln Gln Lys Ala
                115                 120                 125

Asp Lys Lys Ala Ile Ser Glu Lys Gln Val Ala Asn Asn Asp Ala Ile
            130                 135                 140

Asn Thr Val Ile Ala Asn Gln Gln Lys Leu Ala Asp Asp Ala Gln Ala
    145                 150                 155                 160

Leu Thr Thr Lys Gln Ala Glu Leu Lys Ala Ala Glu Leu Ser Leu Ala
                    165                 170                 175

Ala Glu Lys Ala Thr Ala Glu Gly Glu Lys Ala Ser Leu Leu Glu Gln
                    180                 185                 190

Lys Ala Ala Glu Ala Glu Ala Arg Ala Ala Val Ala Glu Ala
                195                 200                 205

Ala Tyr Lys Glu Lys Arg Ala Ser Gln Gln Ser Val Leu Ala Ser
            210                 215                 220

Ala Asn Thr Asn Leu Thr Ala Gln Val Gln Ala Val Ser Glu Ser Ala
    225                 230                 235                 240

Ala Ala Pro Val Arg Ala Lys Val Arg Pro Thr Tyr Ser Thr Asn Ala
                    245                 250                 255

Ser Ser Tyr Pro Ile Gly Glu Cys Thr Trp Gly Val Lys Thr Leu Ala
                    260                 265                 270

Pro Trp Ala Gly Asp Tyr Trp Gly Asn Gly Ala Gln Trp Ala Thr Ser
                    275                 280                 285

Ala Ala Ala Gly Phe Arg Thr Gly Ser Thr Pro Gln Val Gly Ala
            290                 295                 300

Ile Ala Cys Trp Asn Asp Gly Gly Tyr Gly His Val Ala Val Val Thr
    305                 310                 315                 320

Ala Val Glu Ser Thr Thr Arg Ile Gln Val Ser Glu Ser Asn Tyr Ala
                    325                 330                 335

Gly Asn Arg Thr Ile Gly Asn His Arg Gly Trp Phe Asn Pro Thr Thr
                    340                 345                 350

Thr Ser Glu Gly Phe Val Thr Tyr Ile Tyr Ala Asp
                    355                 360

<210> SEQ ID NO 132
<211> LENGTH: 309
<212> TYPE: PRT
<213> ORGANISM: Artificial Sequence
<220> FEATURE:
<223> OTHER INFORMATION: based on pneumococcus

<400> SEQUENCE: 132

Met Lys Lys Leu Gly Thr Leu Leu Val Leu Phe Leu Ser Ala Ile Ile
    1               5                   10                  15

Leu Val Ala Cys Ala Ser Gly Lys Lys Asp Thr Thr Ser Gly Gln Lys
```

```
                 20                  25                  30
Leu Lys Val Val Ala Thr Asn Ser Ile Ile Ala Asp Ile Thr Lys Asn
             35                  40                  45

Ile Ala Gly Asp Lys Ile Asp Leu His Ser Ile Val Pro Ile Gly Gln
 50                  55                  60

Asp Pro His Glu Tyr Glu Pro Leu Pro Glu Asp Val Lys Lys Thr Ser
 65                  70                  75                  80

Glu Ala Asn Leu Ile Phe Tyr Asn Gly Ile Asn Leu Glu Thr Gly Gly
                 85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
            115                 120                 125

Gly Gln Asn Glu Lys Gly Lys Glu Asp Pro His Ala Trp Leu Asn Leu
130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
            195                 200                 205

Lys Tyr Phe Ser Lys Ala Tyr Gly Val Pro Ser Ala Tyr Ile Trp Glu
            210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
            275                 280                 285

Gly Asp Ser Tyr Tyr Ser Met Met Lys Tyr Asn Leu Asp Lys Ile Ala
            290                 295                 300

Glu Gly Leu Ala Lys
305

<210> SEQ ID NO 133
<211> LENGTH: 303
<212> TYPE: PRT
<213> ORGANISM: Artificial Sequence
<220> FEATURE:
<223> OTHER INFORMATION: based on pneumococcus

<400> SEQUENCE: 133

Leu Ile Leu Leu Ala Ser Leu Val Leu Val Ala Ala Ser Leu Ile Trp
 1               5                  10                  15

Ile Leu Ser Arg Thr Pro Ala Thr Ile Ala Ile Pro Asp Val Ala Gly
             20                  25                  30

Gln Thr Val Ala Glu Ala Lys Ala Thr Leu Lys Lys Ala Asn Phe Glu
             35                  40                  45

Ile Gly Glu Glu Lys Thr Glu Ala Ser Glu Lys Val Glu Glu Gly Arg
 50                  55                  60

Ile Ile Arg Thr Asp Pro Gly Ala Gly Thr Gly Arg Lys Glu Gly Thr
```

65                  70                  75                  80
Lys Ile Asn Leu Val Val Ser Ser Gly Lys Gln Ser Phe Gln Ile Ser
                    85                  90                  95

Asn Tyr Val Gly Arg Lys Ser Ser Asp Val Ile Ala Glu Leu Lys Glu
            100                 105                 110

Lys Lys Val Pro Asp Asn Leu Ile Lys Ile Glu Glu Glu Ser Asn
        115                 120                 125

Glu Ser Glu Ala Gly Thr Val Leu Lys Gln Ser Leu Pro Glu Gly Thr
    130                 135                 140

Thr Tyr Asp Leu Ser Lys Ala Thr Gln Ile Val Leu Thr Val Ala Lys
145                 150                 155                 160

Lys Ala Thr Thr Ile Gln Leu Gly Asn Tyr Ile Gly Arg Asn Ser Thr
                165                 170                 175

Glu Val Ile Ser Glu Leu Lys Gln Lys Val Pro Glu Asn Leu Ile
            180                 185                 190

Lys Ile Glu Glu Glu Ser Ser Glu Ser Glu Pro Gly Thr Ile Met
        195                 200                 205

Lys Gln Ser Pro Gly Ala Gly Thr Thr Tyr Asp Val Ser Lys Pro Thr
    210                 215                 220

Gln Ile Val Leu Thr Val Ala Lys Lys Val Thr Ser Val Ala Met Pro
225                 230                 235                 240

Ser Tyr Ile Gly Ser Ser Leu Glu Phe Thr Lys Asn Asn Leu Ile Gln
                245                 250                 255

Ile Val Gly Ile Lys Glu Ala Asn Ile Glu Val Val Glu Val Thr Thr
            260                 265                 270

Ala Pro Ala Gly Ser Ala Glu Gly Met Val Val Glu Gln Ser Pro Arg
        275                 280                 285

Ala Gly Glu Lys Val Asp Leu Asn Lys Thr Arg Val Lys Ile Ser
    290                 295                 300

<210> SEQ ID NO 134
<211> LENGTH: 9385
<212> TYPE: DNA
<213> ORGANISM: Artificial Sequence
<220> FEATURE:
<223> OTHER INFORMATION: based on pneumococcus

<400> SEQUENCE: 134
agatctagcc cgcctaatga gcgggctttt ttttaattcg caattccccg atgcataatg      60
tgcctgtcaa atggacgaag caggattct gcaaaccta tgctactccg tcaagccgtc     120
aattgtctga ttcgttacca attatgacaa cttgacggct acatcattca cttttcttc     180 acaaccggca cggaactcgc tcgggctggc cccggtgcat ttttaaata cccgcgagaa     240 atagagttga tcgtcaaaac caacattgcg accgacggtg gcgataggca tccgggtggt     300
gctcaaaagc agcttcgcct ggctgatacg ttggtcctcg cgccagctta agacgctaat     360
ccctaactgc tggcggaaaa gatgtgacag acgcgacggc gacaagcaaa catgctgtgc     420
gacgctggcg atatcaaaat tgctgtctgc caggtgatcg ctgatgtact gacaagcctc     480
gcgtacccga ttatccatcg gtggatggag cgactcgtta atcgcttcca tgcgccgcag     540
taacaattgc tcaagcagat ttatcgccag cagctccgaa tagcgccctt cccttgccc     600 ggcgttaatg atttgcccaa acaggtcgct gaaatgcggc tggtgcgctt catccgggcg     660
aaagaacccc gtattggcaa atattgacgg ccagttaagc cattcatgcc agtaggcgcg     720
cggacgaaag taaacccact ggtgatacca ttcgcgagcc tccggatgac gaccgtagtg     780

```
atgaatctct cctggcggga acagcaaaat atcacccggt cggcaaacaa attctcgtcc    840
ctgattttc accacccct gaccgcgaat ggtgagattg agaatataac ctttcattcc     900
cagcggtcgg tcgataaaaa aatcgagata accgttggcc tcaatcggcg ttaaacccgc    960
caccagatgg gcattaaacg agtatcccgg cagcagggga tcattttgcg cttcagccat   1020
acttttcata ctcccgccat tcagagaaga aaccaattgt ccatattgca tcagacattg   1080
ccgtcactgc gtcttttact ggctcttctc gctaaccaaa ccgtaaccc cgcttattaa    1140
aagcattctg taacaaagcg ggaccaaagc catgacaaaa acgcgtaaca aaagtgtcta   1200
taatcacggc agaaaagtcc acattgatta tttgcacggc gtcacacttt gctatgccat   1260
agcatttta tccataagat tagcggatcc tacctgacgc tttttatcgc aactctctac    1320
tgtttctcca tacccgtttt tttgggctag cgaattctga gaacaaacta aatggataaa   1380
tttcgtgttc aggggccaac gaagctccag ggcgaagtca caatttccgg cgctaaaaat   1440
gctgctctgc ctatccttt tgccgcacta ctggcggaag aaccggtaga gatccagaac    1500
gtcccgaaac tgaaagacgt cgatacatca atgaagctgc taagccagct gggtgcgaaa   1560
gtagaacgta atggttctgt gcatattgat gcccgcgacg ttaatgtatt ctgcgcacct   1620
tacgatctgg ttaaaaccat gcgtgcttct atctgggcgc tggggccgct ggtagcgcgc   1680
tttggtcagg gcaagtttc actacctggc ggttgtacga tcggtgcgcg tccggttgat    1740
ctacacattt ctggcctcga acaattaggc gcgaccatca aactggaaga aggttacgtt   1800
aaagcttccg tcgatggtcg tttgaaaggt gcacatatcg tgatggataa agtcagcgtt   1860
ggcgcaacgg tgaccatcat gtgtgctgca accctggcgg aaggcaccac gattattgaa   1920
aacgcagcgc gtgaaccgga aatcgtcgat accgcgaact tcctgattac gctgggtgcg   1980
aaaattagcg gtcagggcac cgatcgtatc gtcatcgaag gtgtggaacg tttaggcggc   2040
ggtgtctatc gcgttctgcc ggatcgtatc gaaaccggta cttttcctggt ggcggcggcg  2100
atttctcgcg gcaaaattat ctgccgtaac gcgcagccag atactctcga cgccgtgctg   2160
gcgaaactgc gtgacgctgg agcggacatc gaagtcggcg aagactggat tagcctggat   2220
atgcatggca aacgtccgaa ggctgttaac gtacgtaccg cgccgcatcc ggcattcccg   2280
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgc aaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aagcgaata agaattcagg   2640
aaaaaaacgc tgtgaaaaat gttggtttta tcggctggcg cggaatggtc ggctctgttc   2700
tcatgcaacg catggtagag gagcgcgatt tcgacgctat tcgccctgtt ttctttcta    2760
cctcccagtt tggacaggcg gcgcccacct tcggcgacac ctccaccggc acgctacagg   2820
acgcttttga tctggatgcg ctaaaagcgc tcgatatcat cgtgacctgc caggggcggcg   2880
attataccaa cgaaatttat ccaaagctgc gcgaaagcgc atggcagggt tactggattg   2940
atgcggcttc tacgctgcgc atgaaagatg atgccattat tattctcgac ccggtcaacc   3000
aggacgtgat taccgacggc ctgaacaatg gcgtgaagac ctttgtgggc ggtaactgta   3060
ccgttagcct gatgttgatg tcgctgggcg gtctctttgc ccataatctc gttgactggg   3120
```

```
tatccgtcgc gacctatcag gccgcctccg gcggcggcgc gcgccatatg cgcgagctgt    3180
taacccagat gggtcagttg tatggccatg tcgccgatga actggcgacg ccgtcttccg    3240
caattcttga tattgaacgc aaagttacgg cattgacccg cagcggcgag ctgccggttg    3300
ataactttgg cgtaccgctg gcgggaagcc tgatcccctg gatcgacaaa cagctcgata    3360
acggccagag ccgcgaagag tggaaaggcc aggcggaaac caacaagatt ctcaatactg    3420
cctctgtgat tccggttgat ggtttgtgtg tgcgcgtcgg cgcgctgcgc tgtcacagcc    3480
aggcgttcac catcaagctg aaaaagagg tatccattcc gacggtggaa gaactgctgg    3540
cggcacataa tccgtgggcg aaagtggtgc cgaacgatcg tgatatcact atgcgcgaat    3600
taaccccggc ggcggtgacc ggcacgttga ctacgccggt tggtcgtctg cgtaagctga    3660
acatggggcc agagttcttg tcggcgttta ccgtaggcga ccagttgtta tgggcgccg    3720 ccgagccgct gcgtcgaatg ctgcgccagt tggcgtagtc tagctgcacg ataccgtcga    3780
cttgtacata gactcgctcc gaaattaaag aacacttaaa ttatctacta aaggaatctt    3840
tagtcaagtt tatttaagat gacttaacta tgaatacaca attgatgggt gagcgtagga    3900
gcatgcttat gcgaaaggcc atcctgacgg atggcctttt tggatcttcc ggaagacctt    3960
ccattctgaa atgagctgtt gacaattaat catccggctc gtataatgtg tggaattgtg    4020
agcggataac aatttcacac aggaaacaga ccatgatgaa aaagatttgg ctggcgctgg    4080
ctggtatggt tttagctttt agcgcctcgg cagcacagat cagcgacgaa ttcgaaacga    4140
ctgatgacaa aattgctgct caagataata aaattagtaa cttaacagca caacaacaag    4200
aagcccaaaa acaagttgac caaattcagg agcaagtatc agctattcaa gctgagcagt    4260
ctaacttgca agctgaaaat gatagattac aagcagaatc taagaaactc gagggtgaga    4320
ttacagaact ttctaaaaac attgtttctc gtaaccaatc gttggaaaaa caagctcgta    4380
gtgctcaaac aaatggagcc gtaactagct atatcaatac cattgtaaac tcaaaatcaa    4440
ttacagaagc tatttcacgt gttgctgcaa tgagtgaaat cgtatctgca acaacaaaa    4500 tgttagaaca acaaaaggca gataaaaag ctatttctga aaaacaagta gcaaataatg    4560
atgctatcaa tactgtaatt gctaatcaac aaaaattggc tgatgatgct caagcattga    4620
ctacgaaaca ggcagaacta aaagctgctg aattaagtct tgctgctgag aaagcgacag    4680
ctgaagggga aaaagcaagt ctattagagc aaaaagcagc agctgaggca gaggctcgtg    4740
cagctgcggt agcagaagca gcttataaag aaaaacgagc tagccaacaa caatcagtac    4800
ttgcttcagc aaaacactaac ttaacagctc aagtgcaagc agtatctgaa tctgcagcag    4860
cacctgtccg tgcaaaagtt cgtccaacat acagtacaaa cgcttcaagt tatccaattg    4920
gagaatgtac atggggagta aaacattgg caccttgggc tggagactac tggggtaatg    4980
gagcacagtg ggctacaagt gcagcagcag caggtttccg tacaggttca acacctcaag    5040
ttggagcaat tgcatgttgg aatgatggtg gatatggtca cgtagcggtt gttacagctg    5100
ttgaatcaac aacacgtatc caagtatcag aatcaaatta tgcaggtaat cgtacaattg    5160
gaaatcaccg tggatggttc aatccaacaa caacttctga aggttttgtt acatatattt    5220
atgcagatta aaggaaacag accatgaaag ctactaaact ggtactgggc gcggtaatcc    5280
tgggttctac tctgctggca ggttgctcca gcaagaattc cttgtagcat gtgctagcgg    5340
aaaaaaagat acaacttctg gtcaaaaact aaaagttgtt gctacaaaact caatcatcgc    5400 tgatattact aaaaatattg ctggtgacaa aattgacctt catagtatcg ttccgattgg    5460
gcaagaccca cacgaatacg aaccacttcc tgaagacgtt aagaaaactt ctgaggctaa    5520
```

```
tttgattttc tataacggta tcaaccttga aacaggtggc aatgcttggt ttacaaaatt   5580
ggtagaaaat gccaagaaaa ctgaaaacaa agactacttc gcagtcagcg acggcgttga   5640
tgttatctac cttgaaggtc aaaatgaaaa aggaaaagaa gacccacacg cttggcttaa   5700
ccttgaaaac ggtattattt ttgctaaaaa tatcgccaaa caattgagcg ccaaagaccc   5760
taacaataaa gagttctatg aaaaaaatct caaagaatat actgataagt tagacaaact   5820
tgataaagaa agtaaggata aatttaataa gatccctgct gaaaagaaac tcattgtaac   5880
cagcgaagga gcattcaaat acttctctaa agcctatggt gtcccaagtg cttacatctg   5940
ggaaatcaat actgaagaag aaggaactcc tgaacaaatc aagaccttgg ttgaaaaact   6000
tcgccaaaca aaagttccat cactctttgt agaatcaagt gtggatgacc gtccaatgaa   6060
aactgtttct caagacacaa acatcccaat ctacgctcaa atctttactg actctatcgc   6120
agaacaaggt aaagaaggcg acagctacta cagcatgatg aaatacaacc ttgacaagat   6180
tgctgaagga ttggcaaaat aaataggaga tataccccat ggcaaataaa ggagtaaatg   6240
actttatcct ggctatgaat tacgataaaa agaaactctt gacccatcag ggtgaaagta   6300
ttgaaaatcg tttcatcaaa gagggtaatc agctgccgga tgagtttgtt gttatcgaac   6360
gtaagaagcg tagcttgtcg acaaatacaa gtgatatttc tgtaacagct accaacgaca   6420
gtcgcctcta tcctggtgca cttctcgtag tggatgagac cttgttagag aataatccga   6480
ctcttcttgc ggttgatcgt gctccgatga cttatagtat tgatttgcct ggtttggcaa   6540
gtagcgatag ctttctccaa gtggaagacc cgagcaattc aagtgttcgc ggtgcggtaa   6600
acgatttgtt ggctaagtgg catcaagatt atggtcaggt caataatgtc ccagctcgta   6660
tgcagtatga aaaaatcacg gctcacagca tggaacaact caaggtcaag tttggttctg   6720
actttgaaaa gacagggaat tctcttgata ttgattttaa ctctgtccat tcaggtgaaa   6780
agcagattca gattgttaat tttaagcaga tttattatac agtcagcgta gacgctgtta   6840
aaaatccagg agatgtgttt caagatactg taacggtaga ggatttaaaa cagcgtggaa   6900
tttctgcaga gcgtccttg gtctatattt cgagtgttgc ttatgggcgc caagtctatc   6960
tcaagttgga accacgagt aagagtgatg aagtagaggc tgcttttgaa gctttgatca   7020
aaggtgtcaa ggtagctcct cagacagagt ggaagcagat tttggacaat acagaagtga   7080
aggcggttat tttagggggc gacccaagtt cgggtgcccg tgttgtaaca ggcaaggtgg   7140
atatggtaga ggacttgatt caagaaggca gtcgctttac agcagatcat ccaggcttgc   7200
cgatttccta tacaacttct tttttacgtg acaatgtagt tgcgaccttt caaaacagta   7260
cagactatgt tgagactaag gttacagctt accgtaacgg agatttactg ctggatcata   7320
gtggtgccta tgttgcccaa tattatatta cttgggatga attatcctat gatcatcaag   7380
gtaaggaagt cttgactcct aaggcttggg accgtaatgg gcaggatttg acggctcact   7440
ttaccactag tattccttta aaagggaatg ttcgtaatct ctctgtcaaa attcgtgagt   7500
gtaccgggct tgccttcgaa tggtggcgta cggtttatga aaaaaccgat ttgccactgg   7560
tgcgtaagcg tacgatttct atttggggta caactctcta tcctcaggta gaggataagg   7620
tagaaaatga ctaatcccgg ggatccgtcg acctgcagcc aagctcccaa gcttggctgt   7680
tttggcggat gagagaagat tttcagcctg atacagatta aatcagaacg cagaagcggt   7740
ctgataaaac agaatttgcc tggcggcagt agcgcggtgg tcccacctga ccccatgccg   7800
aactcagaag tgaaacgccg tagcgccgat ggtagtgtgg ggtctcccca tgcgagagta   7860
```

-continued

```
gggaactgcc aggcatcaaa taaaacgaaa ggctcagtcg aaagactggg cctttcgttt    7920
tatctgttgt ttgtcggtga acgctctcct gagtaggaca atccgccgg gagcggattt     7980
gaacgttgcg aagcaacggc ccggagggtg gcgggcagga cgcccgccat aaactgccag    8040
gcatcaaatt aagcagaagg ccatcctgac ggatggcctt tttgcgtttc tacaaactct    8100
tttgtttatt tttctaaata cattcaaata tgtatccgct catgagacaa taaccctgat    8160
aaatgcttca ataatggaag atcttccaac atcacaggta acagaaacg tcgggtcgat     8220
cgggaaattc tttcccggac ggcgcggggt tgggcaagcc gcaggcgcgt cagtgctttt    8280
agcgggtgtc ggggcgcagc catgacccag tcacgtagcg atagcggagt gtatactggc    8340
ttaactatgc ggcatcagag cagattgtac tgagagtgca ccatatgcgg tgtgaaatac    8400
cgcacagatg cgtaaggaga aaataccgca tcaggcgctc ttccgcttcc tcgctcactg    8460
actcgctgcg ctcggtcgtt cggctgcggc gagcggtatc agctcactca aaggcggtaa    8520
tacggttatc cacagaatca ggggataacg caggaaagaa catgtgagca aaaggccagc    8580
aaaaggccag gaaccgtaaa aaggccgcgt tgctggcgtt tttccatagg ctccgccccc    8640
ctgacgagca tcacaaaaat cgacgctcaa gtcagaggtg gcgaaacccg acaggactat    8700
aaagatacca ggcgtttccc cctggaagct ccctcgtgcg ctctcctgtt ccgaccctgc    8760
cgcttaccgg atacctgtcc gcctttctcc cttcgggaag cgtggcgctt tctcatagct    8820
cacgctgtag gtatctcagt tcggtgtagg tcgttcgctc caagctgggc tgtgtgcacg    8880
aaccccccgt tcagcccgac cgctgcgcct tatccggtaa ctatcgtctt gagtccaacc    8940
cggtaagaca cgacttatcg ccactggcag cagccactgg taacaggatt agcagagcga    9000
ggtatgtagg cggtgctaca gagttcttga agtggtggcc taactacggc tacactagaa    9060
ggacagtatt tggtatctgc gctctgctga agccagttac cttcggaaaa agagttggta    9120
gctcttgatc cggcaaacaa accaccgctg gtagcggtgg ttttttttgtt tgcaagcagc    9180
agattacgcg cagaaaaaaa ggatctcaag aagatccttt gatcttttct acggggtctg    9240
acgctcagtg gaacgaaaac tcacgttaag ggattttggt catgagatta tcaaaaagga    9300
tcttcaccta gatcctttta aattaaaaat gaagttttaa atcaatctaa agtatatatg    9360
agtaaacttg gtctgacagt ctaga                                          9385
```

<210> SEQ ID NO 135
<211> LENGTH: 364
<212> TYPE: PRT
<213> ORGANISM: Artificial Sequence
<220> FEATURE:
<223> OTHER INFORMATION: based on pneumococcus

<400> SEQUENCE: 135

```
Thr Thr Asp Asp Lys Ile Ala Ala Gln Asp Asn Lys Ile Ser Asn Leu
1               5                   10                  15

Thr Ala Gln Gln Gln Glu Ala Gln Lys Gln Val Asp Gln Ile Gln Glu
            20                  25                  30

Gln Val Ser Ala Ile Gln Ala Glu Gln Ser Asn Leu Gln Ala Glu Asn
        35                  40                  45

Asp Arg Leu Gln Ala Glu Ser Lys Lys Leu Glu Gly Glu Ile Thr Glu
    50                  55                  60

Leu Ser Lys Asn Ile Val Ser Arg Asn Gln Ser Leu Glu Lys Gln Ala
65                  70                  75                  80

Arg Ser Ala Gln Thr Asn Gly Ala Val Thr Ser Tyr Ile Asn Thr Ile
                85                  90                  95
```

Val Asn Ser Lys Ser Ile Thr Glu Ala Ile Ser Arg Val Ala Ala Met
                100                 105                 110

Ser Glu Ile Val Ser Ala Asn Lys Met Leu Glu Gln Gln Lys Ala
            115                 120                 125

Asp Lys Lys Ala Ile Ser Glu Lys Gln Val Ala Asn Asn Asp Ala Ile
130                 135                 140

Asn Thr Val Ile Ala Asn Gln Gln Lys Leu Ala Asp Asp Ala Gln Ala
145                 150                 155                 160

Leu Thr Thr Lys Gln Ala Glu Leu Lys Ala Ala Glu Leu Ser Leu Ala
                165                 170                 175

Ala Glu Lys Ala Thr Ala Glu Gly Glu Lys Ala Ser Leu Leu Glu Gln
            180                 185                 190

Lys Ala Ala Glu Ala Glu Ala Arg Ala Ala Val Ala Glu Ala
195                 200                 205

Ala Tyr Lys Glu Lys Arg Ala Ser Gln Gln Gln Ser Val Leu Ala Ser
        210                 215                 220

Ala Asn Thr Asn Leu Thr Ala Gln Val Gln Ala Val Ser Glu Ser Ala
225                 230                 235                 240

Ala Ala Pro Val Arg Ala Lys Val Arg Pro Thr Tyr Ser Thr Asn Ala
                245                 250                 255

Ser Ser Tyr Pro Ile Gly Glu Cys Thr Trp Gly Val Lys Thr Leu Ala
            260                 265                 270

Pro Trp Ala Gly Asp Tyr Trp Gly Asn Gly Ala Gln Trp Ala Thr Ser
        275                 280                 285

Ala Ala Ala Gly Phe Arg Thr Gly Ser Thr Pro Gln Val Gly Ala
            290                 295                 300

Ile Ala Cys Trp Asn Asp Gly Gly Tyr Gly His Val Ala Val Val Thr
305                 310                 315                 320

Ala Val Glu Ser Thr Thr Arg Ile Gln Val Ser Glu Ser Asn Tyr Ala
                325                 330                 335

Gly Asn Arg Thr Ile Gly Asn His Arg Gly Trp Phe Asn Pro Thr Thr
            340                 345                 350

Thr Ser Glu Gly Phe Val Thr Tyr Ile Tyr Ala Asp
        355                 360

<210> SEQ ID NO 136
<211> LENGTH: 309
<212> TYPE: PRT
<213> ORGANISM: Artificial Sequence
<220> FEATURE:
<223> OTHER INFORMATION: based on pneumococcus

<400> SEQUENCE: 136

Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
    50                  55                  60

Asp Pro His Glu Tyr Glu Pro Leu Pro Glu Asp Val Lys Lys Thr Ser
65                  70                  75                  80

Glu Ala Asn Leu Ile Phe Tyr Asn Gly Ile Asn Leu Glu Thr Gly Gly
                85                  90                  95

```
Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
290                 295                 300

Glu Gly Leu Ala Lys
305

<210> SEQ ID NO 137
<211> LENGTH: 471
<212> TYPE: PRT
<213> ORGANISM: Artificial Sequence
<220> FEATURE:
<223> OTHER INFORMATION: based on pneumococcus

<400> SEQUENCE: 137

Met Ala Asn Lys Gly Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140
```

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Glu Lys Gln Ile Gln Ile
        180                 185                 190

Val Asn Phe Lys Gln Ile Tyr Tyr Thr Val Ser Val Asp Ala Val Lys
    195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
        260                 265                 270

Ala Pro Gln Thr Glu Trp Lys Gln Ile Leu Asp Asn Thr Glu Val Lys
    275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
            325                 330                 335

Arg Asp Asn Val Val Ala Thr Phe Gln Asn Ser Thr Asp Tyr Val Glu
        340                 345                 350

Thr Lys Val Thr Ala Tyr Arg Asn Gly Asp Leu Leu Leu Asp His Ser
    355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
        420                 425                 430

Phe Glu Trp Trp Arg Thr Val Tyr Glu Lys Thr Asp Leu Pro Leu Val
    435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 138
<211> LENGTH: 15
<212> TYPE: DNA
<213> ORGANISM: Artificial Sequence
<220> FEATURE:
<223> OTHER INFORMATION: based on salmonella

<400> SEQUENCE: 138
agggtggtga atgtg                                                  15

<210> SEQ ID NO 139
<211> LENGTH: 15

```
<212> TYPE: DNA
<213> ORGANISM: Artificial Sequence
<220> FEATURE:
<223> OTHER INFORMATION: based on salmonella

<400> SEQUENCE: 139
aggatggtga atatg                                             15

<210> SEQ ID NO 140
<211> LENGTH: 15
<212> TYPE: DNA
<213> ORGANISM: Artificial Sequence
<220> FEATURE:
<223> OTHER INFORMATION: based on salmonella

<400> SEQUENCE: 140
aggatggtga atatg                                             15
```